United States Patent
Li et al.

(10) Patent No.: US 11,286,243 B2
(45) Date of Patent: Mar. 29, 2022

(54) FERROPORTIN INHIBITORS AND METHODS OF USE

(71) Applicant: GLOBAL BLOOD THERAPEUTICS, INC., South San Francisco, CA (US)

(72) Inventors: Zhe Li, San Diego, CA (US); Qing Xu, Foster City, CA (US); Brian Walter Metcalf, Moraga, CA (US); Calvin Wesley Yee, Daly City, CA (US); Peter Michael Rademacher, San Francisco, CA (US); Carsten Alt, Fremont, CA (US)

(73) Assignee: Global Blood Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 16/712,628

(22) Filed: Dec. 12, 2019

(65) Prior Publication Data

US 2020/0190045 A1    Jun. 18, 2020

Related U.S. Application Data

(60) Provisional application No. 62/939,416, filed on Nov. 22, 2019, provisional application No. 62/779,362, filed on Dec. 13, 2018.

(51) Int. Cl.
| | | |
|---|---|---|
| *C07D 498/04* | (2006.01) | |
| *C07D 513/04* | (2006.01) | |
| *C07D 277/62* | (2006.01) | |
| *A61P 7/00* | (2006.01) | |
| *C07D 233/96* | (2006.01) | |
| *A61K 45/06* | (2006.01) | |

(52) U.S. Cl.
CPC .............. *C07D 277/62* (2013.01); *A61P 7/00* (2018.01); *C07D 233/96* (2013.01); *C07D 498/04* (2013.01); *C07D 513/04* (2013.01); *A61K 45/06* (2013.01)

(58) Field of Classification Search
CPC .......................... C07D 498/04; C07D 513/04
See application file for complete search history.

(56) References Cited

U.S. PATENT DOCUMENTS

| | | | |
|---|---|---|---|
| 3,845,770 | A | 11/1974 | Theeuwes et al. |
| 4,326,525 | A | 4/1982 | Swanson et al. |
| 4,902,514 | A | 2/1990 | Barclay et al. |
| 4,992,445 | A | 2/1991 | Lawter et al. |
| 5,001,139 | A | 3/1991 | Lawter et al. |
| 5,023,252 | A | 6/1991 | Hseih |
| 5,616,345 | A | 4/1997 | Geoghegan et al. |
| 9,315,545 | B2 | 4/2016 | Merutka |
| 9,695,166 | B2 | 7/2017 | Li et al. |

FOREIGN PATENT DOCUMENTS

| | | |
|---|---|---|
| CN | 104011066 A | 8/2017 |
| WO | WO 2010/065815 A2 | 6/2010 |
| WO | WO 2011/029832 A1 | 3/2011 |
| WO | WO 2013/086143 A1 | 6/2013 |
| WO | WO 2014/145561 A2 | 9/2014 |
| WO | WO 2015/042515 A1 | 3/2015 |
| WO | WO 2015/157283 A1 | 10/2015 |
| WO | WO 2015/200916 A2 | 12/2015 |
| WO | WO 2016/109363 A1 | 7/2016 |
| WO | WO 2017/068089 A2 | 4/2017 |
| WO | WO 2017/068090 A1 | 4/2017 |
| WO | WO 2018/128828 A1 | 7/2018 |
| WO | WO 2018/192973 A1 | 10/2018 |

OTHER PUBLICATIONS

Arezes et al., "Hepcidin-induced hypoferremia is a critical host defense mechanism against the siderophilic bacterium Vibrio vulnificus," Cell Host Microbe, 17(1):47-57, (2015).
Blanchette et al., "Modulation of hepcidin to treat iron deregulation: potential clinical applications," Expert Rev. Hematol., 9(2):169-186, (2016).
Carreau et al., "Ironing out the details of iron overload in myelofibrosis: Lessons from myelodysplastic syndromes," Blood Rev., 30(5):349-356, (2016).
Casu et al., "Minihepcidin peptides as disease modifiers in mice affected by β-thalassemia and polycythemia vera," Blood, 128(2)265-276, (2016).
Cravatt et al., "Ligand and Target Discovery by Fragment-Based Screening in Human Cells," Cell, 168(3):527-541, (2017).
Cui et al., "Serum iron metabolism and erythropoiesis in patients with myelodysplastic syndrome not receiving RBC transfusions," Leuk. Res., 38(5):545-550, (2014).
Fukuda et al., "Synthesis and SAR studies of 3,6-disubstituted indazole derivatives as potent hepcidin production inhibitors," Bioorganic & Medicinal Chemistry Letters, 27:2148-2152, (2017).

(Continued)

*Primary Examiner* — Brian E McDowell
(74) *Attorney, Agent, or Firm* — Alston & Bird LLP

(57) ABSTRACT

The subject matter described herein is directed to Ferroportin inhibitor compounds of Formula I and pharmaceutical salts thereof, methods of preparing the compounds, pharmaceutical compositions comprising the compounds and methods of administering the compounds for prophylaxis and/or treatment of diseases caused by a lack of hepcidin or iron metabolism disorders, particularly iron overload states, such as thalassemia, sickle cell disease and hemochromatosis. The compounds of Formula I and pharmaceutical salts thereof have the following structure:

I

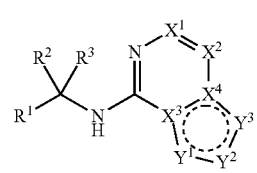

wherein $R^1$, $R^2$, $R^3$, $X^1$, $X^2$, $X^3$, $X^4$, $Y^1$, $Y^2$, and $Y^3$ are as described herein.

24 Claims, No Drawings

(56) References Cited

OTHER PUBLICATIONS

Ganz, Tomas, "Hepcidin and its role in regulating systemic iron metabolism," Hematol Am Soc Hemtaol Educ Program, 2006(1):29-35, (2006), 507.
Hentze et al., "Balancing acts: molecular control of mammalian iron metabolism," Cell, 117(3):285-297, (2004).
Hunter et al., "The solution structure of human hepcidin, a peptide hormone with antimicrobial activity that is involved in iron uptake and hereditary hemochromatosis," J Biol Chem, 277(40):37597-37603, (2002).
Jordan et al., "Hepcidin revisited, disulfide connectivity, dynamics, and structure," J Biol Chem, 284(36:)24155-24167, (2009).
Kang et al., "Design, Synthesis, and Acetylcholinesterase Inhibition Assay of Novel 9-(1-(Substituted-benzyl)piperidin-4-yl)-2-chloro-9H-purin-6-amine Derivatives," Journal of Chemistry, 2013(107302):1-9, (2013).
Krause et al., "LEAP-1, a novel highly disulfide-bonded human peptide, exhibits antimicrobial activity," FEBS Lett., 480(2-3):147-150, (2000).
Nemeth et al., "The N-terminus of hepcidin is essential for its interaction with ferroportin: structure-function study," Blood, 107(1):328-333, (2006).
Origa et al., "Liver iron concentrations and urinary hepcidin in beta-thalassemia," Haematologica, 92(5):583-588, (2007).
Park et al., "Hepcidin, a urinary antimicrobial peptide synthesized in the liver," J Biol Chem, 276(11):7806-7810,(2001).
Powell et al., "Haemochromatosis," The Lancet, 388(10045):706-716, (2016).
Preza et al., "Minihepcidins are rationally designed small peptides that mimic hepcidin activity in mice and may be useful for the treatment of iron overload," J. Clin. Invest., 121 (12):4880-4888, (2011).
PubChem Accession No. 24900775, "N-Hydroxy-4-[[[4-[[(1R)-1-phenylethyl]amino]-7H-pyrrolo[2,3-d]pyrimidin-6-yl]methylamino]methyl]benzamide," Sep. 22, 2008.
PubChem Accession No. 86949463, "1-[6-(Benzylamino)purin-9-yl]-3-[benzyl(methyl)amino]propan-2-ol," Feb. 7, 2015.
Santini et al., "Hepcidin levels and their determinants in different types of myelodysplastic syndromes," PLoS ONE, 6(8):e23109, (2011).
Sebastiani et al., "Pharmacological Targeting of the Hepcidin/Ferroportin Axis," Front. Pharmacol., 7:160, 11 pages, (2016).
Temraz et al., "Iron overload and chelation therapy in myelodysplastic syndromes," Crit. Rev. Oncol. Hematol., 91(1):64-73, (2014).
Walker et al., "Targeting Iron Homeostasis in Acute Kidney Injury," Semin Nephrol., 36(1):62-70, (2016).
Walter et al., "Iron metabolism and iron chelation in sickle cell disease," Acta Haematol., 122(2-3):174-183, (2009).
Zeng et al., "Hepatic hepcidin protects against polymicrobial sepsis in mice by regulating host iron status," Anesthesiology, 122(2):374-386, (2015).
Zhao et al., "MEK1/2 inhibitors reverse acute vascular occlusion in mouse models of sickle cell disease," The FASEB Journal, 30(3):1171-1186, (2016).
WIPO Application No. PCT/US2019/066053, PCT International Search Report and Written Opinion of the International Searching Authority dated Mar. 9, 2020.
Ferron et al., "Cyclic guanidines: synthesis and antiplatelet activity of 4,6,7, 8-tetrahydro-1H-imidazo[1,2-a]pyrazolo[3,4-d]pyrimidin-7-ones and 1,4,6,7,8,9-hexahydropyrazolo [3',4':4,5]pyrimido[2,1-c] [1,2,4]triazin-7-ones," Arzneimittelforschung, 40(12):1328-1331, (1990).
Foster, Allan B., "Deuterium Isotope Effects in Studies of Drug Metabolism," Trends Pharmacol. Sci., 5(12):524-527, (1984).
Schmidt et al., "Heilmittelchemische Studien in der heterocyclischen Reihe. 22. Mitteilung. Pyrazolo-pyrimidine II. Pyrazolo[3,4-d]pyrimidine mit Koffein-ähnlicher Struktur und Wirkung," Helvetica Chimica Acta, 41(4):1052-1060, (1958).
Wamhoff et al., "Notizen Heterocyclic β-Enamino Esters, 39. Synthesis of 1H-Pyrazolo[3,4-d]pyrimidines," Liebigs Annalen der Chemie, 1985(9):1910-1916, (1985).

FERROPORTIN INHIBITORS AND METHODS OF USE

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application No. 62/779,362, filed Dec. 13, 2018, and U.S. Provisional Application No. 62/939,416, filed Nov. 22, 2019.

FIELD

The subject matter described herein is directed to ferroportin inhibitor compounds, methods of making the compounds, pharmaceutical compositions and their use in the prophylaxis and/or treatment of diseases caused by a lack of hepcidin or iron metabolism disorders, particularly iron overload states, such as thalassemia, sickle cell disease and hemochromatosis.

BACKGROUND

In nearly all organisms, iron is an essential trace element. In humans, iron is a critical component for oxygen transport, oxygen uptake, cell functions such as mitochondrial electron transport, cognitive functions, and energy metabolism. Iron is present in enzymes, hemoglobin and myoglobin, as well as in depots in the form of ferritin and hemosiderin. With respect to hemoglobin, approximately half of all iron is present as heme iron, bound in the hemoglobin of the erythrocytes. The human body contains on average approximately 4 to 5 g iron. The iron requirement of a human adult is between 0.5 to 1.5 mg per day, whereas infants and women during pregnancy require 2 to 5 mg of iron per day.

In a healthy human adult, the normal daily loss of iron of about 1 mg is usually replaced via food intake. Iron balance is primarily regulated by recycling and iron recovery from hemoglobin of aging erythrocytes and the duodenal absorption of dietary iron in the form of divalent as well as trivalent iron ions.

Absorption is regulated by the organism depending on the iron requirement and the size of the iron depot. Usually, Fe(III) compounds are dissolved in the stomach at a sufficiently acidic pH value and thus made available for absorption. The absorption of the iron is carried out in the upper small intestine by mucosal cells. Trivalent non-heme iron is first reduced in the intestinal cell membrane to Fe(II) for absorption, for example by ferric reductase (membrane-bound duodenal cytochrome b), so that it can then be transported into the intestinal cells by means of the transport protein DMT1 (divalent metal transporter 1). In contrast, heme iron enters the enterocytes through the cell membrane without any change. In the enterocytes, iron is either stored in ferritin as depot iron, or released into the blood by the transport protein ferroportin. The divalent iron transported into the blood by ferroportin is converted into trivalent iron by oxidases (ceruloplasmin, hephaestin). The trivalent iron is then transported to its destination in the organism by transferrin. ("Balancing acts: molecular control of mammalian iron metabolism," M. W. Hentze, Cell, 1:17, 2004, 285-297). Hepcidin plays a central role in this process because it is the essential regulating factor of iron absorption. The hepcidin-ferroportin system directly regulates iron metabolism.

Iron uptake and storage is regulated by hepcidin. Hepcidin Antimicrobial Peptide (HAMP; also known as LEAP-1; further referred to as Hepcidin) is a 25 amino acid peptide (Krause et al., FEBS Lett. 480, 147-150, 2000). Hepcidin has a hairpin structure with 8 cysteines that form 4 disulfide bridges (Jordan et al., J Biol Chem. 284, 24155-24167, 2009). The N-terminus appears to be important for the iron-regulatory function since deletion of the first 5 amino acids resulted in complete loss of bioactivity (Nemeth et al., Blood, 107, 328-333, 2006). Hepcidin is produced in the liver and functions as the master iron regulatory hormone controlling intestinal iron uptake, and also regulates iron storage in other organs (Ganz, Hematol. Am. Soc. Hematol. Educ. Program, 29-35, 507 2006; Hunter et al., J. Biol. Chem. 277, 37597-37603, 2002; Park et al., J. Biol. Chem. 276, 7806-7810, 2001). Hepcidin limits iron-uptake by binding to the iron transport molecule ferroportin and causing its degradation (Sebastiani et al., Front. Pharmacol. 7, 160, 2016).

The formation of hepcidin is regulated in direct correlation to the organism's iron level, i.e., if the organism is supplied with sufficient iron and oxygen, more hepcidin is formed; if iron and oxygen levels are low, or in case of increased erythropoiesis, less hepcidin is formed. In the small intestinal mucosal cells and in the macrophages hepcidin binds with the transport protein ferroportin, which conventionally transports the phagocytotically recycled iron from the interior of the cell into the blood.

Ferroportin is an iron transporter that plays a key role in regulating iron uptake and distribution in the body and thus in controlling iron levels in the blood. The transport protein ferroportin is a transmembrane protein consisting of 571 amino acids which is formed in the liver, spleen, kidneys, heart, intestine and placenta. In particular, ferroportin is localized in the basolateral membrane of intestinal epithelial cells. Ferroportin bound in this way thus acts to export the iron into the blood. In this case, it is most probable that ferroportin transports iron as $Fe^{2+}$. If hepcidin binds to ferroportin, ferroportin is transported into the interior of the cell, where its breakdown takes place so that the release of the phagocytotically recycled iron from the cells is then almost completely blocked. If the ferroportin is inactivated, for example by hepcidin, so that it is unable to export the iron which is stored in the mucosal cells, the stored iron is lost with the natural shedding of cells via the stools. The absorption of iron in the intestine is therefore reduced, when ferroportin is inactivated or inhibited, for example by hepcidin.

A decrease of hepcidin results in an increase of active ferroportin, thus allowing an enhanced release of stored iron and an enhanced iron uptake, e.g., from the food, resulting in an increase in serum iron levels, i.e., iron overload. Iron overload causes many diseases and undesired medical conditions. Iron overload can be treated by removal of the iron from the body. This treatment includes regularly scheduled phlebotomies (bloodletting). For patients unable to tolerate routine blood draws, there are chelating agents available for use. A disadvantage in the treatment of iron overload by chelation therapy is the removal of the chelated iron from the body when the iron overload has already occurred instead of preventing the occurrence of the disorder.

What is therefore needed and not effectively addressed by the art are compounds that act as ferroportin inhibitors that have desired efficacy and therapeutic potential. This problem as well as others stemming from iron imbalance are addressed by the subject matter described herein.

BRIEF SUMMARY

In certain embodiments, the subject matter described herein is directed to a compound of Formula I or a pharmaceutically acceptable salt thereof.

In certain embodiments, the subject matter described herein is directed to a pharmaceutical composition comprising a compound of Formula I or a pharmaceutically acceptable salt thereof.

In certain embodiments, the subject matter described herein is directed to methods of inhibiting iron transport mediated by ferroportin in a subject, comprising administering to the subject an effective amount of a compound of Formula I or a pharmaceutically acceptable salt thereof.

In certain embodiments, the subject matter described herein is directed to methods of treating a subject afflicted with a disease related to or caused by reduced hepcidin levels, increased iron levels, increased iron absorption, iron overload, increased erythropoiesis, stress erythropoiesis, or ineffective erythropoiesis, comprising administering to the subject an effective amount of a compound of Formula I or a pharmaceutically acceptable salt thereof.

In certain embodiments, the subject matter described herein is directed to methods of preparing compounds of Formula I.

Other embodiments are also described.

DETAILED DESCRIPTION

Described herein are ferroportin inhibitor compounds of Formula I, methods of making the compounds, pharmaceutical compositions comprising the compounds and their use in the prophylaxis and/or treatment of diseases caused by a lack of hepcidin or iron metabolism disorders, particularly iron overload states, such as thalassemia, sickle cell disease and hemochromatosis. Ferroportin is the iron transport protein responsible for the uptake of the released iron via the intestine and its transfer into the blood circulation, where ultimately the iron is delivered to the appropriate tissues and organs. Inactivation or inhibition of the ferroportin reduces or prevents the export of the iron, thereby reducing the absorption of iron in the intestine and ultimately the amount of iron in the body. These compounds, compositions and methods can be used for an effective therapy for the prophylaxis and treatment of iron metabolism disorders which are associated with increased iron levels. It is desirable to provide compounds, compositions and methods that exhibit few side effects, have very low toxicity and good bioavailability and compatibility.

Iron overload has been associated with a variety of diseases (Blanchette et al., Expert Rev. Hematol. 9, 169-186, 2016). Hereditary hemochromatosis is the most common inherited disease in Europe and is caused by lack of, or insensitivity to, hepcidin (Powell et al., The Lancet 388, 706-716, 2016). The clinical manifestation of hemochromatosis are hepatic cirrhosis, diabetes, and skin pigmentation (Powell et al., The Lancet 388, 706-716, 2016). While this disease can be managed by phlebotomy, this approach may be cumbersome and does not treat the cause of the disease.

Iron-loading anemias such as beta-thalassemia are also associated with reduced hepcidin levels (Origa et al., Haematologica 92, 583-588, 2007). Treatment of this disease with hepcidin mimetics may not only address the iron overload, but has also been shown to improve the ineffective erythropoiesis that occurs in this disease (Casu et al., Blood 128, 265-276, 2016). This may be of major benefit for thalassemia patients who may be less dependent on blood transfusions, which can contribute to the iron overload in these patients.

Myelofibrosis, myelodysplastic syndrome, and sickle cell disease are diseases that are also characterized by ineffective erythropoiesis and that may require frequent blood transfusions (Carreau et al., Blood Rev. 30, 349-356, 2016; Temraz et al., Crit. Rev. Oncol. Hematol. 91, 64-73, 2014; Walter et al., Acta Haematol. 122, 174-183, 2009). Reduced hepcidin levels have been described in some of these patients (Cui et al., Leuk. Res. 38, 545-550, 2014; Santini et al., PLoS ONE 6, e23109, 2011). Hepcidin mimetics may also be beneficial in these patients.

Polycythemia vera is a disease characterized by increased erythropoiesis. It has been shown in animal models that high doses of hepcidin mimetics can ameliorate this disease by diminishing erythropoiesis (Casu et al., Blood 128, 265-276, 2016).

Reduction of iron uptake and thereby serum iron levels may even be beneficial in diseases where iron load is normal, such as kidney diseases (Walker and Agarwal, Nephrol. 36, 62-70, 2016), infections with iron-dependent bacteria (Arezes et al., Cell Host Microbe 17, 47-57, 2015), and polymicrobial sepsis (Zeng et al., Anesthesiology, 122, 374-386, 2015).

Hepcidin itself is limited in its use as a drug because of its complex structure which requires a complicated manufacturing, and also its limited in vivo duration of action. Continuous efforts have been made to search for hepcidin mimetics and chemical compounds that could be used to increase hepcidin levels.

A common approach relates to small hepcidin-derived or hepcidin-like peptides, which can be produced affordably, and can be used to treat hepcidin-related diseases and disorders such as those described herein. Such so-called mini-hepcidins are rationally designed small peptides that mimic hepcidin activity and may be useful for the treatment of iron overload, and also iron overload related disease symptoms.

Such mini-hepcidin peptides are described for example in WO 2010/065815 A2 and WO 2013/086143 A1. WO 2015/157283 A1 and the corresponding U.S. Pat. No. 9,315,545 B2 describe hepcidin mimetic peptides and the use thereof in hepcidin-related disorders, such as iron overload, beta-thalassemia, hemochromatosis etc. and cover a development compound M012 of the company Merganser Biotech, having been under evaluation in a Phase 1 clinical program as a potentially transformative therapy for a number of hematological diseases including beta-thalassemia, low risk myelodysplasia and polycythemia vera.

WO 2014/145561 A2 and WO 2015/200916 A2 describe further small hepcidin peptide analogues and the use thereof in the treatment or prevention of a variety of hepcidin-related diseases, including iron overload diseases and iron-loading anemias, and further related disorders. Further, WO2015/042515 A1 relates to hepcidin and its peptide fragments, which are particularly intended for treating renal ischemia reperfusion injury or acute kidney injury. Further, mini-hepcidin analogs are described for example by Preza et al., J. Clin. Invest., 121 (12), 4880-4888, 2011 or in CN 104 011 066 and in WO 2016/109363 A1.

Ferroportin inhibitors as well as compounds that have hepcidin-like activity are needed that also possess additional beneficial properties such as improved solubility, stability, and/or potency. An advantage of the ferroportin inhibitor compounds of Formula I described herein is their preparation in sufficient yields by the synthetic routes disclosed herein.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. Unless otherwise defined, all technical and scientific terms used herein have the same meaning as commonly understood by one of ordinary skill in this field. All publications, patent applications, patents, and other references mentioned herein are incorporated by reference in their entirety. In the event that one or more of the incorporated literature, patents, and similar materials differs from or contradicts this application, including but not limited to defined terms, term usage, described techniques, or the like, this application controls.

I. Definitions

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line or a dashed line drawn through or perpendicular across the end of a line in a structure indicates a specified point of attachment of a group. Unless chemically or structurally required, no directionality or stereochemistry is indicated or implied by the order in which a chemical group is written or named.

The prefix "$C_u$-$C_v$" indicates that the following group has from u to v carbon atoms. For example, "$C_1$-$C_6$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±50%. In certain other embodiments, the term "about" includes the indicated amount ±20%. In certain other embodiments, the term "about" includes the indicated amount ±10%. In other embodiments, the term "about" includes the indicated amount ±5%. In certain other embodiments, the term "about" includes the indicated amount ±1%. In certain other embodiments, the term "about" includes the indicated amount ±0.5% and in certain other embodiments, 0.1%. Such variations are appropriate to perform the disclosed methods or employ the disclosed compositions. Also, to the term "about x" includes description of "x". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_1$-$C_{20}$ alkyl), 1 to 12 carbon atoms (i.e., $C_1$-$C_{12}$ alkyl), 1 to 8 carbon atoms (i.e., $C_1$-$C_8$ alkyl), 1 to 6 carbon atoms (i.e., $C_1$-$C_6$ alkyl), 1 to 4 carbon atoms (i.e., $C_1$-$C_4$ alkyl), or 1 to 3 carbon atoms (i.e., $C_1$-$C_3$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH(CH$_3$)$_2$) and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g., arylalkyl or aralkyl, the last mentioned group contains the atom by which the moiety is attached to the rest of the molecule.

"Alkenyl" refers to an alkyl group containing at least one carbon-carbon double bond and having from 2 to 20 carbon atoms (i.e., $C_2$-$C_{20}$ alkenyl), 2 to 8 carbon atoms (i.e., $C_2$-$C_8$ alkenyl), 2 to 6 carbon atoms (i.e., $C_2$-$C_6$ alkenyl) or 2 to 4 carbon atoms (i.e., $C_2$-$C_4$ alkenyl). Examples of alkenyl groups include, e.g., ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_2$-$C_{20}$ alkynyl), 2 to 8 carbon atoms (i.e., $C_2$-$C_8$ alkynyl), 2 to 6 carbon atoms (i.e., $C_2$-$C_6$ alkynyl) or 2 to 4 carbon atoms (i.e., $C_2$-$C_4$ alkynyl). The term "alkynyl" also includes those groups having one triple bond and one double bond.

"Alkoxy" refers to the group "alkyl-O—". Examples of alkoxy groups include, e.g., methoxy, ethoxy, n-propoxy, iso-propoxy, n-butoxy, tert-butoxy, sec-butoxy, n-pentoxy, n-hexoxy and 1,2-dimethylbutoxy.

"Alkylthio" refers to the group "alkyl-S—". "Alkylsulfinyl" refers to the group "alkyl-S(O)—". "Alkylsulfonyl" refers to the group "alkyl-S(O)$_2$—". "Alkylsulfonylalkyl" refers to -alkyl-S(O)$_2$-alkyl.

"Acyl" refers to a group —C(O)R$^y$, wherein R$^y$ is hydrogen, alkyl, alkenyl, alkynyl, cycloalkyl, heterocyclyl, aryl, heteroalkyl or heteroaryl; each of which may be optionally substituted, as defined herein. Examples of acyl include, e.g., formyl, acetyl, cyclohexylcarbonyl, cyclohexylmethylcarbonyl and benzoyl.

"Amido" refers to both a "C-amido" group which refers to the group —C(O)NR$^y$R$^z$ and an "N-amido" group which refers to the group —NR$^y$C(O)R$^z$, wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein, or R$^y$ and R$^z$ are taken together to form a cycloalkyl or heterocyclyl; each of which may be optionally substituted, as defined herein.

"Amino" refers to the group —NR$^y$R$^z$ wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Amidino" refers to —C(NR$^y$)(NR$^z{}_2$), wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_6$-$C_{20}$ aryl), 6 to 12 carbon ring atoms (i.e., $C_6$-$C_{12}$ aryl), or 6 to 10 carbon ring atoms (i.e., $C_6$-$C_{10}$ aryl). Examples of aryl groups include, e.g., phenyl, naphthyl, fluorenyl and anthryl. Aryl, however, does not encompass or overlap in any way with heteroaryl defined below. If one or more aryl groups are fused with a heteroaryl, the resulting ring system is heteroaryl regardless of the point of attachment. If one or more aryl groups are fused with a heterocyclyl, the resulting ring system is heterocyclyl regardless of the point of attachment.

"Arylalkyl" or "Aralkyl" refers to the group "aryl-alkyl-", such as benzyl.

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Carboxyl ester" or "ester" refer to both —OC(O)R$^x$ and —C(O)OR$^x$, wherein R$^x$ is alkyl, alkenyl, alkynyl, cycloalkyl, heterocyclyl, aryl, heteroalkyl or heteroaryl; each of which may be optionally substituted, as defined herein.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e., the cyclic group having at least one double bond) and carbocyclic fused ring systems having at least one $sp^3$ carbon atom (i.e., at least one non-aromatic ring). As used herein, cycloalkyl has from 3 to 20 ring carbon atoms (i.e., $C_3$-$C_{20}$ cycloalkyl), 3 to 12 ring carbon atoms (i.e., $C_3$-$C_{12}$ cycloalkyl), 3 to 10 ring carbon atoms (i.e., $C_3$-$C_{10}$ cycloalkyl), 3 to 8 ring carbon atoms (i.e., $C_3$-$C_8$ cycloalkyl), 3 to 7 ring carbon atoms (i.e., $C_3$-$C_7$ cycloalkyl), or 3 to 6 ring carbon atoms (i.e., $C_3$-$C_6$ cycloalkyl). Monocyclic groups include, for example, cyclopropyl, cyclobutyl, cyclopentyl, cyclohexyl, cycloheptyl and cyclooctyl. Polycyclic groups include, for example, bicyclo[2.2.1]heptanyl, bicyclo[2.2.2]octanyl, adamantyl, norbornyl, decalinyl, 7,7-dimethyl-bicyclo[2.2.1]heptanyl and the like. Further, the term cycloalkyl is intended to encompass any non-aromatic ring which may be fused to an aryl ring, regardless of the attachment to the remainder of the molecule. Still further, cycloalkyl also includes "spirocycloalkyl" when there are two positions for substitution on the same carbon atom, for example spiro[2.5]octanyl, spiro[4.5]decanyl, or spiro[5.5]undecanyl.

"Cycloalkylalkyl" refers to the group "cycloalkyl-alkyl-", such as ($C_3$-$C_6$ cycloalkyl)-$C_1$-$C_3$ alkyl.

"Guanidino" refers to —NR$^y$C(=NR$^z$)(NR$^y$R$^z$), wherein each R$^y$ and R$^z$ are independently hydrogen, alkyl, alkynyl, cycloalkyl, heterocyclyl, aryl, heteroalkyl or heteroaryl; each of which may be optionally substituted, as defined herein.

"Hydrazino" refers to —NHNH$_2$.

"Imino" refers to a group —C(NR$^y$)R$^z$, wherein R$^y$ and R$^z$ are each independently hydrogen, alkyl, alkenyl, alkynyl, cycloalkyl, heterocyclyl, aryl, heteroalkyl or heteroaryl; each of which may be optionally substituted, as defined herein.

"Imido" refers to a group —C(O)NR$^y$C(O)R$^z$, wherein R$^y$ and R$^z$ are each independently hydrogen, alkyl, alkenyl, alkynyl, cycloalkyl, heterocyclyl, aryl, heteroalkyl or heteroaryl; each of which may be optionally substituted, as defined herein.

"Halogen" or "halo" refers to atoms occupying group VIIA of the periodic table, such as fluoro (fluorine), chloro (chlorine), bromo (bromine) or iodo (iodine).

"Haloalkyl" refers to an unbranched or branched alkyl group as defined above, wherein one or more (e.g., 1 to 6, or 1 to 3) hydrogen atoms are replaced by a halogen. For example, halo-$C_1$-$C_3$ alkyl refers to an alkyl group of 1 to 3 carbons wherein at least one hydrogen atom is replaced by a halogen. Where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl and the like.

"Haloalkoxy" refers to an alkoxy group as defined above, wherein one or more (e.g., 1 to 6, or 1 to 3) hydrogen atoms are replaced by a halogen.

"Hydroxyalkyl" refers to an alkyl group as defined above, wherein one or more (e.g., 1 to 6, or 1 to 3) hydrogen atoms are replaced by a hydroxy group.

"Heteroalkyl" refers to an alkyl group in which one or more of the carbon atoms (and any associated hydrogen atoms) are each independently replaced with the same or different heteroatomic group, provided the point of attachment to the remainder of the molecule is through a carbon atom. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR$^y$—, —O—, —S—, —S(O)—, —S(O)$_2$—, and the like, wherein R$^y$ is hydrogen, alkyl, alkenyl, alkynyl, cycloalkyl, heterocyclyl, aryl, heteroalkyl or heteroaryl; each of which may be optionally substituted, as defined herein. Examples of heteroalkyl groups include, e.g., ethers (e.g., —CH$_2$OCH$_3$, —CH(CH$_3$)OCH$_3$, —CH$_2$CH$_2$OCH$_3$, —CH$_2$CH$_2$OCH$_2$CH$_2$OCH$_3$, etc.), thioethers (e.g., —CH$_2$SCH$_3$, —CH(CH$_3$)SCH$_3$, —CH$_2$CH$_2$SCH$_3$, —CH$_2$CH$_2$SCH$_2$CH$_2$SCH$_3$, etc.), sulfones (e.g., —CH$_2$S(O)$_2$CH$_3$, —CH(CH$_3$)S(O)$_2$CH$_3$, —CH$_2$CH$_2$S(O)$_2$CH$_3$, —CH$_2$CH$_2$S(O)$_2$CH$_2$CH$_2$OCH$_3$, etc.) and amines (e.g., —CH$_2$NR$^y$CH$_3$, —CH(CH$_3$)NR$^y$CH$_3$, —CH$_2$CH$_2$NR$^y$CH$_3$, —CH$_2$CH$_2$NR$^y$CH$_2$CH$_2$NR$^y$CH$_3$, etc., where R$^y$ is hydrogen, alkyl, alkenyl, alkynyl, cycloalkyl, heterocyclyl, aryl, heteroalkyl, or heteroaryl; each of which may be optionally substituted, as defined herein). As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings or multiple fused rings, with one or more ring heteroatoms independently selected from nitrogen, oxygen, and sulfur. As used herein, heteroaryl includes 1 to 20 ring carbon atoms (i.e., $C_1$-$C_{20}$ heteroaryl), 3 to 12 ring carbon atoms (i.e., $C_3$-$C_{12}$ heteroaryl), or 3 to 8 carbon ring atoms (i.e., $C_3$-$C_8$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 9-10 membered ring systems (i.e., 9-10 membered heteroaryl), 5-10 membered ring systems (i.e., 5-10 membered heteroaryl), 5-7 membered ring systems (i.e., 5-7 membered heteroaryl), 5-6 membered ring systems (i.e., 5-6 membered heteroaryl), or 4-6 membered ring systems (i.e., 4-6 membered heteroaryl), each independently having 1 to 4 ring heteroatoms, 1 to 3 ring heteroatoms, 1 to 2 ring heteroatoms, or 1 ring heteroatom independently selected from nitrogen, oxygen and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heteroarylalkyl" refers to the group "heteroaryl-alkyl-".

"Heterocyclyl" refers to a saturated or partially unsaturated cyclic alkyl group, with one or more ring heteroatoms independently selected from nitrogen, oxygen and sulfur. The term "heterocyclyl" includes heterocycloalkenyl groups (i.e., the heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro, and may comprise one or more (e.g., 1 to 3) oxo (=O) or N-oxide (—O—) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_2$-$C_{20}$ heterocyclyl), 2 to 12 ring carbon atoms (i.e., $C_2$-$C_{12}$ heterocyclyl), 2 to 10 ring carbon atoms (i.e., $C_2$-$C_{10}$ heterocyclyl), 2 to 8 ring carbon atoms (i.e., $C_2$-$C_8$ heterocyclyl), 3 to 12 ring carbon atoms (i.e., $C_3$-$C_{12}$ heterocyclyl), 3 to 8 ring carbon atoms (i.e., $C_3$-$C_8$ heterocyclyl), or 3 to 6 ring carbon atoms (i.e., $C_3$-$C_6$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. When the heterocycle ring contains 4- to 6-ring atoms, it is also referred to herein as a 4- to 6-membered heterocycle. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), tetrahydropyranyl, thiomorpholinyl, thiamorpholinyl, 1-oxo-thiomorpholinyl and 1,1-dioxo-thiomorpholinyl. The term "heterocyclyl" also includes "spiroheterocyclyl" when there are two positions for substitution on the same carbon atom. Examples of the spiro-heterocyclyl rings include, e.g., bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system.

"Heterocyclylalkyl" refers to the group "heterocyclyl-alkyl-."

"Oxime" refers to the group —CR$^y$(=NOH) wherein R$^y$ is hydrogen, alkyl, alkenyl, alkynyl, cycloalkyl, heterocyclyl, aryl, heteroalkyl or heteroaryl; each of which may be optionally substituted, as defined herein.

"Sulfonyl" refers to the group —S(O)$_2$R$^y$, where R$^y$ is hydrogen, alkyl, alkenyl, alkynyl, cycloalkyl, heterocyclyl, aryl, heteroalkyl or heteroaryl; each of which may be optionally substituted, as defined herein. Examples of sulfonyl are methylsulfonyl, ethylsulfonyl, phenylsulfonyl and toluenesulfonyl.

"Sulfinyl" refers to the group —S(O)R$^y$, where R$^y$ is hydrogen, alkyl, alkenyl, alkynyl, cycloalkyl, heterocyclyl, aryl, heteroalkyl or heteroaryl; each of which may be optionally substituted, as defined herein. Examples of sulfinyl are methylsulfinyl, ethylsulfinyl, phenylsulfinyl and toluenesulfinyl.

"Sulfonamido" refers to the groups —SO$_2$NR$^y$R$^z$ and —NR$^y$SO$_2$R$^z$, where R$^y$ and R$^z$ are each independently hydrogen, alkyl, alkenyl, alkynyl, cycloalkyl, heterocyclyl, aryl, heteroalkyl or heteroaryl; each of which may be optionally substituted, as defined herein.

The terms "optional" or "optionally" means that the subsequently described event or circumstance may or may not occur and that the description includes instances where said event or circumstance occurs and instances in which it does not. Also, the term "optionally substituted" refers to any one or more (e.g., 1 to 5, 1 to 4, or 1 to 3) hydrogen atoms on the designated atom or group may or may not be replaced by a moiety other than hydrogen.

The term "substituted" used herein means any of the above groups (i.e., alkyl, alkenyl, alkynyl, alkylene, alkoxy, haloalkyl, haloalkoxy, cycloalkyl, aryl, heterocyclyl, heteroaryl, and/or heteroalkyl) wherein at least one (e.g., 1 to 5, 1 to 4, or 1 to 3) hydrogen atom is replaced by a bond to a non-hydrogen atom such as, but not limited to alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanidino, halo, haloalkyl, haloalkoxy, hydroxyalkyl, heteroalkyl, heteroaryl, heteroarylalkyl, heterocyclyl, heterocyclylalkyl, —NHNH$_2$, =NNH$_2$, imino, imido, hydroxy, oxo, oxime, nitro, sulfonyl, sulfinyl, alkylsulfonyl, alkylsulfinyl, thiocyanate, —S(O)OH, —S(O)$_2$OH, sulfonamido, thiol, thioxo, N-oxide or —Si(R$^y$)$_3$, wherein each R$^y$ is independently hydrogen, alkyl, alkenyl, alkynyl, heteroalkyl, cycloalkyl, aryl, heteroaryl or heterocyclyl.

In certain embodiments, "substituted" includes any of the above alkyl, alkenyl, alkynyl, cycloalkyl, heterocyclyl, aryl or heteroaryl groups in which one or more (e.g., 1 to 5, 1 to 4, or 1 to 3) hydrogen atoms are independently replaced with deuterium, halo, cyano, nitro, azido, oxo, alkyl, alkenyl, alkynyl, haloalkyl, cycloalkyl, heterocyclyl, aryl, heteroaryl, —NR$^g$R$^h$, —NR$^g$C(=O)R$^h$, —NR$^g$C(=O)NR$^g$R$^h$, —NR$^g$C(=O)OR$^h$, —NR$^g$S(=O)$_{1-2}$R$^h$, —C(=O)R$^g$, —C(=O)OR$^g$, —OC(=O)OR$^g$, —OC(=O)R$^g$, —C(=O)NR$^g$R$^h$, —OC(=O)NR$^g$R$^h$, —OR$^g$, —SR$^g$, —S(=O)R$^g$, —S(=O)$_2$R$^g$, —OS(=O)$_{1-2}$R$^g$, —S(=O)$_{1-2}$OR$^g$, —NR$^g$S(=O)$_{1-2}$NR$^g$R$^h$, =NSO$_2$R$^g$, =NOR$^g$, —S(=O)$_{1-2}$NR$^g$R$^h$, —SF$_5$, —SCF$_3$ or —OCF$_3$. In certain embodiments, "substituted" also means any of the above groups in which one or more (e.g., 1 to 5, 1 to 4, or 1 to 3) hydrogen atoms are replaced with —C(=O)R$^g$, —C(=O)OR$^g$, —C(=O)NR$^g$R$^h$, —CH$_2$SO$_2$R$^g$, or —CH$_2$SO$_2$NR$^g$R$^h$. In the foregoing, R$^g$ and R$^h$ are the same or different and independently hydrogen, alkyl, alkenyl, alkynyl, alkoxy, thioalkyl, aryl, aralkyl, cycloalkyl, cycloalkylalkyl, haloalkyl, heterocyclyl, heterocyclylalkyl, heteroaryl, and/or heteroarylalkyl. In certain embodiments, "substituted" also means any of the above groups in which one or more (e.g., 1 to 5, 1 to 4, or 1 to 3) hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, and/or heteroarylalkyl, or two of R$^g$ and R$^h$ and R$^i$ are taken together with the atoms to which they are attached to form a heterocyclyl ring optionally substituted with oxo, halo or alkyl optionally substituted with oxo, halo, amino, hydroxyl, or alkoxy.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein.

In certain embodiments, as used herein, the phrase "one or more" refers to one to five. In certain embodiments, as used herein, the phrase "one or more" refers to one to four. In certain embodiments, as used herein, the phrase "one or more" refers to one to three.

Any compound or structure given herein, is intended to represent unlabeled forms as well as isotopically labeled forms (isotopologues) of the compounds. These forms of compounds may also be referred to as and include "isotopically enriched analogs." Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F, $^3$H, $^{11}$C labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium. Further, in some embodiments, the corresponding deuterated analog is provided.

In many cases, the compounds of this disclosure are capable of forming acid and/or base salts by virtue of the presence of amino and/or carboxyl groups or groups similar thereto.

Provided also are a pharmaceutically acceptable salt, isotopically enriched analog, deuterated analog, isomer (such as a stereoisomer), mixture of isomers (such as a mixture of stereoisomers), prodrug, and metabolite of the compounds described herein.

"Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include, e.g., hydrochloric acid, hydrobromic acid, sulfuric acid, nitric acid, phosphoric acid and the like. Salts derived from organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Likewise, pharmaceutically acceptable base addition salts can be prepared from inorganic and organic bases. Salts derived from inorganic bases include, by way of example only, sodium, potassium, lithium, aluminum, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., $HN(alkyl)_2$), trialkyl amines (i.e., $N(alkyl)_3$), substituted alkyl amines (i.e., $NH_2$(substituted alkyl)), di(substituted alkyl) amines (i.e., $HN(substituted\ alkyl)_2$), tri(substituted alkyl) amines (i.e., $N(substituted\ alkyl)_3$), alkenyl amines (i.e., $NH_2$(alkenyl)), dialkenyl amines (i.e., $HN(alkenyl)_2$), trialkenyl amines (i.e., $N(alkenyl)_3$), substituted alkenyl amines (i.e., $NH_2$(substituted alkenyl)), di(substituted alkenyl) amines (i.e., $HN(substituted\ alkenyl)_2$), tri(substituted alkenyl) amines (i.e., $N(substituted\ alkenyl)_3$, mono-, di- or tri-cycloalkyl amines (i.e., $NH_2$(cycloalkyl), $HN(cycloalkyl)_2$, $N(cycloalkyl)_3$), mono-, di- or tri-arylamines (i.e., $NH_2$(aryl), $HN(aryl)_2$, $N(aryl)_3$) or mixed amines, etc. Specific examples of suitable amines include, by way of example only, isopropylamine, trimethyl amine, diethyl amine, tri (iso-propyl) amine, tri(n-propyl) amine, ethanolamine, 2-dimethylaminoethanol, piperazine, piperidine, morpholine, N-ethylpiperidine and the like.

The term "hydrate" refers to the complex formed by the combining of a compound described herein and water.

A "solvate" refers to an association or complex of one or more solvent molecules and a compound of the disclosure. Examples of solvents that form solvates include, but are not limited to, water, isopropanol, ethanol, methanol, dimethylsulfoxide, ethylacetate, acetic acid and ethanolamine.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The compounds of the invention, or their pharmaceutically acceptable salts include an asymmetric center and may thus give rise to enantiomers, diastereomers, and other stereoisomeric forms that may be defined, in terms of absolute stereochemistry, as (R)- or (S)- or, as (D)- or (L)-for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC). When the compounds described herein contain olefinic double bonds or other centres of geometric asymmetry, and unless specified otherwise, it is intended that the compounds include both E and Z geometric isomers.

A "stereoisomer" refers to a compound made up of the same atoms bonded by the same bonds but having different three-dimensional structures, which are not interchangeable. The present invention contemplates various stereoisomers and mixtures thereof and includes "enantiomers," which refers to two stereoisomers whose molecules are nonsuperimposeable mirror images of one another.

"Diastereomers" are stereoisomers that have at least two asymmetric atoms, but which are not mirror-images of each other.

Relative centers of the compounds as depicted herein are indicated graphically using the "thick bond" style (bold or parallel lines) and absolute stereochemistry is depicted using wedge bonds (bold or parallel lines).

"Prodrugs" means any compound which releases an active parent drug according to a structure described herein in vivo when such prodrug is administered to a mammalian subject. Prodrugs of a compound described herein are prepared by modifying functional groups present in the compound described herein in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate and benzoate derivatives), amides, guanidines, carbamates (e.g., N,N-dimethylaminocarbonyl) of hydroxy functional groups in compounds described herein and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

The term, "metabolite," as used herein refers to a resulting product formed when a compound disclosed herein is metabolized. As used herein, the term "metabolized" refers to the sum of processes (including but not limited to hydrolysis reactions and reactions catalyzed by enzymes) by which a particular substance, such as a compound disclosed herein, is changed by an organism. For example, an aldehyde moiety (—C(O)H) of the compounds of the invention may be reduced in vivo to a —CH$_2$OH moiety.

Use of the word "inhibitor," "inhibit" or "inhibition," herein refers to activity of a compound of Formula I or a pharmaceutically acceptable salt on ferroportin, unless specified otherwise. By "inhibit" herein is meant to decrease the activity of ferroportin, as compared to the activity of ferroportin in the absence of the compound. In some embodiments, the term "inhibit" means a decrease in ferroportin activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in ferroportin activity of about 5% to about 25%, about 25% to about 50%, about 50% to about 75%, or about 75% to 100%. In some embodiments, inhibit means a decrease in ferroportin activity of about 95% to 100%, e.g., a decrease in activity of 95%, 96%, 97%, 98%, 99%, or 100%. Such decreases can be measured using a variety of techniques that would be recognizable by one of skill in the art, including in vitro assays.

As used herein, the term "ferroportin inhibitor" and the like refers to a compound that reduces, inhibits, or otherwise diminishes one or more of the biological activities of ferroportin, for instance by inducing internalization of ferroportin. The activity could decrease by a statistically significant amount including, for example, a decrease of at least about 5%, 10%, 15%, 20%, 25%, 30%, 35%, 40%, 45%, 50%, 55%, 60%, 65%, 70%, 75%, 80%, 85%, 95% or 100% of the activity of ferroportin compared to an appropriate control.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a sickle cell disease. The therapeutically effective amount may vary depending on the subject, and disease or condition being treated, the weight and age of the subject, the severity of the disease or condition, and the manner of administering, which can readily be determined by one of ordinary skill in the art.

Additional definitions may also be provided below as appropriate.

II. Compounds

In certain embodiments, the subject matter described herein is directed to compounds of Formula I:

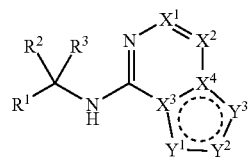

I wherein,
the dashed circle in this portion of the molecule

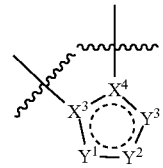

represents single or double bonds in an aromatic or non-aromatic ring system depending on the value of variables $X^3$, $X^4$, $Y^1$, $Y^2$ and $Y^3$, as described herein, $R^1$ is phenyl or a 6-membered heteroaryl, wherein the heteroaryl contains up to two ring heteroatoms, wherein the phenyl and heteroaryl are optionally substituted with one, two, three, or four substituents, each of which is independently selected from
the group consisting of $C_1$-$C_6$ alkyl, halogen, —OR$^a$, —NR$^{1b}$R$^{1c}$, —N$_3$, and —CN;
wherein R$^{1a}$, R$^{1b}$, and R$^{1c}$ are each independently selected from the group consisting of hydrogen and $C_1$-$C_6$ alkyl;

$R^2$ and $R^3$ are each independently hydrogen or $C_1$-$C_6$ alkyl; or $R^2$ and $R^3$ taken together with the carbon to which they are attached form a $C_3$-$C_6$ cycloalkyl;

$X^1$ and $X^2$ are each independently N or CR$^{10}$; wherein
R$^{10}$ is selected from the group consisting of hydrogen, halogen, —CN, $C_1$-$C_3$ alkyl, —OR$^{15}$, and —NR$^{16}$R$^{17}$;
wherein $R^{15}$, $R^{16}$, and $R^{17}$ are each independently selected from the group consisting of hydrogen, $C_1$-$C_6$ alkyl, optionally substituted $C_3$-$C_7$ cycloalkyl, and —$NR^g$(CO)$R^h$; wherein $R^g$ and $R^h$ are independently selected from the group consisting of hydrogen and $C_1$-$C_3$ alkyl;

$X^3$ and $X^4$ are each independently N or C;

$Y^1$ is N, O, S, $CR^{18}$, or $NR^{18}$; and $Y^2$ and $Y^3$ are each independently N, O, S, $CR^{18}$, $CJ^1$, $NR^{18}$, or $NJ^1$, provided that at least one, preferably only one, of $Y^2$ and $Y^3$ is $CJ^1$ or $NJ^1$; wherein $R^{18}$ is hydrogen or $C_1$-$C_3$ alkyl; and $J^1$ is

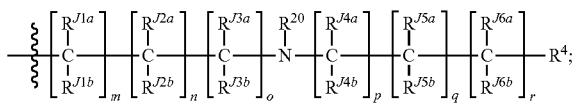

wherein $R^{20}$ is selected from the group consisting of hydrogen and $C_1$-$C_6$ alkyl;

m, n, and o are each independently 0 or 1, provided that the sum of m, n, and o is at least 1;

p, q, and r are each independently 0 or 1, provided that the sum of p, q, and r is at least 1;

each $R^{J1a}$, $R^{J1b}$, $R^{J2a}$, $R^{J2b}$, $R^{J3a}$, $R^{J3b}$, $R^{J4a}$ $R^{J4b}$, $R^{J5a}$, $R^{J5b}$, $R^{J6a}$, and $R^{J6b}$ is independently selected from the group consisting of hydrogen, halogen, hydroxy, $C_1$-$C_3$ alkyl, $C_3$-$C_6$ cycloalkyl, and a 4- to 6-membered heterocycle;

wherein two of $R^{J1a}$, $R^{J2a}$, $R^{J3a}$, and $R^{20}$ or two of $R^{J4a}$, $R^{J5a}$, $R^{J6a}$, and $R^{20}$ or one of $R^{J1a}$, $R^{J2a}$, and $R^{J3a}$, and one of $R^{J4a}$, $R^{J5a}$, and $R^{J6a}$ taken together with the atom to which they are attached form a $C_3$-$C_6$ cycloalkyl or a 4- to 6-membered heterocycle; and $R^4$ is $C_6$-$C_{10}$ aryl or 5- to 10-membered heteroaryl, each of which is optionally substituted;

or a pharmaceutically acceptable salt thereof.

In certain embodiments, $R^{15}$, $R^{16}$, and $R^{17}$ are each independently selected from the group consisting of hydrogen and $C_1$-$C_6$ alkyl.

In certain embodiments, $Y^1$ is N or CH. In certain embodiments, $Y^1$ is N.

In certain embodiments, each of $R^{J1a}$, $R^{J1b}$, $R^{J2a}$, $R^{J2b}$, $R^{J3a}$, $R^{J3b}$, $R^{J4a}$ $R^{J4b}$, $R^{J5a}$, $R^{J5b}$, $R^{J6a}$, and $R^{J6b}$ is independently selected from the group consisting of hydrogen, fluorine, methyl, and hydroxy; wherein two of $R^{J1a}$, $R^{J2a}$, $R^{J3a}$, and $R^{20}$ or two of $R^{J4a}$, $R^{J5a}$, $R^{J6a}$, and $R^{20}$ taken together with the atom to which they are attached form a $C_3$-$C_6$ cycloalkyl or a 4- to 6-membered heterocycle.

In certain embodiments, $R^4$ is $C_6$-$C_{10}$ aryl or 5- to 10-membered heteroaryl, wherein the aryl or heteroaryl is optionally substituted with one, two, three, or four substituents, each of which is independently selected from the group consisting of hydrogen, $C_3$-$C_6$ cycloalkyl, phenyl, benzyl, $C_1$-$C_6$ alkyl, —C(O)O—$C_1$-$C_6$ alkyl, halogen, —$OR^{4a}$, —CN, —C(O)$NR^{4b}R^{4c}$, and —$NR^{4b}$(CO)$R^{4c}$; wherein $R^{4a}$ is hydrogen; and $R^{4b}$ and $R^{4c}$ are independently selected from the group consisting of hydrogen and $C_1$-$C_3$ alkyl.

In certain embodiments, $R^4$ is $C_6$-$C_{10}$ aryl or 5- to 10-membered heteroaryl, wherein the aryl or heteroaryl is optionally substituted with one, two, three, or four substituents, each of which is independently selected from the group consisting of hydrogen, $C_3$-$C_6$ cycloalkyl, phenyl, benzyl, halo-$C_1$-$C_3$ alkyl, 5- to 7-membered heteroaryl, ($C_3$-$C_6$ cycloalkyl)-$C_1$-$C_3$ alkyl, $C_1$-$C_6$ alkyl, —C(O)O—$C_1$-$C_6$ alkyl, halogen, —$OR^{4a}$, —CN, —C(O)$NR^{4b}R^{4c}$, and —$NR^{4b}$(CO)$R^{4c}$; wherein the phenyl or 5- to 7-membered heteroaryl is optionally substituted with one, two, or three substituents, each of which is independently selected from the group consisting of halogen, halo-$C_1$-$C_3$ alkyl, and $C_1$-$C_6$ alkyl; wherein $R^{4a}$ is hydrogen; and $R^{4b}$ and $R^{4c}$ are independently selected from the group consisting of hydrogen and $C_1$-$C_3$ alkyl.

In certain embodiments, $R^4$ is $C_6$-$C_{10}$ aryl or 5- to 10-membered heteroaryl, wherein the aryl or heteroaryl is optionally substituted with one, two, three, or four substituents, each of which is independently selected from the group consisting of hydrogen, $C_3$-$C_6$ cycloalkyl, phenyl, benzyl, halo-$C_1$-$C_3$ alkyl, 5- to 7-membered heteroaryl, ($C_3$-$C_6$ cycloalkyl)-$C_1$-$C_3$ alkyl, $C_1$-$C_6$ alkyl, —C(O)O—$C_1$-$C_6$ alkyl, halogen, —$OR^{4a}$, —CN, —C(O)$NR^{4b}R^{4c}$, and —$NR^{4b}$(CO)$R^{4c}$; wherein the phenyl or 5- to 7-membered heteroaryl is optionally substituted with one, two, or three substituents, each of which is independently selected from the group consisting of halogen, halo-$C_1$-$C_3$ alkyl, and $C_1$-$C_3$ alkyl; wherein $R^{4a}$ is hydrogen; and $R^{4b}$ and $R^{4c}$ are independently selected from the group consisting of hydrogen and $C_1$-$C_3$ alkyl.

In certain embodiments, $X^3$ and $X^4$ are each C.

In certain embodiments, $Y^2$ is $CJ^1$ or $NJ^1$.

In certain embodiments, the subject matter described herein is directed to compounds of Formula Ia:

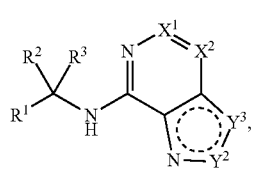

Ia wherein $R^1$, $R^2$, $R^3$, $X^1$, $X^2$, $Y^2$, and $Y^3$ are as defined herein. In certain embodiments of Formula Ia, $Y^3$ is $NR^{18}$, O, or S. In certain embodiments of Formula Ia, $Y^3$ is S or O.

In certain embodiments, the subject matter described herein is directed to compounds of Formula Ib:

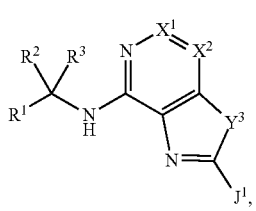

Ib wherein, $R^1$, $R^2$, $R^3$, $X^1$, $X^2$, $Y^3$, and $J^1$ are as defined herein. In certain embodiments of Formula Ib, $Y^3$ is $NR^{18}$, O, or S. In certain embodiments of Formula Ib, $Y^3$ is S or O.

In certain embodiments, the subject described herein is directed to compounds of Formula Ic:

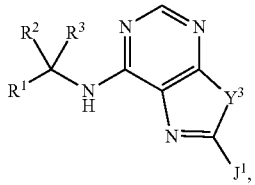

wherein, $R^1$, $R^2$, $R^3$, and $J^1$ are as defined herein.

In certain embodiments, the subject described herein is directed to compounds of Formula Id:

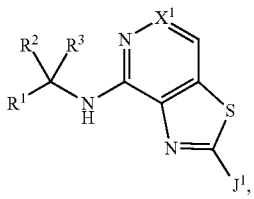

wherein, $R^1$, $R^2$, $R^3$, $X^1$, and $J^1$ are as defined herein.

In certain embodiments, the subject described herein is directed to compounds of Formula Ie:

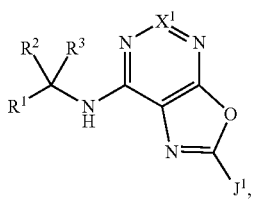

wherein, $R^1$, $R^2$, $R^3$, $X^1$, and $J^1$ are as defined herein.

In certain embodiments, the subject described herein is directed to compounds of Formula If:

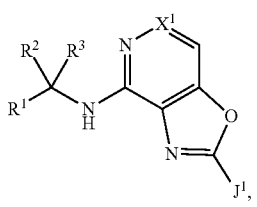

wherein $R^1$, $R^2$, $R^3$, $X^1$, and $J^1$ are as defined herein.

In certain embodiments, the subject described herein is directed to compounds of Formula Ig:

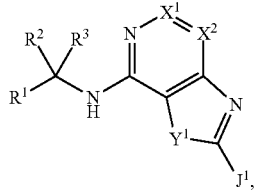

wherein, $R^1$, $R^2$, $R^3$, $X^1$, $X^2$, $Y^1$, and $J^1$ are as defined herein. In certain embodiments, $Y^1$ is $NR^{18}$, O, or S.

In certain embodiments, $R^1$ is an optionally substituted, 6-membered heteroaryl containing one or two ring heteroatoms. In certain embodiments of this aspect, the heteroatoms are each nitrogen. In certain embodiments, $R^1$ is an optionally substituted pyridinyl. In certain embodiments, $R^1$ is pyridinyl singly substituted with a halogen. In certain embodiments, $R^1$ has the following structure:

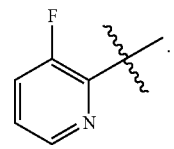

In certain embodiments, $R^2$ and $R^3$ are each hydrogen.
In certain embodiments, $X^1$ is $CR^1$.
In certain embodiments, $X^2$ is N.
In certain embodiments, $R^{10}$ is hydrogen.
In certain embodiments, $R^{20}$ is hydrogen.
In certain embodiments, in $J^1$, the sum of m, n, and o is 2, and the sum of p, q, and r is 2. In certain embodiments, in $J^1$, n, o, p, and q, in each instance is 1. In certain embodiments, in $J^1$, each of $R^{J1a}$, $R^{J1b}$, $R^{J2a}$, $R^{J2b}$, $R^{J3a}$, $R^{J3b}$, $R^{J4a}$, $R^{J4b}$, $R^{J5a}$, $R^{J5b}$, $R^{J6a}$, and $R^{J6b}$, if present, is hydrogen.

In certain embodiments, m is 1; $R^{J1a}$ is fluorine; $R^{J1b}$ is hydrogen or fluorine; and each of $R^{J2a}$, $R^{J2b}$, $R^{J3a}$, $R^{J3b}$, $R^{J4a}$, $R^{J4b}$, $R^{J5a}$, $R^{J5b}$, $R^{J6a}$, and $R^{J6b}$, if present, is hydrogen.

In certain embodiments, m is 1; $R^{J1a}$ is fluorine; $R^{J1b}$ is hydrogen; and each of $R^{J2a}$, $R^{J2b}$, $R^{J3a}$, $R^{J3b}$, $R^{J4a}$, $R^{J4b}$, $R^{J5a}$, $R^{J5b}$, $R^{J6a}$, and $R^{J6b}$, if present, is hydrogen.

In certain embodiments, $R^4$ is a 5- to 10-membered heteroaryl. In certain embodiments, $R^4$ is a 9- to 10-membered heteroaryl. In certain embodiments, $R^4$ is a 9-membered bicyclic heteroaryl. In certain embodiments, $R^4$ is a benzimidazolyl. In certain embodiments of this aspect, $R^4$ has the following structure:

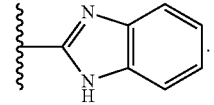 [SMILES: *c1nc2ccccc2[nH]1]

In certain embodiments, $R^4$ is

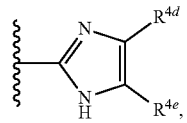

wherein $R^{4d}$ and $R^{4e}$ are independently selected from the group consisting of hydrogen, $C_1$-$C_3$ alkyl, $C_3$-$C_6$ cycloalkyl, phenyl, and benzyl.

In certain embodiments, $R^4$ is

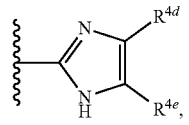

wherein $R^{4d}$ and $R^{4e}$ are independently selected from the group consisting of hydrogen, $C_1$-$C_3$ alkyl, halo-$C_1$-$C_3$ alkyl, 5- to 7-membered heteroaryl, ($C_3$-$C_6$ cycloalkyl)-$C_1$-$C_3$ alkyl, $C_3$-$C_6$ cycloalkyl, phenyl, and benzyl, and wherein said phenyl or 5- to 7-membered heteroaryl is optionally substituted with one, two, or three substituents, each of which is independently selected from the group consisting of halogen, halo-$C_1$-$C_3$ alkyl, and $C_1$-$C_6$ alkyl.

In certain embodiments, $R^4$ is

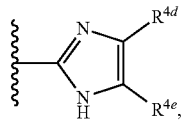

wherein $R^{4d}$ and $R^{4e}$ are independently selected from the group consisting of hydrogen, $C_1$-$C_3$ alkyl, halo-$C_1$-$C_3$ alkyl, 5- to 7-membered heteroaryl, ($C_3$-$C_6$ cycloalkyl)-$C_1$-$C_3$ alkyl, $C_3$-$C_6$ cycloalkyl, phenyl, and benzyl, and wherein said phenyl or 5- to 7-membered heteroaryl is optionally substituted with one, two, or three substituents, each of which is independently selected from the group consisting of halogen, halo-$C_1$-$C_3$ alkyl, and $C_1$-$C_3$ alkyl.

The subject matter described herein includes the following compounds in Table 1, or pharmaceutically acceptable salts thereof:

TABLE 1
| Compound No. | Structure | IUPAC Name | Mass Found (M + 1) |
|---|---|---|---|
| 1 | 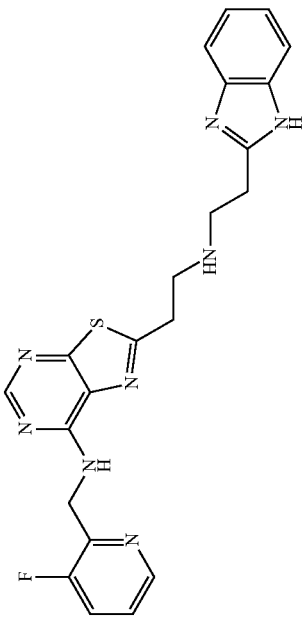 | 2-(2-{[2-(1H-1,3-benzodiazol-2-yl)ethyl]amino}ethyl)-N-[(3-fluoropyridin-2-yl)methyl]-[1,3]thiazolo[5,4-d]pyrimidin-7-amine | 449.2 |
| 2 | 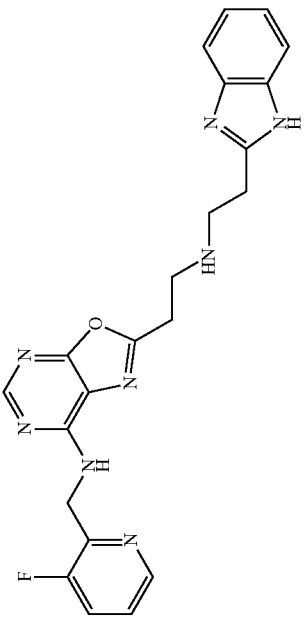 | 2-(2-{[2-(1H-1,3-benzodiazol-2-yl)ethyl]amino}ethyl)-N-[(3-fluoropyridin-2-yl)methyl]-[1,3]oxazolo[5,4-d]pyrimidin-7-amine | 433.2 |
| 3 | 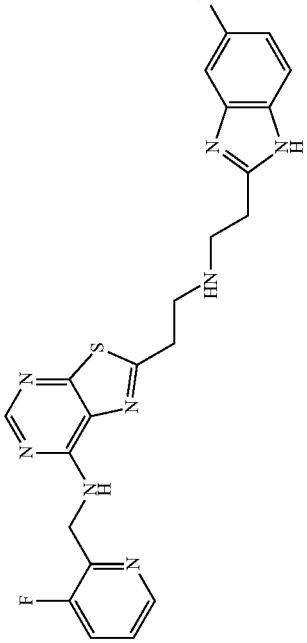 | 2-(2-{[2-(5-fluoro-1H-1,3-benzodiazol-2-yl)ethyl]amino}ethyl)-N-[(3-fluoropyridin-2-yl)methyl]-[1,3]thiazolo[5,4-d]pyrimidin-7-amine | 467.2 |

TABLE 1-continued

| Compound No. | Structure | IUPAC Name | Mass Found (M + 1) |
|---|---|---|---|
| 4 | 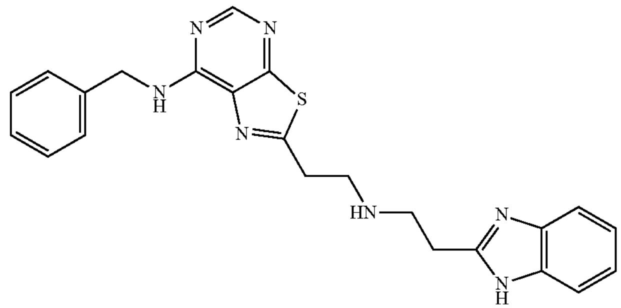 [SMILES: c1ccc(CNc2ncnc3sc(CCNCCc4nc5ccccc5[nH]4)nc23)cc1] | 2-(2-{[2-(1H-1,3-benzodiazol-2-yl)ethyl]amino}ethyl)-N-benzyl-[1,3]thiazolo[5,4-d]pyrimidin-7-amine | 430.4 |
| 5 | 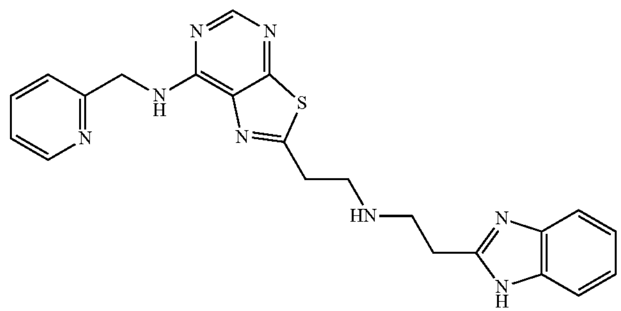 [SMILES: c1ccc(CNc2ncnc3sc(CCNCCc4nc5ccccc5[nH]4)nc23)nc1] | 2-(2-{[2-(1H-1,3-benzodiazol-2-yl)ethyl]amino}ethyl)-N-[(pyridin-2-yl)methyl]-[1,3]thiazolo[5,4-d]pyrimidin-7-amine | 431.2 |
| 6 | 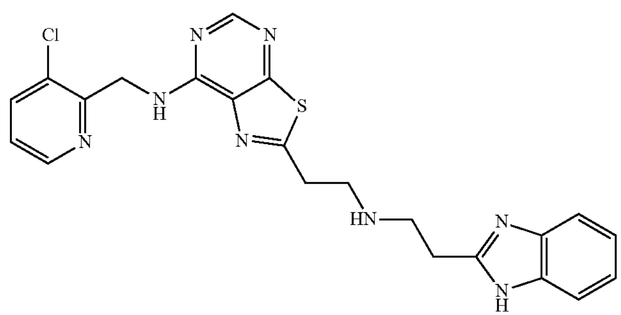 | 2-(2-{[2-(1H-1,3-benzodiazol-2-yl)ethyl]amino}ethyl)-N-[(3-chloropyridin-2-yl)methyl]-[1,3]thiazolo[5,4-d]pyrimidin-7-amine | 465.2 |

TABLE 1-continued

| Compound No. | Structure | IUPAC Name | Mass Found (M + 1) |
|---|---|---|---|
| 7 | 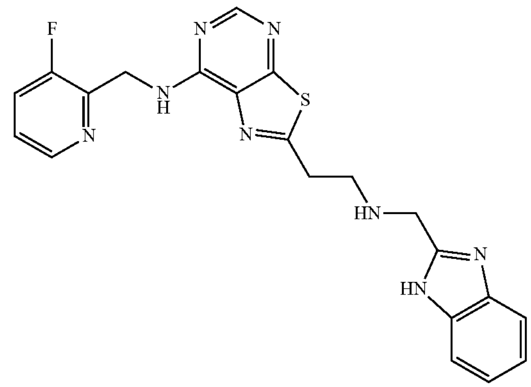 [SMILES: Fc1cccnc1CNc1ncnc2sc(CCNCc3nc4ccccc4[nH]3)nc12] | 2-(2-{[(1H-1,3-benzodiazol-2-yl)methyl]amino}ethyl)-N-[(3-fluoropyridin-2-yl)methyl]-[1,3]thiazolo[5,4-d]pyrimidin-7-amine | 435.1 |
| 8 | 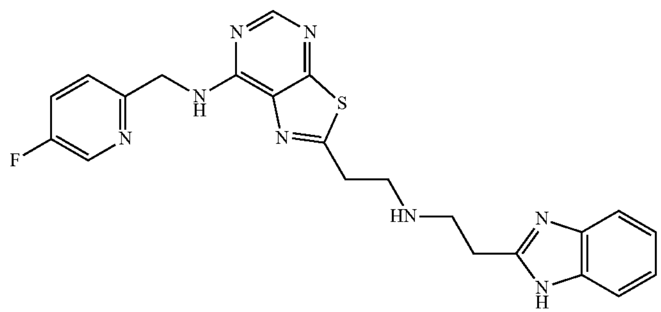 [SMILES: Fc1ccc(CNc2ncnc3sc(CCNCCc4nc5ccccc5[nH]4)nc23)nc1] | 2-(2-{[2-(1H-1,3-benzodiazol-2-yl)ethyl]amino}ethyl)-N-[(5-fluoropyridin-2-yl)methyl]-[1,3]thiazolo[5,4-d]pyrimidin-7-amine | 449.5 |
| 9 | 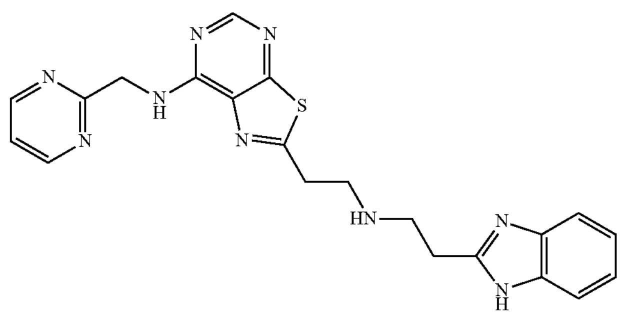 [SMILES: c1cnc(CNc2ncnc3sc(CCNCCc4nc5ccccc5[nH]4)nc23)nc1] | 2-(2-{[2-(1H-1,3-benzodiazol-2-yl)ethyl]amino}ethyl)-N-[(pyrimidin-2-yl)methyl]-[1,3]thiazolo[5,4-d]pyrimidin-7-amine | 432.1 |

TABLE 1-continued

| Compound No. | Structure | IUPAC Name | Mass Found (M + 1) |
|---|---|---|---|
| 10 | 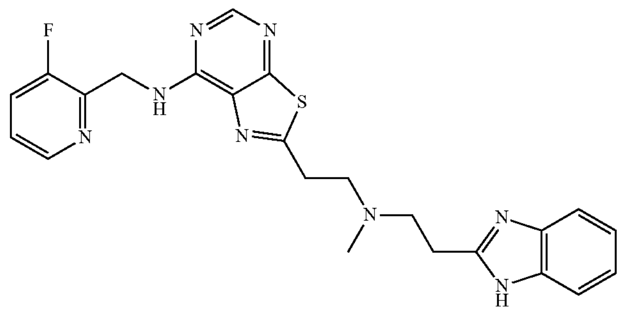 [SMILES: CN(CCc1nc2ccccc2[nH]1)CCc1nc2c(NCc3ncccc3F)ncnc2s1] | 2-(2-{[2-(1H-1,3-benzodiazol-2-yl)ethyl](methyl)amino}ethyl)-N-[(3-fluoropyridin-2-yl)methyl]-[1,3]thiazolo[5,4-d]pyrimidin-7-amine | 463.2 |
| 11 | 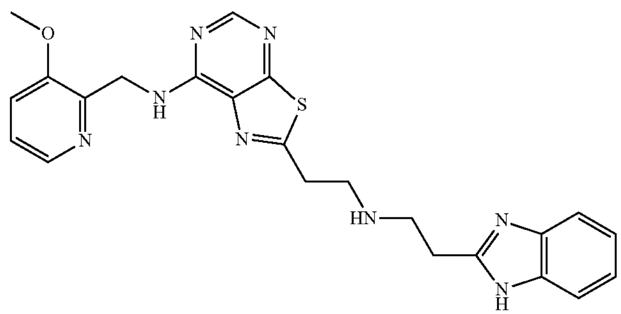 [SMILES: COc1cccnc1CNc1ncnc2sc(CCNCCc3nc4ccccc4[nH]3)nc12] | 2-(2-{[2-(1H-1,3-benzodiazol-2-yl)ethyl]amino}ethyl)-N-[(3-methoxypyridin-2-yl)methyl]-[1,3]thiazolo[5,4-d]pyrimidin-7-amine | 461.2 |
| 12 | 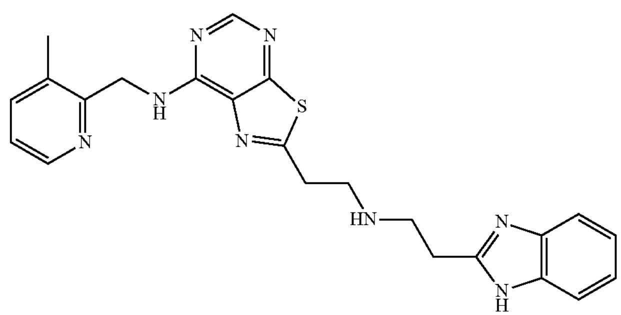 | 2-(2-{[2-(1H-1,3-benzodiazol-2-yl)ethyl]amino}ethyl)-N-[(3-methylpyridin-2-yl)methyl]-[1,3]thiazolo[5,4-d]pyrimidin-7-amine | 445.3 |

TABLE 1-continued
| Compound No. | Structure | IUPAC Name | Mass Found (M + 1) |
|---|---|---|---|
| 13 | 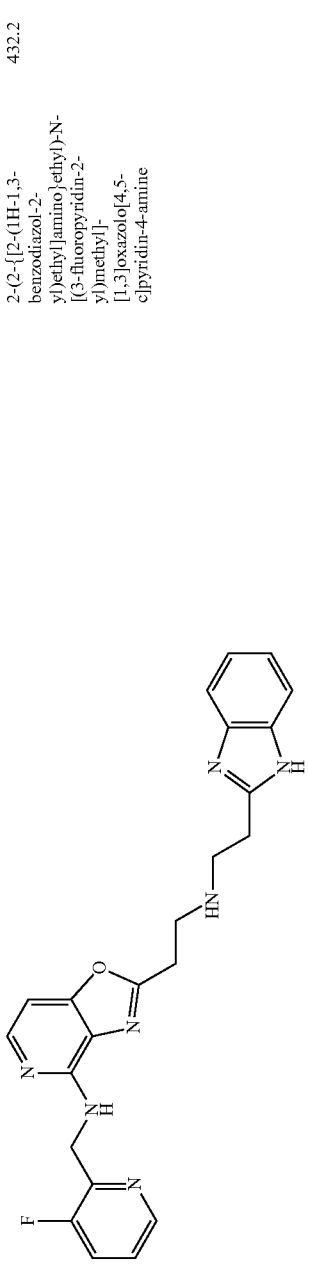 | 2-(2-{[2-(1H-1,3-benzodiazol-2-yl)ethyl]amino}ethyl)-N-[(3-fluoropyridin-2-yl)methyl][1,3]oxazolo[4,5-c]pyridin-4-amine | 432.2 |
| 14 | 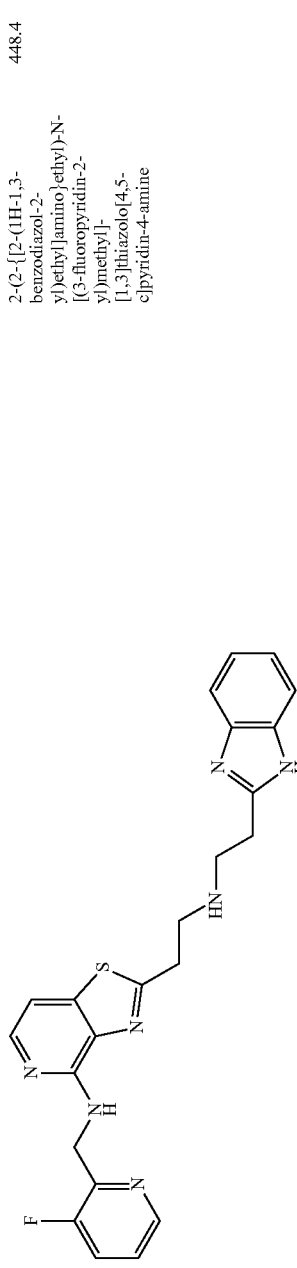 | 2-(2-{[2-(1H-1,3-benzodiazol-2-yl)ethyl]amino}ethyl)-N-[(3-fluoropyridin-2-yl)methyl][1,3]thiazolo[4,5-c]pyridin-4-amine | 448.4 |
| 15 | 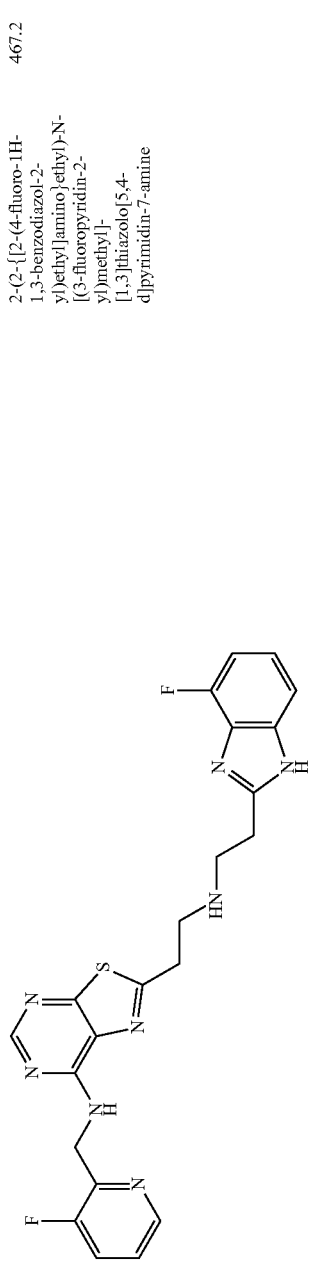 | 2-(2-{[2-(4-fluoro-1H-1,3-benzodiazol-2-yl)ethyl]amino}ethyl)-N-[(3-fluoropyridin-2-yl)methyl][1,3]thiazolo[5,4-d]pyrimidin-7-amine | 467.2 |

TABLE 1-continued

| Compound No. | Structure | IUPAC Name | Mass Found (M + 1) |
|---|---|---|---|
| 16 | 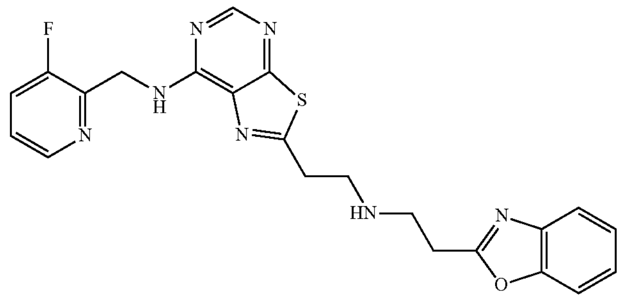 [SMILES: Fc1cccnc1CNc1ncnc2sc(CCNCCc3nc4ccccc4o3)nc12] | 2-(2-{[2-(1,3-benzoxazol-2-yl)ethyl]amino}ethyl)-N-[(3-fluoropyridin-2-yl)methyl]-[1,3]thiazolo[5,4-d]pyrimidin-7-amine | 450.2 |
| 17 | 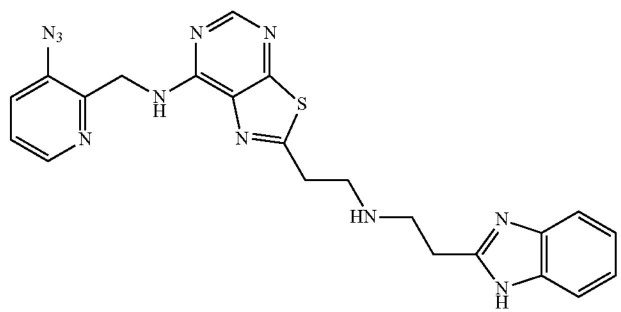 | N-[(3-azidopyridin-2-yl)methyl]-2-(2-{[2-(1H-1,3-benzodiazol-2-yl)ethyl]amino}ethyl)-[1,3]thiazolo[5,4-d]pyrimidin-7-amine | 472.2 |
| 18 | 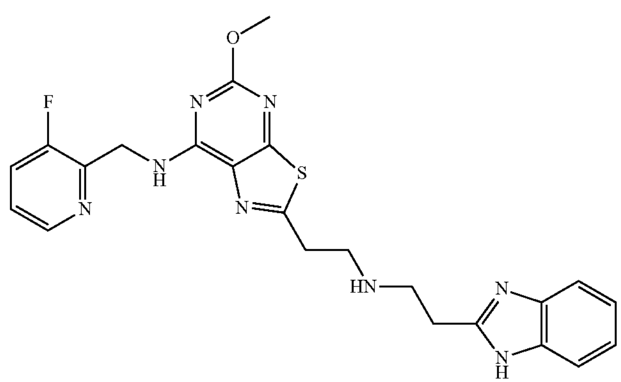 [SMILES: COc1cc2sc(CCNCCc3nc4ccccc4[nH]3)nc2c(NCc2ncccc2F)n1] | 2-(2-{[2-(1H-1,3-benzodiazol-2-yl)ethyl]amino}ethyl)-N-[(3-fluoropyridin-2-yl)methyl]-5-methoxy-[1,3]thiazolo[5,4-d]pyrimidin-7-amine | 479.2 |

TABLE 1-continued
| Compound No. | Structure | IUPAC Name | Mass Found (M + 1) |
|---|---|---|---|
| 19 | 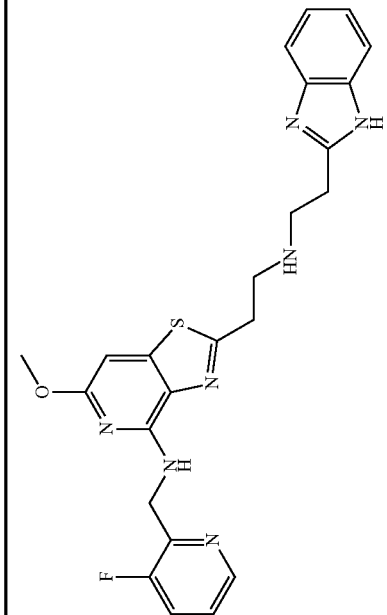 | 2-(2-{[2-(1H-1,3-benzodiazol-2-yl)ethyl]amino}ethyl)-N-[(3-fluoropyridin-2-yl)methyl]-6-methoxy-[1,3]thiazolo[4,5-c]pyridin-4-amine | 478.2 |
| 20 | 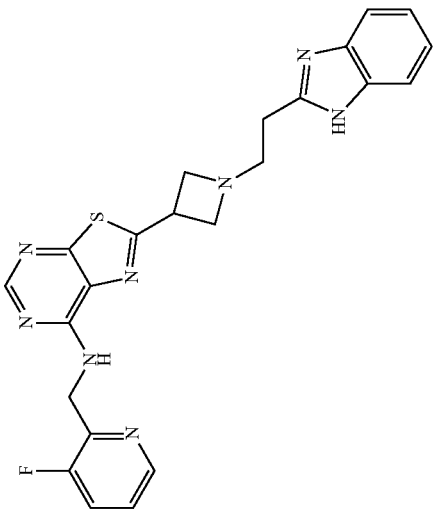 | 2-{1-[2-(1H-1,3-benzodiazol-2-yl)ethyl]azetidin-3-yl}-N-[(3-fluoropyridin-2-yl)methyl]-[1,3]thiazolo[5,4-d]pyrimidin-7-amine | 461.1 |

TABLE 1-continued

| Compound No. | Structure | IUPAC Name | Mass Found (M + 1) |
|---|---|---|---|
| 21 | 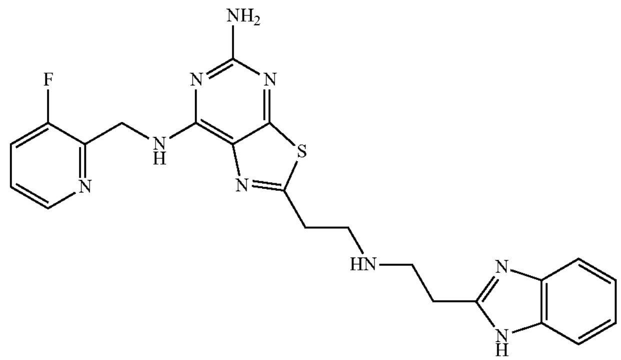 [SMILES: Nc1nc(NCc2ncccc2F)c2nc(CCNCCc3nc4ccccc4[nH]3)sc2n1] | 2-(2-{[2-(1H-1,3-benzodiazol-2-yl)ethyl]amino}ethyl)-N7-[(3-fluoropyridin-2-yl)methyl]-[1,3]thiazolo[5,4-d]pyrimidine-5,7-diamine | 464.2 |
| 22 | 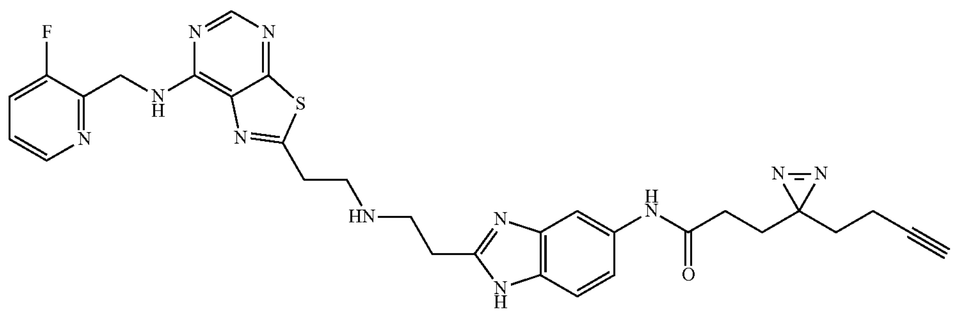 [SMILES: C#CCCC1(CCC(=O)Nc2ccc3[nH]c(CCNCCc4nc5c(NCc6ncccc6F)ncnc5s4)nc3c2)N=N1] | 3-[3-(but-3-yn-1-yl)-3H-diaziren-3-yl]-N-[2-(2-{[2-(7-{[(3-fluoropyridin-2-yl)methyl]amino}-[1,3]thiazolo[5,4-d]pyrimidin-2-yl)ethyl]amino}ethyl)-1H-1,3-benzodiazol-5-yl]propanamide | 612.1 |
| 23 | 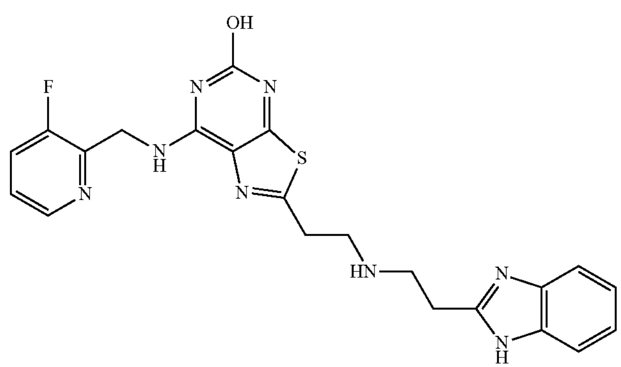 [SMILES: Oc1nc(NCc2ncccc2F)c2nc(CCNCCc3nc4ccccc4[nH]3)sc2n1] | 2-(2-{[2-(1H-1,3-benzodiazol-2-yl)ethyl]amino}ethyl)-7-{[(3-fluoropyridin-2-yl)methyl]amino}-[1,3]thiazolo[5,4-d]pyrimidin-5-ol | 465.1 |

TABLE 1-continued

| Compound No. | Structure | IUPAC Name | Mass Found (M + 1) |
|---|---|---|---|
| 24 | 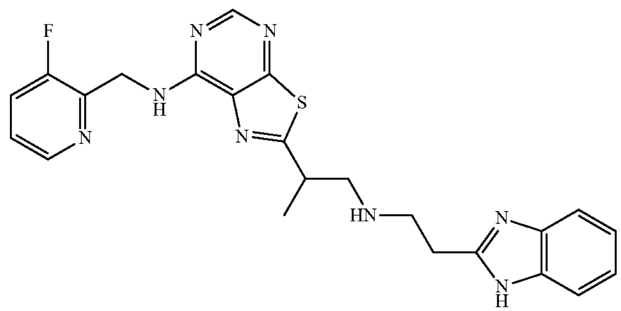 [SMILES: CC(CNCCc1nc2ccccc2[nH]1)c1nc2c(NCc3ncccc3F)ncnc2s1] | 2-(1-{[2-(1H-1,3-benzodiazol-2-yl)ethyl]amino}propan-2-yl)-N-[(3-fluoropyridin-2-yl)methyl]-[1,3]thiazolo[5,4-d]pyrimidin-7-amine | 463.1 |
| 25 | 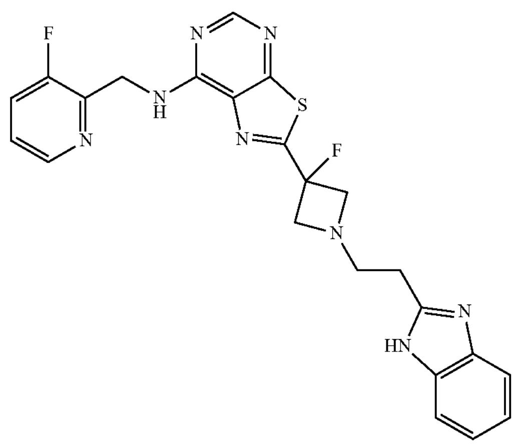 [SMILES: Fc1cccnc1CNc1ncnc2sc(C3(F)CN(CCc4nc5ccccc5[nH]4)C3)nc12] | 2-{1-[2-(1H-1,3-benzodiazol-2-yl)ethyl]-3-fluoroazetidin-3-yl}-N-[(3-fluoropyridin-2-yl)methyl]-[1,3]thiazolo[5,4-d]pyrimidin-7-amine | 479.1 |

TABLE 1-continued

| Compound No. | Structure | IUPAC Name | Mass Found (M + 1) |
|---|---|---|---|
| 26 | 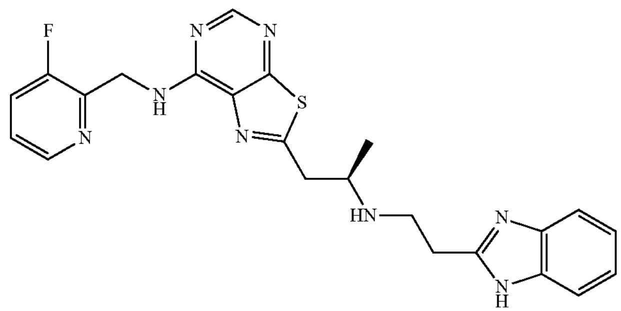 [SMILES: C[C@H](Cc1nc2c(NCc3ncccc3F)ncnc2s1)NCCc1nc2ccccc2[nH]1] | 2-[(2R)-2-{[2-(1H-1,3-benzodiazol-2-yl)ethyl]amino}propyl]-N-[(3-fluoropyridin-2-yl)methyl][1,3]thiazolo[5,4-d]pyrimidin-7-amine | 463 |
| 27 | 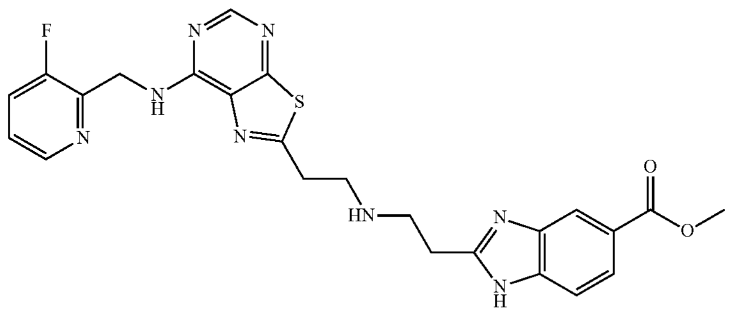 [SMILES: COC(=O)c1ccc2[nH]c(CCNCCc3nc4c(NCc5ncccc5F)ncnc4s3)nc2c1] | methyl 2-(2-{[2-(7-{[(3-fluoropyridin-2-yl)methyl]amino}[1,3]thiazolo[5,4-d]pyrimidin-2-yl)ethyl]amino}ethyl)-1H-1,3-benzodiazole-5-carboxylate | 507.2 |
| 28 | 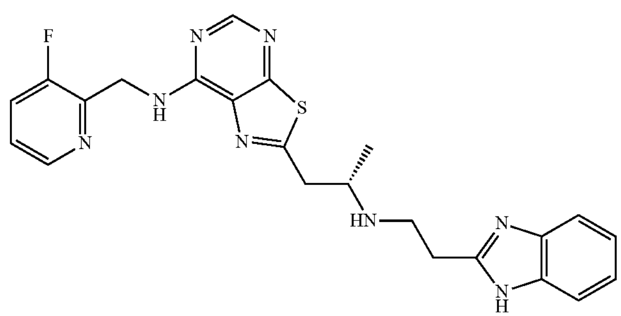 [SMILES: C[C@@H](Cc1nc2c(NCc3ncccc3F)ncnc2s1)NCCc1nc2ccccc2[nH]1] | 2-[(2S)-2-{[2-(1H-1,3-benzodiazol-2-yl)ethyl]amino}propyl]-N-[(3-fluoropyridin-2-yl)methyl][1,3]thiazolo[5,4-d]pyrimidin-7-amine | 463 |

TABLE 1-continued

| Compound No. | Structure | IUPAC Name | Mass Found (M + 1) |
|---|---|---|---|
| 29 | 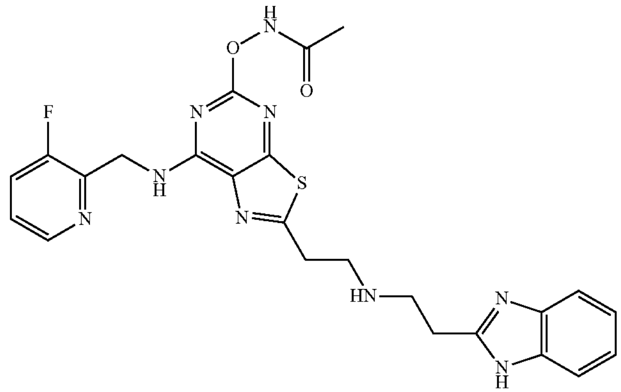 [SMILES: CC(=O)NOc1nc(NCc2ncccc2F)c2nc(CCNCCc3nc4ccccc4[nH]3)sc2n1] | N-{[2-(2-{[2-(1H-1,3-benzodiazol-2-yl)ethyl]amino}ethyl)-7-{[(3-fluoropyridin-2-yl)methyl]amino}-[1,3]thiazolo[5,4-d]pyrimidin-5-yl]oxy}acetamide | 522.2 |
| 30 | 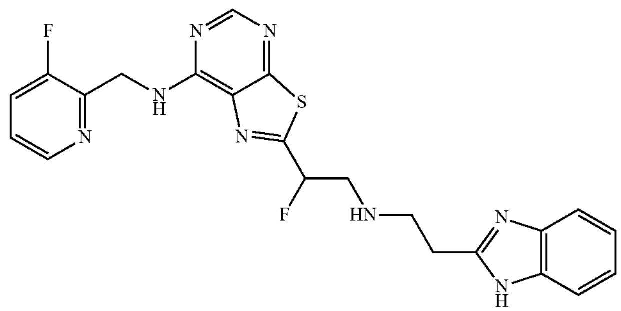 [SMILES: Fc1cccnc1CNc1ncnc2sc(C(F)CNCCc3nc4ccccc4[nH]3)nc12] | 2-(2-{[2-(1H-1,3-benzodiazol-2-yl)ethyl]amino}-1-fluoroethyl)-N-[(3-fluoropyridin-2-yl)methyl]-[1,3]thiazolo[5,4-d]pyrimidin-7-amine | 467.1 |

TABLE 1-continued
| Compound No. | Structure | IUPAC Name | Mass Found (M + 1) |
|---|---|---|---|
| 31 | 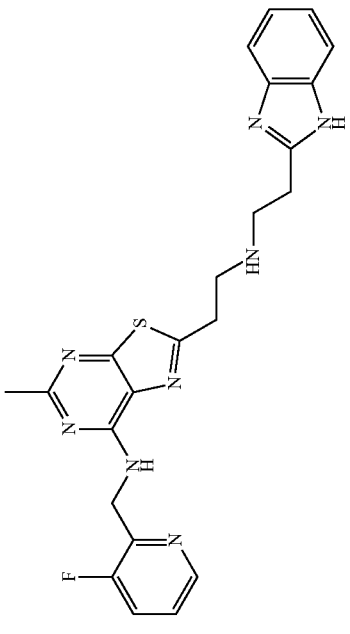 | 2-(2-{[2-(1H-1,3-benzodiazol-2-yl)ethyl]amino}ethyl)-N-[(3-fluoropyridin-2-yl)methyl]-5-methyl-[1,3]thiazolo[5,4-d]pyrimidin-7-amine | 463.3 |
| 32 | 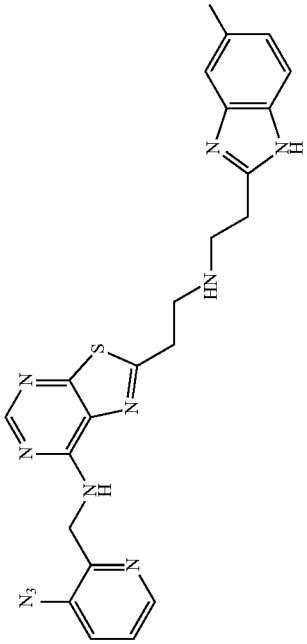 | N-[(3-azidopyridin-2-yl)methyl]-2-(2-{[2-(5-iodo-1H-1,3-benzodiazol-2-yl)ethyl]amino}ethyl)-[1,3]thiazolo[5,4-d]pyrimidin-7-amine | 598.1 |
| 33 | 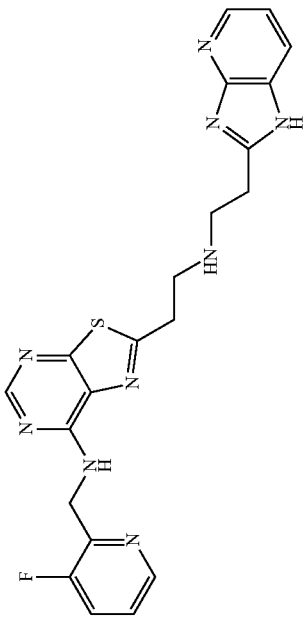 | N-[(3-fluoropyridin-2-yl)methyl]-2-{2-[(2-{1H-imidazo[4,5-b]pyridin-2-yl}ethyl)amino]ethyl}-[1,3]thiazolo[5,4-d]pyrimidin-7-amine | 450.2 |

TABLE 1-continued

| Compound No. | Structure | IUPAC Name | Mass Found (M + 1) |
|---|---|---|---|
| 34 | 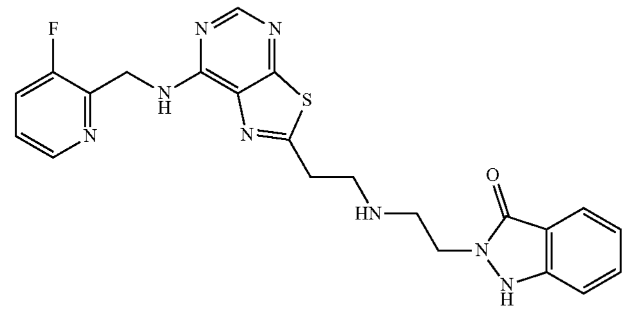 [SMILES: O=c1c2ccccc2[nH]n1CCNCCc1nc2c(NCc3ncccc3F)ncnc2s1] | 2-(2-{[2-(7-{[(3-fluoropyridin-2-yl)methyl]amino}-[1,3]thiazolo[5,4-d]pyrimidin-2-yl)ethyl]amino}ethyl)-2,3-dihydro-1H-indazol-3-one | 465.2 |
| 35 | 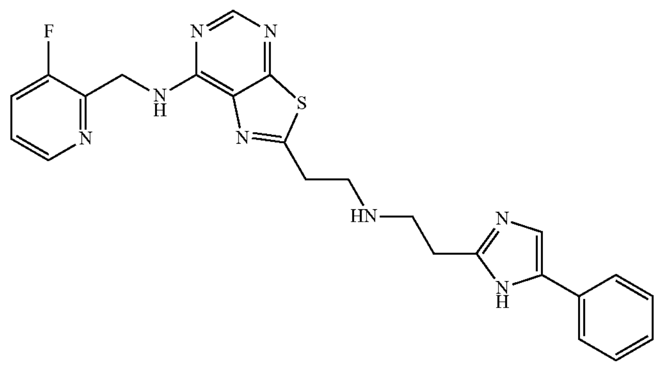 [SMILES: Fc1cccnc1CNc1ncnc2sc(CCNCCc3ncc(-c4ccccc4)[nH]3)nc12] | N-[(3-fluoropyridin-2-yl)methyl]-2-(2-{[2-(5-phenyl-1H-imidazol-2-yl)ethyl]amino}ethyl)-[1,3]thiazolo[5,4-d]pyrimidin-7-amine | 475.2 |

TABLE 1-continued

| Compound No. | Structure | IUPAC Name | Mass Found (M + 1) |
|---|---|---|---|
| 36 | 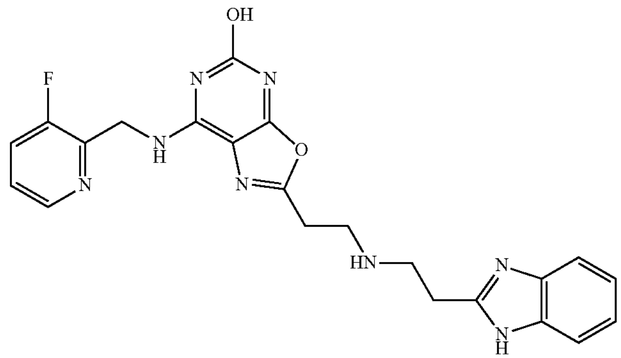 [SMILES: Oc1nc(NCc2ncccc2F)c2nc(CCNCCc3nc4ccccc4[nH]3)oc2n1] | 2-(2-{[2-(1H-1,3-benzodiazol-2-yl)ethyl]amino}ethyl)-7-{[(3-fluoropyridin-2-yl)methyl]amino}-[1,3]oxazolo[5,4-d]pyrimidin-5-ol | 449.1 |
| 37 | 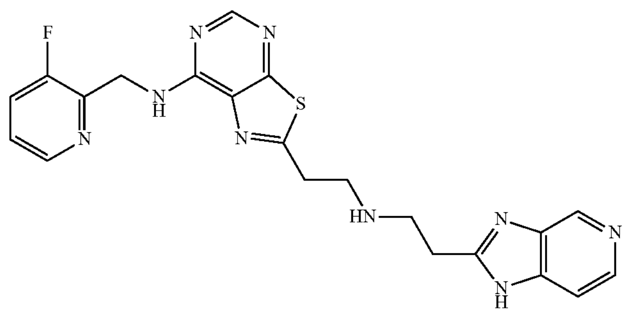 [SMILES: Fc1cccnc1CNc1ncnc2sc(CCNCCc3nc4cnccc4[nH]3)nc12] | N-[(3-fluoropyridin-2-yl)methyl]-2-{2-[(2-{1H-imidazo[4,5-c]pyridin-2-yl})ethyl)amino]ethyl}-[1,3]thiazolo[5,4-d]pyrimidin-7-amine | 450.5 |
| 38 | 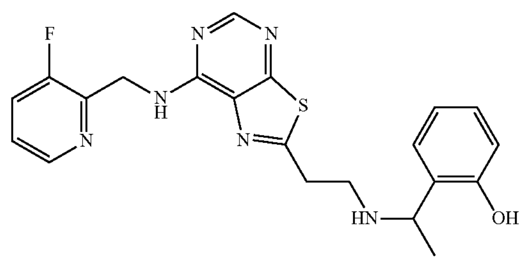 [SMILES: CC(NCCc1nc2c(NCc3ncccc3F)ncnc2s1)c1ccccc1O] | 2-(1-{[2-(7-{[(3-fluoropyridin-2-yl)methyl]amino}-[1,3]thiazolo[5,4-d]pyrimidin-2-yl)ethyl]amino}ethyl)phenol | 425.2 |

TABLE 1-continued

| Compound No. | Structure | IUPAC Name | Mass Found (M + 1) |
|---|---|---|---|
| 39 | 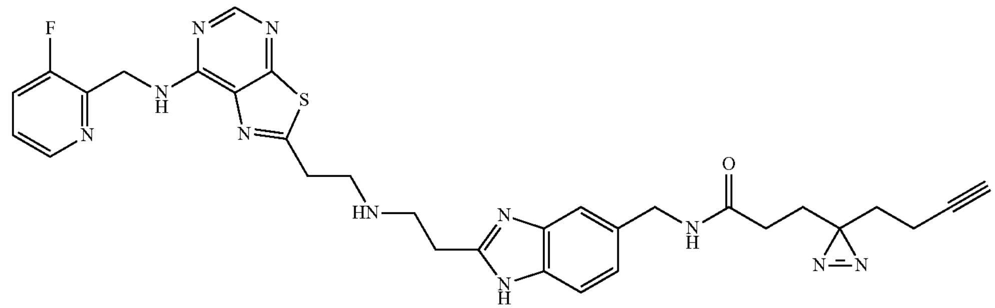 [SMILES: C#CCCC1(CCC(=O)NCc2ccc3[nH]c(CCNCCc4nc5c(NCc6ncccc6F)ncnc5s4)nc3c2)N=N1] | 3-[3-(but-3-yn-1-yl)-3H-diazirin-3-yl]-N-{[2-(2-{[2-(7-{[(3-fluoropyridin-2-yl)methyl]amino}-[1,3]thiazolo[5,4-d]pyrimidin-2-yl)ethyl]amino}ethyl)-1H-1,3-benzodiazol-5-yl]methyl}propanamide | 626.2 |
| 40 | 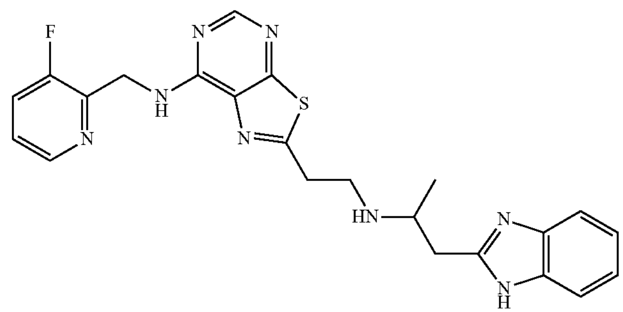 [SMILES: CC(Cc1nc2ccccc2[nH]1)NCCc1nc2c(NCc3ncccc3F)ncnc2s1] | 2-(2-{[1-(1H-1,3-benzodiazol-2-yl)propan-2-yl]amino}ethyl)-N-[(3-fluoropyridin-2-yl)methyl]-[1,3]thiazolo[5,4-d]pyrimidin-7-amine | 463.2 |
| 41 | 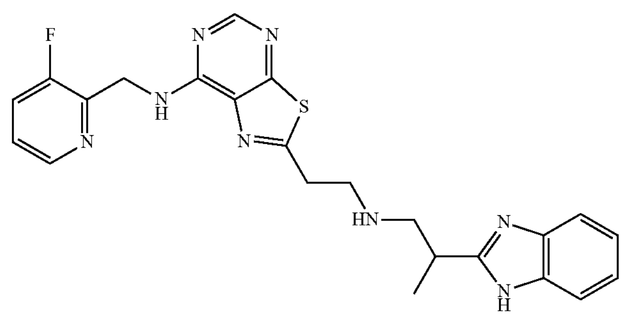 [SMILES: CC(CNCCc1nc2c(NCc3ncccc3F)ncnc2s1)c1nc2ccccc2[nH]1] | 2-(2-{[2-(1H-1,3-benzodiazol-2-yl)propyl]amino}ethyl)-N-[(3-fluoropyridin-2-yl)methyl]-[1,3]thiazolo[5,4-d]pyrimidin-7-amine | 463.1 |

TABLE 1-continued

| Compound No. | Structure | IUPAC Name | Mass Found (M + 1) |
|---|---|---|---|
| 42 | 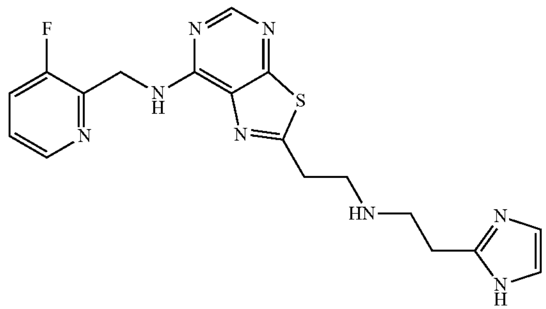 [SMILES: Fc1cccnc1CNc1ncnc2sc(CCNCCc3ncc[nH]3)nc12] | N-[(3-fluoropyridin-2-yl)methyl]-2-(2-(1H-imidazol-2-yl)ethyl]amino}ethyl)[1,3]thiazolo[5,4-d]pyrimidin-7-amine | 399.1 |
| 43 | 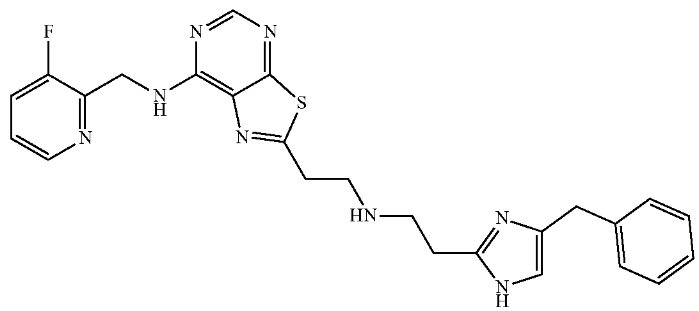 [SMILES: Fc1cccnc1CNc1ncnc2sc(CCNCCc3nc(Cc4ccccc4)c[nH]3)nc12] | 2-(2-{[2-(4-benzyl-1H-imidazol-2-yl)ethyl]amino}ethyl)-N-[(3-fluoropyridin-2-yl)methyl]-[1,3]thiazolo[5,4-d]pyrimidin-7-amine | 489.6 |
| 44 | 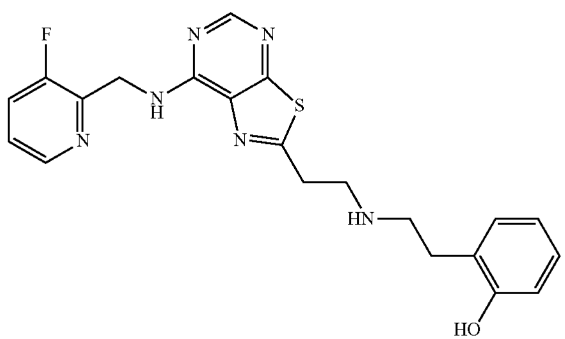 [SMILES: Oc1ccccc1CCNCCc1nc2c(NCc3ncccc3F)ncnc2s1] | 2-(2-{[2-(7-{[(3-fluoropyridin-2-yl)methyl]amino}-[1,3]thiazolo[5,4-d]pyrimidin-2-yl)ethyl]amino}ethyl)phenol | 425.2 |

TABLE 1-continued

| Compound No. | Structure | IUPAC Name | Mass Found (M + 1) |
|---|---|---|---|
| 45 | 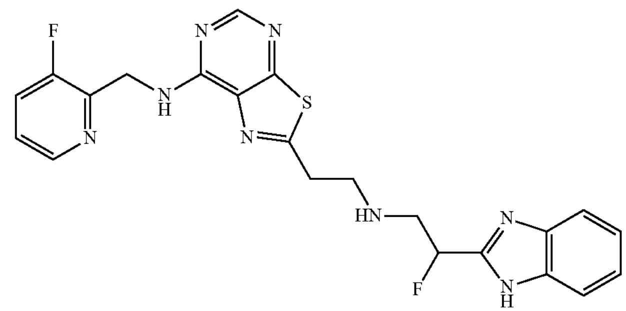 [SMILES: Fc1cccnc1CNc1ncnc2sc(CCNCC(F)c3nc4ccccc4[nH]3)nc12] | 2-(2-{[2-(1H-1,3-benzodiazol-2-yl)-2-fluoroethyl]amino}ethyl)-N-[(3-fluoropyridin-2-yl)methyl][1,3]thiazolo[5,4-d]pyrimidin-7-amine | 467 |
| 46 | 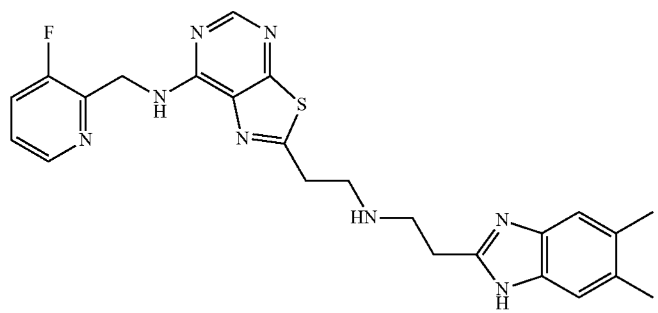 [SMILES: Cc1cc2nc(CCNCCc3nc4c(NCc5ncccc5F)ncnc4s3)[nH]c2cc1C] | 2-(2-{[2-(5,6-dimethyl-1H-1,3-benzodiazol-2-yl)ethyl]amino}ethyl)-N-[(3-fluoropyridin-2-yl)methyl][1,3]thiazolo[5,4-d]pyrimidin-7-amine | 477.2 |

TABLE 1-continued

| Compound No. | Structure | IUPAC Name | Mass Found (M + 1) |
|---|---|---|---|
| 47 | 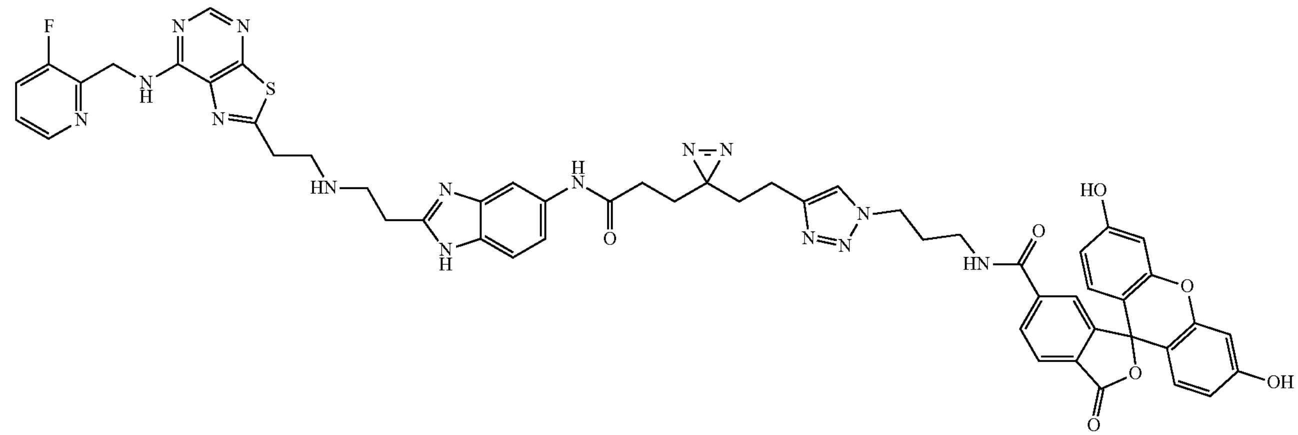 [SMILES: O=C(CCC1(CCc2cn(CCCNC(=O)c3ccc4c(c3)C3(OC4=O)c4ccc(O)cc4Oc4cc(O)ccc43)nn2)N=N1)Nc1ccc2[nH]c(CCNCCc3nc4c(NCc5ncccc5F)ncnc4s3)nc2c1] | N-[3-(4-{2-[3-(2-{[2-(2-{[(3-fluoropyridin-2-yl)methyl]amino}-[1,3]thiazolo[5,4-d]pyrimidin-2-yl)ethyl]amino}ethyl)-1H-1,3-benzodiazol-5-yl]carbamoyl}ethyl)-3H-diazirin-3-yl]ethyl]-1H-1,2,3-triazol-1-yl)propyl]-3′,6′-dihydroxy-3-oxo-3H-spiro[2-benzofuran-1,9′-xanthene]-6-carboxamide | 1071.2 |
| 48 | 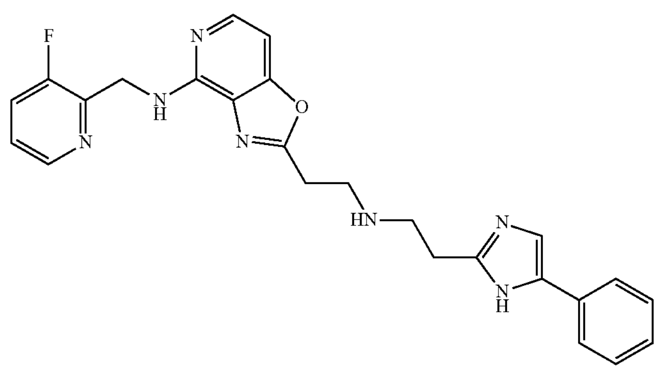 [SMILES: Fc1cccnc1CNc1nccc2oc(CCNCCc3ncc(-c4ccccc4)[nH]3)nc12] | N-[(3-fluoropyridin-2-yl)methyl]-2-(2-{[2-(5-phenyl-1H-imidazol-2-yl)ethyl]amino}ethyl)-[1,3]oxazolo[4,5-c]pyridin-4-amine | 458.1 |

TABLE 1-continued

| Compound No. | Structure | IUPAC Name | Mass Found (M + 1) |
|---|---|---|---|
| 49 | 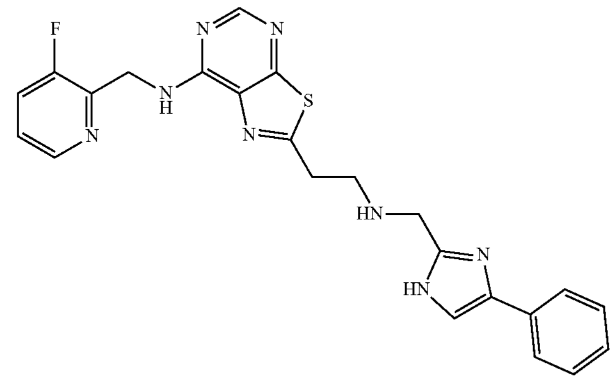 [SMILES: Fc1cccnc1CNc1ncnc2sc(CCNCc3nc(-c4ccccc4)c[nH]3)nc12] | N-[(3-fluoropyridin-2-yl)methyl]-2-(2-{[(4-phenyl-1H-imidazol-2-yl)methyl]amino}ethyl)-[1,3]thiazolo[5,4-d]pyrimidin-7-amine | 461.1 |
| 50 | 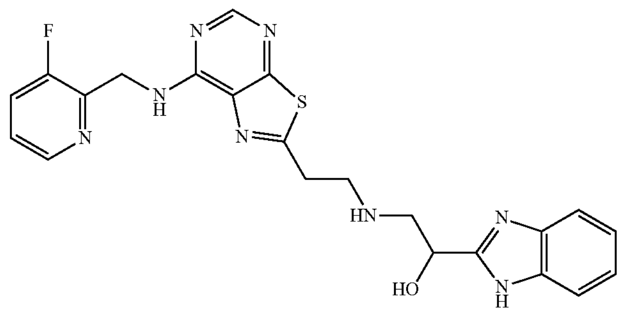 [SMILES: OC(CNCCc1nc2c(NCc3ncccc3F)ncnc2s1)c1nc2ccccc2[nH]1] | 1-(1H-1,3-benzodiazol-2-yl)-2-{[2-(7-{[(3-fluoropyridin-2-yl)methyl]amino}-[1,3]thiazolo[5,4-d]pyrimidin-2-yl)ethyl]amino}ethan-1-ol | 465.2 |
| 51 | 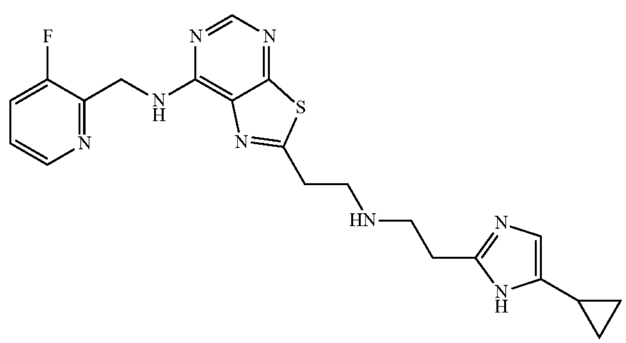 [SMILES: Fc1cccnc1CNc1ncnc2sc(CCNCCc3ncc(C4CC4)[nH]3)nc12] | 2-(2-{[2-(5-cyclopropyl-1H-imidazol-2-yl)ethyl]amino}ethyl)-N-[(3-fluoropyridin-2-yl)methyl]-[1,3]thiazolo[5,4-d]pyrimidin-7-amine | 439.2 |

TABLE 1-continued

| Compound No. | Structure | IUPAC Name | Mass Found (M + 1) |
|---|---|---|---|
| 52 | 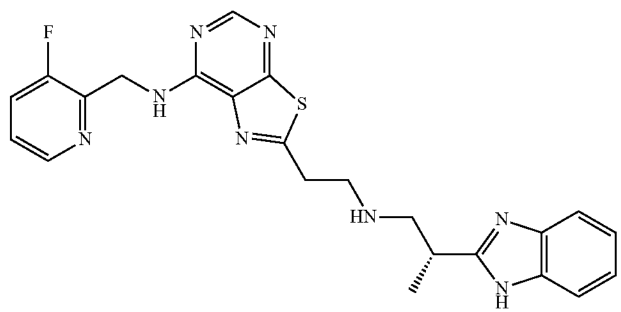 [SMILES: C[C@H](CNCCc1nc2c(NCc3ncccc3F)ncnc2s1)c1nc2ccccc2[nH]1] | 2-(2-{[(2R)-2-(1H-1,3-benzodiazol-2-yl)propyl]amino}ethyl)-N-[(3-fluoropyridin-2-yl)methyl]-[1,3]thiazolo[5,4-d]pyrimidin-7-amine | 463.1 |
| 53 | 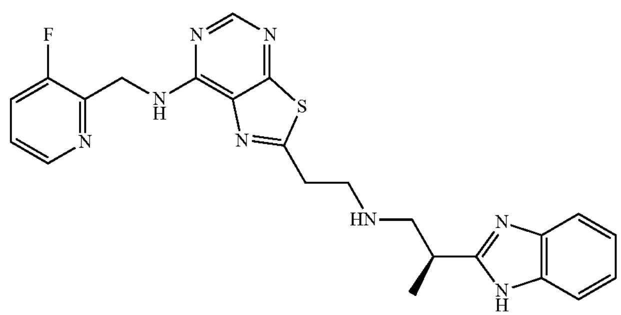 [SMILES: C[C@@H](CNCCc1nc2c(NCc3ncccc3F)ncnc2s1)c1nc2ccccc2[nH]1] | 2-(2-{[(2S)-2-(1H-1,3-benzodiazol-2-yl)propyl]amino}ethyl)-N-[(3-fluoropyridin-2-yl)methyl]-[1,3]thiazolo[5,4-d]pyrimidin-7-amine | 463.2 |
| 54 | 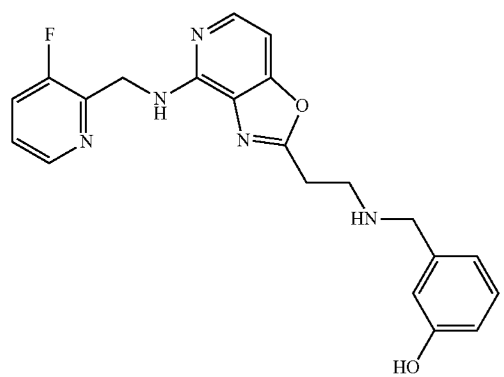 [SMILES: Oc1cccc(CNCCc2nc3c(NCc4ncccc4F)nccc3o2)c1] | 3-({[2-(4-{[(3-fluoropyridin-2-yl)methyl]amino}-[1,3]oxazolo[4,5-c]pyridin-2-yl)ethyl]amino}methyl)phenol | 394.2 |

TABLE 1-continued

| Compound No. | Structure | IUPAC Name | Mass Found (M + 1) |
|---|---|---|---|
| 55 | 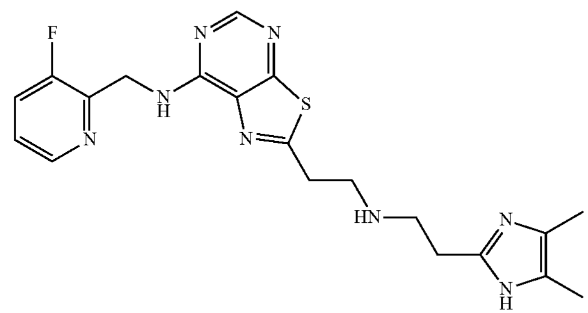 [SMILES: Cc1nc(CCNCCc2nc3c(NCc4ncccc4F)ncnc3s2)[nH]c1C] | 2-(2-{[2-(4,5-dimethyl-1H-imidazol-2-yl)ethyl]amino}ethyl)-N-[(3-fluoropyridin-2-yl)methyl]-[1,3]thiazolo[5,4-d]pyrimidin-7-amine | 427.2 |
| 56 | 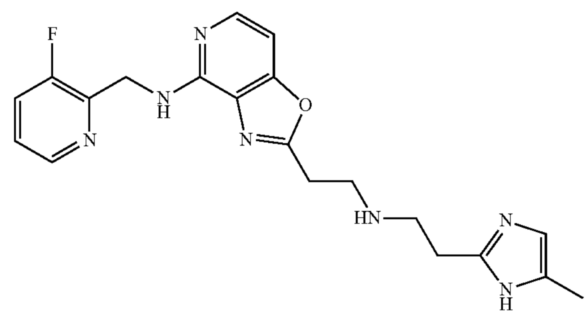 [SMILES: Cc1cnc(CCNCCc2nc3c(NCc4ncccc4F)nccc3o2)[nH]1] | N-[(3-fluoropyridin-2-yl)methyl]-2-(2-{[2-(5-methyl-1H-imidazol-2-yl)ethyl]amino}ethyl)-[1,3]oxazolo[4,5-c]pyridin-4-amine | 396.2 |
| 57 | 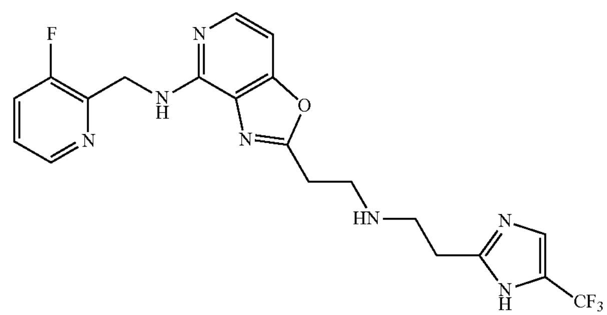 [SMILES: Fc1cccnc1CNc1nccc2oc(CCNCCc3ncc(C(F)(F)F)[nH]3)nc12] | N-[(3-fluoropyridin-2-yl)methyl]-2-[2-({2-[5-(trifluoromethyl)-1H-imidazol-2-yl]ethyl}amino)ethyl]-[1,3]oxazolo[4,5-c]pyridin-4-amine | 450.2 |

TABLE 1-continued

| Compound No. | Structure | IUPAC Name | Mass Found (M + 1) |
|---|---|---|---|
| 58 | 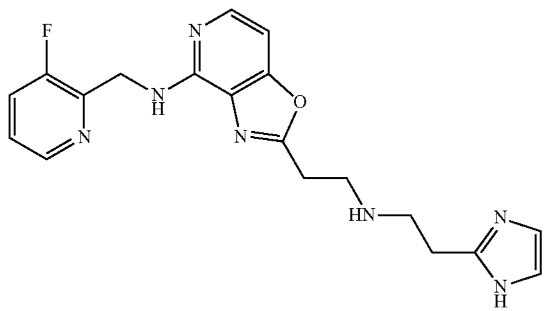 [SMILES: Fc1cccnc1CNc1nccc2oc(CCNCCc3ncc[nH]3)nc12] | N-[(3-fluoropyridin-2-yl)methyl]-2-(2-{[2-(1H-imidazol-2-yl)ethyl]amino}ethyl)[1,3]oxazolo[4,5-c]pyridin-4-amine | 382 |
| 59 | 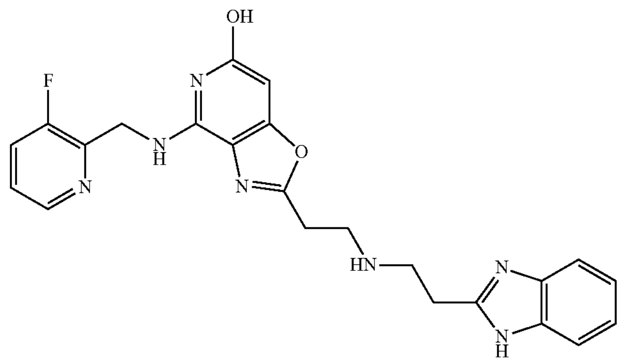 [SMILES: Oc1cc2oc(CCNCCc3nc4ccccc4[nH]3)nc2c(NCc2ncccc2F)n1] | 2-(2-{[2-(1H-1,3-benzodiazol-2-yl)ethyl]amino}ethyl)-4-{[(3-fluoropyridin-2-yl)methyl]amino}-[1,3]oxazolo[4,5-c]pyridin-6-ol | 448.2 |

TABLE 1-continued

| Compound No. | Structure | IUPAC Name | Mass Found (M + 1) |
|---|---|---|---|
| 60 | 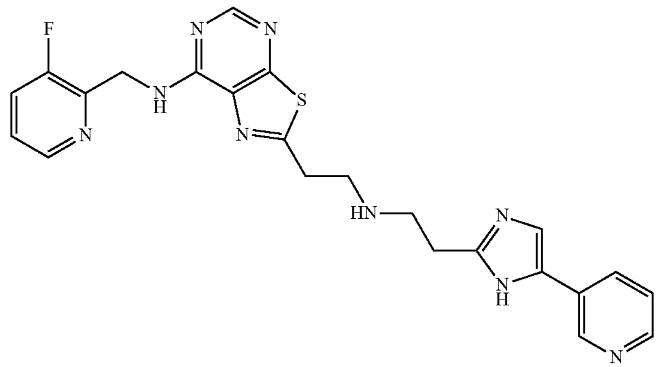 [SMILES: Fc1cccnc1CNc1ncnc2sc(CCNCCc3ncc(-c4cccnc4)[nH]3)nc12] | N-[(3-fluoropyridin-2-yl)methyl]-2-[2-({2-[5-(pyridin-3-yl)-1H-imidazol-2-yl]ethyl}amino)ethyl][1,3]thiazolo[5,4-d]pyrimidin-7-amine | 476.2 |
| 61 | 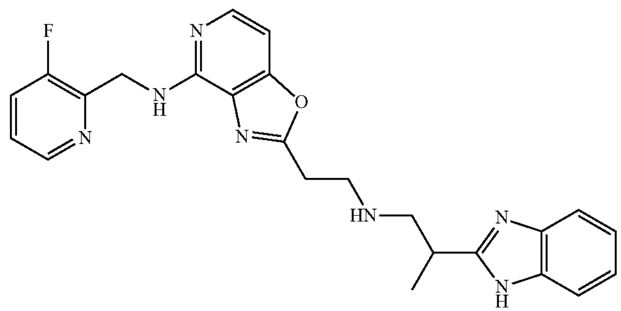 [SMILES: CC(CNCCc1nc2c(NCc3ncccc3F)nccc2o1)c1nc2ccccc2[nH]1] | 2-(2-{[2-(1H-1,3-benzodiazol-2-yl)propyl]amino}ethyl)-N-[(3-fluoropyridin-2-yl)methyl][1,3]oxazolo[4,5-c]pyridin-4-amine | 446.3 |
| 62 | 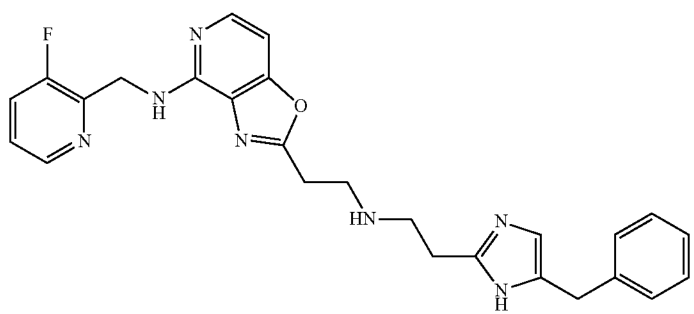 [SMILES: Fc1cccnc1CNc1nccc2oc(CCNCCc3ncc(Cc4ccccc4)[nH]3)nc12] | 2-(2-{[2-(5-benzyl-1H-imidazol-2-yl)ethyl]amino}ethyl)-N-[(3-fluoropyridin-2-yl)methyl][1,3]oxazolo[4,5-c]pyridin-4-amine | 472.4 |

TABLE 1-continued

| Compound No. | Structure | IUPAC Name | Mass Found (M + 1) |
|---|---|---|---|
| 63 | 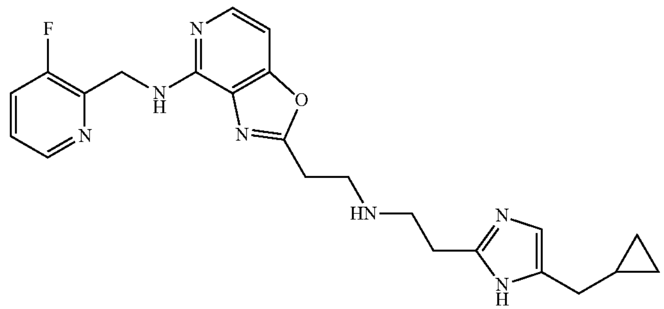 [SMILES: Fc1cccnc1CNc1nccc2oc(CCNCCc3ncc(CC4CC4)[nH]3)nc12] | 2-[2-({2-[5-(cyclopropylmethyl)-1H-imidazol-2-yl]ethyl}amino)ethyl]-N-[(3-fluoropyridin-2-yl)methyl]-[1,3]oxazolo[4,5-c]pyridin-4-amine | 436.2 |
| 64 | 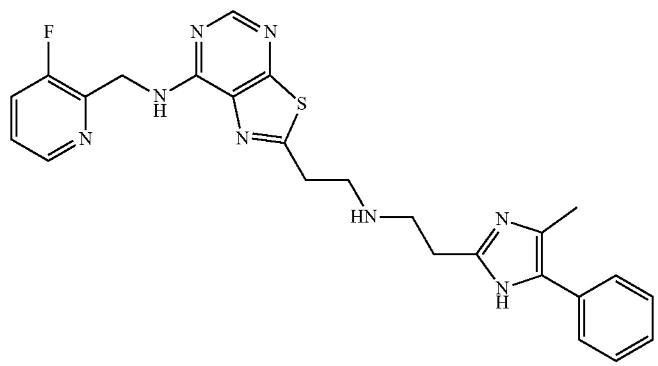 [SMILES: Cc1nc(CCNCCc2nc3c(NCc4ncccc4F)ncnc3s2)[nH]c1-c1ccccc1] | N-[(3-fluoropyridin-2-yl)methyl]-2-(2-{[2-(4-methyl-5-phenyl-1H-imidazol-2-yl)ethyl]amino}ethyl)-[1,3]thiazolo[5,4-d]pyrimidin-7-amine | 489.2 |

TABLE 1-continued

| Compound No. | Structure | IUPAC Name | Mass Found (M + 1) |
|---|---|---|---|
| 65 | 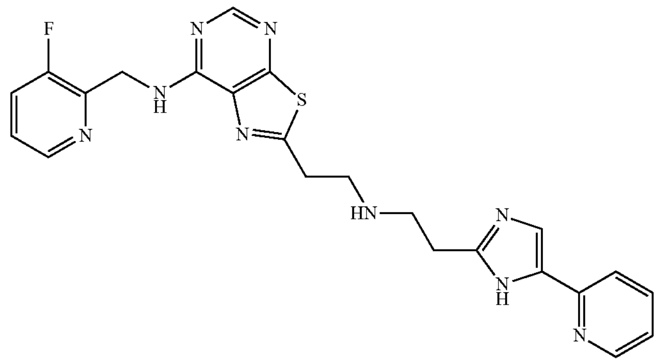 [SMILES: Fc1cccnc1CNc1ncnc2sc(CCNCCc3ncc(-c4ccccn4)[nH]3)nc12] | N-[(3-fluoropyridin-2-yl)methyl]-2-[2-({2-[5-(pyridin-2-yl)-1H-imidazol-2-yl]ethyl}amino)ethyl]-[1,3]thiazolo[5,4-d]pyrimidin-7-amine | 476.2 |
| 66 | 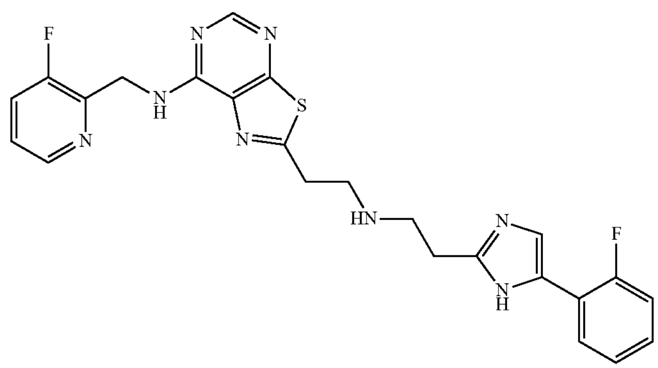 [SMILES: Fc1ccccc1-c1cnc(CCNCCc2nc3c(NCc4ncccc4F)ncnc3s2)[nH]1] | 2-[2-({2-[5-(2-fluorophenyl)-1H-imidazol-2-yl]ethyl}amino)ethyl]-N-[(3-fluoropyridin-2-yl)methyl]-[1,3]thiazolo[5,4-d]pyrimidin-7-amine | 493.2 |

TABLE 1-continued
| Compound No. | Structure | IUPAC Name | Mass Found (M + 1) |
|---|---|---|---|
| 67 | 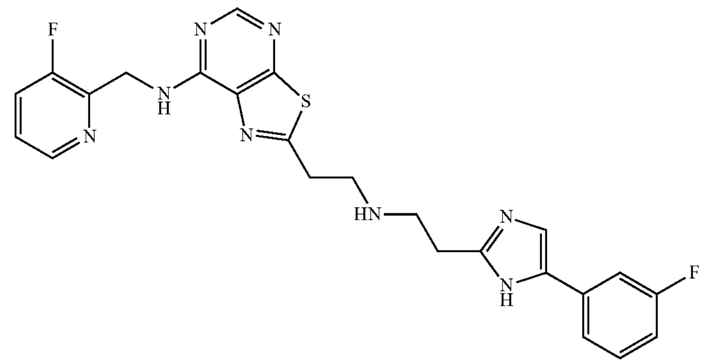 [SMILES: Fc1cccc(-c2cnc(CCNCCc3nc4c(NCc5ncccc5F)ncnc4s3)[nH]2)c1] | 2-[2-({2-[5-(3-fluorophenyl)-1H-imidazol-2-yl]ethyl}amino)ethyl]-N-[(3-fluoropyridin-2-yl)methyl]-[1,3]thiazolo[5,4-d]pyrimidin-7-amine | 493.2 |
| 68 | 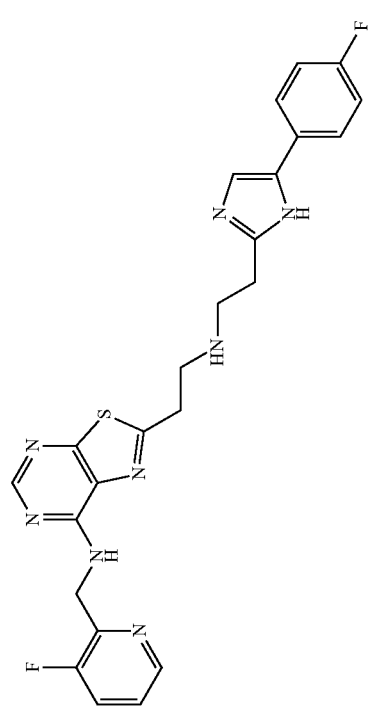 | 2-[2-({2-[5-(4-fluorophenyl)-1H-imidazol-2-yl]ethyl}amino)ethyl]-N-[(3-fluoropyridin-2-yl)methyl]-[1,3]thiazolo[5,4-d]pyrimidin-7-amine | 493.2 |

TABLE 1-continued
| Compound No. | Structure | IUPAC Name | Mass Found (M + 1) |
|---|---|---|---|
| 69 | 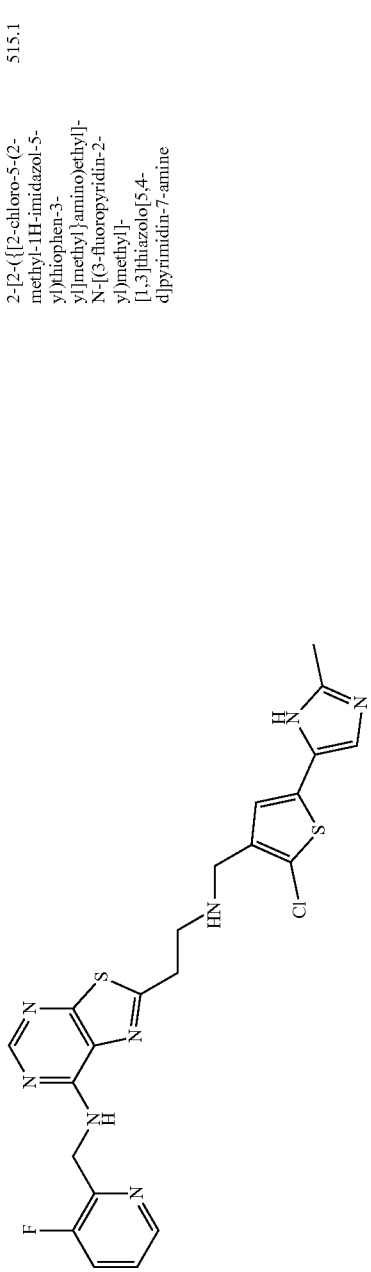 | 2-[2-({[2-chloro-5-(2-methyl-1H-imidazol-5-yl)thiophen-3-yl]methyl}amino)ethyl]-N-[(3-fluoropyridin-2-yl)methyl]-[1,3]thiazolo[5,4-d]pyrimidin-7-amine | 515.1 |
| 70 | 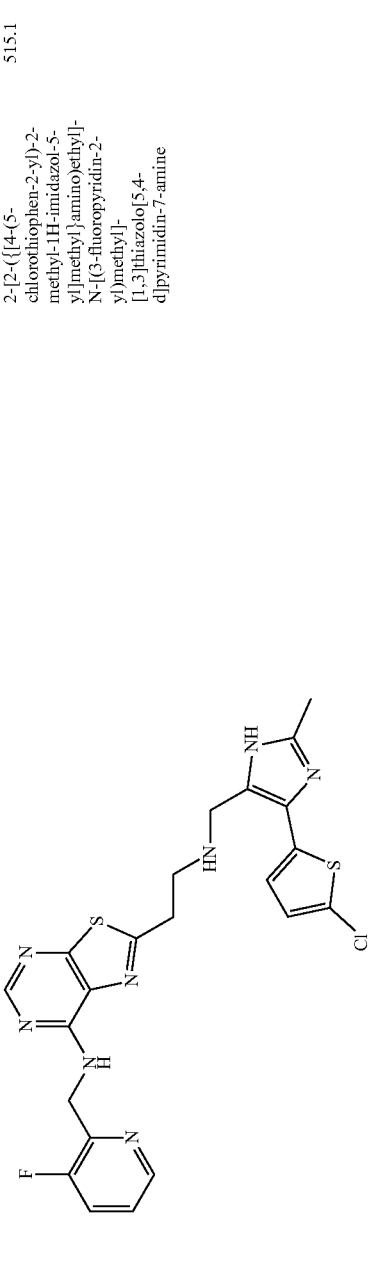 | 2-[2-({[4-(5-chlorothiophen-2-yl)-2-methyl-1H-imidazol-5-yl]methyl}amino)ethyl]-N-[(3-fluoropyridin-2-yl)methyl]-[1,3]thiazolo[5,4-d]pyrimidin-7-amine | 515.1 |

TABLE 1-continued

| Compound No. | Structure | IUPAC Name | Mass Found (M + 1) |
|---|---|---|---|
| 71 | 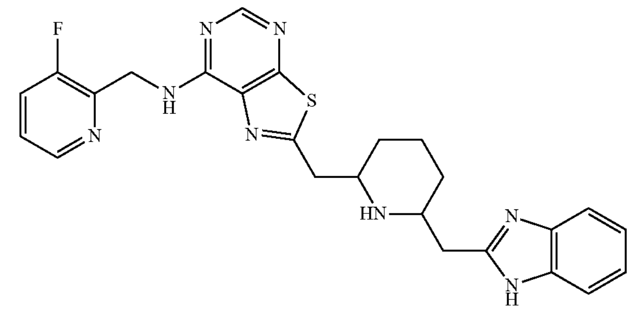 [SMILES: Fc1cccnc1CNc1ncnc2sc(CC3CCCC(Cc4nc5ccccc5[nH]4)N3)nc12] | 2-({6-[(1H-1,3-benzodiazol-2-yl)methyl]piperidin-2-yl}methyl)-N-[(3-fluoropyridin-2-yl)methyl]-[1,3]thiazolo[5,4-d]pyrimidin-7-amine | 489.1 |
| 72 | 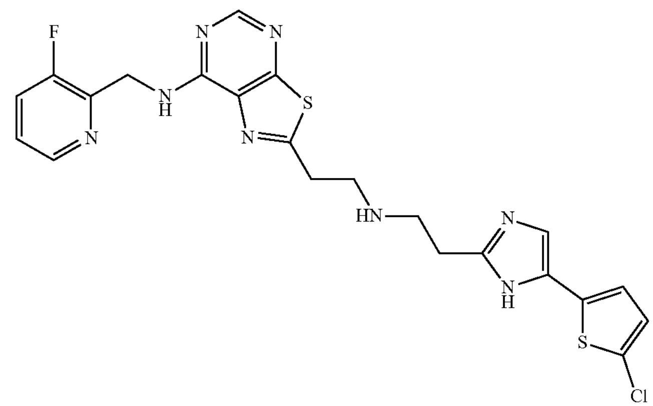 [SMILES: Fc1cccnc1CNc1ncnc2sc(CCNCCc3ncc(-c4ccc(Cl)s4)[nH]3)nc12] | 2-[2-({2-[5-(5-chlorothiophen-2-yl)-1H-imidazol-2-yl]ethyl}amino)ethyl]-N-[(3-fluoropyridin-2-yl)methyl]-[1,3]thiazolo[5,4-d]pyrimidin-7-amine | 515.1 |
| 73 | 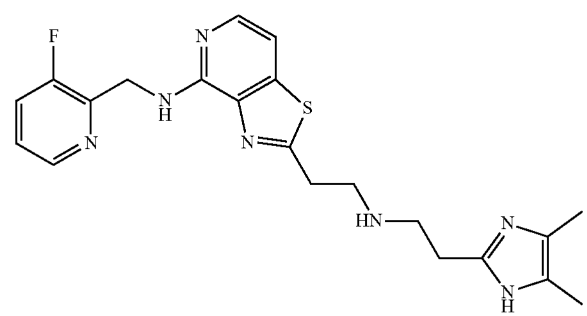 [SMILES: Cc1nc(CCNCCc2nc3c(NCc4ncccc4F)nccc3s2)[nH]c1C] | 2-(2-{[2-(4,5-dimethyl-1H-imidazol-2-yl)ethyl]amino}ethyl)-N-[(3-fluoropyridin-2-yl)methyl]-[1,3]thiazolo[4,5-c]pyridin-4-amine | 426.2 |

TABLE 1-continued

| Compound No. | Structure | IUPAC Name | Mass Found (M + 1) |
|---|---|---|---|
| 74 | 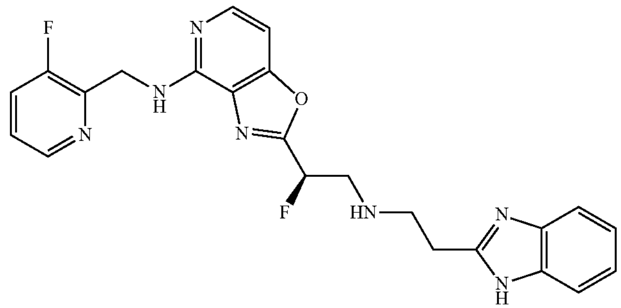 [SMILES: Fc1cccnc1CNc1nccc2oc([C@H](F)CNCCc3nc4ccccc4[nH]3)nc12] | 2-[(1R)-2-{[2-(1H-1,3-benzodiazol-2-yl)ethyl]amino}-1-fluoroethyl]-N-[(3-fluoropyridin-2-yl)methyl][1,3]oxazolo[4,5-c]pyridin-4-amine | 450.2 |
| 75 | 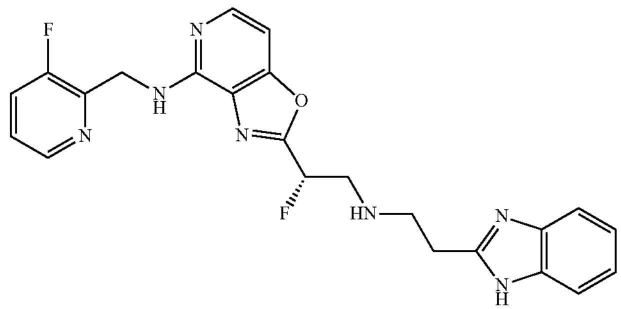 [SMILES: Fc1cccnc1CNc1nccc2oc([C@@H](F)CNCCc3nc4ccccc4[nH]3)nc12] | 2-[(1S)-2-{[2-(1H-1,3-benzodiazol-2-yl)ethyl]amino}-1-fluoroethyl]-N-[(3-fluoropyridin-2-yl)methyl][1,3]oxazolo[4,5-c]pyridin-4-amine | 450.2 |
| 76 | 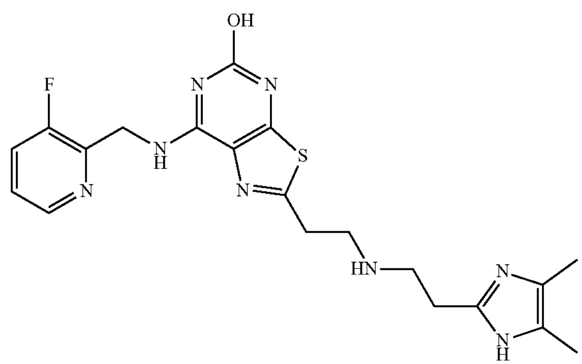 [SMILES: Cc1nc(CCNCCc2nc3c(NCc4ncccc4F)nc(O)nc3s2)[nH]c1C] | 2-(2-{[2-(4,5-dimethyl-1H-imidazol-2-yl)ethyl]amino}ethyl)-7-{[(3-fluoropyridin-2-yl)methyl]amino}[1,3]thiazolo[5,4-d]pyrimidin-5-ol | 443.1 |

TABLE 1-continued

| Compound No. | Structure | IUPAC Name | Mass Found (M + 1) |
|---|---|---|---|
| 77 | 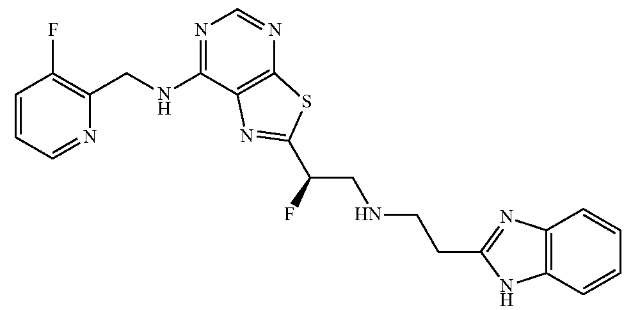 | 2-[(1R)-2-{[2-(1H-1,3-benzodiazol-2-yl)ethyl]amino}-1-fluoroethyl]-N-[(3-fluoropyridin-2-yl)methyl][1,3]thiazolo[5,4-d]pyrimidin-7-amine | 467 |
| 78 | 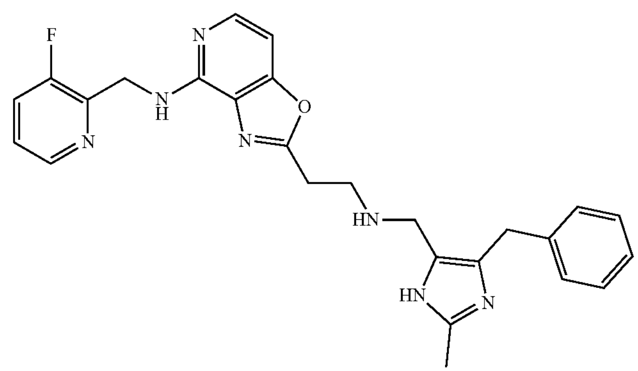 [SMILES: Cc1nc(Cc2ccccc2)c(CNCCc2nc3c(NCc4ncccc4F)nccc3o2)[nH]1] | 2-(2-{[(4-benzyl-2-methyl-1H-imidazol-5-yl)methyl]amino}ethyl)-N-[(3-fluoropyridin-2-yl)methyl][1,3]oxazolo[4,5-c]pyridin-4-amine | 472.3 |

TABLE 1-continued

| Compound No. | Structure | IUPAC Name | Mass Found (M + 1) |
|---|---|---|---|
| 79 | 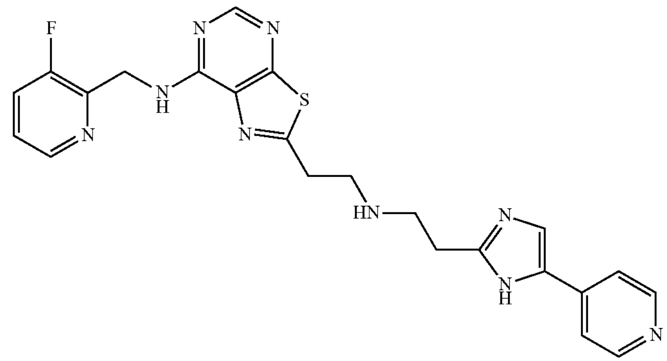 [SMILES: Fc1cccnc1CNc1ncnc2sc(CCNCCc3ncc(-c4ccncc4)[nH]3)nc12] | N-[(3-fluoropyridin-2-yl)methyl]-2-[2-({2-[5-(pyridin-4-yl)-1H-imidazol-2-yl]ethyl}amino)ethyl][1,3]thiazolo[5,4-d]pyrimidin-7-amine | 476.2 |
| 80 | 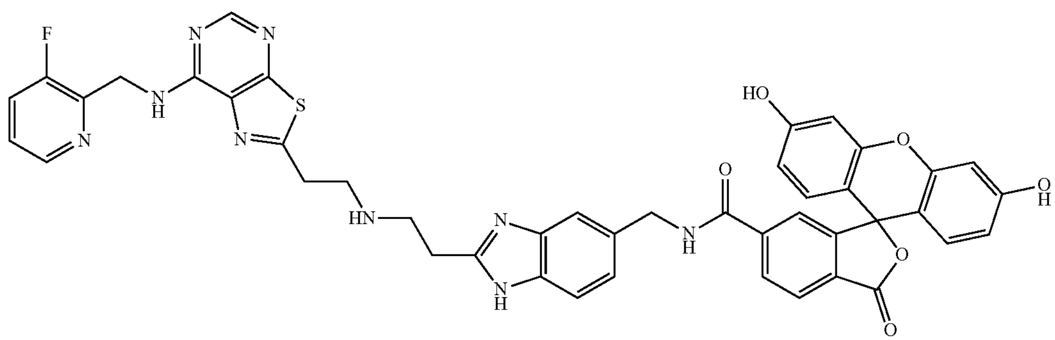 [SMILES: O=C(NCc1ccc2[nH]c(CCNCCc3nc4c(NCc5ncccc5F)ncnc4s3)nc2c1)c1ccc2c(c1)C1(OC2=O)c2ccc(O)cc2Oc2cc(O)ccc21] | N-{[2-(2-{[2-(7-{[(3-fluoropyridin-2-yl)methyl]amino}-[1,3]thiazolo[5,4-d]pyrimidin-2-yl)ethyl]amino}ethyl)-1H-1,3-benzodiazol-5-yl]methyl}-3′,6′-dihydroxy-3-oxo-3H-spiro[2-benzofuran-1,9′-xanthene]-6-carboxamide | 836.4 |
| 81 | 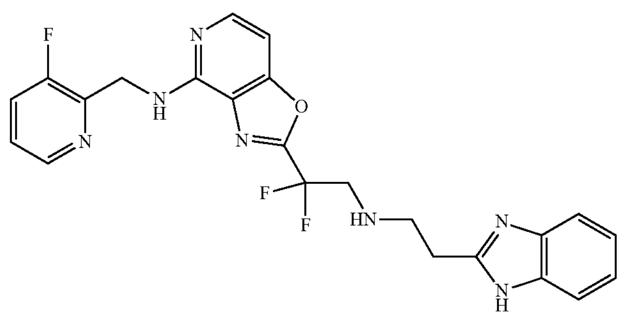 [SMILES: Fc1cccnc1CNc1nccc2oc(C(F)(F)CNCCc3nc4ccccc4[nH]3)nc12] | 2-(2-{[2-(1H-1,3-benzodiazol-2-yl)ethyl]amino}-1,1-difluoroethyl)-N-[(3-fluoropyridin-2-yl)methyl][1,3]oxazolo[4,5-c]pyridin-4-amine | 468.2 |

TABLE 1-continued
| Compound No. | Structure | IUPAC Name | Mass Found (M + 1) |
|---|---|---|---|
| 82 | 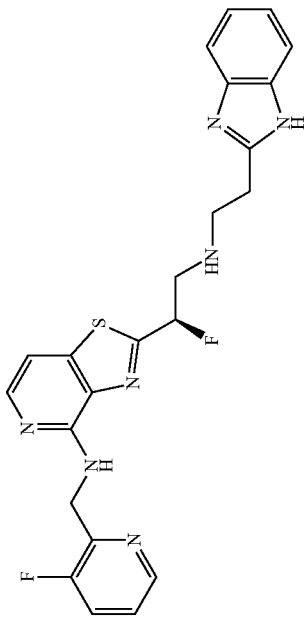 | 2-[(1R)-2-{[2-(1H-1,3-benzodiazol-2-yl)ethyl]amino}-1-fluoroethyl]-N-[(3-fluoropyridin-2-yl)methyl][1,3]thiazolo[4,5-c]pyridin-4-amine | 466.2 |
| 83 | 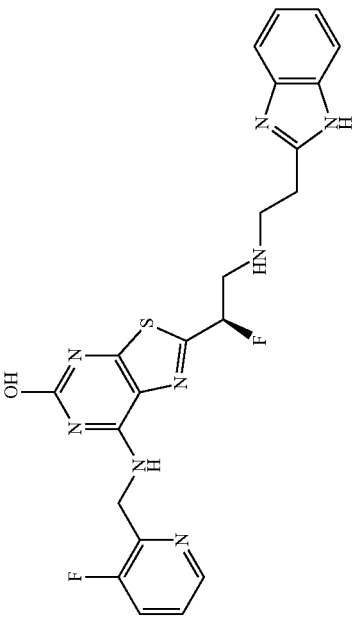 | 2-[(1R)-2-{[2-(1H-1,3-benzodiazol-2-yl)ethyl]amino}-1-fluoroethyl]-7-{[(3-fluoropyridin-2-yl)methyl]amino}[1,3]thiazolo[5,4-d]pyrimidin-5-ol | 483.1 |

In certain embodiments, the subject matter described herein is directed to a compound from Table 1 selected from the group consisting of 1, 2, 3, 4, 5, 6, 7, 8, 9, 10, 11, 12, 13, 14, 15, 16, 17, 18, 19, 20, 21, 23, 24, 25, 26, 27, 28, 29, 30, 31, 32, 33, 34, 35, 36, 37, 38, 40, 41, 42, 43, 44, 45, 46, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 81, 82, and 83, or a pharmaceutically acceptable salt thereof.

In certain embodiments, the subject matter described herein is directed to a compound from Table 1 selected from the group consisting of 1, 13, 23, 74, 75, and 77, or a pharmaceutically acceptable salt thereof.

III. Pharmaceutical Compositions and Modes of Administration

Compounds provided herein are usually administered in the form of pharmaceutical compositions. Thus, provided herein are also pharmaceutical compositions that comprise one or more of the compounds described herein or a pharmaceutically acceptable salt, a stereoisomer, or a mixture of stereoisomers thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, a stereoisomer, or a mixture of stereoisomers thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or a pharmaceutically acceptable salt, a stereoisomer, or a mixture of stereoisomers thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, a stereoisomer, or a mixture of stereoisomers thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

IV. Methods of Treatment

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

The ferroportin inhibition activity of the compounds of Formula I and pharmaceutically acceptable salts thereof provide methods particularly suitable for the use in the inhibition of iron transport mediated by ferroportin. As such, the compounds of Formula I and pharmaceutically acceptable salts thereof are useful in the prophylaxis and/or treatment of iron metabolism disorders leading to increased iron levels, of diseases related to or caused by increased iron levels, increased iron absorption or iron overload, such as in particular of tissue iron overload, of diseases associated with ineffective erythropoiesis, or of diseases caused by reduced levels of hepcidin. Further, the compounds of Formula I are suitable for the use in an adjunctive therapy by limiting the amount of iron available to pathogenic microorganisms, e.g. the siderophilic bacteria *Vibrio vulnificus* and *Yersinia enterocolitica*, and common pathogens (e.g. *Escherichia coli*), thereby preventing or treating infections, inflammation, sepsis, and septic shock caused by said pathogenic microorganisms.

In certain embodiments, the subject matter described herein is directed to a method of inhibiting iron transport mediated by ferroportin in a subject, comprising administering to the subject an effective amount of a compound of Formula I or a pharmaceutically acceptable salt thereof.

In certain embodiments, the subject matter described herein is directed to a method of treating a subject afflicted with a disease related to or caused by reduced hepcidin levels, increased ferroportin levels, reduced sensitivity of ferroportin to hepcidin, increased iron levels, increased iron absorption, iron overload (e.g. due to blood transfusions), increased erythropoiesis, stress erythropoiesis, or ineffective erythropoiesis, comprising administering to the subject an effective amount of a compound of Formula I or a pharmaceutically acceptable salt thereof.

In certain embodiments, the diseases being associated with, being related to, being caused by or leading to increased iron levels, increased iron absorption, iron overload (e.g., tissue iron overload) or ineffective erythropoiesis comprise thalassemia, hemoglobinopathy, such as hemoglobin E disease (HbE), hemoglobin H disease (HbH), haemochromatosis, hemolytic anemia, such as sickle cell anemia and congenital dyserythropoietic anemia. Additional diseases being associated with, being related to, being caused by or leading to increased iron levels, increased iron absorption, iron overload (e.g., tissue iron overload) include neurodegenerative diseases, such as for example Alzheimer's disease, Parkinson's disease, Huntington's disease, multiple sclerosis, Wilson's disease, amyotrophic lateral sclerosis (ALS), and Friedreich's Ataxia, wherein the compounds and methods are considered to be effective by limiting the deposition or increase of iron in tissue or cells; conditions associated with the formation of radicals, reactive oxygen species (ROS) and oxidative stress caused by excess iron or iron overload; cardiac, liver and endocrine damage caused by excess iron or iron overload; inflammation triggered by excess iron or iron overload; diseases associated with ineffective erythropoiesis, such as myelodysplastic syndromes (MDS, myelodysplasia), polycythemia vera, and congenital dyserythropoietic anemia; diseases, disorders and/or disease conditions that comprise iron overload caused by mutations in genes involved in sensing the systemic iron stores, such as hepcidin/hepcidin antimicrobial peptide (HAMP), hemochromatosis protein (HFE), hemojuvelin (HJV) and transferrin receptor 2 (TFR2), such as in particular diseases related to HFE and HJV gene mutations; diseases related to ferroportin mutations; chronic hemolysis associated diseases, sickle cell diseases (including sickle cell anemia (HbSS) as well as hemoglobin SC disease (HbSC), hemoglobin S beta-plus-thalassemia (HbS/β+), and hemoglobin S beta-zero-thalassemia (HbS/β0)), red cell membrane disorders, Glucose-6-phosphate dehydrogenase deficiency (G6PD deficiency), erythropoietic *porphyria*, Friedreich's Ataxia, as well as subgroups of iron overload such as transfusional iron overload, iron intoxication, pulmonary hemosiderosis, osteopenia, insulin resistance, African iron overload, Hallervordan Spatz disease, hyperferritinemia, ceruloplasmin deficiency, neonatal hemochromatosis and red blood cell disorders comprising thalassemia, including alpha thalassemia, beta thalassemia and delta thalassemia, thalassemia *intermedia*, sickle cell disease and myelodysplastic syndrome; liver diseases (e.g. hepatitis B virus infection, hepatitis C virus infection, alcoholic liver disease, autoimmune hepatitis), other conditions including ataxia, Friedreich's ataxia, age-related macular degeneration, age-related cataract, age-related retinal diseases and neurodegenerative disease, such as pantothenate kinase-associated neurodegeneration, restless leg syndrome and Huntington's disease. In certain embodiments, the disease is sickle cell anemia. The ferroportin inhibition activity, for instance by inducing internalization of ferroportin, of the compounds of Formula I and pharmaceutically acceptable salts thereof can be determined by the assays described herein as well as those described in WO2018/192973, incorporated herein by reference in its entirety.

The activity of the compounds of Formula I in the treatment of sickle cell anemia (sickle cell disease) can be determined by using a mouse model, such as e.g. described by Yulin Zhao et al. in "MEK1/2 inhibitors reverse acute vascular occlusion in mouse models of sickle cell disease"; The FASEB Journal Vol. 30, No. 3, pp 1171-1186, 2016. Said mouse model can be suitably adapted to determine the activity of the compounds of Formula I in the treatment of sickle cell anemia. In certain embodiments, the disease is caused by a lack of hepcidin or iron metabolism disorders, particularly iron overload states, such as thalassemia, sickle cell disease and hemochromatosis. In certain embodiments, the disease is related to or caused by reduced hepcidin levels, increased iron levels, increased iron absorption, iron overload, increased erythropoiesis, stress erythropoiesis, or ineffective erythropoiesis. In certain embodiments, the disease is selected from the group consisting of thalassemia, hemoglobinopathy, hemoglobin E disease, hemoglobin H disease, haemochromatosis, and hemolytic anemia.

In certain embodiments, the methods of administering and treating described herein further comprise co-administration of one or more additional pharmaceutically active compounds or in combination with a blood transfusion.

In a combination therapy, the pharmaceutically active compounds can be administered at the same time, in the same formulation, or at different times. Such combination therapy comprises co-administration of a compound of Formula I or a pharmaceutically acceptable salt thereof with at least one additional pharmaceutically active compound. Combination therapy in a fixed dose combination therapy comprises co-administration of a compound of Formula I or a pharmaceutically acceptable salt thereof with at least one additional pharmaceutically active compound in a fixed-dose formulation. Combination therapy in a free dose combination therapy comprises co-administration of a compound of Formula I or a pharmaceutically acceptable salt thereof and at least one additional pharmaceutically active compound in free doses of the respective compounds, either by simultaneous administration of the individual compounds or by sequential use of the individual compounds over a period of time.

The additional pharmaceutically active compound includes in particular drugs for reducing iron overload (e.g., Tmprss6-ASO or siRNA) or iron chelators, in particular curcumin, SSP-004184, Deferitrin, deferasirox, deferoxamine and/or deferiprone, or antioxidants such as n-acetyl cysteine, anti-diabetics such as GLP-1 receptor agonists, antibiotics such as penicillin, vancomycin (Van) or tobramycin, antifungal drugs, anti-viral drugs such as interferon-a or ribavirin, drugs for the treatment of malaria, anticancer agents, drugs for the treatment of neurodegenerative diseases such as Alzheimer's disease and Parkinson's disease (e.g., dopamine agonists such as Levodopa), or immunosuppressants (cyclosporine A or cyclosporine A derivatives), iron supplements, vitamin supplements, red cell production stimulators (e.g., erythropoietin, Epo), anti-inflammatory agents, anti-thrombolytics, statins, vasopressors and inotropic compounds. A further object of the present invention relates to the use of the above combinations for the prophylaxis and/or treatment of diseases caused by a lack of hepcidin or iron metabolism disorders, such as particularly iron overload states such as in particular thalassemia, sickle cell disease and hemochromatosis and other disorders as described in the present application.

V. Methods of Preparing Compounds of Formula I and Pharmaceutically Acceptable Salts Thereof Compounds can be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g., Volume 3; Liebigs Annalen der Chemie, (9):1910-16, (1985); Helvetica Chimica Acta, 41:1052-60, (1958); Arzneimittel-Forschung, 40(12): 1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database). DTT refers to dithiothreitol. DHAA refers to dehydroascorbic acid.

Synthetic chemistry transformations and protecting group methodologies (protection and deprotection) useful in synthesizing compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

Compounds may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus, according to a further aspect, there is provided a compound library comprising at least 2 compounds, or pharmaceutically acceptable salts thereof.

The General Procedures and Examples provide exemplary methods for preparing compounds. Those skilled in the art will appreciate that other synthetic routes may be used to synthesize the compounds. Although specific starting materials and reagents are depicted and discussed in the Schemes, General Procedures, and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

General Synthetic Schemes

General synthetic approaches to compound 1a and 1b. In certain embodiments, Compound 1a and 1b can be synthesized by two synthetic pathways as shown in schemes 1-3. In scheme 1, bicyclic core intermediate 2a is coupled first with various amines to give intermediate 3a, deprotection via method B leads to the free amine intermediate 4a, which was transformed via Michael addition method C and ring closure method D to produce final compound 1a. Compound 1a can also be synthesized via scheme 2, amine intermediate 4a was coupled with alkene 7a directly to give 1a via method E.

Compound 1b could be synthesized as shown in scheme 3. The amine intermediate 4a can be coupled directly with aldehyde 8a via reductive amination method F to give intermediate 9a, which was then converted to compound 1b.

Modifications and variations to schemes 1-3 can be made based on the availability of starting materials, synthetic compatibility of reagents and starting materials or intermediates, this should be obvious to those who are familiar with the art. For example, X could be H, halogen; Y could be tert-butyloxycarbonyl, benzyloxycarbonyl or other common amine protecting group, G could be substituted aryl, heteroaryl, alkyl or cycloalkyl, A, D, E, F could be N, O, S or CH; P could be Trityl, Dimethylsulfamyl or other common imidazole protecting group.

As used herein, the term "Cbz" is an abbreviation for carboxybenzyl or benzyloxycarbonyl.

The term "Boc" is an abbreviation for tert-butyloxycarbonyl.

The term "trt" is an abbreviation for trityl or triphenylmethyl.

The term "Mso" is an abbreviation for methanesulfonate or mesylate.

The term "TBS" is an abbreviation for tert-Butyldimethylsilyl.

Scheme 1 depicts a method for preparing exemplary compounds using Method A, Method B, Method C and Method D.

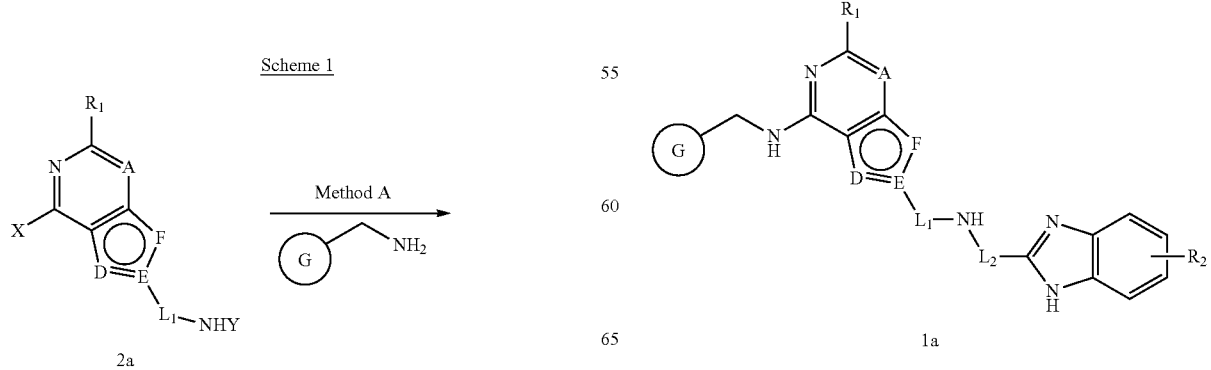

Scheme 2 depicts a method for preparing exemplary compounds using Method E.

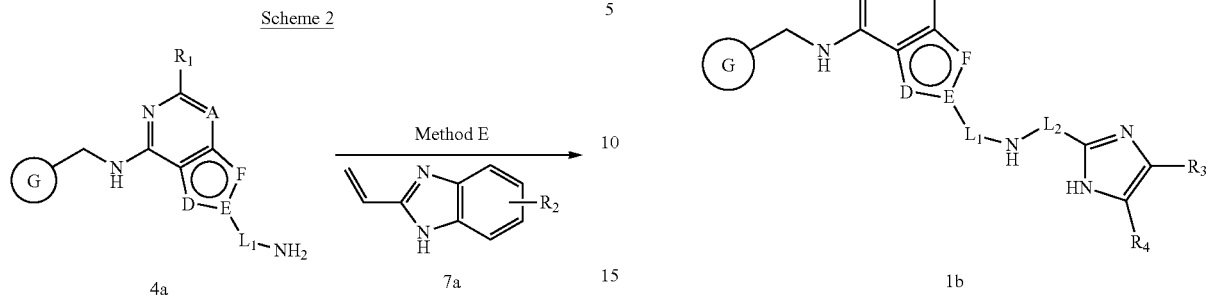

Scheme 3 depicts a method for preparing exemplary compounds using Method F and Method G.

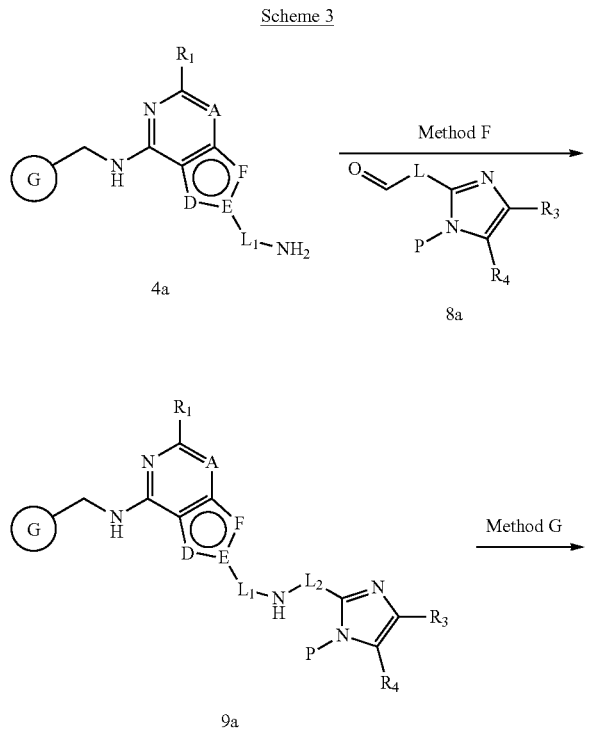

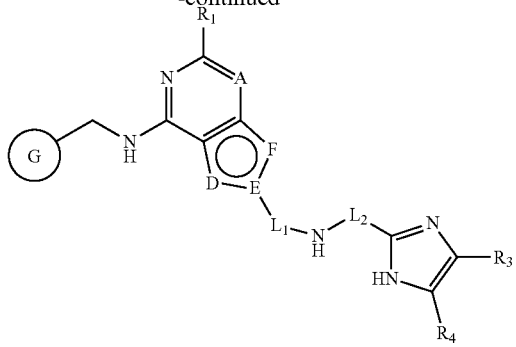

The conditions and reagents for Methods A-G are provided in the below Examples. The following examples are offered by way of illustration and not by way of limitation.

1. SYNTHETIC EXAMPLES

Example 1.1

Method A: General Synthetic Method for Nucleophilic Coupling of Amine to Bicyclic Intermediates Amine coupling procedure-1: Into a round-bottom flask purged and maintained with an inert atmosphere of nitrogen, was placed a solution of bicyclic intermediate 2a (X=Cl) (1.0 equiv) in aprotic solvent such as dimethylformamide (DMF) or acetonitrile (MeCN), amine (1.1 to 2 equiv), base such as $K_2CO_3$ (2.0-4.0 equiv). The resulting solution was stirred for 0.5 hr to 24 hr at a heated temperature between 45 to 125° C., cooled down and the solids were filtered out. The resulting solution was diluted with $H_2O$. The resulting solution was extracted with ethyl acetate and the organic layers combined and dried over anhydrous sodium sulfate and concentrated. The residue was purified by chromatography on silica gel column to give the desired intermediate 3a.

Amine coupling procedure-2 (via N-oxide as intermediate): Into a round-bottom flask, was placed bicyclic intermediate 2a (X=H) (1 equiv) in dichloromethane (DCM). This was followed by the addition of meta-chloroperoxybenzoic acid (m-CPBA) (1.5 to 4 equiv), in portions at 0° C. The resulting solution was stirred for up to 36 h at room temperature. The resulting mixture was washed with Sat. $NaHCO_3$, dried by $Na_2SO_4$. The residue was applied onto a silica gel column with dichloromethane/methanol (3%) to give N-oxide product.

Into a round-bottom flask, was placed above N-oxide (1 equiv), amine (1.1 to 2 equiv), tetrahydrofuran (THF), N,N-diisopropylethylamine (DIEA) (2 to 5 equiv). This was followed by the addition of bromo-tris-pyrrolidino-phosphonium hexafluorophosphate (PyBrOP) (1.1 to 2.5 equiv), in portions at room temperature. The resulting solution was stirred for up to 36 h at room temperature. The resulting solution was extracted with ethyl acetate and the organic layers combined and dried over anhydrous sodium sulfate and concentrated. The residue was purified by chromatography on silica gel column to give the desired intermediate 3a.

Example 1.2

Method B: General Synthetic Method for Amine Protection Group Removal

Procedure-1: Into a round-bottom flask, was placed benzyloxycarbonyl-bicyclic intermediate 3a (Y=benzyl- oxycarbonyl) (1.0 equiv), HBr in acetic acid (AcOH) (40%) (5 to 25 mL). The resulting solution was stirred for 0.5 hr to 12 hr at room temperature and diluted with 50 mL of $H_2O$. The resulting solution was extracted with ethyl acetate and the aqueous layers combined. The pH value of the solution was adjusted to 12 with NaOH (10%). The resulting solution was extracted with ethyl acetate and the organic layers combined and dried over anhydrous sodium sulfate and concentrated. The residue was purified by chromatography on silica gel column or preparative HPLC to give the amine 4a.

Procedure-2: Into a round-bottom flask, was placed tert-butyloxycarbonyl protected bicyclic intermediate 3a (Y=t-butyloxycarbonyl) (1 equiv). This was followed by the addition of HCl in ethyl acetate (EtOAc) dropwise with stirring at 0° C. The resulting solution was stirred for 0.5 hr to 12 h at room temperature. The pH value of the solution was adjusted to 10 with Sat.$Na_2CO_3$. The resulting solution was extracted with ethyl acetate and the organic layers combined and dried over anhydrous sodium sulfate and concentrated to give the amine 4a.

Example 1.3

Method C: General Synthetic Method for Michael Addition

Into a round-bottom flask, was placed bicyclic alkylamine 4a (1.0 equiv), N-(2-nitrophenyl)prop-2-enamide 5a (1.0 to 1.8 equiv), tosylic acid (TsOH) (0.2 to 1.0 equiv), and acetonitrile (AcCN). The resulting solution was stirred for 0.5 to 24 hr at 25 to 65° C. (e.g., 40° C.), cooled down and concentrated. The resulting solution was diluted with 20 mL of $H_2O$. The resulting solution was extracted with ethyl acetate and the organic layers combined and dried over anhydrous sodium sulfate and concentrated. The residue was purified by chromatography on silica gel column to give Michael addition adduct 6a.

Example 1.4

Method D: General Synthetic Method for Imidazole Ring Formation

Into a round-bottom flask, was placed a solution of Michael addition adduct 6a (mmol, 1.0 equiv) in AcOH and Fe (2.0 to 10.0 equiv). The resulting solution was stirred for 0.5 hr to 12 hr at heated temperature between 30 to 90° C., cooled down and concentrated. The resulting solution was diluted with AcCN. The solids were filtered out. The filtrate was concentrated and purified by reverse phase HPLC or silica gel chromatography to give final compound 1a.

Example 1.5

Method E: General Synthetic Method for Hydroamination of Alkene

Into a vial was placed bicyclclic alkylamine 4a (1 equiv), 2-ethenyl-1H-1,3-benzodiazole (1 to 1.5 equiv), $CH_3CN$ and $Et_3N$ (2 to 5 equiv). The resulting solution was stirred for 1 to 36 h at heated temperature between 30 to 80° C. in an oil bath. The reaction mixture was cooled to room temperature. The crude product was purified by reverse phase Prep-HPLC to give final compound 1a.

Example 1.6

Method F: General Synthetic Method for Coupling of Amine and Aldehydes or Ketones Using Reductive Amination Into a round-bottom flask was placed bicyclic alkylamine 4a (1.0 equiv), EtOH, aldehyde 8a (1.1 to 2.0 equiv). The resulting solution was stirred for 1 to 24 hr at room temperature. $NaBH_4$ or $NaBH_3CN$ (2.0 to 4 equiv) was added and the resulting solution was stirred for 0.5 to 12 hr at room temperature. The reaction was then quenched by the addition of water/ice. The resulting solution was diluted with DMF and was purified by reverse flash chromatography or silica gel column chromatography to give reductive amination product 9a.

Example 1.7

Method G: General Synthetic Method for Imidazole Protection Group Removal

Procedure-1: Into a round-bottom flask, was placed trityl protected imidazole 9a (P=Trityl) (1.00 equiv), DCM, HCl (gas) in 1,4-dioxane (large excess). The resulting solution was stirred for 1 to 24 hr at 25° C., concentrated and diluted with 5 mL of ACN. The crude product was purified by reverse phase Prep-HPLC to give final compound 1b.

Procedure-2: Into a round-bottom flask, was placed sulfamyl protected imidazole 9a (P=Dimethylsulfamyl) (1.00 equiv), HCl (2M) (4 to 20 equiv.). The resulting solution was stirred for 1 to 12 hr at heated temperature between 30 to 90° C., cooled down and filtered. The crude product was purified by reverse phase Prep-HPLC to give final compound 1b.

Example 1.8

Experimental Procedures for Common Reference Compounds: Preparation of Reference Compound Int-1

Scheme 4 depicts a synthetic route for preparing compound Int-1.

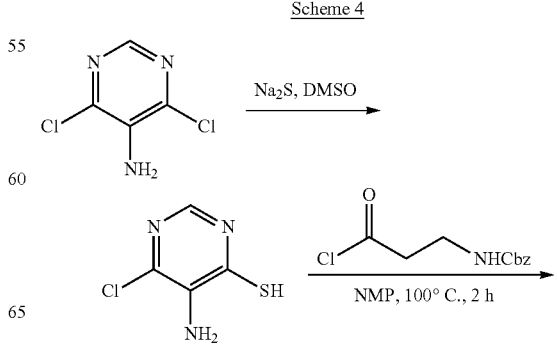

Scheme 4

-continued

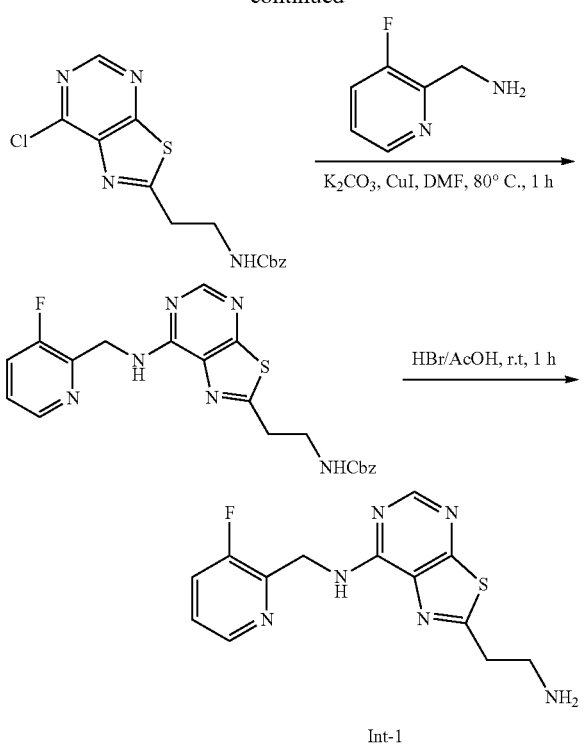

Step 1:

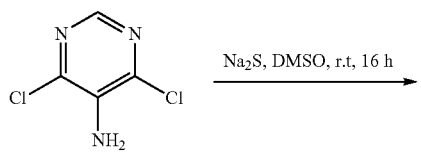

Into a 250-mL round-bottom flask, was placed a solution of 4,6-dichloropyrimidin-5-amine (8.5 g, 51.83 mmol, 1.0 equiv) in dimethyl sulfoxide (DMSO) (100 mL), Na$_2$S (4.04 g, 51.83 mmol, 1.0 equiv). The resulting solution was stirred for 16 hr at room temperature and diluted with 50 mL of H$_2$O, and then 20 ml con. HCl was added. The solids were collected by filtration. This resulted in 7.0 g (83.5%) of 5-amino-6-chloropyrimidine-4-thiol as yellow solid. LCMS [M−1]⁻ m/z: 160.0.

Step 2:

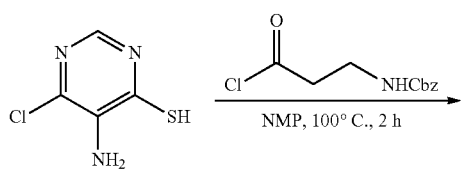

-continued

Into a 250-mL round-bottom flask, was placed a solution of 3-[[(benzyloxy)carbonyl]amino]propanoic acid (10 g, 44.79 mmol, 1.0 equiv) in dichloromethane (DCM) (100 mL). This was followed by the addition of oxalic dichloride (11.37 g, 89.59 mmol, 2.0 equiv) dropwise with stirring at 0° C. The resulting solution was stirred for 16 hr at room temperature and concentrated. This resulted in 10.7 g (98.8%) of benzyl N-(3-chloro-3-oxopropyl) carbamate as colorless oil.

Into a 250-mL round-bottom flask, was placed a solution of 5-amino-6-chloropyrimidine-4-thiol (7 g, 43.31 mmol, 1.00 equiv) in NMP (60 mL). This was followed by the addition of a solution of above synthesized benzyl N-(3-chloro-3-oxopropyl)carbamate (12.56 g, 51.97 mmol, 1.2 equiv) in NMP (40 mL) dropwise with stirring at 0° C. The resulting solution was stirred for 2 hr at 100° C., cooled down and diluted with 100 mL of H$_2$O. The resulting solution was extracted with 3×100 mL of ethyl acetate and the organic layers combined and dried over anhydrous sodium sulfate and concentrated. The residue was applied onto a silica gel column with ethyl acetate/petroleum ether (1:1). This resulted in 8.5 g (56.2%) of benzyl N-(2-[7-chloro-[1,3]thiazolo[5,4-d]pyrimidin-2-yl]ethyl)carbamate as white solid. LCMS [M+1]⁺ m/z: 349.0.

Step 3:

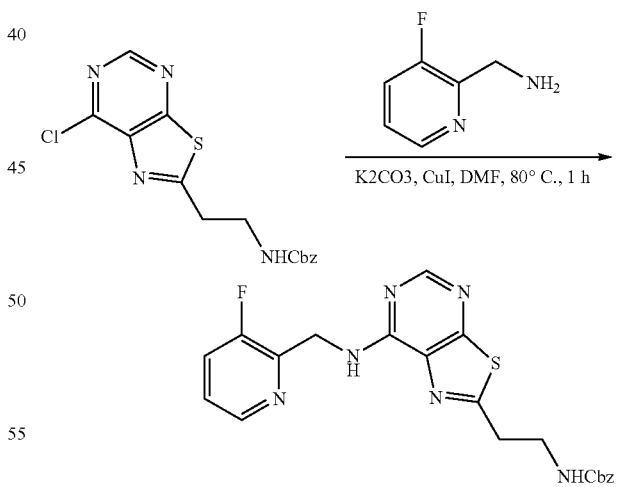

Into a 100-mL round-bottom flask purged and maintained with an inert atmosphere of nitrogen, was placed a solution of benzyl N-(2-[7-chloro-[1,3]thiazolo[5,4-d]pyrimidin-2-yl]ethyl)carbamate (1.4 g, 4.01 mmol, 1.0 equiv) in dimethylformamide (DMF) (15 mL), 1-(3-fluoropyridin-2-yl)methanamine (0.61 g, 4.81 mmol, 1.2 equiv), K$_2$CO$_3$ (1.11 g, 8.02 mmol, 2.0 equiv) and CuI (76 mg, 0.40 mmol, 0.10 equiv). The resulting solution was stirred for 1 hr at 80° C., cooled down and the solids were filtered out. The resulting solution was diluted with 50 mL of H₂O. The resulting solution was extracted with 3×50 mL of ethyl acetate and the organic layers combined and dried over anhydrous sodium sulfate and concentrated. The residue was applied onto a silica gel column with ethyl acetate/petroleum ether (2:1). This resulted in 900 mg (51.1%) of benzyl N-[2-(7-[[(3-fluoropyridin-2-yl)methyl]amino]-[1,3]thiazolo[5,4-d]pyrimidin-2-yl)ethyl]carbamate as yellow oil. $^1$H NMR (300 MHz, DMSO-d$_6$) δ 8.44-8.29 (m, 3H), 7.70 (t, J=9.2 Hz, 1H), 7.59-7.49 (m, 1H), 7.45-7.26 (m, 6H), 5.02 (s, 2H), 4.89 (d, J=5.9 Hz, 2H), 3.49 (s, 2H), 3.25 (s, 2H). [M+1]⁺ m/z: 439.1

Step 4:

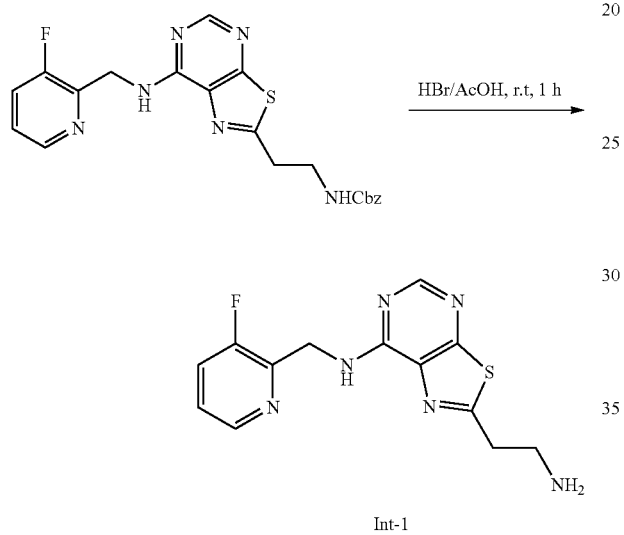

Into a 100-mL round-bottom flask, was placed benzyl N-[2-(7-[[(3-fluoropyridin-2-yl)methyl]amino]-[1,3]thiazolo[5,4-d]pyrimidin-2-yl)ethyl]carbamate (900 mg, 2.05 mmol, 1.0 equiv), HBr in AcOH (40%) (10 mL). The resulting solution was stirred for 1 hr at room temperature and diluted with 50 mL of H₂O. The resulting solution was extracted with 3×30 mL of ethyl acetate and the aqueous layers combined. The pH value of the solution was adjusted to 12 with NaOH (10%). The resulting solution was extracted with 4×50 mL of ethyl acetate and the organic layers combined and dried over anhydrous sodium sulfate and concentrated. This resulted in 500 mg (80.0%) of 2-(2-aminoethyl)-N-[(3-fluoropyridin-2-yl)methyl]-[1,3]thiazolo[5,4-d]pyrimidin-7-amine as white solid. $^1$H NMR (300 MHz, DMSO-d$_6$) δ 8.55 (t, J=5.9 Hz, 1H), 8.39-8.27 (m, 3H), 7.71 (ddd, J=10.1, 8.4, 1.3 Hz, 1H), 7.40 (dt, J=8.6, 4.5 Hz, 1H), 4.91 (dd, J=6.1, 2.0 Hz, 2H), 3.32 (t, J=6.5 Hz, 2H), 3.19 (t, J=6.2 Hz, 2H). LCMS [M+1]⁺ m/z: 305.1

Example 1.9

Experimental Procedures for Common Reference Compounds: Preparation of Reference Compound Int-2

Scheme 5 depicts a synthetic route for preparing compound Int-2.

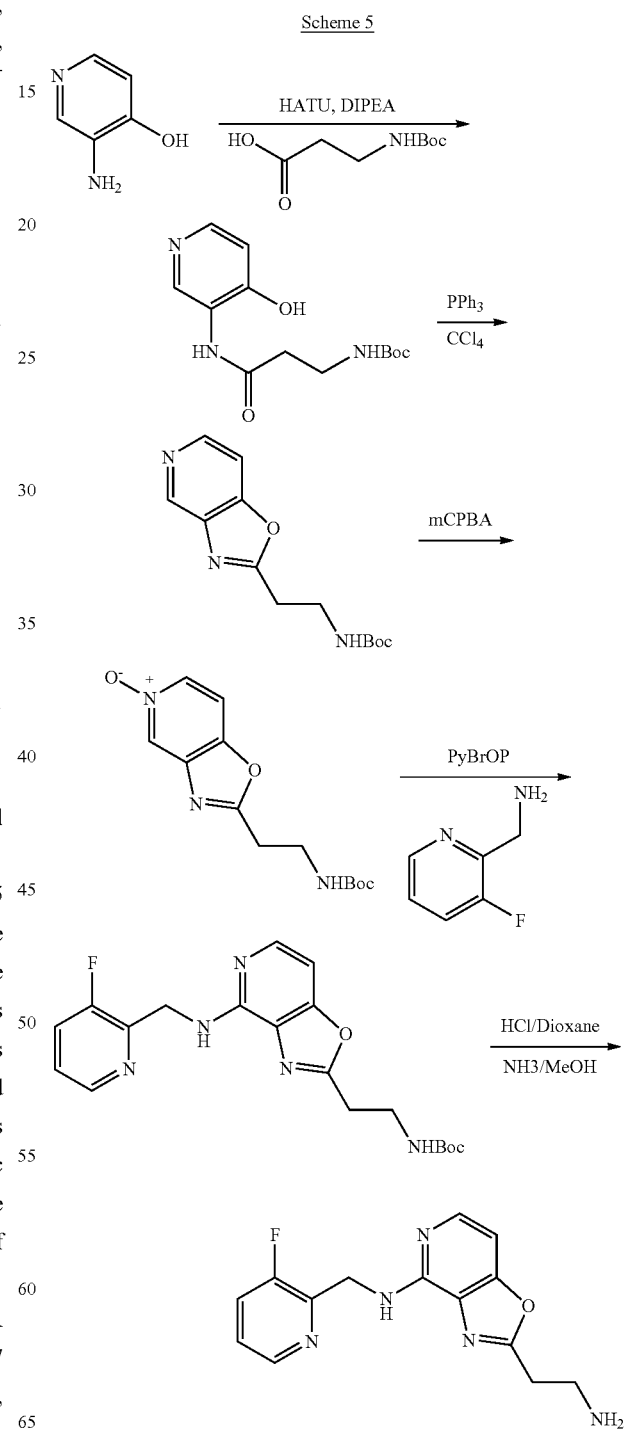

Step 1:

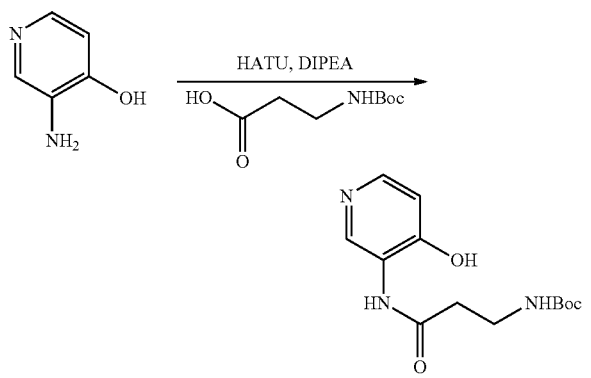

To a solution of 3-amino-4-pyridinol (2.50 g; 22.70 mmol; 1.00 eq.) in DMF (45 mL) was added N-(tert-butoxycarbonyl)-beta-alanine (4.30 g; 22.70 mmol; 1.00 eq.) triethylamine (6.35 mL; 45.41 mmol; 2.00 eq.) and 1-[Bis(dimethylamino)methylene]-1H-1,2,3-triazolo[4,5-b]pyridinium 3-oxid hexafluorophosphate (HATU) (10.36 g; 27.24 mmol; 1.20 eq.). The solution was stirred at room temperature for 15 h. The solution was diluted with water and extracted with EtOAc, organic layers were combined and washed with brine, dried and concentrated to give crude oil, the crude oil was purified by column chromatography (Hexanes/EtOAc=0:100) to give tert-butyl N-{2-[(4-hydroxypyridin-3-yl)carbamoyl]ethyl)}carbamate (5.7 g, 89%). LCMS [M+1]+ m/z: 281.9.

Step 2:

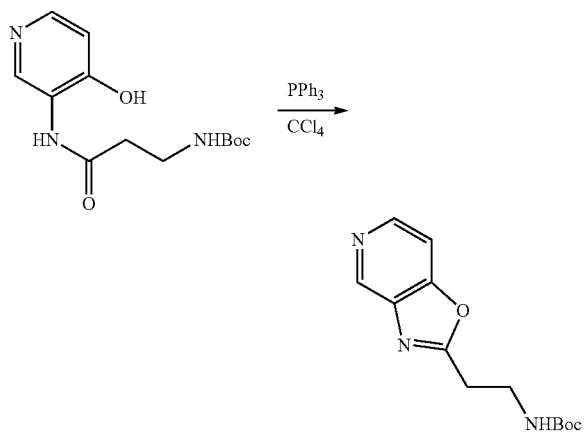

To polymer supported PPh₃ (7 g) in DCM (5 mL) was added 1,1,1,2,2,2-hexachloroethane (1.47 g; 0.01 mol; 1.25 eq.) and triethylamine (3.48 mL; 24.88 mmol; 5.00 eq.), after 5 min, the solid sample of tert-butyl N-{2-[(4-hydroxypyridin-3-yl)carbamoyl]ethyl}carbamate (1.40 g; 4.98 mmol; 1.00 eq.) was added. The mixture was stirred for 1 hr at room temperature, additional 1,1,1,2,2,2-hexachloroethane (1.0 g) and Triethylamine (1 mL) were added. After stirred for additional 10 min, HPLC showed the reaction was mostly completed. The mixture was diluted with DCM and AcCN, filtered to remove the resin, and the filtrate was concentrated to give crude product, which was purified by column chromatography (Hexanes/EtOAc=100:0 to 0 to 95%) to give tert-butyl N-(2-{[1,3]oxazolo[4,5-c]pyridin-2-yl}ethyl)carbamate (0.8 g, 61% yield). ¹H NMR (400 MHz, Chloroform-d) δ 8.94 (d, J=1.0 Hz, 1H), 8.48 (d, J=5.5 Hz, 1H), 7.41 (dd, J=5.6, 1.0 Hz, 1H), 5.37 (s, 1H), 3.65 (q, J=6.2 Hz, 2H), 3.12 (t, J=6.2 Hz, 2H), 1.37 (s, 9H). LCMS [M+1]+ m/z: 263.7.

Step 3:

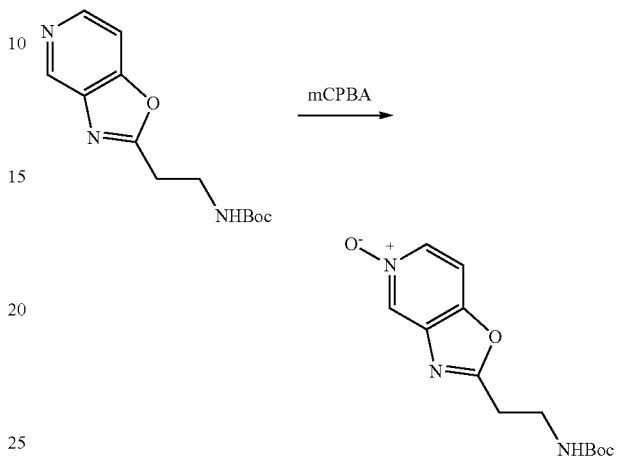

To a solution of tert-butyl N-(2-{[1,3]oxazolo[4,5-c]pyridin-2-yl}ethyl)carbamate (0.90 g; 3.42 mmol; 1.00 eq.) in DCM (15 mL) at 0° C. was added 3-chloroperoxybenzoic acid (1.18 g; 6.84 mmol; 2.00 eq.), after stirred at 0° C. for 2 h, the mixture was warmed to room temperature and was further stirred for 3 h. The mixture was diluted with DCM, washed with Sat. NaHCO₃ and brine, dried and concentrated to give crude product, which was purified by column chromatography (DCM/MeOH/NH₃=90:9:1) to give 2-(2-{[(tert-butoxy)carbonyl]amino}ethyl)-[1,3]oxazolo[4,5-c]pyridin-5-ium-5-olate (0.68 g, 71.2%). ¹H NMR (400 MHz, DMSO-d₆) δ 8.77 (d, J=1.8 Hz, 1H), 8.19 (dd, J=7.0, 1.9 Hz, 1H), 7.80 (d, J=7.0 Hz, 1H), 7.01 (t, J=5.8 Hz, 1H), 3.38 (q, J=6.4 Hz, 2H), 3.04 (t, J=6.6 Hz, 2H), 1.30 (s, 9H), 1.26 (s, 1H). LCMS [M+1]+ m/z: 280.8.

Step 4:

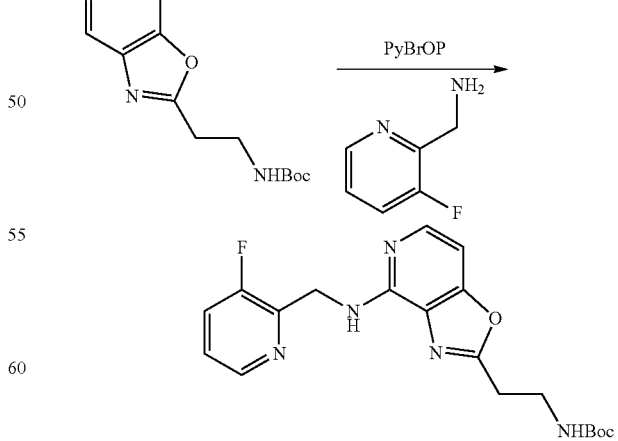

To a solution of (3-fluoropyridin-2-yl)methanamine bis HCl salt (0.73 g; 3.65 mmol; 1.50 eq.) and 2-(2-{[(tert-butoxy)carbonyl]amino}ethyl)-[1,3]oxazolo[4,5-c]pyridin-5-ium-5-olate (0.68 g, 2.43 mmol; 1.00 eq.) in THF (10 mL)

was added Hunig's base DIPEA (1.70 mL; 9.74 mmol; 4.00 eq.) and bromo[tri(1-pyrrolidinyl)]phosphonium hexafluorophosphate (1.70 g; 3.65 mmol; 1.50 eq.). The mixture was stirred for 6 h at room temperature, and was diluted with EtOAc, washed with Sat. NH₄Cl and Sat. NaHCO₃ and brine. The organic layer was separated, dried and concentrated to give crude product, which was purified by column chromatography (DCM/MeOH/NH₃=90:9:1) to give tert-butyl N-[2-(4-{[(3-fluoropyridin-2-yl)methyl]amino}-[1,3]oxazolo[4,5-c]pyridin-2-yl)ethyl]carbamate (1.5 g, >100%)). LCMS [M+1]⁺ m/z: 388.2.

Step 5:

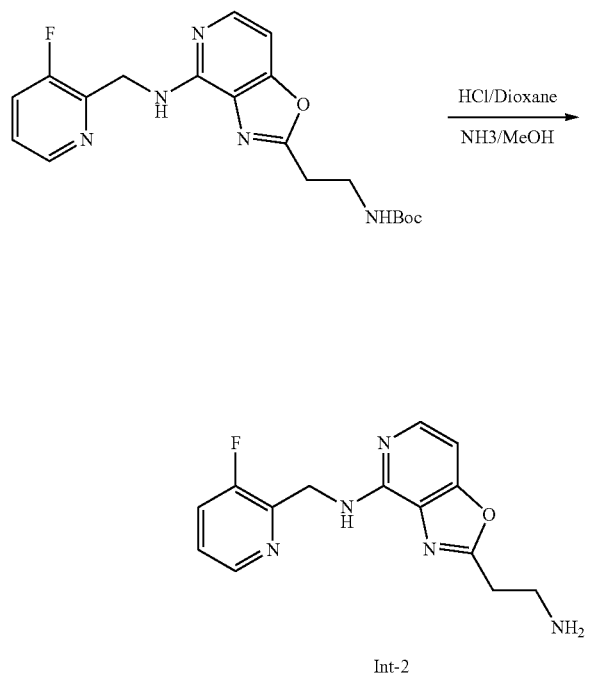

To the above intermediate from step 4 tert-butyl N-[2-(4-{[(3-fluoropyridin-2-yl)methyl]amino}-[1,3]oxazolo[4,5-c]pyridin-2-yl)ethyl]carbamate (1.5 g) was added 4N HCl in dioxane (6 mL, 16 mmol). The mixture was stirred until completion, the solvent was decanted and the remaining solid was concentrated and added NH₃ in MeOH (7 N) to pH=9, the resulting mixture was concentrated again, the residue was diluted with water, the resulting precipitate was collected by filtration, dried under vacuum to give 2-(2-aminoethyl)-N-[(3-fluoropyridin-2-yl)methyl]-[1,3]oxazolo[4,5-c]pyridin-4-amine (0.51 g, 73% from step 4) ¹H NMR (400 MHz, DMSO-d₆) δ 8.39-8.26 (m, 1H), 7.89 (dd, J=5.8, 2.1 Hz, 1H), 7.74-7.58 (m, 1H), 7.37 (dt, J=8.6, 4.4 Hz, 1H), 6.93 (dd, J=5.8, 1.9 Hz, 1H), 4.84 (d, J=5.6 Hz, 2H), 3.29 (s, 6H), 2.99 (d, J=4.6 Hz, 1H). LCMS [M+1]⁺ m/z: 388.2.

Example 1.10

Synthesis of 2-(2-{[2-(1H-1,3-benzodiazol-2-yl)ethyl]amino}ethyl)-N-[(3-fluoropyridin-2-yl)methyl]-[1,3]oxazolo[4,5-c]pyridin-4-amine (Compound 13)

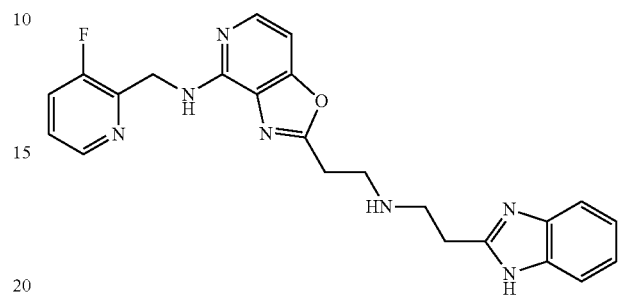

Scheme 6 depicts a synthetic route for preparing an exemplary compound.

Scheme 6

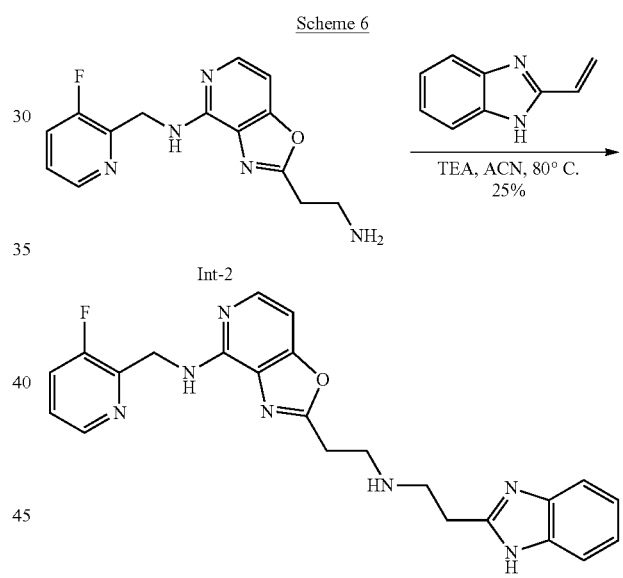

Into a 20-mL vial, was placed 2-(2-aminoethyl)-N-[(3-fluoropyridin-2-yl)methyl]-[1,3]oxazolo[4,5-c]pyridin-4-amine Int-2 (150 mg, 0.498 mmol, 1 equiv), 2-ethenyl-1H-1,3-benzodiazole (71.75 mg, 0.498 mmol, 1 equiv), CH₃CN (4 mL), Et₃N (151.07 mg, 1.493 mmol, 3 equiv). The resulting solution was stirred for 16 h at 80° C. in an oil bath. The reaction mixture was cooled to room temperature. The crude product was purified by Prep-HPLC with the following conditions: Column, SunFire Prep C18 OBD, 19*150 mm 5 um 10 nm; mobile phase, water (0.1% FA) and ACN; Detector, 254 nm. This resulted in 54.3 mg (25.29%) of 2-(2-{[2-(1H-1,3-benzodiazol-2-yl)ethyl]amino}ethyl)-N-[(3-fluoropyridin-2-yl)methyl]-[1,3]oxazolo[4,5-c]pyridin-4-amine as a brown solid. H-NMR (300 MHz, DMSO-d₆, ppm): δ 8.36 (dt, J=4.7, 1.5 Hz, 1H), 7.87 (d, J=5.8 Hz, 1H), 7.72-7.65 (m, 1H), 7.44-7.32 (m, 3H), 7.23-7.03 (m, 3H), 6.90 (d, J=5.8 Hz, 1H), 4.85-4.54 (m, 2H), 3.16-2.88 (m, 8H); LCMS: (ES, m/z): [M+1]⁺: 432.

Example 1.11

Synthesis of 2-(2-{[2-(1H-1,3-benzodiazol-2-yl)ethyl]amino}ethyl)-N-[(3-fluoropyridin-2-yl)methyl]-[1,3]oxazolo[5,4-d]pyrimidin-7-amine (Compound 2)

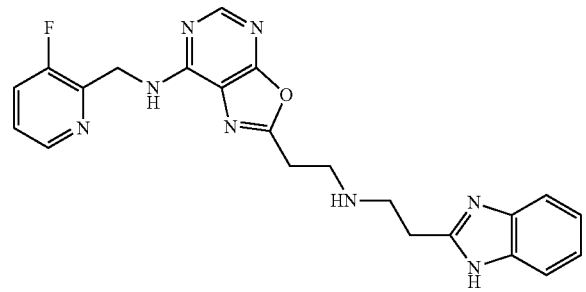 [SMILES: Fc1cccnc1CNc1ncnc2oc(CCNCCc3nc4ccccc4[nH]3)nc12]

Scheme 7 depicts a synthetic route for the preparation of an exemplary compound.

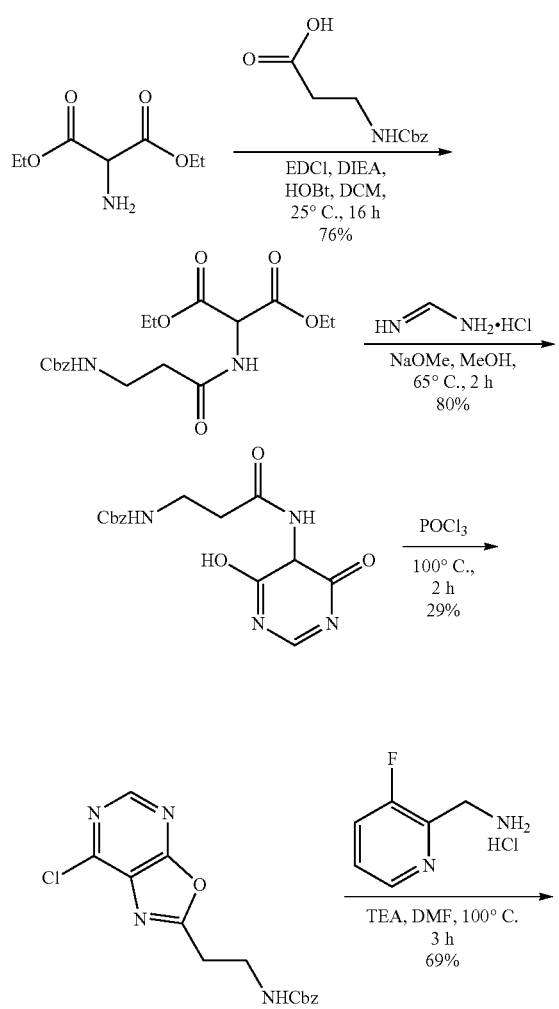

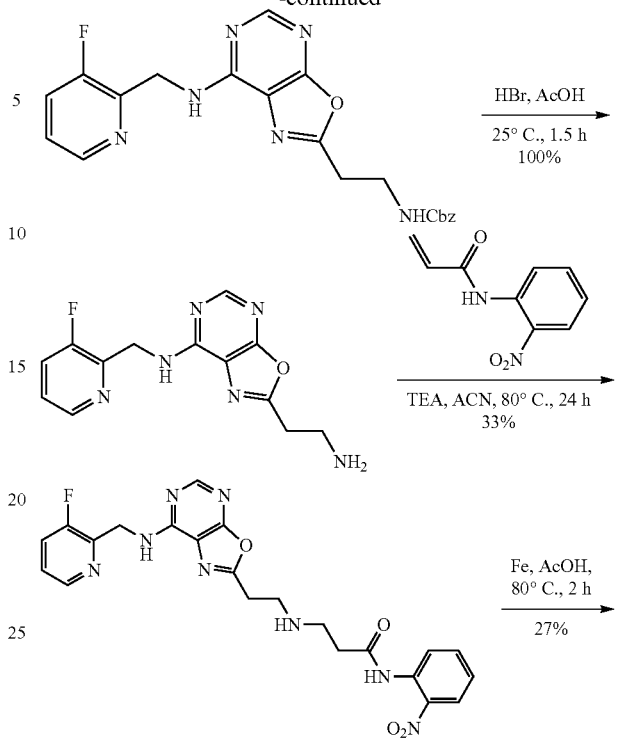

Step 1:

Into a 250-mL 3-necked round-bottom flask, was placed 1,3-diethyl 2-aminopropanedioate (3 g, 17.12 mmol, 1 equiv), 3-[[(benzyloxy)carbonyl]amino]propanoic acid (3.82 g, 17.11 mmol, 1.00 equiv), hydroxybenzotriazole (HOBT) (2.31 g, 17.11 mmol, 1.00 equiv), N,N-diisopropylethylamine (DIEA) (4.43 g, 34.22 mmol, 2.00 equiv), and DCM (50 mL). This was followed by the addition of N-(3-dimethylaminopropyl)-N'-ethylcarbodiimide hydrochloride (EDC.HCl) (4.92 g, 25.66 mmol, 1.50 equiv), in portions at 0° C. The resulting solution was stirred for 16 h at 25° C. The reaction was then quenched by the addition of 100 mL of water/ice. The resulting solution was extracted with 3×50 mL of dichloromethane, dried over anhydrous sodium sulfate, and concentrated. The residue was applied onto a silica gel column and eluted with ethyl acetate/petroleum ether (1:1). This resulted in 5 g (76%) of 1,3-diethyl 2-(3-[[(benzyloxy)carbonyl]amino]propanamido)propanedioate as white solid. LCMS (ES) [M+1]+ m/z: 381.2

Step 2:

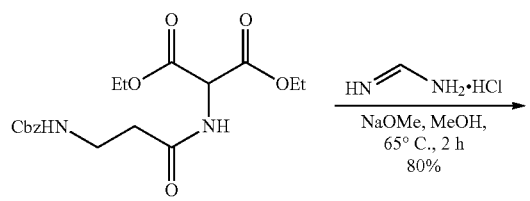

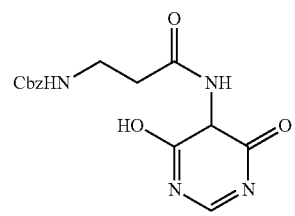

Into a 250-mL 3-necked round-bottom flask purged and maintained with an inert atmosphere of nitrogen, was placed 1,3-diethyl 2-(3-[[(benzyloxy)carbonyl]amino]propanamido)propanedioate (3 g, 7.88 mmol, 1.00 equiv), methanimidamide hydrochloride (698.5 mg, 8.67 mmol, 1.10 equiv), MeOH (30 mL) and CH₃ONa (894.7 mg, 16.56 mmol, 2.10 equiv). The resulting solution was stirred for 2 h at 65° C. in an oil bath. The reaction was then quenched by the addition of 100 mL of water/ice. The resulting solution was extracted with 3×50 mL of ethyl acetate and organic layer combined. Organic layer was washed with 1×100 mL of Brine, dried over anhydrous sodium sulfate, and concentrated. The residue was applied onto a silica gel column and eluted with ethyl acetate/petroleum ether (1:1). This resulted in 2.1 g (80%) of benzyl N-[2-[(6-hydroxy-4-oxo-4,5-dihydropyrimidin-5-yl)carbamoyl]ethyl]carbamate as white solid. LCMS (ES) [M+1]+ m/z: 333.1.

Step 3:

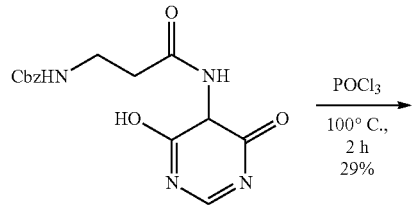

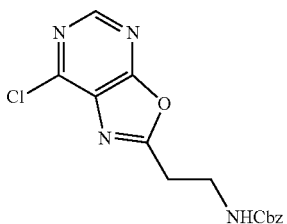

Into a 100-mL round-bottom flask, was placed benzyl N-[2-[(6-hydroxy-4-oxo-4,5-dihydropyrimidin-5-yl)carbamoyl]ethyl]carbamate (2 g, 6.01 mmol, 1.00 equiv), POCl₃ (20 mL, 214.56 mmol, 35.65 equiv). The resulting solution was stirred for 2 h at 100° C. in an oil bath, cooled down, and concentrated. The reaction was then quenched by the addition of 100 mL of water/ice. The pH value of the solution was adjusted to 7 with solid Na₂CO₃. The resulting solution was extracted with 3×50 mL of dichloromethane and dried over anhydrous sodium sulfate and concentrated. The residue was applied onto a silica gel column and eluted with ethyl acetate/petroleum ether (1:1). This resulted in 600 mg (29%) of benzyl N-(2-[7-chloro-[1,3]oxazolo[5,4-d]pyrimidin-2-yl]ethyl)carbamate as yellow solid. LCMS (ES) [M+1]+ m/z: 333.1.

Step 4:

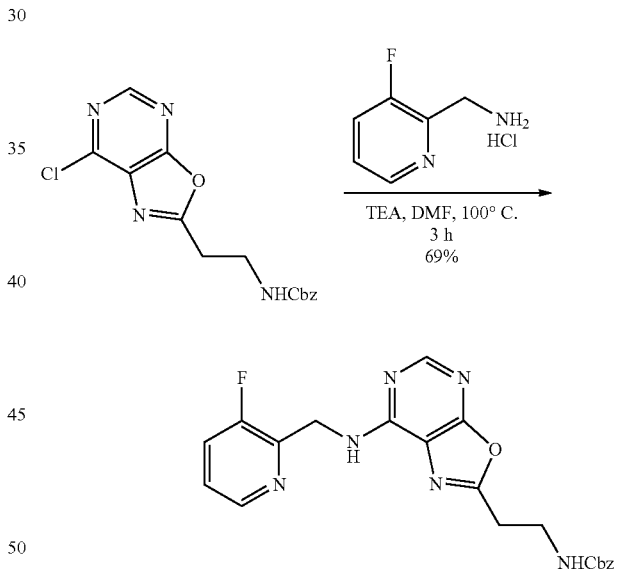

Into a 40-mL vial, was placed benzyl N-(2-[7-chloro-[1,3]oxazolo[5,4-d]pyrimidin-2-yl]ethyl)carbamate (600 mg, 1.80 mmol, 1.00 equiv), 1-(3-fluoropyridin-2-yl)methanamine (227.5 mg, 1.80 mmol, 1.00 equiv), DMF (5 mL), triethylamine (TEA) (273.7 mg, 2.70 mmol, 1.50 equiv). The resulting solution was stirred for 3 h at 100° C. in an oil bath, cooled down and diluted with 20 mL of ethyl acetate (EA). Organic layer was washed with 3×20 ml of brine, dried over anhydrous sodium sulfate, filtered and concentrated. The residue was purified by flash column eluted with ethyl acetate. This resulted in 530 mg (69%) of benzyl N-[2-(7-[[(3-fluoropyridin-2-yl)methyl]amino]-[1,3]oxazolo[5,4-d]pyrimidin-2-yl)ethyl]carbamate as yellow solid. LCMS (ES) [M+1]+ m/z: 422.2.

Step 5:

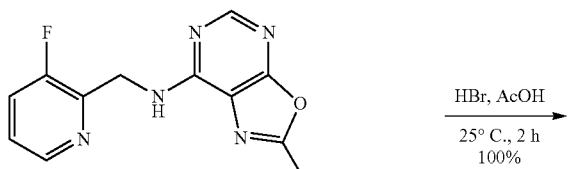

Into a 40-mL vial, was placed benzyl N-[2-(7-[[(3-fluoropyridin-2-yl)methyl]amino]-[1,3]oxazolo[5,4-d]pyrimidin-2-yl)ethyl]carbamate (530 mg, 1.25 mmol, 1.00 equiv), HBr in AcOH (40%, 5 mL). The resulting solution was stirred for 2 h at 25° C. The resulting mixture was concentrated under vacuum. The reaction was then quenched by the addition of 20 mL of water/ice. The pH value of the solution was adjusted to 7-8 with solid $Na_2CO_3$. The resulting solution was extracted with 3×20 mL of dichloromethane, dried over anhydrous sodium sulfate, and concentrated under vacuum. This resulted in 365 mg (100%) of 2-(2-aminoethyl)-N-[(3-fluoropyridin-2-yl)methyl]-[1,3]oxazolo[5,4-d]pyrimidin-7-amine as yellow solid. LCMS (ES) [M+1]+ m/z: 288.1.

Step 6:

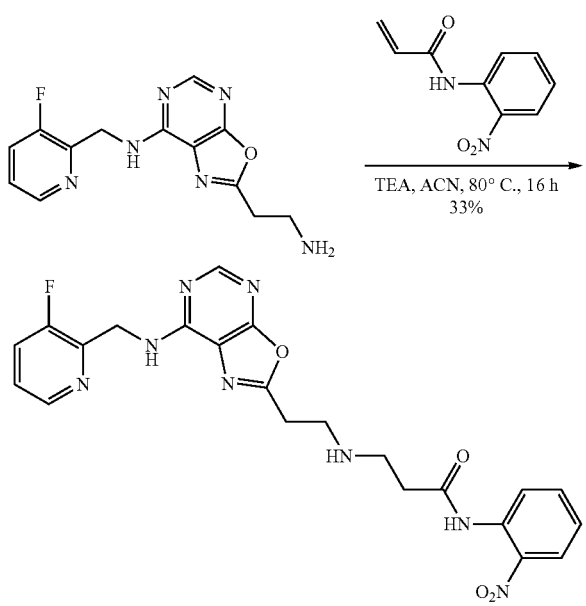

Into a 40-mL vial, was placed 2-(2-aminoethyl)-N-[(3-fluoropyridin-2-yl)methyl]-[1,3]oxazolo[5,4-d]pyrimidin-7-amine (365 mg, 1.26 mmol, 1.00 equiv), N-(2-nitrophenyl) prop-2-enamide (243.3 mg, 1.26 mmol, 1.00 equiv), ACN (5 mL), TEA (256.2 mg, 2.52 mmol, 2.00 equiv). The resulting solution was stirred for 16 h at 80° C. in an oil bath, cooled down, and concentrated. The residue was applied onto a silica gel column and eluted with ethyl acetate. This resulted in 202 mg (33%) of 3-[[2-(7-[[(3-fluoropyridin-2-yl)methyl]amino]-[1,3]oxazolo[5,4-d]pyrimidin-2-yl)ethyl]amino]-N-(2-nitrophenyl)propanamide as white solid. LCMS (ES) [M+1]+ m/z: 481.2.

Step 7:

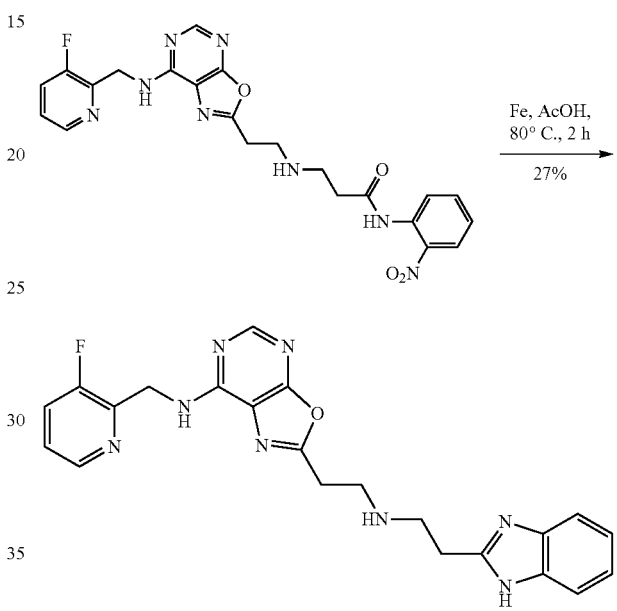

Into a 40-mL vial, was placed 3-[[2-(7-[[(3-fluoropyridin-2-yl)methyl]amino]-[1,3]oxazolo[5,4-d]pyrimidin-2-yl)ethyl]amino]-N-(2-nitrophenyl)propanamide (202 mg, 0.420 mmol, 1 equiv), Fe (70.4 mg, 1.261 mmol, 3.00 equiv), AcOH (5 mL). The reaction was stirred at 80° C. for 2 h, cooled down and concentrated. The residue was diluted with 10 mL of $H_2O$. The pH value was adjusted to 7-8 with saturated $Na_2CO_3$ aq. and extracted with 3×20 mL of dichloromethane. The organic layer was washed with 30 ml of brine, dried over anhydrous sodium sulfate, filtered and concentrated. The crude reaction mixture was filtered again and subjected to reverse preparative HPLC (Prep-C18, 5 mM XBridge column, 19×150 mm, waters; gradient elution of 5% MeCN in water to 5% MeCN in water over a 2 min period, 5% MeCN in water to 30% MeCN in water over another 12 min period, where both solvents contain 0.1% FA). This resulted in 51.0 mg (27%) of 2-(2-{[2-(1H-1,3-benzodiazol-2-yl)ethyl]amino}ethyl)-N-[(3-fluoropyridin-2-yl)methyl]-[1,3]oxazolo[5,4-d]pyrimidin-7-amine as white solid. 1H NMR (300 MHz, DMSO-$d_6$) δ 12.15 (s, 1H), 8.40 (s, 1H), 8.33-8.32 (m, 1H), 8.22 (s, 1H), 7.72-7.66 (m, 1H), 7.42-7.35 (m, 3H), 7.71-7.07 (m, 2H), 4.87 (s, 2H), 3.06-2.93 (m, 8H). LCMS (ES) [M+1]+ m/z: 433.2.

Example 1.12

Synthesis of 2-(2-{[2-(1H-1,3-benzodiazol-2-yl)ethyl]amino}ethyl)-N-[(3-fluoropyridin-2-yl)methyl]-[1,3]thiazolo[4,5-c]pyridin-4-amine (Compound 14)

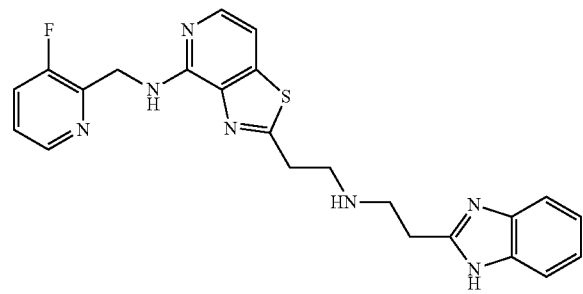 [SMILES: Fc1cccnc1CNc1ncnc2oc(CCNCCc3nc4ccccc4[nH]3)nc12]

Scheme 8 depicts a synthetic route for preparing an exemplary compound.

Scheme 8

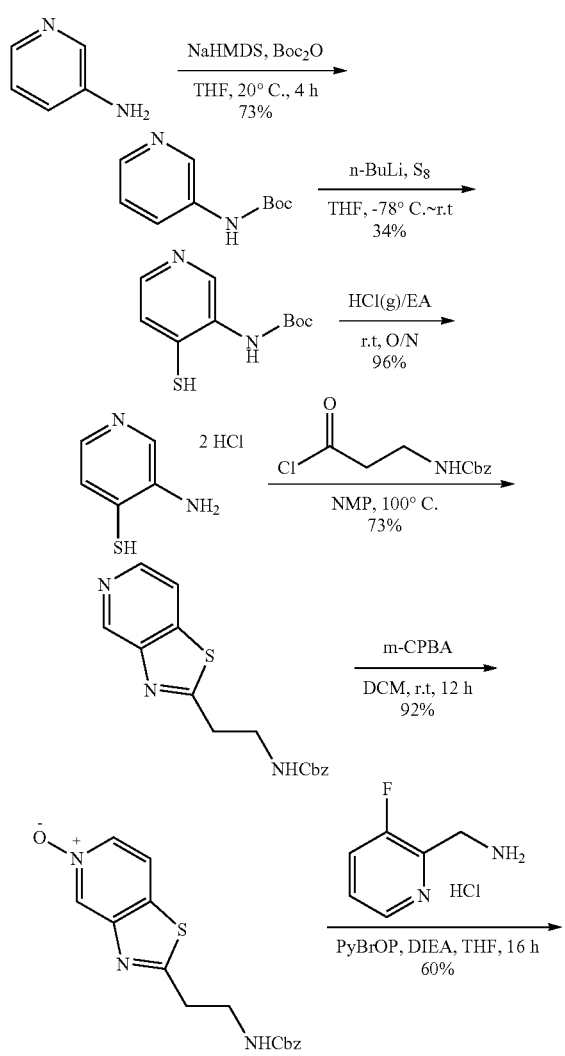

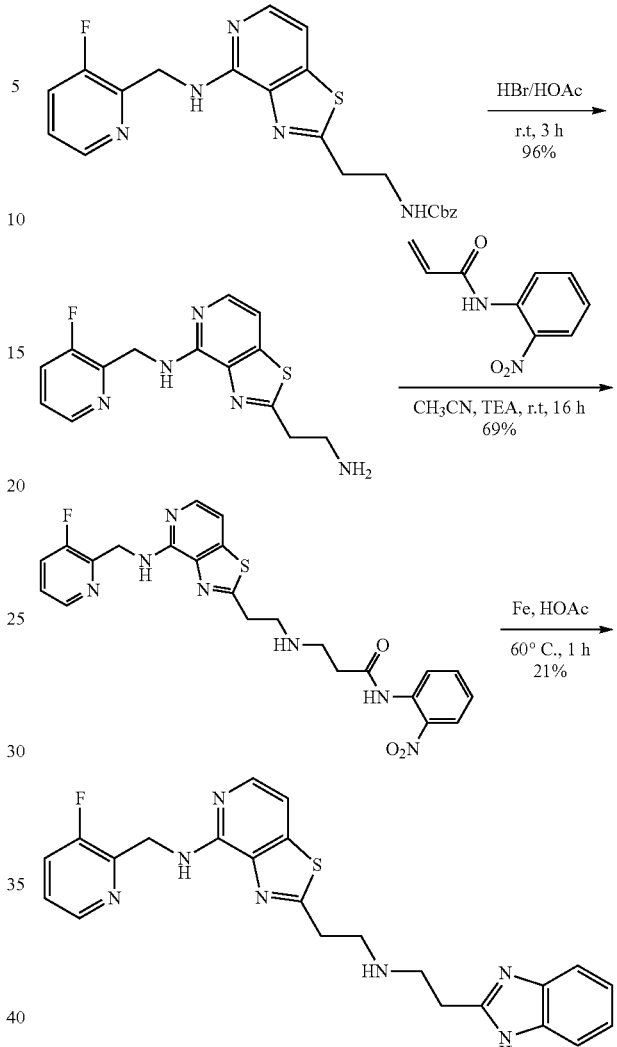

Step 1:

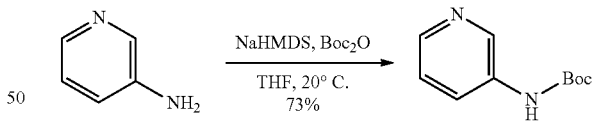

Into a 2-L 3-necked round-bottom flask, was placed pyridin-3-amine (20 g, 212.50 mmol, 1.0 equiv), THF (500 mL). This was followed by the addition of sodium bis(trimethylsilyl)amide (NaHMDS) (1 M in THF) (426 mL, 2.0 equiv) dropwise at 20° C. After addition, the mixture was stirred for 1 h. To the mixture was added di-tert-butyl dicarbonate (Boc₂O) (51.0 g, 233.75 mmol, 1.1 equiv), in portions and stirred for 3 hr at room temperature. The reaction was then quenched by the addition of 1 L of water, extracted with 2×1 L of ethyl acetate, and dried over anhydrous sodium sulfate. Filtered and concentrated under vacuum, the residue was purified by silica gel column with ethyl acetate/petroleum ether (1:2). 30 g (73%) of tert-butyl N-(pyridin-3-yl)carbamate was obtained as yellow solid.

Step 2:

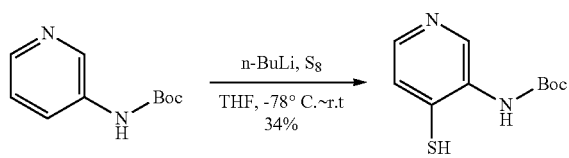

Into a 1-L 3-necked round-bottom flask purged and maintained with an inert atmosphere of nitrogen, was placed tert-butyl N-(pyridin-3-yl)carbamate (18 g, 92.78 mmol, 1.0 equiv), THF (300 mL). This was followed by the addition of n-BuLi (2.5 M in hexane) (93 mL, 93.00 mmol, 2.5 equiv) dropwise with stirring at −78° C. After addition the mixture was warmed to 0° C. and stirred for 2 hr. The temperature was cooled to −78° C. again, $S_8$ (3.56 g, 111.25 mmol, 1.2 equiv) was added in one portion. The mixture was stirred for 1 hr at room temperature. The reaction was then quenched by the addition of 100 mL of water. The pH value of the solution was adjusted to 3-4 with HCl (3N in $H_2O$), extracted with 2×200 ml of dichloromethane, dried over anhydrous sodium sulfate. Filtered, the filtrate was concentrated. The residue was purified by column chromatography with dichloromethane/methanol (25:1). 7.2 g (34%) of tert-butyl N-(4-sulfanylpyridin-3-yl)carbamate was obtained as yellow solid.

Step 3:

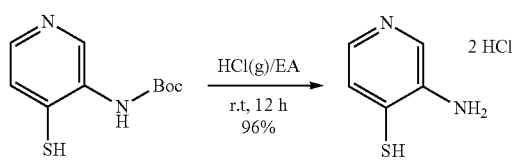 [SMILES: CC(C)(C)OC(=O)Nc1cnccc1S ; "HCl(g)/EA" ; Nc1cnccc1S]

Into a 500-mL round-bottom flask, was placed tert-butyl N-(4-sulfanylpyridin-3-yl)carbamate (7.2 g, 1.0 equiv), DCM (100 mL), HCl (g)(2 M in EA, 32 mL, 2 equiv). The mixture was stirred for 12 hr at room temperature. Filtered and the solid was collected and used to the next step directly without further purification. 6.1 g (96%) of 3-aminopyridine-4-thiol dihydrochloride was obtained as yellow solid.

Step 4:

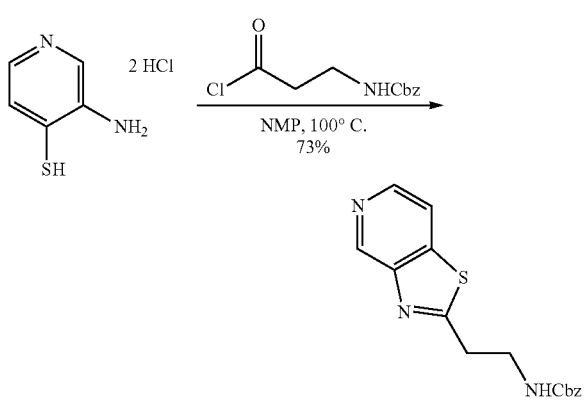

Into a 250-mL round-bottom flask, was placed benzyl N-(3-chloro-3-oxopropyl)carbamate (8.7 g, 36.00 mmol, 1.2 equiv), N-Methyl-2-pyrrolidone (NMP) (100 mL), 3-aminopyridine-4-thiol dihydrochloride (6 g, 30.14 mmol, 1.0 equiv). The mixture was stirred for 2 hr at 100° C. The reaction mixture was cooled to room temperature. The pH value of the solution was adjusted to 8 with $NaHCO_3$ (aq, 100 mL), extracted with 3×100 mL of ethyl acetate. The organic phase was washed with 3×100 ml of brine, dried over anhydrous sodium sulfate. Filtered, the filtrate was concentrated under vacuum. The residue was purified by column chromatography with (EA/PE=1:1). 6.9 g (73%) of benzyl N-(2-[[1,3]thiazolo[4,5-c]pyridin-2-yl]ethyl)carbamate was obtained as dark yellow solid.

Step 5:

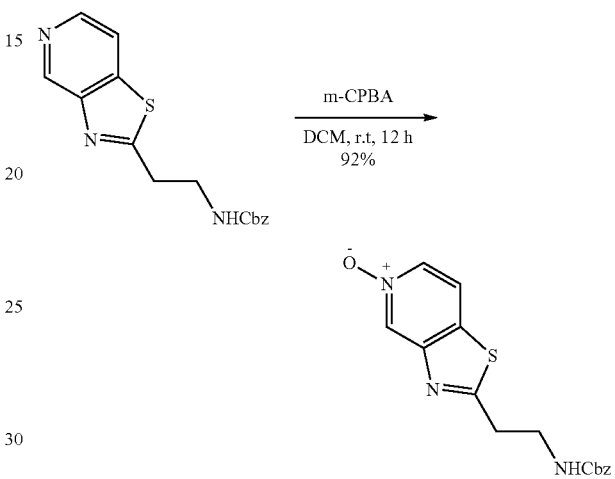

Into a 500-mL round-bottom flask, was placed benzyl N-(2-[[1,3]thiazolo[4,5-c]pyridin-2-yl]ethyl)carbamate (7.0 g, 22.34 mmol, 1.0 equiv), DCM (140 mL), m-CPBA (7.7 g, 44.67 mmol, 2.0 equiv). The mixture was stirred for 12 hr at room temperature. Extracted with 100 mL of $NaHCO_3$(aq) and the organic layers was combined and dried over anhydrous sodium sulfate. Filtered and the filtrate was concentrated under vacuum. The residue was purified by column chromatography with dichloromethane/methanol (100:3). 6.8 g (92%) of 2-(2-[[(benzyloxy)carbonyl]amino]ethyl)-[1,3]thiazolo[4,5-c]pyridin-5-ium-5-olate was obtained as white solid.

Step 6:

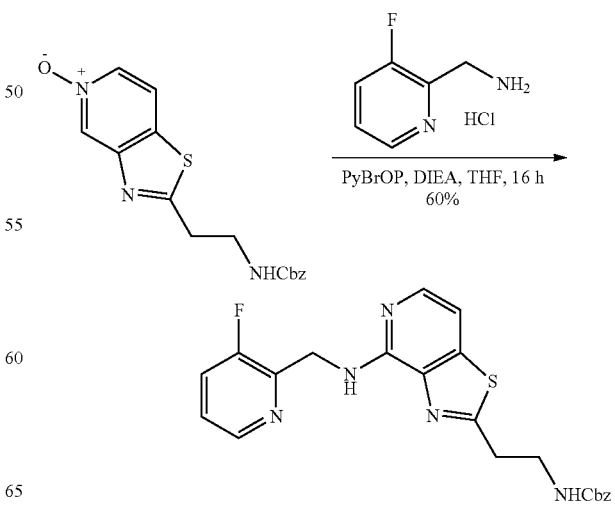

Into a 100-mL round-bottom flask purged and maintained with an inert atmosphere of nitrogen, was placed 2-(2-[[(benzyloxy)carbonyl]amino]ethyl)-[1,3]thiazolo[5,4-c]pyridin-5-ium-5-olate (1.5 g, 4.55 mmol, 1.0 equiv), THF (30 mL), 1-(3-fluoropyridin-2-yl)methanamine hydrochloride (1.1 g, 6.83 mmol, 1.5 equiv), DIEA (5.9 g, 45.54 mmol, 10.0 equiv), PyBrOP (3.2 g, 6.83 mmol, 1.5 equiv). The mixture was stirred for 16 hr at 25° C. The reaction solution was diluted with 30 mL of H$_2$O, extracted with 100 mL of ethyl acetate, dried over anhydrous sodium sulfate. Filter out the solid, the filtrate was concentrated under vacuum. The residue was purified by silica gel column with ethyl acetate/petroleum ether (1:2). 1.2 g (60.%) of benzyl N-[2-(4-[[(3-fluoropyridin-2-yl)methyl]amino]-[1,3]thiazolo[5,4-c]pyridin-2-yl)ethyl]carbamate was obtained as white solid.

Step 7:

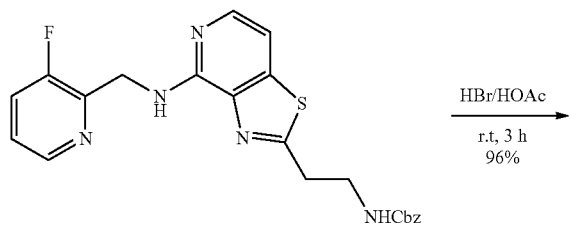

Into a 50-mL round-bottom flask, was placed benzyl N-[2-(4-[[(3-fluoropyridin-2-yl)methyl]amino]-[1,3]thiazolo[4,5-c]pyridin-2-yl)ethyl]carbamate (1.2 g, 1.0 equiv), HBr in AcOH (15%) (12 mL). The mixture was stirred for 3 hr at room temperature. The reaction solution was diluted with 30 mL of H$_2$O, extracted with 3×50 mL of ethyl acetate and the aqueous layers was combined. The pH value of the solution was adjusted to 10 with K$_2$CO$_3$ solid. Then extracted with 2×100 mL of dichloromethane and the organic layers was combined and dried over anhydrous sodium sulfate and concentrated. 800 mg (96%) of 2-(2-aminoethyl)-N-[(3-fluoropyridin-2-yl)methyl]-[1,3]thiazolo[4,5-c]pyridin-4-amine was obtained as white solid.

Step 8:

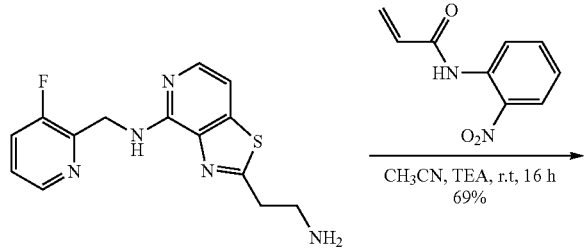

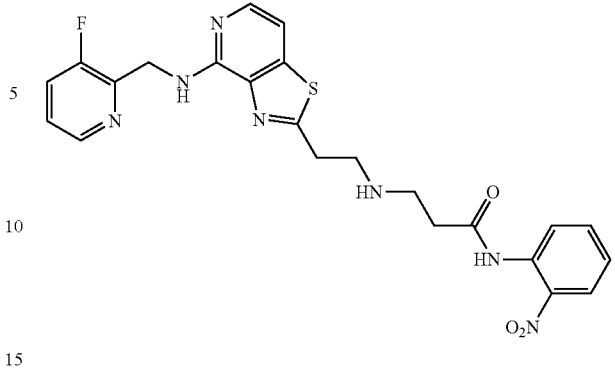

Into a 40-mL vial, was placed 2-(2-aminoethyl)-N-[(3-fluoropyridin-2-yl)methyl]-[1,3]thiazolo[4,5-c]pyridin-4-amine (400 mg, 1.32 mmol, 1.0 equiv), CH$_3$CN (10 mL), N-(2-nitrophenyl)prop-2-enamide (253.4 mg, 1.32 mmol, 1.0 equiv), TEA (133.4 mg, 1.32 mmol, 1.0 equiv). The mixture was stirred for 16 hr at room temperature. The residue was purified directly by Prep-HPLC with the following conditions: Column, C18-120 g; mobile phase, CH$_3$CN/H$_2$O (0.05% NH$_4$OH) from 30% to 100% within 12 min, 70 mL/min, Detector 254 nm. 450 mg (69%) of 3-[[2-(4-[[(3-fluoropyridin-2-yl)methyl]amino]-[1,3]thiazolo[4,5-c]pyridin-2-yl)ethyl]amino]-N-(2-nitrophenyl)propanamide was obtained as yellow oil.

Step 9:

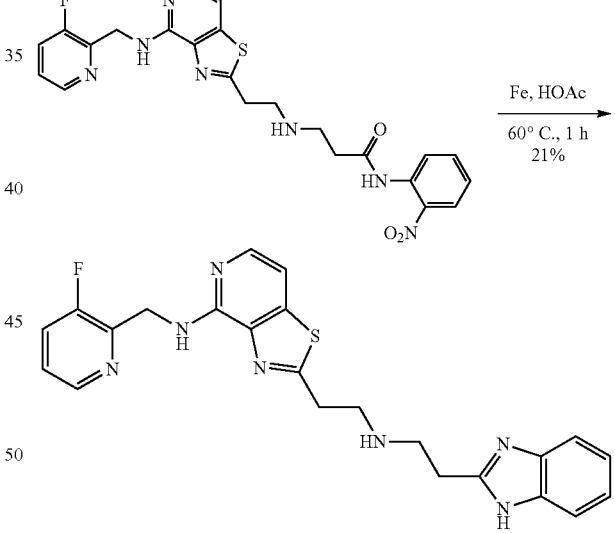

Into a 40-mL vial, was placed 3-[[2-(4-[[(3-fluoropyridin-2-yl)methyl]amino]-[1,3]thiazolo[4,5-c]pyridin-2-yl)ethyl]amino]-N-(2-nitrophenyl)propanamide (450 mg, 0.91 mmol, 1.0 equiv), HOAc (5 mL), Fe (202.9 mg, 3.63 mmol, 4.0 equiv). The mixture was stirred for 1 hr at 60° C. The reaction mixture was cooled and diluted with 30 mL of H$_2$O. The pH value of the solution was adjusted to 8 with K$_2$CO$_3$ solid, extracted with 2×60 mL of ethyl acetate, dried over anhydrous sodium sulfate. The crude product was purified by Prep-HPLC with the following conditions (IntelFlash-1): Column, C18-120 g; mobile phase, CH$_3$CN/H$_2$O (0.05% NH$_4$OH) from 20% to 100% within 12 min, 70 mL/min, detector 254 nm. 86.7 mg (21%) of 2-(2-[[2-(1H-1,3-benzodiazol-2-yl)ethyl]amino]ethyl)-N-[(3-fluoropyridin-2-yl)methyl]-[1,3]thiazolo[4,5-c]pyridin-4-amine was obtained as a light yellow solid. $^1$H-NMR (300 MHz, DMSO-d$_6$): δ 8.40-8.37 (m, 1H), 7.85 (d, J=5.4 Hz, 1H), 7.74-7.67 (m, 1H), 7.46-7.37 (m, 3H), 7.30-7.26 (m, 1H), 7.14-7.09 (m, 3H), 4.85 (dd, J=5.4, 1.8 Hz, 2H), 3.23 (t, J=6.6 Hz, 2H), 3.09-2.96 (m, 6H). LC-MS (ES, m/z): [M+H]: 448.

Example 1.13

Synthesis of 2-(2-{[2-(1H-1,3-benzodiazol-2-yl)ethyl]amino}ethyl)-N-[(3-fluoropyridin-2-yl)methyl]-[1,3]thiazolo[5,4-d]pyrimidin-7-amine (Compound 1)

Scheme 9 depicts a synthetic route for preparing an exemplary compound.

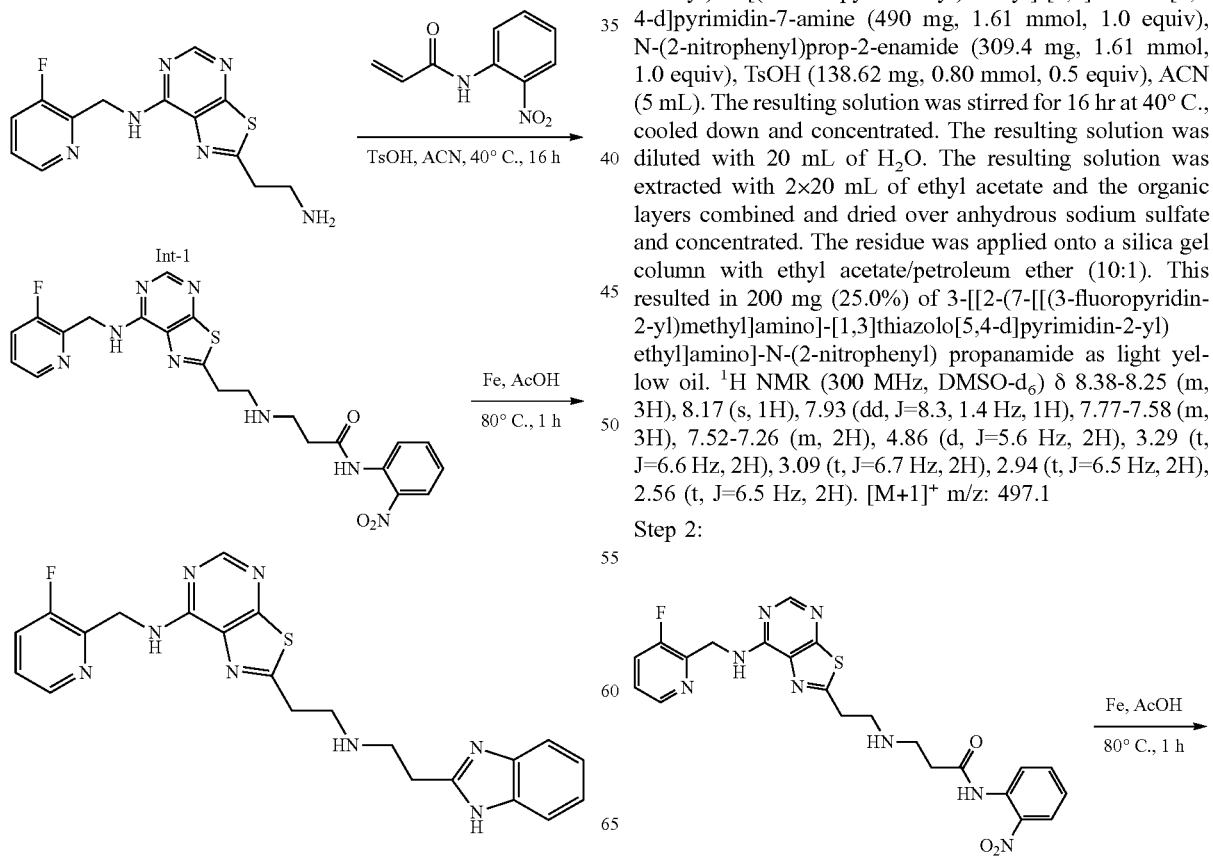

Scheme 9

Step 1:

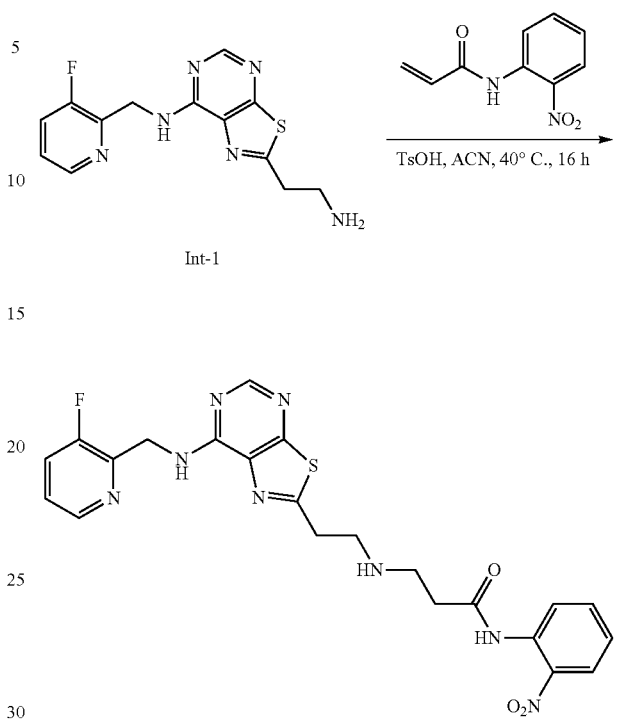

Into a 50-mL round-bottom flask, was placed 2-(2-aminoethyl)-N-[(3-fluoropyridin-2-yl)methyl]-[1,3]thiazolo[5,4-d]pyrimidin-7-amine (490 mg, 1.61 mmol, 1.0 equiv), N-(2-nitrophenyl)prop-2-enamide (309.4 mg, 1.61 mmol, 1.0 equiv), TsOH (138.62 mg, 0.80 mmol, 0.5 equiv), ACN (5 mL). The resulting solution was stirred for 16 hr at 40° C., cooled down and concentrated. The resulting solution was diluted with 20 mL of H$_2$O. The resulting solution was extracted with 2×20 mL of ethyl acetate and the organic layers combined and dried over anhydrous sodium sulfate and concentrated. The residue was applied onto a silica gel column with ethyl acetate/petroleum ether (10:1). This resulted in 200 mg (25.0%) of 3-[[2-(7-[[(3-fluoropyridin-2-yl)methyl]amino]-[1,3]thiazolo[5,4-d]pyrimidin-2-yl)ethyl]amino]-N-(2-nitrophenyl) propanamide as light yellow oil. $^1$H NMR (300 MHz, DMSO-d$_6$) δ 8.38-8.25 (m, 3H), 8.17 (s, 1H), 7.93 (dd, J=8.3, 1.4 Hz, 1H), 7.77-7.58 (m, 3H), 7.52-7.26 (m, 2H), 4.86 (d, J=5.6 Hz, 2H), 3.29 (t, J=6.6 Hz, 2H), 3.09 (t, J=6.7 Hz, 2H), 2.94 (t, J=6.5 Hz, 2H), 2.56 (t, J=6.5 Hz, 2H). [M+1]$^+$ m/z: 497.1

Step 2:

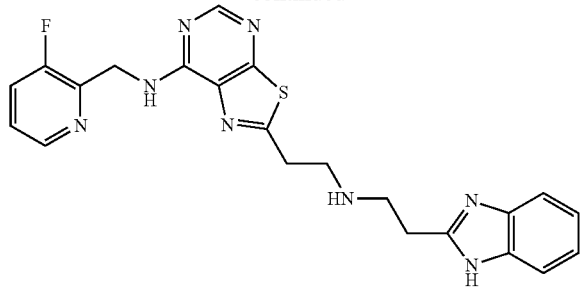 [SMILES: Fc1cccnc1CNc1ncnc2sc(CCNCCc3nc4ccccc4[nH]3)nc12]

Into a 50-mL round-bottom flask, was placed a solution of 3-[[2-(7-[[(3-fluoropyridin-2-yl)methyl]amino]-[1,3]thiazolo[5,4-d]pyrimidin-2-yl)ethyl]amino]-N-(2-nitrophenyl)propanamide (200 mg, 0.40 mmol, 1.0 equiv) in AcOH (3 mL), Fe (89.98 mg, 1.61 mmol, 4.0 equiv). The resulting solution was stirred for 1 hr at 80° C., cooled down and concentrated. The resulting solution was diluted with 3 mL of ACN. The solids were filtered out. The residue was purified by reverse flash chromatography with the following conditions: column, C18 silica gel; mobile phase, ACN in water, 10% to 50% gradient in 10 min; detector, UV 254 nm. This resulted in 89.6 mg (49.5%) of 2-(2-{[2-(1H-1,3-benzodiazol-2-yl)ethyl]amino}ethyl)-N-[(3-fluoropyridin-2-yl)methyl]-[1,3]thiazolo[5,4-d]pyrimidin-7-amine as grey solid. $^1$H NMR (300 MHz, DMSO-$d_6$) δ8.38-8.25 (m, 3H), 7.70 (ddd, J=10.2, 8.4, 1.3 Hz, 1H), 7.48-7.32 (m, 3H), 7.15-7.03 (m, 2H), 4.88 (d, J=5.5 Hz, 2H), 3.23 (t, J=6.5 Hz, 2H), 3.10-2.90 (m, 6H). LCMS: [M+1]$^+$ m/z: 449.2

Example 1.14

Synthesis of 2-(2-{[2-(1H-1,3-benzodiazol-2-yl)ethyl]amino}ethyl)-N-benzyl-[1,3]thiazolo[5,4-d]pyrimidin-7-amine (Compound 4)

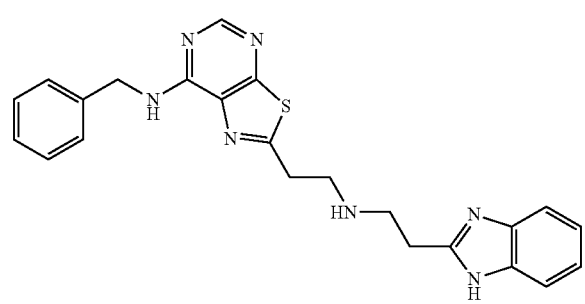 [SMILES: c1ccc(CNc2ncnc3sc(CCNCCc4nc5ccccc5[nH]4)nc23)cc1]

Scheme 10 depicts a synthetic route for preparing an exemplary compound.

Scheme 10

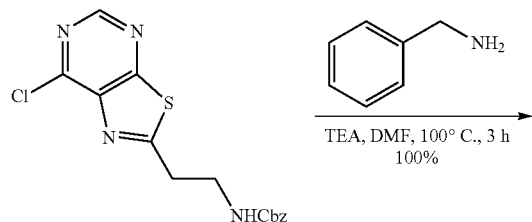

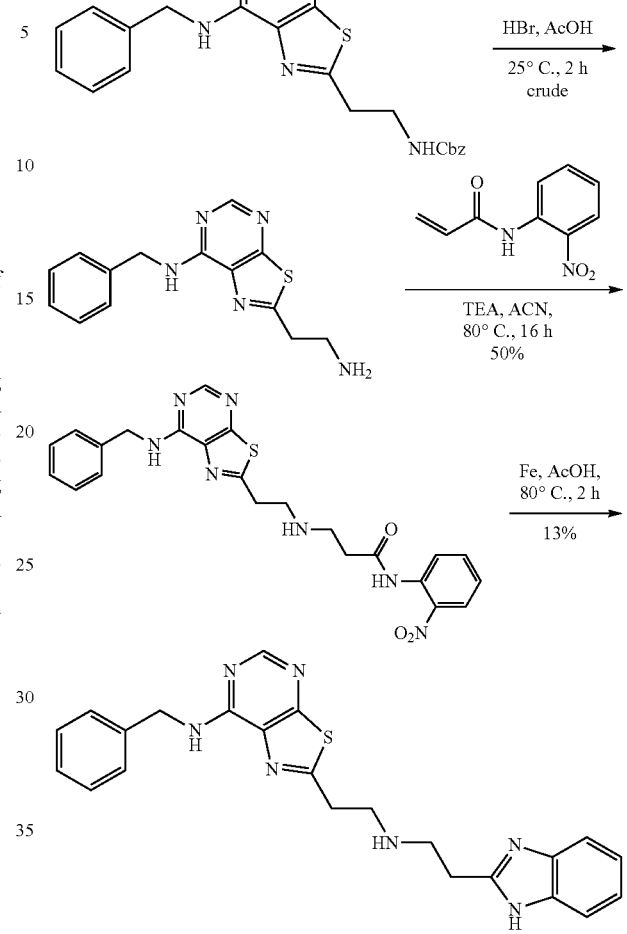

Step 1:

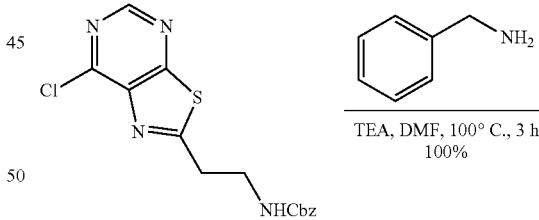

Into a 40-mL vial, was placed benzyl N-(2-[7-chloro-[1,3]thiazolo[5,4-d]pyrimidin-2-yl]ethyl)carbamate (620 mg, 1.77 mmol, 1.00 equiv), 1-phenylmethanamine (190.47 mg, 1.77 mmol, 1.00 equiv), DMF (5 mL), TEA (269.79 mg, 2.66 mmol, 1.5 equiv). The reaction was stirred for 3 h at 100° C. cooled down and diluted with 20 mL of EA. Organic layer was washed with 3×20 ml of brine, dried over anhydrous sodium sulfate, filtered and concentrated. The residue was purified by flash column eluted with ethyl acetate. This resulted in 780 mg (100%) of benzyl N-[2-(7-[[(3-methoxypyridin-2-yl)methyl]amino]-[1,3]thiazolo[5,4-d]pyrimidin-2-yl)ethyl]carbamate as yellow solid. LCMS (ES) [M+1]+ m/z: 420.1.

Step 2:

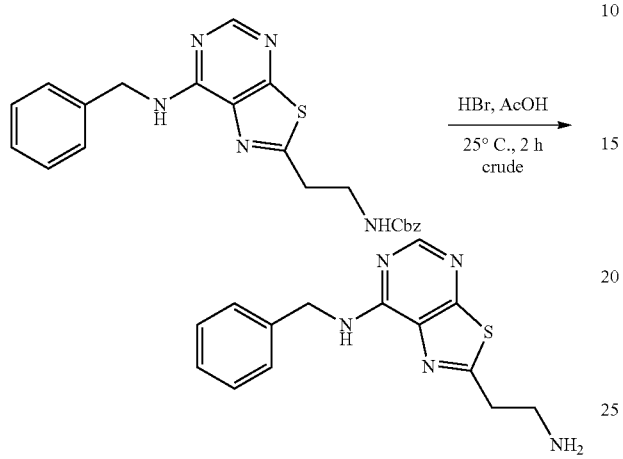

Into a 40-mL vial, was placed benzyl N-[2-[7-(benzylamino)-[1,3]thiazolo[5,4-d]pyrimidin-2-yl]ethyl]carbamate (780 mg, 1.85 mmol, 1.00 equiv), HBr in AcOH (40%) (10 mL). The resulting solution was stirred for 2 h at 25° C. The resulting mixture was concentrated under vacuum. The reaction was then quenched by the addition of 20 mL of water/ice. The pH value of the solution was adjusted to 7-8 with solid Na₂CO₃. The resulting solution was extracted with 3×20 mL of dichloromethane dried over anhydrous sodium sulfate and concentrated under vacuum. This resulted in 600 mg (crude) of 2-(2-aminoethyl)-N-benzyl-[1,3]thiazolo[5,4-d]pyrimidin-7-amine as yellow solid. LCMS (ES) [M+1]+ m/z: 286.1.

Step 3:

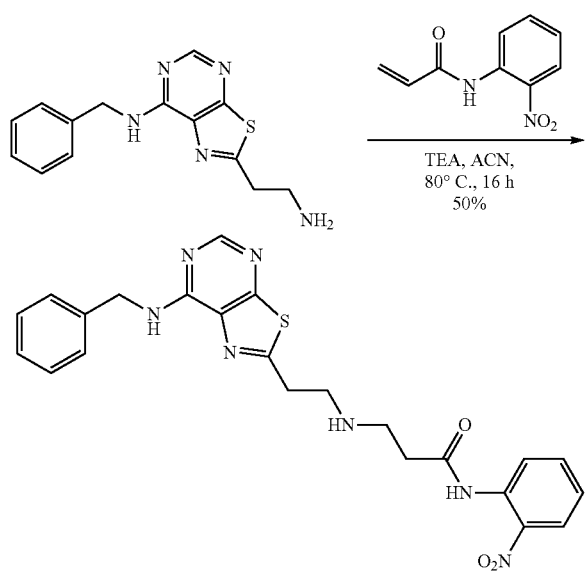

Into a 40-mL vial, was placed 2-(2-aminoethyl)-N-benzyl-[1,3]thiazolo[5,4-d]pyrimidin-7-amine (590 mg, 2.06 mmol, 1 equiv), N-(2-nitrophenyl)prop-2-enamide (397 mg, 2.06 mmol, 1.00 equiv), ACN (10 mL), TEA (331 mg, 3.27 mmol, 1.5 equiv). The reaction was stirred for 16 h at 80° C., cooled down and concentrated. The residue was purified by a flash column eluted with ethyl acetate/petroleum ether (1/1). This resulted in 500 mg (50%) of 3-([2-[7-(benzylamino)-[1,3]thiazolo[5,4-d]pyrimidin-2-yl]ethyl]amino)-N-(2-nitrophenyl)propanamide as yellow solid. LCMS (ES) [M+1]+ m/z: 429.2.

Step 4:

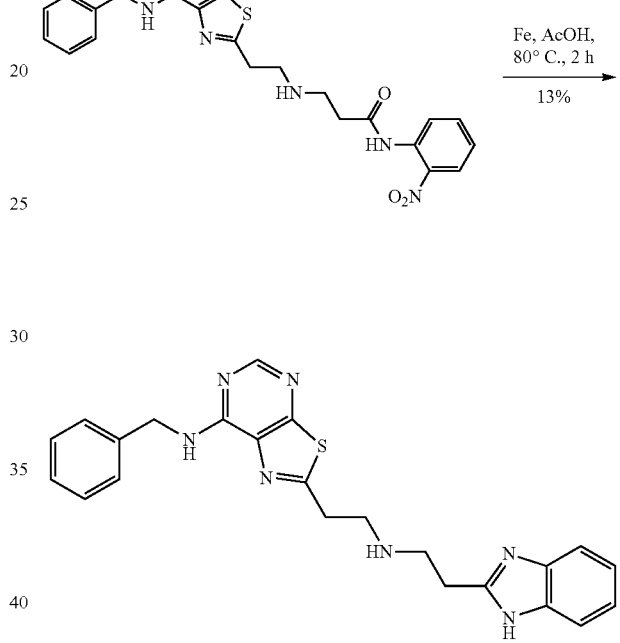

Into a 40-mL vial, was placed 3-([2-[7-(benzylamino)-[1,3]thiazolo[5,4-d]pyrimidin-2-yl]ethyl]amino)-N-(2-nitrophenyl)propanamide (500 mg, 1.04 mmol, 1.00 equiv), Fe (175.4 mg, 3.12 mmol, 3.00 equiv), AcOH (10 mL). The reaction was stirred at 80° C. for 2 h, cooled down and concentrated. The residue was diluted with 10 mL of H₂O. The pH value was adjusted to 7-8 with saturated Na₂CO₃ aq. and extracted with 3×20 mL of dichloromethane. The organic layer was washed with 30 ml of brine, dried over anhydrous sodium sulfate, filtered and concentrated. The crude reaction mixture was filtered again and subjected to reverse preparative HPLC (Prep-C18, 5 mM XBridge column, 19×150 mm, waters; gradient elution of 5% MeCN in water to 5% MeCN in water over a 2 min period, 5% MeCN in water to 30% MeCN in water over another 12 min period, where both solvents contain 0.1% FA). This resulted in 59 mg (13%) of 2-(2-[[2-(3a,7a-dihydro-1H-1,3-benzodiazol-2-yl)ethyl]amino]ethyl)-N-benzyl-[1,3]thiazolo[5,4-d]pyrimidin-7-amine as white solid. $^1$H NMR (300 MHz, DMSO-d₆) δ 12.15 (s, 1H), 8.63-8.59 (m, 1H), 8.32 (s, 1H), 7.43-7.34 (m, 2H), 7.32-7.21 (m, 4H), 7.19-7.10 (m, 1H), 7.09-7.07 (m, 2H), 4.71-4.69 (d, J=6 Hz, 2H), 3.24-3.19 (m, 2H), 3.04-2.96 (m, 6H). LCMS (ES) [M+1]+ m/z: 430.4.

Example 1.15

Synthesis of 2-(2-{[2-(1H-1,3-benzodiazol-2-yl) ethyl]amino}ethyl)-N-[(pyridin-2-yl)methyl]-[1,3] thiazolo[5,4-d]pyrimidin-7-amine (Compound 5)

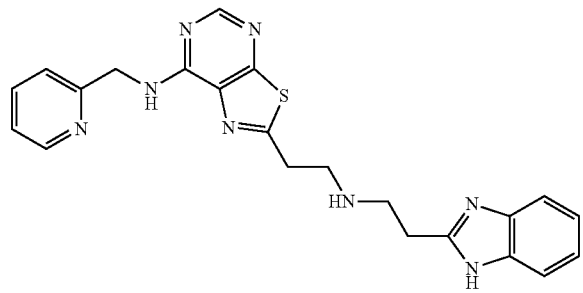 [SMILES: c1ccc(CNc2ncnc3sc(CCNCCc4nc5ccccc5[nH]4)nc23)nc1]

Example 15 was synthesized similar to Example 14 replacing 1-phenylmethanamine with pyridin-2-ylmethanamine. $^1$H NMR (300 MHz, DMSO-$d_6$) δ 8.56-8.40 (m, 2H), 8.32 (s, 1H), 8.22 (s, 2H), 7.77-7.65 (m, 1H), 7.43 (d, J=4.4 Hz, 2H), 7.34-7.19 (m, 2H), 7.15-7.06 (m, 2H), 4.84-4.75 (m, 2H), 3.30 (s, 2H), 3.13 (s, 4H), 3.04 (s, 2H). [M+1]$^+$ m/z: 431.2

Example 1.16

Synthesis of 2-(2-{[2-(1H-1,3-benzodiazol-2-yl) ethyl]amino}ethyl)-N-[(5-fluoropyridin-2-yl) methyl]-[1,3]thiazolo[5,4-d]pyrimidin-7-amine (Compound 8)

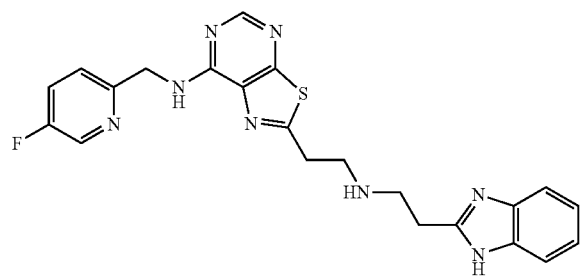 [SMILES: Fc1ccc(CNc2ncnc3sc(CCNCCc4nc5ccccc5[nH]4)nc23)nc1]

Example 16 was synthesized similar to Example 14 replacing 1-phenylmethanamine with (5-fluoropyridin-2-yl) methanamine. $^1$H NMR (300 MHz, DMSO-$d_6$) δ12.16 (s, 1H), 8.59 (m, 1H), 8.49-8.48 (m, 1H), 8.30 (s, 1H), 7.66-7.59 (m, 1H), 7.42-7.34 (m, 3H), 7.10-7.07 (m, 2H), 4.77 (d, J=6.0 Hz, 2H), 3.25-3.20 (m, 2H), 3.02-2.96 (m, 6H). LCMS (ES) [M+1]$^+$ m/z: 449.5.

Example 1.17

Synthesis of 2-(2-{[2-(1H-1,3-benzodiazol-2-yl) ethyl]amino}ethyl)-N-[(pyrimidin-2-yl)methyl]-[1,3] thiazolo[5,4-d]pyrimidin-7-amine (Compound 9)

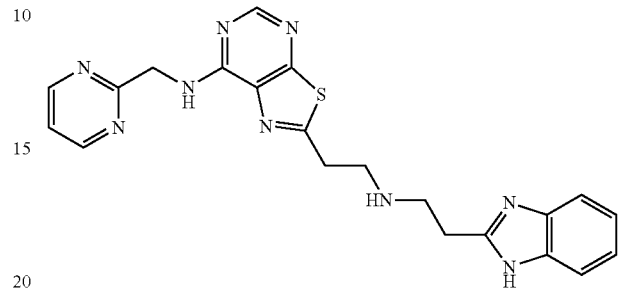

Example 17 was synthesized similar to Example 14 replacing 1-phenylmethanamine with 1-(pyrimidin-2-yl) methanamine. $^1$H NMR (300 MHz, DMSO-$d_6$, ppm): 12.16 (br, 1H), 8.74 (d, J=4.8 Hz, 2H), 8.41 (br, 1H), 8.26 (s, 1H), 7.43-7.36 (m, 3H), 7.11-7.08 (m, 2H), 4.87 (d, J=6.0 Hz, 2H), 3.26-3.22 (m, 2H), 3.30-2.97 (m, 6H). LCMS (ES) [M+1]$^+$ m/z 432.1.

Example 1.18

Synthesis of 2-(2-{[2-(1H-1,3-benzodiazol-2-yl) ethyl]amino}ethyl)-N-[(3-methoxypyridin-2-yl) methyl]-[1,3]thiazolo[5,4-d]pyrimidin-7-amine (Compound 11)

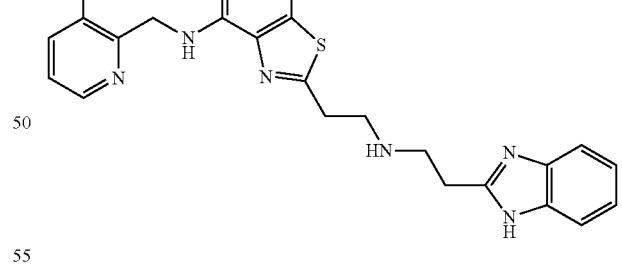

Example 18 was synthesized similar to Example 14 replacing 1-phenylmethanamine with 1-(3-methoxypyridin-2-yl)methanamine. $^1$H NMR (300 MHz, DMSO-$d_6$) δ 8.34 (s, 1H), 8.27-8.17 (m, 1H), 8.09 (dd, J=4.7, 1.3 Hz, 1H), 8.06-7.97 (m, 1H), 7.50-7.40 (m, 3H), 7.31 (dd, J=8.3, 4.7 Hz, 1H), 7.15-7.06 (m, 2H), 4.77 (d, J=5.2 Hz, 2H), 3.90 (s, 3H), 3.28 (t, J=6.6 Hz, 2H), 3.18-3.05 (m, 4H), 3.05-2.96 (m, 2H). LCMS (ES) [M+1]$^+$ m/z: 461.2.

Example 1.19

Synthesis of 2-(2-{[2-(1H-1,3-benzodiazol-2-yl)ethyl]amino}ethyl)-N-[(3-chloropyridin-2-yl)methyl]-[1,3]thiazolo[5,4-d]pyrimidin-7-amine (Compound 6)

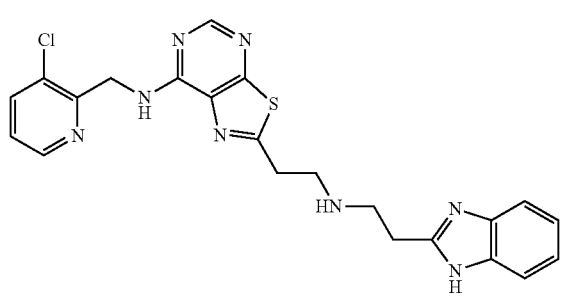 [SMILES: Clc1cccnc1CNc1ncnc2sc(CCNCCc3nc4ccccc4[nH]3)nc12]

Example 19 was synthesized similar to Example 14 replacing 1-phenylmethanamine with 1-(3-chloropyridin-2-yl)methanamine. $^1$H NMR (300 MHz, DMSO-d$_6$, ppm) δ 8.47-8.45 (m, 1H), 8.33-8.32 (m, 1H), 8.25-8.18 (m, 2H), 7.97-7.94 (m, 1H), 7.48-7.35 (m, 3H), 7.12-7.08 (m, 2H), 4.89-4.87 (m, 2H), 3.29-3.25 (m, 2H), 3.13-2.99 (m, 6H). LCMS (ES) [M+1]$^+$ m/z: 465.2.

Example 1.20

Synthesis of 2-(2-{[2-(1H-1,3-benzodiazol-2-yl)ethyl]amino}ethyl)-N-[(3-methylpyridin-2-yl)methyl]-[1,3]thiazolo[5,4-d]pyrimidin-7-amine (Compound 12)

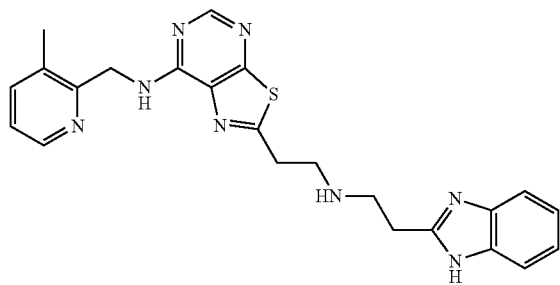

Example 20 was synthesized similar to Example 14 replacing 1-phenylmethanamine with 1-(3-methylpyridin-2-yl)methanamine. $^1$H NMR (300 MHz, DMSO-d$_6$) δ12.15 (s, 1H), 8.39-80.37 (m, 2H), 8.19-8.16 (m, 1H), 7.63 (d, J=9 Hz, 1H), 7.44-7.42 (m, 2H), 7.26-7.22 (m, 1H), 7.12-7.06 (m, 2H), 4.77 (d, J=3 Hz, 2H), 3.26-3.22 (m, 2H), 3.05-2.94 (m, 6H), 2.35 (s, 3H). LCMS (ES) [M+1]$^+$ m/z: 445.3.

Example 1.21

Synthesis of 2-(2-{[2-(4-fluoro-1H-1,3-benzodiazol-2-yl)ethyl]amino}ethyl)-N-[(3-fluoropyridin-2-yl)methyl]-[1,3]thiazolo[5,4-d]pyrimidin-7-amine (Compound 15)

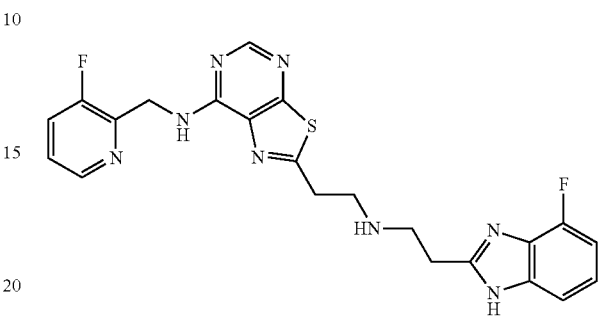

Scheme 11 depicts a synthetic route for preparing an exemplary compound.

Scheme 11

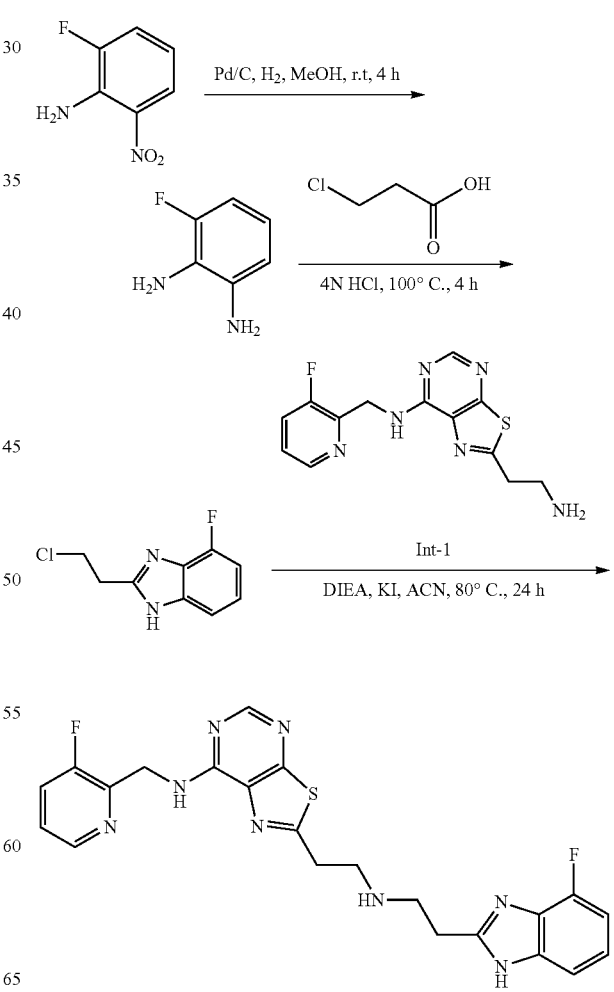

Step 1:

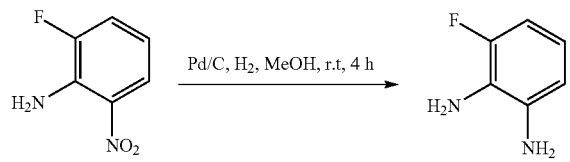

Into a 100-mL round-bottom flask, was placed 2-fluoro-6-nitroaniline (1.0 g, 6.40 mmol, 1.0 equiv), MeOH (20 mL), 10% Pd/C (100 mg). The resulting solution was stirred for 4 hr at room temperature under H₂ (2.0 atm). The solids were filtered out and concentrated. The residue was purified by flash column eluted with ethyl acetate/petroleum ether (1/2). This resulted in 700 mg (86.6%) of 3-fluorobenzene-1,2-diamine as black solid. [M+1]⁺ m/z: 127.1

Step 2:

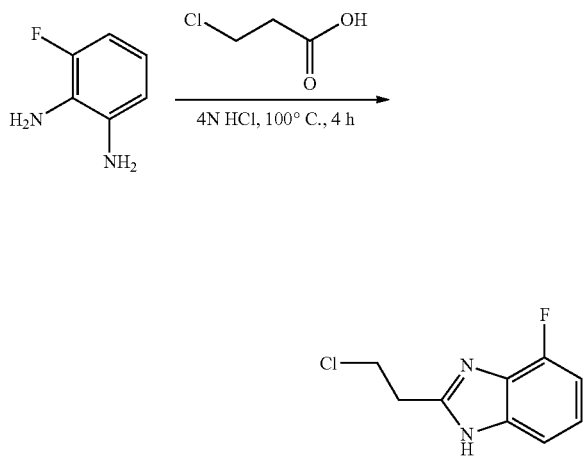

Into a 50-mL round-bottom flask, was placed 3-fluorobenzene-1,2-diamine (500 mg, 3.96 mmol, 1.0 equiv), 3-chloropropanoic acid (645.27 mg, 5.94 mmol, 1.5 equiv), HCl (4M, 10 mL). The resulting solution was stirred for 4 hr at 100° C., cooled down and purified by reverse flash chromatography with the following conditions: column, C18 silica gel; mobile phase, ACN in water (0.1% FA), 5% to 35% gradient in 10 min; detector, UV 254 nm. This resulted in 200 mg (25.4%) of 2-(2-chloroethyl)-4-fluoro-1H-1,3-benzodiazole as white solid. [M+1]⁺ m/z: 199.0

Step 3:

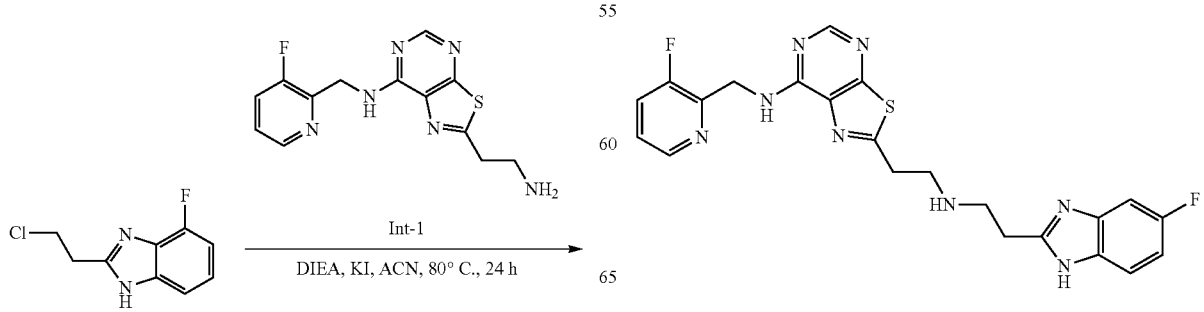

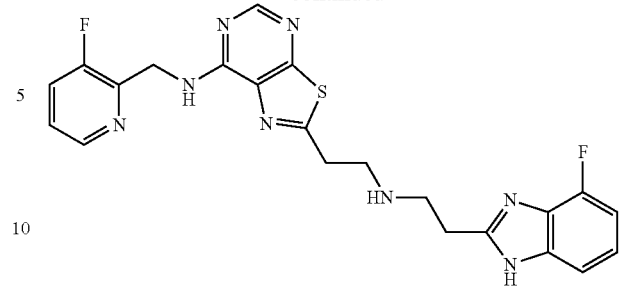

Into a 50-mL round-bottom flask, was placed 2-(2-aminoethyl)-N-[(3-fluoropyridin-2-yl)methyl]-[1,3]thiazolo[5,4-d]pyrimidin-7-amine (150 mg, 0.49 mmol, 1.0 equiv), ACN (3 mL), 2-(2-chloroethyl)-4-fluoro-1H-1,3-benzodiazole (97.9 mg, 0.49 mmol, 1.0 equiv), DIEA (191.1 mg, 1.48 mmol, 3.0 equiv), KI (81.8 mg, 0.49 mmol, 1.0 equiv). The resulting solution was stirred for 24 hr at 80° C., cooled down and diluted with 5 mL of ACN. The solids were filtered out. The crude product was purified by Prep-HPLC with the following conditions (Prep-HPLC-013): Column, SunFire Prep C18 OBD Column, 19*150 mm 5 um 10 nm; mobile phase, Water (0.1% FA) and ACN (7% Phase B up to 22% in 8 min); Detector, uv. This resulted in 37.2 mg (16.1%) of 2-(2-[[2-(4-fluoro-1H-1,3-benzodiazol-2-yl)ethyl]amino]ethyl)-N-[(3-fluoropyridin-2-yl)methyl]-[1,3]thiazolo[5,4-d]pyrimidin-7-amine as white solid. ¹H NMR (300 MHz, DMSO-d₆) δ 8.38-8.25 (m, 3H), 8.21 (s, 1H), 7.70 (ddd, J=10.0, 8.3, 1.3 Hz, 1H), 7.38 (dt, J=8.6, 4.4 Hz, 1H), 7.25 (d, J=8.0 Hz, 1H), 7.08 (td, J=8.0, 4.9 Hz, 1H), 6.97-6.84 (m, 1H), 4.87 (d, J=5.7 Hz, 2H), 3.24 (t, J=6.5 Hz, 2H), 3.15-3.02 (m, 6H). [M+1]⁺ m/z: 467.2

Example 1.22

Synthesis of 2-(2-{[2-(5-fluoro-1H-1,3-benzodiazol-2-yl)ethyl]amino}ethyl)-N-[(3-fluoropyridin-2-yl)methyl]-[1,3]thiazolo[5,4-d]pyrimidin-7-amine (Compound 3)

Scheme 12 depicts a synthetic route for preparing an exemplary compound.

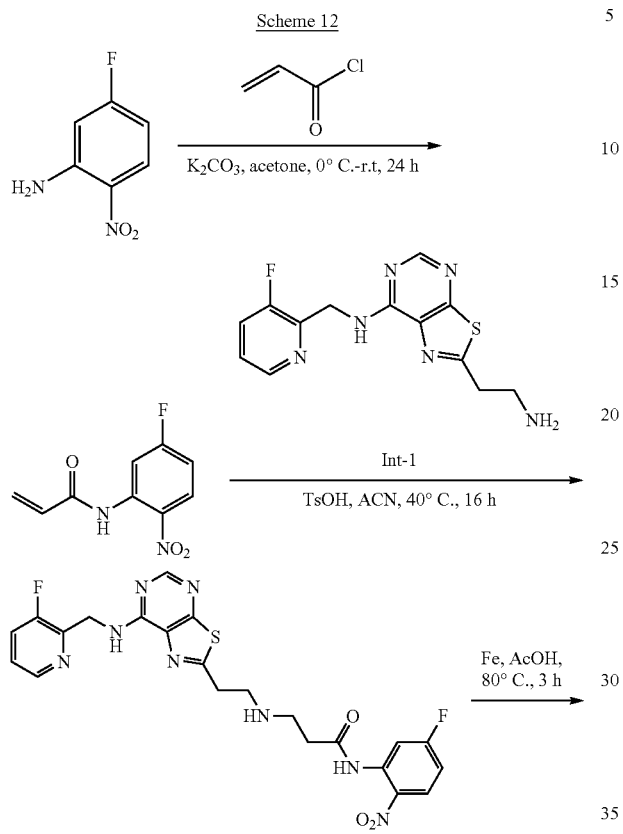

Step 1:

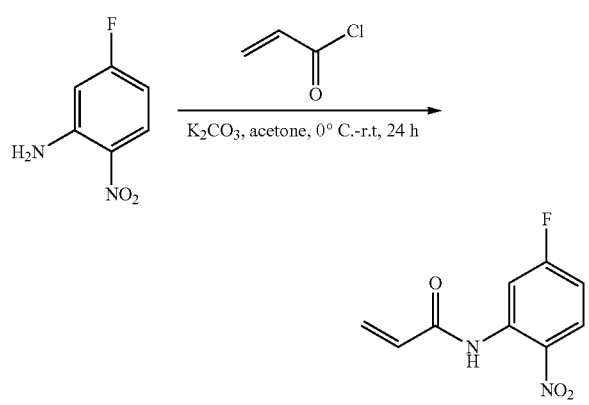

Into a 250-mL 3-necked round-bottom flask, was placed 5-fluoro-2-nitroaniline (5.0 g, 32.02 mmol, 1.0 equiv), acetone (100 mL), $K_2CO_3$ (17.71 g, 128.11 mmol, 4.0 equiv). This was followed by the addition of prop-2-enoyl chloride (8.70 g, 96.08 mmol, 3.0 equiv) dropwise with stirring at 0° C. The resulting solution was stirred for 24 hr at room temperature. The reaction was then quenched by the addition of 100 mL of water. The resulting solution was extracted with 3×100 mL of ethyl acetate and the organic layers combined and dried over anhydrous sodium sulfate and concentrated. The residue was applied onto a silica gel column with ethyl acetate/petroleum ether (1:50). This resulted in 2.7 g (40.1%) of N-(5-fluoro-2-nitrophenyl)prop-2-enamide as yellow solid. $[M+1]^+$ m/z: 211.0

Step 2:

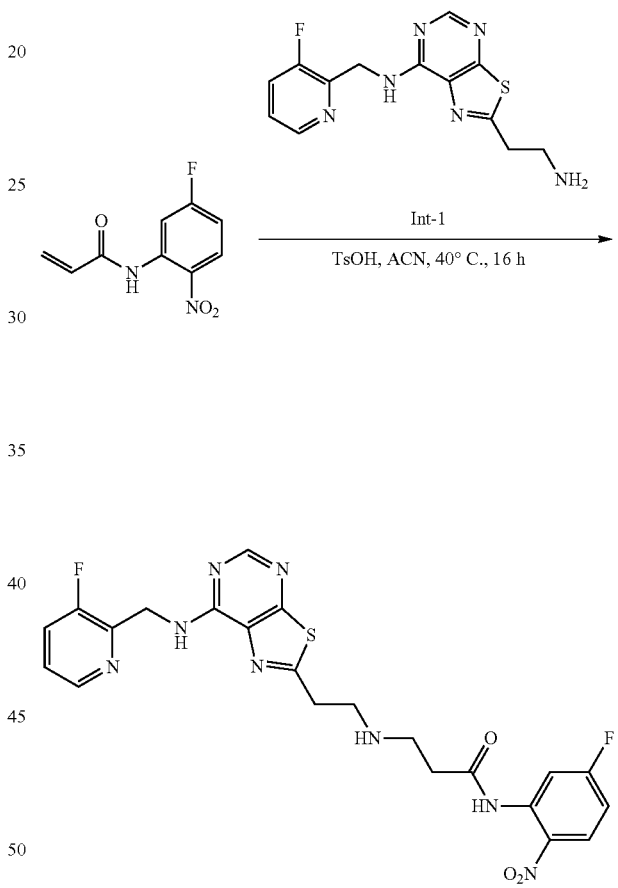

Into a 100-mL round-bottom flask, was placed 2-(2-aminoethyl)-N-[(3-fluoropyridin-2-yl)methyl]-[1,3]thiazolo[5,4-d]pyrimidin-7-amine (400 mg, 1.31 mmol, 1.0 equiv), ACN (5 mL), N-(5-fluoro-2-nitrophenyl)prop-2-enamide (276.2 mg, 1.34 mmol, 1.0 equiv), TsOH (113.2 mg, 0.65 mmol, 0.5 equiv). The resulting solution was stirred for 16 hr at 40° C., cooled down and diluted with 5 mL of $H_2O$. The residue was purified by reverse flash chromatography with the following conditions: column, C18 silica gel; mobile phase, ACN in water, 30% to 90% gradient in 15 min; detector, UV 254 nm. This resulted in 290 mg (42.9%) of N-(5-fluoro-2-nitrophenyl)-3-[[2-(7-[[(3-fluoropyridin-2-yl)methyl]amino]-[1,3]thiazolo[5,4-d]pyrimidin-2-yl)ethyl]amino]propanamide as yellow oil. $[M+1]^+$ m/z: 515.1

Step 3:

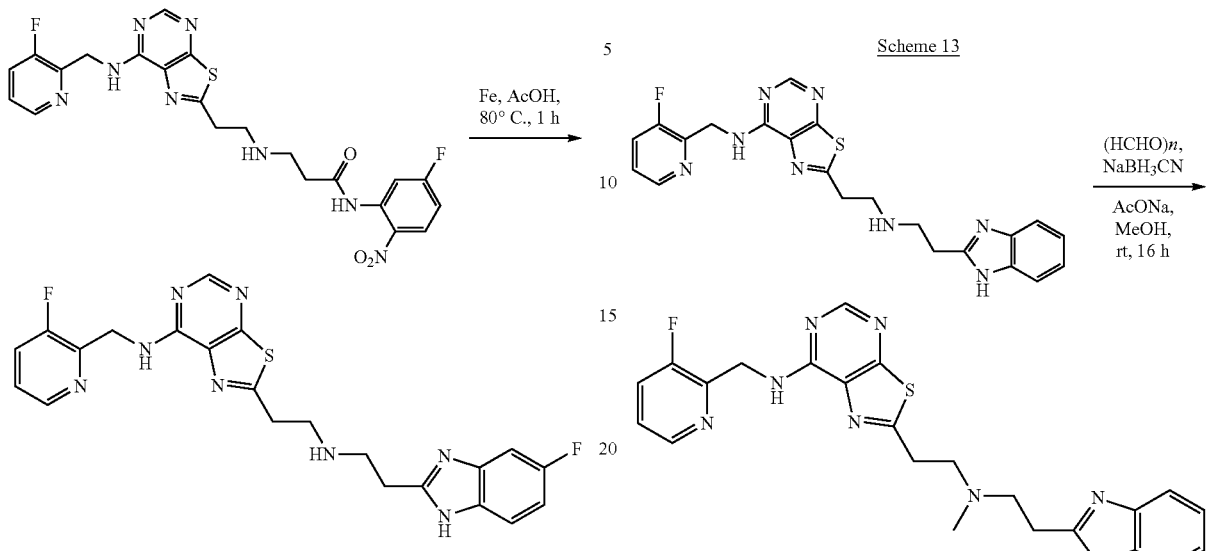

Into a 50-mL round-bottom flask, was placed N-(5-fluoro-2-nitrophenyl)-3-[[2-(7-[[(3-fluoropyridin-2-yl)methyl]amino]-[1,3]thiazolo[5,4-d]pyrimidin-2-yl)ethyl]amino]propanamide (200 mg, 0.39 mmol, 1.0 equiv), AcOH (3 mL), Iron powder (86.8 mg, 1.55 mmol, 4.0 equiv). The resulting solution was stirred for 1 hr at 80° C., cooled down and diluted with 5 mL ACN. The solids were filtered out. The residue was purified by reverse flash chromatography with the following conditions: column, C18 silica gel; mobile phase, ACN in water (0.1% NH$_4$H$_2$O), 10% to 50% gradient in 10 min; detector, UV 254 nm. This resulted in 31.7 mg (17.5%) of 2-(2-{[2-(5-fluoro-1H-1,3-benzodiazol-2-yl)ethyl]amino}ethyl)-N-[(3-fluoropyridin-2-yl)methyl]-[1,3]thiazolo[5,4-d]pyrimidin-7-amine as yellow solid. $^1$H NMR (300 MHz, DMSO-d$_6$) δ 8.38-8.25 (m, 3H), 8.19 (s, 1H), 7.70 (ddd, J=10.1, 8.3, 1.3 Hz, 1H), 7.44-7.36 (m, 2H), 7.23 (dd, J=9.6, 2.5 Hz, 1H), 6.94 (ddd, J=9.9, 8.7, 2.5 Hz, 1H), 4.92-4.83 (m, 2H), 3.26 (t, J=6.6 Hz, 2H), 3.06-2.99 (m, 6H). [M+1]$^+$ m/z: 467.2

Example 1.23

Synthesis of 2-(2-{[2-(1H-1,3-benzodiazol-2-yl)ethyl](methyl)amino}ethyl)-N-[(3-fluoropyridin-2-yl)methyl]-[1,3]thiazolo[5,4-d]pyrimidin-7-amine (Compound 10)

Scheme 13 depicts a synthetic route for preparing an exemplary compound.

Scheme 13

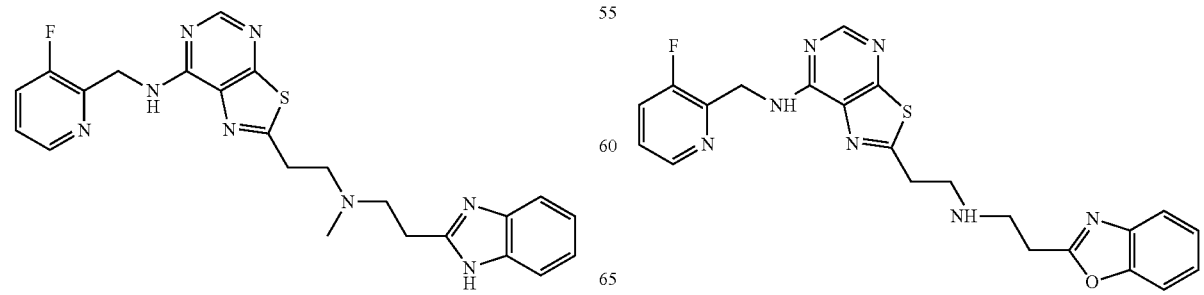

Into a 8-mL vial, was placed a mixture of 2-(2-[[2-(1H-1,3-benzodiazol-2-yl)ethyl]amino]ethyl)-N-[(3-fluoropyridin-2-yl)methyl]-[1,3]thiazolo[5,4-d]pyrimidin-7-amine (250 mg, 0.56 mmol, 1 equiv), (HCHO)n (33 mg, 1.12 mmol, 2 equiv), NaBH$_3$CN (105 mg, 1.672 mmol, 3 equiv), sodium acetate (AcONa) (137 mg, 1.67 mmol, 3 equiv) and MeOH (3.0 mL). The reaction mixture was stirred for 16 hours at room temperature. The mixture was diluted with 10 mL of H$_2$O, extracted with 3×10 mL of dichloromethane, the combined organic layers were dried over anhydrous sodium sulfate and concentrated. The crude product was purified by Prep-HPLC with the following conditions: Column, XBridge Shield RP18 OBD Column, 5 um, 19*150 mm; mobile phase, Water (0.05% NH$_3$H$_2$O) and ACN (21% Phase B up to 36% in 8 min); Detector, UV 254 nm. This resulted in 120.5 mg (47%) of 2-(2-[[2-(1H-1,3-benzodiazol-2-yl)ethyl](methyl)amino]ethyl)-N-[(3-fluoropyridin-2-yl)methyl]-[1,3]thiazolo[5,4-d]pyrimidin-7-amine as white solid. $^1$H NMR (300 MHz, DMSO-d$_6$, ppm): 12.13 (br, 1H), 8.38-8.30 (m, 3H), 7.73-7.67 m, 1H), 7.43-7.36 (m, 3H), 7.12-7.06 (m, 2H), 4.89-4.87 (m, 2H), 3.30-3.24 (m, 2H), 3.00-2.81 (m, 6H), 2.35 (s, 3H). LCMS (ES) [M+1]$^+$ m/z 463.2.

Example 1.24

Synthesis of 2-(2-{[2-(1,3-benzoxazol-2-yl)ethyl]amino}ethyl)-N-[(3-fluoropyridin-2-yl)methyl]-[1,3]thiazolo[5,4-d]pyrimidin-7-amine (Compound 16)

Scheme 14 depicts a synthetic route for preparing an exemplary compound.

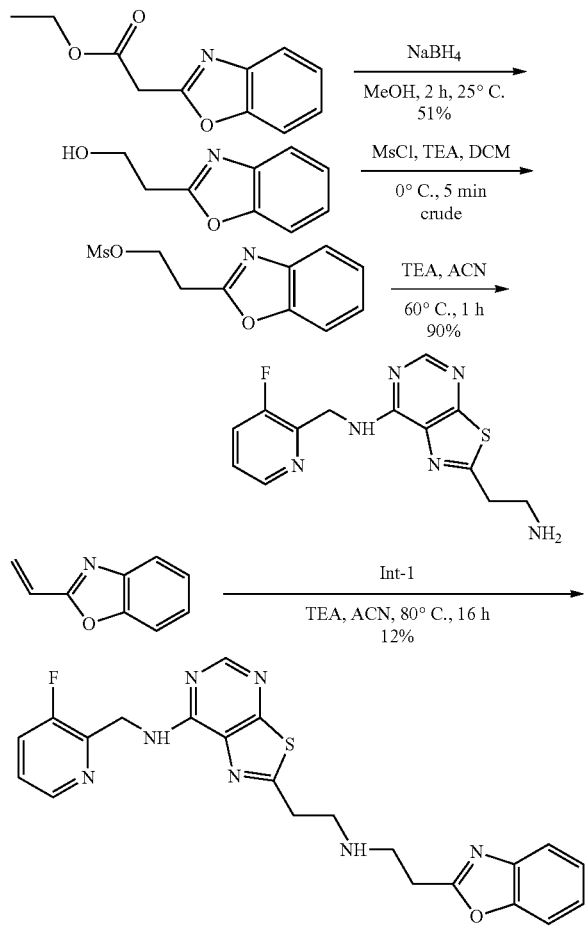

Step 1:

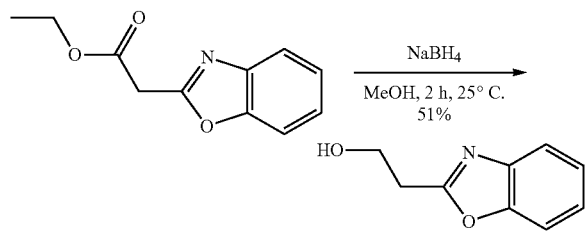

Into a 100-mL 3-necked round-bottom flask purged and maintained with an inert atmosphere of nitrogen, was placed ethyl 2-(3a,7a-dihydro-1,3-benzoxazol-2-yl)acetate (1.2 g, 5.79 mmol, 1.00 equiv), MeOH (15 mL). This was followed by the addition of NaBH$_4$ (0.44 g, 11.58 mmol, 2.00 equiv) in portions at 0° C. The resulting solution was stirred for 2 h at 25° C. The reaction was then quenched by the addition of 100 mL of water/ice. The resulting solution was extracted with 3×50 mL of ethyl acetate, dried over anhydrous sodium sulfate and concentrated under vacuum. The residue was applied onto a silica gel column and eluted with ethyl acetate/petroleum ether (1/1). This resulted in 490 mg (51%) of 2-(benzo[d]oxazol-2-yl)ethan-1-ol as yellow oil. LCMS (ES) [M+1]$^+$ m/z: 164.1.

Step 2:

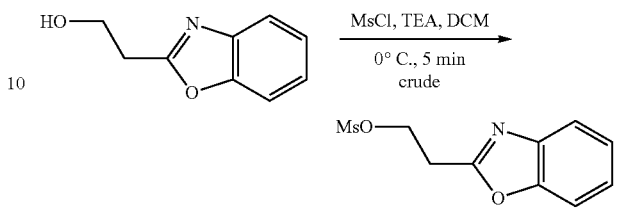

Into a 50-mL 3-necked round-bottom flask purged and maintained with an inert atmosphere of nitrogen, was placed 2-(3a,7a-dihydro-1,3-benzoxazol-2-yl)ethan-1-ol (100 mg, 0.60 mmol, 1.00 equiv), DCM (5 mL), TEA (128.6 mg, 1.27 mmol, 2.10 equiv). This was followed by the addition of a solution of methanesulfonyl chloride (MsCl) (72.8 mg, 0.63 mmol, 1.05 equiv) in DCM (1 mL) dropwise with stirring at 0° C. The resulting solution was stirred for 5 min at 0° C. in a water/ice bath. The reaction was then quenched by the addition of 30 mL of water/ice. The resulting solution was extracted with 3×5 mL of dichloromethane, dried over anhydrous sodium sulfate and concentrated under vacuum. This resulted in 170 mg (crude) of 2-(benzo[d]oxazol-2-yl) ethyl methanesulfonate as yellow solid. LCMS (ES) [M+1]$^+$ m/z: 242.0.

Step 3:

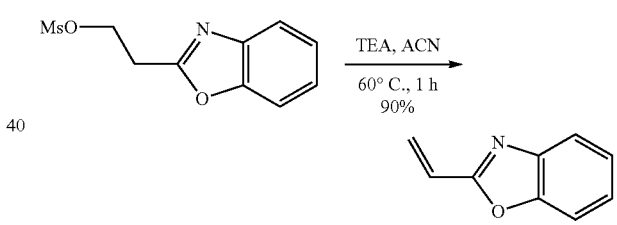

Into a 40-mL vial, was placed 2-(3a,7a-dihydro-1,3-benzoxazol-2-yl)ethyl methanesulfonate (200 mg, 0.82 mmol, 1.00 equiv), ACN, TEA (166.38 mg, 1.64 mmol, 2.00 equiv). The resulting solution was stirred for 1 h at 60° C. in an oil bath. The reaction was then quenched by the addition of 20 mL of water/ice. The resulting solution was extracted with 3×5 mL of dichloromethane and washed with 1×10 mL of brine. The mixture was dried over anhydrous sodium sulfate and concentrated under vacuum. The residue was applied onto a silica gel column and eluted with ethyl acetate/petroleum ether (1/20) to give 2-vinylbenzo[d]oxazole 110 mg (90%) as yellow oil. LCMS (ES) [M+1]$^+$ m/z: 146.2.

Step 4:

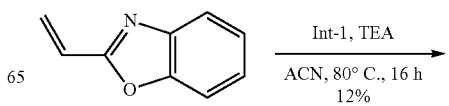

-continued

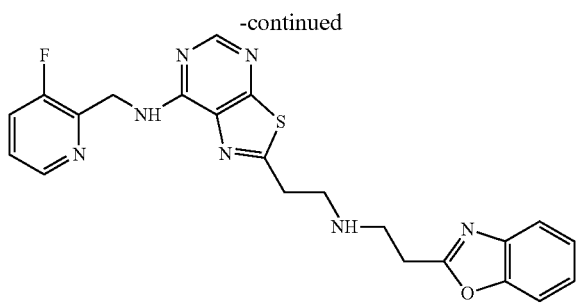

Into a 40-mL vial, was placed 2-(2-aminoethyl)-N-[(3-fluoropyridin-2-yl)methyl]-[1,3]thiazolo[5,4-d]pyrimidin-7-amine (110 mg, 0.36 mmol, 1.00 equiv), 2-ethenyl-3a,7a-dihydro-1,3-benzoxazole (53 mg, 0.36 mmol, 1.00 equiv), ACN (5 mL), TEA (55 mg, 0.54 mmol, 1.50 equiv). The reaction was stirred at 80° C. for 16 h, cooled down and concentrated. The residue was diluted with 10 mL of H₂O and extracted with 3×10 mL of dichloromethane. The organic layer was washed with 20 ml of brine, dried over anhydrous sodium sulfate, filtered and concentrated. The crude reaction mixture was filtered again and subjected to reverse preparative HPLC (Prep-C18, 5 mM XBridge column, 19×150 mm, waters; gradient elution of 5% MeCN in water to 5% MeCN in water over a 2 min period, 5% MeCN in water to 30% MeCN in water over another 12 min period, where both solvents contain 0.1% FA). This resulted in 20.8 mg (12%) of 2-(2-[[2-(1,3-benzoxazol-2-yl)ethyl]amino]ethyl)-N-[(3-fluoropyridin-2-yl)methyl]-[1,3]thiazolo[5,4-d]pyrimidin-7-amine as yellow solid. ¹H NMR (300 MHz, DMSO-d₆) δ8.35-8.24 (m, 3H), 7.77-7.61 (m, 3H), 7.41-7.28 (m, 3H), 4.87 (d, J=6 Hz, 2H), 3.54-3.34 (m, 2H), 3.19-3.06 (m, 4H), 3.04-2.99 (m, 2H). LCMS (ES) [M+1]⁺ m/z: 450.2.

Example 1.25

Synthesis of 2-(2-{[(1H-1,3-benzodiazol-2-yl)methyl]amino}ethyl)-N-[(3-fluoropyridin-2-yl)methyl]-[1,3]thiazolo[5,4-d]pyrimidin-7-amine (Compound 7)

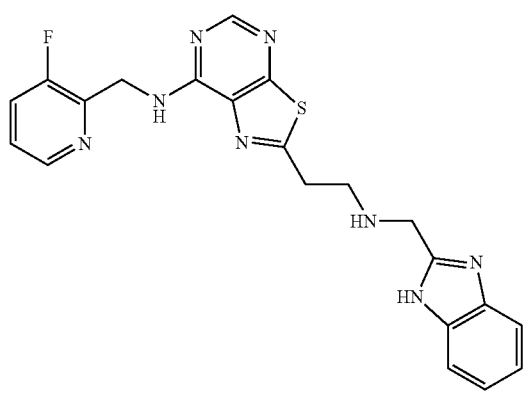 [SMILES: Fc1cccnc1CNc1ncnc2sc(CCNCc3nc4ccccc4[nH]3)nc12]

Scheme 15 depicts a synthetic route for preparing an exemplary compound.

Scheme 15

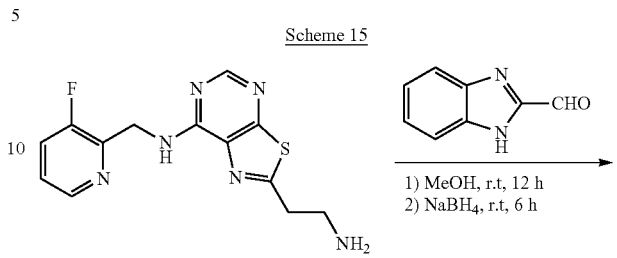

Into a 100-mL round-bottom flask, was placed 2-(2-aminoethyl)-N-[(3-fluoropyridin-2-yl)methyl]-[1,3]thiazolo[5,4-d]pyrimidin-7-amine (150 mg, 0.49 mmol, 1.0 equiv), EtOH (5 mL), 1H-1,3-benzodiazole-2-carbaldehyde (108 mg, 0.74 mmol, 1.5 equiv). The resulting solution was stirred for 12 hr at room temperature. NaBH₄ (37.3 mg, 0.98 mmol, 2.0 equiv) was added and the resulting solution was stirred for 6 hr at room temperature. The reaction was then quenched by the addition of 5 mL of water/ice. The resulting solution was diluted with 10 mL of DMF and purified by reverse flash chromatography with the following conditions: column, C18 silica gel; mobile phase, ACN in water, 20% to 50% gradient in 15 min; detector, UV 254 nm. This resulted in 54.3 mg (25.3%) of 2-(2-{[(1H-1,3-benzodiazol-2-yl)methyl]amino}ethyl)-N-[(3-fluoropyridin-2-yl)methyl]-[1,3]thiazolo[5,4-d]pyrimidin-7-amine as white solid. ¹H NMR (300 MHz, DMSO-d₆) δ 8.38-8.27 (m, 3H), 8.16 (s, 1H), 7.70 (dd, J=10.3, 8.4 Hz, 1H), 7.48 (d, J=5.4 Hz, 2H), 7.38 (dt, J=8.6, 4.4 Hz, 1H), 7.13-7.11 (m, 2H), 4.88 (d, J=5.4 Hz, 2H), 3.99 (s, 2H), 3.27 (t, J=6.8 Hz, 2H), 3.04 (t, J=6.4 Hz, 2H). LCMS [M+1]⁺ m/z: 435.1.

Example 1.26

Synthesis of 2-{1-[2-(1H-1,3-benzodiazol-2-yl)ethyl]azetidin-3-yl}-N-[(3-fluoropyridin-2-yl)methyl]-[1,3]thiazolo[5,4-d]pyrimidin-7-amine (Compound 20)

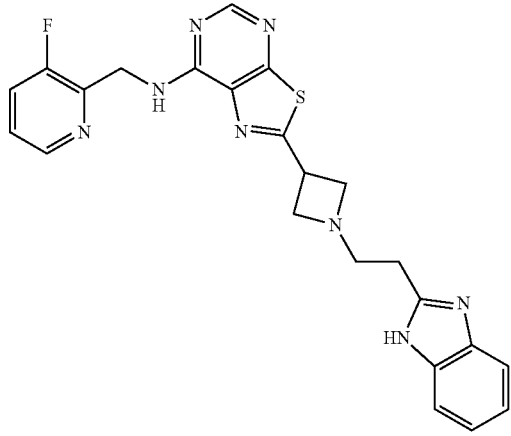 [SMILES: Fc1cccnc1CNc1ncnc2sc(C3CN(CCc4nc5ccccc5[nH]4)C3)nc12]

Scheme 16 depicts a synthetic route for preparing an exemplary compound.

Scheme 16

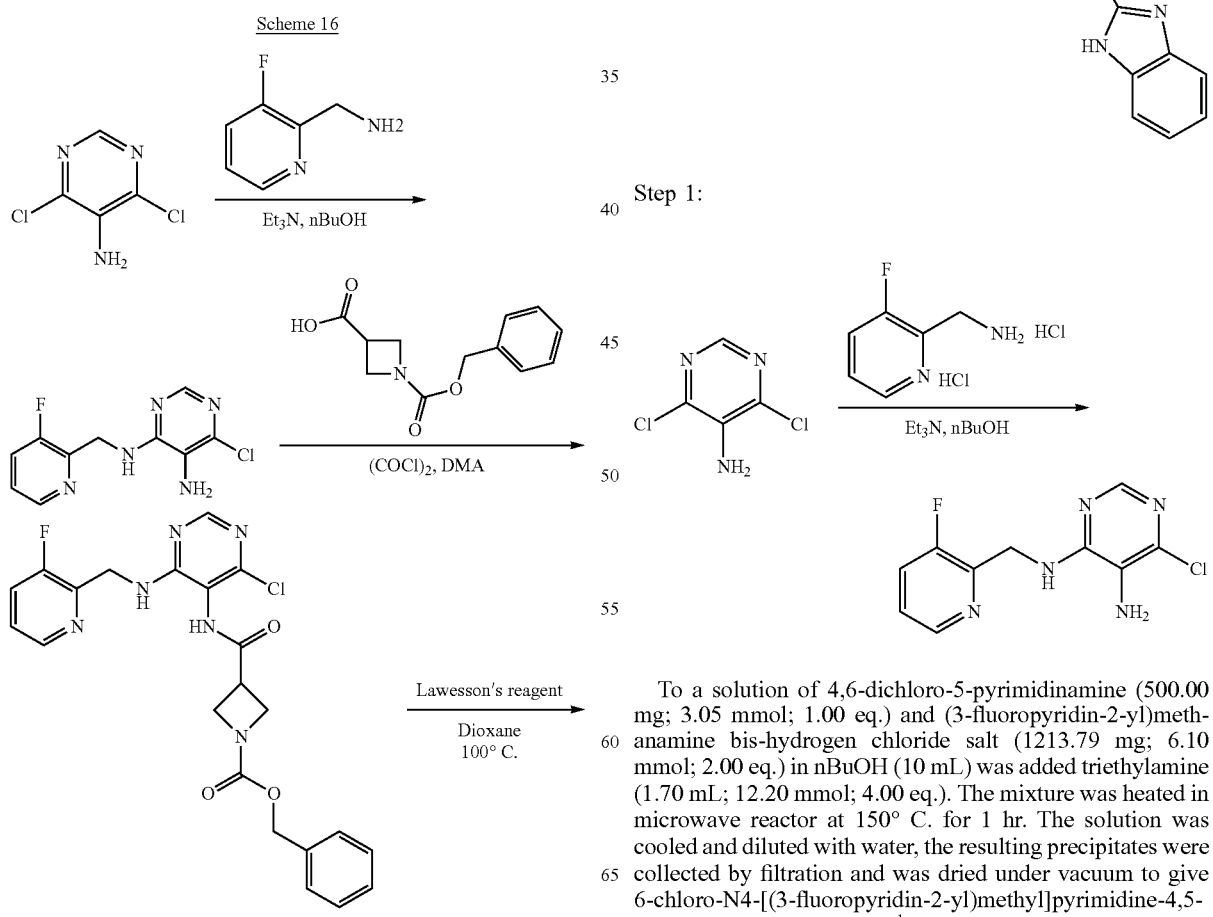

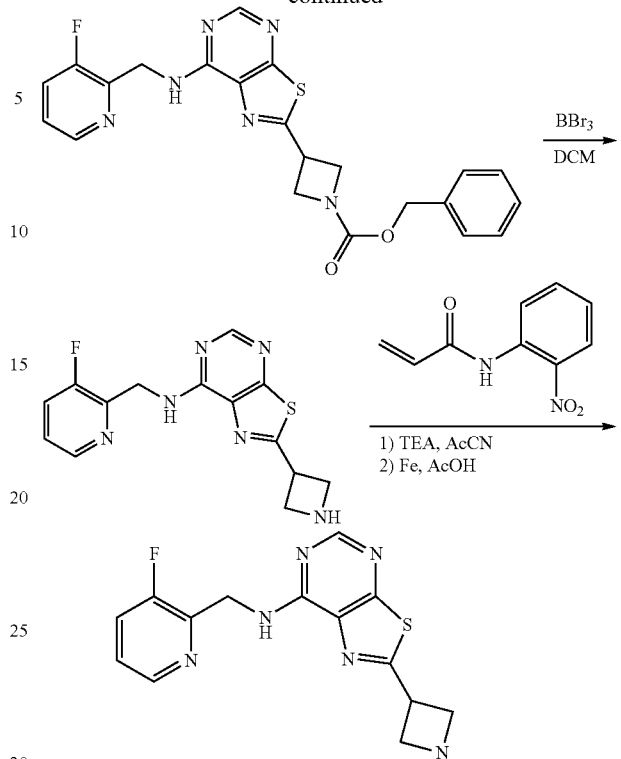

Step 1:

To a solution of 4,6-dichloro-5-pyrimidinamine (500.00 mg; 3.05 mmol; 1.00 eq.) and (3-fluoropyridin-2-yl)methanamine bis-hydrogen chloride salt (1213.79 mg; 6.10 mmol; 2.00 eq.) in nBuOH (10 mL) was added triethylamine (1.70 mL; 12.20 mmol; 4.00 eq.). The mixture was heated in microwave reactor at 150° C. for 1 hr. The solution was cooled and diluted with water, the resulting precipitates were collected by filtration and was dried under vacuum to give 6-chloro-N4-[(3-fluoropyridin-2-yl)methyl]pyrimidine-4,5-diamine 900 mg (>100%). $^1$H NMR (400 MHz, DMSO-d$_6$)

δ 8.35 (dt, J=4.7, 1.5 Hz, 1H), 7.68 (ddd, J=10.0, 8.3, 1.3 Hz, 1H), 7.67 (s, 1H), 7.43-7.31 (m, 2H), 5.12 (s, 2H), 4.76 (dd, J=5.5, 1.8 Hz, 2H). LCMS [M+1]⁺ m/z 253.2, 255.4.

Step 2:

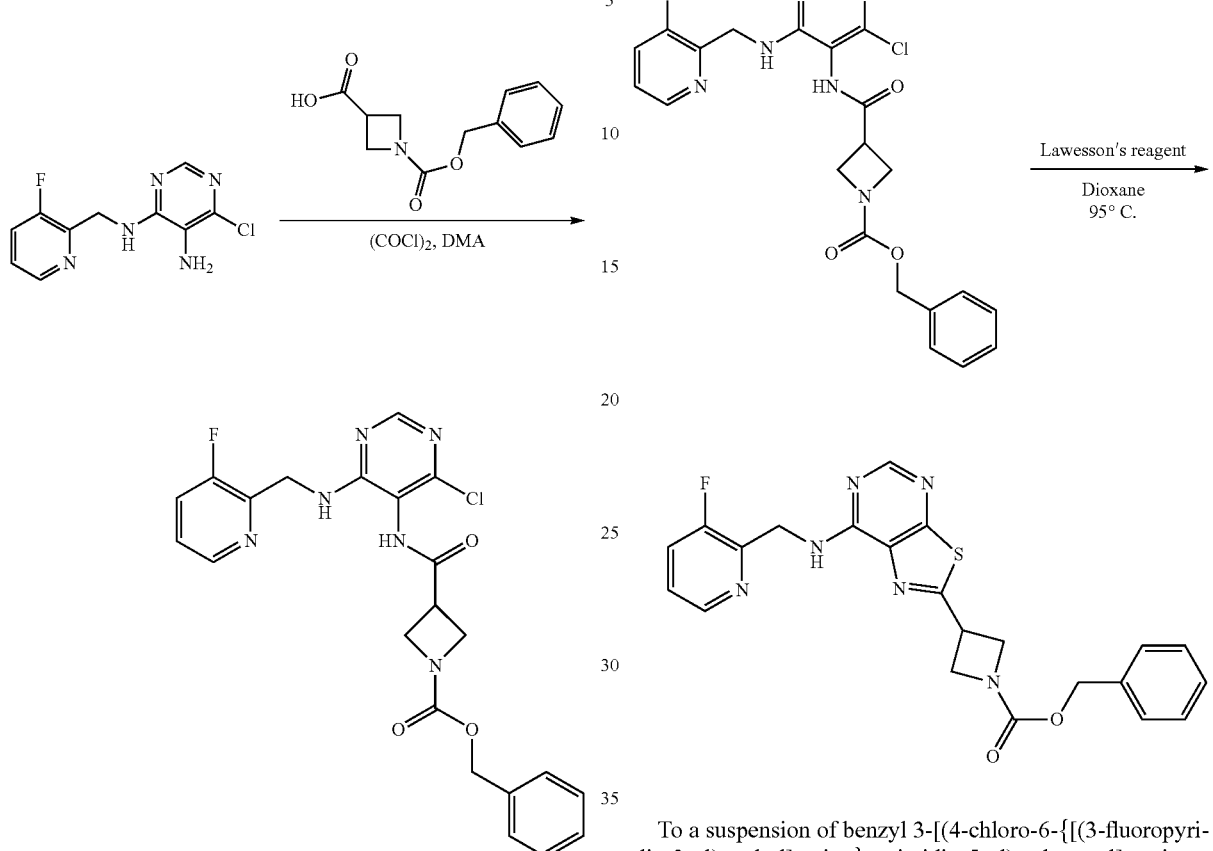

To a solution of 1-[(benzyloxy)carbonyl]azetidine-3-carboxylic acid (370.94 mg; 1.58 mmol; 2.00 eq.) in DCM (1 mL) was added 1 drop of DMF followed by oxalyl chloride (0.14 mL; 1.58 mmol; 2.00 eq.) at room temperature. The mixture was stirred for 1.5 h and was concentrated to give benzyl 3-(chlorocarbonyl)azetidine-1-carboxylate as crude oil. The crude acid chloride was diluted with DMA (dimethylacetamide, 1 mL) and was added 6-chloro-N4-[(3-fluoropyridin-2-yl)methyl]pyrimidine-4,5-diamine (200.00 mg; 0.79 mmol; 1.00 eq.). After stirred for 1 h, the mixture was diluted with EtOAc and Sat. NaHCO₃, the organic layers were combined and concentrated, and the solid was washed with DCM/Hexane and isolated by filtration to give benzyl 3-[(4-chloro-6-{[(3-fluoropyridin-2-yl)methyl]amino}pyrimidin-5-yl)carbamoyl]azetidine-1-carboxylate 370 mg (99%). ¹H NMR (400 MHz, DMSO-d₆) δ 9.64 (s, 1H), 8.30 (s, 1H), 8.18-8.13 (m, 1H), 7.86 (s, 1H), 7.67 (t, J=9.5 Hz, 1H), 7.37-7.32 (m, 6H), 5.03 (d, J=2.9 Hz, 2H), 4.72 (s, 2H), 4.09 (s, 4H), 3.58 (s, 1H). LCMS [M+1]⁺ m/z 471.1.

Step 3:

To a suspension of benzyl 3-[(4-chloro-6-{[(3-fluoropyridin-2-yl)methyl]amino}pyrimidin-5-yl)carbamoyl]azetidine-1-carboxylate (70.00 mg; 0.15 mmol; 1.00 eq.) in Dioxane (1.5 mL) was added 2,4-bis(4-methoxyphenyl)-1,3,2,4-dithiadiphosphetane 2,4-disulfide (81.17 mg; 0.20 mmol; 1.35 eq.). The mixture was heated at 95° C. for 25 min, cooled and was concentrated to give a crude oil. Purification by column chromatography (Hexanes/EtOAc=1:9, 1% Et3N) gave benzyl 3-(7-{[(3-fluoropyridin-2-yl)methyl]amino}-[1,3]thiazolo[5,4-d]pyrimidin-2-yl)azetidine-1-carboxylate 36 mg (54%). ¹H NMR (400 MHz, Chloroform-d) δ 8.51 (d, J=3.4 Hz, 1H), 8.44 (s, 1H), 7.47-7.23 (m, 7H), 5.14 (d, J=3.3 Hz, 2H), 5.00 (s, 2H), 4.46 (td, J=9.0, 3.0 Hz, 2H), 4.39 (q, J=7.5, 5.7 Hz, 2H), 4.19 (dd, J=7.6, 3.8 Hz, 1H), 4.19-4.07 (m, 1H). LCMS [M+1]⁺ m/z: 451.1.

Step 4:

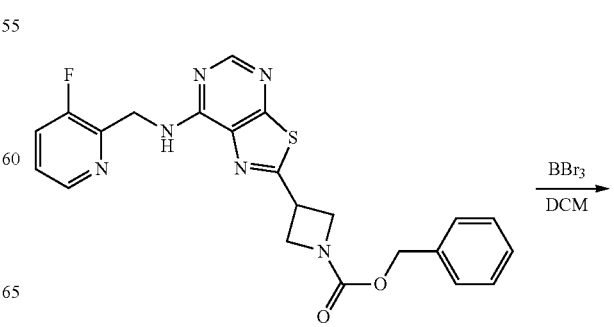

-continued

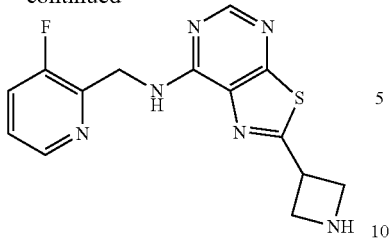

To a solution of 3-(7-{[(3-fluoropyridin-2-yl)methyl]amino}-[1,3]thiazolo[5,4-d]pyrimidin-2-yl)azetidine-1-carboxylate (160 mg 0.36 mmol, 1.00 eq)) in DCM (3 mL) was added boron tribromide (0.70 mL; 1.00 mol/L; 0.70 mmol; 1.94 eq.). The mixture was stirred at room temperature for 30 min, and was concentrated to give a crude product, the crude product was diluted with water, extracted with EtOAc, the aq layer was separated and was treated with NaOH, the aqueous layer was extracted again with EtOAc (3×), organic layers combined, dried and concentrated to give 2-(azetidin-3-yl)-N-[(3-fluoropyridin-2-yl)methyl]-[1,3]thiazolo[5,4-d]pyrimidin-7-amine (88 mg), which was used for next step without purification. LCMS [M+1]$^+$ m/z: 317.0.

Step 5:

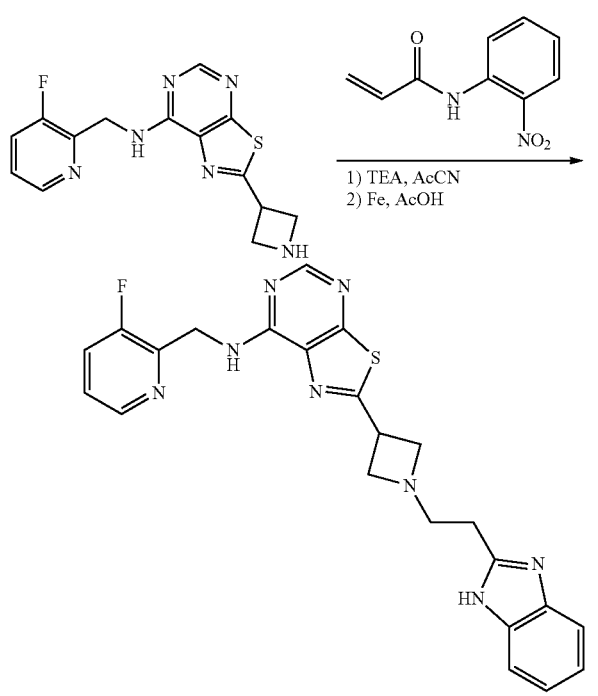

To a solution of 2-(azetidin-3-yl)-N-[(3-fluoropyridin-2-yl)methyl]-[1,3]thiazolo[5,4-d]pyrimidin-7-amine (45.00 mg; 0.14 mmol; 1.00 eq.) in AcCN (2 mL) was added N-(2-nitrophenyl)prop-2-enamide (30.07 mg; 0.16 mmol; 1.10 eq.) and triethylamine (0.04 mL; 0.28 mmol; 2.00 eq.). The mixture was stirred for 15 hr and was then concentrated and diluted with AcOH (2 mL); iron (23.83 mg; 0.43 mmol; 3.00 eq.) was added, and the mixture was heated at 80° C. for 2 h, cooled and concentrated to give a crude product, which was diluted with AcCN and water. The insoluble solid was filtered off and the filtrate was concentrated to give a crude oil, which was purified by prep HPLC to give 2-{1-[2-(1H-1,3-benzodiazol-2-yl)ethyl]azetidin-3-yl}-N-[(3-fluoropyridin-2-yl)methyl]-[1,3]thiazolo[5,4-d]pyrimidin-7-amine (23 mg, 35% yield). $^1$H NMR (400 MHz, DMSO-d$_6$) δ 8.38-8.27 (m, 3H), 8.19 (s, 1H), 7.68 (t, J=9.7 Hz, 1H), 7.45 (q, J=4.3 Hz, 2H), 7.37 (dd, J=8.8, 4.4 Hz, 1H), 7.09 (dd, J=6.0, 3.4 Hz, 2H), 4.86 (s, 2H), 4.02 (d, J=8.6 Hz, 1H), 3.66 (d, J=7.8 Hz, 2H), 2.89 (d, J=6.1 Hz, 2H), 2.84 (d, J=6.3 Hz, 2H). LCMS [M+1]$^+$ m/z: 461.1.

Example 1.27

Synthesis of N-[(3-fluoropyridin-2-yl)methyl]-2-(2-{[2-(1H-imidazol-2-yl)ethyl]amino)}ethyl)-[1,3]thiazolo[5,4-d]pyrimidin-7-amine (Compound 42)

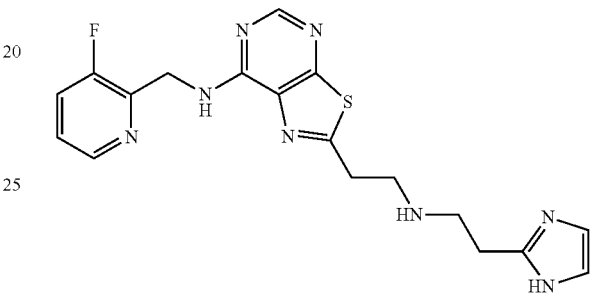

Scheme 17 depicts a synthetic route for preparing an exemplary compound.

Scheme 17

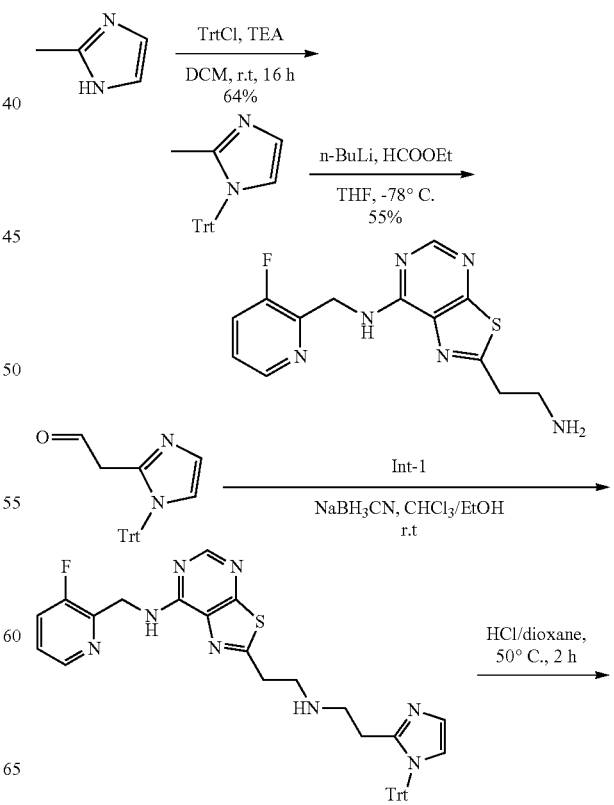

-continued

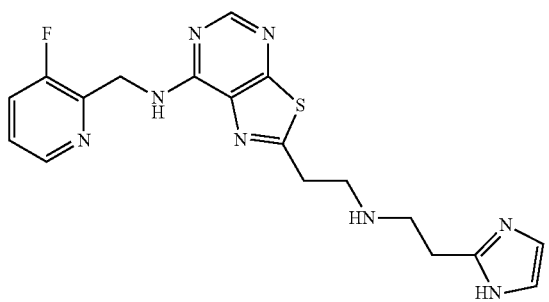 [SMILES: Fc1cccnc1CNc1ncnc2sc(CCNCCc3ncc[nH]3)nc12]

Step 1:

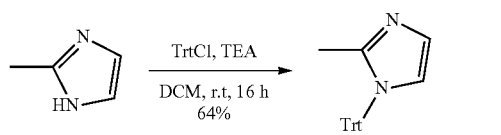

Into a 100-mL 3-neck round-bottom flask, was placed 2-methyl-1H-imidazole (3.0 g, 36.54 mmol, 1.0 equiv), DCM (30 mL), TEA (7.4 g, 73.13 mmol, 2.0 equiv). The mixture was cooled to 0° C., followed by the addition of (chlorodiphenylmethyl)benzene (10.7 g, 38.38 mmol, 1.05 equiv), which was added dropwise. The reaction was stirred overnight for 16 h at room temperature. The reaction was quenched with $H_2O$ (50 mL), the organic phase was separated out, dried over anhydrous $Na_2SO_4$, filtered, and concentrated in vacuum. The residue was purified by silica gel column with dichloromethane. 8 g (64%) of 2-methyl-1-(triphenylmethyl)-1H-imidazole was obtained as a white solid. LCMS (ES) [M+1]+ m/z: 325.

Step 2:

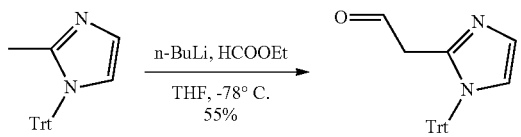

Into a 250-mL 3-necked round-bottom flask purged and maintained with an inert atmosphere of nitrogen, was placed 2-methyl-1-(1,1,2-triphenylethyl)-1H-imidazole (5.0 g, 14.77 mmol, 1.0 equiv), THF (50 mL). This was followed by the addition of n-BuLi (2.5 M in THF) (4.17 mL, 65.17 mmol, 3.0 equiv) at −78° C. After addition, the mixture was stirred for 1 h at the same temperature. Then, HCOOEt (5.47 g, 73.86 mmol, 5.0 equiv) was added and stirred for 1.5 h at −78° C. The reaction was quenched by the addition of 20 mL of $NHCl_4$ (aq.), extracted with 3×100 mL of ethyl acetate, the organic phase combined, dried over anhydrous $Na_2SO_4$, filtered, and the filtrate was concentrated in vacuum. The residue was purified by silica gel column with ethyl acetate/petroleum ether (1:9). 3 g (55%) of 2-[1-(triphenylmethyl)-1H-imidazol-2-yl]acetaldehyde as light yellow solid. LCMS (ES) [M+1]+ m/z: 353.

Step 3:

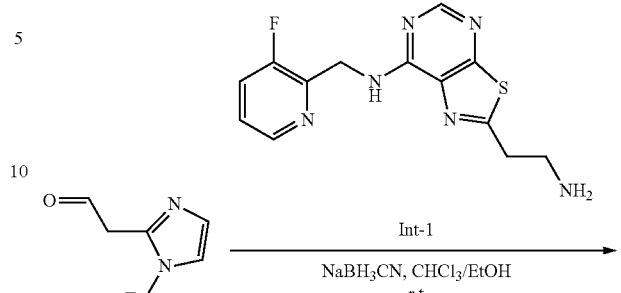

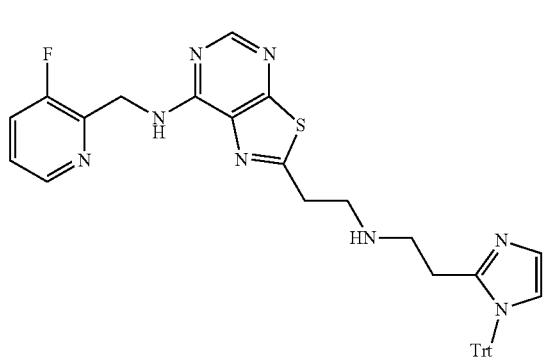

Into a 50-mL round-bottom flask, was placed 2-(2-aminoethyl)-N-[(3-fluoropyridin-2-yl)methyl]-[1,3]thiazolo[5,4-d]pyrimidin-7-amine (300 mg, 0.99 mmol, 1.0 equiv), 2-[1-(triphenylmethyl)imidazolidin-2-yl]ethan-1-ol (521 mg, 1.45 mmol, 1.5 equiv), $CHCl_3$/EtOH=3/1 (8 mL), and AcOH (119 mg, 1.98 mmol, 2.0 equiv). The mixture was stirred overnight at room temperature. This was followed by the addition $NaBH_3CN$ (186 mg, 2.96 mmol, 3.0 equiv) and stirred for 2 h. The reaction was quenched by the addition of 5 mL of water. The resulting solution was extracted with 3×20 mL of dichloromethane, the organic phase combined, dried over anhydrous $Na_2SO_4$, filtered and concentrated in vacuum. 300 mg (crude) of N-[(3-fluoropyridin-2-yl)methyl]-2-[2-({2-[1-(triphenylmethyl)-1H-imidazol-2-yl]ethyl}amino)ethyl]-[1,3]thiazolo[5,4-d]pyrimidin-7-amine was obtained as a brown solid and used in the next step directly without further purification. LCMS (ES) [M+1]+ m/z: 641.

Step 4:

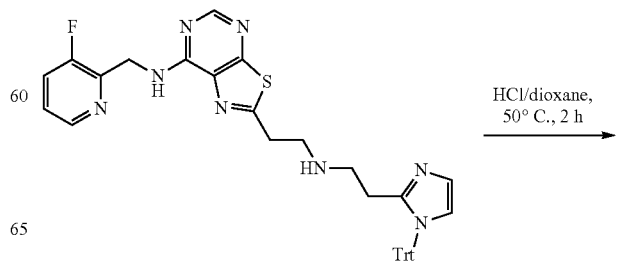

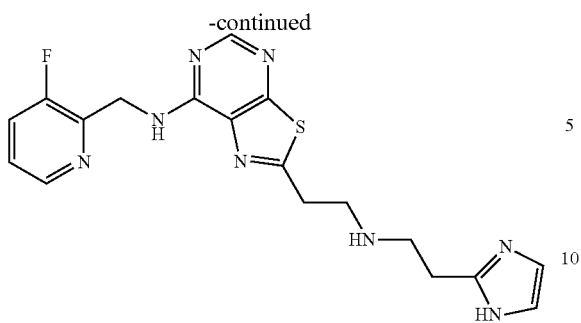

Into a 50-mL round-bottom flask, was placed N-[(3-fluoropyridin-2-yl)methyl]-2-[2-([2-[1-(triphenylmethyl)-1H-imidazol-2-yl]ethyl]amino)ethyl]-[1,3]thiazolo[5,4-d]pyrimidin-7-amine (300 mg, crude of last step), DCM (5 mL), and 4N HCl in dioxane (10 mL). The mixture was stirred for 2 h at 50° C. After cooled to room temperature, the reaction was concentrated in vacuum. The reside was purified by Prep-HPLC with the following conditions: SunFire Prep C18 5 um 19*150 mm, CH$_3$CN/H$_2$O (0.2% FA), from 5% to 35% in 10 min, 20 mL/min, detector, UV 220 nm. 81.8 mg of N-[(3-fluoropyridin-2-yl)methyl]-2-(2-{[2-(1H-imidazol-2-yl)ethyl]amino}ethyl)-[1,3]thiazolo[5,4-d]pyrimidin-7-amine was obtained as a white solid in formic acid salt (partial). $^1$HNMR: (300 MHz, DMSO-d6, ppm): δ 8.45 (br, 1H), 8.36-8.33 (m, 2H), 7.75-7.69 (m, 1H), 7.43-7.37 (m, 1H), 7.14 (s, 2H), 4.92 (d, 2H, J=5.7 Hz), 3.53-3.40 (m, 4H), 3.32-3.12 (m, 4H). LCMS: (ES, m/z): [M−HCOOH+H]$^+$: 399.

Example 1.28

Synthesis of N-[(3-fluoropyridin-2-yl)methyl]-2-(2-{[2-(5-phenyl-1H-imidazol-2-yl)ethyl]amino}ethyl)-[1,3]thiazolo[5,4-d]pyrimidin-7-amine (Compound 35)

Scheme 18 depicts a synthetic route for preparing an exemplary compound.

Scheme 18

Step 1:

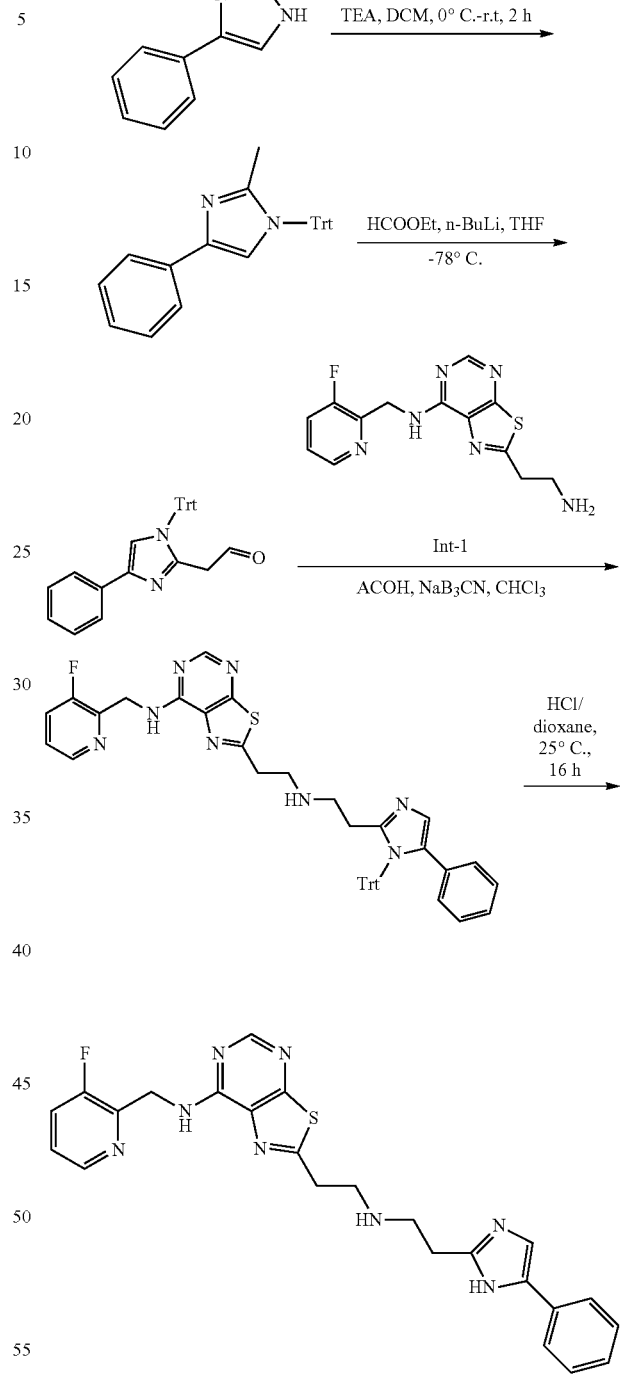

-continued

Into a 100-mL round-bottom flask, was placed (NH$_4$)$_2$CO$_3$ (3.62 g, 37.68 mmol, 3.00 equiv), and AcOH (30.00 mL). The resulting solution was stirred for 30 min at 100° C., and phenacyl bromide (2.50 g, 12.56 mmol, 1.00 equiv) was added. The resulting solution was stirred for 5 hr at 100° C., cooled down, and diluted with 50 mL of H$_2$O. The pH value of the solution was adjusted to 12 with aq NaOH (10%). The resulting solution was extracted with 3×40 mL of dichloromethane and the organic layers were combined. The resulting mixture was washed with 50 mL of brine, dried over anhydrous sodium sulfate, and concentrated. This resulted in 800 mg (40.2%) of 2-methyl-4-phenyl-1H-imidazole as a light yellow solid. [M+1]$^+$ m/z: 159.1

Step 2:

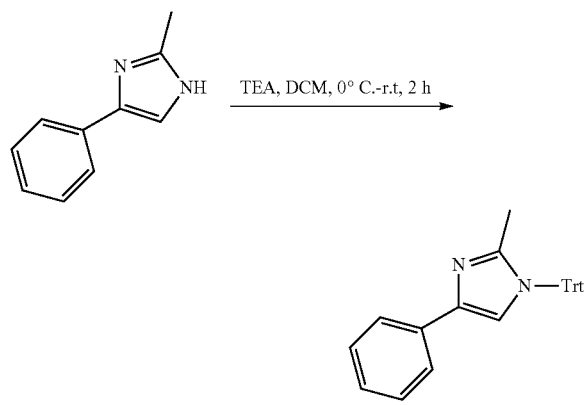

Into a 100-mL 3-necked round-bottom flask, was placed 2-methyl-4-phenyl-1H-imidazole (800 mg, 5.05 mmol, 1.00 equiv), DCM (10.00 mL), and TEA (1023 mg, 10.11 mmol, 2.00 equiv). This was followed by the addition of triphenylmethyl chloride (1691 mg, 6.06 mmol, 1.20 equiv) in portions at 0° C. The resulting solution was stirred for 2 hr at room temperature. The resulting mixture was concentrated, and the residue was applied onto a silica gel column with ethyl acetate/petroleum ether (1/8). This resulted in 1.7 g (83.94%) of 2-methyl-4-phenyl-1-(triphenylmethyl)imidazole as a white solid. [M+1]$^+$ m/z: 401.2.

Step 3:

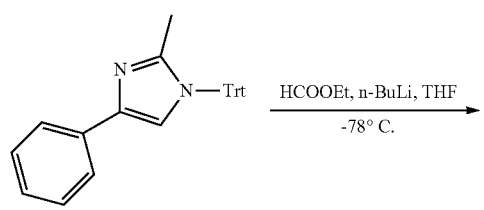

-continued

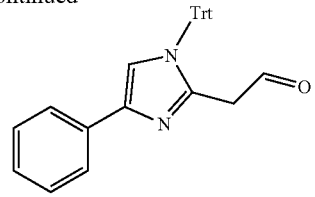

Into a 100-mL 3-necked round-bottom flask, was placed 2-methyl-4-phenyl-1-(triphenylmethyl) imidazole (1.7 g, 4.24 mmol, 1.00 equiv), and THF (20 mL). This was followed by the addition of n-BuLi in hexanes (5.10 mL, 12.75 mmol, 3.00 equiv) dropwise with stirring at −78° C. The resulting solution was stirred for 1 hr at −78° C. To this was added HCOOEt (1.57 g, 21.21 mmol, 5.00 equiv) dropwise with stirring. The resulting solution was stirred for 30 min at −78° C., and then quenched by the addition of 10 mL of NH$_4$Cl. The resulting solution was extracted with 3×50 mL of ethyl acetate and the organic layers were combined, washed with 30 mL of brine, dried over anhydrous sodium sulfate, and concentrated. The residue was applied onto a silica gel column with ethyl acetate/petroleum ether (1/10). This resulted in 1.2 g (65.97%) of 2-[4-phenyl-1-(triphenylmethyl)imidazol-2-yl]acetaldehyde as white solid. [M+1]$^+$ m/z: 429.2.

Step 4:

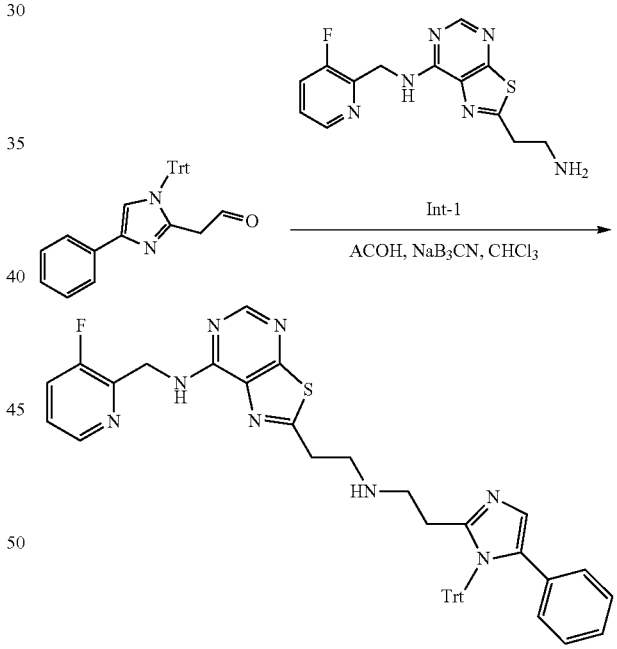

Into a 50-mL round-bottom flask, was placed 2-(2-aminoethyl)-N-[(3-fluoropyridin-2-yl)methyl]-[1,3]thiazolo[5,4-d]pyrimidin-7-amine (400 mg, 1.31 mmol, 1.00 equiv), CH$_3$Cl (6.00 mL), EtOH (2.00 mL), and 2-[4-phenyl-1-(triphenylmethyl)imidazol-2-yl]acetaldehyde (675 mg, 1.57 mmol, 1.20 equiv). The resulting solution was stirred for 16 hr at room temperature. To this was added NaBH$_3$CN (206 mg, 3.28 mmol, 2.50 equiv) at 0° C. The resulting solution was stirred for 2 hr at room temperature, and then quenched by the addition of 10 mL of NH$_4$Cl. The resulting solution was extracted with 2×20 mL of dichloromethane and the organic layers were combined. The resulting mixture was washed with 30 mL of brine, dried over anhydrous sodium sulfate, and concentrated. This resulted in 500 mg (53.07%) of N-[(3-fluoropyridin-2-yl)methyl]-2-[2-([2-[5-phenyl-1-(triphenylmethyl)imidazol-2-yl]ethyl]amino)ethyl]-[1,3]thiazolo[5,4-d]pyrimidin-7-amine as a light yellow oil. [M+1]+ m/z: 717.3.

Step 5:

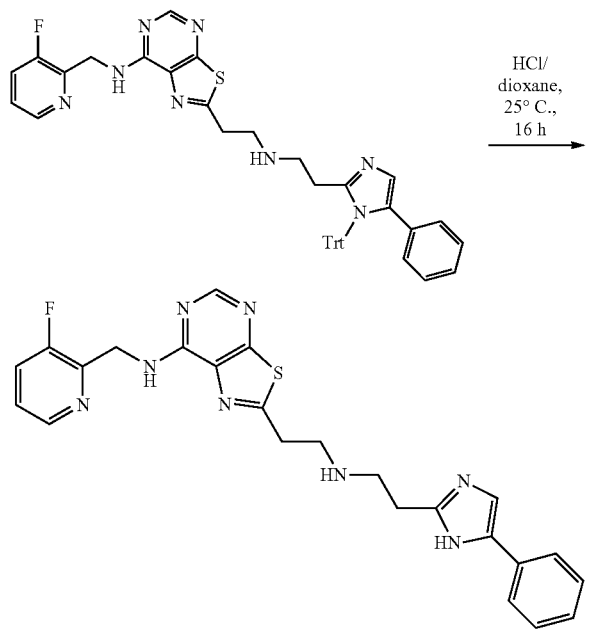

Into a 50-mL round-bottom flask, was placed N-[(3-fluoropyridin-2-yl)methyl]-2-[2-([2-[5-phenyl-1-(triphenylmethyl)imidazol-2-yl]ethyl]amino)ethyl]-[1,3]thiazolo[5,4-d]pyrimidin-7-amine (500 mg, 0.69 mmol, 1.00 equiv), DCM (3.00 mL), and HCl (gas) in 1,4-dioxane (3.00 mL, 98.73 mmol, 141.56 equiv). The resulting solution was stirred for 16 hr at 25° C., concentrated, and diluted with 5 mL of ACN. The crude product was purified by Prep-HPLC with the following conditions (Prep-HPLC-013): Column, SunFire Prep C18 OBD Column, 19*150 mm 5 um 10 nm; mobile phase, Water (0.1% FA) and ACN (7% Phase B up to 22% in 8 min); Detector, uv. This resulted in 106.3 mg (32.12%) of N-[(3-fluoropyridin-2-yl)methyl]-2-(2-[[2-(4-phenyl-3H-imidazol-2-yl)ethyl]amino]ethyl)-[1,3]thiazolo[5,4-d]pyrimidin-7-amine as a white solid. $^1$H NMR (300 MHz, DMSO-d$_6$) δ 8.38-8.28 (m, 3H), 8.25 (d, J=6.5 Hz, 1H), 7.74-7.64 (m, 3H), 7.44-7.35 (m, 2H), 7.35-7.25 (m, 2H), 7.20-7.10 (m, 1H), 4.89 (d, J=5.5 Hz, 2H), 3.30 (t, J=5.9 Hz, 2H), 3.22-2.98 (m, 4H), 2.88 (q, J=6.4 Hz, 2H). [M+1]+ m/z: 475.2.

Example 1.29

Synthesis of 2-(2-{[2-(5-benzyl-1H-imidazol-2-yl)ethyl]amino}ethyl)-N-[(3-fluoropyridin-2-yl)methyl]-[1,3]thiazolo[5,4-d]pyrimidin-7-amine (Compound 43)

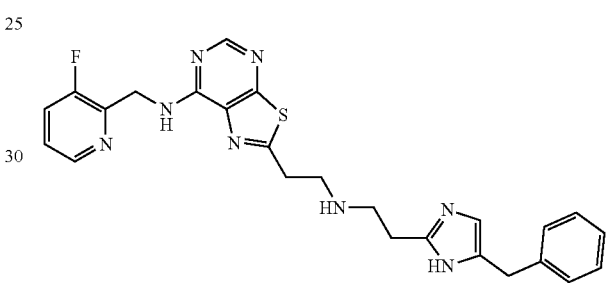

Scheme 19 depicts a synthetic route for preparing an exemplary compound.

Scheme 19

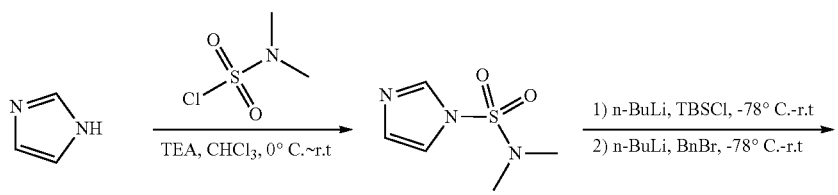

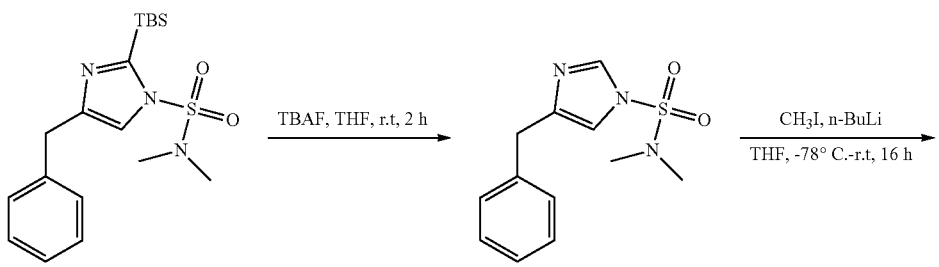

153                                                                                                              154
-continued

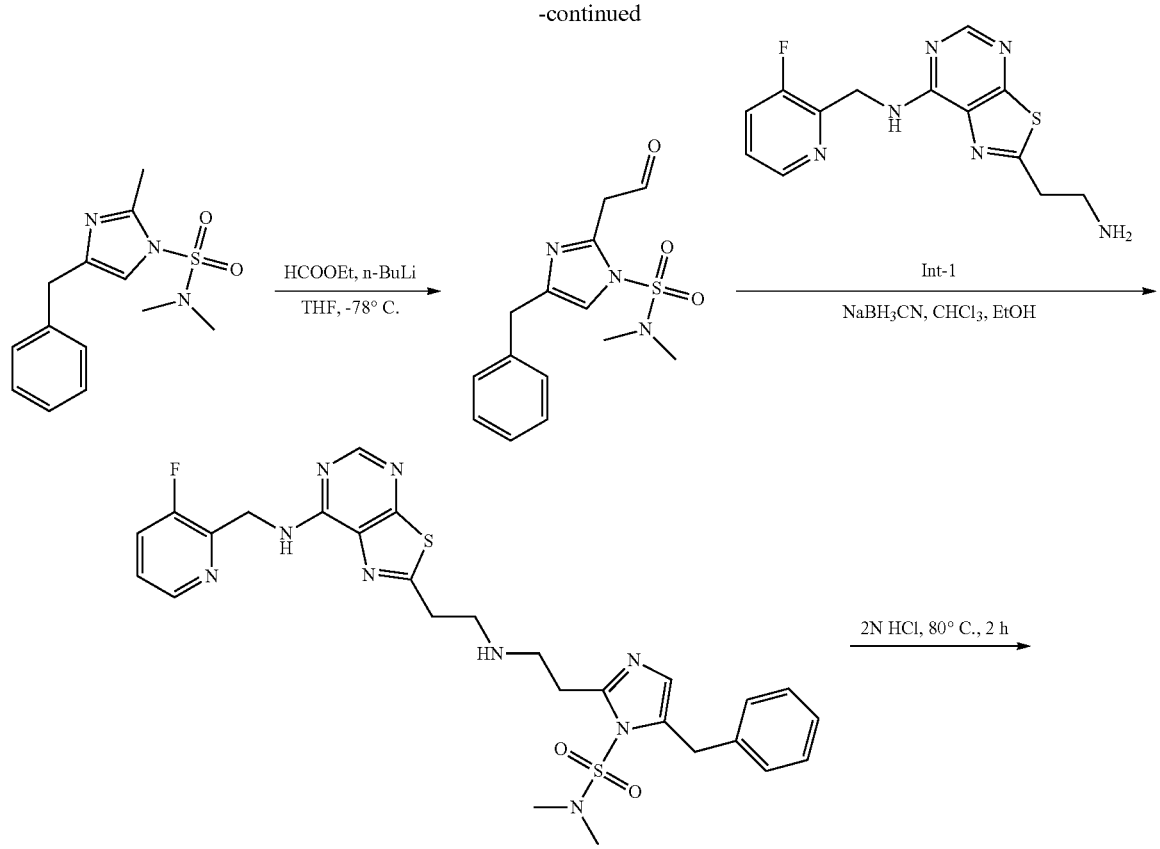

Step 1:

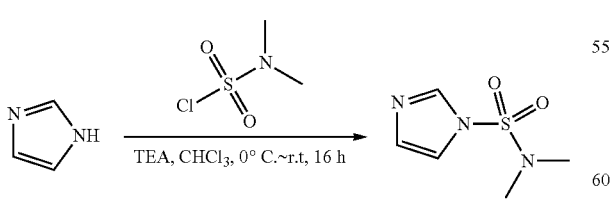

Into a 250-mL 3-necked round-bottom flask, was placed imidazole (10.00 g, 146.88 mmol, 1.00 equiv), CHCl₃ (200.00 mL), and TEA (22.30 g, 220.33 mmol, 1.50 equiv). This was followed by the addition of dimethylsulphamoyl-chloride (23.20 g, 161.57 mmol, 1.10 equiv) dropwise with stirring at 0° C. The resulting solution was stirred for 16 hr at room temperature, diluted with 100 mL of CHCl₃, and washed with 2×200 mL of brine. The mixture was dried over anhydrous sodium sulfate and concentrated. The residue was applied onto a silica gel column with ethyl acetate/petroleum ether (1/1). This resulted in 23.0 g (89.37%) of N,N-dimethylimidazole-1-sulfonamide as a white solid. [M+1]⁺ m/z: 176.0.

Step 2:

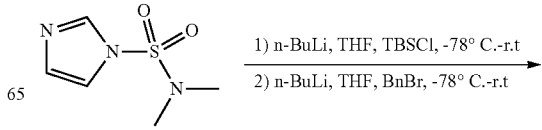

Step 4:

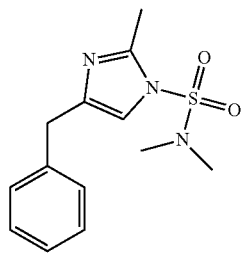

Into a 100-mL 3-necked round-bottom flask, was placed 4-benzyl-N,N-dimethylimidazole-1-sulfonamide (1.60 g, 6.03 mmol, 1.00 equiv) and THF (20.00 mL). This was followed by the addition of n-BuLi (2.52 mL, 6.27 mmol, 1.04 equiv) dropwise with stirring at −78° C. The resulting solution was stirred for 30 min at −78° C. To this was added CH₃I (0.89 g, 6.27 mmol, 1.04 equiv) dropwise. The resulting solution was stirred for 16 hr at room temperature, and quenched by the addition of 20 mL of NH₄Cl. The resulting solution was extracted with 3×30 mL of ethyl acetate and the organic layers were combined. The resulting mixture was washed with 2×20 mL of brine, dried over anhydrous sodium sulfate, and concentrated. The residue was applied onto a silica gel column with ethyl acetate/petroleum ether (1/4). This resulted in 1.1 g (65.30%) of 4-benzyl-N,N,2-trimethylimidazole-1-sulfonamide as a light yellow oil. LCMS [M+1]⁺ m/z: 280.1.

Step 5:

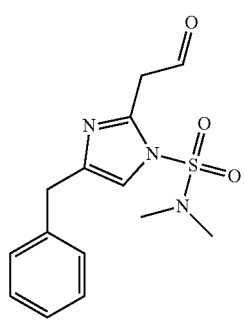

Into a 100-mL 3-necked round-bottom flask, was placed 4-benzyl-N,N,2-trimethylimidazole-1-sulfonamide (1.20 g, 4.29 mmol, 1.00 equiv) and THF (20.00 mL). This was followed by the addition of n-BuLi (5.15 mL, 12.85 mmol, -continued

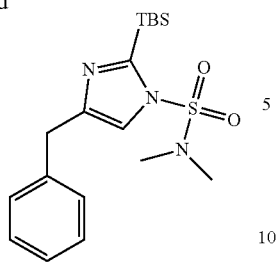

Into a 250-mL 3-necked round-bottom flask, was placed N,N-dimethylimidazole-1-sulfonamide (10.00 g, 57.07 mmol, 1.00 equiv) and THF (150.00 mL). This was followed by the addition of n-BuLi in hexane (24.00 mL, 60.00 mmol, 1.05 equiv) dropwise with stirring at −78° C. The resulting solution was stirred for 15 min at −78° C. To this was added TBSCl (8.60 g, 57.07 mmol, 1.00 equiv) and the mixture stirred for 1 hr at room temperature. To the mixture was added n-BuLi in hexane (23 mL, 57.07 mmol, 1.00 equiv) dropwise with stirring at −78° C. The resulting solution was stirred for 30 min at −78° C. BnBr (9.76 g, 57.07 mmol, 1.00 equiv) was added. The resulting solution was stirred for 16 hr at room temperature, and quenched by the addition of 30 mL of NH₄Cl. The resulting solution was extracted with 3×200 mL of ethyl acetate and the organic layers were combined. The resulting mixture was washed with 2×200 mL of brine, dried over anhydrous sodium sulfate, and concentrated. The residue was applied onto a silica gel column with ethyl acetate/petroleum ether (1/10). This resulted in 4.8 g (22.16%) of 4-benzyl-2-(tert-butyldimethylsilyl)-N,N-dimethylimidazole-1-sulfonamide as a white solid. LCMS [M+1]⁺ m/z: 380.2.

Step 3:

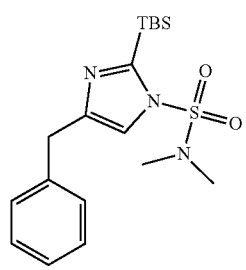

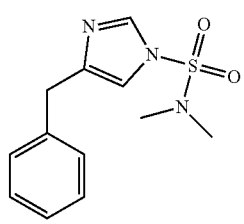

Into a 100-mL round-bottom flask, was placed 4-benzyl-2-(tert-butyldimethylsilyl)-N,N-dimethylimidazole-1-sulfonamide (4.80 g, 12.64 mmol, 1.00 equiv), THF (50.00 mL), and tetra-n-butylammonium fluoride (TBAF) (1N in THF) (15.17 mL, 15.17 mmol, 1.20 equiv). The resulting solution was stirred for 2 hr at room temperature, concentrated, and the residue was purified by silica gel column with ethyl acetate/petroleum ether (1/3). This resulted in 2.5 g (74.51%) of 4-benzyl-N,N-dimethylimidazole-1-sulfonamide as a white solid. LCMS [M+1]⁺ m/z: 266.1.

3.00 equiv) dropwise with stirring at −78° C. The resulting solution was stirred for 1 hr at −78° C. To this was added HCOOEt (1.59 g, 21.47 mmol, 5.00 equiv) dropwise and the mixture was stirred for 30 min at −78° C. and quenched by the addition of 20 mL of NH₄Cl. The resulting solution was extracted with 3×20 mL of ethyl acetate and the organic layers were combined. The resulting mixture was washed with 20 mL of brine, dried over anhydrous sodium sulfate, and concentrated. The residue was applied onto a silica gel column with ethyl acetate/petroleum ether (1/3). This resulted in 300 mg (22.72%) of 4-benzyl-N,N-dimethyl-2-(2-oxoethyl)imidazole-1-sulfonamide as a light yellow oil. LCMS [M+1]⁺ m/z: 308.1.

Step 6:

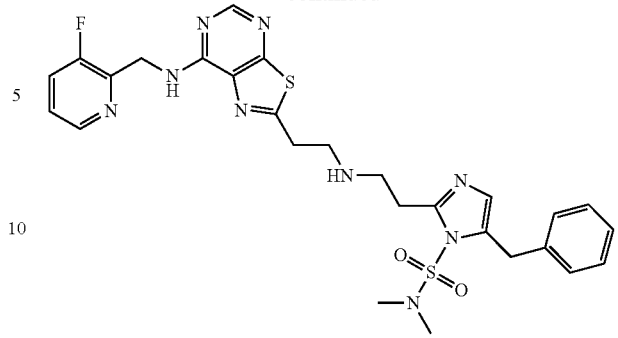

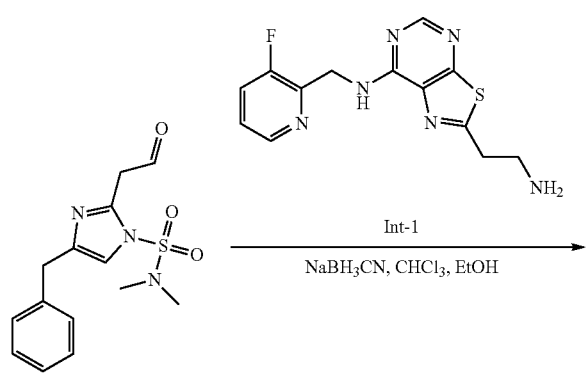

Into a 100-mL round-bottom flask, was placed 2-(2-aminoethyl)-N-[(3-fluoropyridin-2-yl)methyl]-[1,3]thiazolo[5,4-d]pyrimidin-7-amine (297 mg, 0.97 mmol, 1.00 equiv), CHCl₃ (3.00 mL), EtOH (1.00 mL), 4-benzyl-N,N-dimethyl-2-(2-oxoethyl)imidazole-1-sulfonamide (300.00 mg, 0.97 mmol, 1.00 equiv), and AcOH (5.8 mg, 0.10 mmol, 0.1 equiv). The resulting solution was stirred for 16 hr at room temperature. To this was added NaBH₃CN (153 mg, 2.44 mmol, 2.50 equiv) at 0° C. The resulting solution was stirred for 2 hr at room temperature, and diluted with 10 mL of H₂O. The resulting solution was extracted with 3×10 mL of dichloromethane and the organic layers were combined. The resulting mixture was washed with 20 mL of brine, dried over anhydrous sodium sulfate, and concentrated. This resulted in 400 mg (68.80%) of 5-benzyl-2-(2-[[2-(7-[[(3-fluoropyridin-2-yl)methyl]amino]-[1,3]thiazolo[5,4-d]pyrimidin-2-yl)ethyl]amino]ethyl)-N,N-dimethylimidazole-1-sulfonamide as a light yellow solid. LCMS [M+1]⁺ m/z: 596.2.

Step 7:

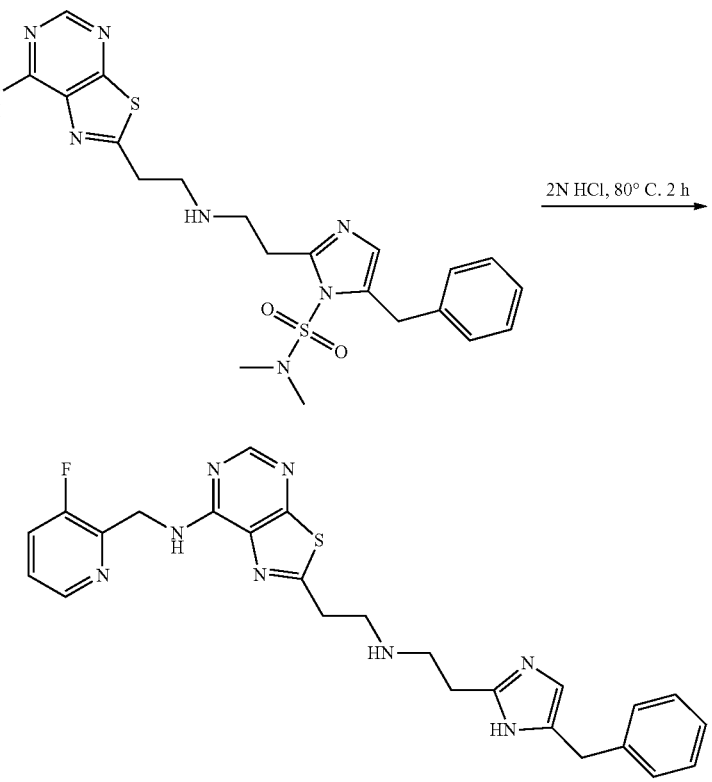

Into a 100-mL round-bottom flask, was placed 5-benzyl-2-(2-[[2-(7-[[(3-fluoropyridin-2-yl)methyl]amino]-[1,3]thiazolo[5,4-d]pyrimidin-2-yl)ethyl]amino]ethyl)-N,N-dimethylimidazole-1-sulfonamide (400 mg, 0.67 mmol, 1.00 equiv), HCl (2M) (5.00 mL). The resulting solution was stirred for 2 hr at 80° C., cooled down, and filtered. The crude product was purified by Prep-HPLC with the following conditions (Prep-HPLC-013): Column, SunFire Prep C18 OBD Column, 19*150 mm 5 um 10 nm; mobile phase, Water (0.1% FA) and ACN (10% Phase B up to 25% in 10 min); Detector, uv 254 nm. This resulted in 39.1 mg (11.92%) of 2-(2-[[2-(4-benzyl-3H-imidazol-2-yl)ethyl]amino]ethyl)-N-[(3-fluoropyridin-2-yl)methyl]-[1,3]thiazolo[5,4-d]pyrimidin-7-amine as white solid. $^1$H NMR (300 MHz, DMSO-d$_6$) δ 8.39-8.28 (m, 3H), 8.20 (s, 1H), 7.71 (ddd, J=10.1, 8.4, 1.3 Hz, 1H), 7.39 (dt, J=8.6, 4.5 Hz, 1H), 7.30-7.11 (m, 5H), 6.57 (d, J=0.8 Hz, 1H), 4.89 (d, J=5.6 Hz, 2H), 3.24 (t, J=6.5 Hz, 2H), 3.05 (t, J=6.5 Hz, 2H), 2.93 (t, J=7.2 Hz, 2H), 2.74 (t, J=6.9 Hz, 2H). LCMS [M+1]$^+$ m/z: 489.6.

Example 1.30

Synthesis of N-[(3-azidopyridin-2-yl)methyl]-2-(2-{[2-(1H-1,3-benzodiazol-2-yl)ethyl]amino}ethyl)-[1,3]thiazolo[5,4-d]pyrimidin-7-amine (Compound 17)

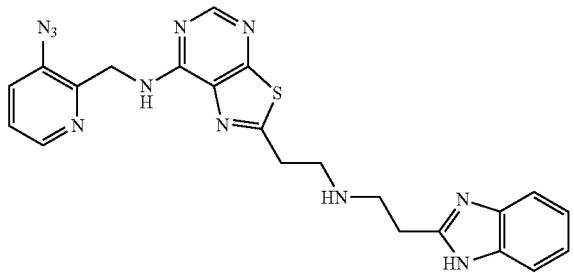 [SMILES: [N-]=[N+]=Nc1cccnc1CNc1ncnc2sc(CCNCCc3nc4ccccc4[nH]3)nc12]

Scheme 20 depicts a synthetic route for preparing an exemplary compound.

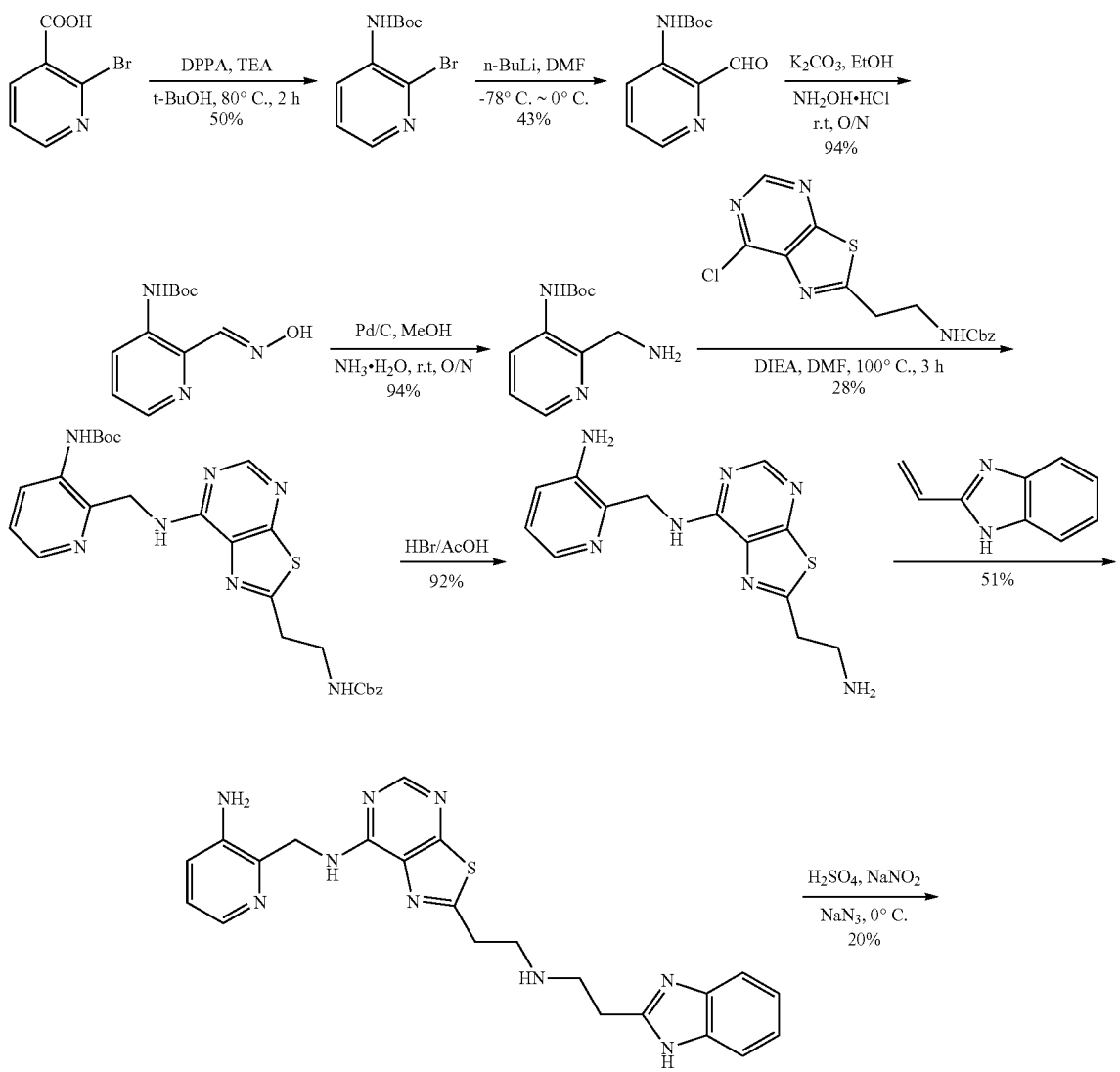

-continued

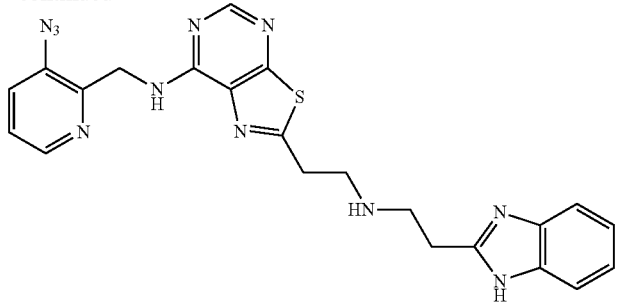

Step 1

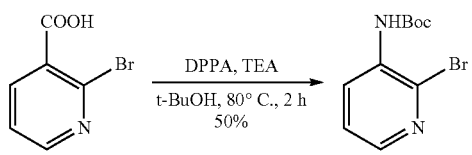 [SMILES: O=C(O)c1cccnc1Br ; CC(C)(C)OC(=O)Nc1cccnc1Br]

Into a 250-mL 3-necked round-bottom flask purged and maintained with an inert atmosphere of nitrogen, was placed 2-bromopyridine-3-carboxylic acid (10 g, 49.5 mmol, 1.0 equiv), TEA (5.5 g, 54.5 mmol, 1.1 equiv), and t-BuOH (150 mL). The flask was evacuated and flushed three times with nitrogen. This was followed by the addition of DPPA (14.3 g, 52.0 mmol, 1.05 equiv). The mixture was stirred for 2 hr at 80° C. in an oil bath. The reaction mixture was cooled to room temperature, quenched with H$_2$O (100 mL), extracted with 3×100 mL of ethyl acetate, and the organic phase was washed with 2×25 ml of Na$_2$CO$_3$ and 2×25 mL of brine. The mixture was dried over anhydrous sodium sulfate, filtered, and concentrated. The residue was purified by silica gel column with ethyl acetate/petroleum ether (3:1). 6.7 g (50%) of tert-butyl N-(2-bromopyridin-3-yl)carbamate was obtained as a white solid. LCMS (ES) [M+1]$^+$ m/z: 273.

Step 2

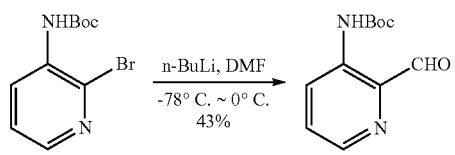 [SMILES: CC(C)(C)OC(=O)Nc1cccnc1Br ; CC(C)(C)OC(=O)Nc1cccnc1C=O]

Into a 1-L 4-necked round-bottom flask purged and maintained with an inert atmosphere of nitrogen, was placed tert-butyl N-(2-bromopyridin-3-yl)carbamate (33.8 g, 123.8 mmol, 1.0 equiv) in THF (500 mL). The reaction was cooled to −78° C. This was followed by the addition of n-BuLi (124.2 mL, 1318.5 mmol, 2.5 equiv) and the reaction stirred for 1 h at the same temperature. DMF (10.9 g, 148.5 mmol, 1.2 equiv) was added and the temperature was allowed to warm to 0° C. Following this, the reaction was stirred for 1 h. The reaction was then quenched by the addition of NH$_4$Cl(aq) (300 mL). The resulting solution was extracted with 3×200 mL of ethyl acetate, dried over anhydrous sodium sulfate, filtered, and concentrated. The residue was purified by silica gel column with ethyl acetate/petroleum ether (3:1). 11.9 g (43%) of tert-butyl N-(2-formylpyridin-3-yl)carbamate was obtained as a yellow solid. LCMS (ES) [M+1]$^+$ m/z: 222.

Step 3

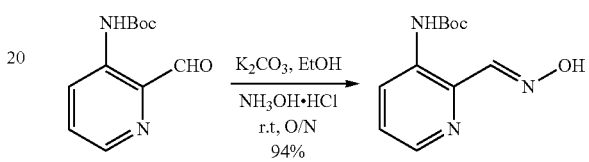

Into a 500-mL 3-necked round-bottom flask purged and maintained with an inert atmosphere of nitrogen, was placed tert-butyl N-(2-formylpyridin-3-yl)carbamate (11.9 g, 53.5 mmol, 1.0 equiv) in EtOH (200 mL). This was followed by the addition of a solution of NH$_2$OH.HCl (3.91 g, 56.2 mmol, 1.05 equiv) in K$_2$CO$_3$ (1 mol/L in H$_2$O) with stirring. The reaction was stirred at r.t overnight. The mixture was concentrated and extracted with 3×100 mL of dichloromethane. The organic phase was dried over anhydrous sodium sulfate, filtered, and concentrated. 11.9 g (93%) of tert-butyl N-[2-[(1E)-(hydroxyimino)methyl]pyridin-3-yl]carbamate was obtained as a yellow solid and used in the next step directly without further purification. LCMS (ES) [M+1]$^+$ m/z: 238.

Step 4

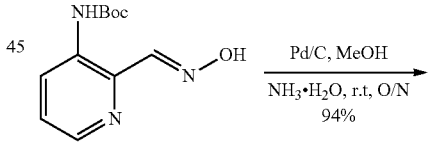

Into a 250-mL round-bottom flask, was placed tert-butyl N-[2-[(1E)-(hydroxyimino)methyl]pyridin-3-yl]carbamate (2.5 g, 10.5 mmol, 1.0 equiv) in MeOH (100 mL), NH$_3$—H$_2$O (20 mL), and Pd/C (250 mg, 10% Wt). The flask was evacuated and flushed three times with nitrogen, followed by flushing with hydrogen. The mixture was stirred overnight at room temperature under an atmosphere of hydrogen. Following this, the mixture was filtered, and the filtrate was concentrated. The residue was purified by silica gel column with ethyl acetate/petroleum ether (1:1). 2.2 g (94%) of tert-butyl N-[2-(aminomethyl)pyridin-3-yl]carbamate was obtained as a yellow oil. LCMS (ES) [M+1]+m/z: 224.

Step 5

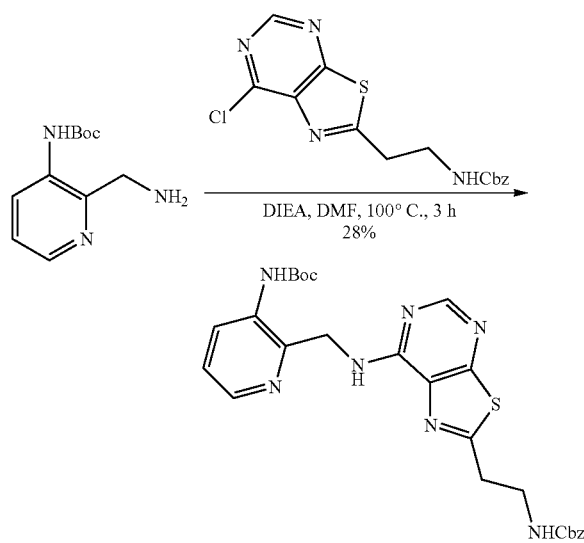

Into a 40-mL sealed tube, was placed tert-butyl N-[2-(aminomethyl)pyridin-3-yl]carbamate (2.2 g, 9.9 mmol, 1.0 equiv), benzyl N-(2-[7-chloro-[1,3]thiazolo[5,4-d]pyrimidin-2-yl]ethyl)carbamate (3.4 g, 9.9 mmol, 1.0 equiv), DMF (20 mL), and DIEA (2.6 g, 19.7 mmol, 2.0 equiv). The mixture was stirred for 3 h at 100° C. in an oil bath. After cooling to room temperature, the reaction solution was diluted with cold water (20 mL). The mixture was extracted with ethyl acetate (50 mL*2). The organic phase was washed with brine and dried over $Na_2SO_4$, filtered, and the filtrate was concentrated in vacuo. The residue was purified by silica gel column with ethyl acetate/petroleum ether (1:1). 1.45 g (28%) of benzyl N-[2-(7-[[(3-[[(tert-butoxy)carbonyl]amino]pyridin-2-yl)methyl]amino]-[1,3]thiazolo[5,4-d]pyrimidin-2-yl)ethyl]carbamate was obtained as a brown solid. LCMS (ES) $[M+1]^+$ m/z: 536.

Step 6

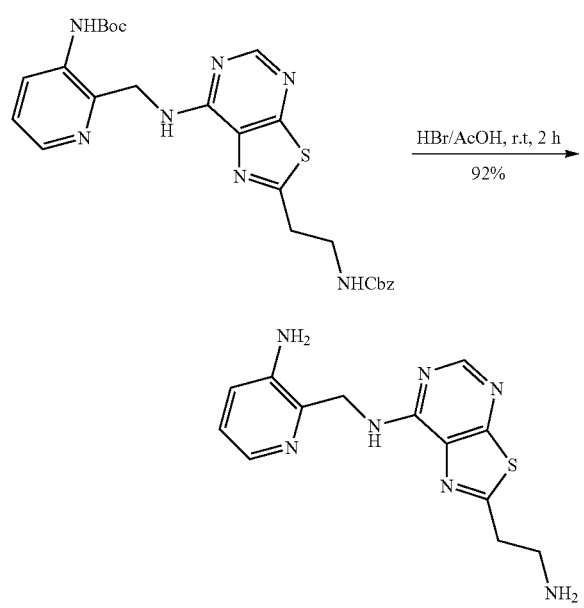 [SMILES: CC(C)(C)OC(=O)Nc1cccnc1CNc1ncnc2sc(CCNC(=O)OCc3ccccc3)nc12 ; NCCc1nc2c(NCc3ncccc3N)ncnc2s1]

Into a 20-mL vial, was placed benzyl N-[2-(7-[[(3-[[(tert-butoxy)carbonyl]amino]pyridin-2-yl)methyl]amino]-[1,3]thiazolo[5,4-d]pyrimidin-2-yl)ethyl]carbamate (793 mg, 1.5 mmol, 1.0 equiv), AcOH (3 mL), and HBr/AcOH (33%) (3 mL). The mixture was stirred for 2 h at room temperature. The residue was dissolved in 20 ml of $H_2O$, extracted with 3×20 mL of ethyl acetate, and the aqueous layers combined. The pH value of the solution was adjusted to 9 with $K_2CO_3$ solid, extracted with DCM/MeOH=10:1 (50 mL*3), and dried over $Na_2SO_4$. After filtration, the filtrate was concentrated in vacuo, 409 mg (92%) of 2-([[2-(2-aminoethyl)-[1,3]thiazolo[5,4-d]pyrimidin-7-yl]amino]methyl)pyridin-3-amine was obtained as a brown solid. LCMS (ES) $[M+1]^+$ m/z: 302.

Step 7

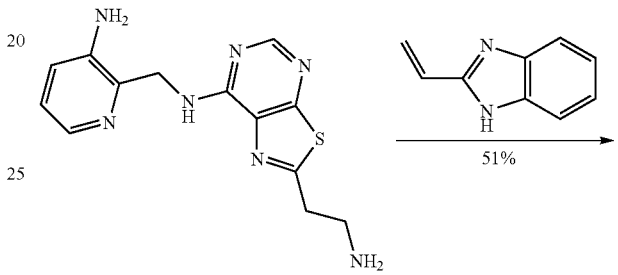

Into a 100-mL 3-necked round-bottom flask, was placed 2-([[2-(2-aminoethyl)-[1,3]thiazolo[5,4-d]pyrimidin-7-yl]amino]methyl)pyridin-3-amine (409 mg, 1.4 mmol, 1.0 equiv), ACN (40 mL, 1.0 mmol), $NH_4OAc$ (104.6 mg, 1.4 mmol, 1.0 equiv), and 2-ethenyl-1H-1,3-benzodiazole (195.7 mg, 1.4 mmol, 1.0 equiv). The mixture was stirred for 6 h at 80° C. in an oil bath. The reaction mixture was cooled to room temperature, extracted with 3×40 mL of DCM/MeOH=10:1, and the organic layers were combined and concentrated. 309 mg (51%) of 2-([[2-(2-[[2-(1H-1,3-benzodiazol-2-yl)ethyl]amino]ethyl)-[1,3]thiazolo[5,4-d]pyrimidin-7-yl]amino]methyl)pyridin-3-amine was obtained as a brown solid. LCMS (ES) $[M+1]^+$ m/z: 446.

Step 8

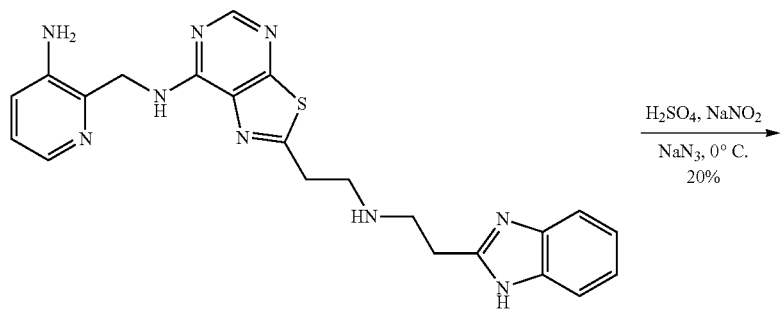

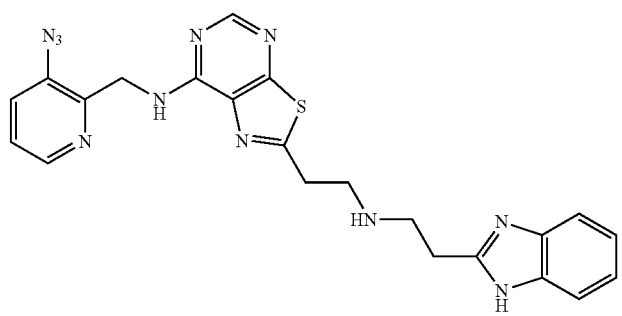

Into a 50-mL 3-necked round-bottom flask, was placed H₂SO₄(c) 0.4 mL in H₂O (8 mL), and 2-([[2-(2-[[2-(1H-1,3-benzodiazol-2-yl)ethyl]amino]ethyl)-[1,3]thiazolo[5,4-d]pyrimidin-7-yl]amino]methyl)pyridin-3-amine (320 mg, 0.72 mmol, 1.0 equiv). The mixture was cooled to 0° C., followed by the addition of a solution of NaNO₂ (59.5 mg, 0.86 mmol, 1.2 equiv) in H₂O (2 ml) dropwise with stirring. After stirring for 20 min, a solution of NaN₃ (70.1 mg, 1.08 mmol, 1.5 equiv) in H₂O (4 ml) was added dropwise with stirring at 0° C. The resulting solution was stirred for 1 hr at 0° C. The pH of the solution was adjusted to 9 and extracted with DCM (30 mL*2). After concentrated in vacuo, the residue was purified by Prep-HPLC (Prep-HPLC-006): Column, XBridge Prep C18 OBD Column, 19 cm, 150 mm, 5 um; mobile phase, Water (10 mmol/L NH₄HCO₃+0.1% NH₃.H₂O) and ACN (33% Phase B up to 45% in 7 min), Detector, UV. 68.9 mg (20%) of N-[(3-azidopyridin-2-yl)methyl]-2-(2-[[2-(1H-1,3-benzodiazol-2-yl)ethyl]amino]ethyl)-[1,3]thiazolo[5,4-d]pyrimidin-7-amine was obtained as a light yellow solid. LCMS (ES, m/z): [M+H]⁺: 472. ¹H NMR (300 MHz, CDCl₃, ppm): δ 8.54 (s, 1H), 8.28 (dd, J=4.8, 1.2 Hz, 1H), 7.61-7.43 (m, 2H), 7.40-7.33 (m, 2H), 7.26-7.24 (m, 2H), 7.16-7.08 (m, 2H), 4.76 (d, J=4.5 Hz, 2H), 3.49-3.31 (m, 4H), 3.28-3.12 (m, 4H).

Example 1.31

Synthesis of 2-(2-{[2-(1H-1,3-benzodiazol-2-yl)ethyl]amino}ethyl)-N-[(3-fluoropyridin-2-yl)methyl]-5-methoxy-[1,3]thiazolo[5,4-d]pyrimidin-7-amine (Compound 18)

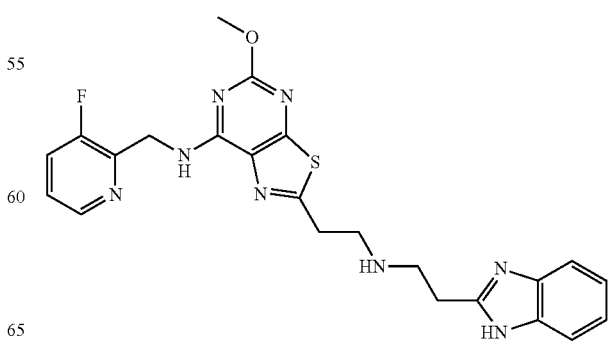

Scheme 21 depicts a synthetic route for preparing an exemplary compound.

Scheme 21

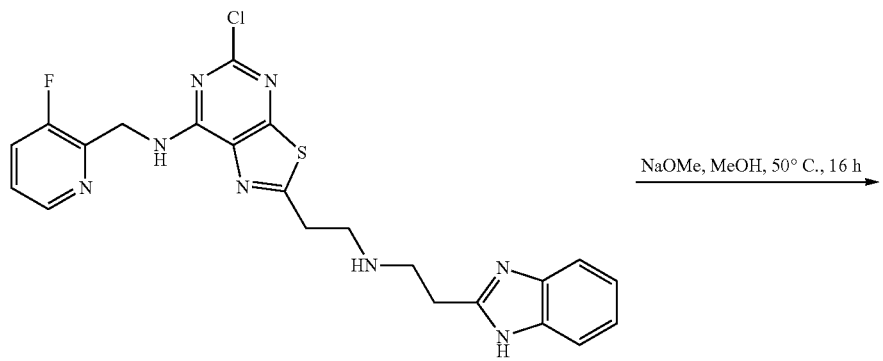

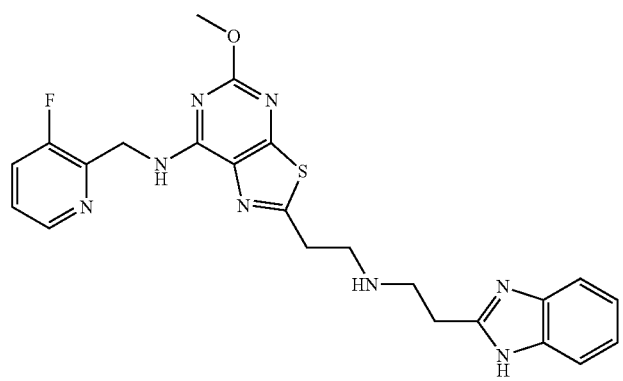

Into a 50-mL round-bottom flask, was placed 2-(2-((2-(1H-benzo[d]imidazol-2-yl)ethyl)amino)ethyl)-5-chloro-N-((3-fluoropyridin-2-yl)methyl)thiazolo[5,4-d]pyrimidin-7-amine (60 mg, 0.12 mmol, 1.00 equiv), MeOH (2.00 mL), and MeONa (7 mg, 0.13 mmol, 1.05 equiv). The resulting solution was stirred for 16 hr at 50° C., cooled, and concentrated. The crude product was purified by Prep-HPLC with the following conditions: Column, XBridge Prep C18 OBD Column, 19*150 mm 5 um; mobile phase, Water (10 MMOL/L NH$_4$HCO$_3$+0.1% NH$_3$.H$_2$O) and ACN (30% Phase B up to 40% in 7 min); Detector, UV. This resulted in 30 mg (50.4%) of 2-(2-((2-(1H-benzo[d]imidazol-2-yl)ethyl)amino)ethyl)-N-((3-fluoropyridin-2-yl)methyl)-5-methoxythiazolo[5,4-d]pyrimidin-7-amine as a white solid. $^1$H NMR (300 MHz, DMSO-d$_6$) δ 12.14 (s, 1H), 8.35 (dt, J=4.7, 1.5 Hz, 2H), 7.70 (ddd, J=10.2, 8.4, 1.3 Hz, 1H), 7.52-7.30 (m, 3H), 7.16-7.05 (m, 2H), 4.81 (d, J=5.4 Hz, 2H), 3.77 (s, 3H), 3.16 (t, J=6.5 Hz, 2H), 3.08-2.92 (m, 6H), 2.27 (s, 1H). LCMS [M+1]$^+$ m/z: 479.2.

Example 1.32

Synthesis of 2-(2-{[2-(1H-1,3-benzodiazol-2-yl)ethyl]amino}ethyl)-N7-[(3-fluoropyridin-2-yl)methyl]-[1,3]thiazolo[5,4-d]pyrimidine-5,7-diamine (Compound 21)

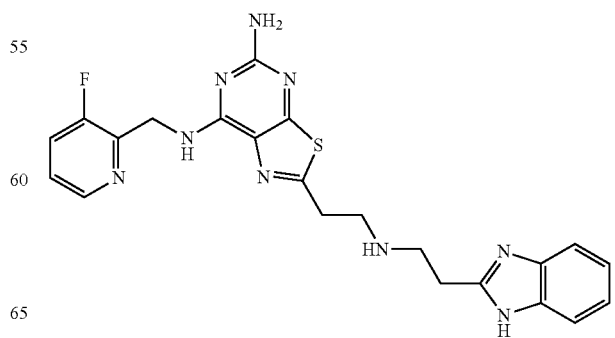

Scheme 22 depicts a synthetic route for preparing an exemplary compound.
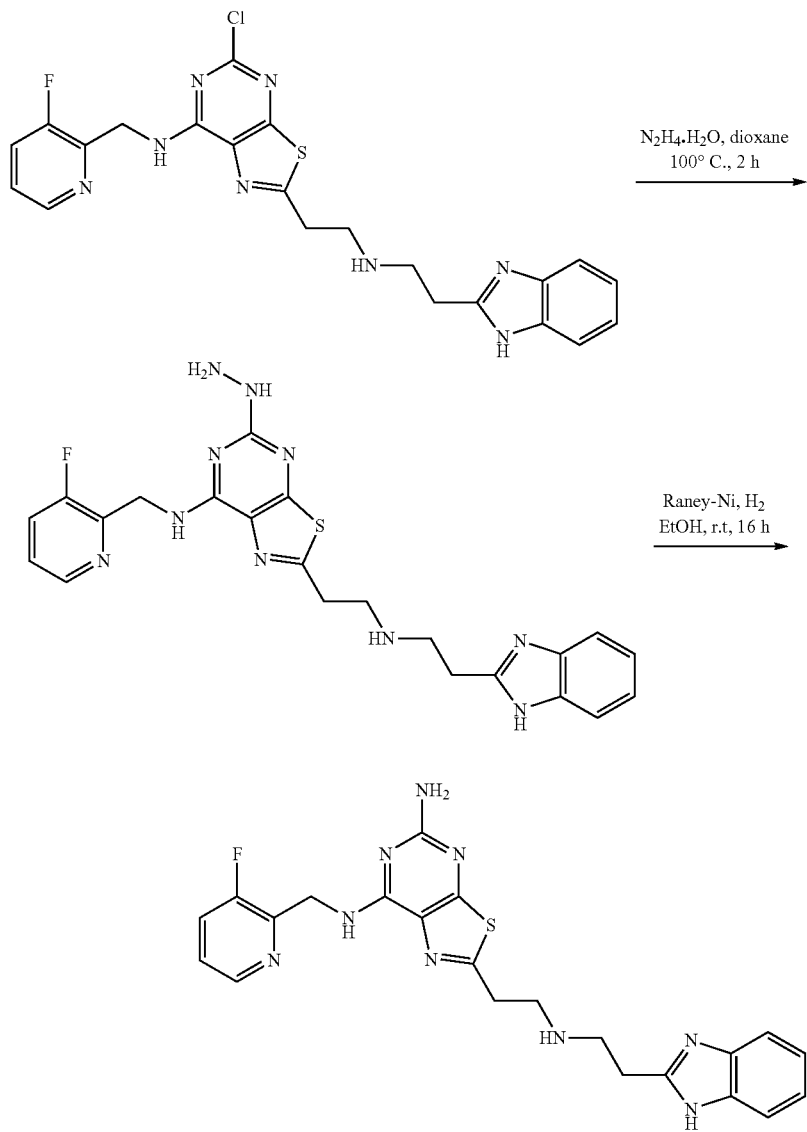
Step 1
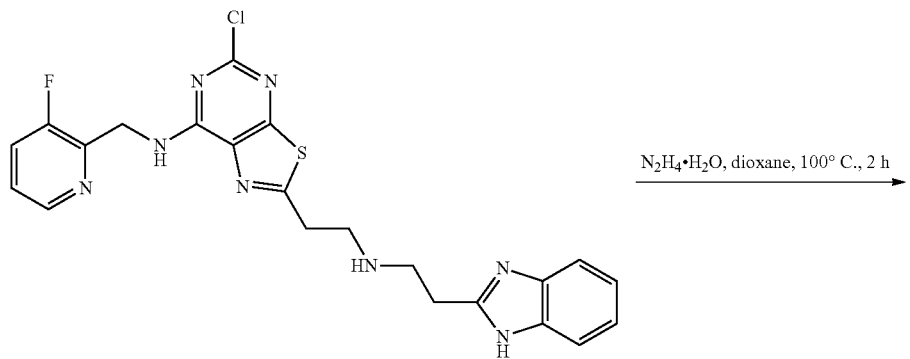

-continued

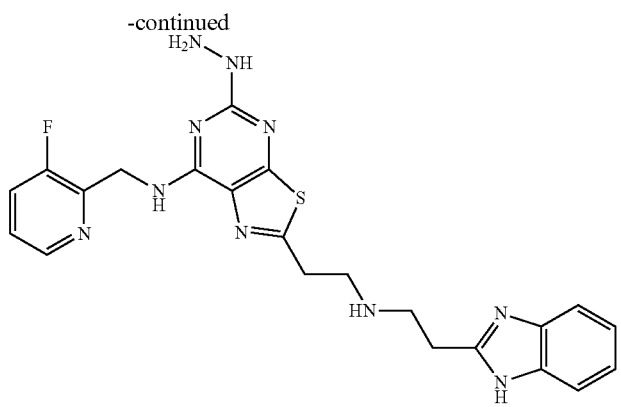

Into a 100-mL round-bottom flask was placed 2-(2-[[2-(1H-1,3-benzodiazol-2-yl)ethyl]amino]ethyl)-5-chloro-N-[(3-fluoropyridin-2-yl)methyl]-[1,3]thiazolo[5,4-d]pyrimidin-7-amine (500 mg, 1.03 mmol, 1.00 equiv), dioxane (5.00 mL), and hydrazine hydrate (518 mg, 10.35 mmol, 10.00 equiv). The resulting solution was stirred for 2 hr at 100° C., cooled, and concentrated. This resulted in 270 mg (54.5%) of 2-(2-[[2-(1H-1,3-benzodiazol-2-yl)ethyl]amino]ethyl)-N-[(3-fluoropyridin-2-yl)methyl]-5-hydrazinyl-[1,3]thiazolo[5,4-d]pyrimidin-7-amine as a light yellow oil without further purification. [M+1]$^+$ m/z: 197.9.

Step 2

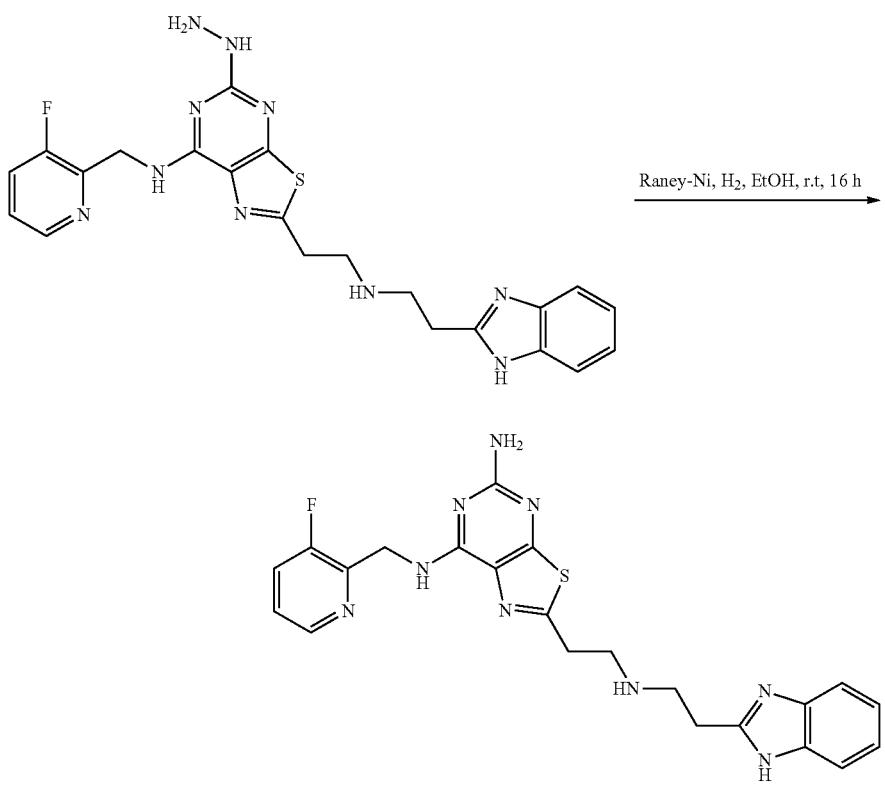

Into a 50-mL pressure tank reactor was placed 2-(2-((2-(1H-benzo[d]imidazol-2-yl)ethyl)amino)ethyl)-N-((3-fluoropyridin-2-yl)methyl)-5-hydrazineylthiazolo[5,4-d]pyrimidin-7-amine (200 mg, 0.41 mmol, 1.00 equiv), EtOH (10.00 mL), and Raney Ni (50 mg). The resulting solution was stirred for 16 hr at room temperature under an H$_2$ atmosphere (10 atm), filtered, and concentrated. The crude product was purified by Prep-HPLC with the following conditions: Column, XBridge Prep C$^{18}$ OBD Column, 19*150 mm 5 um; mobile phase, Water (0.1% TFA) and ACN (30% Phase B up to 40% in 7 min); Detector, UV 254 nm. This resulted in 52.5 mg (27.1%) of 2-(2-((2-(1H-benzo[d]imidazol-2-yl)ethyl)amino)ethyl)-N7-((3-fluoropyridin-2-yl)methyl)thiazolo[5,4-d]pyrimidine-5,7-diamine as a white solid. $^1$H NMR (300 MHz, DMSO-d$_6$) δ 8.36 (dt, J=4.8, 1.5 Hz, 1H), 7.72 (ddd, J=10.0, 8.3, 1.3 Hz, 1H), 7.65 (dd, J=6.1, 3.2 Hz, 2H), 7.41 (dt, J=8.6, 4.5 Hz, 1H), 7.36 (dd, J=6.2, 3.2 Hz, 2H), 4.84 (d, J=5.5 Hz, 2H), 3.62 (t, J=7.1 Hz, 2H), 3.53 (d, J=6.8 Hz, 2H), 3.44 (t, J=6.5 Hz, 4H). [M+1]$^+$ m/z: 464.2.

Example 1.33
Synthesis of 3-[3-(but-3-yn-1-yl)-3H-diazirin-3-yl]-N-[2-(2-{[2-(7-{[(3-fluoropyridin-2-yl)methyl]amino}-[1,3]thiazolo[5,4-d]pyrimidin-2-yl)ethyl]amino}ethyl)-1H-1,3-benzodiazol-5-yl]propanamide (Compound 22)
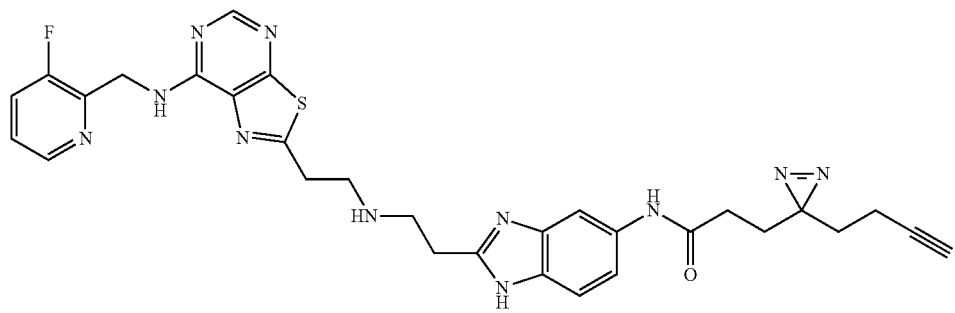
Scheme 23 depicts a synthetic route for preparing an exemplary compound.
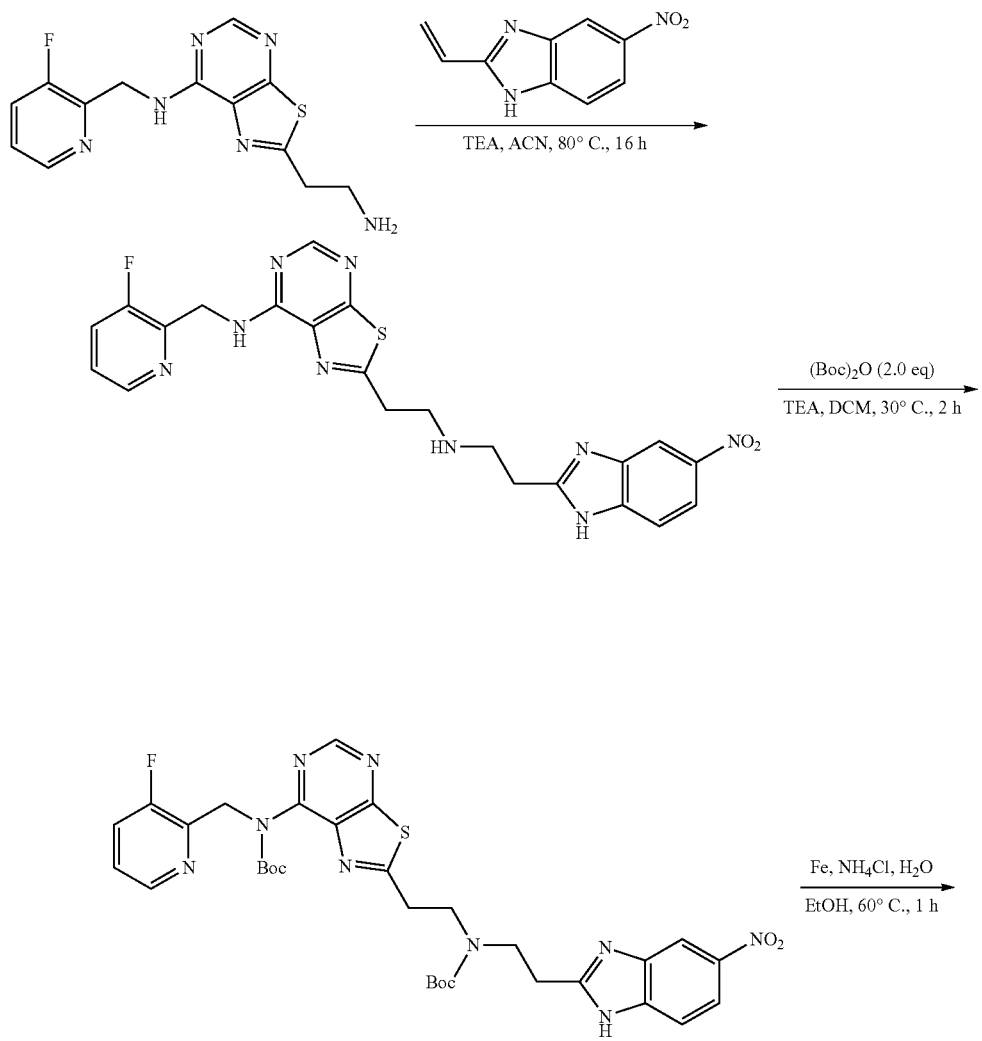

175 176
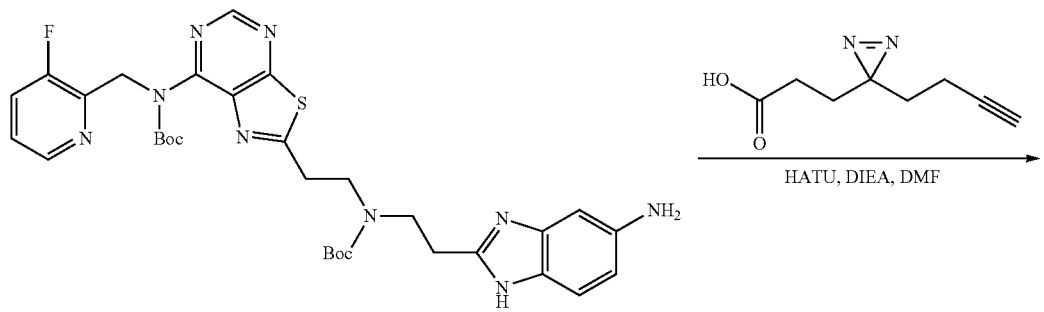
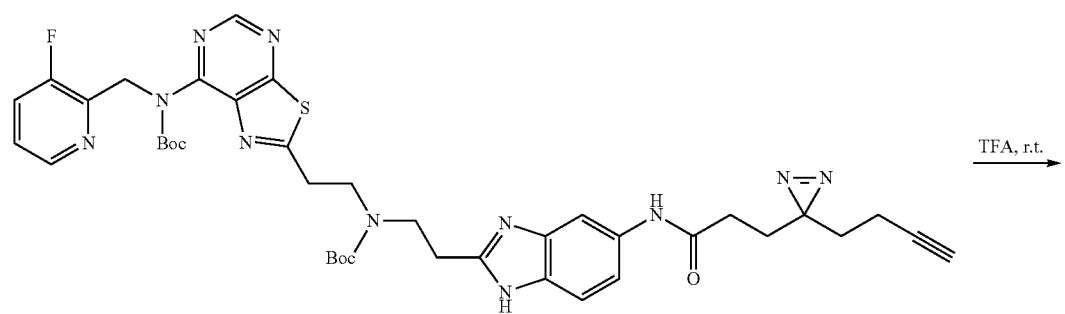
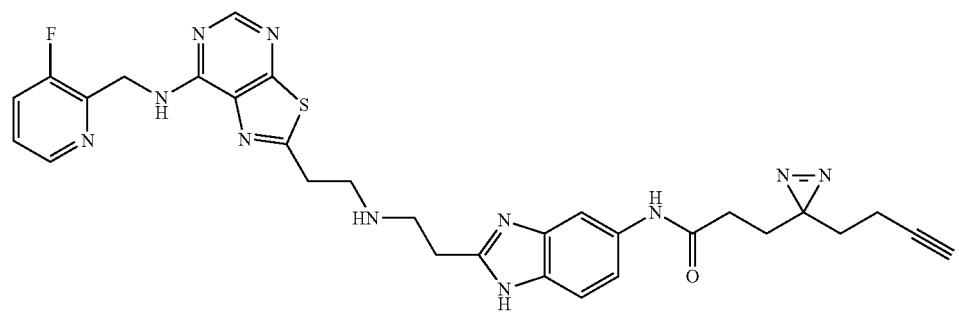 [SMILES: C#CCCC1(CCC(=O)Nc2ccc3[nH]c(CCNCCc4nc5c(NCc6ncccc6F)ncnc5s4)nc3c2)N=N1]

Step 1:

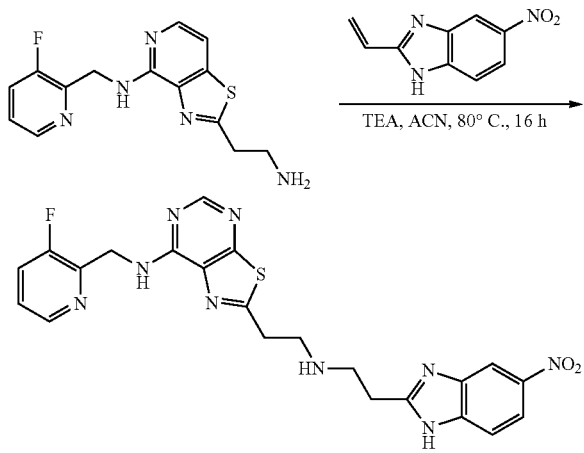

Into a 40-mL vial, was placed 2-(2-aminoethyl)-N-[(2-fluorophenyl)methyl]-[1,3]thiazolo[5,4-d]pyrimidin-7-amine (460 mg, 1.516 mmol, 1 equiv), 2-ethenyl-5-nitro-1H-1,3-benzodiazole (286.85 mg, 1.516 mmol, 1.00 equiv), TEA (306.88 mg, 3.033 mmol, 2.0 equiv), and ACN (10 mL, 190.247 mmol, 125.46 equiv). The resulting solution was stirred for 16 hr at 80° C. in an oil bath. The resulting mixture was concentrated under vacuum. The residue was applied onto a silica gel column with ethyl acetate/petroleum ether (1:1). This resulted in 190 mg (25.44%) of N-[(2-fluorophenyl)methyl]-2-(2-[[2-(5-nitro-1H-1,3-benzodiazol-2-yl)ethyl]amino]ethyl)-[1,3]thiazolo[5,4-d]pyrimidin-7-amine as a brown solid. LCMS (ES) [M+1]$^+$ m/z: 494

Step 2:

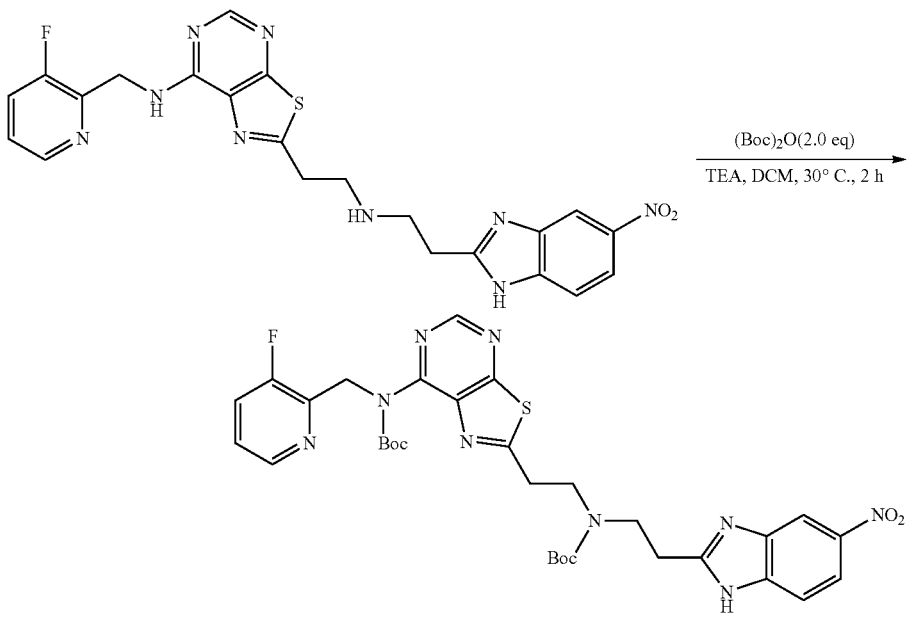

Into a 40-mL vial, was placed N-[(3-fluoropyridin-2-yl)methyl]-2-(2-[[2-(5-nitro-1H-1,3-benzodiazol-2-yl)ethyl]amino]ethyl)-[1,3]thiazolo[5,4-d]pyrimidin-7-amine (190 mg, 0.386 mmol, 1 equiv), DCM (20 mL, 314.601 mmol, 815.53 equiv), TEA (156.14 mg, 1.543 mmol, 4.0 equiv), and Boc$_2$O (168.38 mg, 0.772 mmol, 2.00 equiv). The resulting solution was stirred for 2 hr at 30° C. The reaction was then quenched by the addition of 50 mL of water/ice. The resulting solution was extracted with 3×20 mL of dichloromethane; the organic layer was combined, dried over anhydrous sodium sulfate, and concentrated under vacuum. The residue was applied onto a silica gel column with dichloromethane/methanol (10:1). This resulted in 240 mg (89.81%) of tert-butyl N-[2-(7-[[(tert-butoxy)carbonyl][(3-fluoropyridin-2-yl)methyl]amino]-[1,3]thiazolo[5,4-d]pyrimidin-2-yl)ethyl]-N-[2-(5-nitro-1H-1,3-benzodiazol-2-yl)ethyl]carbamate as a yellow solid. LCMS (ES) [M+1]$^+$ m/z: 694

Step 3

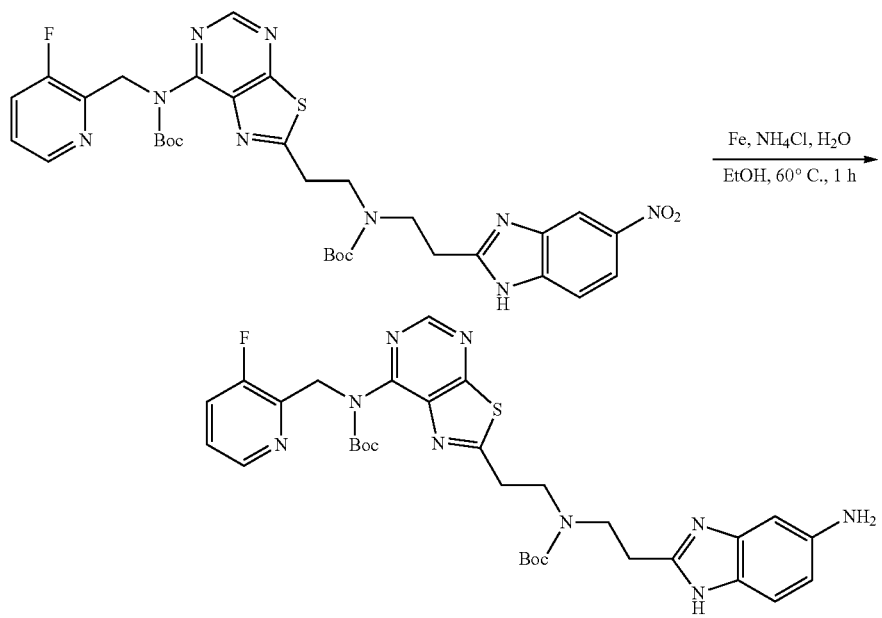

Into a 100-mL round-bottom flask, was placed tert-butyl N-[2-(7-[[(tert-butoxy)carbonyl][(3-fluoropyridin-2-yl) methyl]amino]-[1,3]thiazolo[5,4-d]pyrimidin-2-yl)ethyl]-N-[2-(5-nitro-1H-1,3-benzodiazol-2-yl)ethyl]carbamate (240 mg, 0.346 mmol, 1 equiv), Fe (58.04 mg, 1.039 mmol, 3.00 equiv), NH$_4$Cl (55.59 mg, 1.039 mmol, 3.0 equiv), water (5 mL), and EtOH (5 mL). The resulting solution was stirred for 1 hr at 60° C. in an oil bath. The reaction was then quenched by the addition of 50 mL of water/ice. The resulting solution was extracted with 3×20 mL of ethyl acetate and the organic layer was combined. The resulting mixture was washed with 1×20 mL of Brine. The mixture was dried over anhydrous sodium sulfate and concentrated under vacuum. The residue was applied onto a silica gel column with dichloromethane/methanol (10:1). This resulted in 154 mg (67.07%) of tert-butyl N-[2-(5-amino-1H-1,3-benzodiazol-2-yl)ethyl]-N-[2-(7-[[(tert-butoxy)carbonyl][(3-fluoropyridin-2-yl)methyl]amino]-[1,3]thiazolo [5,4-d]pyrimidin-2-yl)ethyl]carbamate as a yellow solid. LCMS (ES) [M+1]$^+$ m/z: 664.

Step 4

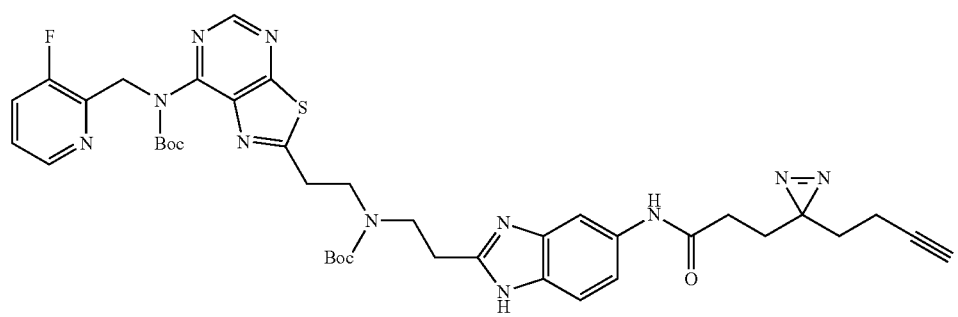

Into a 40-mL vial, was placed tert-butyl N-[2-(5-amino-1H-1,3-benzodiazol-2-yl)ethyl]-N-[2-(7-[[(tert-butoxy)carbonyl][(3-fluoropyridin-2-yl)methyl]amino]-[1,3]thiazolo[5,4-d]pyrimidin-2-yl)ethyl]carbamate (154 mg, 0.232 mmol, 1 equiv), 3-[3-(but-3-yn-1-yl)-3H-diazirin-3-yl]propanoic acid (38.61 mg, 0.232 mmol, 1.00 equiv), DMF (4 mL), DIEA (60.06 mg, 0.465 mmol, 2.0 equiv), and HATU (132.52 mg, 0.349 mmol, 1.5 equiv). The resulting solution was stirred for 2 hr at 25° C. The reaction was then quenched by the addition of 0.5 mL of water. The crude product (5 mL) was purified by Flash-Prep-HPLC with the following conditions (IntelFlash-1): Column, C18 silica gel; mobile phase, ACN/water (0.5% NH$_3$H$_2$O)=45/55 increasing to ACN/water (0.5% NH$_3$H$_2$O)=75/25 within 7; Detector, UV 254 nm. This resulted in 115 mg (61.03%) of tert-butyl N-[2-(5-[3-[3-(but-3-yn-1-yl)-3H-diazirin-3-yl]propanamido]-1H-1,3-benzodiazol-2-yl)ethyl]-N-[2-(7-[[(tert-butoxy)carbonyl][(3-fluoropyridin-2-yl)methyl]amino]-[1,3]thiazolo[5,4-d]pyrimidin-2-yl)ethyl]carbamate as a yellow solid. LCMS (ES) [M+1]$^+$ m/z: 812.

Step 5 yl)ethyl]-N-[2-(7-[[(tert-butoxy)carbonyl][(3-fluoropyridin-2-yl)methyl]amino]-[1,3]thiazolo[5,4-d]pyrimidin-2-yl)ethyl]carbamate (100 mg, 0.123 mmol, 1 equiv), and TFA (2 mL). The resulting solution was stirred for 1 hr at room temperature. The reaction mixture was poured into 5 mL of ice water, and then adjusted to pH 8 with saturated aqueous sodium bicarbonate. The resulting solution was extracted with 3×10 mL of DCM. The organic layers were combined, washed with sodium carbonate (aq.) and brine, dried, and concentrated under vacuum. The crude reaction mixture was filtered and subjected to reverse preparative HPLC (Prep-C18, 5 mM XBridge column, 19×150 mm, waters; gradient elution of 35% MeCN in water to 50% MeCN in water over a 7 min period, where the aqueous phase contains 10 uM NH$_4$HCO$_3$+0.5% ammonia) to provide 14.7 mg (19.27%) of 3-[3-(but-3-yn-1-yl)-3H-diazirin-3-yl]-N-[2-(2-[[2-(7-[[(3-fluoropyridin-2-yl)methyl]amino]-[1,3]thiazolo[5,4-d]pyrimidin-2-yl)ethyl]amino]ethyl)-1H-1,3-benzodiazol-5-yl]propanamide as a white solid. $^1$H NMR (300 MHz, DMSO-d$_6$) δ 12.05 (br, 1H), 9.85 (d, J=14.9 Hz, 1H), 8.34 (s, 1H), 8.32 (d, J=8.4 Hz, 2H), 7.87 (d, J=12.8 Hz, 1H), 7.70 (ddd,

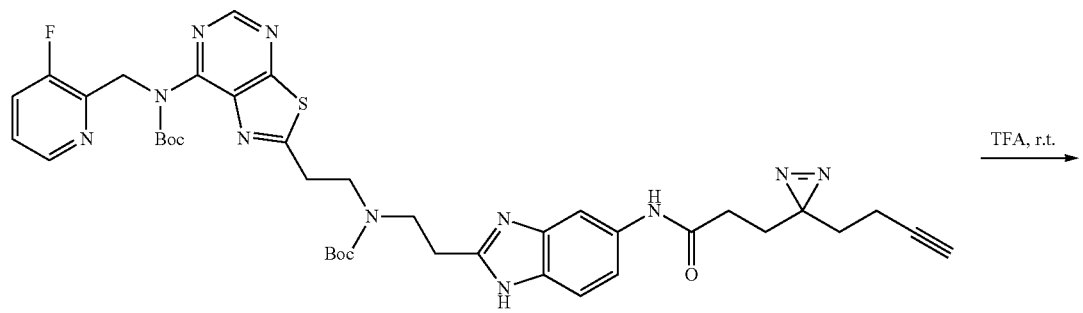

Into a 25-mL round-bottom flask, was placed tert-butyl N-[2-(5-[3-[3-(but-3-yn-1-yl)-3H-diazirin-3-yl]propanamido]-1H-1,3-benzodiazol-2-yl)ethyl]-N-[2-(7-[[(tert-butoxy)carbonyl] [(3-fluoropyridin-2-yl)methyl]amino]-[1,3]thiazolo[5,4-d]pyrimidin-2-yl)ethyl]carbamate (100 mg, 0.123 mmol, 1 equiv) tert-butyl N-[2-(5-[3-[3-(but-3-yn-1-yl)-3H-diazirin-3-yl]propanamido]-1H-1,3-benzodiazol-2-

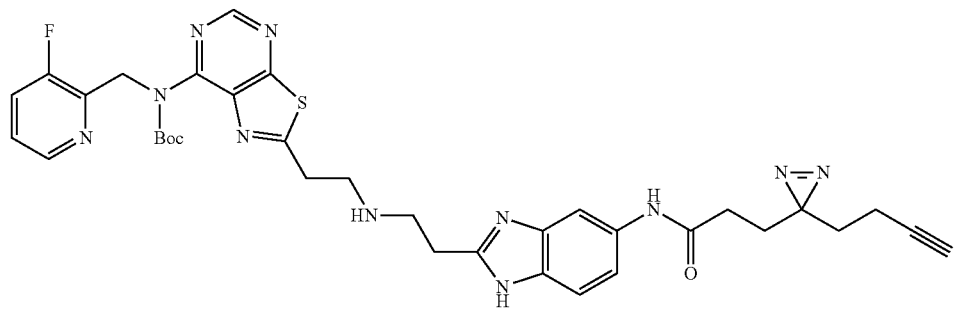

J=10.1, 8.3, 1.4 Hz, 1H), 7.39 (dt, J=8.7, 4.5 Hz, 1H), 7.33 (s, 1H), 7.14 (s, 1H), 4.88 (s, 2H), 3.81-3.53 (m, 2H), 3.35-3.21 (m, 2H), 3.07-2.91 (m, 5H), 2.84 (t, J=2.6 Hz, 1H), 2.14 (dd, J=8.6, 6.7 Hz, 2H), 2.03 (td, J=7.4, 2.7 Hz, 2H), 1.77 (dd, J=8.7, 6.7 Hz, 2H), 1.62 (t, J=7.4 Hz, 2H). LCMS (ES) [M+1]$^+$ m/z: 612.

Example 1.34
Synthesis of 2-(2-{[2-(1H-1,3-benzodiazol-2-yl)ethyl]amino}ethyl)-7-{[(3-fluoropyridin-2-yl)methyl]amino}-[1,3]thiazolo[5,4-d]pyrimidin-5-ol (Compound 23)
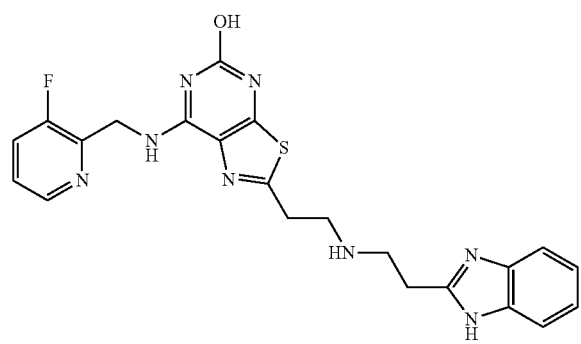 [SMILES: Oc1nc(NCc2ncccc2F)c2nc(CCNCCc3nc4ccccc4[nH]3)sc2n1]
Scheme 24 depicts a synthetic route for preparing an exemplary compound.
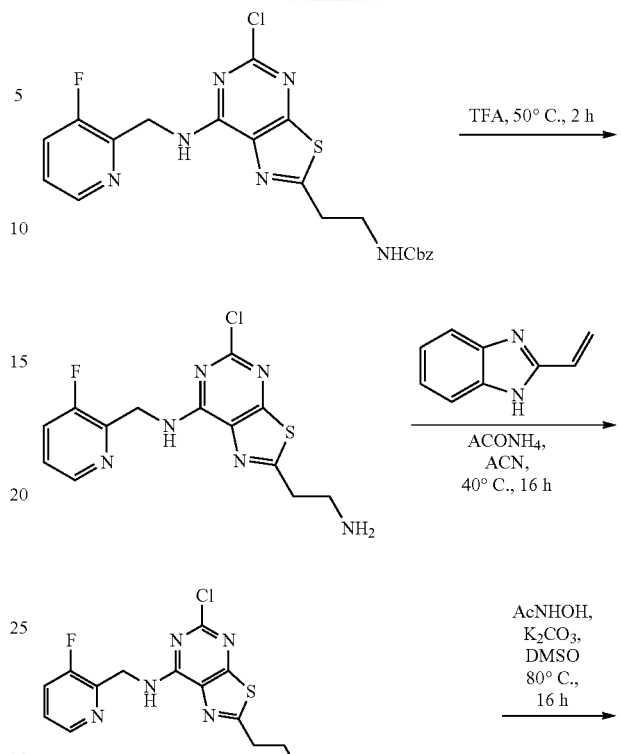
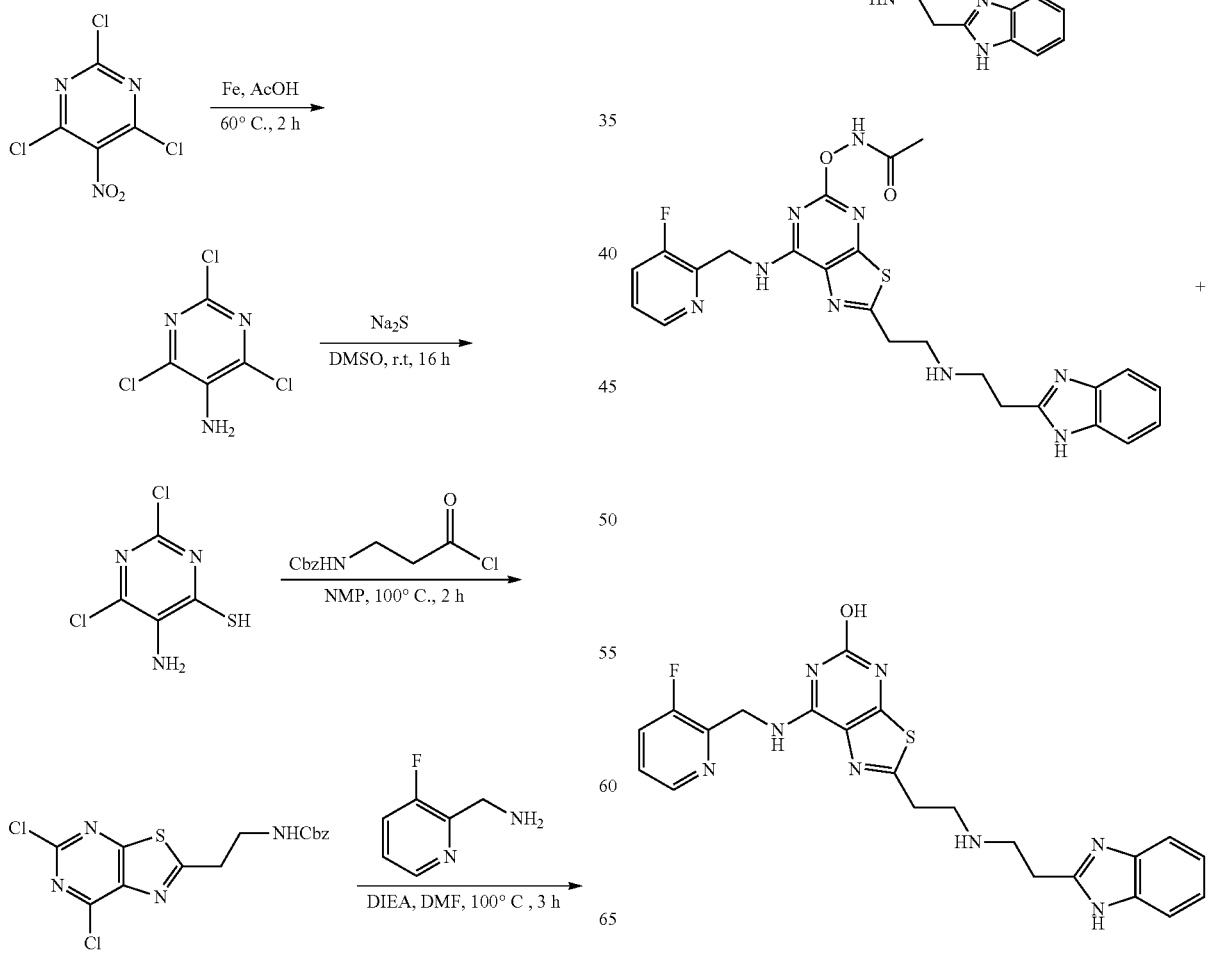

Step 1:

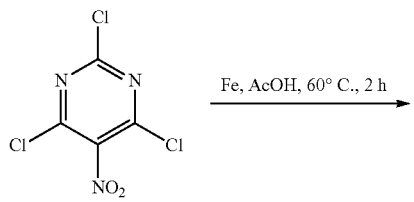

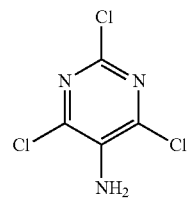

Into a 500-mL round-bottom flask, was placed 2,4,6-trichloro-5-nitropyrimidine (20.00 g, 87.56 mmol, 1.00 equiv), EtOH (300.00 mL), and Fe (19.56 g, 350.24 mmol, 4.00 equiv). This was followed by the addition of AcOH (10.52 g, 175.12 mmol, 2.00 equiv) dropwise with stirring. The resulting solution was stirred for 2 hr at 60° C., cooled down, and diluted with 500 mL of $H_2O$. The pH value of the solution was adjusted to 7 with $NaHCO_3$ (10%). The solids were filtered out. The resulting solution was extracted with 3×200 mL of ethyl acetate and the organic layers combined and dried over anhydrous sodium sulfate and concentrated. The residue was applied onto a silica gel column with ethyl acetate/petroleum ether (1/3). This resulted in 8.0 g (46.0%) of 2,4,6-trichloropyrimidin-5-amine as a white solid. $[M+1]^+$ m/z: 197.9.

Step 2

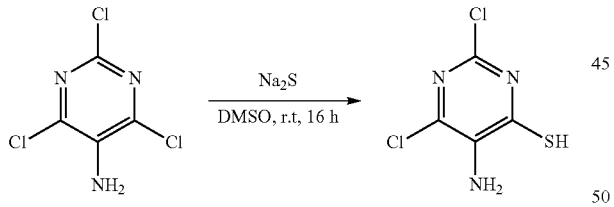

Into a 500-mL round-bottom flask, was placed 2,4,6-trichloropyrimidin-5-amine (8.00 g, 40.31 mmol, 1.00 equiv), DMSO (100 mL), and disodium sulfane (3.23 g, 40.31 mmol, 1.00 equiv). The resulting solution was stirred for 16 hr at room temperature, and diluted with 200 mL of $H_2O$. The resulting solution was extracted with 2×100 mL of ethyl acetate and the aqueous layers were combined. The pH value of the solution was adjusted to 2 with conc.HCl. The resulting solution was extracted with 2×100 mL of ethyl acetate and the organic layers were combined and dried over anhydrous sodium sulfate and concentrated. This resulted in 5.0 g (63.2%) of 5-amino-2,6-dichloropyrimidine-4-thiol as a yellow solid. $[M+1]^+$ m/z: 195.9

Step 3

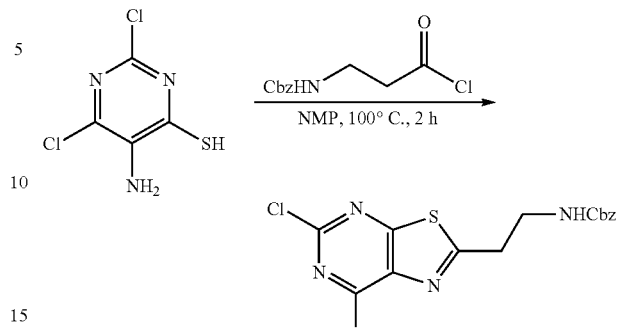

Into a 250-mL round-bottom flask, was placed 5-amino-2,6-dichloropyrimidine-4-thiol (5.00 g, 25.50 mmol, 1.00 equiv), NMP (60.00 mL), and benzyl N-(3-chloro-3-oxo-propyl)carbamate (9.25 g, 38.25 mmol, 1.50 equiv). The resulting solution was stirred for 2 hr at 100° C., cooled down, and diluted with 100 mL of $H_2O$. The resulting solution was extracted with 3×100 mL of ethyl acetate and the organic layers were combined and dried over anhydrous sodium sulfate and then concentrated. The residue was applied onto a silica gel column with ethyl acetate/petroleum ether (1/4). This resulted in 4.0 g (40.9%) of benzyl (2-(5,7-dichlorothiazolo[5,4-d]pyrimidin-2-yl)ethyl)carbamate as a light yellow solid. $[M+1]^+$ m/z: 383.0.

Step 4

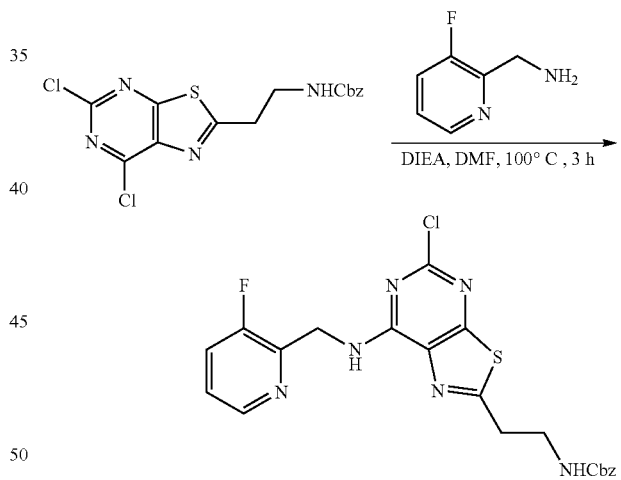

Into a 100-mL round-bottom flask, was placed benzyl (2-(5,7-dichlorothiazolo[5,4-d]pyrimidin-2-yl)ethyl)carbamate (4.00 g, 10.43 mmol, 1.00 equiv), DMF (50.00 mL), DIEA (2.70 g, 20.87 mmol, 2.00 equiv), and 1-(3-fluoro-pyridin-2-yl)methanamine (1.58 g, 12.52 mmol, 1.20 equiv). The resulting solution was stirred for 3 hr at 100° C., cooled down, and diluted with 100 mL of $H_2O$. The resulting solution was extracted with 3×50 mL of ethyl acetate and the organic layers were combined and dried in an oven under reduced pressure, and then concentrated. The residue was applied onto a silica gel column with ethyl acetate/petroleum ether (5/1). This resulted in 2.9 g (58.7%) of benzyl (2-(5-chloro-7-(((3-fluoropyridin-2-yl)methyl)amino)thiazolo[5,4-d]pyrimidin-2-yl)ethyl)carbamate as a light yellow solid. $[M+1]^+$ m/z: 473.1

Step 5

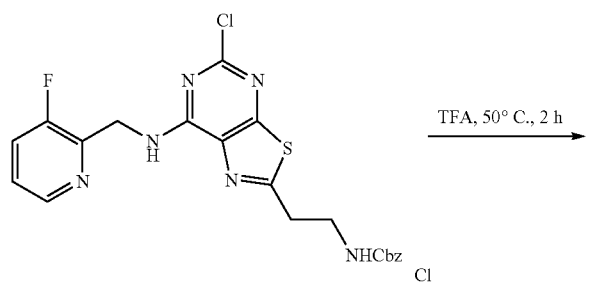

Into a 100-mL round-bottom flask, was placed benzyl (2-(5-chloro-7-(((3-fluoropyridin-2-yl)methyl)amino)thiazolo[5,4-d]pyrimidin-2-yl)ethyl)carbamate (2.90 g, 6.13 mmol, 1.00 equiv) and TFA (30.00 mL). The resulting solution was stirred for 2 hr at 50° C., cooled down, and diluted with 50 mL of H$_2$O. The pH value of the solution was adjusted to 8 with NaOH (10%). The crude product was purified by Flash-Prep-HPLC with the following conditions (IntelFlash-1): Column, C18 silica gel; mobile phase, H$_2$O (0.1% NH$_3$.H$_2$O)/ACN=10/1 increasing to H$_2$O (0.1% NH$_3$.H$_2$O)/ACN=3/1 within 15 min; Detector, UV. This resulted in 1.6 g (77.0%) of 2-(2-aminoethyl)-5-chloro-N-((3-fluoropyridin-2-yl)methyl)thiazolo[5,4-d]pyrimidin-7-amine as a light yellow oil. [M+1]$^+$ m/z: 339.1

Step 6

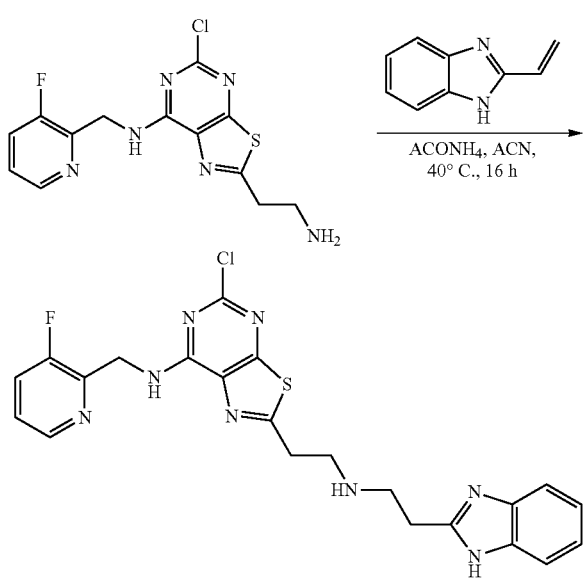

Into a 100-mL round-bottom flask, was placed 2-(2-aminoethyl)-5-chloro-N-((3-fluoropyridin-2-yl)methyl)thiazolo[5,4-d]pyrimidin-7-amine (1.60 g, 4.72 mmol, 1.00 equiv), ACN (20 mL), 2-ethenyl-1H-1,3-benzodiazole (0.68 g, 4.72 mmol, 1.00 equiv), and AcONH$_4$ (0.73 g, 9.44 mmol, 2.00 equiv). The resulting solution was stirred for 16 hr at 40° C., cooled down, and diluted with 20 mL of MeOH. The crude product was purified by Flash-Prep-HPLC with the following conditions (IntelFlash-1): Column, C18 silica gel; mobile phase, H$_2$O (0.1% HCOOH)/ACN=10/1 increasing to H$_2$O (0.1% HCOOH)/ACN=3/1 within 12 min; Detector, UV. This resulted in 980 mg (42.9%) of 2-(2-((2-(1H-benzo[d]imidazol-2-yl)ethyl)amino)ethyl)-5-chloro-N-((3-fluoropyridin-2-yl)methyl)thiazolo[5,4-d]pyrimidin-7-amine as a yellow solid. [M+1]$^+$ m/z: 483.1

Step 7

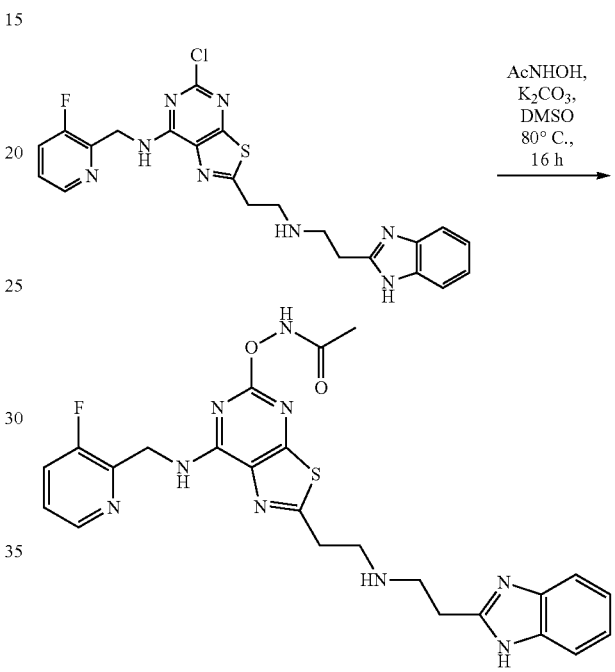

Into a 50-mL round-bottom flask, was placed 2-(2-((2-(1H-benzo[d]imidazol-2-yl)ethyl)amino)ethyl)-5-chloro-N-((3-fluoropyridin-2-yl)methyl)thiazolo[5,4-d]pyrimidin-7-amine (650.00 mg, 1.34 mmol, 1.00 equiv), DMSO (10.00 mL), K$_2$CO$_3$ (1.30 g, 9.421 mmol, 7.00 equiv), and N-hydroxyacetamide (303 mg, 4.03 mmol, 3.00 equiv). The resulting solution was stirred for 16 hr at 80° C., cooled down, and filtered. The crude product was purified by Prep-HPLC with the following conditions (Prep-HPLC-006): Column, XBridge Prep C$^{18}$ OBD Column, 19*150 mm 5 um; mobile phase, Water (10 MMOL/L NH$_4$HCO$_3$+0.1% NH$_3$.H$_2$O) and ACN (30% Phase B up to 40% in 7 min);

Detector, UV 254 nm. This resulted in 20.9 mg (3.0%) of N-((2-(2-((2-(1H-benzo[d]imidazol-2-yl)ethyl)amino)ethyl)-7-(((3-fluoropyridin-2-yl)methyl)amino)thiazolo[5,4-d]pyrimidin-5-yl)oxy)acetamide as a white solid and 101.3 mg (16.2%) of 2-(2-((2-(1H-benzo[d]imidazol-2-yl)ethyl)amino)ethyl)-7-(((3-fluoropyridin-2-yl)methyl)amino)thiazolo[5,4-d]pyrimidin-5-ol as a white solid. $^1$H NMR (300 MHz, DMSO-$d_6$) δ 8.37 (dt, J=4.7, 1.5 Hz, 1H), 8.19 (s, 1H), 7.71 (ddd, J=10.1, 8.4, 1.3 Hz, 1H), 7.50-7.34 (m, 3H), 7.10 (dd, J=6.0, 3.2 Hz, 2H), 4.79 (d, J=5.0 Hz, 2H), 3.15-2.89 (m, 8H). [M+1]$^+$ m/z: 465.2

Example 1.35

Synthesis of 2-(1-{[2-(1H-1,3-benzodiazol-2-yl)ethyl]amino}propan-2-yl)-N-[(3-fluoropyridin-2-yl)methyl]-[1,3]thiazolo[5,4-d]pyrimidin-7-amine (Compound 24)

Scheme 25 depicts a synthetic route for preparing an exemplary compound.

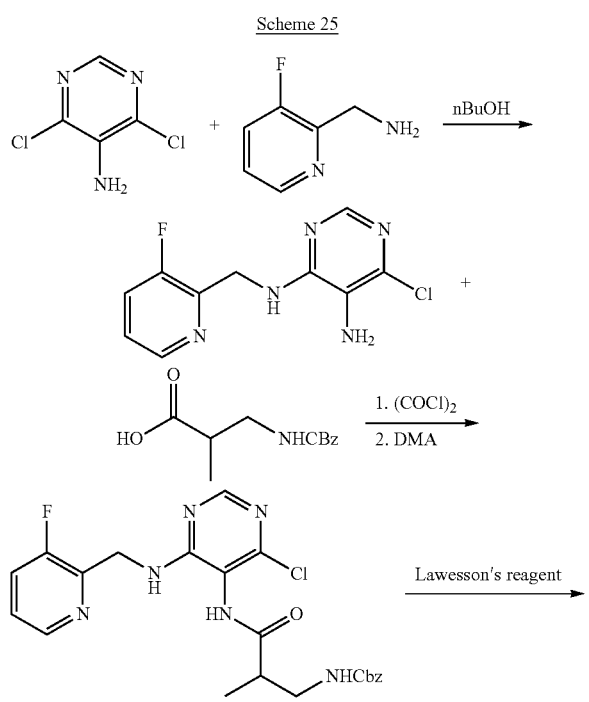

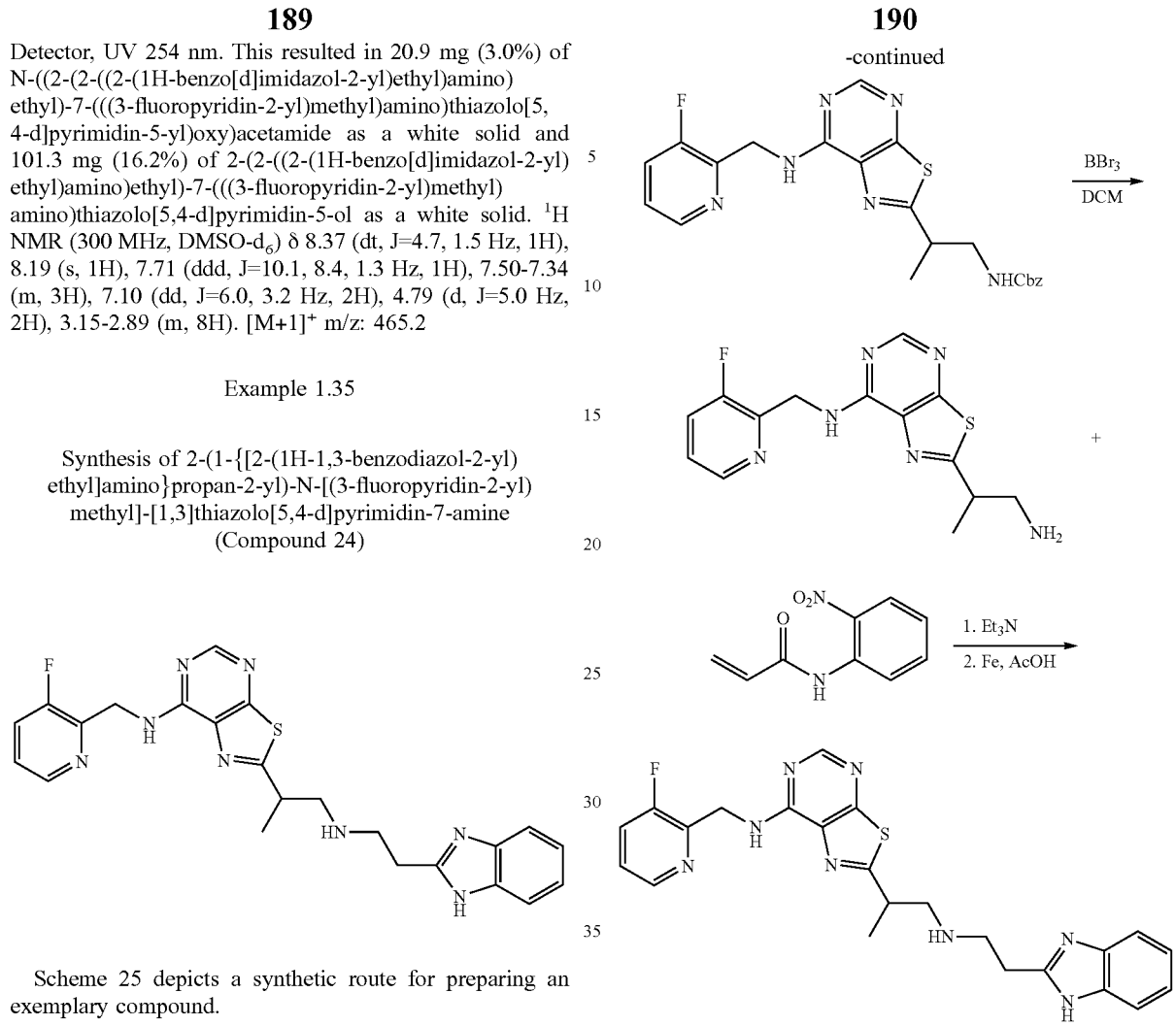

Step 1:

To a solution of 4,6-dichloro-5-pyrimidinamine (500.00 mg; 3.05 mmol; 1.00 eq.) and (3-fluoropyridin-2-yl)methanamine bis hydrogen chloride salt (769.39 mg 1213.79 mg; 6.10 mmol; 2.00 eq.) in nBuOH (10 mL) was added triethylamine (1.70 mL; 12.20 mmol; 4.00 eq.) and the mixture was heated in a microwave oven at 150° C. for 1 h. The mixture was cooled and diluted with water, and the resulting precipitates were collected by filtration, and dried under high vacuum to give 6-chloro-N4-((3-fluoropyridin-2-yl)methyl)pyrimidine-4,5-diamine (900 mg).

Step 2:

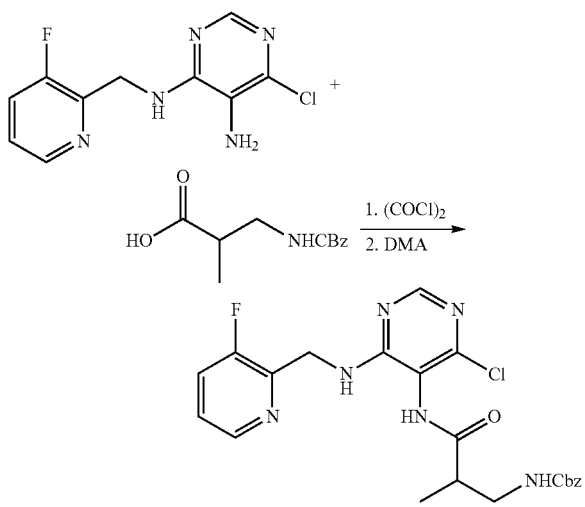

To a solution of 3-{[(benzyloxy)carbonyl]amino}-2-methylpropanoic acid (587.37 mg; 2.48 mmol; 2.00 eq.) (670.00 mg; 2.65 mmol; 2.00 eq.) in DCM (5 mL) was added 5 drops of DMF followed by oxalyl chloride (0.30 mL; 3.47 mmol; 2.80 eq.) at room temperature. The mixture was stirred at room temperature for 1.5 h, and concentrated to give crude acid chloride. The crude acid chloride was diluted with DMA (dimethylacetamide, 4 mL) and 6-chloro-N4-((3-fluoropyridin-2-yl)methyl)pyrimidine-4,5-diamine (314.00 mg; 1.24 mmol; 1.00 eq.) was added. After stirring for 1 h, the mixture was diluted with EtOAc and the Sat. NaHCO₃, organic layer was separated and concentrated. The resulting solid was washed with DCM/Hexane and isolated by filtration to give N-{2-[(4-chloro-6-{[(3-fluoropyridin-2-yl)methyl]amino}pyrimidin-5-yl)carbamoyl]-2-methylethyl}carbamate (330 mg). LCMS [M+1]⁺ m/z: 473.2.

Step 3

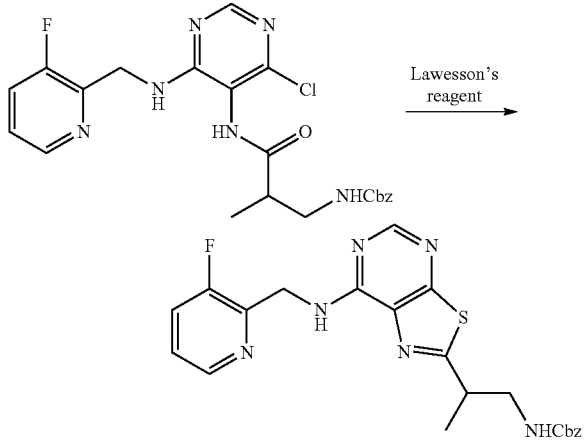

To a solution of benzyl N-{2-[(4-chloro-6-{[(3-fluoropyridin-2-yl)methyl]amino}pyrimidin-5-yl)carbamoyl]-2-methylethyl}carbamate (330.00 mg; 0.70 mmol; 1.00 eq.) in Dioxane (7.5 mL) was added 2,4-bis(4-methoxyphenyl)-1,3,2,4-dithiadiphosphetane 2,4-disulfide (381.03 mg; 0.94 mmol; 1.35 eq.). After degassing and stirring at 95° C. for 2 h, the mixture was cooled and concentrated. The crude residue was purified by column chromatography to give benzyl N-[2-(7-{[(3-fluoropyridin-2-yl)methyl]amino}-[1,3]thiazolo[5,4-d]pyrimidin-2-yl)propyl]carbamate (120 mg)

Step 4

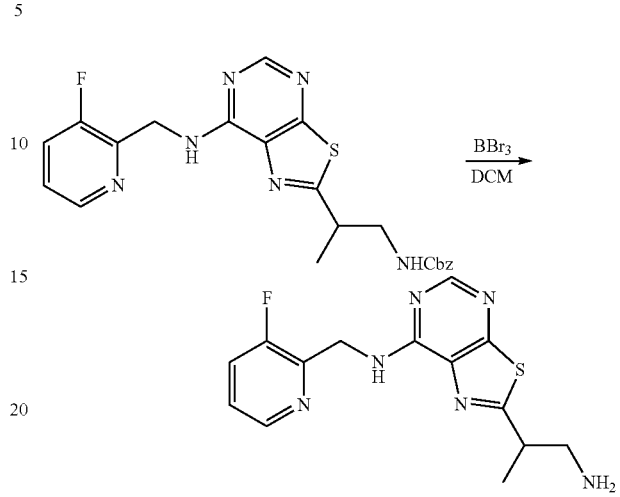

To a solution of benzyl N-[2-(7-{[(3-fluoropyridin-2-yl)methyl]amino}-[1,3]thiazolo[5,4-d]pyrimidin-2-yl)propyl]carbamate (190.00 mg; 0.42 mmol; 1.00 eq.) in DCM (3.5 mL) was added boron tribromide (0.84 mL; 1.00 mol/L; 0.84 mmol; 2.00 eq.). After stirring for 2 h, the mixture was concentrated and washed with ether. The solid was filtered and the filtered solid was diluted with EtOAc and Sat. NaHCO₃. The organic layer was then separated and concentrated to give 2-(1-aminopropan-2-yl)-N-[(3-fluoropyridin-2-yl)methyl]-[1,3]thiazolo[5,4-d]pyrimidin-7-amine as a crude solid, which was used in the next step without purification.

Step 5

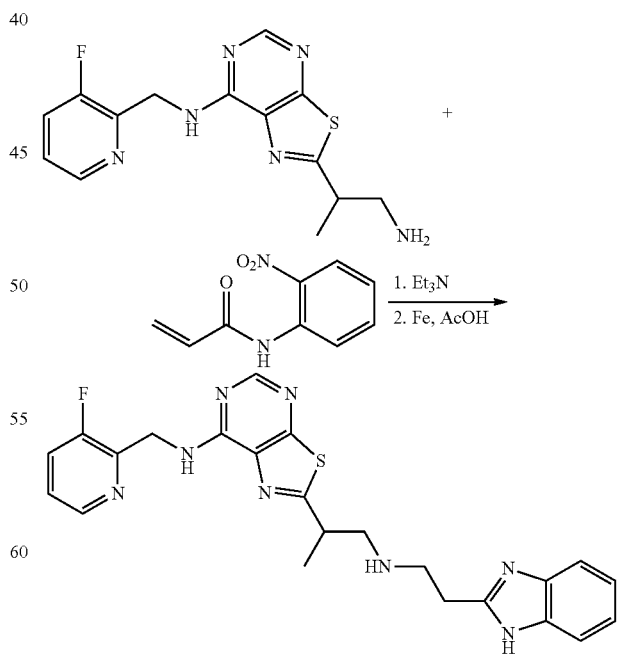

To a suspension of 2-(1-aminopropan-2-yl)-N-[(3-fluoropyridin-2-yl)methyl]-[1,3]thiazolo[5,4-d]pyrimidin-7- amine (120.00 mg; 0.38 mmol; 1.00 eq.) and N-(2-nitrophenyl)prop-2-enamide (72.43 mg; 0.38 mmol; 1.00 eq.) in AcCN (2 mL) was added triethylamine (0.08 mL; 0.57 mmol; 1.50 eq.). The mixture was further stirred at room temperature for 4 h. The mixture was concentrated, the residue diluted with AcOH (2 mL), and then was added iron (210.49 mg; 3.77 mmol; 10.00 eq.). The resulting mixture was heated at 80° C. for 2 h, cooled, and diluted with AcCN and water. Insoluble material was filtered, and the filtrate was subjected to preparative HPLC to give 2-(1-{[2-(1H-1,3-benzodiazol-2-yl)ethyl]amino}propan-2-yl)-N-[(3-fluoropyridin-2-yl)methyl]-[1,3]thiazolo[5,4-d]pyrimidin-7-amine (47.3 mg). $^1$H NMR (400 MHz, DMSO-d$_6$) δ 8.37-8.22 (m, 4H), 7.72-7.63 (m, 1H), 7.39 (dd, J=5.9, 3.2 Hz, 2H), 7.36 (dd, J=8.3, 4.2 Hz, 1H), 7.06 (dt, J=7.0, 3.5 Hz, 2H), 4.86 (d, J=5.5 Hz, 2H), 2.94 (td, J=15.4, 15.0, 7.3 Hz, 6H), 2.05 (s, 0H), 1.37 (d, J=6.9 Hz, 3H). [M+1]$^+$ m/z: 463.1.

Example 1.36

Synthesis of 2-{1-[2-(1H-1,3-benzodiazol-2-yl)ethyl]-3-fluoroazetidin-3-yl}-N-[(3-fluoropyridin-2-yl)methyl]-[1,3]thiazolo[5,4-d]pyrimidin-7-amine (Compound 25)

Compound 25 was synthesized in a similar manner to that of Compound 24, replacing 3-{[(benzyloxy)carbonyl]amino}-2-methylpropanoic acid with 1-[(benzyloxy)carbonyl]-3-fluoroazetidine-3-carboxylic acid. $^1$H NMR (400 MHz, DMSO-d$_6$) δ 12.18 (s, 1H), 8.61 (s, 1H), 8.33 (d, J=20.2 Hz, 2H), 7.69 (ddd, J=9.9, 8.3, 1.3 Hz, 1H), 7.44 (s, 2H), 7.37 (dt, J=8.6, 4.4 Hz, 1H), 7.09 (dt, J=7.3, 3.7 Hz, 2H), 4.89 (d, J=5.8 Hz, 2H), 3.92 (dd, J=19.0, 9.3 Hz, 2H), 3.75 (d, J=9.4 Hz, 1H), 3.70 (d, J=9.5 Hz, 1H), 3.05 (t, J=7.2 Hz, 2H), 2.88 (t, J=7.2 Hz, 2H). [M+1]$^+$ m/z: 477.0.

Example 1.37

Synthesis of 2-[(2R)-2-{[2-(1H-1,3-benzodiazol-2-yl)ethyl]amino}propyl]-N-[(3-fluoropyridin-2-yl)methyl]-[1,3]thiazolo[5,4-d]pyrimidin-7-amine (Compound 26)

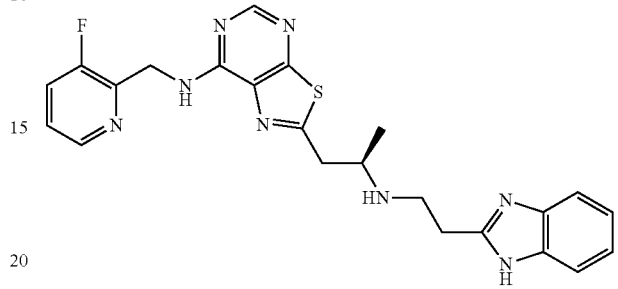

Compound 26 was synthesized in a similar manner to that of Compound 24, replacing 3-{[(benzyloxy)carbonyl]amino}-2-methylpropanoic acid with (3R)-3-{[(benzyloxy)carbonyl]amino}butanoic acid. $^1$H NMR (400 MHz, DMSO-d$_6$) δ 8.30 (d, J=7.6 Hz, 3H), 8.21 (s, 1H), 7.67 (ddd, J=9.9, 8.2, 1.2 Hz, 1H), 7.38 (ddt, J=12.9, 8.5, 3.8 Hz, 3H), 7.07 (dt, J=5.9, 3.5 Hz, 2H), 4.85 (d, J=5.6 Hz, 2H), 3.23-3.10 (m, 4H), 3.10-2.99 (m, 2H), 2.98 (d, J=6.7 Hz, 1H), 1.12 (d, J=4.6 Hz, 3H). [M+1]$^+$ m/z: 463.0.

Example 1.38

Synthesis of Methyl 2-(2-{[2-(7-{[(3-fluoropyridin-2-yl)methyl]amino}-[1,3]thiazolo[5,4-d]pyrimidin-2-yl)ethyl]amino}ethyl)-1H-1,3-benzodiazole-5-carboxylate (Compound 27)

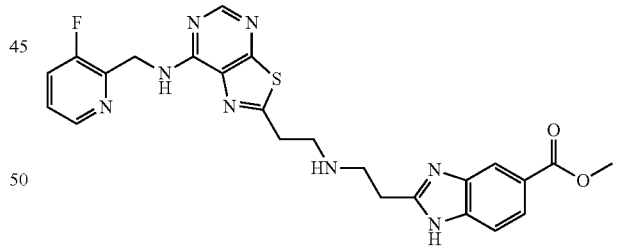

Scheme 26 depicts a synthetic route for preparing an exemplary compound.

Scheme 26

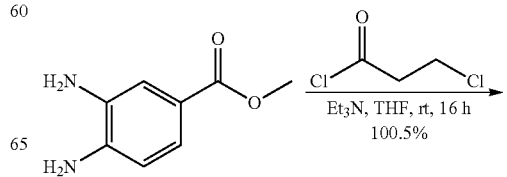

-continued

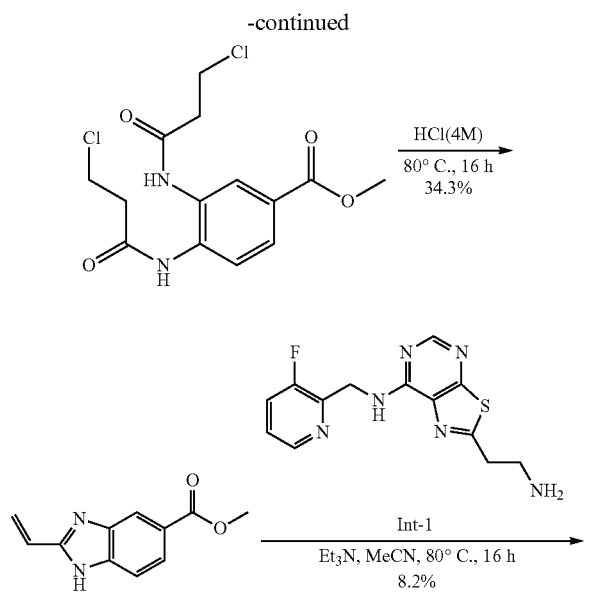

Step 1

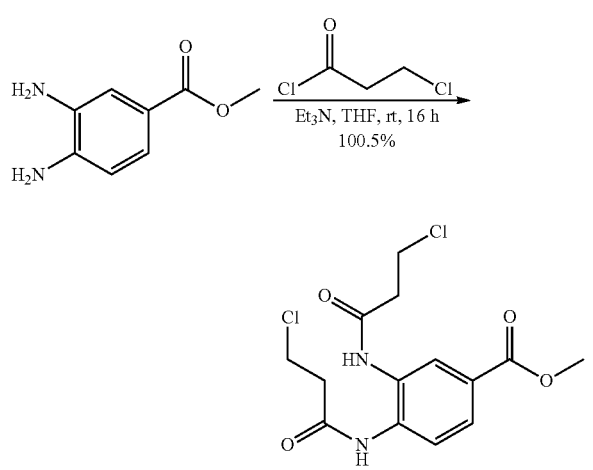

Into a 250-mL round-bottom flask, was placed methyl 3,4-diaminobenzoate (5.00 g, 30.088 mmol, 1.00 equiv), THF (100.00 mL), triethylamine (6.089 g, 60.176 mmol, 2.00 equiv), and 3-chloropropanoyl chloride (11.459 g, 90.264 mmol, 3.00 equiv). The resulting solution was stirred for 16 hr at room temperature. The reaction was then quenched by the addition of 1000 mL of water. The solids were collected by filtration. This resulted in 10.5 g (100.5%) of methyl 3,4-bis(3-chloropropanamido)benzoate as a yellow solid. LCMS (ES) [M+1]$^+$ m/z 347.1.

Step 2

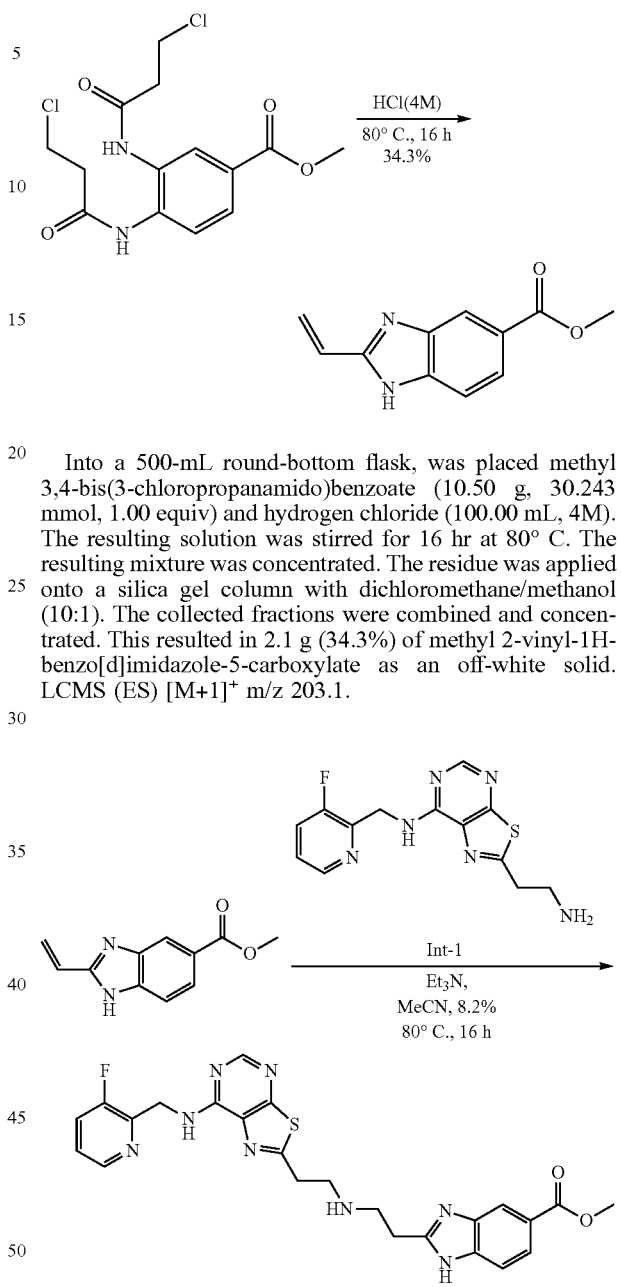

Into a 500-mL round-bottom flask, was placed methyl 3,4-bis(3-chloropropanamido)benzoate (10.50 g, 30.243 mmol, 1.00 equiv) and hydrogen chloride (100.00 mL, 4M). The resulting solution was stirred for 16 hr at 80° C. The resulting mixture was concentrated. The residue was applied onto a silica gel column with dichloromethane/methanol (10:1). The collected fractions were combined and concentrated. This resulted in 2.1 g (34.3%) of methyl 2-vinyl-1H-benzo[d]imidazole-5-carboxylate as an off-white solid. LCMS (ES) [M+1]$^+$ m/z 203.1.

Into a 50-mL round-bottom flask, was placed methyl 2-vinyl-1H-benzo[d]imidazole-5-carboxylate (100.00 mg, 0.495 mmol, 1.00 equiv), triethylamine (150.00 mg, 1.482 mmol, 3.00 equiv), acetonitrile (10.00 mL, 0.731 mmol, 1.48 equiv), and 2-(2-aminoethyl)-N-((3-fluoropyridin-2-yl)methyl)thiazolo[5,4-d]pyrimidin-7-amine (150.50 mg, 0.494 mmol, 1.00 equiv). The resulting solution was stirred for 16 hr at 80° C. The resulting mixture was concentrated. The crude reaction mixture was filtered and subjected to reverse phase preparative HPLC (Prep-C18, 5 uM SunFire column, 19×150 mm, Waters; gradient elution of 20% MeCN in water to 30% MeCN in water over a 10 min period, where both solvents contained 0.1% FA) to provide the title compound as an off-white solid. (22.4 mg, 8.2%). LCMS (ES) [M+1]$^+$ m/z 507.2.

Example 1.39

Synthesis of 2-[(2S)-2-{[2-(1H-1,3-benzodiazol-2-yl)ethyl]amino}propyl]-N-[(3-fluoropyridin-2-yl)methyl]-[1,3]thiazolo[5,4-d]pyrimidin-7-amine (Compound 28)

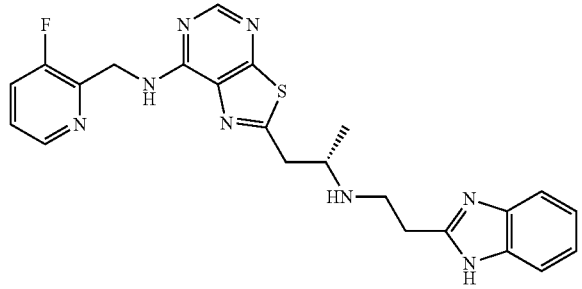

Compound 28 was synthesized in a similar manner to that of Compound 24, replacing 3-{[(benzyloxy)carbonyl]amino}-2-methylpropanoic acid with (3 S)-3-{[(benzyloxy)carbonyl]amino}butanoic acid. $^1$H NMR (400 MHz, DMSO-$d_6$) δ 8.35-8.29 (m, 1H), 8.28 (s, 1H), 8.26 (d, J=5.6 Hz, 1H), 8.19 (s, 1H), 7.68 (ddd, J=10.0, 8.3, 1.3 Hz, 1H), 7.38 (ddt, J=12.8, 8.5, 3.8 Hz, 3H), 7.07 (dd, J=6.0, 3.2 Hz, 2H), 4.85 (d, J=5.6 Hz, 2H), 3.11 (d, J=14.9 Hz, 5H), 3.04-2.92 (m, 3H), 1.09 (d, J=4.9 Hz, 3H). [M+1]$^+$ m/z: 463.0.

Example 1.40

Synthesis of 2-(2-{[2-(1H-1,3-benzodiazol-2-yl)ethyl]amino}-1-fluoroethyl)-N-[(3-fluoropyridin-2-yl)methyl]-[1,3]thiazolo[5,4-d]pyrimidin-7-amine (Compound 30)

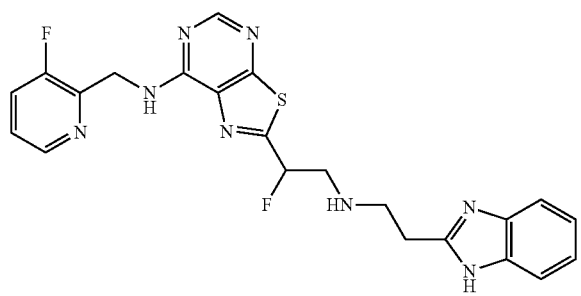 [SMILES: CC(CNCCc1nc2ccccc2[nH]1)c1nc2c(NCc3ncccc3F)ncnc2s1]

Compound 30 was synthesized in a similar manner to that of Compound 24, replacing 3-{[(benzyloxy)carbonyl]amino}-2-methylpropanoic acid with 3-{[(benzyloxy)carbonyl]amino}-2-fluoropropanoic acid. $^1$H NMR (400 MHz, DMSO-$d_6$) δ 8.53 (t, J=5.8 Hz, 1H), 8.35 (s, 1H), 8.31 (d, J=4.7 Hz, 1H), 8.22 (s, 1H), 7.69 (dd, J=10.3, 8.6 Hz, 1H), 7.42 (dd, J=5.9, 3.3 Hz, 1H), 7.37 (dt, J=8.5, 4.4 Hz, 1H), 7.08 (dd, J=6.0, 3.2 Hz, 2H), 6.59 (s, 1H), 6.06 (d, J=5.0 Hz, 1H), 5.95 (s, 1H), 4.88 (d, J=5.7 Hz, 2H), 3.06 (d, J=8.0 Hz, 1H), 2.96 (t, J=6.9 Hz, 2H). [M+1]$^+$ m/z: 467.1.

Example 1.41

Synthesis of 2-(2-{[2-(1H-1,3-benzodiazol-2-yl)ethyl]amino}ethyl)-N-[(3-fluoropyridin-2-yl)methyl]-5-methyl-[1,3]thiazolo[5,4-d]pyrimidin-7-amine (Compound 31)

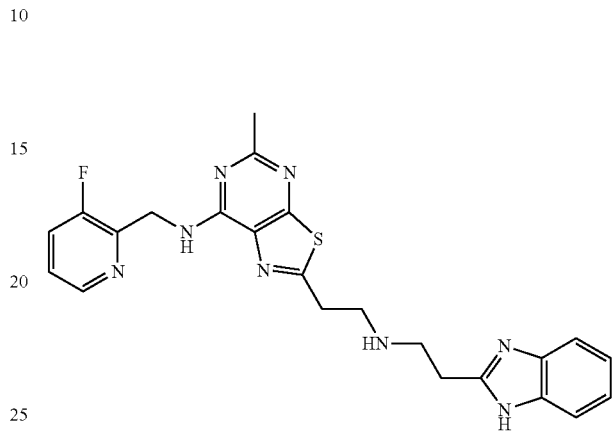

Compound 31 was synthesized in a similar manner to that of Compound 24, replacing 4,6-dichloro-5-pyrimidinamine with 4,6-dichloro-2-methyl-5-pyrimidinamine. $^1$H NMR (400 MHz, DMSO-$d_6$) δ 8.34 (d, J=4.7 Hz, 1H), 8.18 (s, 1H), 8.10 (t, J=5.7 Hz, 1H), 7.68 (ddd, J=10.0, 8.3, 1.3 Hz, 1H), 7.41 (dd, J=6.0, 3.2 Hz, 2H), 7.37 (dd, J=8.6, 4.4 Hz, 1H), 7.07 (dd, J=6.0, 3.2 Hz, 2H), 4.83 (d, J=5.5 Hz, 2H), 3.19 (t, J=6.6 Hz, 2H), 3.01 (t, J=6.4 Hz, 4H), 2.95 (t, J=6.5 Hz, 2H), 2.38 (s, 3H). [M+1]$^+$ m/z: 463.3.

Example 1.42

Synthesis of N-[(3-azidopyridin-2-yl)methyl]-2-(2-{[2-(5-iodo-1H-1,3-benzodiazol-2-yl)ethyl]amino}ethyl)-[1,3]thiazolo[5,4-d]pyrimidin-7-amine (Compound 32)

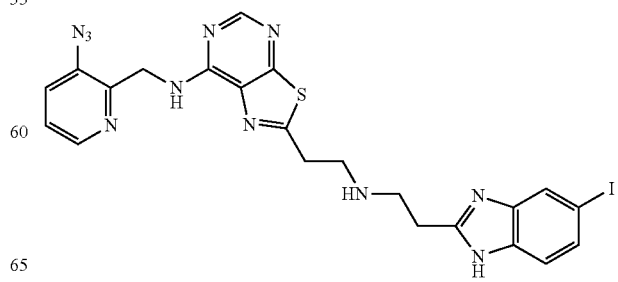

Scheme 27 depicts a synthetic route for preparing an exemplary compound.
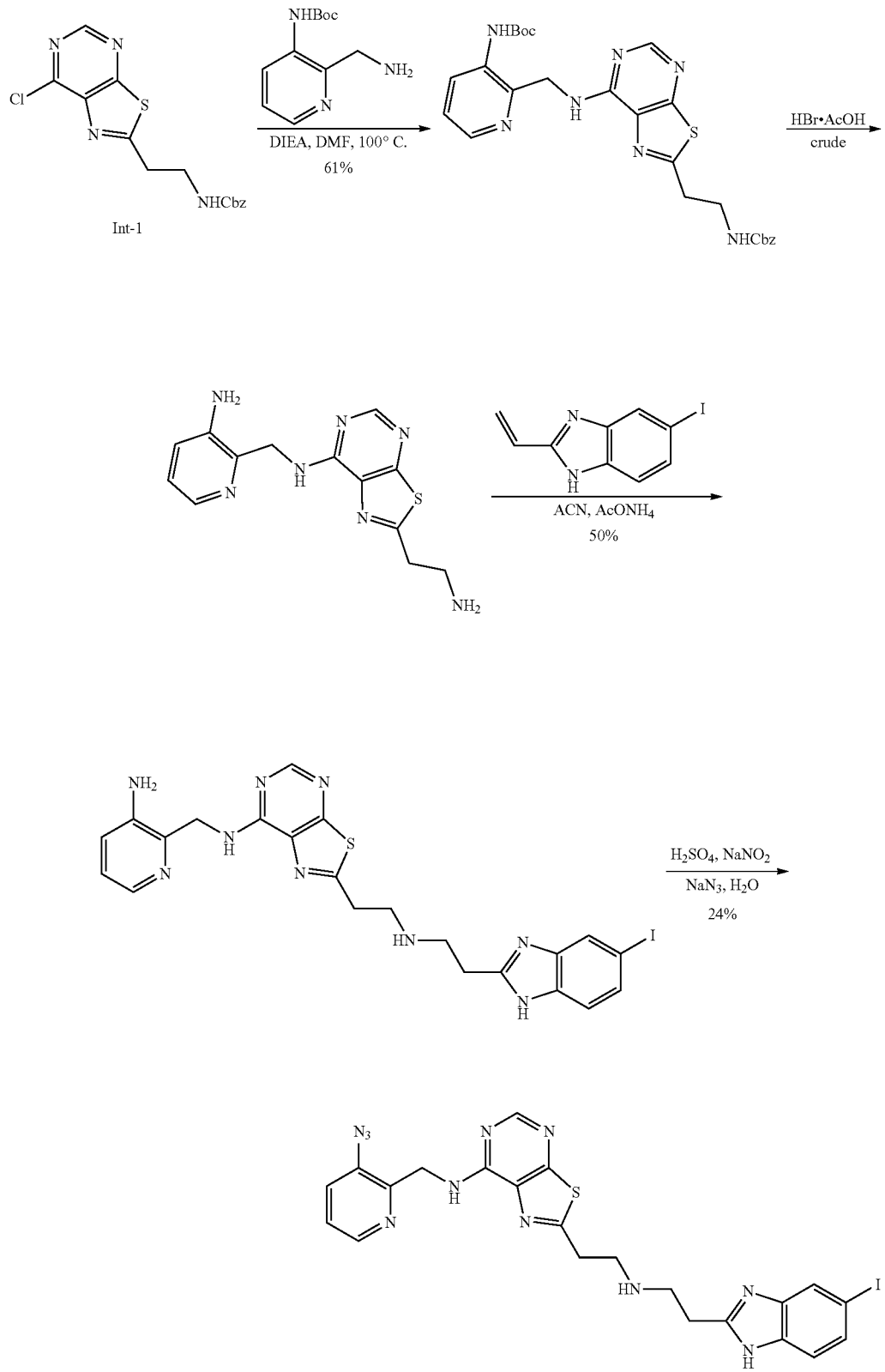
Scheme 27

Step 1:

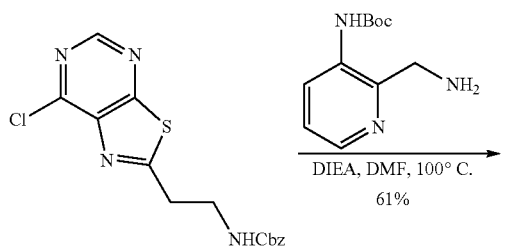

Into a 100-mL round-bottom flask, was placed benzyl N-(2-[7-chloro-[1,3]thiazolo[5,4-d]pyrimidin-2-yl]ethyl) carbamate (1.5 g, 0.004 mmol, 1 equiv), tert-butyl N-[2-(aminomethyl)pyridin-3-yl]carbamate (0.96 g, 0.004 mmol, 1 equiv), DIEA (1.67 g, 0.013 mmol, 3 equiv), and DMF (30 mL). The resulting solution was stirred for 4 hr at 100° C. in an oil bath. The resulting mixture was concentrated. The residue was applied onto a silica gel column with ethyl acetate/petroleum ether (1:3-1:1). The collected fractions were combined and concentrated. This resulted in 1.4 g (60.78%) of benzyl N-[2-(7-[[(3-[[(tert-butoxy)carbonyl]amino]pyridin-2-yl)methyl]amino]-[1,3]thiazolo[5,4-d]pyrimidin-2-yl)ethyl]carbamate as a yellow solid. LCMS (ES) [M+1]+ m/z 536.

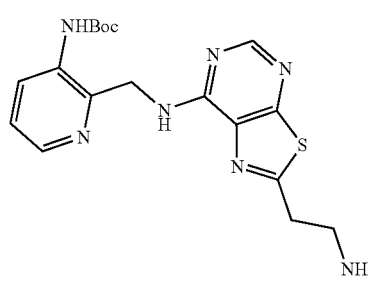

Into a 50-mL round-bottom flask, was placed benzyl N-[2-(7-[[(3-[[(tert-butoxy)carbonyl]amino]pyridin-2-yl)methyl]amino]-[1,3]thiazolo[5,4-d]pyrimidin-2-yl)ethyl] carbamate (1.4 g, 1 equiv), AcOH (5 mL), and ethanecarboperoxoyl bromide (5 mL). The resulting solution was stirred for 2 hr at room temperature. The resulting mixture was concentrated. The resulting solution was diluted with 80 mL of water. The pH value of the solution was adjusted to 10 with $K_2CO_3$. The resulting solution was extracted with 1×100 mL of DCM:MeOH=10:1 and the organic layer was combined, dried over anhydrous sodium sulfate, and concentrated. This resulted in 0.81 g (crude) of 2-([[2-(2-aminoethyl)-[1,3]thiazolo[5,4-d]pyrimidin-7-yl]amino] methyl)pyridin-3-amine as a brown solid. LCMS (ES) [M+1]+ m/z 302.

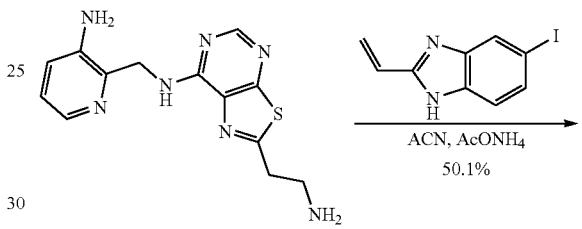

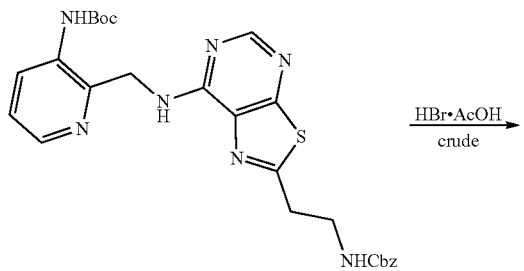

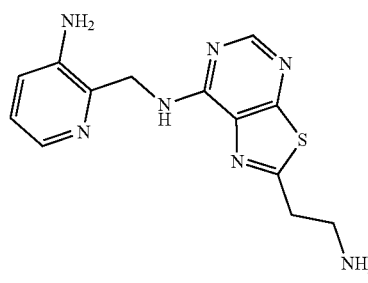

Into a 100-mL round-bottom flask, was placed 2-([[2-(2-aminoethyl)-[1,3]thiazolo[5,4-d]pyrimidin-7-yl]amino] methyl)pyridin-3-amine (270 mg, 0.896 mmol, 1 equiv), 2-ethenyl-5-iodo-1H-1,3-benzodiazole (266.16 mg, 0.985 mmol, 1.1 equiv), AcONH4 (345.29 mg, 4.479 mmol, 5.00 equiv), and ACN (60 mL, 1.462 mmol, 1.63 equiv). The resulting solution was stirred for 1 overnight at 80° C. in an oil bath. The resulting mixture was concentrated. The crude product was purified by Flash-Prep-HPLC. This resulted in 200 mg (50.10%) of 2-([[2-(2-[[2-(5-iodo-1H-1,3-benzodiazol-2-yl)ethyl]amino]ethyl)-[1,3]thiazolo[5,4-d]pyrimidin-7-yl]amino]methyl)pyridin-3-amine as a white solid. LCMS (ES) [M+1]+ m/z 572.

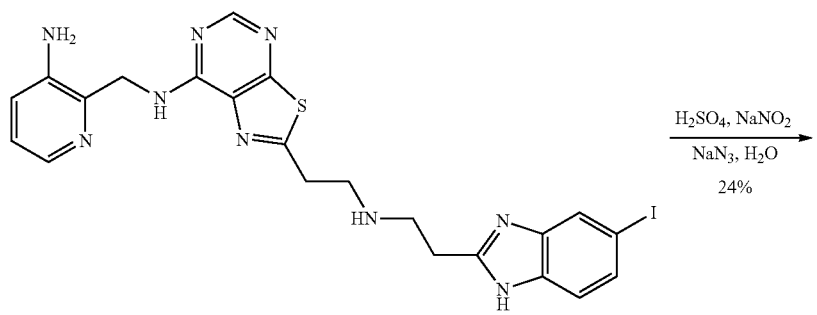

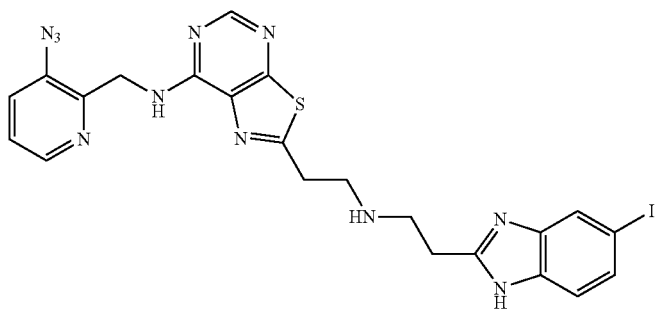

Into an 8-mL vial, was placed a solution of $H_2SO_4$ (0.05 mL, 0.001 mmol, 0.01 equiv) in $H_2O$ (0.3 mL), 2-({[2-(2-[[2-(5-iodo-1H-1,3-benzodiazol-2-yl)ethyl]amino]ethyl)-[1,3]thiazolo[5,4-d]pyrimidin-7-yl]amino}methyl)pyridin-3-amine (50 mg, 0.087 mmol, 1 equiv). This was followed by the addition of a solution of $NaNO_2$ (12.07 mg, 0.175 mmol, 2 equiv) in $H_2O$ (0.2 mL) dropwise with stirring at 0° C. in 1 min. The resulting solution was stirred for 40 min at 0° C. in an ice/salt bath. To this was added a solution of $NaN_3$ (17.06 mg, 0.262 mmol, 3 equiv) in $H_2O$ (0.3 mL) at OC. The resulting solution was stirred for 1 hr at 0° C. in an ice/salt bath. The reaction was then quenched by the addition of 1 mL of $Na_2CO_3$. The resulting solution was extracted with 4×20 mL of dichloromethane and the organic layer was concentrated. The reaction was repeated 3 times. The crude product was purified by Flash-Prep-HPLC (Prep-C18, 20-45M, 120 g, Tianjin Bonna-Agela Technologies; gradient elution of 25% MeCN in water to 40% MeCN in water over a 10 min period, where both solvents contained 0.1% FA). This resulted in 49.8 mg (23.82%) of N-[(3-azidopyridin-2-yl)methyl]-2-(2-[[2-(5-iodo-1H-1,3-benzodiazol-2-yl)ethyl]amino]ethyl)-[1,3]thiazolo[5,4-d]pyrimidin-7-amine as an off-white solid. $^1H$ NMR (300 MHz, DMSO-$d_6$) δ 8.37-8.20 (m, 3H), 8.10 (br, 1H), 7.84-7.72 (m, 2H), 7.44-7.34 (m, 2H), 7.27 (d, J=8.3 Hz, 1H), 4.73 (d, J=5.5 Hz, 2H), 3.31-3.20 (m, 2H), 3.10-2.91 (m, 6H). LCMS (ES) [M+1]$^+$ m/z 598.1.

Example 1.43

Synthesis of N-[(3-fluoropyridin-2-yl)methyl]-2-{2-[(2-{1H-imidazo[4,5-b]pyridin-2-yl}ethyl)amino]ethyl}-[1,3]thiazolo[5,4-d]pyrimidin-7-amine (Compound 33)

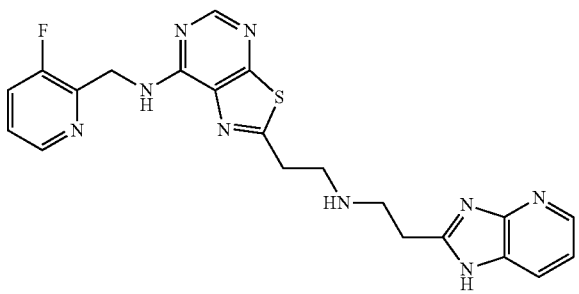

Compound 33 was synthesized in a similar manner to that of Compound 1, replacing N-(2-nitrophenyl)prop-2-enamide with N-(3-nitropyridin-2-yl)acrylamide. $^1H$ NMR (300 MHz, DMSO-$d_6$) δ 8.34 (dt, J=4.8, 1.5 Hz, 1H), 8.31 (s, 2H), 8.23 (dd, J=4.8, 1.5 Hz, 1H), 7.84 (dd, J=7.9, 1.5 Hz, 1H), 7.70 (ddd, J=10.0, 8.3, 1.3 Hz, 1H), 7.39 (dt, J=8.6, 4.4 Hz, 1H), 7.14 (dd, J=8.0, 4.8 Hz, 1H), 4.89 (d, J=5.6 Hz, 2H), 3.22 (t, J=6.5 Hz, 2H), 3.05 (tt, J=8.5, 3.5 Hz, 6H). [M+1]$^+$ m/z: 450.2

Example 1.44

Synthesis of 2-(2-{[2-(7-{[(3-fluoropyridin-2-yl)methyl]amino}-[1,3]thiazolo[5,4-d]pyrimidin-2-yl)ethyl]amino}ethyl)-2,3-dihydro-1H-indazol-3-one (Compound 34)

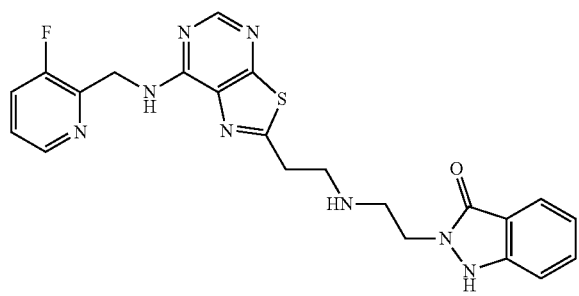 [SMILES: O=c1c2ccccc2[nH]n1CCNCCc1nc2c(NCc3ncccc3F)ncnc2s1]

Scheme 28 depicts a synthetic route for preparing an exemplary compound.

Scheme 28

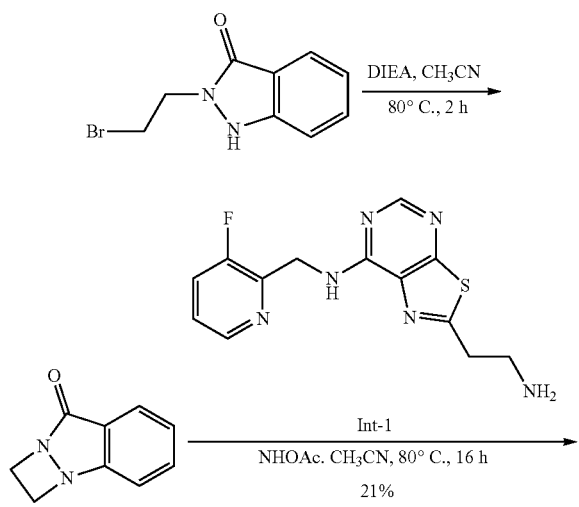

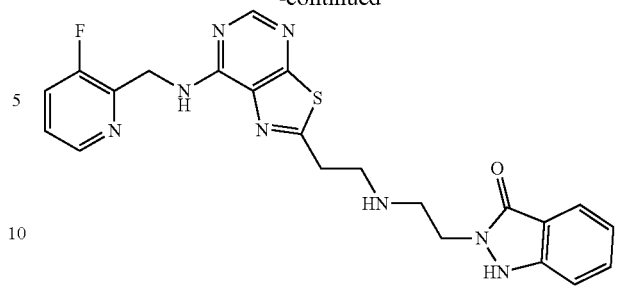

Step 1

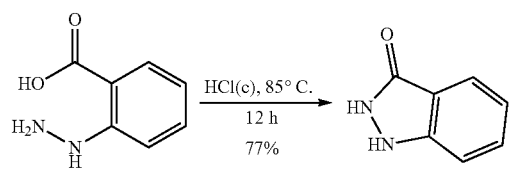 [SMILES: NNc1ccccc1C(=O)O ; O=c1[nH][nH]c2ccccc12]

Into a 250-mL round-bottom flask, was placed 2-hydrazinylbenzoic acid (5 g, 32.9 mmol, 1.0 equiv) and HCl (c) (100 mL). The mixture was stirred for 12 h at 85° C. After being cooled to room temperature, the resulting mixture was concentrated in vacuo. The residue was diluted with 20 mL of H₂O, and the pH value of the solution was adjusted to 8-9 with K₂CO₃ solid. The solution was concentrated again in vacuo, and then the residue was dissolved in DCM/MeOH (2:1) 200 mL and filtered out of the solid. The filtrate was then concentrated in vacuo. 3.4 g (77%) of 2,3-dihydro-1H-indazol-3-one was obtained as a brown solid and used in the next step directly without further purification.

Step 2

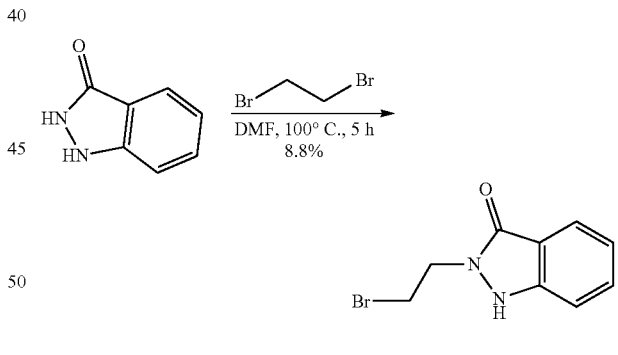

Into a 100-mL round-bottom flask, was placed 2,3-dihydro-1H-indazol-3-one (3.4 g, 25.3 mmol, 1.0 equiv), DMF (60 mL), and 1,2-dibromoethane (4.7 g, 25.3 mmol, 1.0 equiv). The mixture was stirred for 5 hr at 100° C. After being cooled to room temperature, the residue was purified by Prep HPLC with the following conditions: C18 column- 120 g, CH₃CN/H₂O (0.05% TFA), from 5% to 70% within 15 min. The product was concentrated in vacuo to remove CH₃CN and the residue was adjusted to pH 7 with K₂CO₃ solid, and then extracted with DCM (50 mL*2). The product was then combined in the organic phase, dried over Na₂SO₄, filtered, and the filtrate was concentrated in vacuo. 540 mg (8.8%) of 2-(2-bromoethyl)-2,3-dihydro-1H-indazol-3-one was obtained as a yellow solid.

Step 3

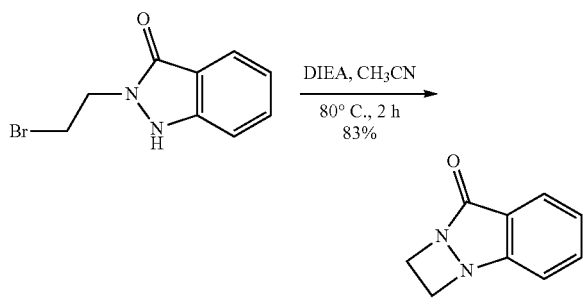

Into a 40-mL vial, was placed 2-(2-bromoethyl)-2,3-dihydro-1H-indazol-3-one (540 mg, 2.24 mmol, 1.0 equiv), CH₃CN (10 mL), and DIEA (870 mg, 6.75 mmol, 3.0 equiv). The mixture was stirred for 2 hr at 80° C. The reaction mixture was cooled and concentrated in vacuo. The residue was purified by silica gel column with ethyl acetate/petroleum ether (1:3). 300 mg (83%) of 1H,2H,8H-[1,2]diazeto[1,2-a]indazol-8-one was obtained as a white solid.

Step 4

Into a 40-mL vial, was placed 2-(2-aminoethyl)-N-[(3-fluoropyridin-2-yl)methyl]-[1,3]thiazolo[5,4-d]pyrimidin-7-amine (190 mg, 0.62 mmol, 1.0 equiv), CH₃CN (8 mL), 1H,2H,8H-[1,2]diazeto[1,2-a]indazol-8-one (100 mg, 0.62 mmol, 1.0 equiv), and NH₄OAc (48 mg, 0.62 mmol, 1.0 equiv). The mixture was stirred for 16 h at 80° C. The reaction mixture was cooled and directly purified by Prep-HPLC with the following conditions: Column, Xbridge shield RP18 OBD, mobile phase, CH₃CN/water (0.05% NH₄OH) from 15% to 80% within 8 min; Detector UV 254 nm. 60.1 mg (21%) of 2-([[2-(7-[[(3-fluoropyridin-2-yl)methyl]amino]-[1,3]thiazolo[5,4-d]pyrimidin-2-yl)ethyl]amino]methyl)-2,3,3a,7a-tetrahydro-1H-indazol-3-one was obtained as a light brown solid. ¹H NMR (300 MHz, DMSO-d₆) δ 8.36-8.33 (m, 3H), 7.74-7.69 (m, 2H), 7.42-7.37 (m, 1H), 7.29 (d, J=8.7 Hz, 1H), 7.11-7.05 (m, 1H), 6.77-6.72 (m, 1H), 6.05 (t, J=6.3 Hz, 1H), 5.02 (t, J=4.5 Hz, 1H), 4.91 (d, J=6.0 Hz, 2H), 4.25 (t, J=6.0 Hz, 2H), 3.92 (q, J=6.6, 12.9 Hz, 2H), 3.80 (q, J=5.4, 11.1 Hz, 2H), 3.41 (t, J=6.3 Hz, 2H). LCMS (ES) [M+1]⁺ m/z: 465.

Example 1.45

Synthesis of 2-(2-{[2-(1H-1,3-benzodiazol-2-yl)ethyl]amino}ethyl)-7-{[(3-fluoropyridin-2-yl)methyl]amino}-[1,3]oxazolo[5,4-d]pyrimidin-5-ol (Compound 36)

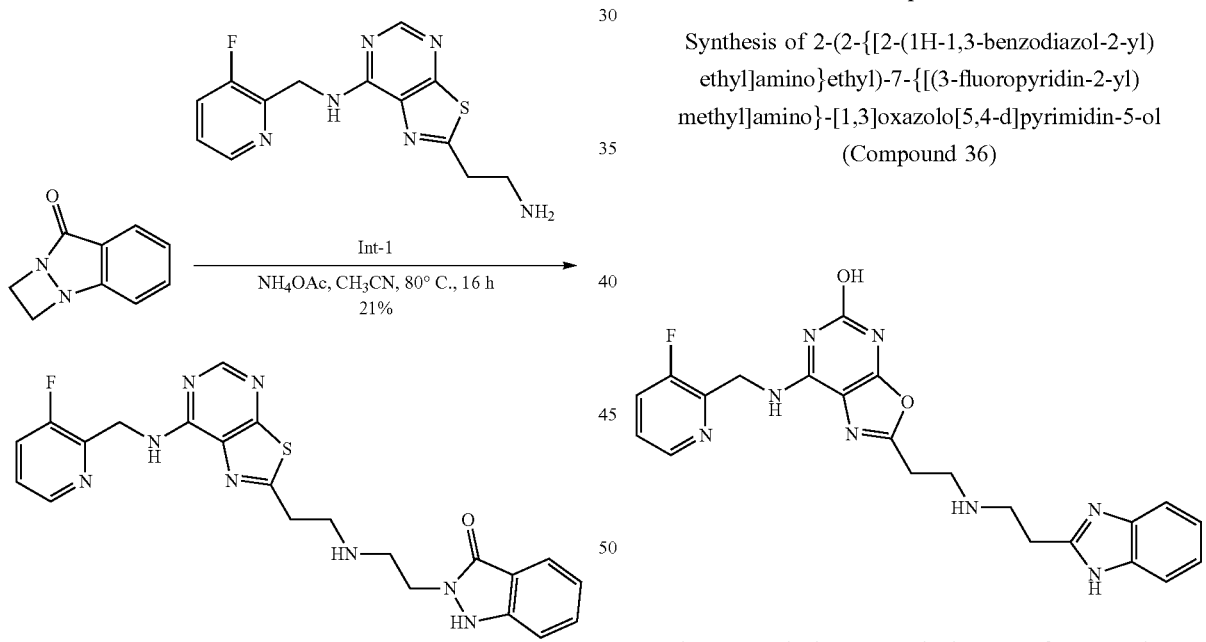

Scheme 29 depicts a synthetic route for preparing an exemplary compound.

Scheme 29

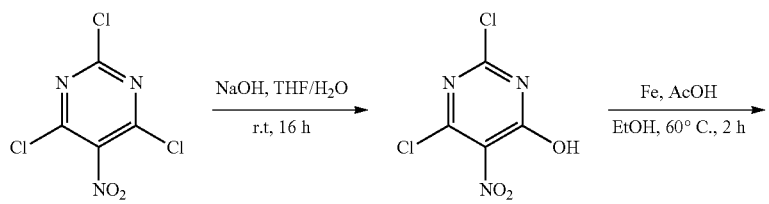

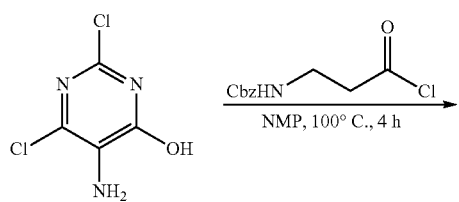
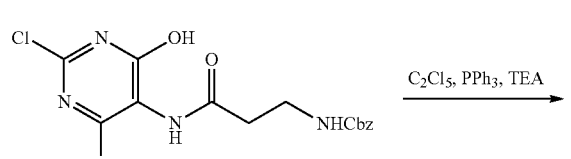
-continued
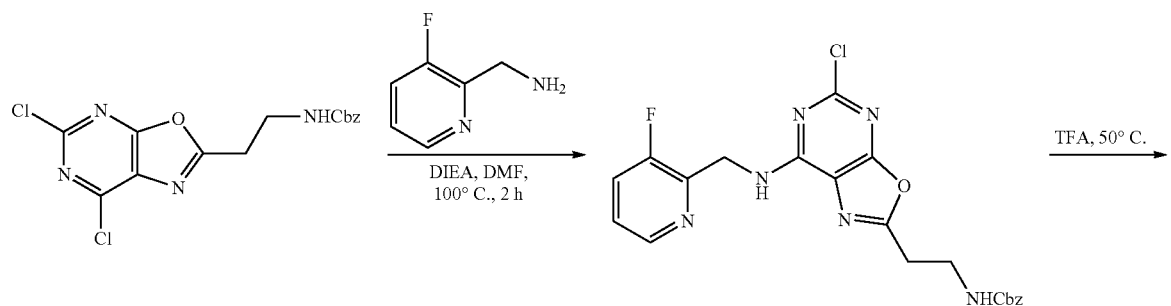
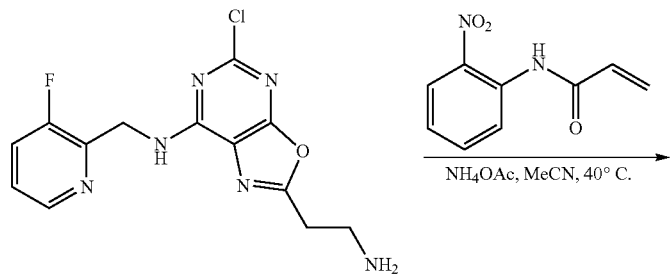
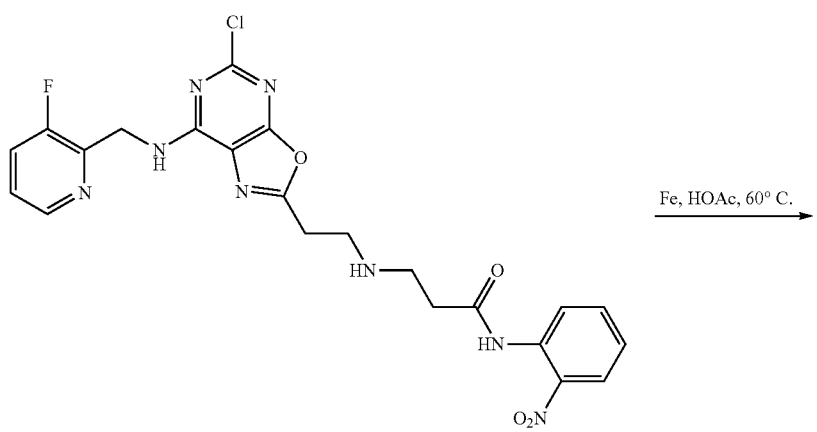
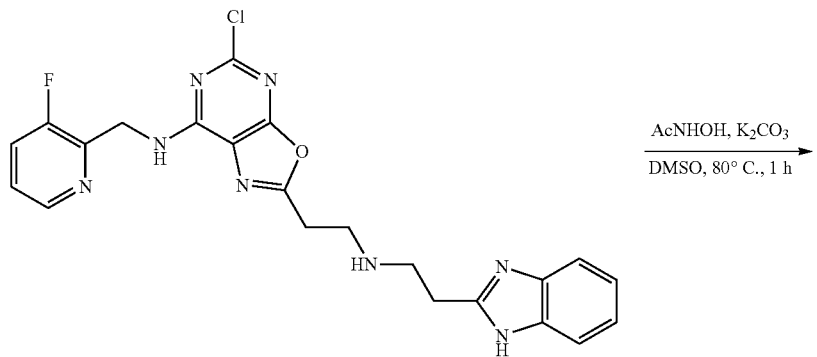

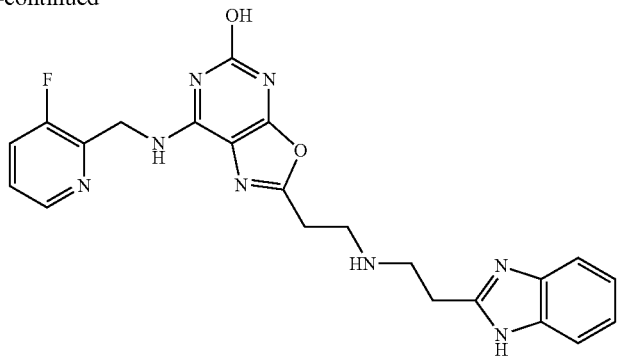

Step 1

Into a 250-mL round-bottom flask purged and maintained with an inert atmosphere of nitrogen, was placed a solution of 2,4,6-trichloro-5-nitropyrimidine (10.00 g, 1.00 equiv) in THF (50 mL). This was followed by the addition of a solution of caustic soda (1.76 g, 1.00 equiv) in H$_2$O (50 mL) dropwise with stirring at room temperature. The resulting solution was stirred for 2 hr at room temperature. The pH value of the solution was adjusted to 2-3 with HCl (1 mol/L). The resulting solution was extracted with 3×100 mL of dichloromethane dried over anhydrous sodium sulfate and concentrated. This resulted in 8.5 g (92%) of 2,6-dichloro-5-nitropyrimidin-4-ol as a light yellow solid. LCMS (ES) [M+1]$^+$ m/z: 210.

Step 2

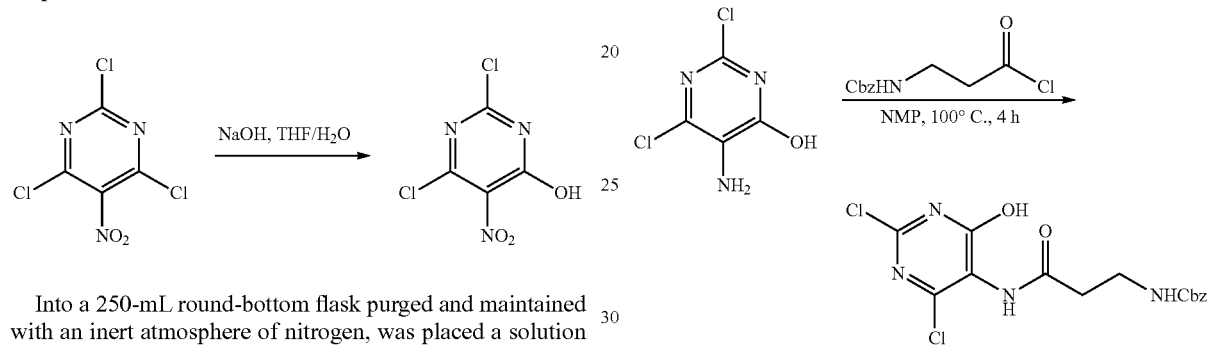

Into a 250-mL 3-necked round-bottom flask purged and maintained with an inert atmosphere of nitrogen, was placed a solution of 2,6-dichloro-5-nitropyrimidin-4-ol (8.50 g, 1.00 equiv) in EtOH (50 mL) and HOAc (50.00 mL). Iron (9.11 g, 4.00 equiv) was added in portion. The resulting solution was stirred for 2 hr at 60° C. in an oil bath. The solids were filtered out. The resulting solution was extracted with 3×100 mL of dichloromethane and the organic layers were combined and dried over anhydrous sodium sulfate and concentrated. The residue was applied onto a silica gel column with ethyl acetate/petroleum ether (4:5). This resulted in 6.1 g (83.6%) of 5-amino-2,6-dichloropyrimidin-4-ol as an off-white solid. LCMS (ES) [M+1]$^+$ m/z: 180.

Into a 250-mL round-bottom flask, was placed 5-amino-2,6-dichloropyrimidin-4-ol (6.10 g, 33.891 mmol, 1.00 equiv) and benzyl N-(3-chloro-3-oxopropyl)carbamate (9.83 g, 40.669 mmol, 1.20 equiv) in NMP (100 mL). The resulting solution was stirred for 4 hr at 100° C. in an oil bath. The crude product was purified by Prep-HPLC with the following conditions: Column, SunFire Prep C18 OBD; mobile phase, water (0.1% FA)/ACN; Detector, 220 nm. This resulted in 5.1 g (39.07%) of benzyl N-[2-[(2,4-dichloro-6-hydroxypyrimidin-5-yl)carbamoyl]ethyl]carbamate as a light yellow oil. LCMS (ES) [M+1]$^+$ m/z: 385.

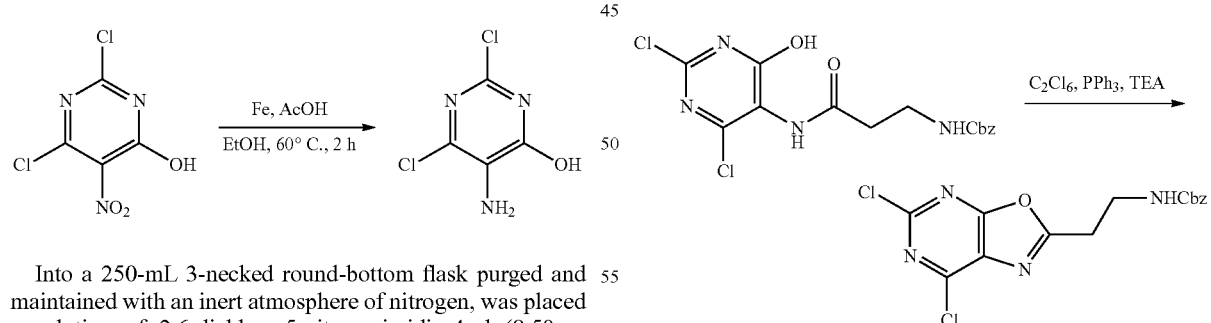

Into a 250-mL round-bottom flask purged and maintained with an inert atmosphere of nitrogen, was placed C$_2$Cl$_6$ (7.81 g, 33.100 mmol, 2.50 equiv), PPh$_3$ (10.42 g, 39.720 mmol, 3.00 equiv), TEA (10.72 g, 105.919 mmol, 8.00 equiv), and benzyl N-[2-[(2,4-dichloro-6-hydroxypyrimidin-5-yl)carbamoyl]ethyl]carbamate (5.10 g, 13.240 mmol, 1.00 equiv). The resulting solution was stirred for 20 min at room temperature. The resulting solution was allowed to react, with stirring, for an additional 20 min at room temperature.

The reaction was then quenched by the addition of water. The resulting solution was extracted with 3×100 mL of dichloromethane dried over anhydrous sodium sulfate and concentrated. The residue was applied onto a silica gel column with ethyl acetate/petroleum ether (3:1). This resulted in 1.8 g (37.03%) of benzyl N-(2-[5,7-dichloro-[1,3]oxazolo[5,4-d]pyrimidin-2-yl]ethyl)carbamate as a light yellow solid. LCMS (ES) [M+1]⁺ m/z: 367.

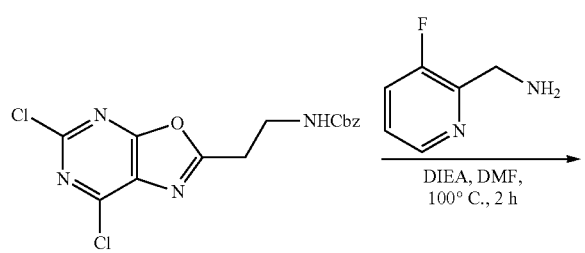

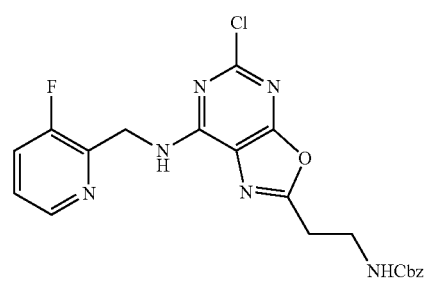

Into a 50-mL round-bottom flask purged and maintained with an inert atmosphere of nitrogen, was placed benzyl N-(2-[5,7-dichloro-[1,3]oxazolo[5,4-d]pyrimidin-2-yl]ethyl)carbamate (1.80 g, 4.902 mmol, 1.00 equiv), 1-(3-fluoropyridin-2-yl)methanamine hydrochloride (1.20 g, 7.353 mmol, 1.50 equiv), DIEA (1.90 g, 14.706 mmol, 3.00 equiv), and DMF (20.00 mL, 281.571 mmol, 57.44 equiv). The resulting solution was stirred for 2 hr at 100° C. in an oil bath. The reaction was then quenched by the addition of water (50 mL). The resulting solution was extracted with 3×100 mL of ethyl acetate and the organic layers were combined and dried over anhydrous sodium sulfate and concentrated. The residue was applied onto a silica gel column with ethyl acetate/petroleum ether (1:2). This resulted in 1.6 g (71.44%) of benzyl N-[2-(5-chloro-7-[[(3-fluoropyridin-2-yl)methyl]amino]-[1,3]oxazolo[5,4-d]pyrimidin-2-yl)ethyl]carbamate as a light yellow solid. LCMS (ES) [M+1]⁺ m/z: 457.

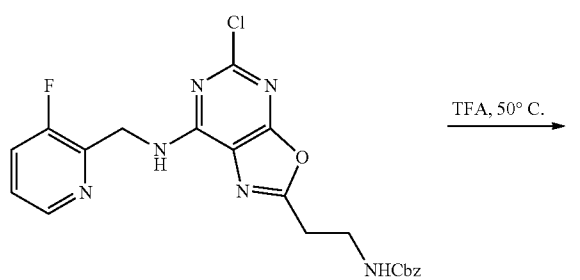

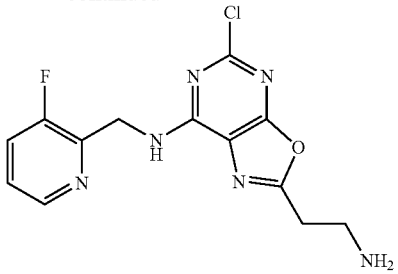

Into a 50-mL round-bottom flask purged and maintained with an inert atmosphere of nitrogen, was placed benzyl N-[2-(5-chloro-7-[[(3-fluoropyridin-2-yl)methyl]amino]-[1,3]oxazolo[5,4-d]pyrimidin-2-yl)ethyl]carbamate (1.50 g, 3.283 mmol, 1.00 equiv), and trifluoroacetaldehyde (20 mL). The resulting solution was stirred for 3 hr at 50° C. in an oil bath. The pH value of the solution was adjusted to 7-8 with NaHCO₃ (1 mol/L). The resulting solution was extracted with 3×100 mL of ethyl acetate dried over anhydrous sodium sulfate and concentrated. The residue was applied onto a silica gel column with ethyl acetate/petroleum ether (1:1). This resulted in 700 mg (66.06%) of 2-(2-aminoethyl)-5-chloro-N-[(3-fluoropyridin-2-yl)methyl]-[1,3]oxazolo[5,4-d]pyrimidin-7-amine as a light brown solid. LCMS (ES) [M+1]⁺ m/z: 323.

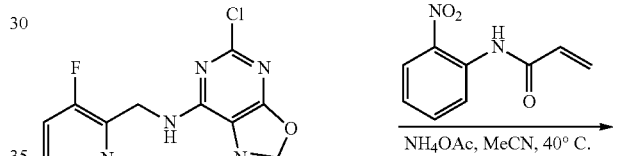

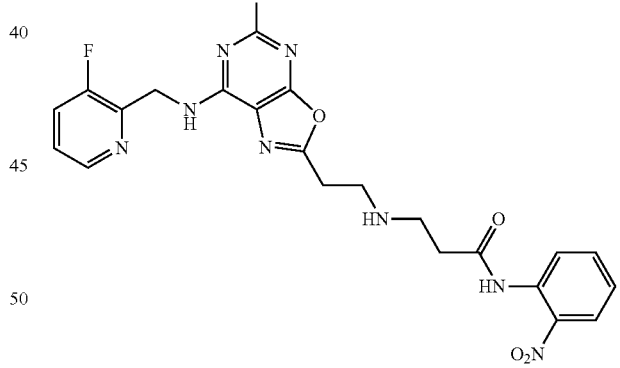

Into a 50-mL round-bottom flask purged and maintained with an inert atmosphere of nitrogen, was placed 2-(2-aminoethyl)-5-chloro-N-[(3-fluoropyridin-2-yl)methyl]-[1,3]oxazolo[5,4-d]pyrimidin-7-amine (480 mg, 1.487 mmol, 1.00 equiv), N-(2-nitrophenyl)prop-2-enamide (285.82 mg, 1.487 mmol, 1.00 equiv), NH₄OAc (229.29 mg, 2.975 mmol, 2.00 equiv), and MeCN (20.00 mL, 380.494 mmol, 255.83 equiv). The resulting solution was stirred overnight at 40° C. The resulting mixture was concentrated. The residue was applied onto a silica gel column with ethyl acetate/petroleum ether (1:1). This resulted in 350 mg (45.70%) of 3-[[2-(5-chloro-7-[[(3-fluoropyridin-2-yl)methyl]amino]-[1,3]oxazolo[5,4-d]pyrimidin-2-yl)ethyl]amino]-N-(2-nitrophenyl)propanamide as an off-white solid. LCMS (ES) [M+1]⁺ m/z: 515.

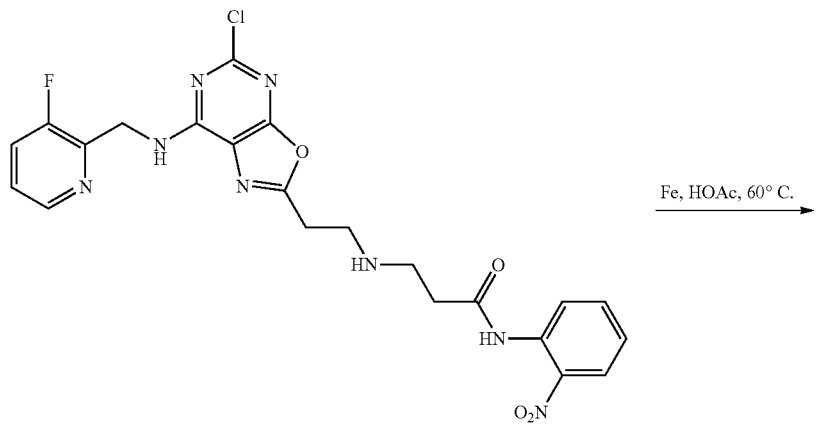

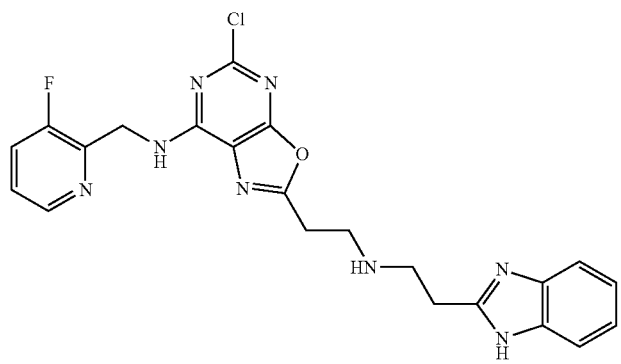

Into a 25-mL round-bottom flask purged and maintained with an inert atmosphere of nitrogen, was placed 3-[[2-(5-chloro-7-[[(3-fluoropyridin-2-yl)methyl]amino]-[1,3]oxazolo[5,4-d]pyrimidin-2-yl)ethyl]amino]-N-(2-nitrophenyl) propanamide (350 mg, 0.680 mmol, 1.00 equiv), and HOAc (10.00 mL, 174.515 mmol, 256.74 equiv). This was followed by the addition of Fe (151.84 mg, 2.719 mmol, 4.00 equiv) in several batches at 60° C. The resulting solution was stirred for 2 hr at 60° C. The solids were filtered out. The crude product was purified by Prep-HPLC with the following conditions: Column, SunFire Prep C18 OBD; mobile phase, water (0.1% FA)/ACN; Detector, 220 nm. This resulted in 230 mg (72.47%) of 2-(2-[[2-(1H-1,3-benzodiazol-2-yl)ethyl]amino]ethyl)-5-chloro-N-[(3-fluoropyridin-2-yl)methyl]-[1,3]oxazolo[5,4-d]pyrimidin-7-amine as an off-white solid. LCMS (ES) [M+1]$^+$ m/z: 467.

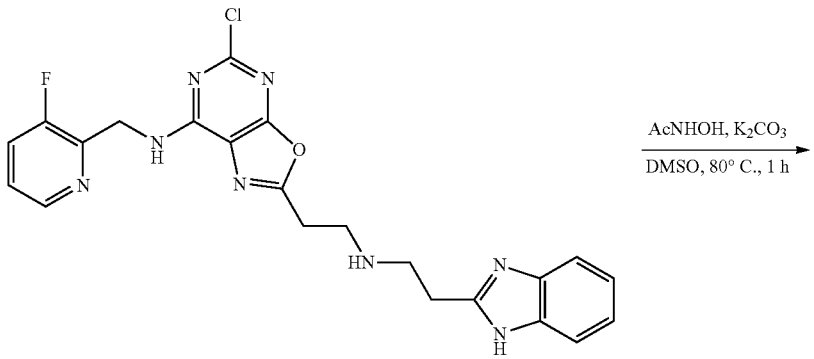

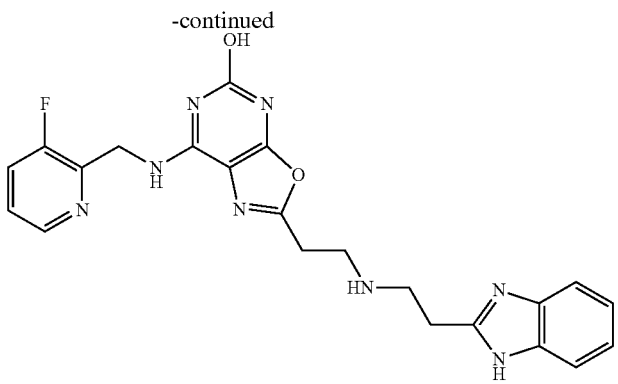

Into a 25-mL round-bottom flask purged and maintained with an inert atmosphere of nitrogen, was placed 2-(2-[[2-(1H-1,3-benzodiazol-2-yl)ethyl]amino]ethyl)-5-chloro-N-[(3-fluoropyridin-2-yl)methyl]-[1,3]oxazolo[5,4-d]pyrimidin-7-amine (230.00 mg, 0.493 mmol, 1.00 equiv), potassium carbonate (342.88 mg, 2.463 mmol, 5.00 equiv), acetohydroxamic acid (110.93 mg, 1.478 mmol, 3.00 equiv), and DMSO (10.00 mL, 140.786 mmol, 285.80 equiv). The resulting solution was stirred for 1 hr at 80° C. The crude product was purified by Prep-HPLC with the following conditions: Column, SunFire Prep C18 OBD, 19*150 mm 5 um 10 nm; mobile phase, water (0.1% FA) and ACN; Detector, 254. This resulted in 26.6 mg (12.04%) of 2-(2-[[2-(1H-1,3-benzodiazol-2-yl)ethyl]amino]ethyl)-7-[[(3-fluoropyridin-2-yl)methyl]amino]-[1,3]oxazolo[5,4-d]pyrimidin-5-ol as a white solid. $^1$H-NMR (300 MHz, DMSO-d$_6$, ppm): δ 8.38 (d, J=5.1 Hz, 1H), 8.30 (br, 2H), 7.72 (ddd, J=10.0, 8.4, 1.3 Hz, 1H), 7.49-7.36 (m, 3H), 7.09 (dd, J=6.0, 3.2 Hz, 2H), 4.91 (s, 2H), 3.35-2.67 (m, 8H). LCMS: (ES, m/z): [M+H]$^+$:449.

Example 1.46

Synthesis of N-[(3-fluoropyridin-2-yl)methyl]-2-{2-[(2-{1H-imidazo[4,5-c]pyridin-2-yl}ethyl)amino]ethyl}-[1,3]thiazolo[5,4-d]pyrimidin-7-amine (Compound 37)

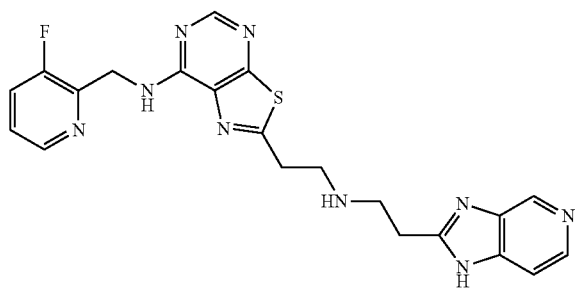 [SMILES: Fc1cccnc1CNc1ncnc2sc(CCNCCc3nc4cnccc4[nH]3)nc12]

Compound 37 was synthesized in a similar manner to that of Compound 1, replacing N-(2-nitrophenyl)prop-2-enamide with N-(3-nitropyridin-4-yl)acrylamide as a solid. $^1$H NMR (300 MHz, DMSO-d$_6$) δ 8.77 (d, J=1.1 Hz, 1H), 8.34 (dt, J=4.8, 1.5 Hz, 1H), 8.30 (d, J=4.5 Hz, 2H), 8.22 (d, J=5.5 Hz, 1H), 7.70 (ddd, J=10.2, 8.4, 1.3 Hz, 1H), 7.45 (dd, J=5.5, 1.1 Hz, 1H), 7.39 (dt, J=8.6, 4.4 Hz, 1H), 4.88 (d, J=5.6 Hz, 2H), 3.22 (t, J=6.6 Hz, 2H), 3.12-2.95 (m, 6H). [M+1]$^+$ m/z: 450.2.

Example 1.47

Synthesis of 2-(1-{[2-(7-{[(3-fluoropyridin-2-yl)methyl]amino}-[1,3]thiazolo[5,4-d]pyrimidin-2-yl)ethyl]amino}ethyl)phenol (Compound 38)

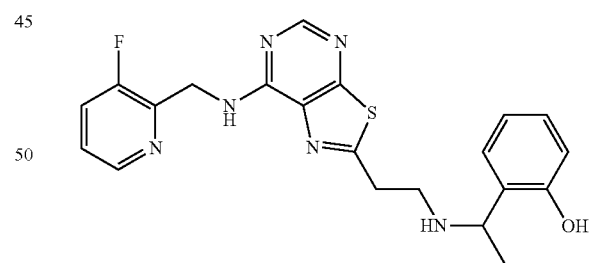

Compound 38 was synthesized in a similar manner to that of Compound 27, using 2-Vinylphenol to replace methyl 2-vinyl-1H-benzo[d]imidazole-5-carboxylate. $^1$H NMR (300 MHz, DMSO-d$_6$) δ 8.32 (m, 3H), 8.20 (s, 1H), 7.70 (m, 1H), 7.40 (m, 1H), 7.08 (m, 2H), 6.72 (m, 2H), 4.88 (d, J=3.9 Hz, 2H), 4.01 (d, J=6.6 Hz, 1H), 3.29 (m, 2H), 2.95 (m, 2H), 1.31 (d, J=6.6 Hz, 3H). [M+1]$^+$ m/z: 425.2.

Example 1.48
Synthesis of 3-[3-(but-3-yn-1-yl)-3H-diazirin-3-yl]-N-{[2-(2-{[2-(7-{[(3-fluoropyridin-2-yl)methyl]amino}-[1,3]thiazolo[5,4-d]pyrimidin-2-yl)ethyl]amino}ethyl)-1H-1,3-benzodiazol-5-yl]methyl}propanamide (Compound 39)
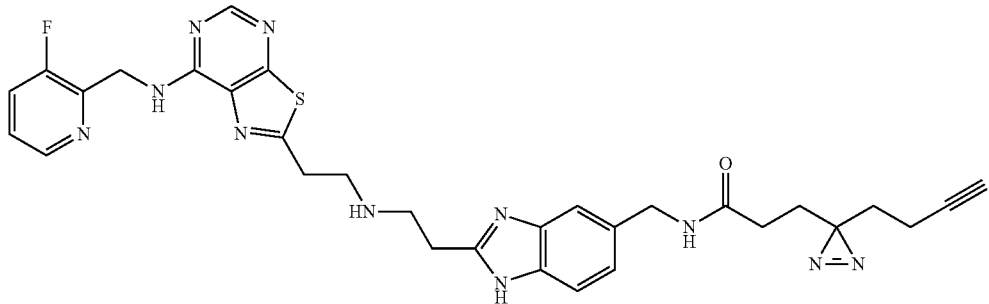 [SMILES: C#CCCC1(CCC(=O)NCc2ccc3[nH]c(CCNCCc4nc5c(NCc6ncccc6F)ncnc5s4)nc3c2)N=N1]
Scheme 30 depicts a synthetic route for preparing an exemplary compound.
Scheme 30
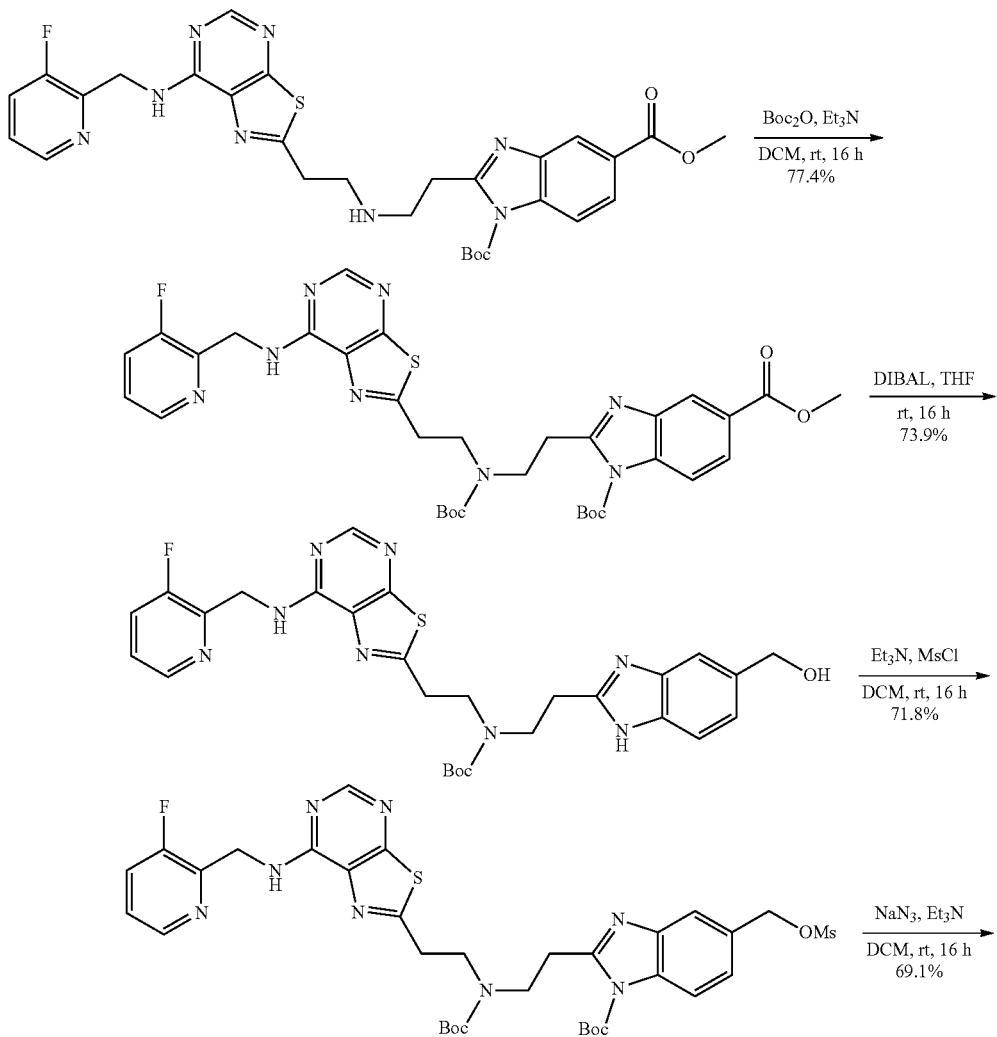

221 222
-continued
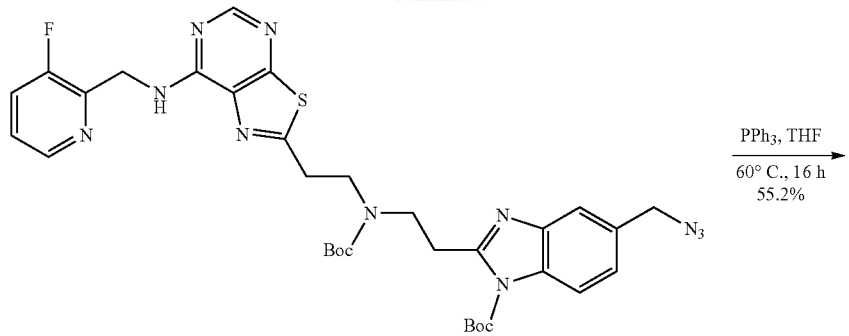
PPh₃, THF
60° C., 16 h
55.2%
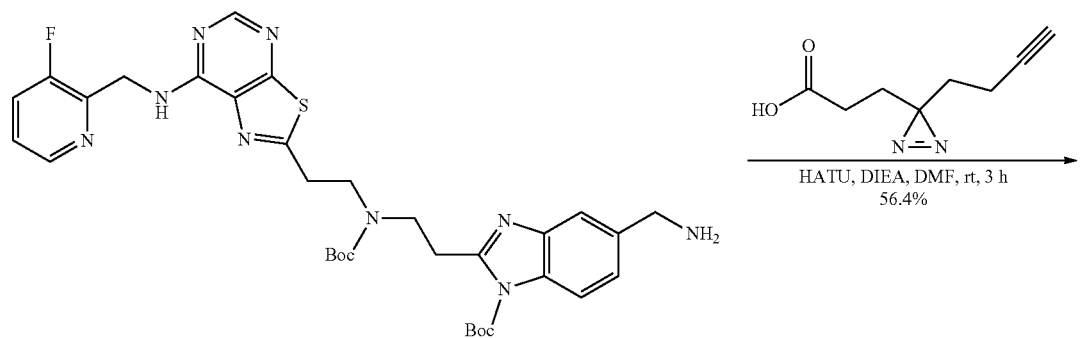
HATU, DIEA, DMF, rt, 3 h
56.4%
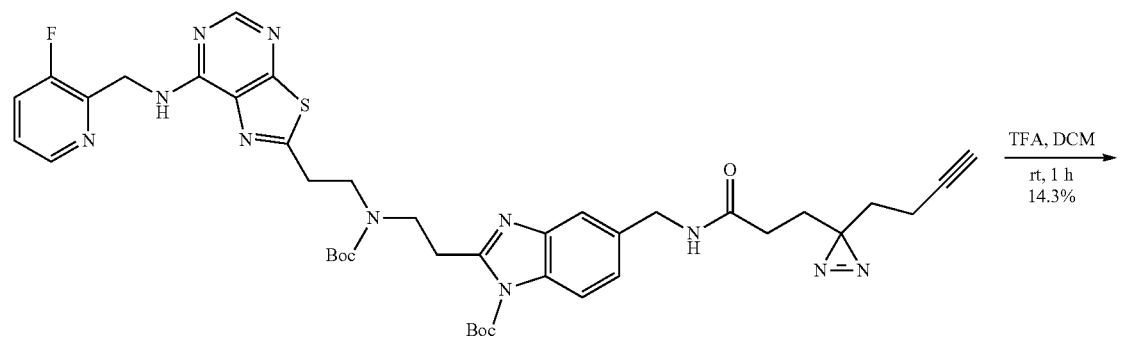
TFA, DCM
rt, 1 h
14.3%
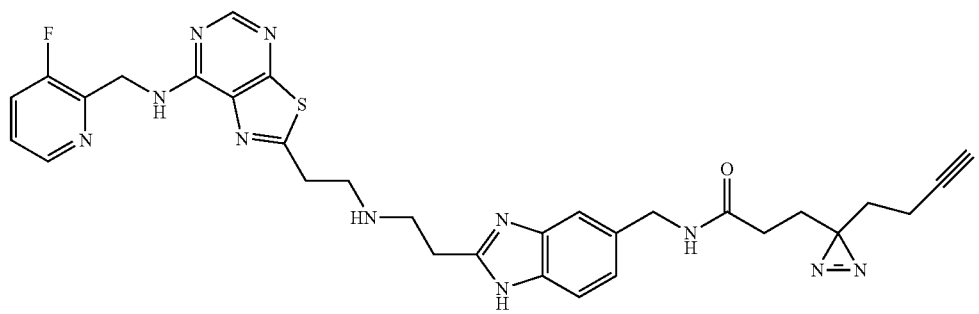

Step 1

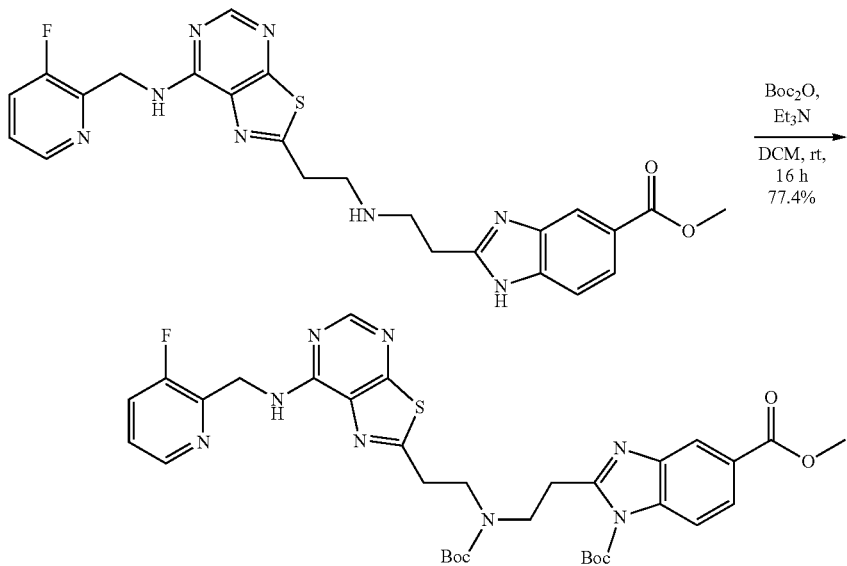

Into a 50-mL round-bottom flask, was placed methyl 2-(2-((2-(7-(((3-fluoropyridin-2-yl)methyl)amino)thiazolo[5,4-d]pyrimidin-2-yl)ethyl)amino)ethyl)-1H-benzo[d]imidazole-5-carboxylate (500.00 mg, 0.987 mmol, 1.00 equiv), DCM (20.00 mL), triethylamine (300.00 mg, 2.965 mmol, 3.00 equiv), and di-tert-butyl dicarbonate (431.00 mg, 1.975 mmol, 2.00 equiv). The resulting solution was stirred for 16 hr at room temperature. The resulting mixture was concentrated. The residue was applied onto a silica gel column with ethyl acetate/petroleum ether (2:1). The collected fractions were combined and concentrated. This resulted in 540 mg (77.4%) of 1-(tert-butyl) 5-methyl 2-(2-((tert-butoxycarbonyl)(2-(7-(((3-fluoropyridin-2-yl)methyl)amino)thiazolo[5,4-d]pyrimidin-2-yl)ethyl)amino)ethyl)-1H-benzo[d]imidazole-1,5-dicarboxylate as an off-white solid. LCMS (ES) [M+1]$^+$ m/z 707.3.

Step 2

Into a 50-mL round-bottom flask, was placed 1-(tert-butyl) 5-methyl 2-(2-((tert-butoxycarbonyl)(2-(7-(((3-fluoropyridin-2-yl)methyl)amino)thiazolo[5,4-d]pyrimidin-2-yl)ethyl)amino)ethyl)-1H-benzo[d]imidazole-1,5-dicarboxylate (500.00 mg, 0.707 mmol, 1.00 equiv), and THF (20.00 mL). Then, DIBAL (14 mL, 1M, 14.147 mmol, 20.00 equiv) was added dropwise at −78° C. The resulting solution was stirred for 16 hr at room temperature. The reaction was then quenched by the addition of 10 mL of water. The resulting solution was extracted with 3×50 mL of ethyl acetate and dried under reduced pressure. The residue was applied onto a silica gel column with dichloromethane/methanol (10:1). The collected fractions were combined and concentrated. This resulted in 355 mg (73.9%) of tert-butyl (2-(7-(((3-fluoropyridin-2-yl)methyl)amino)thiazolo[5,4-d]pyrimidin-2-yl)ethyl)(2-(5-(hydroxymethyl)-1H-benzo[d]imidazol-2-yl)ethyl)carbamate as an off-white solid. LCMS (ES) [M+1]$^+$ m/z 579.2.

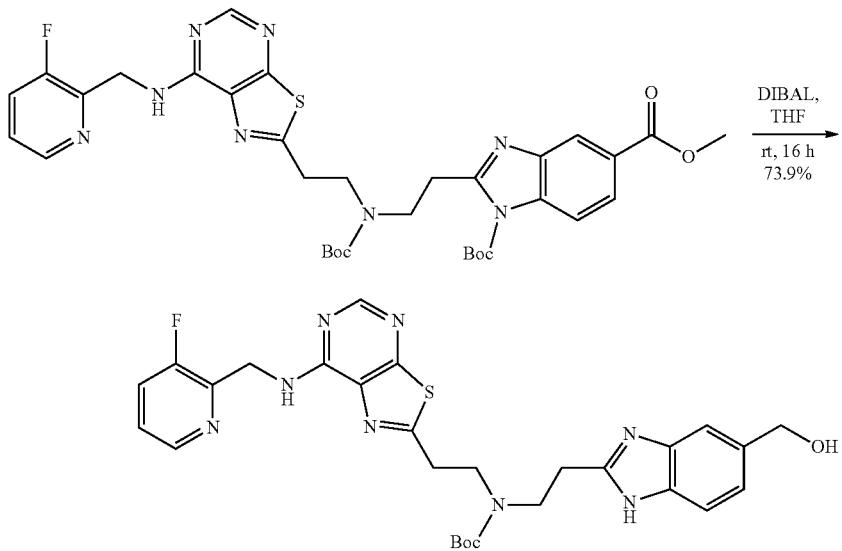

Step 3

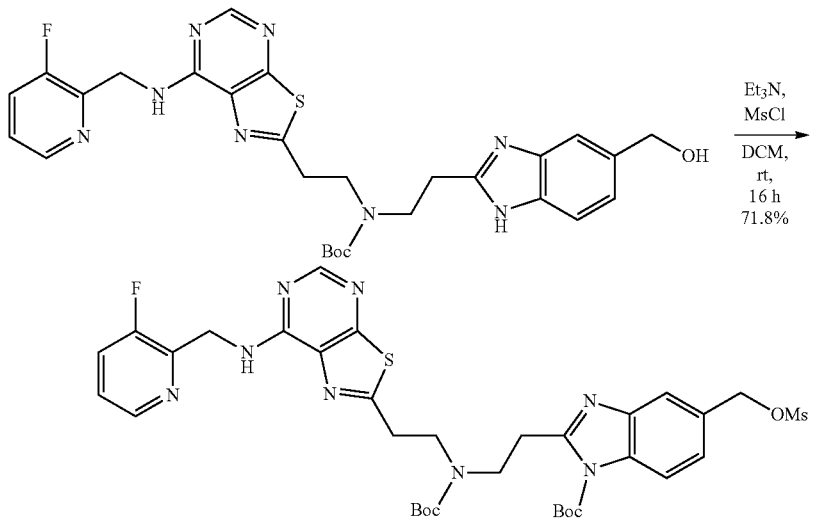

Into a 50-mL round-bottom flask, was placed tert-butyl (2-(7-(((3-fluoropyridin-2-yl)methyl)amino)thiazolo[5,4-d]pyrimidin-2-yl)ethyl)(2-(5-(hydroxymethyl)-1H-benzo[d]imidazol-2-yl)ethyl)carbamate (350.00 mg, 0.516 mmol, 1.00 equiv), DCM (20.00 mL), Et₃N (104.50 mg, 1.033 mmol, 2.00 equiv), and methanesulfonyl chloride (59.00 mg, 0.515 mmol, 1.00 equiv). The resulting solution was stirred for 16 hr at room temperature. The resulting mixture was washed with 2×10 mL water. The mixture was then dried over anhydrous sodium sulfate and concentrated. This resulted in 280 mg (71.8%) of tert-butyl 2-(2-((tert-butoxycarbonyl)(2-(7-(((3-fluoropyridin-2-yl)methyl)amino)thiazolo[5,4-d]pyrimidin-2-yl)ethyl)amino)ethyl)-5-(((methylsulfonyl)oxy)methyl)-1H-benzo[d]imidazole-1-carboxylate as a light yellow solid. LCMS (ES) [M+1]⁺ m/z 757.3.

Step 4

Into a 50-mL round-bottom flask, was placed tert-butyl 2-(2-((tert-butoxycarbonyl)(2-(7-(((3-fluoropyridin-2-yl)methyl)amino)thiazolo[5,4-d]pyrimidin-2-yl)ethyl)amino)ethyl)-5-(((methylsulfonyl)oxy)methyl)-1H-benzo[d]imidazole-1-carboxylate (280.00 mg, 0.370 mmol, 1.00 equiv), DCM (20.00 mL), Et₃N (112.00 mg, 1.107 mmol, 2.99 equiv), and azidosodium (36.00 mg, 0.554 mmol, 1.50 equiv). The resulting solution was stirred for 16 hr at room temperature. The resulting mixture was washed with 3×10 mL of water. The mixture was dried over anhydrous sodium sulfate and concentrated. The residue was applied onto a silica gel column with dichloromethane/methanol (10:1). The collected fractions were combined and concentrated. This resulted in 180 mg (69.1%) of tert-butyl 5-(azidomethyl)-2-(2-((tert-butoxycarbonyl)(2-(7-(((3-fluoropyridin-2-yl)methyl)amino)thiazolo[5,4-d]pyrimidin-2-yl)ethyl)amino)ethyl)-1H-benzo[d]imidazole-1-carboxylate as a light yellow solid.

LCMS (ES) [M+1]⁺ m/z 704.3.

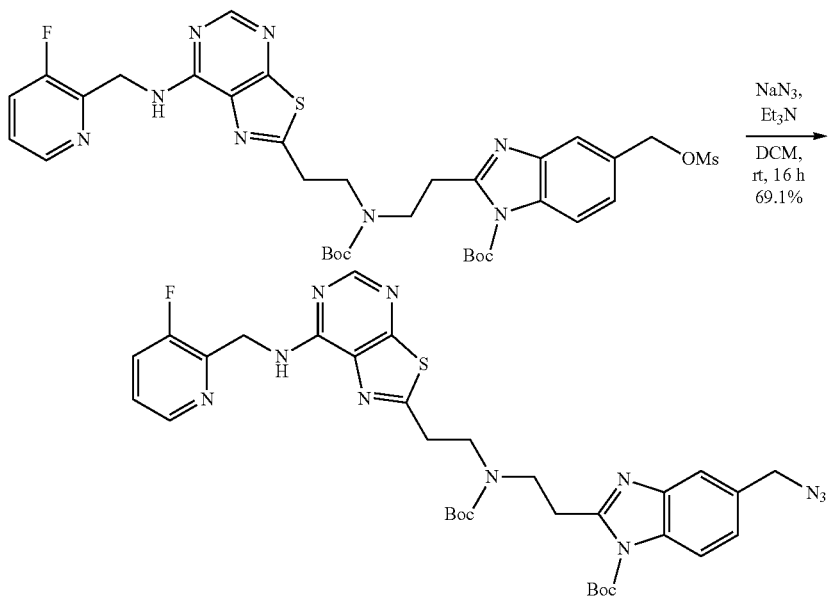

Step 5

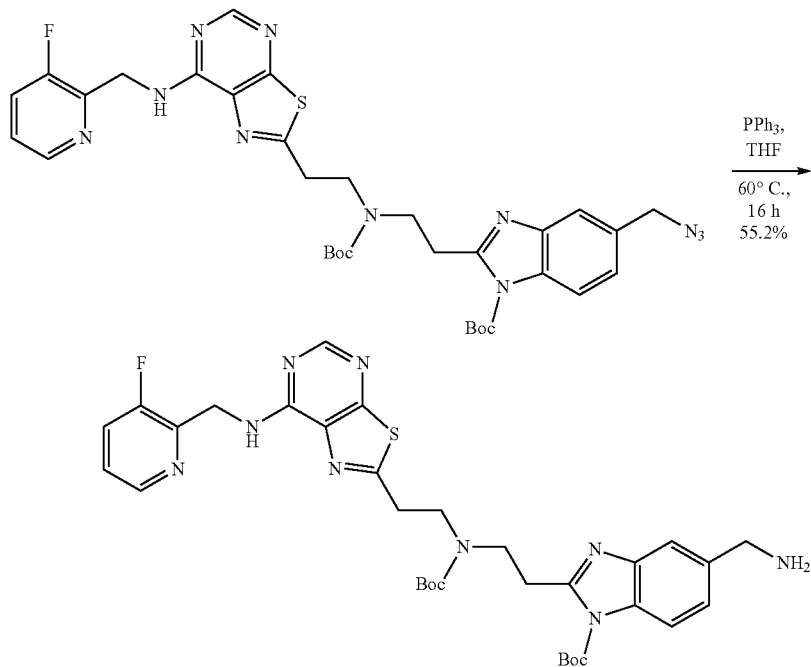

Into a 50-mL round-bottom flask, was placed tert-butyl 5-(azidomethyl)-2-(2-(((tert-butoxycarbonyl)(2-(7-(((3-fluoropyridin-2-yl)methyl)amino)thiazolo[5,4-d]pyrimidin-2-yl)ethyl)amino)ethyl)-1H-benzo[d]imidazole-1-carboxylate (160.00 mg, 0.227 mmol, 1.00 equiv), THF (10.00 mL), and triphenylphosphane (119.26 mg, 0.455 mmol, 2.00 equiv). The resulting solution was stirred for 16 hr at 60° C. The resulting mixture was concentrated. The residue was applied onto a silica gel column with dichloromethane+0.1% NH$_3$H$_2$O/methanol (10:1). The collected fractions were combined and concentrated. This resulted in 85 mg (55.2%) of tert-butyl 5-(aminomethyl)-2-(2-(((tert-butoxycarbonyl)(2-(7-(((3-fluoropyridin-2-yl)methyl)amino)thiazolo[5,4-d]pyrimidin-2-yl)ethyl)amino)ethyl)-1H-benzo[d]imidazole-1-carboxylate as a yellow solid. LCMS (ES) [M+1]+ m/z 678.3.

Step 6

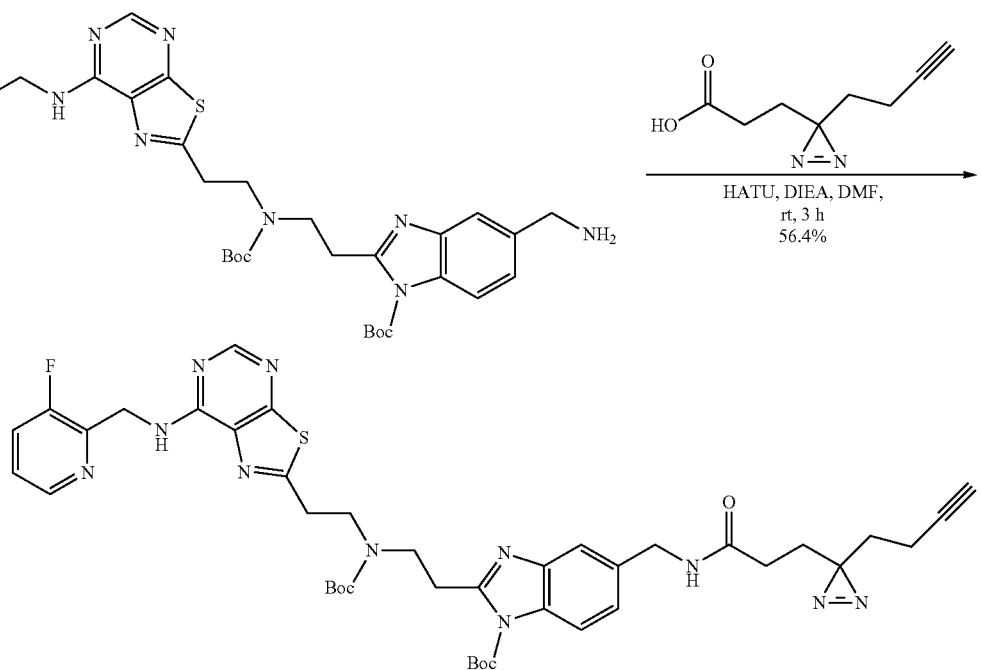

Into a 50-mL round-bottom flask, was placed tert-butyl 5-(aminomethyl)-2-(2-((tert-butoxycarbonyl)(2-(7-(((3-fluoropyridin-2-yl)methyl)amino)thiazolo[5,4-d]pyrimidin-2-yl)ethyl)amino)ethyl)-1H-benzo[d]imidazole-1-carboxylate (80.00 mg, 0.118 mmol, 1.00 equiv), DCM (5.00 mL), 3-[3-(but-3-yn-1-yl)-3H-diazirin-3-yl]propanoic acid (19.50 mg, 0.117 mmol, 0.99 equiv), HATU (67.00 mg, 0.176 mmol, 1.49 equiv), and DIEA (45.50 mg, 0.352 mmol, 2.98 equiv). The resulting solution was stirred for 3 hr at room temperature. The resulting mixture was concentrated. The residue was applied onto a silica gel column with dichloromethane/methanol (10:1). The collected fractions were combined and concentrated. This resulted in 55 mg (56.4%) of tert-butyl 5-((3-(3-(but-3-yn-1-yl)-3H-diazirin-3-yl)propanamido)methyl)-2-(2-((tert-butoxycarbonyl)(2-(7-(((3-fluoropyridin-2-yl)methyl)amino)thiazolo[5,4-d]pyrimidin-2-yl)ethyl)amino)ethyl)-1H-benzo[d]imidazole-1-carboxylate as a light yellow solid. LCMS (ES) [M+1]+m/z 826.4.

Step 7

Into a 50-mL round-bottom flask, was placed tert-butyl 5-((3-(3-(but-3-yn-1-yl)-3H-diazirin-3-yl)propanamido)methyl)-2-(2-((tert-butoxycarbonyl)(2-(7-(((3-fluoropyridin-2-yl)methyl)amino)thiazolo[5,4-d]pyrimidin-2-yl)ethyl)amino)ethyl)-1H-benzo[d]imidazole-1-carboxylate (50.00 mg, 0.061 mmol, 1.00 equiv), DCM (3.00 mL), and 2,2,2-trifluoroacetaldehyde (1.00 mL). The resulting solution was stirred for 1 hr at room temperature. The resulting mixture was concentrated. The crude reaction mixture was filtered and subjected to reverse phase preparative HPLC (Prep-C18, 5 uM SunFire column, 19×150 mm, Waters; gradient elution of 20% MeCN in water to 30% MeCN in water over a 10 min period, where both solvents contain 0.1% FA) to provide the title compound as a yellow solid. (5.4 mg, 14.3%). $^1$H NMR (300 MHz, CD$_3$OD): δ8.58 (s, 1H), 8.37 (s, 1H), 8.29 (d, J=4.6 Hz, 1H), 7.60 (t, J=9.1 Hz, 1H), 7.37 (dt, J=8.5, 4.5 Hz, 1H), 7.28 (dd, J=5.0, 3.2 Hz, 2H), 7.11 (d, J=8.4 Hz, 1H), 4.78-4.54 (m, 2H), 4.42 (s, 2H), 3.46 (d, J=4.4 Hz, 4H), 3.39 (d, J=6.7 Hz, 2H), 3.22 (t, J=6.8 Hz, 2H), 2.26 (t, J=2.7 Hz, 1H), 2.15-1.95 (m, 4H), 1.79 (dd, J=8.5, 6.8 Hz, 2H), 1.61 (t, J=7.5 Hz, 2H). LCMS (ES) [M+1]$^+$ m/z 626.2.

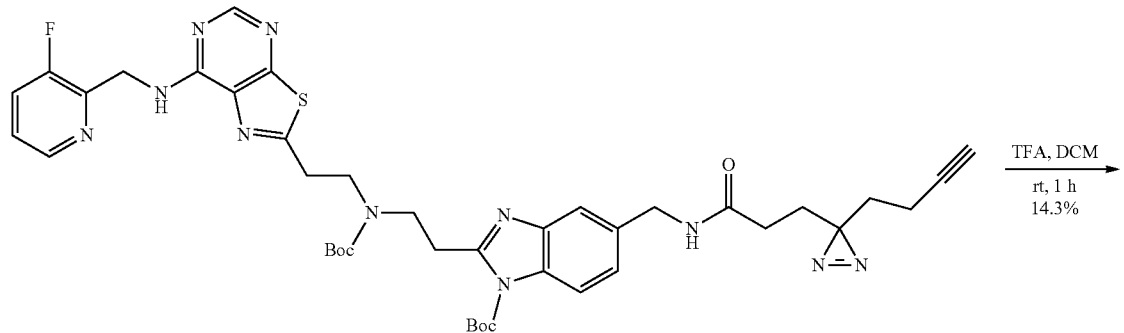

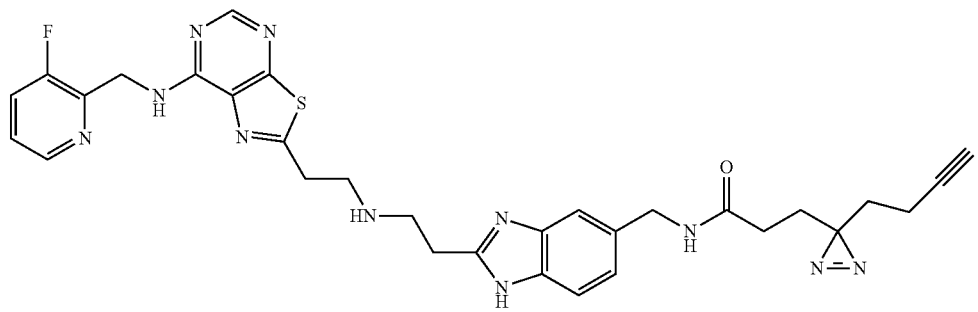

Example 1.49
Synthesis of 2-(2-{[1-(1H-1,3-benzodiazol-2-yl)propan-2-yl]amino}ethyl)-N-[(3-fluoropyridin-2-yl)methyl]-[1,3]thiazolo[5,4-d]pyrimidin-7-amine (Compound 40)
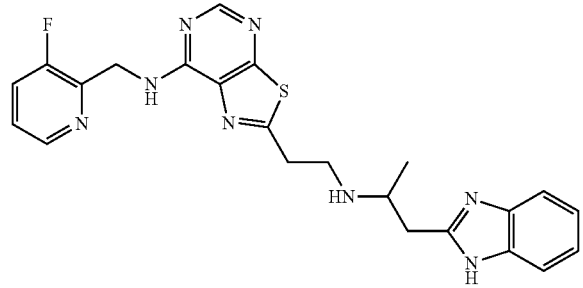 [SMILES: CC(Cc1nc2ccccc2[nH]1)NCCc1nc2c(NCc3ncccc3F)ncnc2s1]
Scheme 31 depicts a synthetic route for preparing an exemplary compound.
Scheme 31
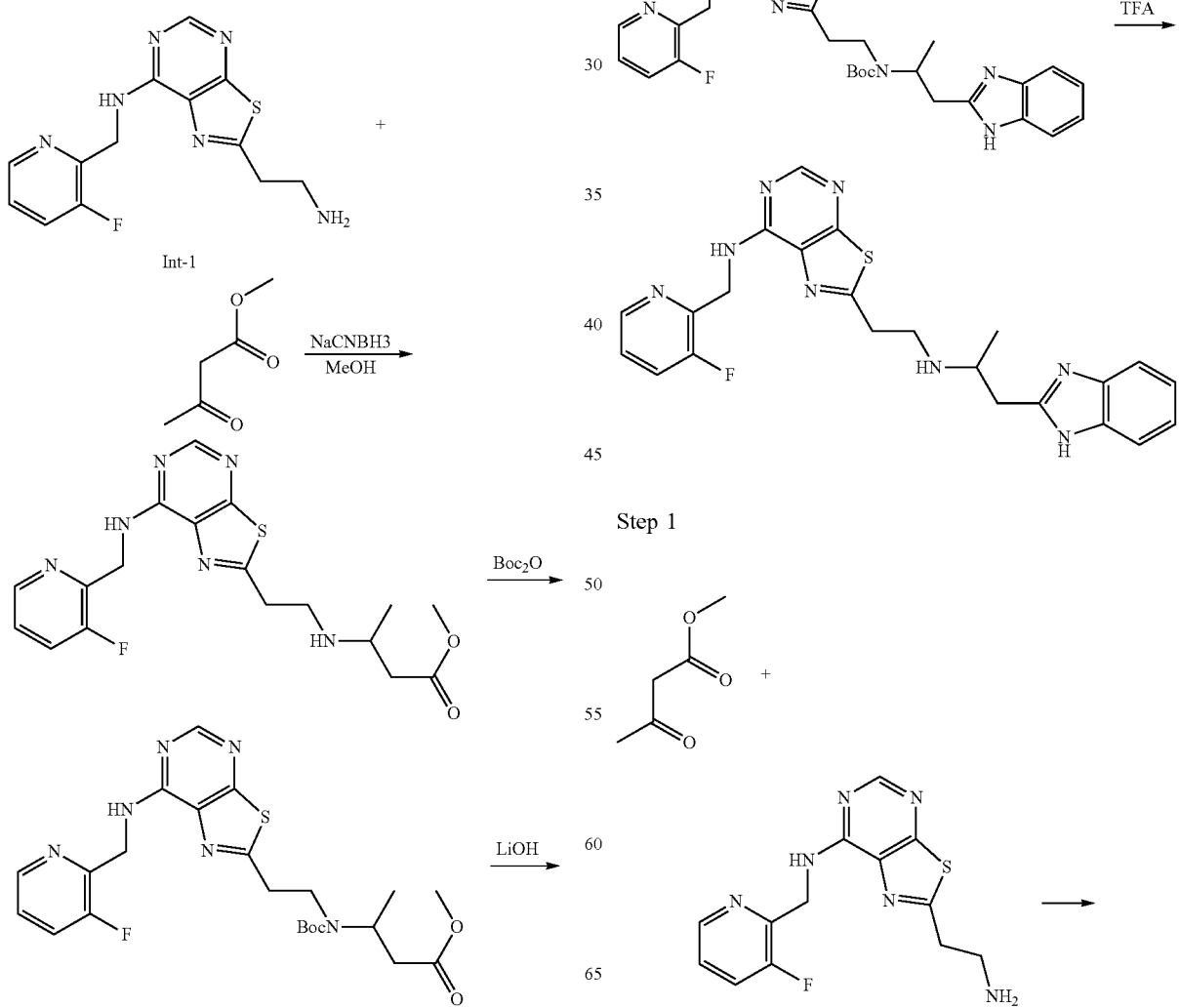
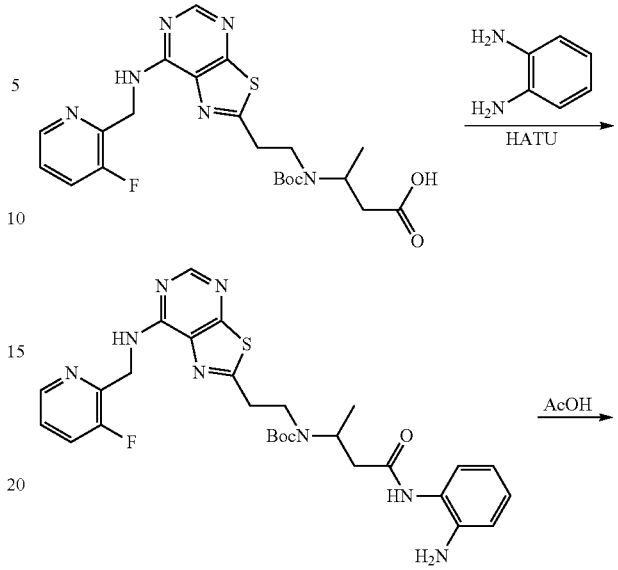
Step 1

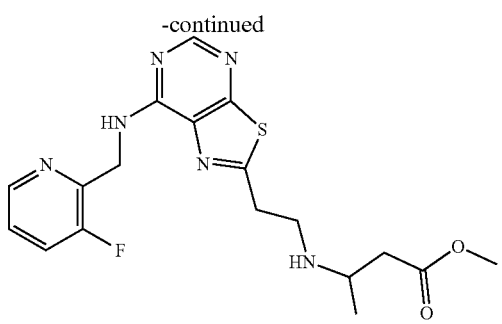

2-(2-Aminoethyl)-N-[(3-fluoropyridin-2-yl)methyl]-[1,3]thiazolo[5,4-d]pyrimidin-7-amine (140.00 mg; 0.46 mmol; 1.00 eq.) [Int-1] was dissolved in methanol (5 ml). Acetic acid (26.33 µL; 0.46 mmol; 1.00 eq.) and methyl 3-oxobutanoate (74.5 µL; 0.69 mmol; 1.50 eq.) were added, followed by 3A mol. sieves (activated, 0.9 g). After 1 h, the reaction was cooled in an ice bath. Sodium cyanoborohydride (57.8 mg; 0.92 mmol; 2.00 eq.) was added and the reaction was stirred for 64 h at 30° C. Sodium bicarbonate solution (20 ml) was added and the organic solvent was evaporated. The aqueous phase was extracted with ethyl acetate (2×100 ml) and the combined organic phases were dried over sodium sulfate. After evaporation of the solvent, the residue was purified by silica gel chromatography (0.1% NH$_4$OH/methanol/dichloromethane gradient) to give methyl 3-{[2-(7-{[(3-fluoropyridin-2-yl)methyl]amino}-[1,3]thiazolo[5,4-d]pyrimidin-2-yl)ethyl]amino}butanoate (60 mg, 32%). MS (ES+): (M+H)$^+$=405.0.

Step 2

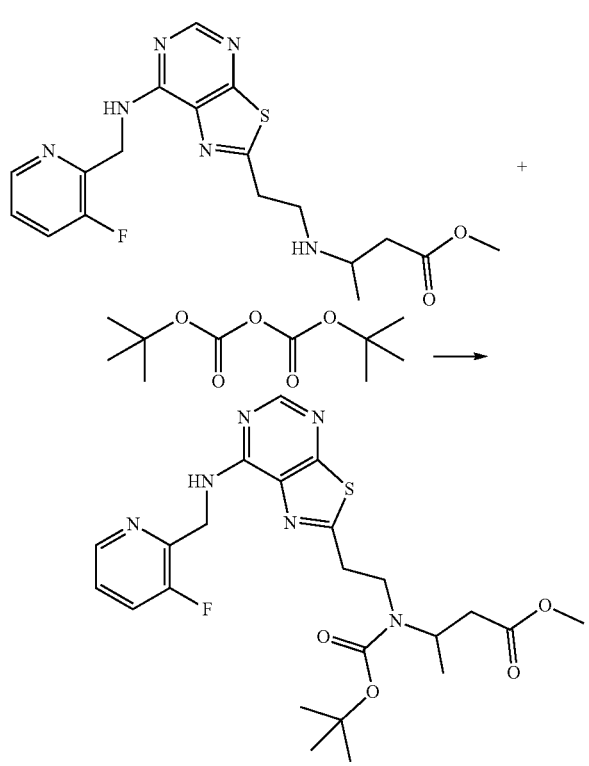

1-(1H-Benzimidazol-2-yl)ethanone (0.85 g; 5.30 mmol; 1.00 eq.) was dissolved in dichloromethane (2 ml). Triethylamine (0.04 mL; 0.31 mmol; 1.50 eq.), and then di-tert-butyl dicarbonate (53.74 mg; 0.25 mmol; 1.20 eq.) were added. After 15 h, more di-tert-butyl dicarbonate (25 mg) in dichloromethane (1 ml) was added and stirring continued for 7 h. Sodium bicarbonate solution (20 ml) and ethyl acetate (50 ml) were then added. The phases were separated, the aqueous phase was extracted with more ethyl acetate (2×25 ml), and the combined organic phases were washed with sodium chloride solution (10 ml) and dried over sodium sulfate. After evaporation of the solvent, the residue was purified by silica gel chromatography (ethyl acetate/dichloromethane gradient) to give methyl 3-{[(tert-butoxy)carbonyl][2-(7-{[(3-fluoropyridin-2-yl)methyl]amino}-[1,3]thiazolo[5,4-d]pyrimidin-2-yl)ethyl]amino}butanoate (74 mg, 71%). MS (ES+): (M+H)$^+$=505.2.

Step 3

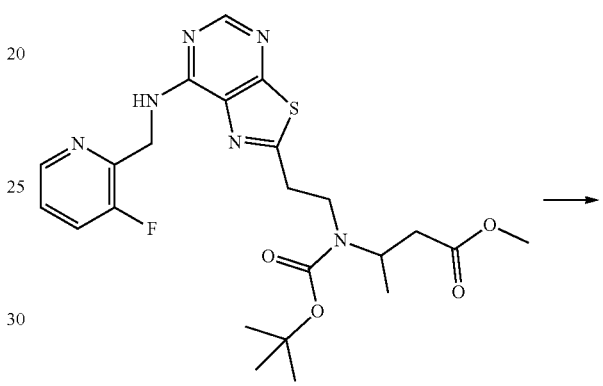

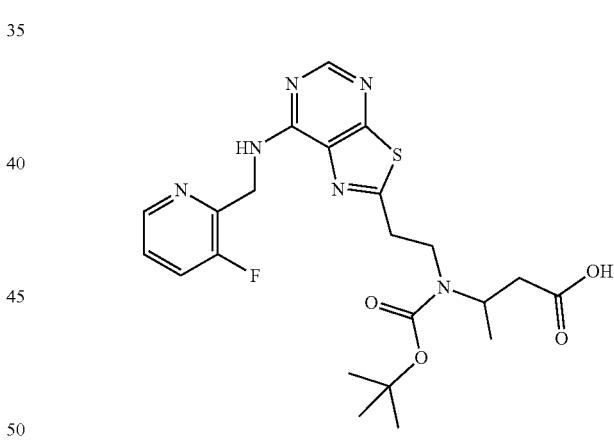

Methyl 3-{[(tert-butoxy)carbonyl][2-(7-{[(3-fluoropyridin-2-yl)methyl]amino}-[1,3]thiazolo[5,4-d]pyrimidin-2-yl)ethyl]amino}butanoate (74.00 mg; 0.15 mmol; 1.00 eq.) was dissolved in THF (2 ml) and methanol (0.5 ml) and stirred in an ice water bath. Lithium hydroxide (10.5 mg; 0.44 mmol; 3.00 eq.) dissolved in water (1 ml) was then added slowly and the reaction was stirred to 25° C. After 24 h, solvents were evaporated. Ethyl acetate (10 ml) was added and the solution was acidified carefully with 6 M HCl to pH 3. The solution was then evaporated to dryness, the residue was co-evaporated with toluene twice and dried under high vacuum. The residue of 3-{[(tert-butoxy)carbonyl][2-(7-{[(3-fluoropyridin-2-yl)methyl]amino}-[1,3]thiazolo[5,4-d]pyrimidin-2-yl)ethyl]amino}butanoic acid was used directly in the next step. MS (ES+): (M+H)$^+$=491.

Step 4

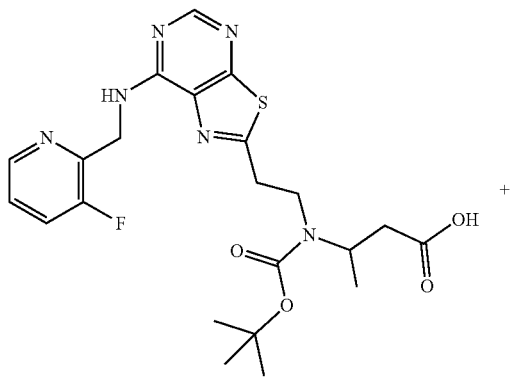

+

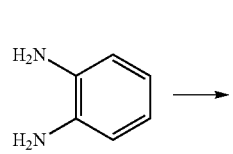

→

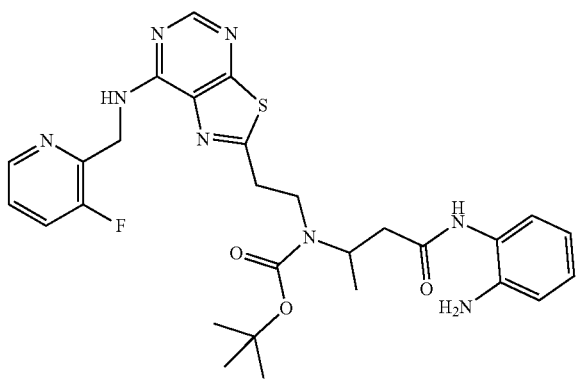

3-{[(Tert-butoxy)carbonyl][2-(7-{[(3-fluoropyridin-2-yl)methyl]amino}-[1,3]thiazolo[5,4-d]pyrimidin-2-yl)ethyl]amino}butanoic acid (72.00 mg; 0.15 mmol; 1.00 eq.) was dissolved in N,N-dimethylformamide (2 ml). 1,2-Benzenediamine (21.5 mg; 0.20 mmol; 1.35 eq.), and N,N-diisopropylethylamine (0.03 mL; 0.20 mmol; 1.35 eq.) and then 1-[bis(dimethylamino)methylene]-1H-1,2,3-triazolo[4,5-b]pyridinium 3-oxid hexafluorophosphate (HATU, 75.5 mg; 0.20 mmol; 1.35 eq.) were added. After 15 h, the reaction was taken up in ethyl acetate (50 ml) and sodium bicarbonate solution (20 ml). The phases were separated, and the aqueous phase was extracted with more ethyl acetate (20 ml). The combined organic phases were then dried over sodium sulfate. Solvents were evaporated, and the residue was purified by silica gel chromatography (methanol/dichloromethane gradient) to give tert-butyl N-{1-[(2-aminophenyl)carbamoyl]propan-2-yl}-N-[2-(7-{[(3-fluoropyridin-2-yl)methyl]amino}-[1,3]thiazolo[5,4-d]pyrimidin-2-yl)ethyl]carbamate (75 mg, 88%). MS (ES+): (M+H)$^+$=581.2.

Step 5

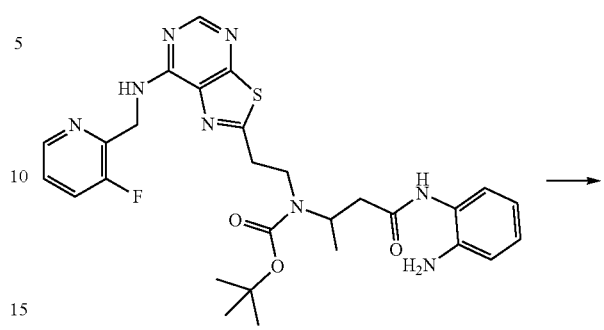

→

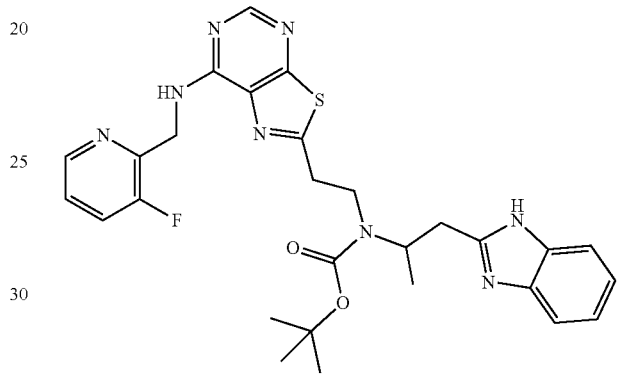

Tert-butyl N-{1-[(2-aminophenyl)carbamoyl]propan-2-yl}-N-[2-(7-{[(3-fluoropyridin-2-yl)methyl]amino}-[1,3]thiazolo[5,4-d]pyrimidin-2-yl)ethyl]carbamate (75.00 mg; 0.13 mmol; 1.00 eq.) was dissolved in acetic acid (2 ml) and stirred in a heat block at 80° C. After 30 m, the reaction was concentrated. The residue was taken up in ethyl acetate (50 ml) and washed with sodium bicarbonate solution (10 ml). The phases were separated, and the aqueous phase was extracted with ethyl acetate (2×50 ml). The combined organic phases were dried over sodium sulfate. Solvent was evaporated to give a residue of tert-butyl N-[1-(1H-1,3-benzodiazol-2-yl)propan-2-yl]-N-[2-(7-{[(3-fluoropyridin-2-yl)methyl]amino}-[1,3]thiazolo[5,4-d]pyrimidin-2-yl)ethyl]carbamate, which was used directly in the next step. MS (ES+): (M+H)$^+$=563.3.

Step 6

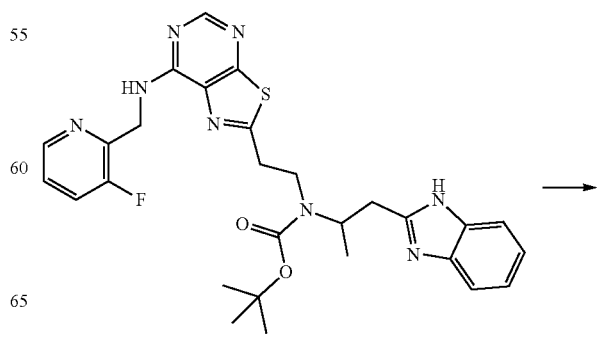

→

-continued

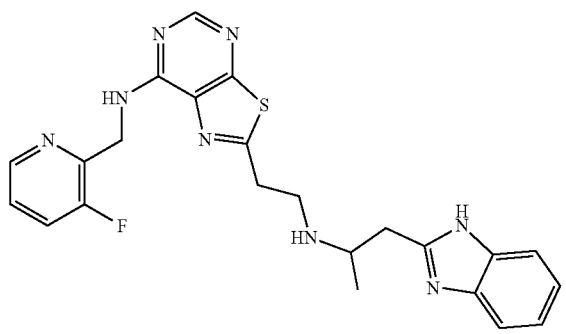

Tert-butyl N-{1-[(2-aminophenyl)carbamoyl]propan-2-yl}-N-[2-(7-{[(3-fluoropyridin-2-yl)methyl]amino}-[1,3]thiazolo[5,4-d]pyrimidin-2-yl)ethyl]carbamate (75.00 mg; 0.13 mmol; 1.00 eq.) was dissolved in dichloromethane (1.5 ml) and cooled in an ice bath. Trifluoroacetic acid (0.65 ml) was added slowly and the reaction was stirred at 25° C. for 2 h. The reaction was then evaporated to dryness and purified by reverse phase chromatography (Waters XSelect CSH C18 column, 0-50% acetonitrile/0.1% aqueous formic acid gradient) to give 2-(2-{[1-(1H-1,3-benzodiazol-2-yl)propan-2-yl]amino}ethyl)-N-[(3-fluoropyridin-2-yl)methyl]-[1,3]thiazolo[5,4-d]pyrimidin-7-amine (57 mg, 87%) as a white solid. $^1$H NMR (400 MHz, DMSO-$d_6$) δ 8.37 (s, 1H), 8.35-8.28 (m, 2H), 7.70 (ddd, J=10.0, 8.3, 1.3 Hz, 1H), 7.64-7.58 (m, 2H), 7.41-7.31 (m, 3H), 4.86 (d, J=5.6 Hz, 2H), 3.96 (q, J=6.7 Hz, 1H), 3.68-3.48 (m, 5H), 3.35-3.28 (m, 1H), 1.37 (d, J=6.5 Hz, 3H). MS (ES+): (M+H)$^+$=463.2.

Example 1.50

Synthesis of 2-(2-{[2-(1H-1,3-benzodiazol-2-yl)propyl]amino}ethyl)-N-[(3-fluoropyridin-2-yl)methyl]-[1,3]thiazolo[5,4-d]pyrimidin-7-amine (Compound 41)

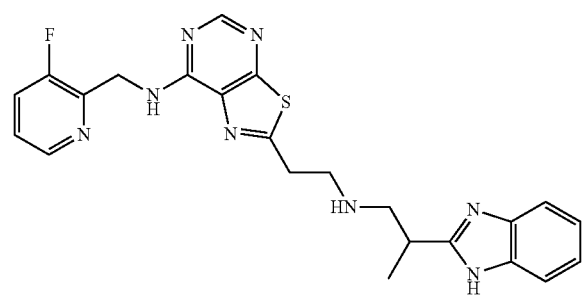

Scheme 32 depicts a synthetic route for preparing an exemplary compound.

Scheme 32

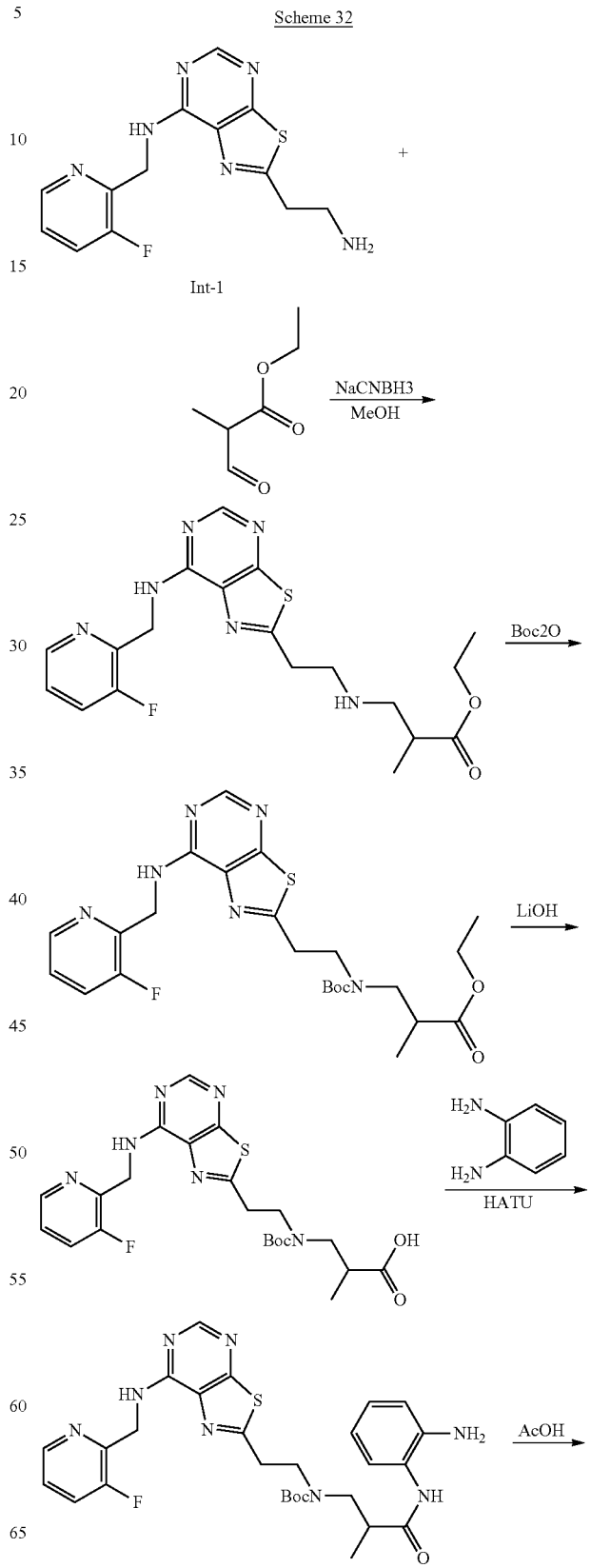

-continued

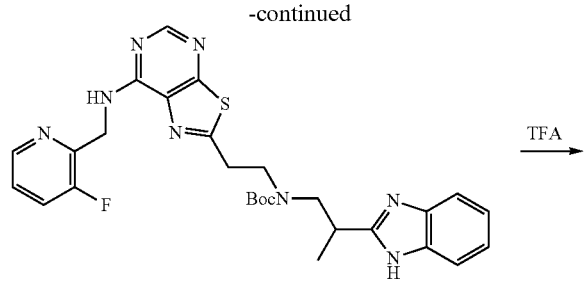

TFA →

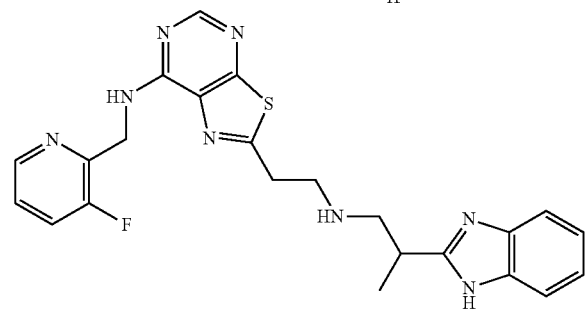

Step 1

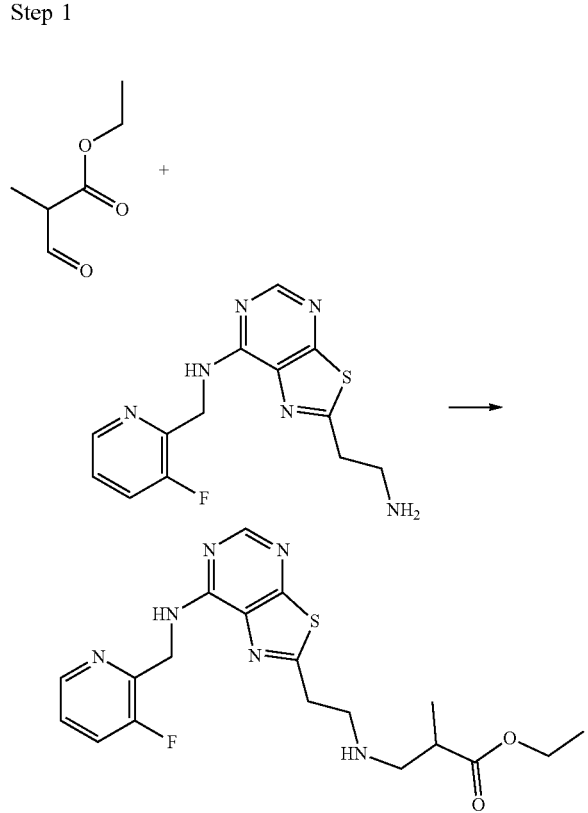

2-(2-Aminoethyl)-N-[(3-fluoropyridin-2-yl)methyl]-[1,3]thiazolo[5,4-d]pyrimidin-7-amine [Int-1] (300.00 mg; 0.99 mmol; 1.00 eq.) was dissolved in methanol (dry, 9 ml). Acetic acid (56 µL; 0.99 mmol; 1.00 eq.) was added to give a turbid soln. Ethyl 2 methyl-3-oxopropanoate (192 mg; 1.48 mmol; 1.50 eq.) and 0.5 g of 3A activated molecular sieves were then added. After two hours, the reaction was cooled in an ice bath. Sodium cyanoborohydride (124 mg; 1.97 mmol; 2.00 eq.) was added in portions and the reaction was stirred at 25° C. After 20 h, sodium bicarbonate solution was added, and organic solvents were evaporated. The remaining aqueous phase was extracted with ethyl acetate (3×50 ml) and the combined organic phases were dried over sodium sulfate. After evaporation, the crude residue was purified by silica gel chromatography (NH₄OH/methanol/dichloromethane gradient) to give a residue of ethyl 3-{[2-(7-{[(3-fluoropyridin-2-yl)methyl]amino}-[1,3]thiazolo[5,4-d]pyrimidin-2-yl)ethyl]amino}-2-methylpropanoate (0.17 g, 41%). MS (ES+): (M+H)⁺=419.1.

Step 2

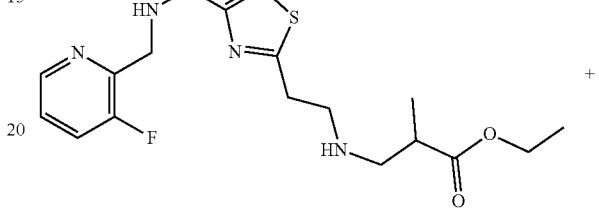

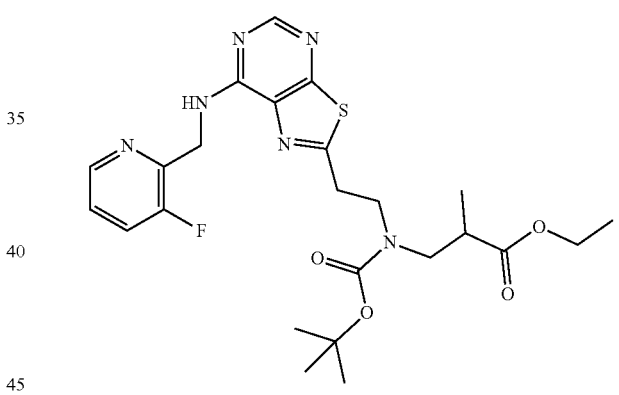

Ethyl 3-{[2-(7-{[(3-fluoropyridin-2-yl)methyl]amino}-[1,3]thiazolo[5,4-d]pyrimidin-2-yl)ethyl]amino}-2-methylpropanoate (170.00 mg; 0.41 mmol; 1.00 eq.) was dissolved in dichloromethane (5 ml). Triethylamine (0.10 mL; 0.71 mmol; 1.75 eq.) and then di-tert-butyl dicarbonate (133 mg; 0.61 mmol; 1.50 eq.) were added and the reaction was stirred at 25° C. After 16 h, more di-tert-butyl dicarbonate (43 mg) in dichloromethane (1 ml) was added and the reaction was stirred for an additional 8 h. Water (10 ml), sodium bicarbonate solution (10 ml), and ethyl acetate (50 ml) were added and the phases were separated. The aqueous phase was extracted (2×50 ml ethyl acetate), the combined organic phases were washed with sodium chloride solution and dried over sodium sulfate. After evaporation of solvent, the crude residue was purified by silica gel chromatography (ethyl acetate/dichloromethane gradient) to give a residue of ethyl 3-{[(tert-butoxy)carbonyl][2-(7-{[(3-fluoropyridin-2-yl)methyl]amino}-[1,3]thiazolo[5,4-d]pyrimidin-2-yl)ethyl]amino}-2-methylpropanoate (178 mg, 84%). MS (ES+): (M+H)⁺=519.2.

Step 3

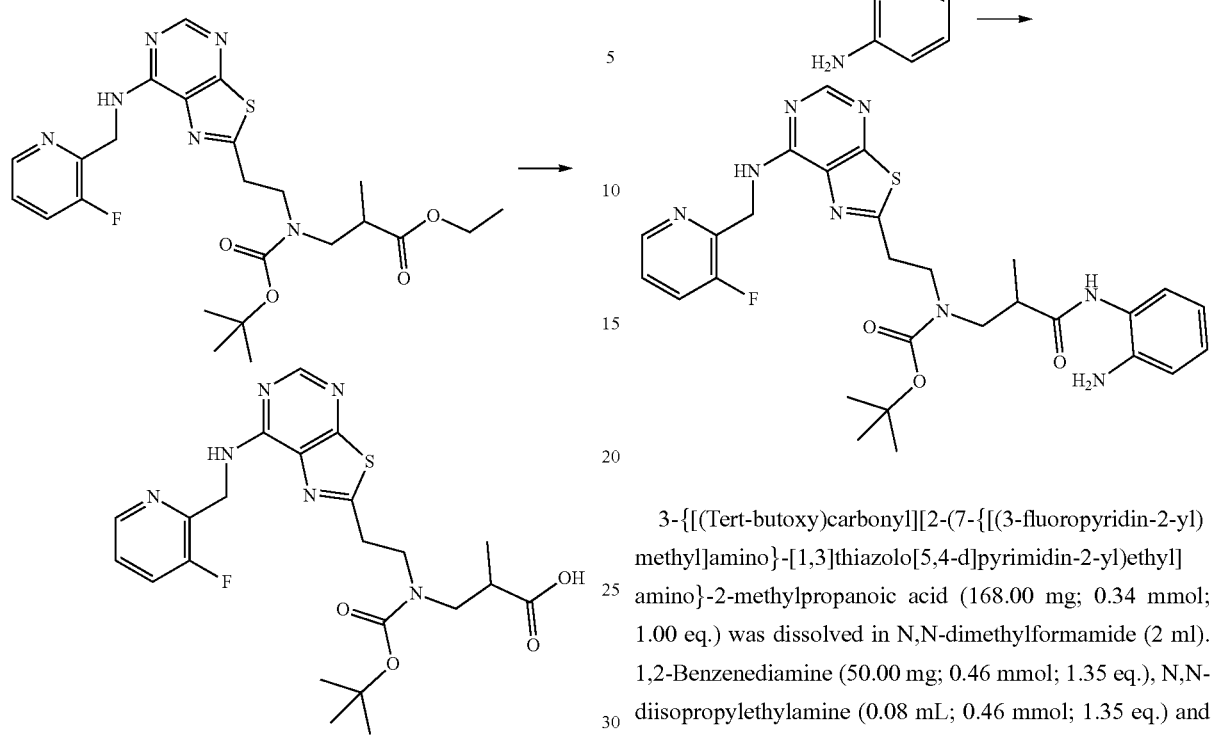

Ethyl 3-{[(tert-butoxy)carbonyl][2-(7-{[(3-fluoropyridin-2-yl)methyl]amino}-[1,3]thiazolo[5,4-d]pyrimidin-2-yl)ethyl]amino}-2-methylpropanoate (178.00 mg; 0.34 mmol; 1.00 eq.) was dissolved in THF (2 ml) and methanol (0.5 ml) and stirred in an ice water bath. Lithium hydroxide (anhydrous) (41 mg; 1.72 mmol; 5.00 eq.) dissolved in water (1 ml) was added slowly. The reaction was stirred to 25° C. over 14 h. 6M HCl was added carefully to the reaction to give a pH of approximately 4. The reaction mixture was evaporated to dryness and the residue was suspended in toluene (20 ml) and evaporated to dryness again. After repeating once more, the residue was dried under high vacuum to give 3-{[(tert-butoxy)carbonyl][2-(7-{[(3-fluoropyridin-2-yl)methyl]amino}-[1,3]thiazolo[5,4-d]pyrimidin-2-yl)ethyl]amino}-2-methylpropanoic acid (0.29 g crude mixture). MS (ES+): (M+H)$^+$=491.1.

Step 4

3-{[(Tert-butoxy)carbonyl][2-(7-{[(3-fluoropyridin-2-yl)methyl]amino}-[1,3]thiazolo[5,4-d]pyrimidin-2-yl)ethyl]amino}-2-methylpropanoic acid (168.00 mg; 0.34 mmol; 1.00 eq.) was dissolved in N,N-dimethylformamide (2 ml). 1,2-Benzenediamine (50.00 mg; 0.46 mmol; 1.35 eq.), N,N-diisopropylethylamine (0.08 mL; 0.46 mmol; 1.35 eq.) and then 1-[bis(dimethylamino)methylene]-1H-1,2,3-triazolo[4,5-b]pyridinium 3-oxid hexafluorophosphate (HATU, 176 mg; 0.46 mmol; 1.35 eq.) were added. After 2 h, the reaction was partitioned into ethyl acetate (50 ml) and sodium bicarbonate solution (50 ml). The phases were separated, and the aqueous phase was extracted with ethyl acetate (50 ml). The combined organic phases were washed with sodium chloride solution and dried over sodium sulfate. After evaporation, the residue was purified by silica gel chromatography (methanol/dichloromethane gradient) to give a residue of tert-butyl N-{2-[(2-aminophenyl)carbamoyl]-2-methylethyl}-N-[2-(7-{[(3-fluoropyridin-2-yl)methyl]amino}-[1,3]thiazolo[5,4-d]pyrimidin-2-yl)ethyl]carbamate (0.22 g). MS (ES+): (M+H)$^+$=581.1.

Step 5

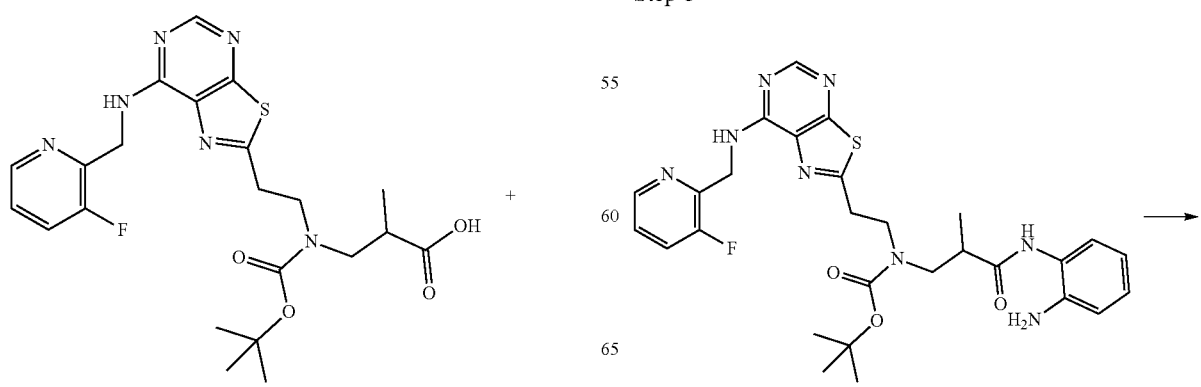

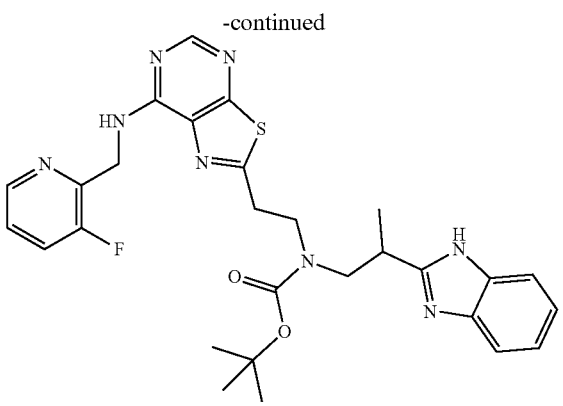

Tert-butyl N-{2-[(2-aminophenyl)carbamoyl]-2-methylethyl}-N-[2-(7-{[(3-fluoropyridin-2-yl)methyl]amino}-[1,3]thiazolo[5,4-d]pyrimidin-2-yl)ethyl]carbamate (0.20 g; 0.34 mmol; 1.00 eq.) was dissolved in acetic acid (4 ml) and stirred in a heat block at 80° C. After 40 m, the reaction was concentrated, the residue was dissolved in ethyl acetate (100 ml) and washed with sodium bicarbonate solution (50 ml). The phases were separated, the aqueous phase was extracted with ethyl acetate (2×50 ml), and the combined organic phases were then dried over sodium sulfate. The residue obtained from evaporation of solvent (tert-butyl N-[2-(1H-1,3-benzodiazol-2-yl)propyl]-N-[2-(7-{[(3-fluoropyridin-2-yl)methyl]amino}-[1,3]thiazolo[5,4-d]pyrimidin-2-yl)ethyl] carbamate) was used directly in the next step. MS (ES+): (M+H)$^+$=563.
Step 6

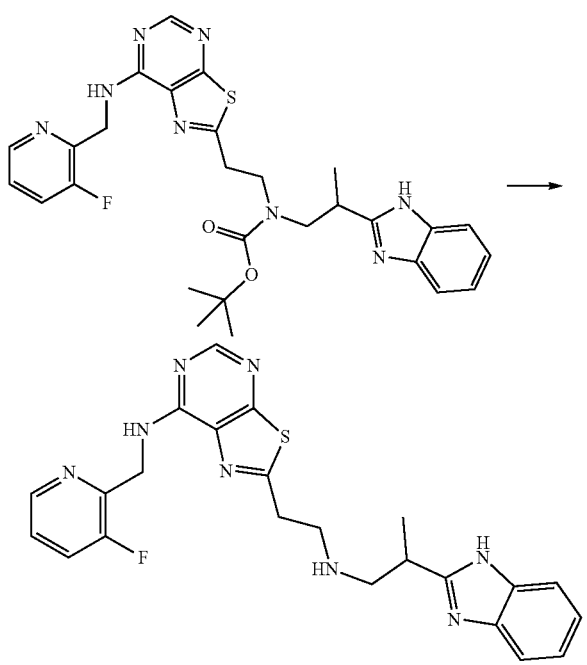

Tert-butyl N-{1-[(2-aminophenyl)carbamoyl]propan-2-yl}-N-[2-(7-{[(3-fluoropyridin-2-yl)methyl]amino}-[1,3]thiazolo[5,4-d]pyrimidin-2-yl)ethyl]carbamate (75.00 mg; 0.13 mmol; 1.00 eq.) was dissolved in dichloromethane (4 ml) and cooled in an ice bath. Trifluoroacetic acid (1.70 mL; 0.20 mol/L; 0.34 mmol; 1.01 eq.) was added slowly and the reaction was stirred at 25° C. After 1 h, the reaction was evaporated and dried under high vacuum. Purification by reverse phase chromatography (Waters XSelect CSH C18 column, 0-50% acetonitrile/0.1% aqueous formic acid gradient) gave 2-(2-{[2-(1H-1,3-benzodiazol-2-yl)propyl]amino}ethyl)-N-[(3-fluoropyridin-2-yl)methyl]-[1,3]thiazolo[5,4-d]pyrimidin-7-amine (0.15 g, 87%). $^1$H NMR (400 MHz, DMSO-d$_6$) δ 8.39-8.27 (m, 3H), 7.70 (ddd, J=10.0, 8.3, 1.3 Hz, 1H), 7.60-7.51 (m, 2H), 7.42-7.35 (m, 1H), 7.32-7.24 (m, 2H), 4.90-4.80 (m, 2H), 3.62-3.50 (m, 7H), 1.47 (d, J=6.2 Hz, 3H). MS (ES+): (M+H)$^+$=463.1.

Example 1.51

Synthesis of 2-(2-{[2-(7-{[(3-fluoropyridin-2-yl)methyl]amino}-[1,3]thiazolo[5,4-d]pyrimidin-2-yl)ethyl]amino}ethyl)phenol (Compound 44)

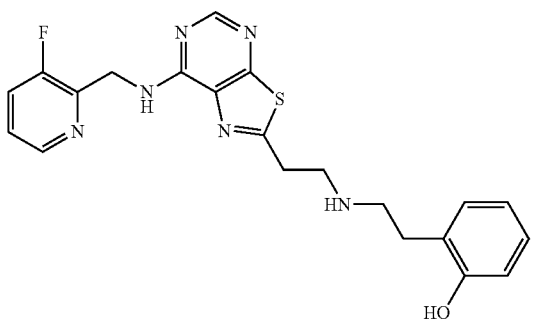 [SMILES: Oc1ccccc1CCNCCc1nc2c(NCc3ncccc3F)ncnc2s1]

Scheme 33 depicts a synthetic route for preparing an exemplary compound.

Scheme 33

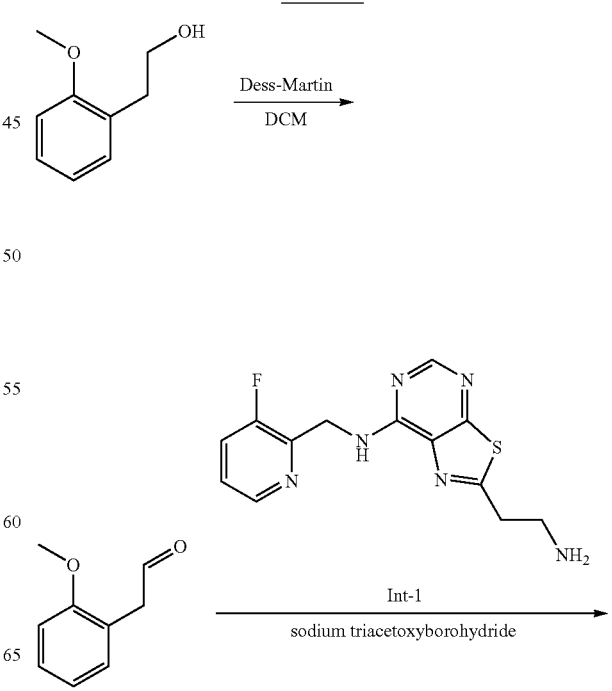

245
-continued

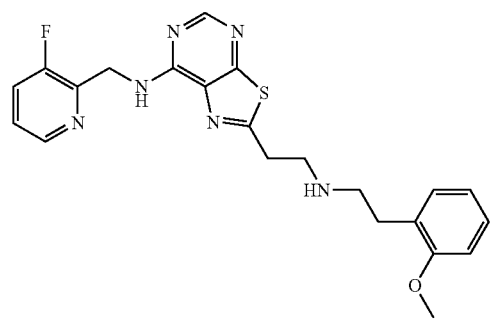

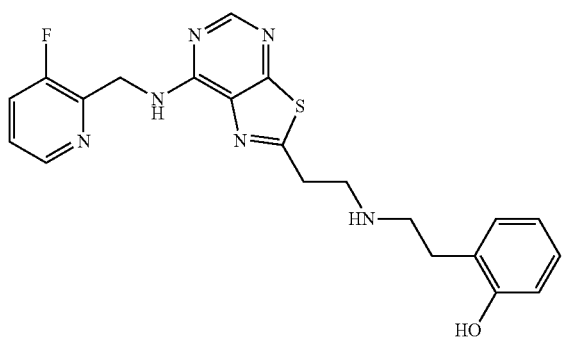

Step 1

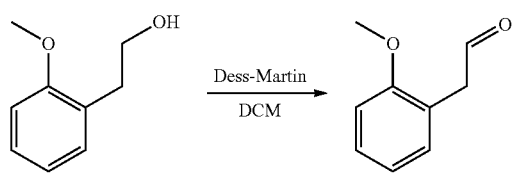

Into a 100-mL round-bottom flask, was placed 2-(2-methoxyphenyl) ethanol (1.00 g, 1 equiv), and DCM (50 mL). This was followed by the addition of Dess-Martin (2.90 g, 1.05 equiv) at 0° C. The resulting solution was stirred for 3 hr at room temperature. The solids were filtered out. The resulting mixture was concentrated. The residue was applied onto a silica gel column with ethyl acetate/petroleum ether (3:1). This resulted in 0.8 g of 2-(2-methoxyphenyl) acetaldehyde as a colorless oil.

Step 2

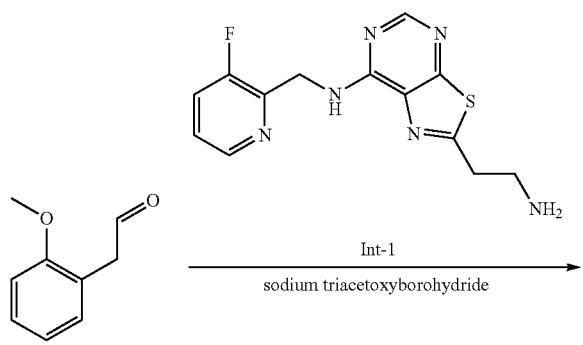

246
-continued

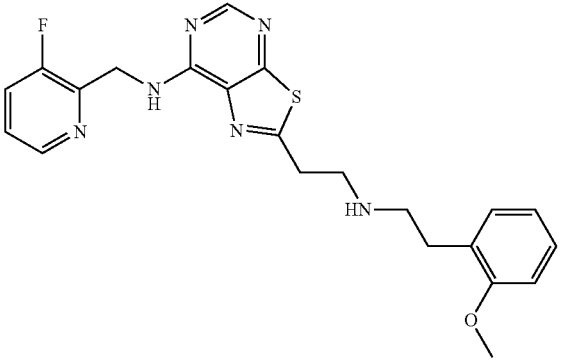

Into a 100-mL round-bottom flask, was placed 2-(2-aminoethyl)-N-[(3-fluoropiperidin-2-yl)methyl]-octahydro-[1,3]thiazolo[5,4-d]pyrimidin-7-amine (700.00 mg, 1.00 equiv), 2-(2-methoxyphenyl)acetaldehyde (420.00 mg, 1.20 equiv), CHCl$_3$ (20.00 mL), and EtOH (6.00 mL). This was followed by the addition of sodium triacetoxyborohydride (1.20 g, 2.50 equiv), in portions at 0° C. The resulting solution was stirred overnight at room temperature. The reaction was then quenched by the addition of 10 mL of water. The resulting solution was extracted with 3×20 mL of ethyl acetate and the organic layers were combined and dried over anhydrous sodium sulfate and concentrated. The residue was applied onto a silica gel column with ethyl acetate/petroleum ether (1:1). This resulted in 300 mg of N-[(3-fluoropyridin-2-yl)methyl]-2-(2-[[2-(2-methoxyphenyl)ethyl]amino]ethyl)-[1,3]thiazolo[5,4-d]pyrimidin-7-amine as a white solid. LCMS (ES) [M+1]$^+$ m/z: 439.

Step 3

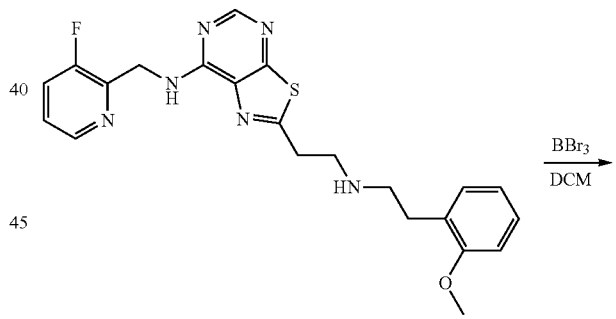

Into a 100-mL round-bottom flask purged and maintained with an inert atmosphere of nitrogen, was placed DCM (50.00 mL), N-[(3-fluoropyridin-2-yl)methyl]-2-(2-[[2-(2-methoxyphenyl)ethyl]amino]ethyl)-[1,3]thiazolo[5,4-d]pyrimidin-7-amine (500.00 mg, 1.00 equiv). This was followed by the addition of BBr₃ (11.40 mL, 10.00 equiv) dropwise with stirring at −50° C. in 10 min. The resulting solution was warmed up to 0° C. and stirred for 2 hr at 0° C. The reaction was then quenched by the addition of 5 mL of water. The resulting solution was extracted with 3×20 mL of concentrated dichloromethane. The crude product was purified by Flash-Prep-HPLC (Prep-C18, 20-45M, 120 g, Tianjin Bonna-Agela Technologies; gradient elution of 30% MeCN in water to 60% MeCN in water over a 10 min period, where both solvents contained 0.05% NH₃.H₂O). This resulted in 55.7 mg (11.3%) of 2-(2-((2-(7-(((3-fluoropyridin-2-yl)methyl)amino)thiazolo[5,4-d]pyrimidin-2-yl)ethyl)amino)ethyl)phenol as an off-white solid. ¹H-NMR: (300 MHz, DMSO-d₆, ppm): δ 8.53 (s, 1H), 8.39 (s, 1H), 8.32 (dt, J=4.8, 1.4 Hz, 1H), 7.65 (ddd, J=9.8, 8.4, 1.3 Hz, 1H), 7.41 (dt, J=8.6, 4.5 Hz, 1H), 7.13 (dd, J=7.4, 1.6 Hz, 1H), 7.06 (td, J=7.7, 1.7 Hz, 1H), 6.82-6.69 (m, 2H), 5.05 (s, 2H), 3.58 (dd, J=13.6, 5.1 Hz, 4H), 3.41-3.32 (m, 2H), 3.04 (t, J=7.3 Hz, 2H). LCMS: (ES, m/z): [M+H]⁺: 425.

Example 1.52

Synthesis of 2-(2-{[2-(1H-1,3-benzodiazol-2-yl)-2-fluoroethyl]amino}ethyl)-N-[(3-fluoropyridin-2-yl)methyl]-[1,3]thiazolo[5,4-d]pyrimidin-7-amine (Compound 45)

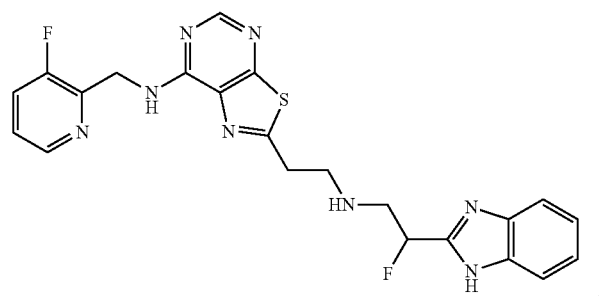 [SMILES: Fc1cccnc1CNc1ncnc2sc(CCNCC(F)c3nc4ccccc4[nH]3)nc12]

Scheme 34 depicts a synthetic route for preparing an exemplary compound.

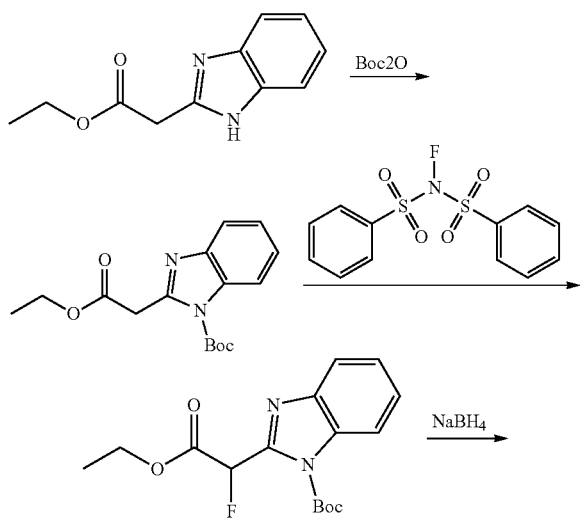

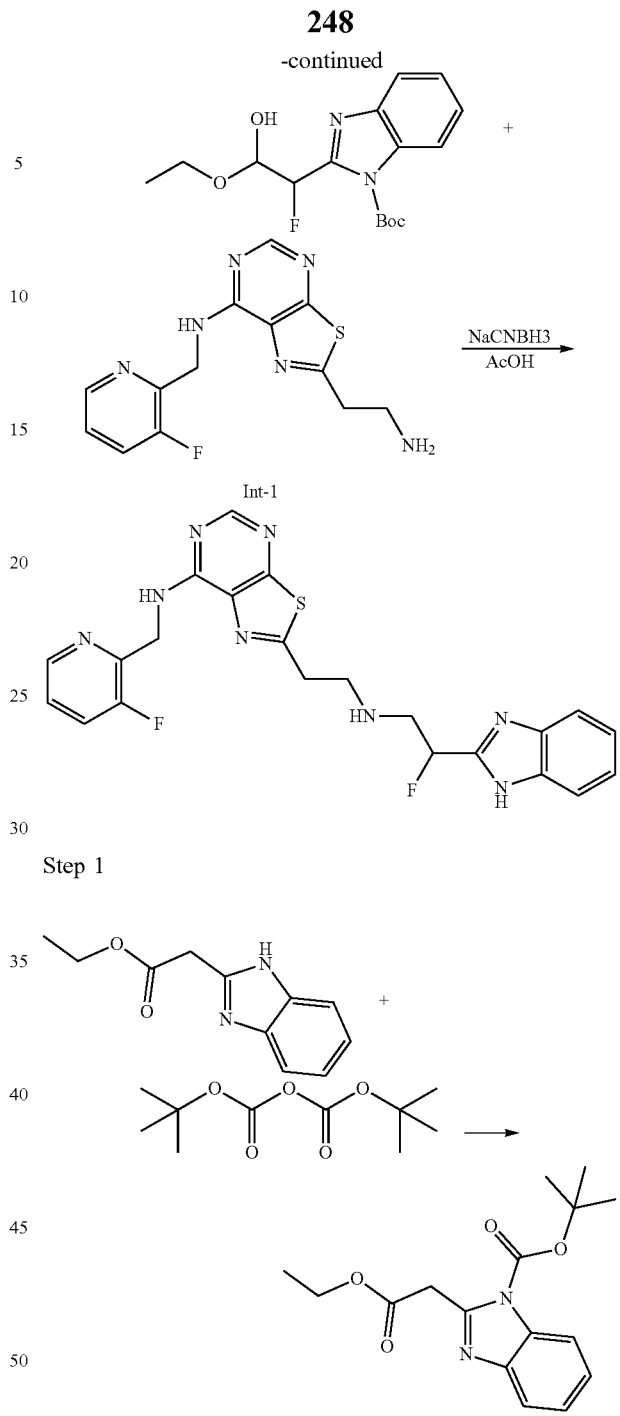

1-(1H-benzimidazol-2-yl)ethanone (0.85 g; 5.30 mmol; 1.00 eq.) was dissolved in THF (48 ml). Triethylamine (0.71 mL; 5.09 mmol; 1.05 eq.), di-tert-butyl dicarbonate (1.27 g; 5.82 mmol; 1.20 eq.) and N,N-dimethylaminopyridine (0.12 g; 0.97 mmol; 0.20 eq.) were then added, and the reaction was stirred at 25° C. After 21 h, water (50 ml), ammonium chloride solution (50 ml), and ethyl acetate (200 ml) were added to the reaction. The phases were separated, and the aqueous phase was extracted with ethyl acetate (1×50 ml). The combined organic phases were washed with sodium chloride solution (50 ml) and dried over sodium sulfate. After evaporation of solvent, the crude residue was purified by silica gel chromatography (ethyl acetate/hexanes gradient) to give an off-white solid of tert-butyl 2-(2-ethoxy-2- oxoethyl)-1H-1,3-benzodiazole-1-carboxylate (1.32 g, 89%). MS (ES+): (M+H)⁺=305.0.

Step 2

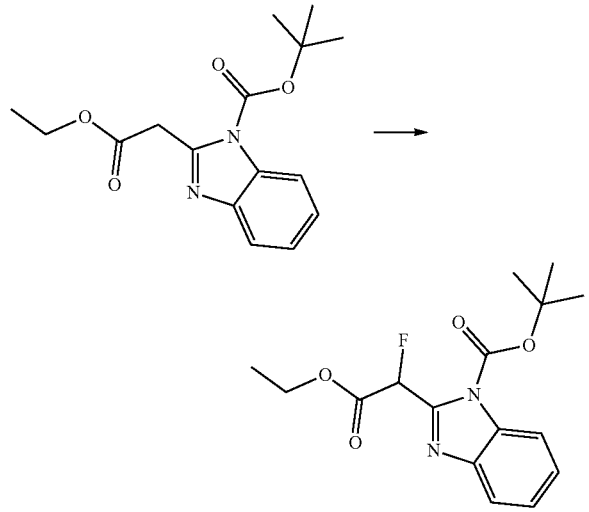

Sodium bis(trimethylsilyl)azanide (0.23 g; 1.23 mmol; 1.50 eq.) was taken up in THF (dry, 5 ml). The solution was cooled in a dry-ice bath. Tert-butyl 2-(2-ethoxy-2-oxoethyl)-1H-1,3-benzodiazole-1-carboxylate (0.25 g; 0.82 mmol; 1.00 eq.) in THF (4 ml) was added slowly. The reaction was stirred in the bath for 1 h. N-Fluoro-N-(phenylsulfonyl)benzenesulfonamide (0.36 g; 1.15 mmol; 1.40 eq.) and 18-crown-6 (0.33 g; 1.23 mmol; 1.50 eq.) dissolved in THF (3 ml), was then added slowly. The reaction was stirred in a cooling bath to 25° C. over 16 h. Ammonium chloride solution (50 ml), water (50 ml) and ethyl acetate (100 ml) were added and the phases were separated. The aqueous phase was extracted with ethyl acetate (2×50 ml) and the combined organic phases were washed with sodium chloride solution and dried over sodium sulfate. After evaporation, the residue was purified by silica gel chromatography (ethyl acetate/hexanes gradient) to give tert-butyl 2-(2-ethoxy-1-fluoro-2-oxoethyl)-1H-1,3-benzodiazole-1-carboxylate (0.22 g, 83%) as a white crystalline solid. MS (ES+): (M+H)⁺=323.0. ¹H NMR (400 MHz, Chloroform-d) δ 7.99-7.92 (m, 1H), 7.85-7.76 (m, 1H), 7.48-7.35 (m, 2H), 6.49 (dd, J=46.3, 1.6 Hz, 1H), 4.36 (qd, J=7.1, 1.6 Hz, 2H), 1.72 (s, 9H), 1.32 (td, J=7.1, 1.6 Hz, 3H).

Step 3

-continued

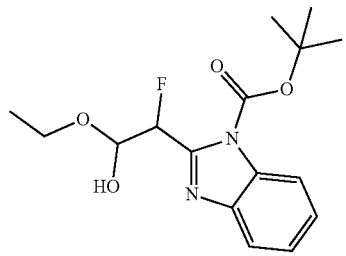

Tert-butyl 2-(2-ethoxy-1-fluoro-2-oxoethyl)-1H-1,3-benzodiazole-1-carboxylate (0.22 g; 0.68 mmol; 1.00 eq.) was dissolved in ethanol (dry, 9 ml) and cooled in an ice bath. To the cloudy mixture, sodium borohydride (38.73 mg; 1.02 mmol; 1.50 eq.) was added and the reaction was stirred in the bath to 25° C. After 2 h, more sodium borohydride (20 mg) was added. After 3 additional hours, the reaction was cooled in an ice bath and 1 M HCl (0.9 ml) was added dropwise. More water (10 ml) and ethyl acetate (100 ml) were then added and the phases were separated. The aqueous phase was extracted with ethyl acetate (3×50 ml) and the combined organic phases were dried over sodium sulfate. After evaporation, the crude residue was purified by silica gel chromatography (ethyl acetate/dichloromethane gradient) to give tert-butyl 2-(2-ethoxy-1-fluoro-2-hydroxyethyl)-1H-1,3-benzodiazole-1-carboxylate (0.13 g, 53%). MS (ES+): (M+H)⁺=324.9. ¹H NMR (400 MHz, Chloroform-d) δ 7.71-7.62 (m, 2H), 7.35-7.27 (m, 2H), 6.24-6.16 (m, 1H), 5.95-5.79 (m, 1H), 4.00-3.79 (m, 1H), 3.78-3.67 (m, 1H), 1.48 (s, 7H), 1.43 (s, 2H), 1.26 (td, J=7.1, 2.4 Hz, 1H), 1.16 (t, J=7.1 Hz, 2H).

Step 4

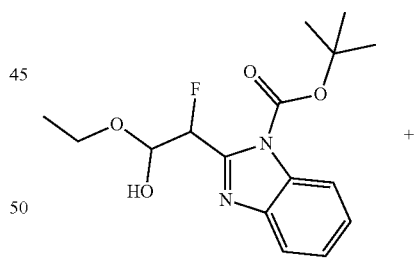

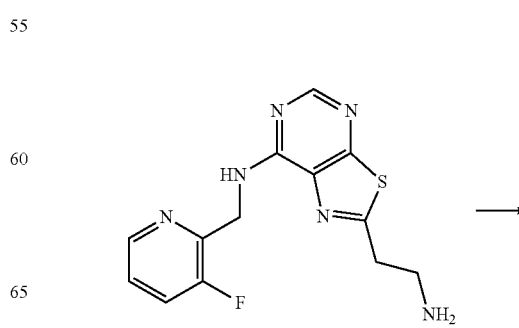

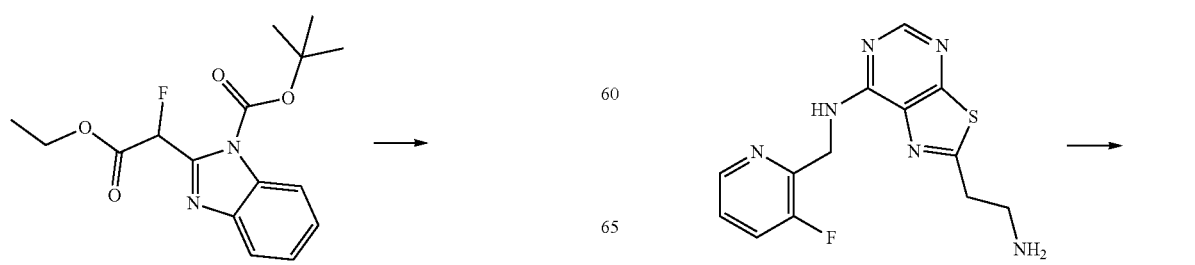

Tert-butyl 2-(2-ethoxy-1-fluoro-2-hydroxyethyl)-1H-1,3-benzodiazole-1-carboxylate (0.13 g; 0.41 mmol; 1.00 eq.) was dissolved in methanol (dry, 5 ml). 2-(2-Aminoethyl)-N-[(3-fluoropyridin-2-yl)methyl]-[1,3]thiazolo[5,4-d]pyrimidin-7-amine (124 mg; 0.41 mmol; 1.00 eq.) [Int-1] and 3A molecular sieves (0.34 g). After 30 m, acetic acid (0.02 mL; 0.41 mmol; 1.00 eq.) was added followed by sodium cyanoborohydride (51 mg; 0.81 mmol; 2.00 eq.) added in portions. After 16 h, the reaction was diluted with toluene (dry, 5 ml) and more 3A molecular sieves (0.3 g) were added. The mixture was gradually heated to 110° C. for 4 h. The reaction was cooled and neutralized with 1 M HCl, taken up in sodium bicarbonate solution (10 ml), and then extracted with ethyl acetate (3×50 ml). The combined organics were filtered, evaporated, and purified by reverse phase chromatography (Waters XSelect CSH C18 column, 0-50% acetonitrile/0.1% aqueous formic acid gradient) to give a white solid of 2-(2-{[2-(1H-1,3-benzodiazol-2-yl)-2-fluoroethyl]amino}ethyl)-N-[(3-fluoropyridin-2-yl)methyl]-[1,3]thiazolo[5,4-d]pyrimidin-7-amine (formate salt, 11.5 mg, 5.5%) MS (ES+): (M+H)$^+$=467.0. $^1$H NMR (400 MHz, DMSO-d$_6$) δ 8.35-8.28 (m, 2H), 8.23 (s, 1H), 7.70 (ddd, J=10.0, 8.3, 1.4 Hz, 1H), 7.59-7.51 (m, 2H), 7.41-7.35 (m, 1H), 7.23-7.17 (m, 2H), 4.88 (d, J=5.8 Hz, 2H), 3.35-3.33 (m, 1H), 3.30-3.28 (m, 1H), 3.28-3.22 (m, 2H), 3.10-3.05 (m, 2H).

Example 1.53

Synthesis of 2-(2-{[2-(5,6-dimethyl-1H-1,3-benzodiazol-2-yl)ethyl]amino}ethyl)-N-[(3-fluoropyridin-2-yl)methyl]-[1,3]thiazolo[5,4-d]pyrimidin-7-amine (Compound 46)

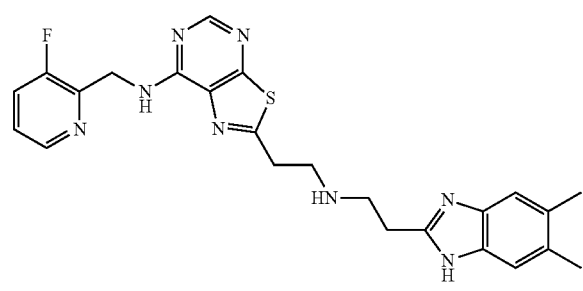 [SMILES: Cc1cc2nc(CCNCCc3nc4c(NCc5ncccc5F)ncnc4s3)[nH]c2cc1C]

Scheme 35 depicts a synthetic route for preparing an exemplary compound.

Scheme 35

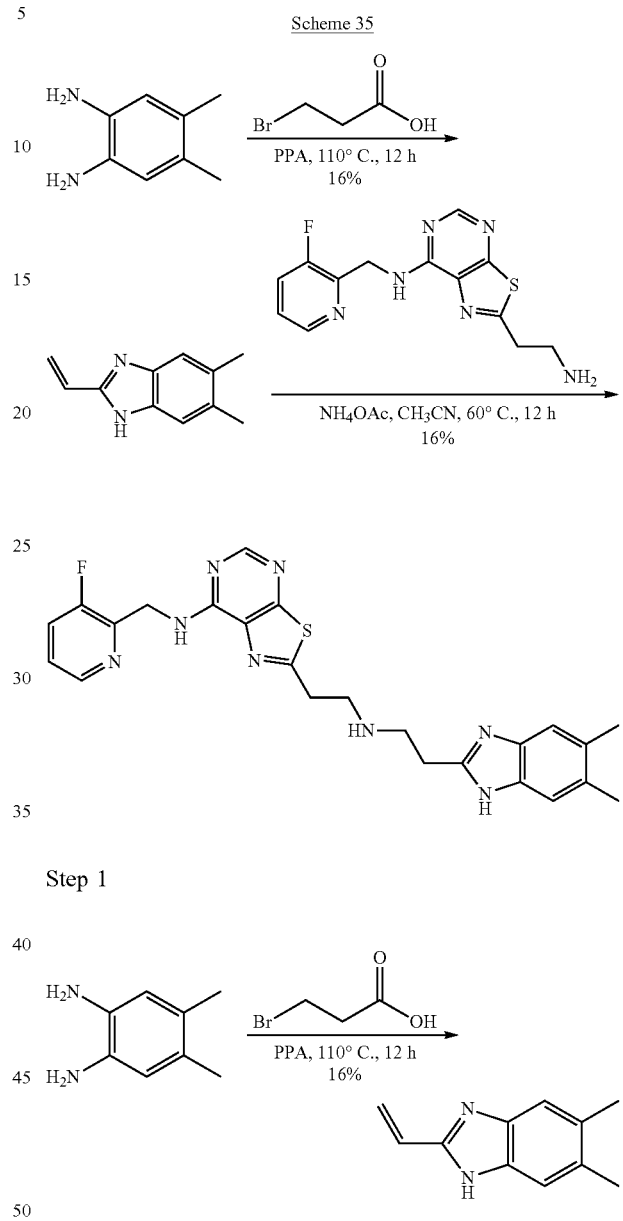

Step 1

Into a 50-mL round-bottom flask, was placed 4,5-dimethylbenzene-1,2-diamine (2.0 g, 14.69 mmol, 1.0 equiv), 3-bromopropanoic acid (2.25 g, 14.69 mmol, 1.0 equiv), and PPA (14.0 mL). The mixture was stirred for 12 h at 110° C. The reaction mixture was poured onto crushed ice. The pH value of the solution was adjusted to 8-9 with NH$_4$OH, extracted with 3×30 mL of ethyl acetate, combined the organic phase, and dried over anhydrous Na$_2$SO$_4$. The solution was filtered, and the filtrate was concentrated under reduced pressure. The residue was purified by flash column with ethyl acetate/petroleum ether (1/2). 400 mg (16%) of 2-ethenyl-5,6-dimethyl-1H-1,3-benzodiazole was obtained as a light-yellow solid. LCMS (ES) [M+1]$^+$ m/z: 173.

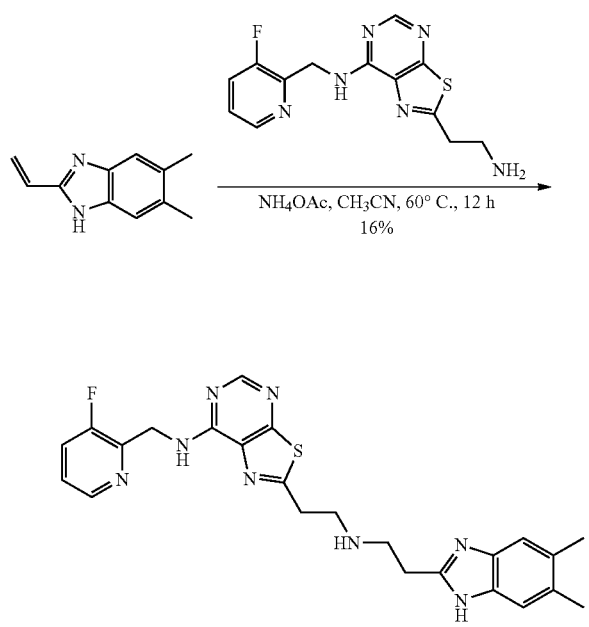

Into a 20-mL round-bottom flask, was placed 2-ethenyl-5,6-dimethyl-1H-1,3-benzodiazole (173 mg, 1.0 mmol, 1.0 equiv), 2-(2-aminoethyl)-N-[(3-fluoropyridin-2-yl)methyl]-[1,3]thiazolo[5,4-d]pyrimidin-7-amine (304 mg, 1.0 mmol, 1.0 equiv), NH₄OAc (77 mg, 1.0 mmol, 1.0 equiv), and CH₃CN (7.0 mL). The reaction solution was stirred for 12 h at 60° C. The mixture was concentrated under reduced pressure. The crude product was purified by Prep-HPLC with the following conditions: Column, Atlantis HILIC OBD Column, 19*150 mm*5 um, mobile phase, H₂O (10 mmol/L NH₄HCO₃) and CH₃CN (17% Phase B up to 35% within 8 min), Detector, UV 220 nm. 75.4 mg (16%) of 2-(2-[[2-(5,6-dimethyl-1H-1,3-benzodiazol-2-yl)ethyl]amino]ethyl)-N-[(3-fluoropyridin-2-yl)methyl]-[1,3]thiazolo[5,4-d]pyrimidin-7-amine was obtained as a white solid. H-NMR-PH-GBT-QX-FP-18-0: (300 MHz, DMSO-$d_6$, ppm): δ 11.84 (br, 1H), 8.35-8.29 (m, 3H), 7.74-7.67 (m, 1H), 7.42-7.36 (m, 1H), 7.21-7.12 (m, 2H), 4.88 (d, J=5.4 Hz, 2H), 3.23 (t, J=6.3 Hz, 2H), 3.02-2.92 (m, 6H), 2.26 (s, 6H). LCMS: (ES, m/z): [M+H]⁺: 477.

Example 1.54

Synthesis of N-[3-(4-{2-[3-(2-{[2-(2-{[2-(7-{[(3-fluoropyridin-2-yl)methyl]amino}-[1,3]thiazolo[5,4-d]pyrimidin-2-yl)ethyl]amino}ethyl)-1H-1,3-benzodiazol-5-yl]carbamoyl}ethyl)-3H-diazirin-3-yl]ethyl}-1H-1,2,3-triazol-1-yl)propyl]-3',6'-dihydroxy-3-oxo-3H-spiro[2-benzofuran-1,9'-xanthene]-6-carboxamide (Compound 47)

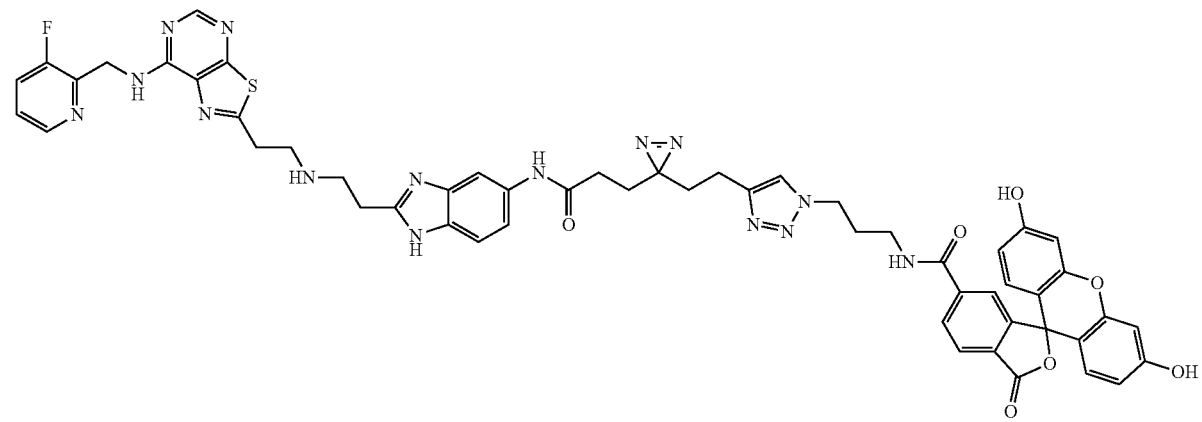 [SMILES: O=C(CCC1(CCc2cn(CCCNC(=O)c3ccc4c(c3)C3(OC4=O)c4ccc(O)cc4Oc4cc(O)ccc43)nn2)N=N1)Nc1ccc2[nH]c(CCNCCc3nc4c(NCc5ncccc5F)ncnc4s3)nc2c1]

Scheme 36 depicts a synthetic route for preparing an exemplary compound

Scheme 36

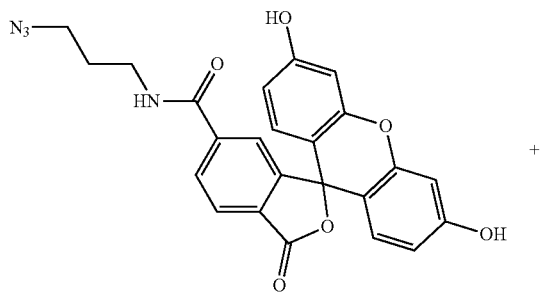

+

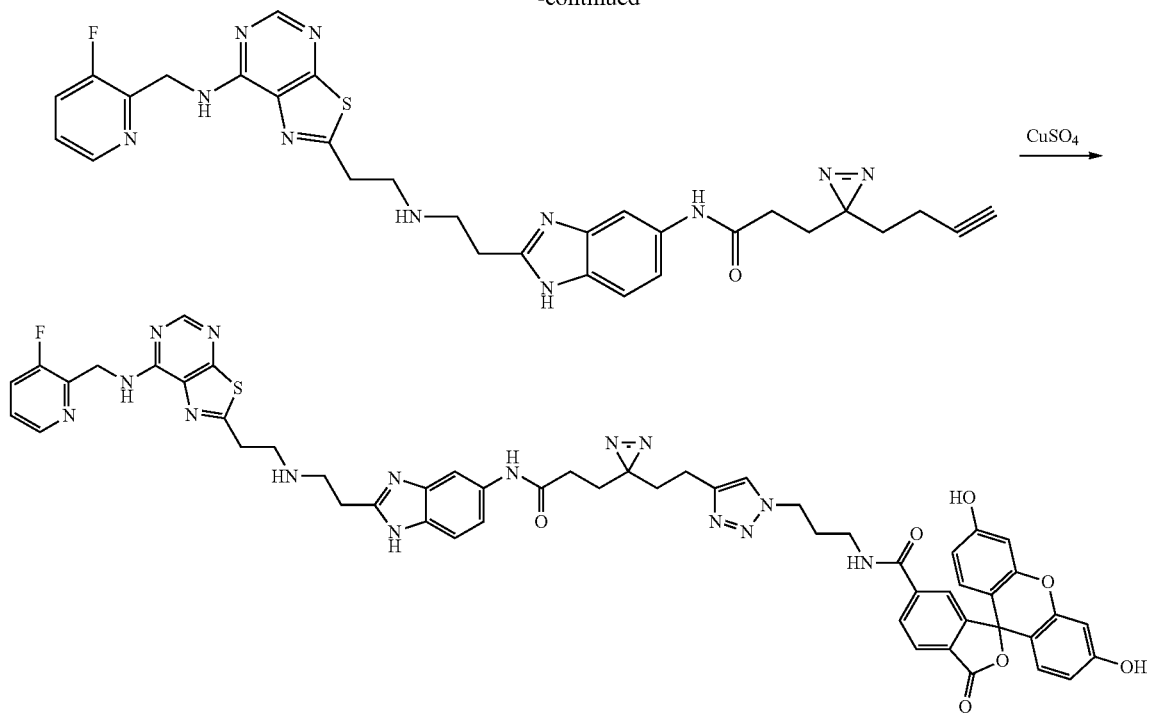

In an Eppendorf tube was added 3-[3-(but-3-yn-1-yl)-3H-diazirin-3-yl]-N-[2-(2-{[2-(7-{[(3-fluoropyridin-2-yl)methyl]amino}-[1,3]thiazolo[5,4-d]pyrimidin-2-yl)ethyl]amino}ethyl)-1H-1,3-benzodiazol-5-yl]propanamide (2.3 mg, 3.76 umol) and 6-FAM azide (2.59 mg, 5.64 umol), followed by the addition of the premixed solution of CuSO$_4$ (37.6 uL, 1 eq), TJPTA (37.6 uL, 2 eq), and Ascorbic acid (20 eq, 188 uL). The tube was capped, and the light green solution was stirred at room temperature. After 1 h of stirring, HPLC indicated still both starting materials left unreacted. To the mixture was added an additional mixed 37.6 uL of CuSO$_4$ and THPTA stock solution. After another 30 min stirring, the reaction was completed by HPLC and the mixture was diluted with water and AcCN and was purified by prep HPLC (95-60% water in AcCN) to give N-[3-(4-{2-[3-(2-{[2-(2-{[2-(7-{[(3-fluoropyridin-2-yl)methyl]amino}-[1,3]thiazolo[5,4-d]pyrimidin-2-yl)ethyl]amino}ethyl)-1H-1,3-benzodiazol-5-yl]carbamoyl}ethyl)-3H-diazirin-3-yl]ethyl}-1H-1,2,3-triazol-1-yl)propyl]-3',6'-dihydroxy-3-oxo-3H-spiro[2-benzofuran-1,9'-xanthene]-6-carboxamide (0.80 mg). LCMS: (ES, m/z): [M+H]$^+$: 1071.2.

Example 1.55

Synthesis of N-[(3-fluoropyridin-2-yl)methyl]-2-(2-{[2-(5-phenyl-1H-imidazol-2-yl)ethyl]amino}ethyl)-[1,3]oxazolo[4,5-c]pyridin-4-amine (Compound 48)

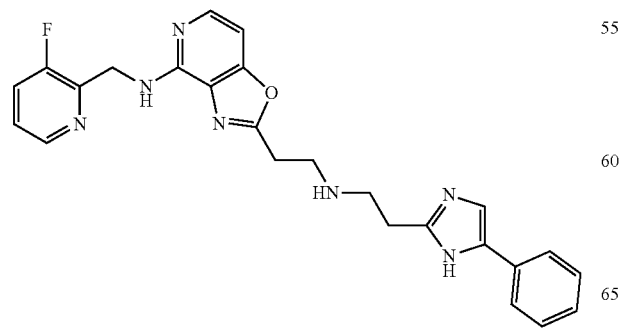

Scheme 37 depicts a synthetic route for preparing an exemplary compound

Scheme 37

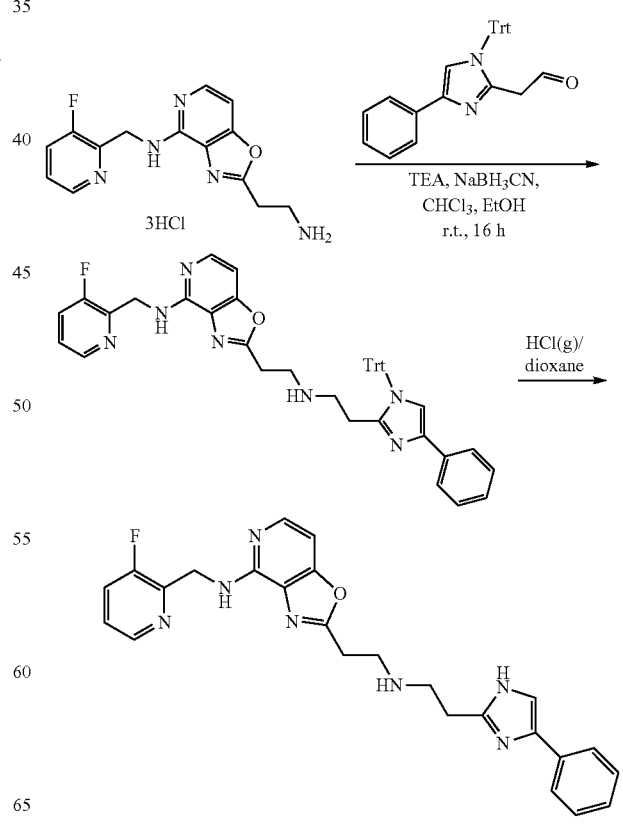

Step 1

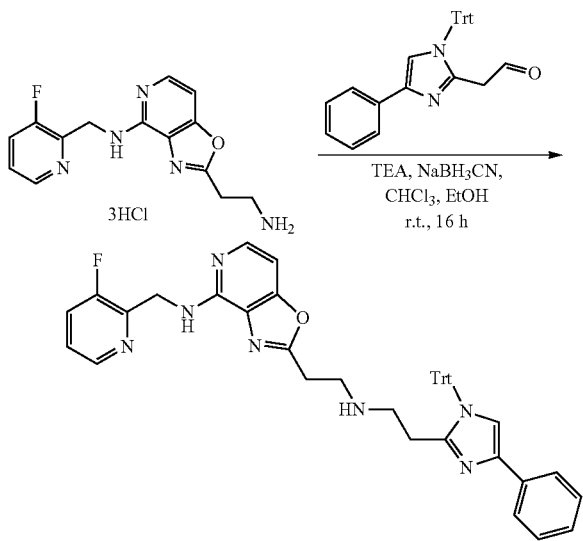

Into a 50-mL round-bottom flask, was placed 2-(2-aminoethyl)-N-[(3-fluoropyridin-2-yl)methyl]-[1,3]oxazolo[4,5-c]pyridin-4-amine (300 mg, 1.04 mmol, 1.00 equiv), CHCl$_3$ (6.00 mL), EtOH (2.00 mL), TEA (316 mg, 3.13 mmol, 3.00 equiv), and 2-[4-phenyl-1-(triphenylmethyl)imidazol-2-yl]acetaldehyde (536 mg, 1.25 mmol, 1.20 equiv). The resulting solution was stirred for 16 hr at room temperature. NaBH$_3$CN (196 mg, 3.13 mmol, 3.00 equiv) was added. The resulting solution was stirred for 2 hr at room temperature, and then quenched by the addition of 10 mL of water. The resulting solution was extracted with 3×10 mL of dichloromethane and the organic layers were combined and dried over anhydrous sodium sulfate and then concentrated. This resulted in 300 mg (41.0%) of N-((3-fluoropyridin-2-yl)methyl)-2-(2-((2-(4-phenyl-1-trityl-1H-imidazol-2-yl)ethyl) amino)ethyl)oxazolo[4,5-c]pyridin-4-amine as a light yellow oil. [M+1]$^+$ m/z: 700.3

Step 2

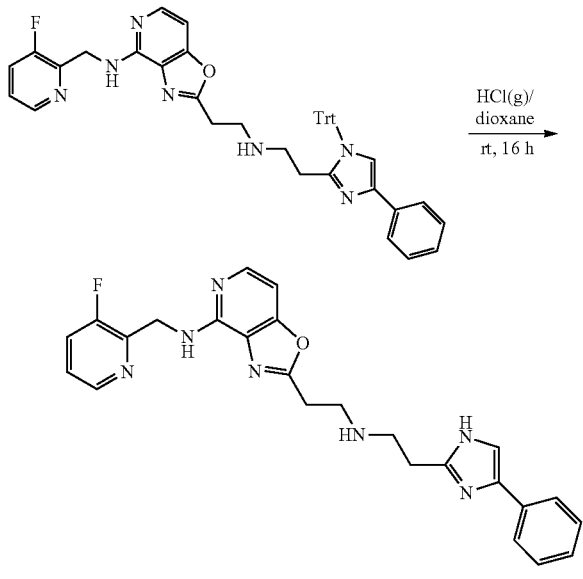

Into a 50-mL round-bottom flask, was placed N-[(3-fluoropyridin-2-yl)methyl]-2-[2-([2-[4-phenyl-1-(triphenylmethyl)imidazol-2-yl]ethyl]amino)ethyl]-[1,3]oxazolo[4,5-c]pyridin-4-amine (300 mg, 0.42 mmol, 1.00 equiv), and HCl (gas) in 1,4-dioxane (5.00 mL). The resulting solution was stirred for 16 hr at room temperature, concentrated. The resulting solution was diluted with 5 mL of ACN. The crude product was purified by Prep-HPLC with the following conditions (Prep-HPLC-006): Column, XBridge Prep $^{18}$C OBD Column, 19*150 mm 5 um; mobile phase, Water (10 mmol/L NH$_4$HCO$_3$+0.1% NH$_3$.H$_2$O) and ACN (30% Phase B up to 40% in 7 min); Detector, UV 254 nm. This resulted in 35.0 mg (17.8%) of N-((3-fluoropyridin-2-yl)methyl)-2-(2-((2-(4-phenyl-1H-imidazol-2-yl)ethyl)amino)ethyl)oxazolo[4,5-c]pyridin-4-amine as a white solid. $^1$H NMR (300 MHz, DMSO-d$_6$) δ 8.35 (dt, J=4.6, 1.5 Hz, 1H), 7.87 (d, J=5.8 Hz, 1H), 7.73-7.63 (m, 3H), 7.41-7.34 (m, 2H), 7.33-7.25 (m, 2H), 7.23-7.11 (m, 2H), 6.92 (d, J=5.8 Hz, 1H), 4.84 (dd, J=5.4, 1.8 Hz, 2H), 3.14 (s, 4H), 2.99 (t, J=7.1 Hz, 2H), 2.82 (t, J=7.0 Hz, 2H). [M+1]$^+$ m/z: 458.1

Example 1.56

Synthesis of N-[(3-fluoropyridin-2-yl)methyl]-2-(2-{[(4-phenyl-1H-imidazol-2-yl)methyl]amino}ethyl)-[1,3]thiazolo[5,4-d]pyrimidin-7-amine (Compound 49)

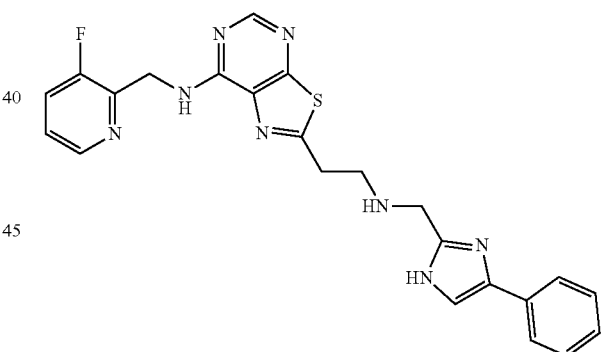

Scheme 38 depicts a synthetic route for preparing an exemplary compound

Scheme 38

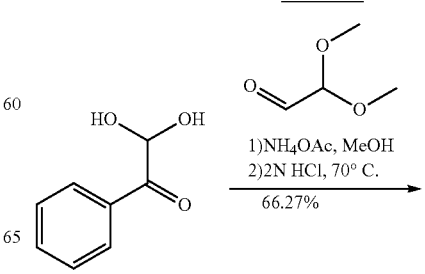

-continued

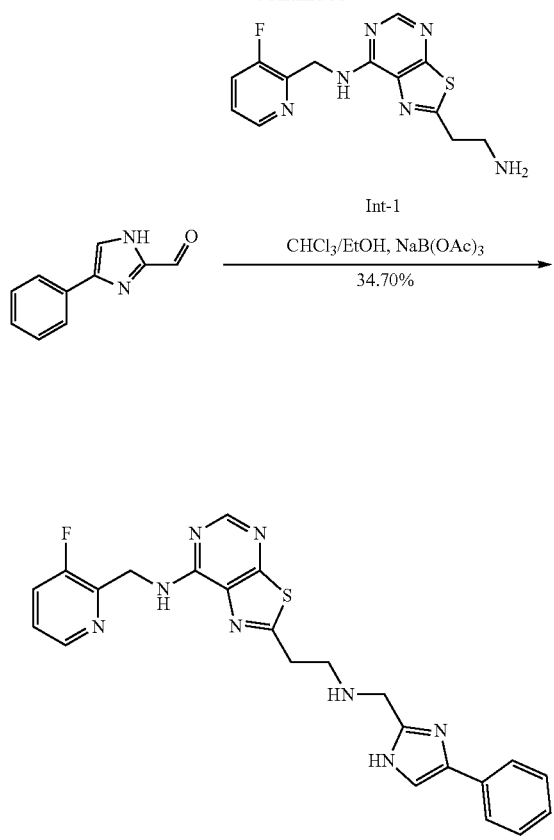

Step 1

Into a 250-mL round-bottom flask, was placed phenylglyoxal (2 g, 13.145 mmol, 1.00 equiv), MeOH (20.00 mL), 2,2-dimethoxyacetaldehyde (3.15 g, 30.234 mmol, 2.30 equiv), and NH₄OAc (3.95 g, 51.266 mmol, 3.90 equiv). The resulting solution was stirred overnight at room temperature. 2N HCl (20 mL) was added and stirred at 70° C. in an oil bath. The reaction progress was monitored by LCMS. The reaction mixture was cooled with a water/ice bath. The solids were collected by filtration. The solid was dried in an oven under reduced pressure. This resulted in 1.5 g (66.27%) of 4-phenyl-1H-imidazole-2-carbaldehyde as a brown solid. LCMS (ES) [M+1]⁺ m/z 173.

Step 2

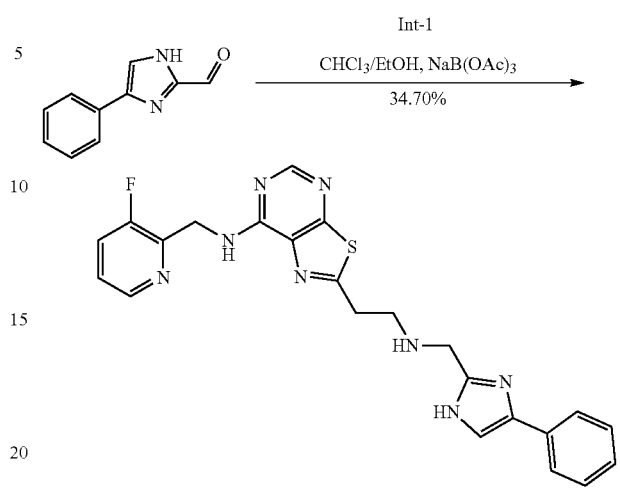

Into a 100-mL round-bottom flask, was placed 4-phenyl-1H-imidazole-2-carbaldehyde (100.00 mg, 0.581 mmol, 1.00 equiv), CHCl₃ (5.00 mL), EtOH (10.00 mL), and Int-1 (176.76 mg, 0.581 mmol, 1.00 equiv). This was followed by the addition of NaBH₃CN (54.74 mg, 0.871 mmol, 1.5 equiv), in portions at 0° C. The resulting solution was stirred for 3 hr at room temperature. The reaction progress was monitored by LCMS. The resulting mixture was concentrated under vacuum. The crude product was purified by Prep-HPLC with the following conditions (Waters-2767): Column, X-bridge RP18, 5 um, 19*100 mm; mobile phase, 0.03% ammonia in water and CH₃CN (20% CH₃CN up to 30% in 5 min); Detector, UV 254 nm. This resulted in 92.8 mg (34.70%) of N-[(3-fluoropyridin-2-yl)methyl]-2-(2-[[(4-phenyl-1H-imidazol-2-yl)methyl]amino]ethyl)-[1,3]thiazolo[5,4-d]pyrimidin-7-amine as an off-white solid. ¹H NMR (300 MHz, DMSO-d₆): δ 11.88 (s, 1H), 8.34-8.30 (m, 3H), 7.75-7.66 (m, 3H), 7.51 (s, 1H), 7.41-7.29 (m, 3H), 7.17-7.15 (m, 1H), 4.87 (d, J=4.8 Hz, 2H), 3.80 (s, 2H), 3.27-3.23 (m, 2H), 3.02-3.0 (m, 2H). LCMS (ES) [M+1]⁺ m/z 461.1

Example 1.57

Synthesis of 1-(1H-1,3-benzodiazol-2-yl)-2-{[2-(7-{[(3-fluoropyridin-2-yl)methyl]amino}-[1,3]thiazolo[5,4-d]pyrimidin-2-yl)ethyl]amino}ethan-1-ol (Compound 50)

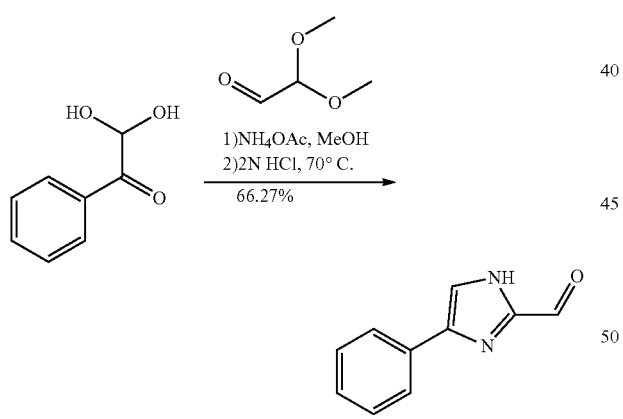

Scheme 39 depicts a synthetic route for preparing an exemplary compound

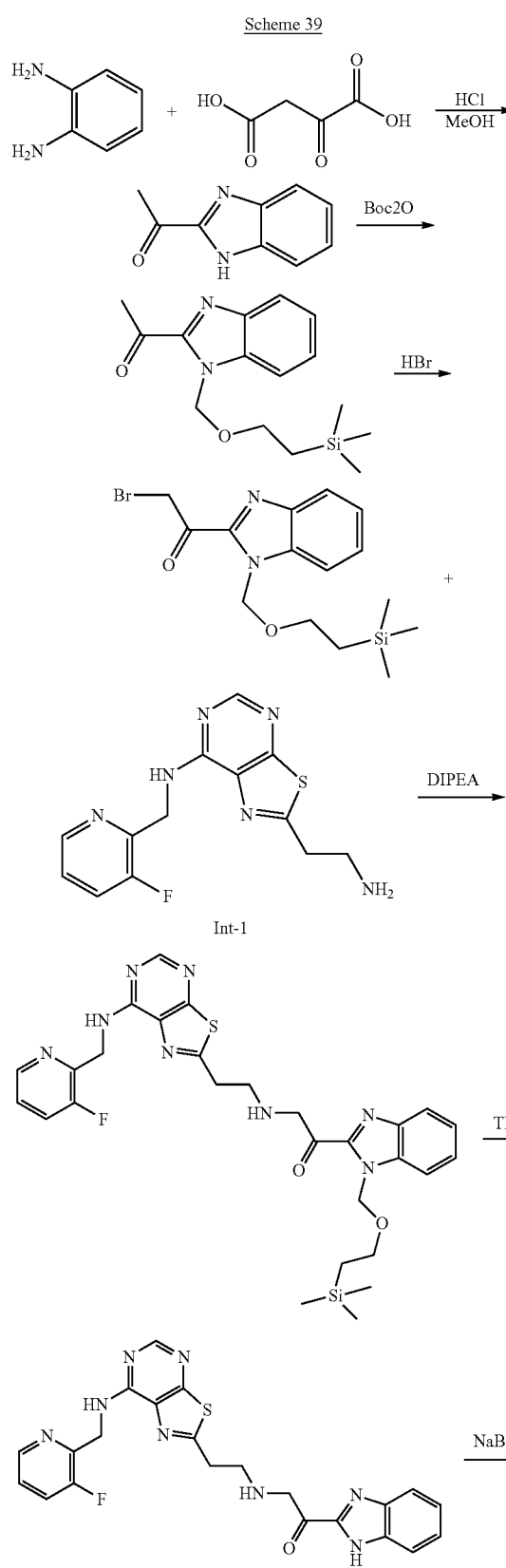

Int-1

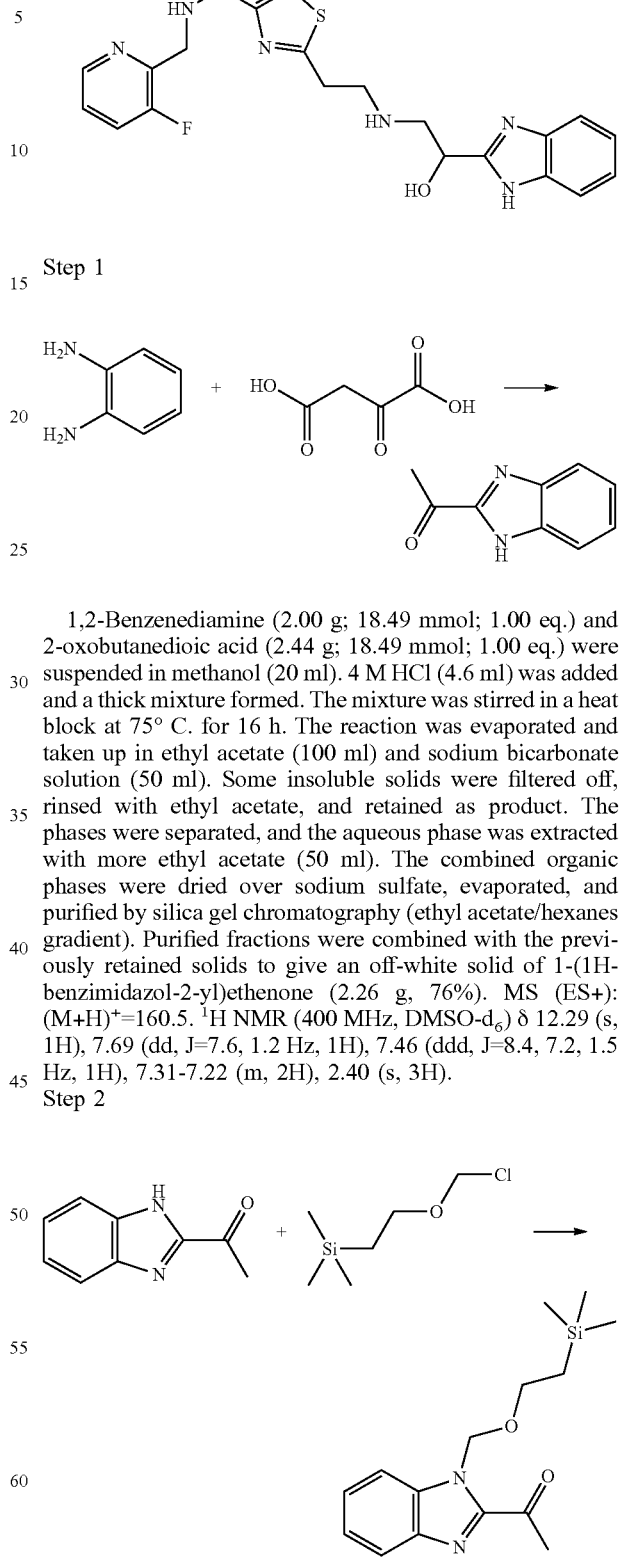

Step 1

1,2-Benzenediamine (2.00 g; 18.49 mmol; 1.00 eq.) and 2-oxobutanedioic acid (2.44 g; 18.49 mmol; 1.00 eq.) were suspended in methanol (20 ml). 4 M HCl (4.6 ml) was added and a thick mixture formed. The mixture was stirred in a heat block at 75° C. for 16 h. The reaction was evaporated and taken up in ethyl acetate (100 ml) and sodium bicarbonate solution (50 ml). Some insoluble solids were filtered off, rinsed with ethyl acetate, and retained as product. The phases were separated, and the aqueous phase was extracted with more ethyl acetate (50 ml). The combined organic phases were dried over sodium sulfate, evaporated, and purified by silica gel chromatography (ethyl acetate/hexanes gradient). Purified fractions were combined with the previously retained solids to give an off-white solid of 1-(1H-benzimidazol-2-yl)ethanone (2.26 g, 76%). MS (ES+): $(M+H)^+=160.5$. $^1$H NMR (400 MHz, DMSO-$d_6$) δ 12.29 (s, 1H), 7.69 (dd, J=7.6, 1.2 Hz, 1H), 7.46 (ddd, J=8.4, 7.2, 1.5 Hz, 1H), 7.31-7.22 (m, 2H), 2.40 (s, 3H).

Step 2

1-(1H-Benzimidazol-2-yl)ethanone (0.37 g; 2.33 mmol; 1.00 eq.) was dissolved in N,N-dimethylformamide (dry, 6 ml). This solution was added dropwise to a mixture of sodium hydride (103 mg; 2.57 mmol; 1.10 eq., 60%) in THF (dry, 1 ml) and the reaction was stirred for 1 h. The reaction was then cooled in an ice bath. [2-(Chloromethoxy)ethyl](trimethyl)silane (0.41 mL; 2.33 mmol; 1.00 eq.) was added slowly and the reaction was stirred to 25° C. After 2.5 h, more 2-(chloromethoxy)ethyl](trimethyl)silane (0.06 ml) was added and stirred for 15 h more. Water (20 ml), ethyl acetate (50 ml), and ammonium chloride solution (10 ml) were added. The phases were separated, and the aqueous phase was extracted with ethyl acetate (2×50 ml). The combined organic phases were washed with sodium chloride solution and dried over sodium sulfate. After evaporation under high vacuum, the residue was purified by silica gel chromatography (ethyl acetate/hexanes gradient) to give a light yellow film of 1-(1-{[2-(trimethylsilyl)ethoxy]methyl}-1H-1,3-benzodiazol-2-yl)ethan-1-one (0.15 g, 22%). MS (ES+): (M+H)⁺=291.0.

Step 3

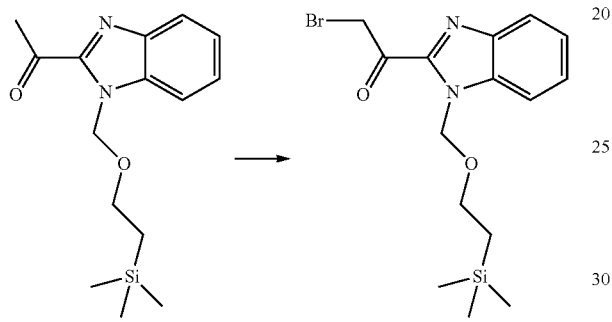

1-(1-{[2-(Trimethylsilyl)ethoxy]methyl}-1H-1,3-benzodiazol-2-yl)ethan-1-one (152.00 mg; 0.52 mmol; 1.00 eq.) was dissolved in THF (dry, 3 ml). Pyrrolidone hydrotribromide (286 mg; 0.58 eq.) and 2-pyrrolidinone (44 µL; 0.58 mmol; 1.10 eq.) were added, and the reaction was stirred in a heat block at 70° C. After 18 h, the mixture was evaporated and purified by silica gel chromatography (ethyl acetate/hexanes gradient) to give a white solid of 2-bromo-1-(1-((2-(trimethylsilyl)ethoxy)methyl)-1H-benzo[d]imidazol-2-yl)ethan-1-one (125 mg, 64%). MS (ES+): (M+H)⁺=369; 370.8.

Step 4

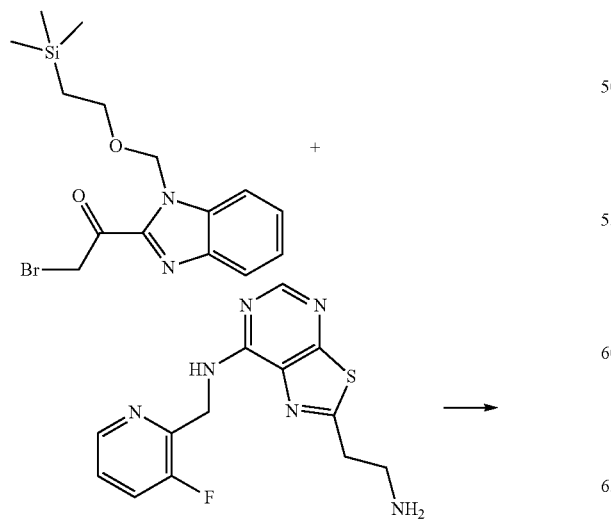

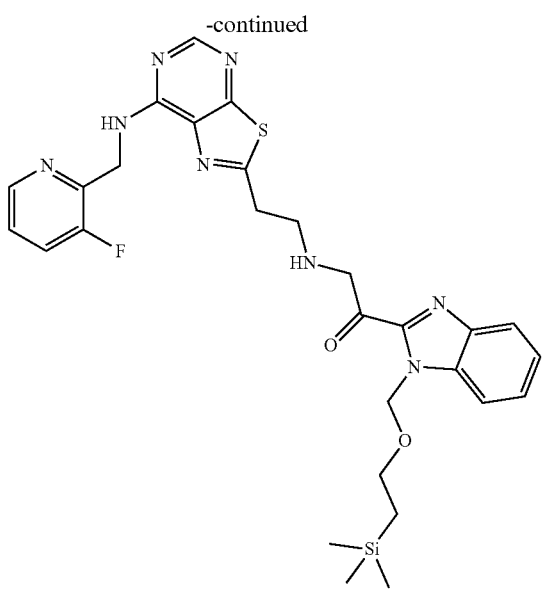

2-(2-Aminoethyl)-N-[(3-fluoropyridin-2-yl)methyl]-[1,3]thiazolo[5,4-d]pyrimidin-7-amine (103 mg; 0.34 mmol; 1.00 eq.) was dissolved in methanol (dry, 2 ml), THF (dry, 2 ml) and N,N-diisopropylethylamine (65 µL; 0.37 mmol; 1.10 eq.) and cooled in an ice bath. 2-Bromo-1-(1-((2-(trimethylsilyl)ethoxy)methyl)-1H-benzo[d]imidazol-2-yl)ethan-1-one (125.00 mg; 0.34 mmol; 1.00 eq.) in THF (3 ml) was added. The solution was then stirred in a bath to 25° C. After 72 h, the reaction was concentrated and the crude residue was purified by reverse phase chromatography (Waters XSelect CSH C18 column, 0-90% acetonitrile/0.1% aqueous formic acid gradient) to give a solid of 2-{[2-(7-{[(3-fluoropyridin-2-yl)methyl]amino}-[1,3]thiazolo[5,4-d]pyrimidin-2-yl)ethyl]amino}-1-(1-{[2-(trimethylsilyl)ethoxy]methyl}-1H-1,3-benzodiazol-2-yl)ethan-1-one (57 mg, 28%). MS (ES+): (M+H)⁺=593.3.

Step 5

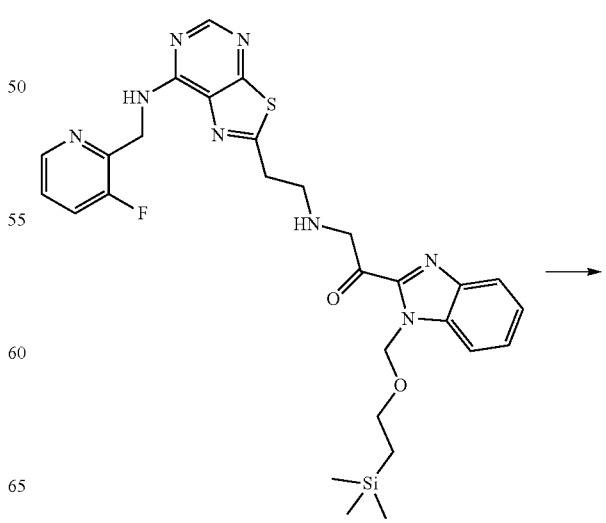

-continued

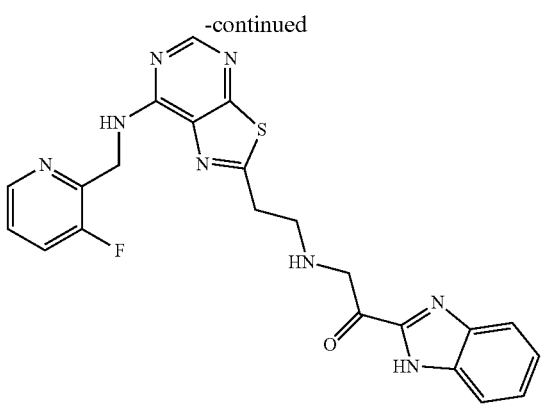

2-{[2-(7-{[(3-Fluoropyridin-2-yl)methyl]amino}-[1,3]thiazolo[5,4-d]pyrimidin-2-yl)ethyl]amino}-1-(1-{[2-(trimethylsilyl)ethoxy]methyl}-1H-1,3-benzodiazol-2-yl)ethan-1-one (57.50 mg; 0.10 mmol; 1.00 eq.) was dissolved in DCM (2 ml). Trifluoroacetic acid (1.00 mL; 0.10 mol/L; 0.10 mmol; 1.03 eq.) was added slowly. The reaction was stirred in a heat block at 35° C. briefly, then evaporated under high vacuum after 45 m. The residue was dissolved in methanol (1 ml), then sodium hydroxide solution (0.73 mL; 2.00 mol/L; 1.46 mmol; 15.00 eq.) was added dropwise, and the reaction was stirred for 2 h. Ammonium chloride solution (2 ml) and ethyl acetate (50 ml) were added and the phases were separated. The aqueous phase was extracted with ethyl acetate (3×20 ml) and the combined organic phases were dried over sodium sulfate. After evaporation of solvent, the residue of 1-(1H-1,3-benzodiazol-2-yl)-2-{[2-(7-{[(3-fluoropyridin-2-yl)methyl]amino}-[1,3]thiazolo[5,4-d]pyrimidin-2-yl)ethyl]amino}ethan-1-one was used directly in the next step. MS (ES+): (M+H)$^+$=462.9.

Step 6

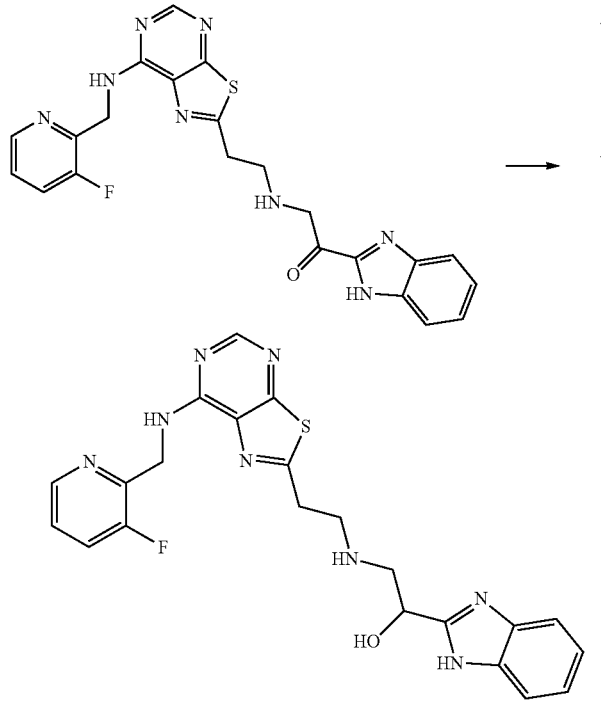

1-(1H-1,3-Benzodiazol-2-yl)-2-{[2-(7-{[(3-fluoropyridin-2-yl)methyl]amino}-[1,3]thiazolo[5,4-d]pyrimidin-2-yl)ethyl]amino}ethan-1-one (45.00 mg; 0.10 mmol; 1.00 eq.) was dissolved in THF (2 ml) and methanol (2 ml) and cooled in an ice bath. Sodium borohydride (7.5 mg; 0.19 mmol; 2.00 eq.) was added and the reaction was stirred at 25° C. After 1 h, more sodium borohydride (3 mg) was added and repeated once more after 1 h. 1 M HCl (0.5 ml) was added after 40 m and the reaction was evaporated to a residue. The residue was purified by reverse phase chromatography (Waters XSelect CSH C18 column, 0-65% acetonitrile/0.1% aqueous formic acid gradient) to give a white solid of 1-(1H-1,3-benzodiazol-2-yl)-2-{[2-(7-{[(3-fluoropyridin-2-yl)methyl]amino}-[1,3]thiazolo[5,4-d]pyrimidin-2-yl)ethyl]amino}ethan-1-ol (13 mg, 28%). MS (ES+): (M+H)+=465.2. $^1$H NMR (400 MHz, DMSO-d$_6$) δ 10.47 (s, 1H), 8.42-8.28 (m, 3H), 7.71 (ddd, J=10.0, 8.3, 1.3 Hz, 1H), 7.42-7.35 (m, 1H), 6.83-6.73 (m, 2H), 6.72-6.67 (m, 1H), 6.67-6.59 (m, 1H), 6.10 (s, 1H), 4.92 (d, J=5.8 Hz, 2H), 4.09 (s, 1H), 3.52-3.35 (m, 4H), 3.20-3.06 (m, 2H).

Example 1.58

Synthesis of 2-(2-{[2-(5-cyclopropyl-1H-imidazol-2-yl)ethyl]amino}ethyl)-N-[(3-fluoropyridin-2-yl)methyl]-[1,3]thiazolo[5,4-d]pyrimidin-7-amine (Compound 51)

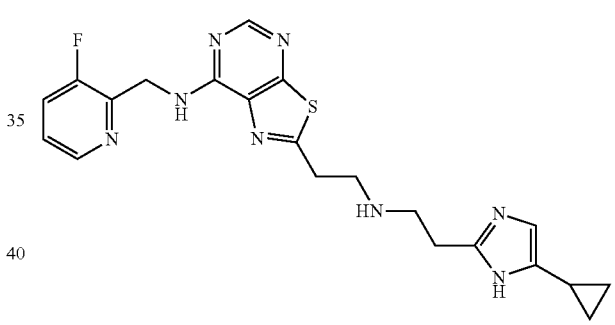

Scheme 40 depicts a synthetic route for preparing an exemplary compound.

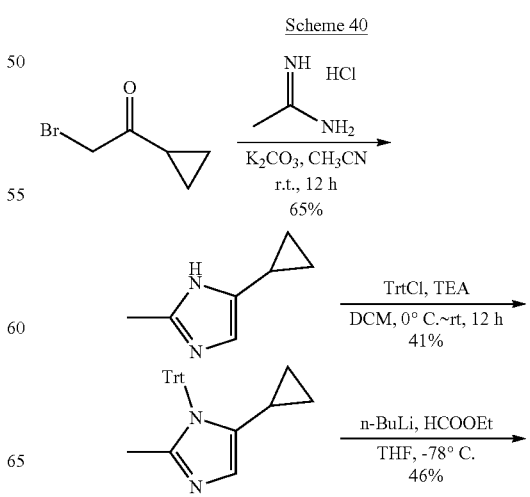

-continued

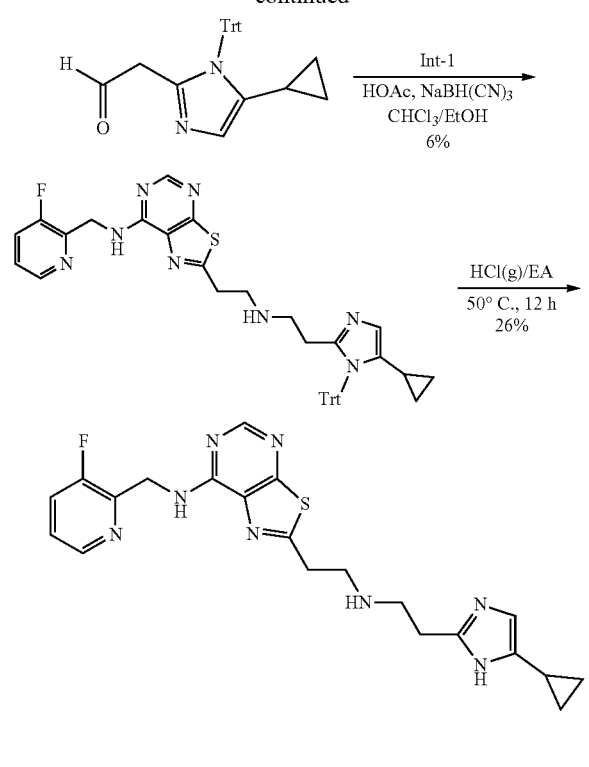

Step 1

Into a 250-mL 3-necked round-bottom flask, was placed acetamidine hydrochloride (10.3 g, 109.90 mmol, 5.0 equiv) and CH₃OH (100 mL). This was followed by the addition of NaOH (4.4 g, 109.90 mmol, 5.0 equiv) at 0° C. The mixture was stirred for 3 h at room temperature. The mixture was then filtered, and the filtrate was concentrated in vacuum, the residue was dissolved in CH₃CN (60 mL), followed by a solution of K₂CO₃ (6.1 g, 43.96 mmol, 2.0 equiv) in H₂O (30 mL), which was added at room temperature. After that, a solution of 2-bromo-1-cyclopropylethanone (3.56 g, 21.98 mmol, 1.0 equiv) in CH₃CN (10 mL) was added and stirred for 12 h at the same temperature. The solution was filtered, and the filtrate was concentrated in vacuum. 1.73 g crude (65%) of 4-cyclopropyl-2-methyl-3H-imidazole was obtained as a yellow oil and used in the next step without further purification. LCMS (ES) [M+1]⁺ m/z: 123.

-continued

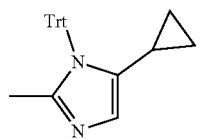

Into a 50-mL 3-necked round-bottom flask, was placed 5-cyclopropyl-2-methyl-1H-imidazole (1.73 g, 14.16 mmol, 1.0 equiv), DCM (17 mL), and TEA (2.87 g, 28.32 mmol, 2.0 equiv). This was followed by the addition of Trt-Cl (4.15 g, 14.89 mmol, 1.05 equiv) at 0° C. The reaction solution was stirred for 12 h at room temperature. The reaction was quenched by the addition of water (20 mL), and extracted with 2×20 mL of dichloromethane. The combined organic phase was dried over anhydrous sodium sulfate, filtered and the filtrate was concentrated under reduced pressure. The residue was purified by silica gel column with ethyl acetate/petroleum ether (6/1). 2.1 g (41%) of 5-cyclopropyl-2-methyl-1-trityl-1H-imidazole was obtained as a white solid. LCMS (ES) [M+1]⁺ m/z: 365.

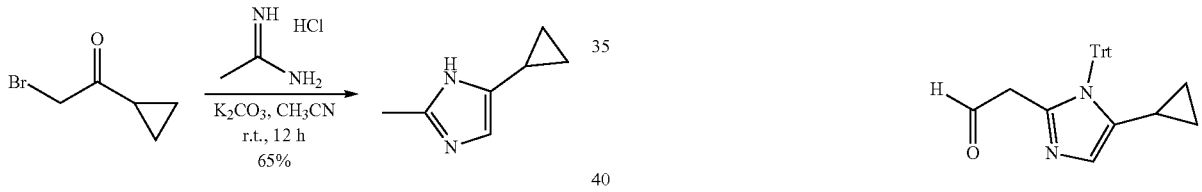

Into a 250-mL 3-necked round-bottom flask, was placed 5-cyclopropyl-2-methyl-1-trityl-1H-imidazole (2.0 g, 5.49 mmol, 1.0 equiv), THF (60 mL). After insertion of N₂, the mixture was cooled to −78° C. This was followed by the addition of n-BuLi (2.5 M in hexane) (6.60 mL, 16.46 mmol, 3.0 equiv) dropwise and then the solution was stirred for 1 h at the same temperature. To this, HCOOEt (2.03 g, 27.44 mmol, 5.0 equiv) was added at −78° C. and stirred for an additional 30 min. The reaction was then quenched by the addition of saturated NH₄Cl in H₂O (20 mL) and extracted with 3×50 mL of ethyl acetate. The combined organic phase was dried over anhydrous sodium sulfate, filtered and the filtrate was concentrated under reduced pressure. 985 mg (46%) of 2-(5-cyclopropyl-1-trityl-1H-imidazol-2-yl)acetaldehyde was obtained as a yellow oil and used in the next step directly without further purification. LCMS (ES) [M+1]⁺ m/z: 393.

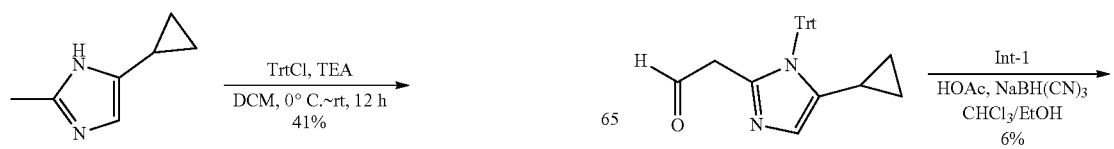

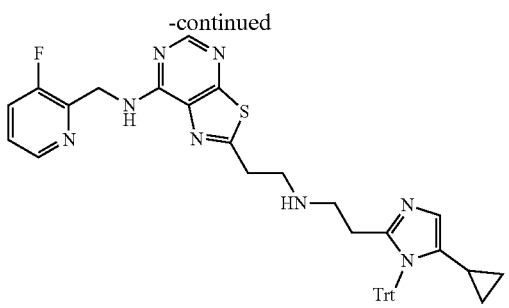

Into a 50-mL round-bottom flask, was placed 2-(5-cyclopropyl-1-trityl-1H-imidazol-2-yl)acetaldehyde (985 mg, 2.51 mmol, 1.2 equiv), 2-(2-aminoethyl)-N-[(3-fluoropyridin-2-yl)methyl]-[1,3]thiazolo[5,4-d]pyrimidin-7-amine (636 mg, 2.09 mmol, 1.0 equiv), CHCl₃ (21 mL), EtOH (7 mL), and AcOH (251 mg, 4.18 mmol, 2.0 eq). The mixture was stirred overnight at room temperature. To this was added NaBH₃CN (395 mg, 6.28 mmol, 3.0 equiv). After the addition, the reaction was stirred for 1 h. The reaction was quenched with H₂O (20 mL), the pH value was adjusted to 8 with NaHCO₃ solid, and then extracted with DCM (30 mL*2). The combined organic phase was dried over anhydrous sodium sulfate, filtered, and the filtrate was concentrated under reduced pressure. The residue was purified by silica gel column with dichloromethane/methanol (9/1). 80 mg (6%) of 2-(2-((2-(5-cyclopropyl-1-trityl-1H-imidazol-2-yl)ethyl)amino)ethyl)-N-((3-fluoropyridin-2-yl)methyl)thiazolo[5,4-d]pyrimidin-7-amine was obtained as a yellow solid. LCMS (ES) [M+1]⁺ m/z: 681.

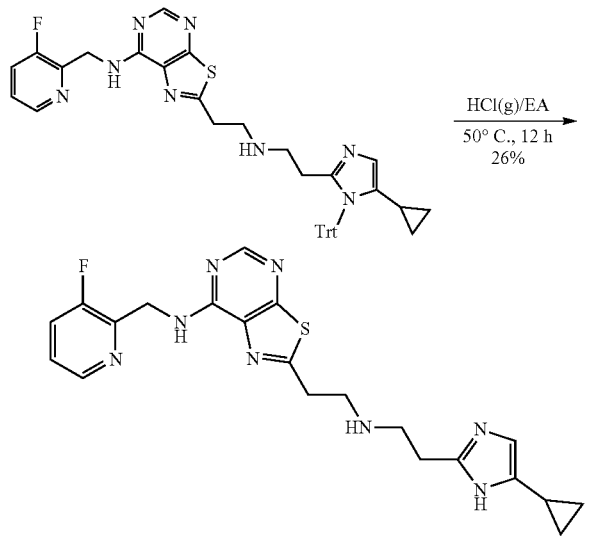

Into an 8-mL vial, was placed 2-(2-((2-(5-cyclopropyl-1-trityl-1H-imidazol-2-yl)ethyl)amino)ethyl)-N-((3-fluoropyridin-2-yl)methyl)thiazolo[5,4-d]pyrimidin-7-amine (80 mg, 0.12 mmol, 1.0 equiv), and HCl (g) (2 M in EA) (2 mL). The reaction solution was stirred for 12 h at 50° C. After cooling to room temperature, the pH value was adjusted to 8 with NH₄OH, and then the solution was extracted with DCM (20 mL*2). The combined organic phase was concentrated in vacuum, the residue was purified by Prep-HPLC with the following conditions (2# SHIMADZU (HPLC-01)): Column, Kinetex EVO C18 Column, 21.2*150, 5 um, mobile phase, Water (0.05% NH₄OH) and CH₃CN (25% Phase B up to 45% within 10 min), Detector, UV 254 nm. 13.7 mg (26%) of 2-(2-((2-(5-cyclopropyl-1H-imidazol-2-yl)ethyl)amino)ethyl)-N-((3-fluoropyridin-2-yl)methyl)thiazolo[5,4-d]pyrimidin-7-amine was obtained as a white solid. ¹H-NMR (300 MHz, DMSO-d₆): δ 8.36-8.33 (m, 3H), 8.32 (s, 1H), 8.20 (s, 1H), 7.71-7.68 (m, 1H), 7.42-7.37 (m, 1H), 6.57 (s, 1H), 4.89 (d, J=4.8 Hz, 2H), 3.24 (t, J=5.7 Hz, 2H), 3.04 (t, J=6.0 Hz, 2H), 2.89 (d, J=6.6 Hz, 2H), 2.71 (t, J=6.9 Hz, 2H), 1.73-1.66 (m, 1H), 0.71-0.67 (m, 2H), 0.55-0.50 (m, 2H). LCMS: (ES, m/z): [M+H]⁺: 439.

Example 1.59

Synthesis of 2-(2-{[(2R)-2-(1H-1,3-benzodiazol-2-yl)propyl]amino}ethyl)-N-[(3-fluoropyridin-2-yl)methyl]-[1,3]thiazolo[5,4-d]pyrimidin-7-amine (Compound 52)

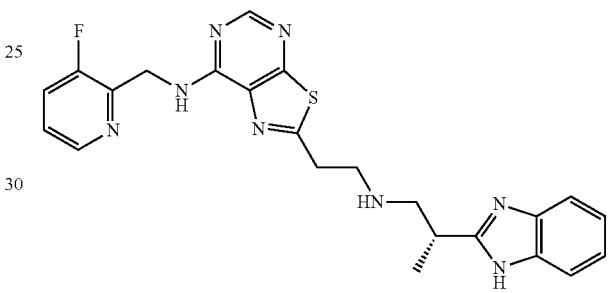

Compound 52 was synthesized in a similar manner to that of Compound 53, replacing Methyl (S)-3-amino-2-methylpropanoate with Methyl (R)-3-amino-2-methylpropanoate. ¹H NMR (400 MHz, DMSO-d₆) δ 8.40-8.27 (m, 3H), 7.70 (ddd, J=10.0, 8.3, 1.3 Hz, 1H), 7.64-7.54 (m, 2H), 7.43-7.35 (m, 1H), 7.31 (dt, J=6.1, 3.6 Hz, 2H), 4.85 (t, J=4.8 Hz, 2H), 3.67-3.46 (m, 8H), 1.47 (d, J=6.3 Hz, 3H). MS (ES+): (M+H)⁺=463.1.

Example 1.60

Synthesis of 2-(2-{[(2S)-2-(1H-1,3-benzodiazol-2-yl)propyl]amino}ethyl)-N-[(3-fluoropyridin-2-yl)methyl]-[1,3]thiazolo[5,4-d]pyrimidin-7-amine (Compound 53)

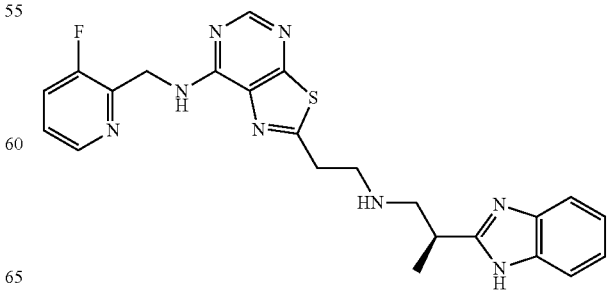

Scheme 41 depicts a synthetic route for preparing an exemplary compound.
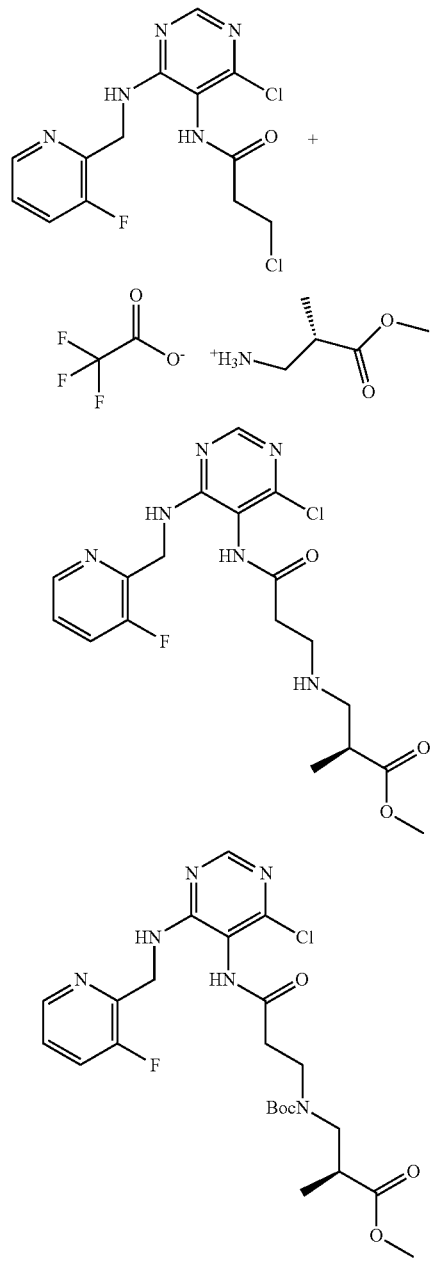
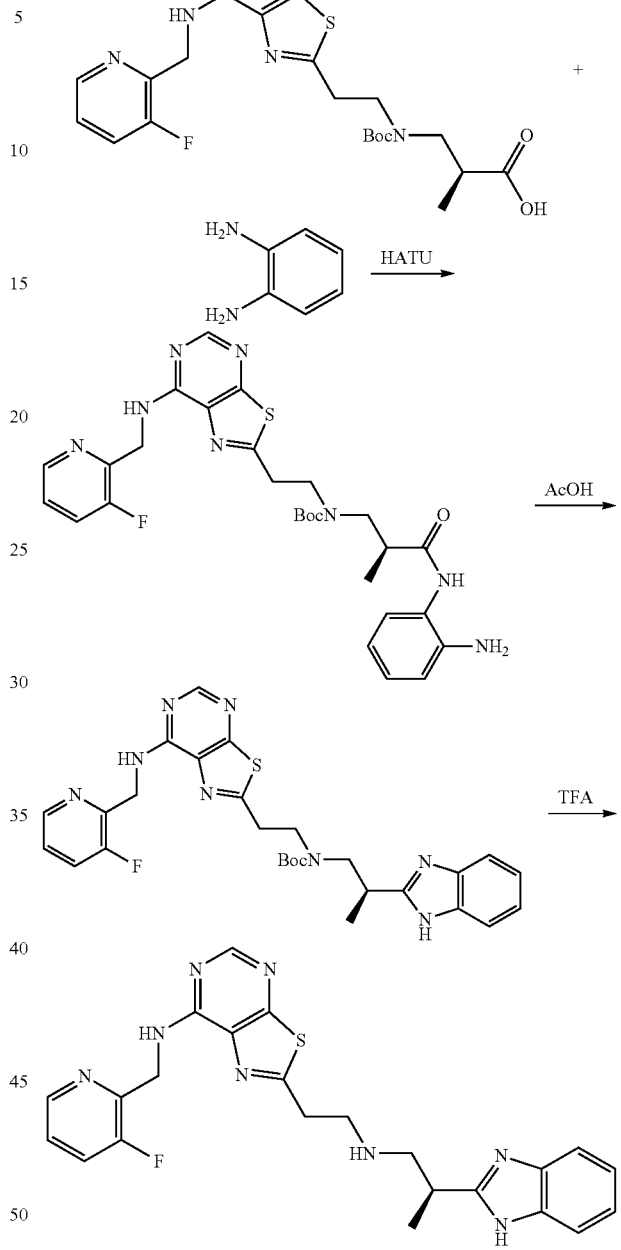
Step 1
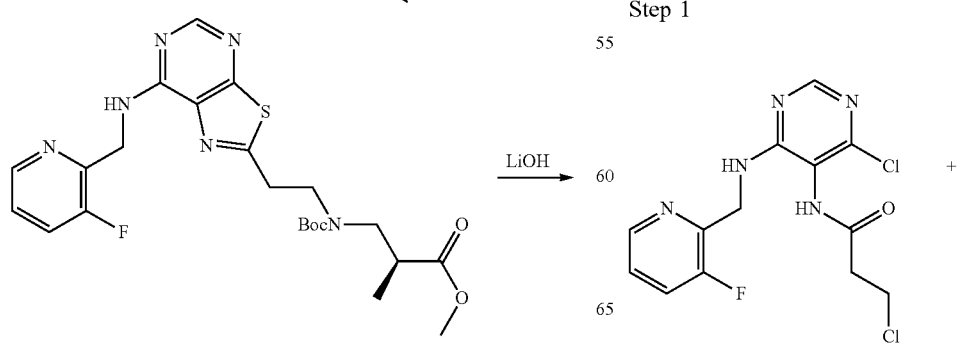

-continued

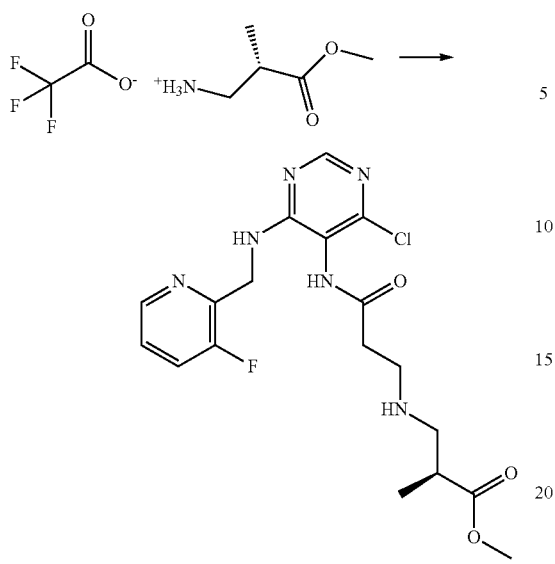

Methyl (S)-3-amino-2-methylpropanoate, TFA salt (272.70 mg; 1.18 mmol; 1.40 eq.) was dissolved in DMF (dry, 2 ml). Sodium iodide (31.58 mg; 0.21 mmol; 0.25 eq.) and 3-chloro-N-(4-chloro-6-{[(3-fluoropyridin-2-yl)methyl]amino}pyrimidin-5-yl)propanamide (290.00 mg; 0.84 mmol; 1.00 eq.) in N,N-dimethylformamide (2 ml) and potassium carbonate (0.17 g; 1.26 mmol; 1.50 eq.) were added. The reaction was stirred in a heat block at 80° C. for 60 h. Ethyl acetate (100 ml) and sodium bicarbonate solution (40 ml) were added, the phases were separated, and the aqueous phase was extracted with ethyl acetate (2×50 ml). The combined organic phases were dried over sodium sulfate, evaporated to a residue, and purified by reverse phase chromatography (Waters XSelect CSH C18 column, 0-65% acetonitrile/0.1% aqueous formic acid gradient) to give methyl (S)-3-((3-((4-chloro-6-(((3-fluoropyridin-2-yl)methyl)amino)pyrimidin-5-yl)amino)-3-oxopropyl)amino)-2-methylpropanoate (77 mg, 21%). MS (ES+): (M+H)$^+$= 425.3.

Step 2

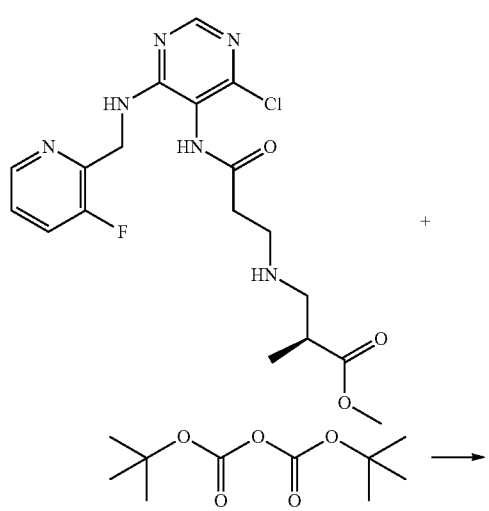

-continued

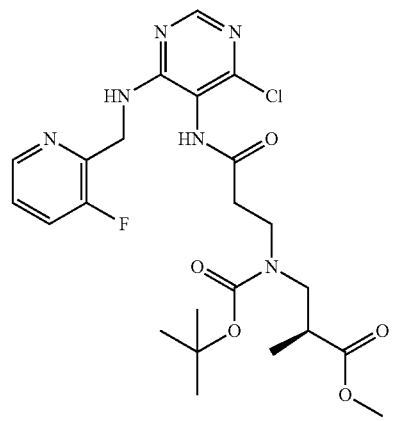

Methyl (S)-3-((3-((4-chloro-6-(((3-fluoropyridin-2-yl)methyl)amino)pyrimidin-5-yl)amino)-3-oxopropyl)amino)-2-methylpropanoate (170.00 mg; 0.41 mmol; 1.00 eq.) was dissolved in DCM (5 ml). N,N-diisopropylethylamine (0.06 mL; 0.32 mmol; 1.75 eq.) and di-tert-butyl dicarbonate (60 mg; 0.27 mmol; 1.50 eq.) in DCM (0.5 ml) were added. The reaction was stirred at 25° C. for 6 h. Water (10 ml), sodium bicarbonate solution (5 ml), and ethyl acetate (50 ml) were added to the mixtures. The phases were separated, and the aqueous phase was extracted with ethyl acetate (2×50 ml). The combined organic phases were washed with sodium chloride solution and dried over sodium sulfate. After evaporation, the crude residue was purified by silica gel chromatography (methanol/dichloromethane gradient) to give methyl (S)-3-((tert-butoxycarbonyl)(3-((4-chloro-6-(((3-fluoropyridin-2-yl)methyl)amino)pyrimidin-5-yl)amino)-3-oxopropyl)amino)-2-methylpropanoate (92 mg, 96%). MS (ES+): (M+H)$^+$=525.2.

Step 3

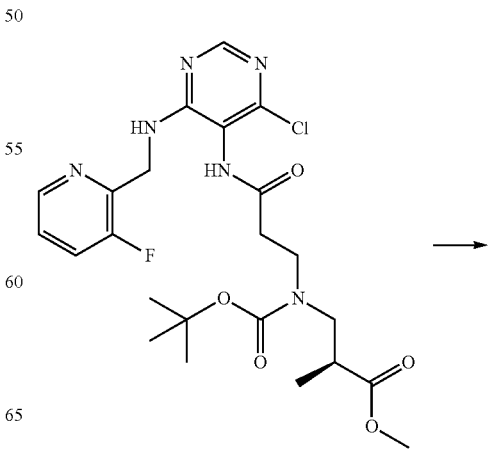

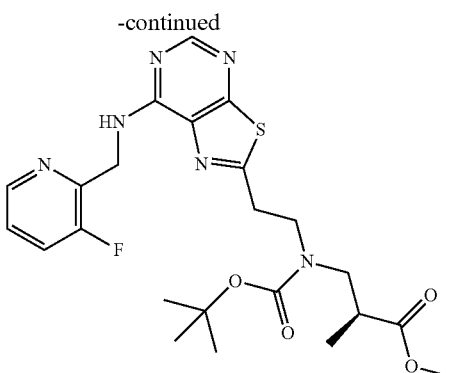

Methyl (S)-3-((tert-butoxycarbonyl)(3-((4-chloro-6-(((3-fluoropyridin-2-yl)methyl)amino)pyrimidin-5-yl)amino)-3-oxopropyl)amino)-2-methylpropanoate (91.00 mg; 0.17 mmol; 1.00 eq.) was dissolved in 1,4-dioxane (dry, 2 ml). 2,4-bis(4-methoxyphenyl)-1,3,2,4-dithiadiphosphetane 2,4-disulfide (87.64 mg; 0.22 mmol; 1.25 eq.) (Lawesson reagent) was added and the reaction was stirred in a heat block at 95° C. After 2 h, more Lawesson reagent (28 mg) was added and the reaction was heated for 1 h more. The solvent was evaporated, and the residue was purified by silica gel chromatography (methanol/dichloromethane gradient) to give methyl (S)-3-((tert-butoxycarbonyl)(2-(7-(((3-fluoropyridin-2-yl)methyl)amino)thiazolo[5,4-d]pyrimidin-2-yl)ethyl)amino)-2-methylpropanoate. MS (ES+): $(M+H)^+$=505.2.

Step 4

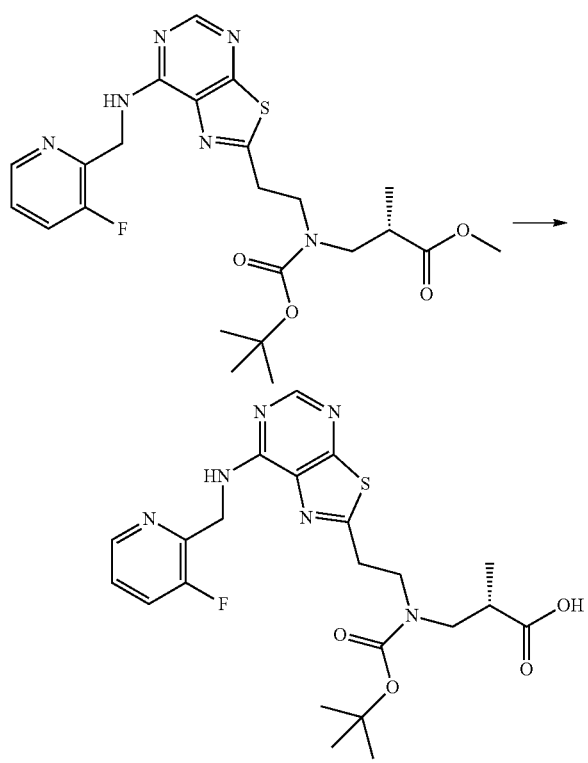

Methyl (S)-3-((tert-butoxycarbonyl)(2-(7-(((3-fluoropyridin-2-yl)methyl)amino)thiazolo[5,4-d]pyrimidin-2-yl)ethyl)amino)-2-methylpropanoate (88.00 mg; 0.17 mmol; 1.00 eq.) was dissolved in THF (2 ml) and methanol (0.5 ml). Lithium hydroxide (anhydrous) (21 mg; 0.87 mmol; 5.00 eq.) dissolved in water (1 ml) was added dropwise. After 8 h, the reaction was diluted with more THF (1 ml) and methanol (0.5 ml). More lithium hydroxide (10 mg in 0.5 ml of water) was added and the reaction was stirred for 1 h. 6 M HCl was added until a pH of 3 was reached. Solvents were evaporated, and the residue was twice evaporated from toluene (10 ml) and dried under vacuum to leave a crude residue of (S)-3-((tert-butoxycarbonyl)(2-(7-(((3-fluoropyridin-2-yl)methyl) amino)thiazolo[5,4-d]pyrimidin-2-yl) ethyl)amino)-2-methylpropanoic acid, which was used directly in the next step. MS (ES+): $(M+H)^+$=491.1.

Step 5

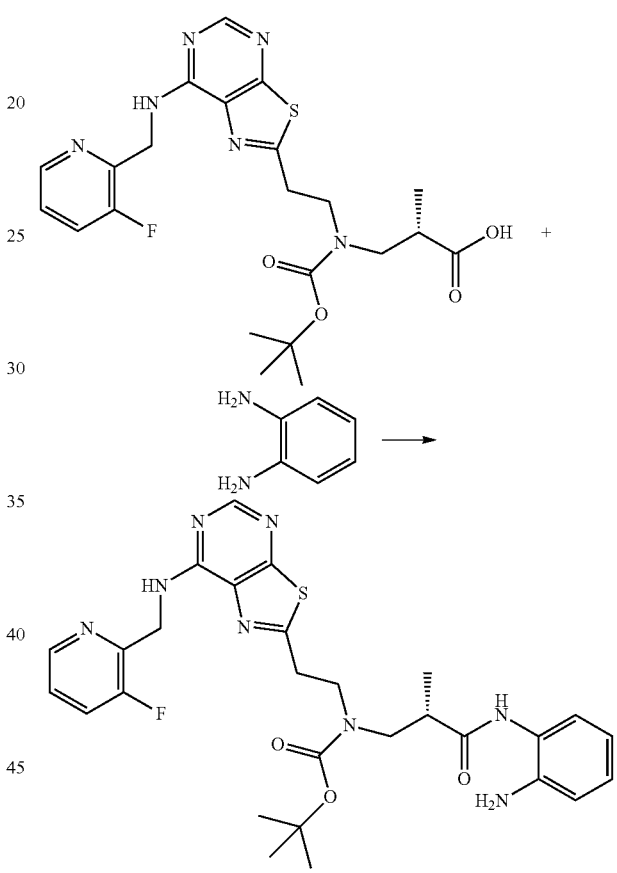

(S)-3-((Tert-butoxycarbonyl)(2-(7-(((3-fluoropyridin-2-yl)methyl)amino)thiazolo[5,4-d]pyrimidin-2-yl)ethyl) amino)-2-methylpropanoic acid (85.50 mg; 0.17 mmol; 1.00 eq.) was dissolved in DMF (2 ml). 1,2-benzenediamine (25.5 mg; 0.24 mmol; 1.35 eq.), N,N-diisopropylethylamine (41 µL; 0.24 mmol; 1.35 eq.) and then 1-[bis(dimethylamino)methylene]-1H-1,2,3-triazolo[4,5-b]pyridinium 3-oxid hexafluorophosphate (HATU, 89.5 mg; 0.24 mmol; 1.35 eq.) were added. After 14 h, another portion of N,N-diisopropylethylamine (20 µL) and 1-[bis(dimethylamino) methylene]-1H-1,2,3-triazolo[4,5-b]pyridinium 3-oxid hexafluorophosphate (HATU, 45 mg) were added, and the reaction was stirred for 2 h more. Ethyl acetate (70 ml) and sodium bicarbonate solution (20 ml) were added, the phases were separated, and the aqueous phase was extracted with ethyl acetate (40 ml). The combined organic phases were dried over sodium sulfate and evaporated. The residue was purified by silica gel chromatography (methanol/dichloromethane gradient) to give a yellow film of tert-butyl (S)-(3-((2-aminophenyl)amino)-2-methyl-3-oxopropyl)(2-(7-(((3-fluoropyridin-2-yl)methyl)amino)thiazolo[5,4-d]pyrimidin-2-yl)ethyl)carbamate (68 mg, 67%). MS (ES+): (M+H)$^+$=581.2.

Step 6

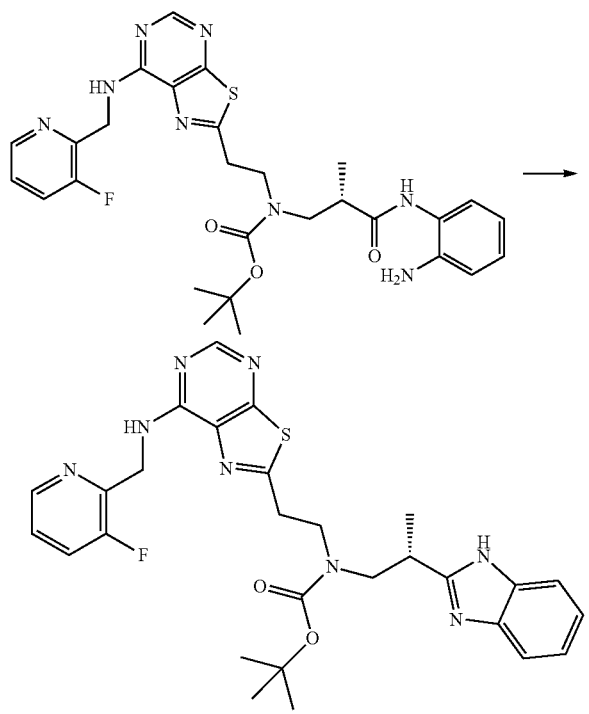

Tert-butyl (S)-(3-((2-aminophenyl)amino)-2-methyl-3-oxopropyl)(2-(7-(((3-fluoropyridin-2-yl)methyl)amino)thiazolo[5,4-d]pyrimidin-2-yl)ethyl)carbamate (68.00 mg; 0.12 mmol; 1.00 eq.) was dissolved in acetic acid (1.5 ml) and stirred in a heat block at 80° C. After 1 h, the reaction was concentrated. The residue was dissolved in ethyl acetate (50 ml) and washed with sodium bicarbonate solution (5 ml). The phases were separated, and the aqueous phase was extracted with ethyl acetate (2×20 ml). The combined organic phases were dried over sodium sulfate and evaporated to give tert-butyl (S)-(2-(1H-benzo[d]imidazol-2-yl)propyl)(2-(7-(((3-fluoropyridin-2-yl)methyl)amino)thiazolo[5,4-d]pyrimidin-2-yl)ethyl)carbamate, which was used directly in the next step. MS (ES+): (M+H)$^+$=563.

Step 7

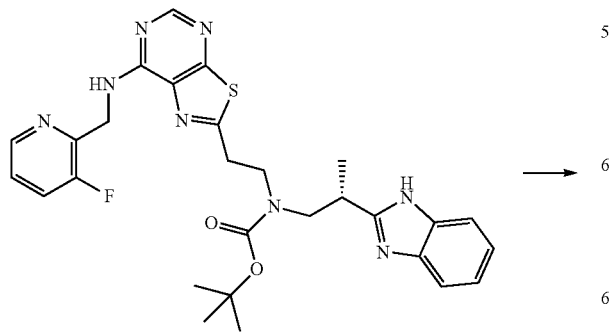

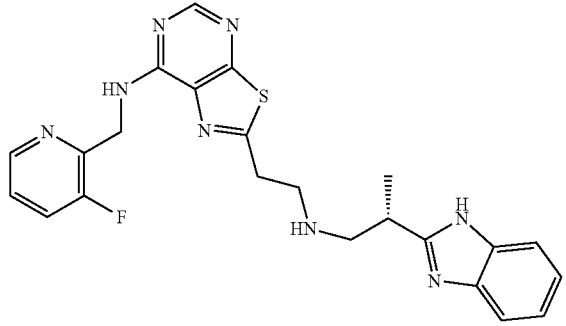

Tert-butyl (S)-(2-(1H-benzo[d]imidazol-2-yl)propyl)(2-(7-(((3-fluoropyridin-2-yl)methyl)amino)thiazolo[5,4-d]pyrimidin-2-yl)ethyl)carbamate (67.00 mg; 0.12 mmol; 1.00 eq.) was dissolved in dichloromethane (2 ml) and cooled in an ice bath. Trifluoroacetic acid (0.60 mL; 0.20 mol/L; 0.12 mmol; 1.01 eq.) (1 ml) was added slowly and the reaction was stirred at 25° C. After 1 h, the solvent was evaporated and then the residue was co-evaporated twice with toluene. The residue was purified by reverse phase chromatography (Waters XSelect CSH C18 column, 0-50% acetonitrile/0.1% aqueous formic acid gradient) to give 2-(2-{[(2S)-2-(1H-1,3-benzodiazol-2-yl)propyl]amino}ethyl)-N-[(3-fluoropyridin-2-yl)methyl]-[,3]thiazolo[5,4-d]pyrimidin-7-amine (formate salt, 39 mg, 64%) as a yellow solid. $^1$H NMR (400 MHz, DMSO-d$_6$) δ 8.38-8.28 (m, 3H), 7.70 (ddd, J=10.0, 8.3, 1.3 Hz, 1H), 7.63-7.54 (m, 2H), 7.44-7.36 (m, 1H), 7.36-7.26 (m, 2H), 4.91-4.79 (m, 2H), 3.65-3.47 (m, 8H), 1.47 (d, J=6.5 Hz, 3H). MS (ES+): (M+H)$^+$=463.2.

Example 1.61

Synthesis of 3-({[2-(4-{[(3-fluoropyridin-2-yl)methyl]amino}-[1,3]oxazolo[4,5-c]pyridin-2-yl)ethyl]amino}methyl)phenol (Compound 54)

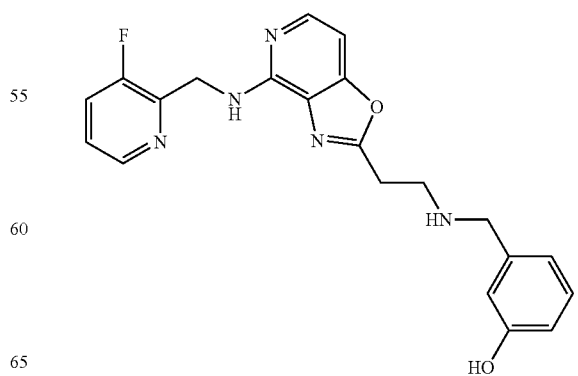

Scheme 42 depicts a synthetic route for preparing an exemplary compound.

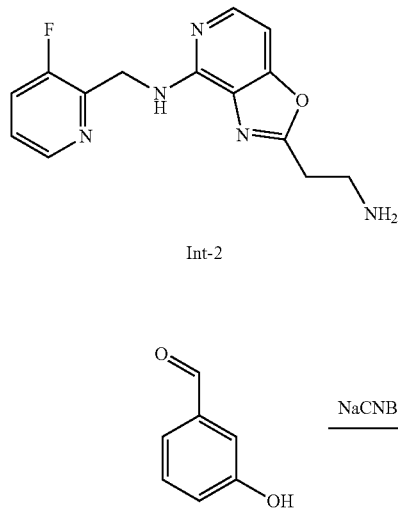

Example 1.62

Synthesis of 2-(2-{[2-(4,5-dimethyl-1H-imidazol-2-yl)ethyl]amino}ethyl)-N-[(3-fluoropyridin-2-yl)methyl]-[1,3]thiazolo[5,4-d]pyrimidin-7-amine (Compound 55)

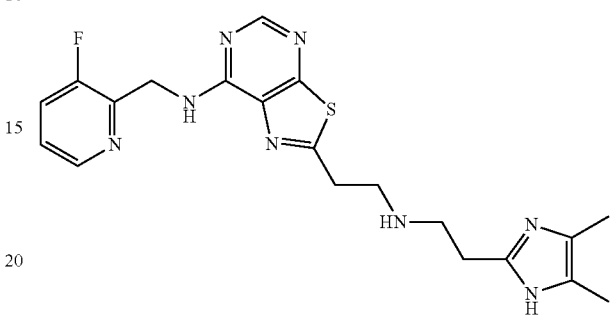

Scheme 43 depicts a synthetic route for preparing an exemplary compound.

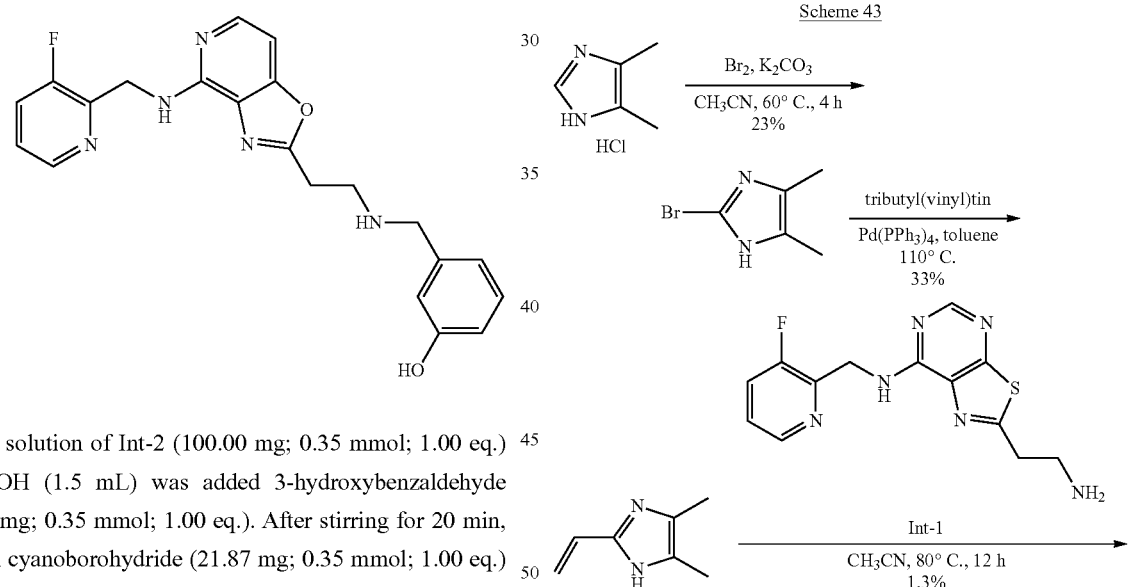

To a solution of Int-2 (100.00 mg; 0.35 mmol; 1.00 eq.) in MeOH (1.5 mL) was added 3-hydroxybenzaldehyde (42.51 mg; 0.35 mmol; 1.00 eq.). After stirring for 20 min, sodium cyanoborohydride (21.87 mg; 0.35 mmol; 1.00 eq.) was added to the mixture. The mixture was further stirred for 15 h, then concentrated and purified by preparative HPLC to give 3-({[2-(4-{[(3-fluoropyridin-2-yl)methyl]amino}-[1,3]oxazolo[4,5-c]pyridin-2-yl)ethyl]amino}methyl)phenol. $^1$H NMR (400 MHz, DMSO-$d_6$) δ 9.24 (s, 1H), 8.33 (dt, J=4.7, 1.5 Hz, 1H), 8.17 (d, J=3.1 Hz, 1H), 7.85 (d, J=5.8 Hz, 1H), 7.66 (ddd, J=10.0, 8.3, 1.3 Hz, 1H), 7.35 (dt, J=8.5, 4.4 Hz, 1H), 7.17 (t, J=5.6 Hz, 1H), 7.06 (t, J=7.7 Hz, 1H), 6.90 (d, J=5.8 Hz, 1H), 6.75-6.67 (m, 2H), 6.59 (ddd, J=8.1, 2.5, 1.1 Hz, 1H), 4.82 (dd, J=5.7, 1.7 Hz, 2H), 4.00 (s, 1H), 3.65 (s, 2H), 3.07 (t, J=7.2 Hz, 2H), 2.96 (t, J=6.7 Hz, 2H). LCMS: (ES, m/z): [M+H]$^+$: 394.2.

Step 1

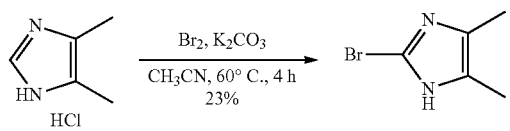

To a mixture of 4,5-dimethyl-1H-imidazole hydrochloride (5.0 g, 37.88 mmol, 1.0 eq), K$_2$CO$_3$ (12.6 g, 90.91 mmol, 2.4 eq) in CH$_3$CN (200 mL), bromine (6.7 g, 41.80 mmol, 1.1 eq) was added at room temperature. After addition, the mixture was heated to 60° C. and stirred for 4 h. The reaction was cooled to room temperature, and then concentrated under reduced pressure. The residue was diluted with H$_2$O (100 mL), and then extracted with EA (50 mL*2). The combined organic phase was dried over anhydrous Na$_2$SO$_4$, filtered, and the filtrate was concentrated under reduced pressure. The residue was purified by silica column, with dichloromethane/methanol (10/1). 1.5 g (23%) 2-bromo-4,5-dimethyl-1H-imidazole was obtained as a brown solid. LCMS (ES) [M+1]$^+$ m/z: 175.

Step 2

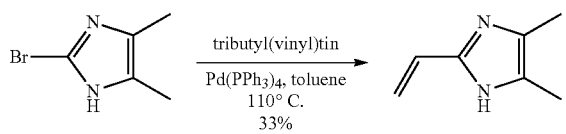

Into a 100-mL 3-necked round-bottom flask, was placed 2-bromo-4,5-dimethyl-1H-imidazole (1.5 g, 8.57 mmol, 1.0 equiv), dioxane (30 mL), tributyl(ethenyl)stannane (5.43 g, 17.12 mmol, 2.0 equiv), and Pd(dppf)Cl$_2$—CH$_2$Cl$_2$ (313 mg, 0.38 mmol, 0.04 equiv). The mixture was stirred overnight at 110° C. The reaction was cooled to room temperature and concentrated under reduced pressure. The residue was purified by silica gel column with dichloromethane/methanol (30/1). 340 mg (33%) of 2-ethenyl-4,5-dimethyl-1H-imidazole was obtained as a brown oil. LCMS (ES) [M+1]$^+$ m/z: 123.

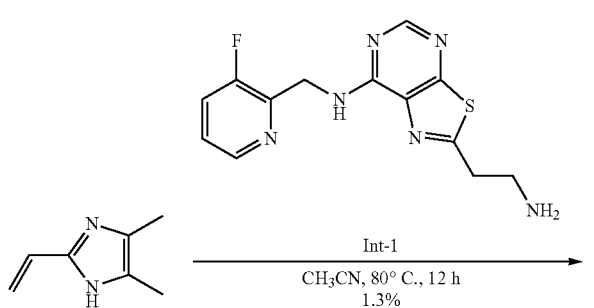

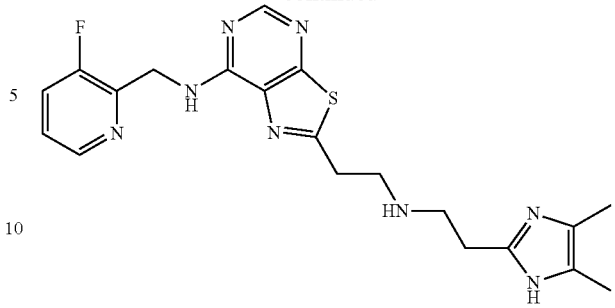

Into a 40-mL vial, was placed 2-ethenyl-4,5-dimethyl-1H-imidazole (340 mg, 2.78 mmol, 1.0 equiv), 2-(2-aminoethyl)-N-[(3-fluoropyridin-2-yl)methyl]-[1,3]thiazolo[5,4-d]pyrimidin-7-amine (847 mg, 2.78 mmol, 1.0 equiv), NH$_4$OAc (215 mg, 2.78 mmol, 1.0 equiv), CH$_3$CN (15 mL). The mixture was stirred for 12 h at 80° C. The reaction was cooled to room temperature and concentrated under reduced pressure. The residue was purified by Prep-HPLC with the following conditions: (2# SHIMADZU (HPLC-01)): Column, Kinetex EVO C18 Column, 21.2*150, 5 um, mobile phase, H$_2$O (0.05% NH$_4$OH)/CH$_3$CN, (20% Phase B up to 50% within 10 min), Detector, uv 254 nm. 15.9 mg (1.3%) of 2-(2-[[2-(4,5-dimethyl-1H-imidazol-2-yl)ethyl]amino]ethyl)-N-[(3-fluoropyridin-2-yl)methyl]-[1,3]thiazolo[5,4-d]pyrimidin-7-amine was obtained as off-white solid. H-NMR-PH-GBT-QX-FP-12-0: (300 MHz, CDCl$_3$) δ 8.52 (s, 1H), 8.41 (d, J=4.8 Hz, 1H), 7.47-7.41 (m, 2H), 7.32-7.28 (m, 1H), 4.96 (d, J=8.7 Hz, 2H), 3.38-3.22 (m, 4H), 3.06 (t, J=5.7 Hz, 2H), 2.95 (d, J=5.4 Hz, 2H), 2.02 (s, 6H). LCMS: (ES, m/z): [M+H]$^+$: 427.

Example 1.63

Synthesis of N-[(3-fluoropyridin-2-yl)methyl]-2-(2-{[2-(5-methyl-1H-imidazol-2-yl)ethyl]amino}ethyl)-[1,3]oxazolo[4,5-c]pyridin-4-amine (Compound 56)

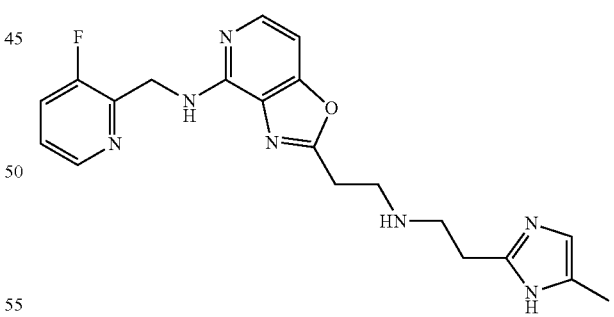

Scheme 44 depicts a synthetic route for preparing an exemplary compound.

Scheme 44

283
-continued

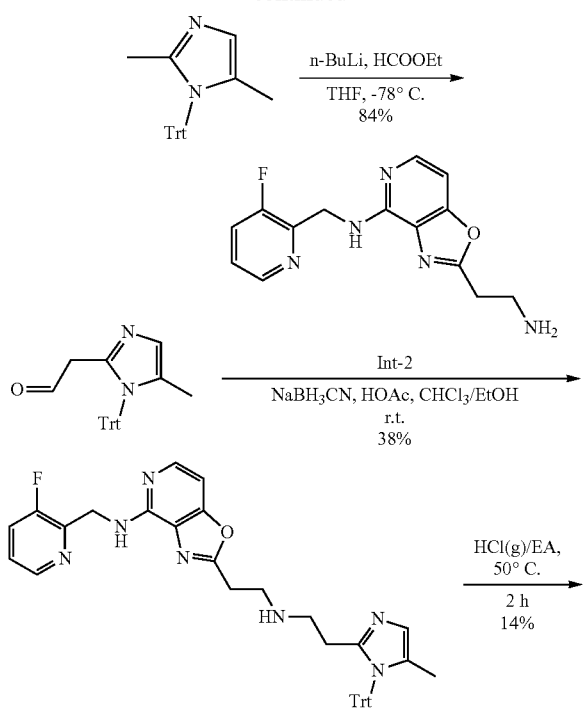

Step 1

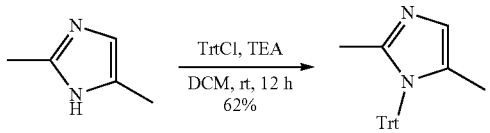

Into a 250-mL round-bottom flask, was placed 2,4-dimethyl-3H-imidazole (5.0 g, 52.01 mmol, 1.0 equiv), DCM (50 mL), and Et₃N (10.53 g, 104.02 mmol, 2.0 equiv). This was followed by the addition of TrtCl (15.22 g, 54.61 mmol, 1.05 equiv) at 0° C. The reaction solution was stirred for 12 h at room temperature. The reaction was diluted with 30 ml of H₂O. The organic phase was separated out and dried over anhydrous Na₂SO₄. This was then filtered, and the filtrate was concentrated under reduced pressure. The residue was purified by silica gel column with ethyl acetate/petroleum ether (1:1). 11 g (62%) of 2,5-dimethyl-1-(triphenylmethyl) imidazole was obtained as a white solid. LCMS (ES) [M+1]⁺ m/z: 339.

Step 2

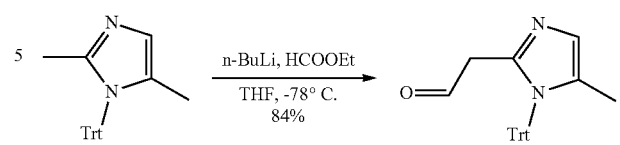

Into a 100-mL 3-necked round-bottom flask purged and maintained with an inert atmosphere of nitrogen, was placed 2,5-dimethyl-1-(triphenylmethyl)imidazole (600 mg, 1.78 mmol, 1.0 equiv) and THF (25 mL). This was followed by the addition of n-BuLi (2.5 M in hexane) (2.14 mL, 5.34 mmol, 3.0 equiv) at −78° C. and stirred for 1 h. HCOOEt (659 mg, 8.90 mmol, 5.0 equiv) was added at the same temperature. After addition, the reaction solution was stirred for 15 min. The reaction was then quenched by the addition of NH₄Cl (aq) (20 mL), and extracted with 3×20 mL of ethyl acetate. The combined organic phase was dried over anhydrous Na₂SO₄. This was then filtered, and the filtrate was concentrated under reduced pressure. 546 mg (84%) crude of 2-[5-methyl-1-(triphenylmethyl)imidazol-2-yl]acetaldehyde was obtained as a yellow oil and used in the next step directly without further purification. LCMS (ES) [M+1]⁺ m/z: 367.

Step 3

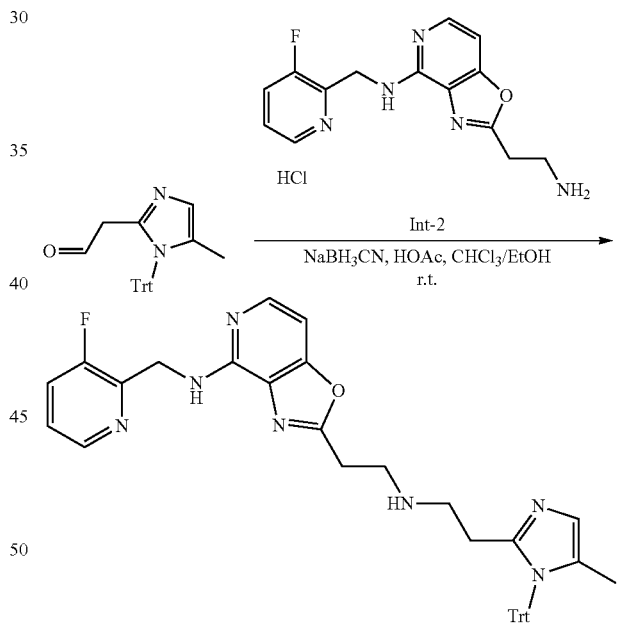

Into a 50-mL round-bottom flask, was placed 2-(2-aminoethyl)-N-[(3-fluoropyridin-2-yl)methyl]-[1,3]oxazolo[4,5-c]pyridin-4-amine hydrochloride (358 mg, 1.25 mmol, 1.0 equiv), CHCl₃ (6 mL), EtOH (2 mL), and TEA (378 mg, 3.74 mmol, 3.0 equiv). The mixture was stirred for 10 min at room temperature. To this was added 2-[5-methyl-1-(triphenylmethyl)imidazol-2-yl]acetaldehyde (548 mg, 1.50 mmol, 1.2 equiv), one drop of AcOH. Following this, the reaction solution was left to stir overnight at room temperature. This was followed by the addition of NaBH₃CN (294 mg, 3.74 mmol, 3.0 equiv). Afterward, the reaction mixture stirred for 2 h at room temperature. The reaction was diluted with H₂O (10 mL), the pH value was adjusted with Na₂CO₃ solid, and then extracted with DCM (20 mL*2). The combined organic phase was dried over anhydrous Na$_2$SO$_4$. This was then filtered, and the filtrate was concentrated under reduced pressure. The residue was purified by silica column with DCM/MeOH (20:1). 300 mg (38%) of N-[(3-fluoropyridin-2-yl)methyl]-2-[2-([2-[5-methyl-1-(triphenylmethyl)imidazol-2-yl]ethyl]amino)ethyl]-[1,3]oxazolo[4,5-c]pyridin-4-amine as a yellow oil was obtained and used in the next step directly without further purification. LCMS (ES) [M+1]$^+$ m/z: 288.

Step 4

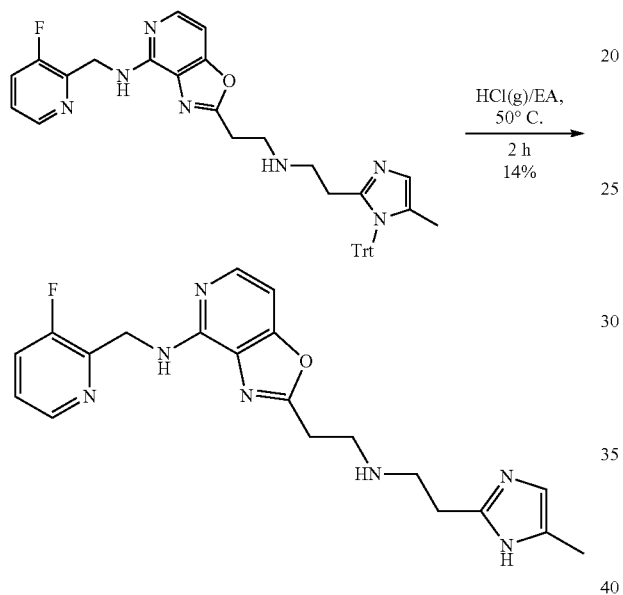

Into a 20-mL vial, was placed N-[(3-fluoropyridin-2-yl)methyl]-2-[2-([2-[5-methyl-1-(triphenylmethyl)imidazol-2-yl]ethyl]amino)ethyl]-[1,3]oxazolo[4,5-c]pyridin-4-amine (300 mg, 0.47 mmol, 1.0 equiv) and HCl (g) (2 M in EA) (4 mL). The mixture was stirred for 2 h at 50° C. After concentrated under reduced pressure, the crude product was purified by Prep-HPLC with the following conditions: (2# SHIMADZU (HPLC-01)): Column, Welch XB-C18, 21.2*250 mm, 5 um, mobile phase, H$_2$O (0.05% NH$_4$OH) and CH$_3$CN (20% Phase B up to 45% within 10 min); Detector, UV 254 nm. 26.2 mg (14%) of N-[(3-fluoropyridin-2-yl)methyl]-2-(2-[[2-(4-methyl-3H-imidazol-2-yl)ethyl]amino]ethyl)-[1,3]oxazolo[4,5-c]pyridin-4-amine was obtained as light yellow solid. $^1$H-NMR (300 MHz, DMSO-d$_6$): δ 8.37 (d, J=4.5 Hz, 1H), 7.87 (d, J=5.7 Hz, 1H), 7.72-7.66 (m, 1H), 7.41-7.36 (m, 1H), 7.21 (br, 1H), 6.93 (d, J=5.7 Hz, 1H), 6.50 (s, 1H), 6.10 (br, 1H), 4.84 (d, J=5.1 Hz, 2H), 3.07-3.00 (m, 4H), 2.81 (t, J=7.5 Hz, 2H), 2.66 (t, J=7.2 Hz, 2H), 2.03 (s, 3H). LCMS (ES, m/z): [M+H]$^+$: 396.2.

Example 1.64

Synthesis of N-[(3-fluoropyridin-2-yl)methyl]-2-[2-({2-[5-(trifluoromethyl)-1H-imidazol-2-yl]ethyl}amino)ethyl]-[1,3]oxazolo[4,5-c]pyridin-4-amine (Compound 57)

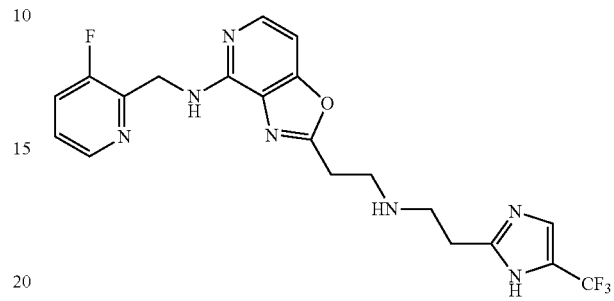

Compound 57 was synthesized in a similar manner to that of Compound 56, replacing 2,4-dimethyl-3H-imidazole with 2-methyl-4-(trifluoromethyl)-3H-imidazole. $^1$H NMR (300 MHz, DMSO-d$_6$) δ 8.36 (dt, J=4.7, 1.5 Hz, 1H), 7.88 (d, J=5.8 Hz, 1H), 7.73-7.66 (m, 1H), 7.59 (d, J=3 Hz, 1H), 7.41-7.36 (m, 1H), 7.20 (t, J=5.6 Hz, 1H), 6.92 (d, J=5.8 Hz, 1H), 4.85 (dd, J=5.6, 1.8 Hz, 2H), 3.12-2.98 (m, 4H), 2.88 (t, J=7.0 Hz, 2H), 2.76 (t, J=7.0 Hz, 2H). LCMS (ESI) m/z, [M+H]$^+$:450.2.

Example 1.65

Synthesis of N-[(3-fluoropyridin-2-yl)methyl]-2-(2-{[2-(1H-imidazol-2-yl)ethyl]amino)}ethyl)-[1,3]oxazolo[4,5-c]pyridin-4-amine (Compound 58)

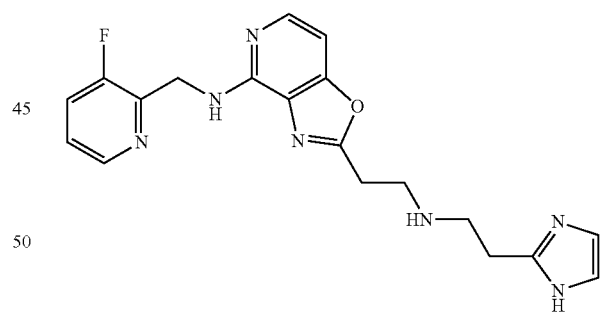

Step 1

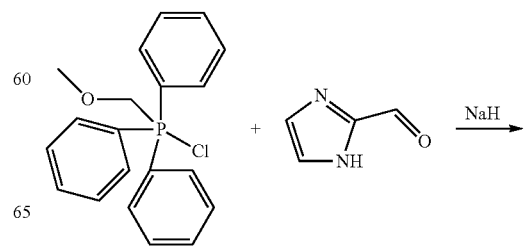

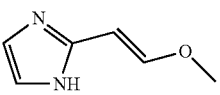

To a suspension of sodium hydride (0.52 g; 13.01 mmol; 2.50 eq.) in DMSO (1 mL) was added chloro(methoxymethyl)triphenyl-λ⁵-phosphane (4.46 g; 13.01 mmol; 2.50 eq.). After stirring for 20 min, 1H-imidazole-2-carbaldehyde (0.50 g; 5.20 mmol; 1.00 eq.) was added to the reaction and the mixture was further stirred at room temperature for 6 h. The mixture was diluted with Sat. NaHCO₃ and extracted with EtOAc (3×). The organic layers were combined, washed with brine, dried, and concentrated to give the crude product, which was purified by silica column chromatography (DCM/MeOH/NH₃=90:9:1) to give 2-[2-methoxyehtenyl]-1H-imidazole.
Step 2

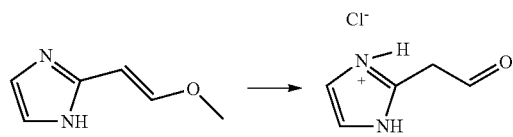

To a solution of 2-[2-methoxyehtenyl]-1H-imidazole (140.00 mg; 1.13 mmol; 1.00 eq.) in THF (2 mL) was added conc HCl (6N, 2 mL). The mixture was heated at 65° C. for 7 h. the mixture was then cooled and concentrated, and lyophilized to give the crude product, which was used directly in the next step.
Step 3

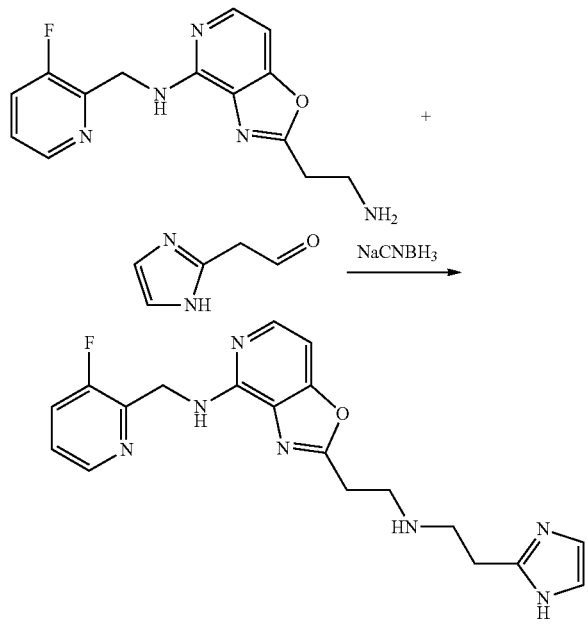

To a solution of 2-(1H-imidazol-2-yl)acetaldehyde (15.00 mg; 0.05 mmol; 1.00 eq.) in MeOH (0.5 mL) was added Int-2 (11.48 mg; 0.08 mmol; 1.50 eq.). After stirring for 20 min, sodium cyanoborohydride (6.56 mg; 0.10 mmol; 2.00 eq.) was added and the reaction was stirred for 15 h. To the reaction mixture was added excess BOc₂O. After 1 h of stirring, the mixture was subjected to purification by HPLC to give the Boc-protected final product, which was treated with TFA and purified by HPLC to give N-[(3-fluoropyridin-2-yl)methyl]-2-(2-{[2-(1H-imidazol-2-yl)ethyl]amino}ethyl)-[1,3]oxazolo[4,5-c]pyridin-4-amine. ¹H NMR (400 MHz, DMSO-d₆) δ 8.32 (d, J=4.8 Hz, 1H), 7.97-7.91 (m, 1H), 7.75 (s, 1H), 7.61 (s, 2H), 7.42 (s, 1H), 4.96 (s, 2H), 3.44 (d, J=27.0 Hz, 8H), 1.24-1.10 (m, 1H), 1.00 (s, 7H). LCMS (ES, m/z): [M+H]⁺: 382.0.

Example 1.66

Synthesis of 2-(2-{[2-(1H-1,3-benzodiazol-2-yl)ethyl]amino}ethyl)-4-{[(3-fluoropyridin-2-yl)methyl]amino}-[1,3]oxazolo[4,5-c]pyridin-6-ol (Compound 59)

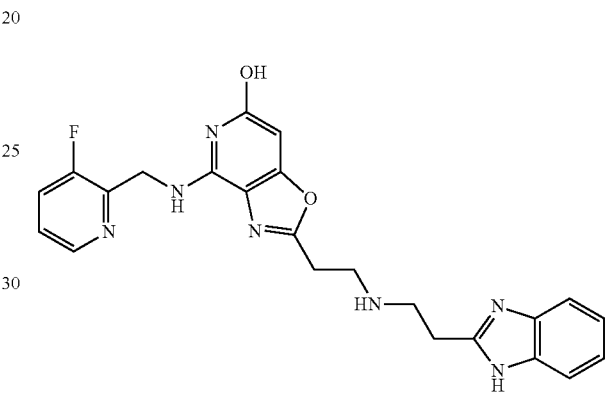

Scheme 45 depicts a synthetic route for preparing an exemplary compound.

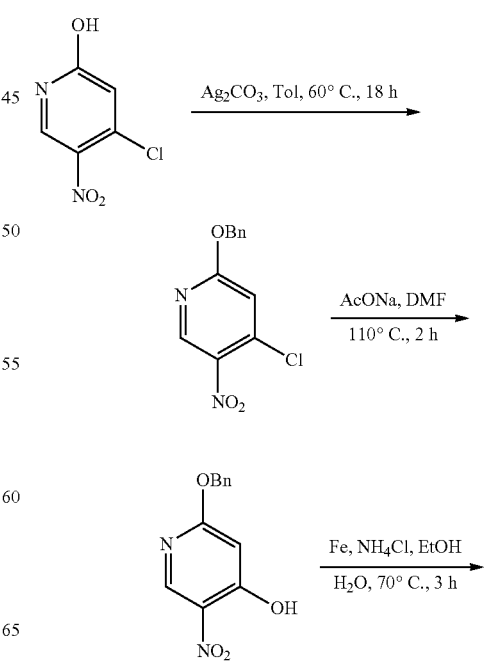

289
-continued

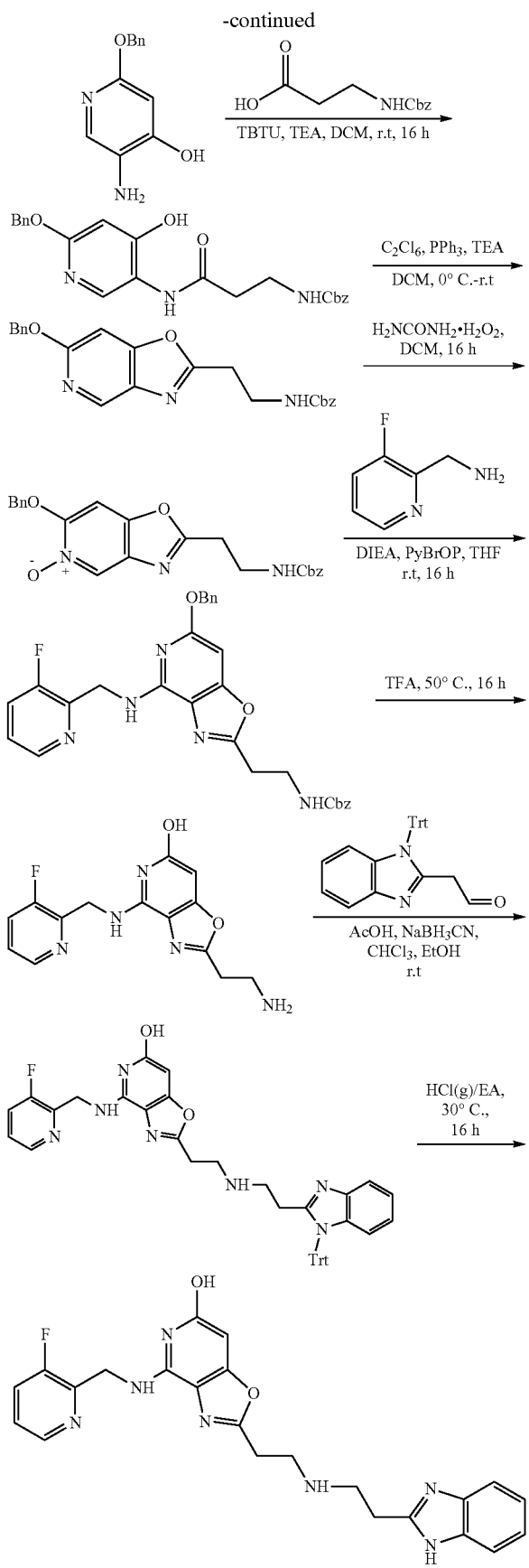

290

Step 1

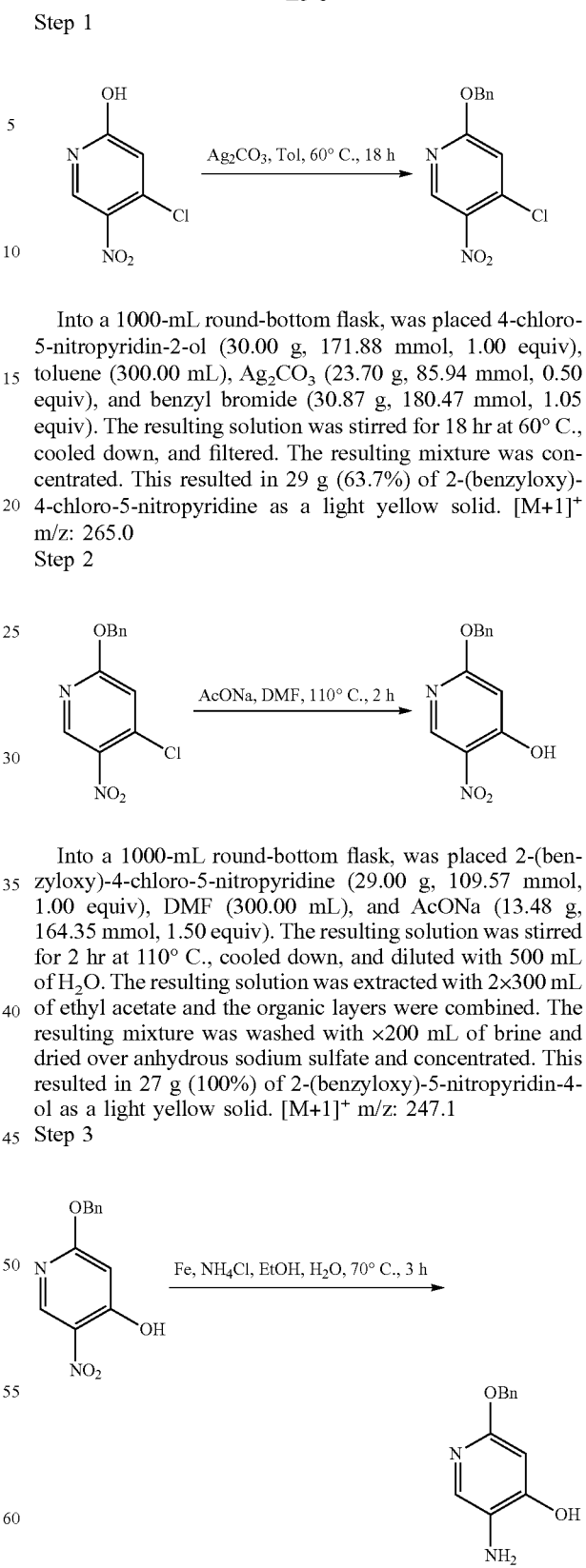

Into a 1000-mL round-bottom flask, was placed 4-chloro-5-nitropyridin-2-ol (30.00 g, 171.88 mmol, 1.00 equiv), toluene (300.00 mL), Ag$_2$CO$_3$ (23.70 g, 85.94 mmol, 0.50 equiv), and benzyl bromide (30.87 g, 180.47 mmol, 1.05 equiv). The resulting solution was stirred for 18 hr at 60° C., cooled down, and filtered. The resulting mixture was concentrated. This resulted in 29 g (63.7%) of 2-(benzyloxy)-4-chloro-5-nitropyridine as a light yellow solid. [M+1]$^+$ m/z: 265.0

Step 2

Into a 1000-mL round-bottom flask, was placed 2-(benzyloxy)-4-chloro-5-nitropyridine (29.00 g, 109.57 mmol, 1.00 equiv), DMF (300.00 mL), and AcONa (13.48 g, 164.35 mmol, 1.50 equiv). The resulting solution was stirred for 2 hr at 110° C., cooled down, and diluted with 500 mL of H$_2$O. The resulting solution was extracted with 2×300 mL of ethyl acetate and the organic layers were combined. The resulting mixture was washed with ×200 mL of brine and dried over anhydrous sodium sulfate and concentrated. This resulted in 27 g (100%) of 2-(benzyloxy)-5-nitropyridin-4-ol as a light yellow solid. [M+1]$^+$ m/z: 247.1

Step 3

Into a 1000-mL round-bottom flask, was placed 2-(benzyloxy)-5-nitropyridin-4-ol (28.00 g, 113.71 mmol, 1.00 equiv), EtOH (300.00 mL), H$_2$O (60.00 mL), NH$_4$Cl (48.66 g, 909.74 mmol, 8.00 equiv), and Fe (25.40 g, 454.87 mmol, 4.00 equiv). The resulting solution was stirred for 3 hr at 70° C., cooled down, and filtered. The resulting mixture was concentrated. The residue was applied onto a silica gel column with dichloromethane/methanol (10/1). This resulted in 6.0 g (24.4%) of 5-amino-2-(benzyloxy)pyridin-4-ol as a yellow solid. [M+1]+ m/z: 217.1

Step 4

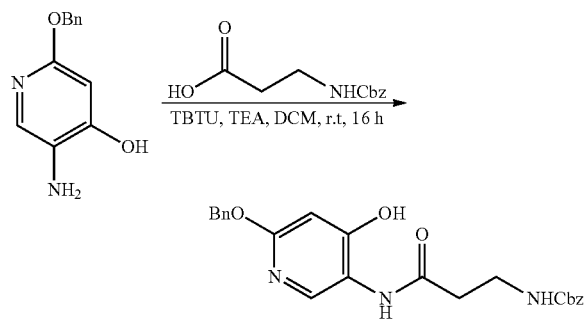

Into a 250-mL round-bottom flask, was placed 5-amino-2-(benzyloxy)pyridin-4-ol (6.00 g, 27.74 mmol, 1.00 equiv), DMF, 3-[[(benzyloxy)carbonyl]amino]propanoic acid (7.43 g, 33.29 mmol, 1.20 equiv), TEA (8.42 g, 83.24 mmol, 3.00 equiv), and TBTU (17.82 g, 55.49 mmol, 2.00 equiv). The resulting solution was stirred for 16 hr at room temperature, and then diluted with 200 mL of H₂O. The resulting solution was extracted with 2×100 mL of ethyl acetate and the organic layers were combined and dried over anhydrous sodium sulfate and concentrated. The residue was applied onto a silica gel column with dichloromethane/methanol (10/1). This resulted in 8.1 g (69.2%) of benzyl (3-((6-(benzyloxy)-4-hydroxypyridin-3-yl)amino)-3-oxopropyl) carbamate as a light yellow oil. [M+1]+ m/z: 422.2

Step 5

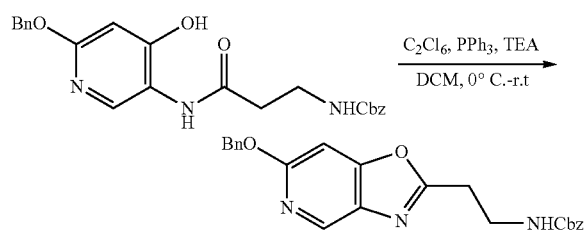

Into a 250-mL round-bottom flask purged and maintained with an inert atmosphere of nitrogen, was placed perchloroethane (11.24 g, 48.04 mmol, 2.50 equiv), DCM (100 mL). PPh₃ (15.12 g, 57.65 mmol, 3.00 equiv) and TEA (15.56 g, 153.75 mmol, 8.00 equiv) were added at 0° C. The resulting solution was stirred for 10 min at 0° C. Benzyl(3-((6-(benzyl oxy)-4-hydroxypyridin-3-yl)amino)-3-oxopropyl)carbamate (8.10 g, 19.219 mmol, 1.00 equiv) was added. The resulting solution was stirred for 1.5 hr at room temperature, and then diluted with 100 mL of DCM. The resulting mixture was washed with 2×100 mL of brine and dried over anhydrous sodium sulfate and concentrated. The residue was applied onto a silica gel column with ethyl acetate/petroleum ether (1/2). This resulted in 1.3 g (16.7%) of benzyl (2-(6-(benzyloxy)oxazolo[4,5-c]pyridin-2-yl)ethyl)carbamate as a light yellow solid. [M+1]+ m/z: 404.2

Step 6

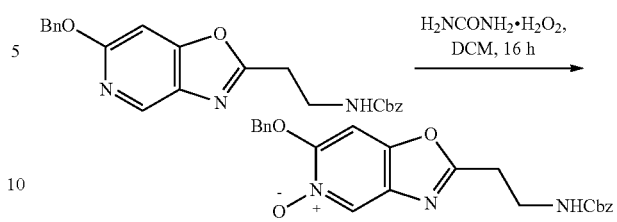

Into a 100-mL 3-necked round-bottom flask, was placed benzyl (2-(6-(benzyloxy)oxazolo[4,5-c]pyridin-2-yl)ethyl) carbamate (1.30 g, 3.22 mmol, 1.00 equiv), DCM (15.00 mL). This was followed by the addition of urea hydrogen peroxide (605 mg, 6.44 mmol, 2.00 equiv) at 0° C. The resulting solution was stirred for 30 min at 0° C. To this was added TFAA (676 mg, 3.22 mmol, 1.00 equiv) at 0° C. The resulting solution was stirred for 16 hr at room temperature, and then diluted with 80 mL of DCM. The resulting mixture was washed with 2×100 mL of Na₂SO₃ (10%). The mixture was dried over anhydrous sodium sulfate and concentrated. The residue was applied onto a silica gel column with ethyl acetate/petroleum ether (10/1). This resulted in 550 mg (40.6%) of 6-(benzyloxy)-2-(2-(((benzyloxy)carbonyl)amino)ethyl)oxazolo[4,5-c]pyri dine 5-oxide as a white solid. [M+1]+ m/z: 420.1

Step 7

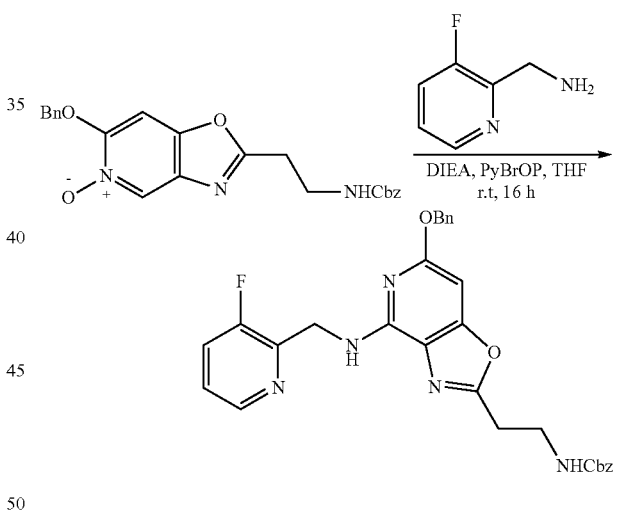

Into a 50-mL round-bottom flask, was placed 6-(benzyloxy)-2-(2-(((benzyloxy)carbonyl)amino)ethyl)oxazolo[4,5-c]pyridine 5-oxide (550 mg, 1.31 mmol, 1.00 equiv), THF (6.00 mL), 1-(3-fluoropyridin-2-yl)methanamine (198 mg, 1.57 mmol, 1.20 equiv), DIEA (1.69 g, 13.11 mmol, 10 equiv), and PyBrOP (916 mg, 1.96 mmol, 1.50 equiv). The resulting solution was stirred for 16 hr at room temperature, and diluted with 20 mL of H₂O. The resulting solution was extracted with 3×30 mL of ethyl acetate and the organic layers were combined. The resulting mixture was washed with 2×20 mL of brine. The mixture was dried over anhydrous sodium sulfate and concentrated. The residue was applied onto a silica gel column with ethyl acetate/petroleum ether (1/1). This resulted in 540 mg (78.0%) of benzyl (2-(6-(benzyloxy)-4-(((3-fluoropyridin-2-yl)methyl)amino)oxazolo[4,5-c]pyridin-2-yl)ethyl)carbamate as a light yellow oil. [M+1]+ m/z: 528.2.

Step 8

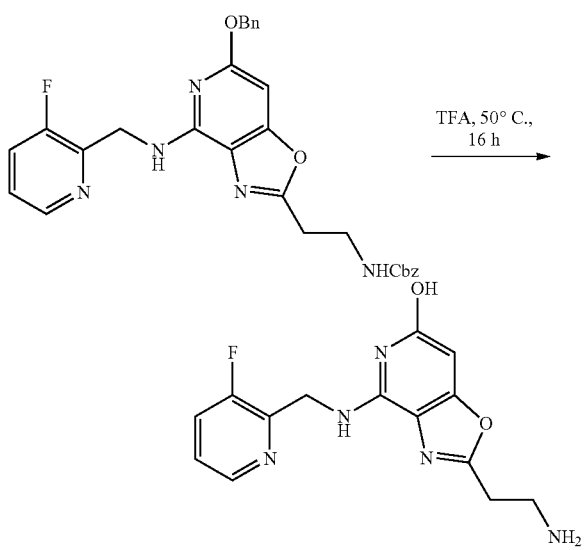

Into a 50-mL round-bottom flask, was placed benzyl (2-(6-(benzyloxy)-4-(((3-fluoropyridin-2-yl)methyl)amino)oxazolo[4,5-c]pyridin-2-yl)ethyl)carbamate (540 mg, 1.02 mmol, 1.00 equiv), and TFA (8.00 mL). The resulting solution was stirred for 16 hr at 50° C., cooled down, and concentrated. The resulting solution was diluted with 10 mL of H$_2$O. The resulting solution was extracted with 3×20 mL of dichloromethane and the organic layers combined and dried over anhydrous sodium sulfate and concentrated. The residue was applied onto a silica gel column with dichloromethane/methanol (10/1). This resulted in 230 mg (74.0%) of 2-(2-aminoethyl)-4-(((3-fluoropyridin-2-yl)methyl)amino)oxazolo[4,5-c]pyridin-6-ol as light yellow solid. [M+1]$^+$ m/z: 304.1.

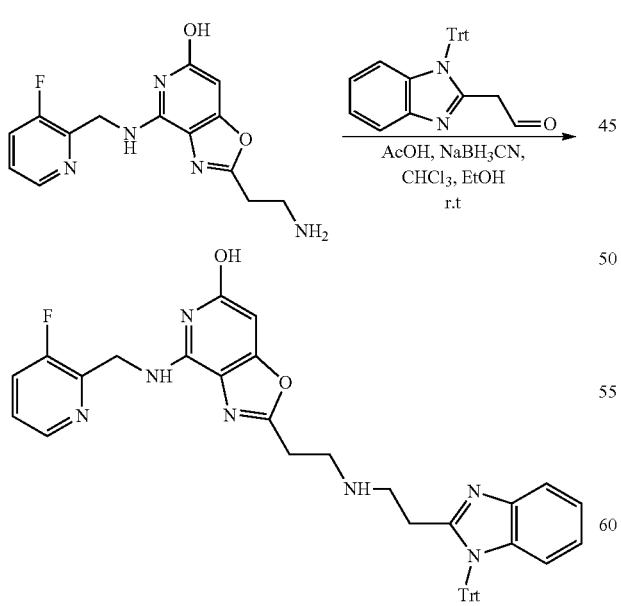

Into a 50-mL round-bottom flask, was placed 2-(2-aminoethyl)-4-(((3-fluoropyridin-2-yl)methyl)amino)oxazolo[4,5-c]pyridin-6-ol (230 mg, 0.75 mmol, 1.00 equiv), CHCl$_3$ (3.00 mL), EtOH (1.00 mL), 2-[1-(triphenylmethyl)-1,3-benzodiazol-2-yl]acetaldehyde (366 mg, 0.91 mmol, 1.20 equiv), AcOH (5 mg, 0.07 mmol, 0.10 equiv). The resulting solution was stirred for 16 hr at room temperature. NaBH$_3$CN (142 mg, 2.27 mmol, 3.00 equiv) was added. The resulting solution was stirred for 2 hr at room temperature, and then quenched by the addition of 10 mL of NH$_4$Cl (10%). The resulting solution was extracted with 2×20 mL of dichloromethane and the organic layers were combined and dried over anhydrous sodium sulfate and concentrated. This resulted in 350 mg (66.9%) of 4-(((3-fluoropyridin-2-yl)methyl)amino)-2-(2-((2-(1-trityl-1H-benzo[d]imidazol-2-yl)ethyl)amino)ethyl)oxazolo[4,5-c]pyridin-6-ol as light yellow solid. [M+1]$^+$ m/z: 690.3

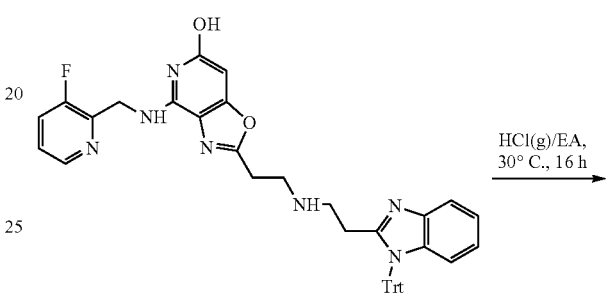

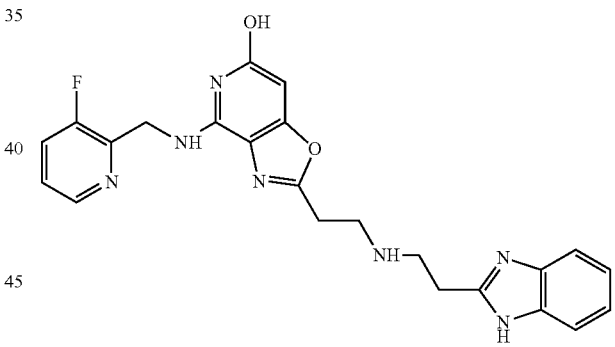

Into a 50-mL round-bottom flask, was placed 4-(((3-fluoropyridin-2-yl)methyl)amino)-2-(2-((2-(1-trityl-1H-benzo[d]imidazol-2-yl)ethyl)amino)ethyl)oxazolo[4,5-c]pyridin-6-ol (350 mg, 0.50 mmol, 1.00 equiv), HCl (g) in EA (5.00 mL). The resulting solution was stirred for 16 hr at 30° C., concentrated, and diluted with 5 mL of ACN. The crude product was purified by Prep-HPLC with the following conditions: Column, Atlantis HILIC OBD Column, 19*150 mm*5 um; mobile phase, Water (10 MMOL/L NH$_4$HCO$_3$+0.10% NH$_3$.H$_2$O) and ACN (5% Phase B up to 50% in 12 min); Detector, uv. This resulted in 69.1 mg (30.4%) of 2-(2-((2-(1H-benzo[d]imidazol-2-yl)ethyl)amino)ethyl)-4-(((3-fluoropyridin-2-yl)methyl)amino)oxazolo[4,5-c]pyridin-6-ol as light yellow solid. $^1$H NMR (300 MHz, DMSO-d$_6$) δ 8.39 (d, J=4.7 Hz, 1H), 7.71 (dd, J=10.3, 8.3 Hz, 1H), 7.48-7.37 (m, 3H), 7.09 (dd, J=6.0, 3.2 Hz, 2H), 7.01 (s, 1H), 5.89 (s, 1H), 4.86 (d, J=5.4 Hz, 2H), 3.03-2.89 (m, 8H). [M+1]$^+$ m/z: 448.2.

Example 1.67

Synthesis of 2-(2-{[2-(1H-1,3-benzodiazol-2-yl)propyl]amino}ethyl)-N-[(3-fluoropyridin-2-yl)methyl]-[1,3]oxazolo[4,5-c]pyridin-4-amine (Compound 61)

Scheme 46 depicts a synthetic route for preparing an exemplary compound.

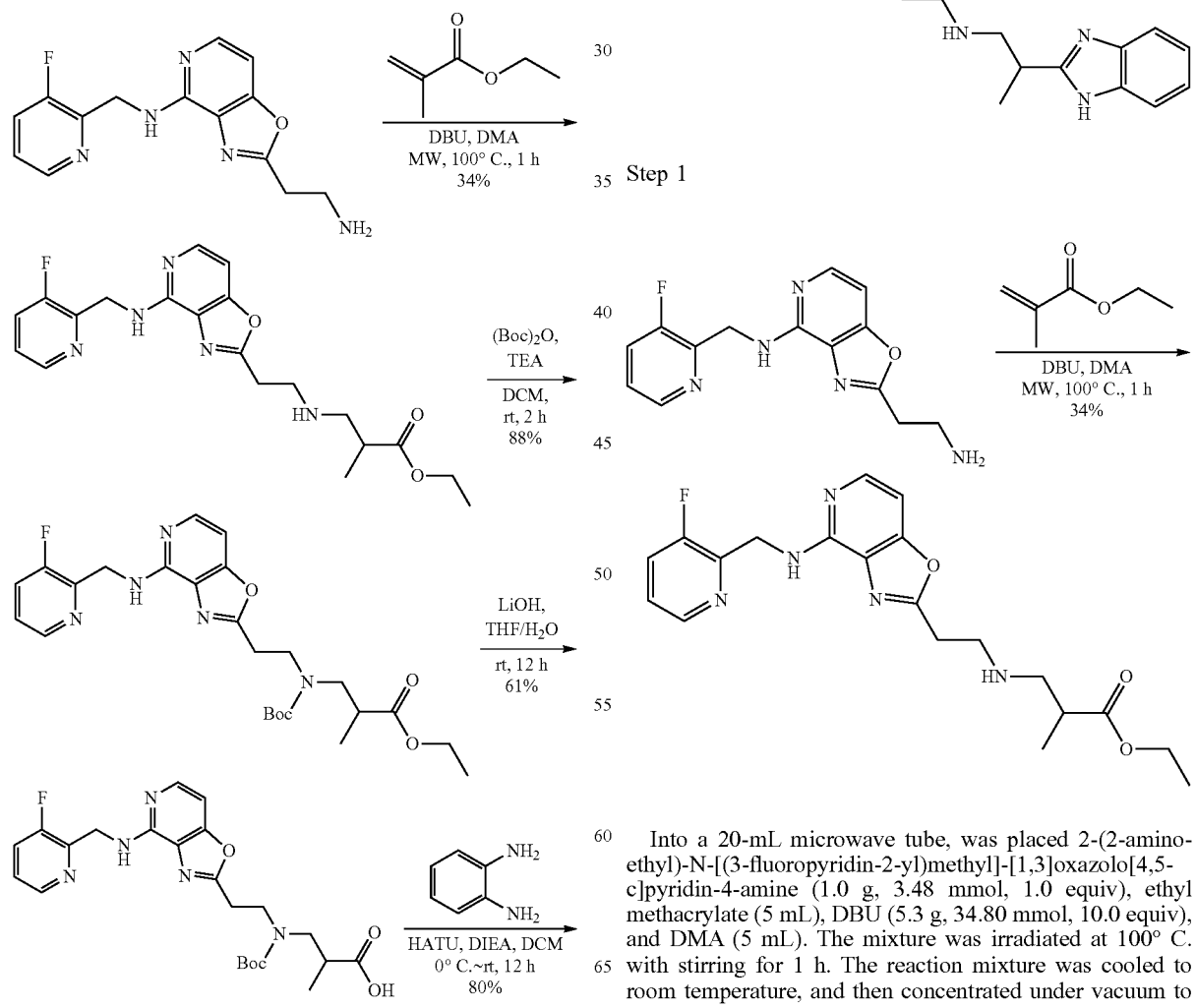

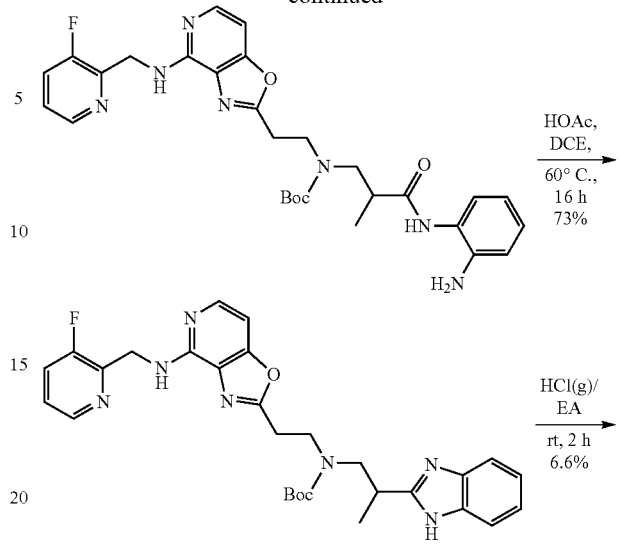

Step 1

Into a 20-mL microwave tube, was placed 2-(2-aminoethyl)-N-[(3-fluoropyridin-2-yl)methyl]-[1,3]oxazolo[4,5-c]pyridin-4-amine (1.0 g, 3.48 mmol, 1.0 equiv), ethyl methacrylate (5 mL), DBU (5.3 g, 34.80 mmol, 10.0 equiv), and DMA (5 mL). The mixture was irradiated at 100° C. with stirring for 1 h. The reaction mixture was cooled to room temperature, and then concentrated under vacuum to remove the solvent. The residue was extracted with 3×30 mL of ethyl acetate, the organic layers combined, and then dried over anhydrous sodium sulfate. This was then filtered, and the filtrate was concentrated under reduced pressure, the crude product was purified by silica gel column with dichloromethane/methanol (20:1). The reaction was repeated three times, scaled up to 3.0 g starting material, and 1.44 g (34%) of 3-((2-(4-(((3-fluoropyridin-2-yl)methyl)amino)oxazolo[4,5-c]pyridin-2-yl)ethyl)amino)-2-methylpropanoate was obtained as a white solid. LCMS (ES) [M+1]$^+$ m/z: 402.

Step 2

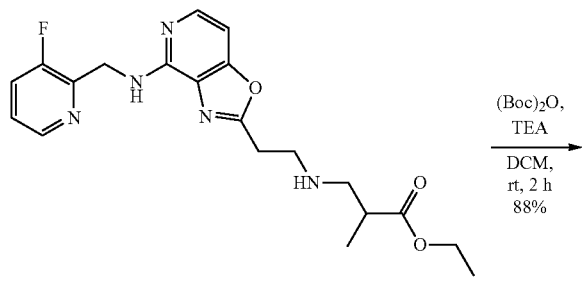

(Boc)$_2$O, TEA
DCM, rt, 2 h
88%

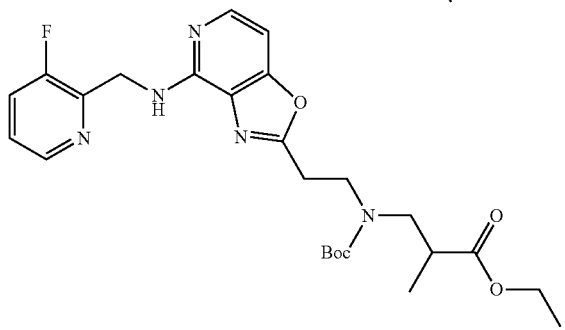

Into a 100-mL round-bottom flask, was placed ethyl 3-((2-(4-(((3-fluoropyridin-2-yl)methyl)amino)oxazolo[4,5-c]pyridin-2-yl)ethyl)amino)-2-methylpropanoate (1.44 g, 3.59 mmol, 1.0 equiv), (Boc)$_2$O (1.17 g, 5.38 mmol, 1.5 equiv), TEA (1.09 g, 10.76 mmol, 3.0 equiv), and DCM (30 mL). The mixture was stirred for 2 h at room temperature. The reaction was quenched with water (20 mL), and then extracted with 3×30 mL of dichloromethane. The combined organic phase was dried over anhydrous sodium sulfate, filtered, and the filtrate was concentrated under vacuum. 1.6 g (88%) of ethyl 3-((tert-butoxycarbonyl)(2-(4-(((3-fluoropyridin-2-yl)methyl)amino)oxazolo[4,5-c]pyridin-2-yl)ethyl)amino)-2-methylpropanoate was obtained as an off-white solid and used in the next step directly without further purification. LCMS (ES) [M+1]$^+$ m/z: 502.

Step 3

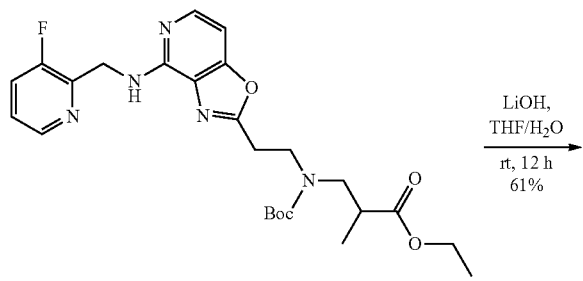

LiOH, THF/H$_2$O
rt, 12 h
61%

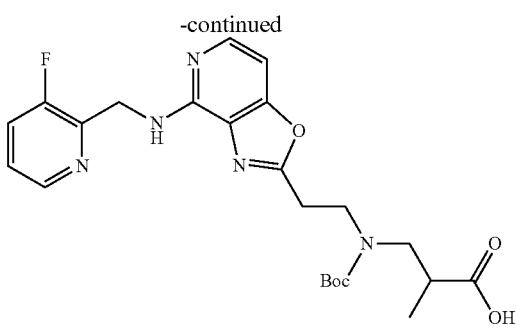

Into a 100-mL round-bottom flask, was placed ethyl 3-((tert-butoxycarbonyl)(2-(4-(((3-fluoropyridin-2-yl)methyl)amino)oxazolo[4,5-c]pyridin-2-yl)ethyl)amino)-2-methylpropanoate (1.90 g, 3.79 mmol, 1.0 equiv), LiOH (0.36 g, 15.03 mmol, 4.0 equiv), H$_2$O (5 mL), and THF (20 mL). The reaction solution was stirred for 12 h at room temperature. The pH value of the solution was adjusted to 5 with citric acid solid, and then extracted with 3×30 mL of ethyl acetate. The combined organic phase was dried over anhydrous sodium sulfate, filtered, and the filtrate was concentrated under vacuum. 1.1 g (61%) of 3-((tert-butoxycarbonyl)(2-(4-(((3-fluoropyridin-2-yl)methyl)amino)oxazolo[4,5-c]pyridin-2-yl)ethyl)amino)-2-methylpropanoic acid was obtained as a light yellow solid. LCMS (ES) [M+1]$^+$ m/z: 474.

Step 4

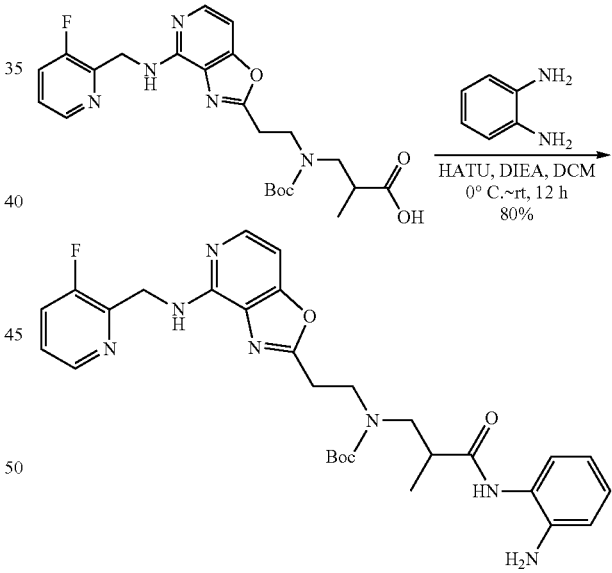

Into a 100-mL 3-necked round-bottom flask purged and maintained with an inert atmosphere of nitrogen, was placed 3-((tert-butoxycarbonyl)(2-(4-(((3-fluoropyridin-2-yl)methyl)amino)oxazolo[4,5-c]pyridin-2-yl)ethyl)amino)-2-methylpropanoic acid (1.10 g, 2.32 mmol, 1.0 equiv), o-phenylenediamine (0.38 g, 3.51 mmol, 1.5 equiv), DIEA (0.60 g, 4.65 mmol, 2.0 equiv), and DCM (30 mL). To the mixture, HATU (1.32 g, 3.49 mmol, 1.5 equiv) was added at 0° C. After addition, the reaction solution was stirred for 12 h at room temperature. The reaction was then quenched by the addition of water (20 mL), and then extracted with 3×30 mL of dichloromethane. The combined organic phase was dried over anhydrous sodium sulfate, filtered, and the filtrate was concentrated under vacuum. The residue was purified by silica gel column with ethyl acetate/petroleum ether (2:3). 1.04 g (79%) of tert-butyl (3-((2-aminophenyl)amino)-2-methyl-3-oxopropyl)(2-(4-(((3-fluoropyridin-2-yl)methyl)amino)oxazolo[4,5-c]pyridin-2-yl)ethyl)carbamate was obtained as a brown solid. LCMS (ES) [M+1]⁺ m/z: 564.

Step 5

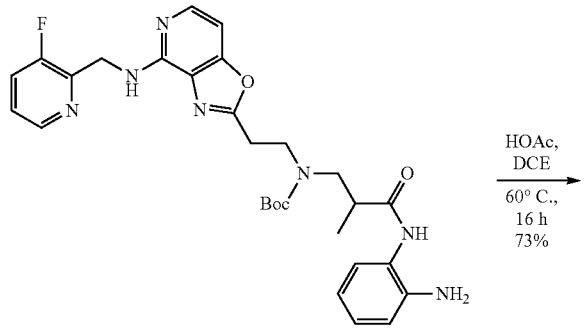

Into a 100-mL round-bottom flask, was placed tert-butyl (3-((2-aminophenyl)amino)-2-methyl-3-oxopropyl)(2-(4-(((3-fluoropyridin-2-yl)methyl)amino)oxazolo[4,5-c]pyridin-2-yl)ethyl)carbamate (950 mg, 1.69 mmol, 1.0 equiv), HOAc (405 mg, 6.74 mmol, 4.0 equiv), and DCE (15 mL). The reaction solution was stirred for 16 h at 60° C. The reaction mixture was cooled and concentrated under vacuum to remove the solvent. 670 mg (73%) of tert-butyl (2-(1H-benzo[d]imidazol-2-yl)propyl)(2-(4-(((3-fluoropyridin-2-yl)methyl)amino)oxazolo[4,5-c]pyridin-2-yl)ethyl)carbamate was obtained as a brown solid. LCMS (ES) [M+1]⁺ m/z: 546.

Step 6

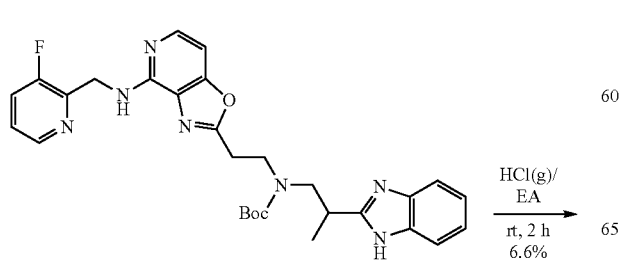

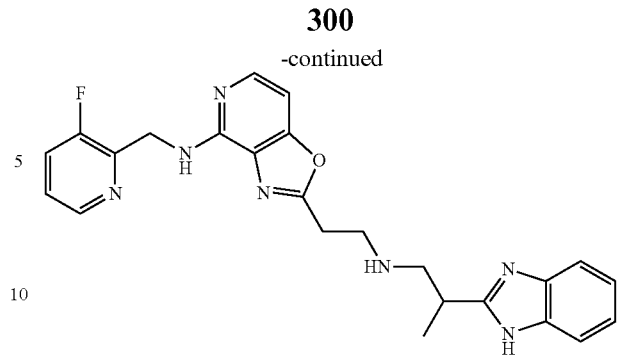

Into a 50-mL round-bottom flask, was placed tert-butyl (2-(1H-benzo[d]imidazol-2-yl)propyl)(2-(4-(((3-fluoropyridin-2-yl)methyl)amino)oxazolo[4,5-c]pyridin-2-yl)ethyl)carbamate (670 mg, 1.23 mmol, 1.0 equiv), and HCl (g) (2 M in EA) (6 mL). The mixture was stirred for 2 h at room temperature. The reaction solution was diluted with ice-water (10 mL), the pH value of the solution was adjusted to 7 with NaHCO₃ solid, and extracted with 3×20 mL of ethyl acetate. The combined organic phase was dried over anhydrous sodium sulfate, filtered, and the filtrate was concentrated under vacuum. The crude product was purified by Prep-HPLC with the following conditions: (Prep-C18, XBridge column, 19*150 mm, gradient elution of 5% to 30% CH₃CN in water within 12 min, both solvents contained 0.1% FA). 35.9 mg (6.6%) of 2-(2-((2-(1H-benzo[d]imidazol-2-yl)propyl)amino)ethyl)-N-((3-fluoropyridin-2-yl)methyl)oxazolo[4,5-c]pyridin-4-amine was obtained as an off-white solid. ¹H-NMR (300 MHz, DMSO-d₆) δ 12.09 (br, 1H), 8.35 (dt, J=4.5, 1.5 Hz, 1H), 7.86 (d, J=5.7 Hz, 1H), 7.72-7.66 (m, 1H), 7.43-7.35 (m, 3H), 7.18-7.06 (m, 3H), 6.89 (d, J=5.7 Hz, 1H), 4.84 (d, J=4.5 Hz, 2H), 3.18-2.96 (m, 6H), 2.82 (dd, J=11.6, 6.5 Hz, 1H), 2.10 (br, 1H), 1.31 (d, J=6.9 Hz, 3H). LCMS (ES) [M+1]⁺ m/z: 446.

Example 1.68

Synthesis of 2-(2-{[2-(1H-1,3-benzodiazol-2-yl)propyl]amino}ethyl)-N-[(3-fluoropyridin-2-yl)methyl]-[1,3]oxazolo[4,5-c]pyridin-4-amine (Compound 62)

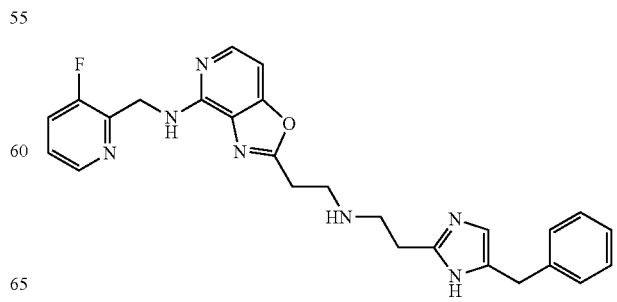

Scheme 47 depicts a synthetic route for preparing an exemplary compound.
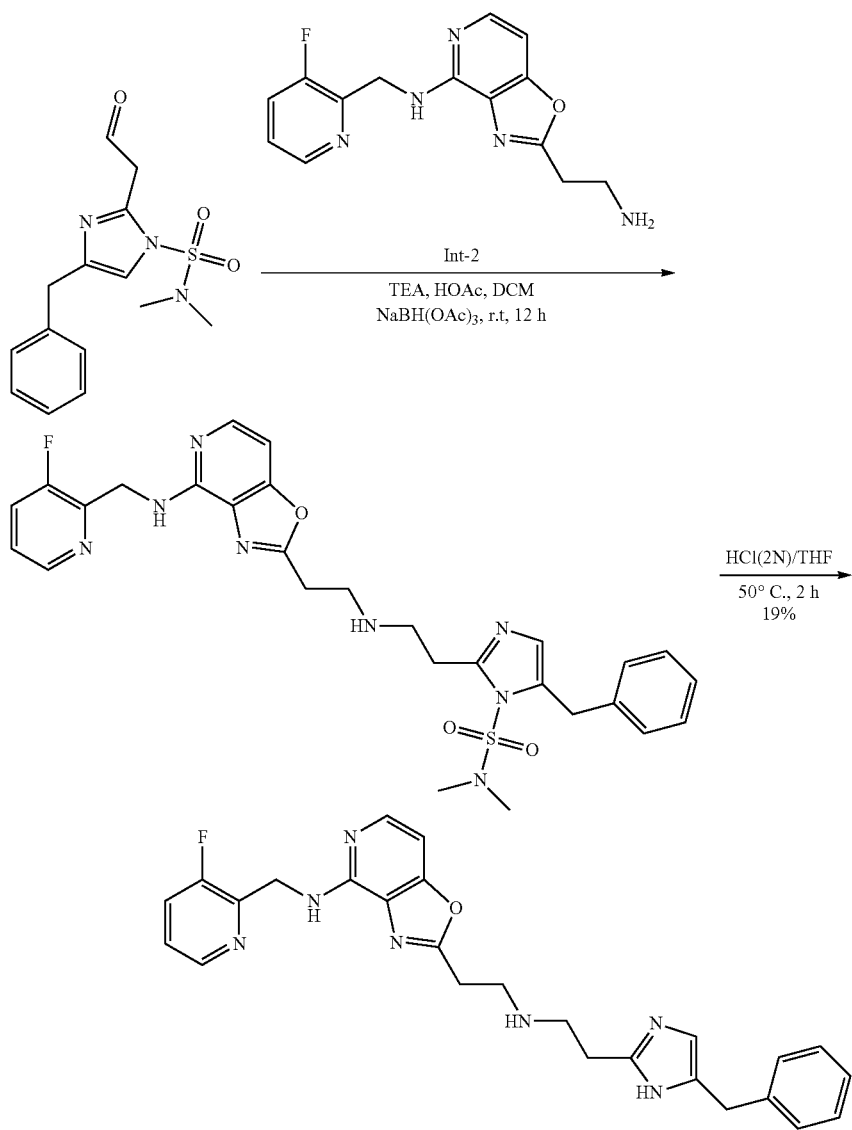
Step 1:
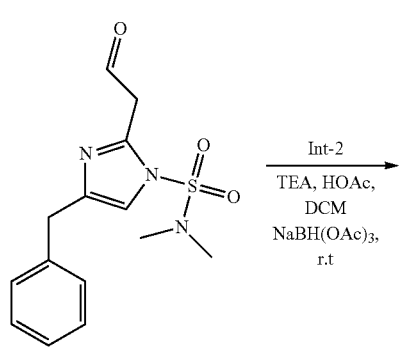
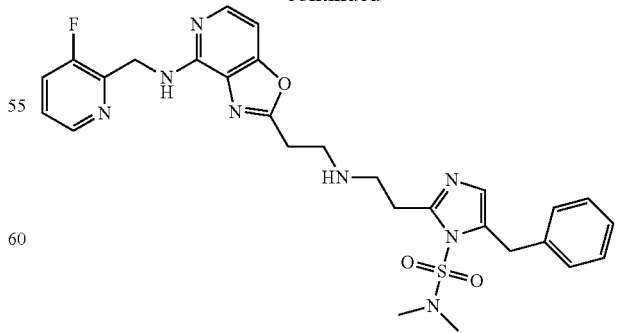
Into a 100-mL round-bottom flask, was placed 2-(2-aminoethyl)-N-((3-fluoropyridin-2-yl)methyl)oxazolo[4,5- c]pyridin-4-amine trihydrochloride (1.16 g, 3.0 mmol, 1.0 equiv), CH$_2$Cl$_2$ (30 mL), 4-benzyl-N,N-dimethyl-2-(2-oxoethyl)imidazole-1-sulfonamide (921 mg, 3.0 mmol, 1.0 equiv), TEA (1.21 g, 12.0 mmol, 4.0 eq), and AcOH (540 mg, 9.0 mmol, 3.0 equiv). The mixture was stirred for 0.5 h at room temperature, followed by the addition of NaBH(OAc)$_3$ (1.91 g, 9.0 mmol, 3.0 equiv), which was added in one portion at 0° C. The reaction solution was stirred overnight at room temperature. The reaction was diluted with 10 mL of H$_2$O, extracted with 2*20 mL of dichloromethane, dried over anhydrous sodium sulfate, filtered, and the filtrate was concentrated under reduced pressure. The residue was purified by silica column, with MeOH/DCM from 0% to 5%, 400 mg (23%) of 5-benzyl-2-(2-((2-(4-(((3-fluoropyridin-2-yl)methyl)amino)oxazolo[4,5-c]pyridin-2-yl)ethyl)amino)ethyl)-N,N-dimethyl-1H-imidazole-1-sulfonamide was obtained as a light yellow solid.
Step 2

Into a 40-mL vial, was placed a mixture of 5-benzyl-2-(2-((2-(4-(((3-fluoropyridin-2-yl)methyl)amino)oxazolo[4,5-c]pyridin-2-yl)ethyl)amino)ethyl)-N,N-dimethyl-1H-imidazole-1-sulfonamide (400 mg, 0.69 mmol, 1.0 eq), HCl (2N)(4 mL), and THF (4 mL). The mixture was stirred for 2 h at 50° C. This was then concentrated under reduced pressure to remove the solvent, and the residue was dissolved in MeOH (5 mL), and then subjected to reverse phase preparative (Prep-HPLC-006): Column, XBridge Shield RP18 OBD Column, 5 um, 19*150 mm; mobile phase, Water (10 mmol/L NH$_4$HCO$_3$+0.1% NH$_3$.H$_2$O) and ACN (16% Phase B up to 34% in 7 min) to provide the title compound as a yellow solid. (61.0 mg, 19%). $^1$H-NMR (300 MHz, DMSO-d$_6$) δ 11.35 (br, 1H), 8.36 (d, 1H, J=4.5 Hz), 7.87 (d, 1H, J=6.0 Hz), 7.72-7.66 (m, 1H), 7.41-7.35 (m, 1H), 7.28-7.16 (m, 6H), 6.92 (d, 1H, J=6.0 Hz), 6.54 (br, 1H), 4.84 (d, 2H, J=4.5 Hz), 3.73 (s, 2H), 3.05-3.01 (m, 4H), 2.82 (t, 2H, J=7.2 Hz), 2.66 (t, 2H, J=7.2 Hz). LCMS (ESI) m/z, [M+H]$^+$: 472.

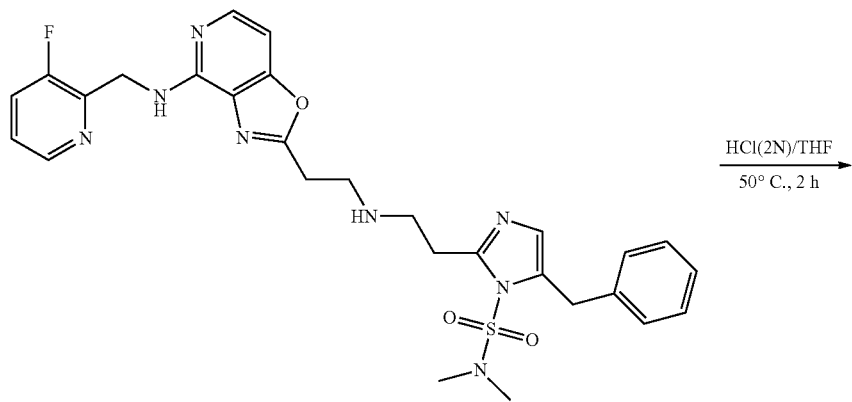

HCl(2N)/THF
50° C., 2 h

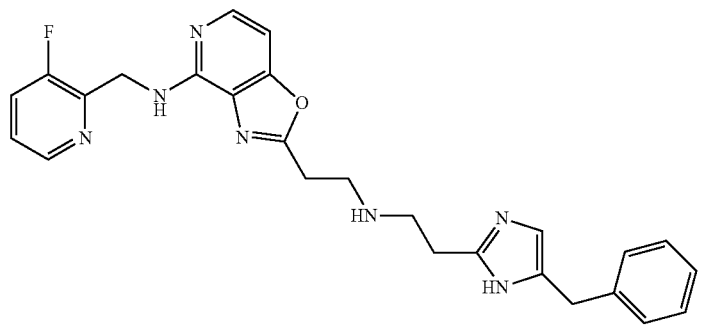

Example 1.69
Synthesis of 2-[2-({2-[5-(cyclopropylmethyl)-1H-imidazol-2-yl]ethyl}amino)ethyl]-N-[(3-fluoropyridin-2-yl)methyl]-[1,3]oxazolo[4,5-c]pyridin-4-amine (Compound 63)
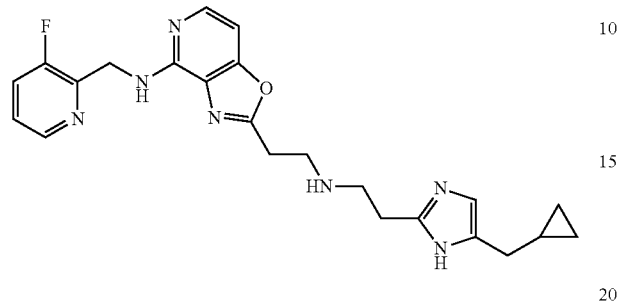
Scheme 48 depicts a synthetic route for preparing an exemplary compound.
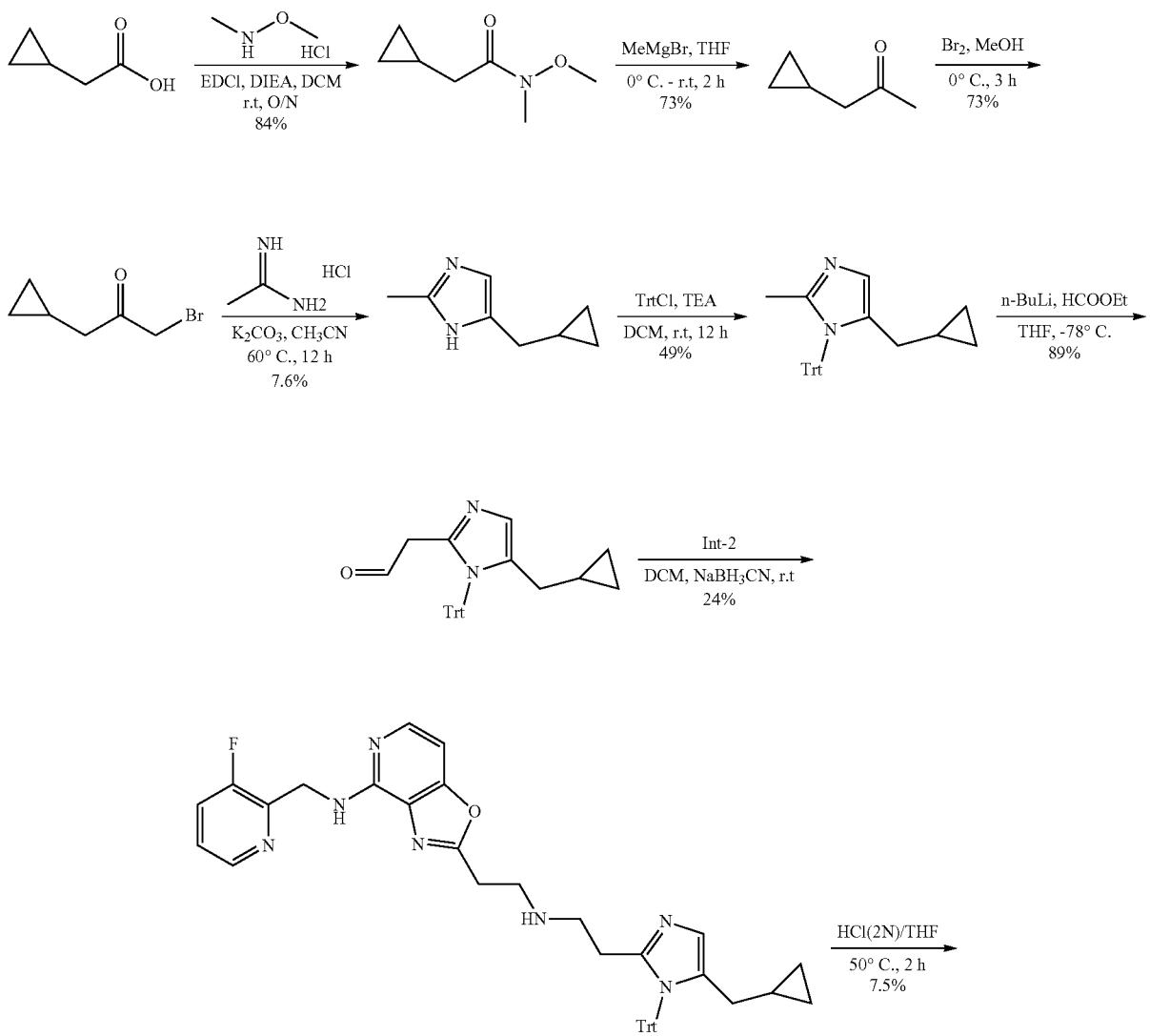

-continued

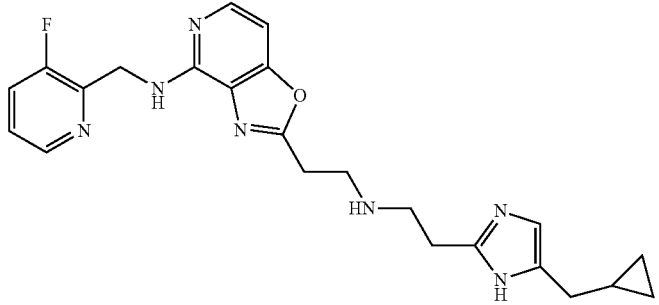

Step 1

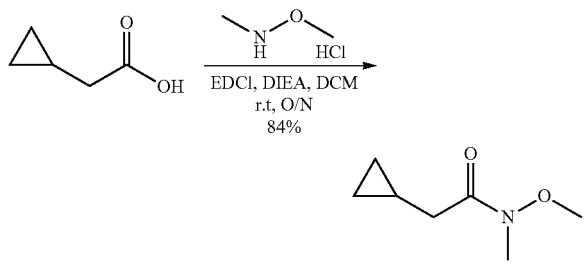

Into a 500-mL round-bottom flask, was placed cyclopropylacetic acid (10.0 g, 100 mmol, 1.0 equiv), DCM (200 mL), N,O-dimethylhydroxylamine hydrochloride (11.7 g, 120 mmol, 1.2 equiv), DIEA (38.7 g, 300 mmol, 3.0 equiv), and EDCI (38.3 g, 200 mmol, 2.0 equiv). The mixture was stirred overnight at room temperature. The reaction was then quenched by the addition of 100 mL of water, separated out the organic phase, washed with 1×100 ml of $Na_2CO_3$(aq), 1×100 mL of brine, dried over anhydrous sodium sulfate, filtered out the solid, and the filtrate was concentrated under reduced pressure. 12 g (84%) of 2-cyclopropyl-N-methoxy-N-methylacetamide was obtained as a yellow solid and used to the next step directly without further purification.

Step 2

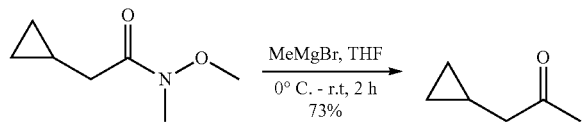

Into a 500-mL 3-necked round-bottom flask purged and maintained with an inert atmosphere of nitrogen, was placed 2-cyclopropyl-N-methoxy-N-methylacetamide (12.0 g, 83.9 mmol, 1.0 equiv), and THF (200 mL). This was followed by the addition of MeMgBr (3 M in THF) (56.0 mL, 167.8 mmol, 2.0 equiv) dropwise with stirring at 0° C. The mixture was stirred for 2 h at room temperature. The reaction was then quenched by the addition of 100 mL of $NH_4Cl$(aq), extracted with 2×100 mL of $Et_2O$, combined with the organic phase, dried over anhydrous sodium sulfate, filtered, and the filtrate was concentrated under reduced pressure. 6.0 g (73%) of 1-cyclopropylpropan-2-one was obtained as a yellow oil and used to the next step directly without further purification.

Step 3

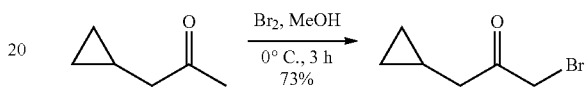

Into a 100-mL round-bottom flask, was placed 1-cyclopropylpropan-2-one (6.0 g, 61.1 mmol, 1.0 equiv) and MeOH (60 mL). $Br_2$ (7.82 g, 48.9 mmol, 0.8 equiv) was added dropwise at 0° C. After addition, the mixture was stirred for 3 h at 0° C. The reaction was then quenched by the addition of $Na_2S_2O_3$(aq)(20 mL), extracted with 2×100 mL of ethyl acetate, combined with the organic phase, dried over anhydrous sodium sulfate, filtered, and the filtrate was concentrated under reduced pressure. 7.9 g (73%) of 1-bromo-3-cyclopropylpropan-2-one was obtained as a yellow oil and used in the next step directly without further purification.

Step 4

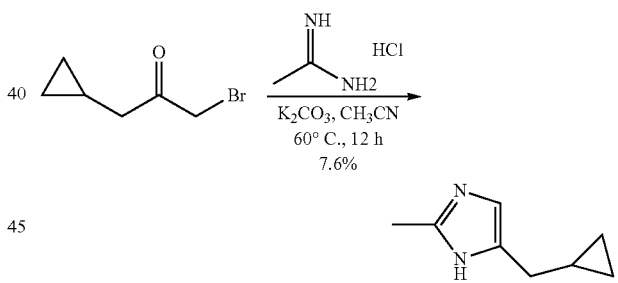

Into a 500-mL round-bottom flask, was placed 1-bromo-3-cyclopropylpropan-2-one (7.90 g, crude, 44.62 mmol, 1.0 equiv), $CH_3CN$ (150 mL), acetamidine hydrochloride (12.66 g, 133.87 mmol, 3.0 equiv), and $K_2CO_3$ (30.84 g, 223.11 mmol, 5.0 equiv). The mixture was stirred for 12 h at 60° C. The reaction mixture was cooled, filtered, and the filtrate was purified by Flash-Prep-HPLC with the following conditions (IntelFlash-1): Column, C18-120 g, mobile phase, $CH_3CN/H_2O$ (1% $NH_4OH$) from 5% to 80% within 12 min; Detector, 220 nm. 460 mg (7.6%) of 4-(cyclopropylmethyl)-2-methyl-3H-imidazole was obtained as a colorless oil.

Step 5

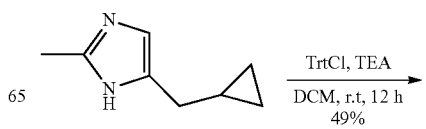

-continued

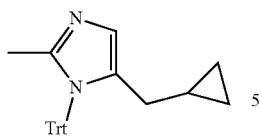

Into a 50-mL round-bottom flask, was placed 4-(cyclopropylmethyl)-2-methyl-3H-imidazole (460.0 mg, 3.38 mmol, 1.0 equiv), DCM (15 mL), TEA (1.03 g, 10.1 mmol, 3.0 equiv), and Trt-Cl (1.13 g, 4.05 mmol, 1.2 equiv). The mixture was stirred for 12 h at room temperature. The reaction solution was diluted with 10 mL of H₂O, the organic phase was separated out, dried over anhydrous Na₂SO₄, filtered, and the filtrate was concentrated under reduced pressure. The residue was purified by silica gel column with ethyl acetate/petroleum ether from 10% to 60%. 630 mg (49%) of 5-(cyclopropylmethyl)-2-methyl-1-(triphenylmethyl)imidazole was obtained as a white solid.

Step 6

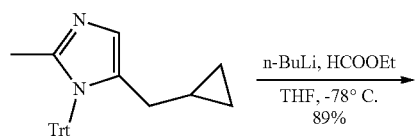

Into a 50-mL 3-necked round-bottom flask purged and maintained with an inert atmosphere of nitrogen, was placed 5-(cyclopropylmethyl)-2-methyl-1-(triphenylmethyl)imidazole (630 mg, 1.66 mmol, 1.0 equiv) and THF (15 mL). This was followed by the addition of n-BuLi (2.0 mL, 21.23 mmol, 3.0 equiv) dropwise with stirring at −78° C. After stirring for 1 h, to this was added HCOOEt (618 mg, 8.35 mmol, 5.0 equiv) dropwise with stirring at −78° C. The reaction solution was stirred for 0.5 h at −78° C. The reaction was then quenched by the addition of 20 mL of NH₄Cl(aq), extracted with 2×100 mL of ethyl acetate, combined with the organic phase, washed with 1×100 ml of brine, dried over anhydrous sodium sulfate, filtered, and the filtrate was concentrated under reduced pressure. 600 mg (89%) of 2-[5-(cyclopropylmethyl)-1-(triphenylmethyl)imidazol-2-yl]acetaldehyde was obtained as a yellow oil and used in the next step directly without further purification.

Step 7

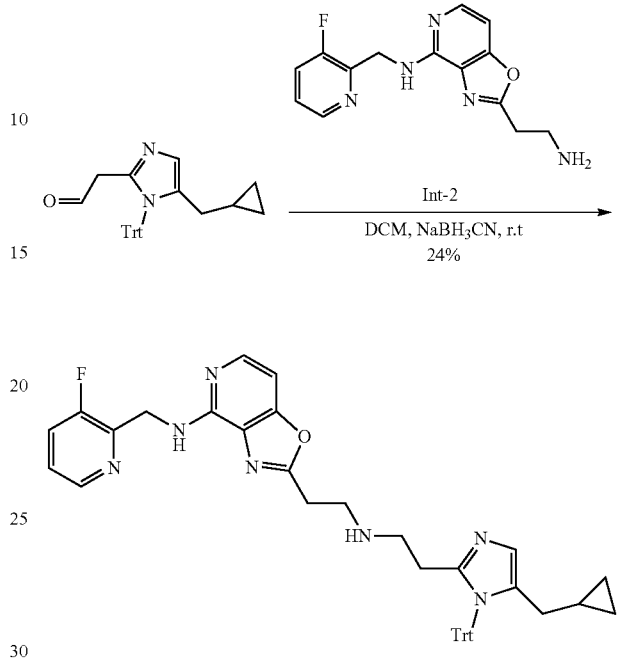

Into a 20-mL round-bottom flask, was placed 2-(2-aminoethyl)-N-[(3-fluoropyridin-2-yl)methyl]-[1,3]oxazolo[4,5-c]pyridin-4-amine trihydrochloride (585 mg, 1.47 mmol, 1.0 equiv), DCM (20 mL), TEA (448 mg, 4.43 mmol, 3.0 equiv), 2-[5-(cyclopropylmethyl)-1-(triphenylmethyl)imidazol-2-yl]acetaldehyde (600 mg, 1.47 mmol, 1.0 equiv), HOAc (266 mg, 4.43 mmol, 3.0 equiv), and NaBH₃CN (186 mg, 2.95 mmol, 2.0 equiv). The mixture was stirred for 12 h at room temperature. The reaction was then quenched by the addition of water (10 mL). The pH value of the solution was adjusted to 8 with Na₂CO₃ solid. The solution was extracted with 2×30 mL of dichloromethane, combined the organic phase, dried over anhydrous sodium sulfate, filtered, and the filtrate was concentrated under reduced pressure. The residue was purified by silica column with MeOH/DCM from 1% to 5%. 244 mg (24%) of 2-[2-([2-[5-(cyclopropylmethyl)-1-(triphenylmethyl)imidazol-2-yl]ethyl]amino)ethyl]-N-[(3-fluoropyridin-2-yl)methyl]-[1,3]oxazolo[4,5-c]pyridin-4-amine was obtained as a yellow solid.

Step 8

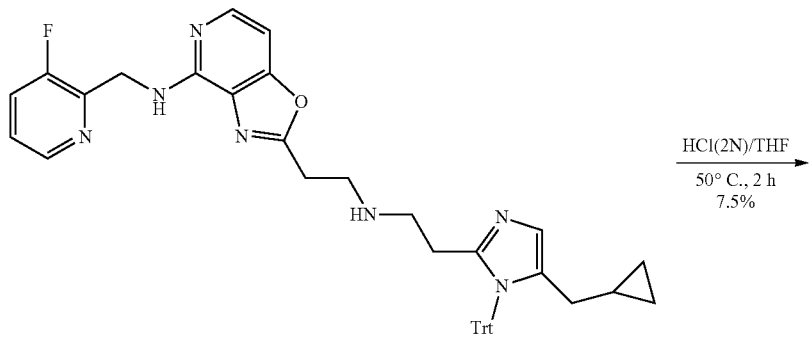

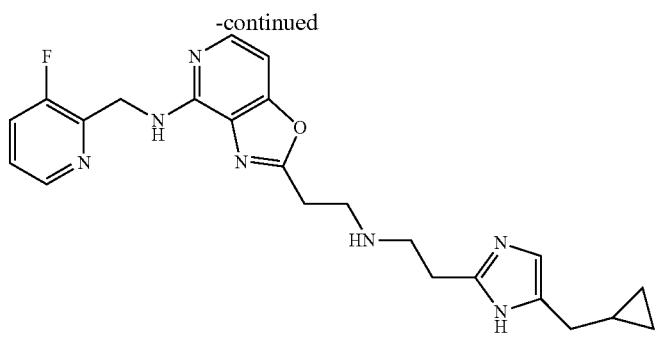

Into a 40-mL vial, was placed a mixture of 2-[2-([2-[5-(cyclopropylmethyl)-1-(triphenylmethyl)imidazol-2-yl]ethyl]amino)ethyl]-N-[(3-fluoropyridin-2-yl)methyl]-[1,3]oxazolo[4,5-c]pyridin-4-amine (244 mg, 0.36 mmol, 1.0 eq), HCl (2N)(4 mL), and THF (4 mL). The mixture was stirred for 2 h at 50° C. The mixture was concentrated under reduced pressure to remove the solvent, and the residue was dissolved in MeOH (5 mL), subjected to reverse phase preparative (Prep-HPLC): Column, XBridge Shield RP18 OBD Column, 5 um, 19*150 mm; mobile phase, Water (10 mmol/L NH$_4$HCO$_3$+0.1% NH$_3$.H$_2$O) and ACN (16% Phase B up to 34% in 7 min) to provide the title compound as a yellow solid, 11.7 mg (7.5%). H NMR (300 MHz, CD$_3$OD) δ 8.39-8.36 (m, 1H), 7.91 (d, 1H, J=6.0 Hz), 7.65-7.53 (m, 1H), 7.43-7.37 (m, 1H), 6.91 (d, 1H, J=5.7 Hz), 6.65 (s, 1H), 4.95 (d, 2H, J=1.2 Hz), 3.18 (s, 4H), 3.03 (t, 2H, J=6.9 Hz), 2.89 (t, 2H, J=6.9 Hz), 2.38 (d, 2H, J=6.9 Hz), 0.98-0.89 (m, 1H), 0.50-0.44 (m, 2H), 0.15-0.10 (m, 2H). LCMS (ESI) m/z, [M+H]$^+$: 436.

Example 1.70

Synthesis of N-[(3-fluoropyridin-2-yl)methyl]-2-(2-{[2-(4-methyl-5-phenyl-1H-imidazol-2-yl)ethyl]amino}ethyl)-[1,3]thiazolo[5,4-d]pyrimidin-7-amine (Compound 64)

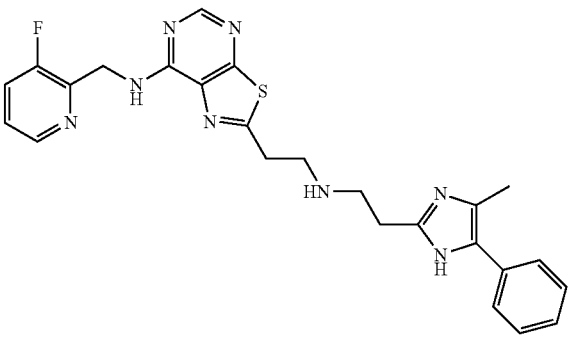 [SMILES: Cc1nc(CCNCCc2nc3c(NCc4ncccc4F)ncnc3s2)[nH]c1-c1ccccc1]

Scheme 49 depicts a synthetic route for preparing an exemplary compound.

Scheme 49

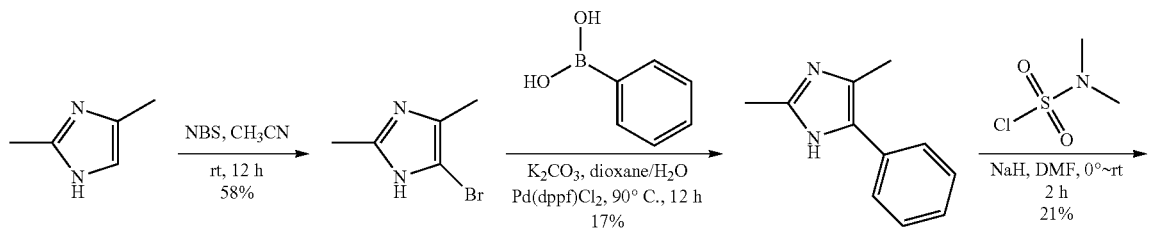

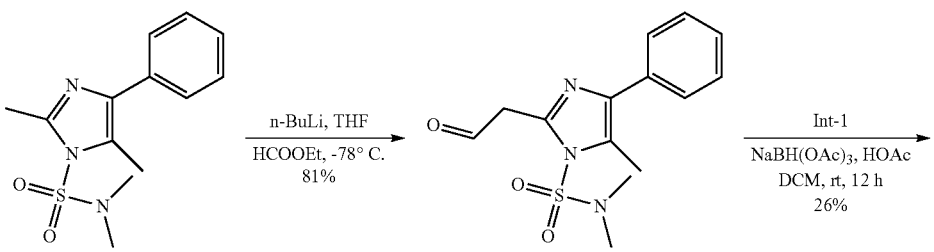

-continued

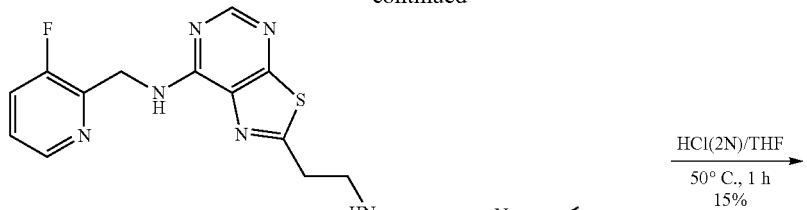

HCl(2N)/THF
50° C., 1 h
15%

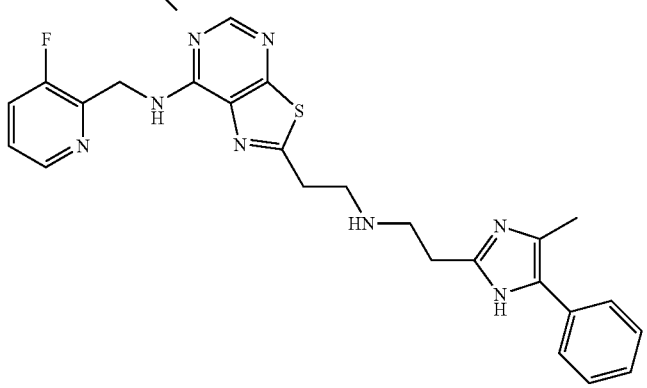

Step 1

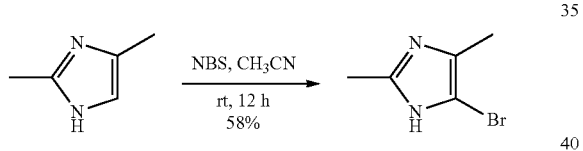

Into a 500-mL 3-necked round-bottom flask, was placed 2,4-dimethyl-1H-imidazole (15.0 g, 156.03 mmol, 1.0 equiv) and CH$_3$CN (150 mL). This was followed by the addition of NBS (29.6 g, 166.31 mmol, 1.05 equiv) at 0° C. The reaction solution was stirred for 12 h at room temperature. After concentrated to remove the solvent, the residue was diluted with 50 mL of H$_2$O and extracted with 3×50 mL of ethyl acetate. The organic phase was combined, dried over anhydrous Na$_2$SO$_4$, filtered, and the filtrate was concentrated under reduced pressure. The residue was purified by silica gel column with dichloromethane/methanol (8/1). 15.87 g (58%) of 4-bromo-2,5-dimethyl-3H-imidazole was obtained as a yellow solid. LCMS (ES) [M+1]$^+$ m/z: 175.

Step 2

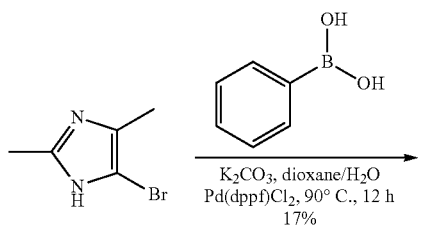

-continued

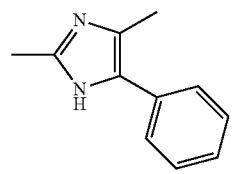

Into a 250-mL 3-necked round-bottom flask purged and maintained with an inert atmosphere of nitrogen, was placed 4-bromo-2,5-dimethyl-3H-imidazole (15.87 g, 90.67 mmol, 1.0 equiv), phenyl boronic acid (13.28 g, 108.92 mmol, 1.2 equiv), K$_2$CO$_3$ (25.03 g, 181.11 mmol, 2.0 equiv), dioxane (150 mL), H$_2$O (15 mL), and Pd(dppf)Cl$_2$ (2.95 g, 4.04 mmol, 0.04 equiv). The mixture was stirred for 12 h at 90° C. After being cooled to room temperature, the reaction mixture was concentrated to remove the solvent. The residue was purified by silica gel column with EA (100%). 2.67 g (17%) of 2,4-dimethyl-5-phenyl-1H-imidazole was obtained as a yellow solid. LCMS (ES) [M+1]$^+$ m/z: 173.

Step 3

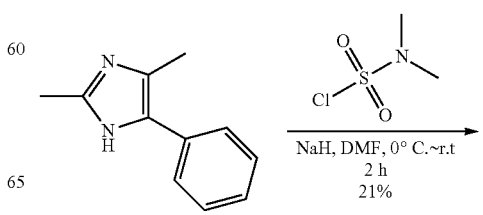

-continued

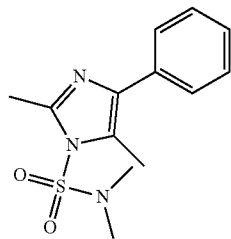

Into a 100-mL 3-necked round-bottom flask, was placed 2,4-dimethyl-5-phenyl-1H-imidazole (2.67 g, 15.50 mmol, 1.0 equiv) and DMF (30 mL). This was followed by the addition of NaH (60% in mineral oil) (931 mg, 23.25 mmol, 1.5 equiv) at 0° C. and stirred for 30 min. To this was added dimethylsulphamoyl-chloride (2.68 g, 18.66 mmol, 1.2 equiv) at 0° C. The reaction solution was allowed to stir for an additional 2 h at room temperature. The reaction was then quenched by the addition of H$_2$O (30 mL), extracted with 3×30 mL of ethyl acetate, washed with 3×20 ml of brine, dried over anhydrous Na$_2$SO$_4$, filtered, and the filtrate was concentrated under reduced pressure. The residue was purified by silica gel column with ethyl acetate/petroleum ether (1/5). 900 mg (21%) of N,N,2,5-tetramethyl-4-phenylimidazole-1-sulfonamide was obtained as a yellow oil. LCMS (ES) [M+1]$^+$ m/z: 280.

Step 4

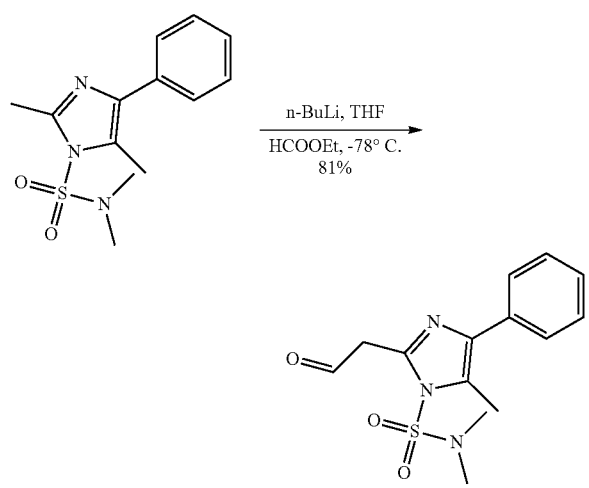

Into a 50-mL 3-necked round-bottom flask purged and maintained with an inert atmosphere of nitrogen, was placed N,N,2,5-tetramethyl-4-phenylimidazole-1-sulfonamide (900 mg, 3.22 mmol, 1.0 equiv) and THF (10 mL). This was followed by the addition of n-BuLi (2.5 M in hexane) (0.91 mL, 14.21 mmol, 3.0 equiv) at −78° C., and then the reaction mixture was stirred for 1 h at −78° C. To this, HCOOEt (1.19 g, 16.11 mmol, 5.0 equiv) was added and stirred for 30 min. The reaction was then quenched by the addition of NH$_4$Cl (aq) (10 mL) and extracted with EA (30 mL*2). The combined organic phase was dried over anhydrous Na$_2$SO$_4$, filtered, and the filtrate was concentrated under reduced pressure. 800 mg (81%) of crude N,N,5-trimethyl-2-(2-oxoethyl)-4-phenylimidazole-1-sulfonamide was obtained as a yellow oil and used in the next step directly without further purification. LCMS (ES) [M+1]$^+$ m/z: 308.

Step 5

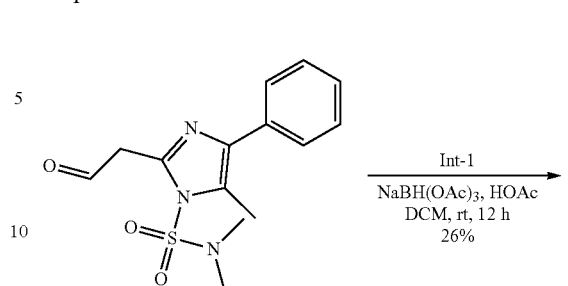

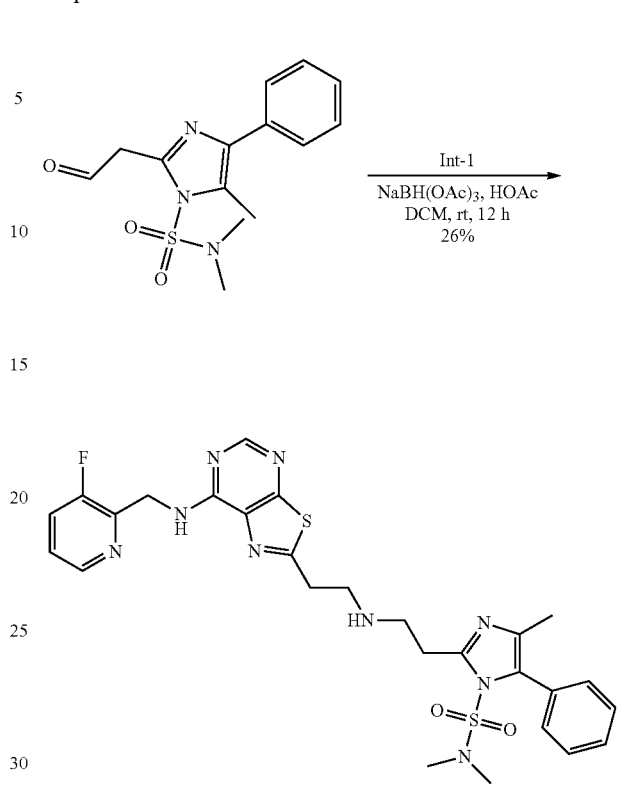

Into a 50-mL round-bottom flask, was placed N,N,5-trimethyl-2-(2-oxoethyl)-4-phenylimidazole-1-sulfonamide (800 mg, 2.61 mmol, 1.0 equiv), 2-(2-aminoethyl)-N-[(3-fluoropyridin-2-yl)methyl]-[1,3]thiazolo[5,4-d]pyrimidin-7-amine (794 mg, 2.61 mmol, 1.0 equiv), AcOH (313 mg, 5.22 mmol, 2.0 equiv), and DCM (10 mL). The mixture was stirred for 0.5 h at room temperature. Following this, NaBH(OAc)$_3$ (1.66 g, 7.83 mmol, 3.0 equiv) was added. The reaction was left to stir for 12 h at room temperature. The reaction was quenched with NaHCO$_3$(aq) (50 mL) and then extracted with 3×10 mL of dichloromethane. The combined organic phase was dried over anhydrous Na$_2$SO$_4$, filtered, and the filtrate was concentrated under reduced pressure. The residue was purified by silica gel column with dichloromethane/methanol (10/1). 400 mg (26%) of 2-(2-[[2-(7-[[(3-fluoropyridin-2-yl)methyl]amino]-[1,3]thiazolo[5,4-d]pyrimidin-2-yl)ethyl]amino]ethyl)-N,N,4-trimethyl-5-phenylimidazole-1-sulfonamide was obtained as a yellow oil. LCMS (ES) [M+1]$^+$ m/z: 596.

Step 6

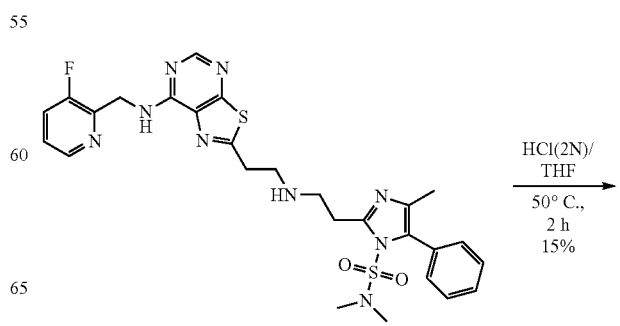

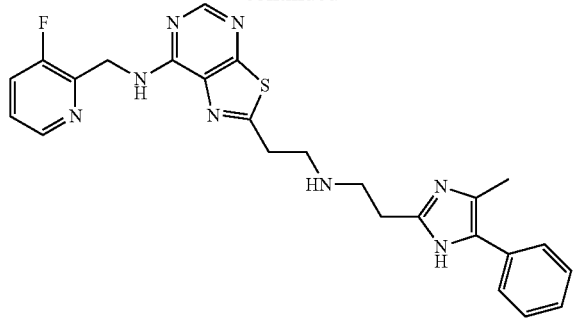

Into a 50-mL round-bottom flask, was placed 2-(2-[[2-(7-[[(3-fluoropyridin-2-yl)methyl]amino]-[1,3]thiazolo[5,4-d]pyrimidin-2-yl)ethyl]amino]ethyl)-N,N,4-trimethyl-5-phenylimidazole-1-sulfonamide (400 mg, 0.67 mmol, 1.0 equiv), THF (10 mL), and HCl (2M) (10 mL). The mixture was stirred for 2 h at 50° C. After being cooled to room temperature, the reaction solution was concentrated to remove the solvent. The pH value of the residue was adjusted to 8 with NH$_3$—H$_2$O. The crude product was purified by Prep-HPLC with the following conditions: Column, XBridge Prep C18 OBD Column, 19 cm, 150 mm, 5 um, mobile phase, Water (10 mmol/L NH$_4$HCO$_3$+0.1% NH$_3$.H$_2$O) and CH$_3$CN (33% Phase B up to 45% within 7 min), Detector, UV 254 nm. 50.6 mg (15%) of N-[(3-fluoropyridin-2-yl)methyl]-2-(2-[[2-(4-methyl-5-phenyl-1H-imidazol-2-yl)ethyl]amino]ethyl)-[1,3]thiazolo[5,4-d]pyrimidin-7-amine was obtained as a white solid. $^1$HNMR: (300 MHz, DMSO-d$_6$): δ 11.61 (br, 1H), 8.35-8.31 (m, 3H), 7.74-7.67 (m, 1H), 7.54 (d, J=7.2 Hz, 2H), 7.42-7.32 (m, 3H), 7.19-7.14 (m, 1H), 4.88 (d, J=4.8 Hz, 2H), 3.23 (t, J=6.3 Hz, 2H), 3.02 (t, J=6.3 Hz, 2H), 2.93 (t, J=6.9 Hz, 2H), 2.75 (t, J=6.9 Hz, 2H), 2.30 (s, 3H). LCMS: (ES, m/z): [M+H]$^+$: 489.

Example 1.71

Synthesis of N-[(3-fluoropyridin-2-yl)methyl]-2-[2-({2-[5-(pyridin-2-yl)-1H-imidazol-2-yl]ethyl}amino)ethyl]-[1,3]thiazolo[5,4-d]pyrimidin-7-amine (Compound 65)

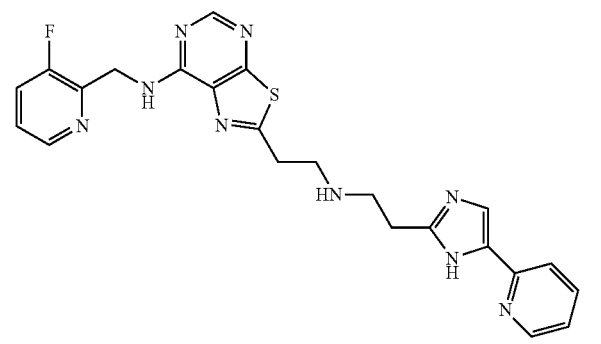 [SMILES: Fc1cccnc1CNc1ncnc2sc(CCNCCc3ncc(-c4ccccn4)[nH]3)nc12]

Scheme 50 depicts a synthetic route for preparing an exemplary compound.

Scheme 50

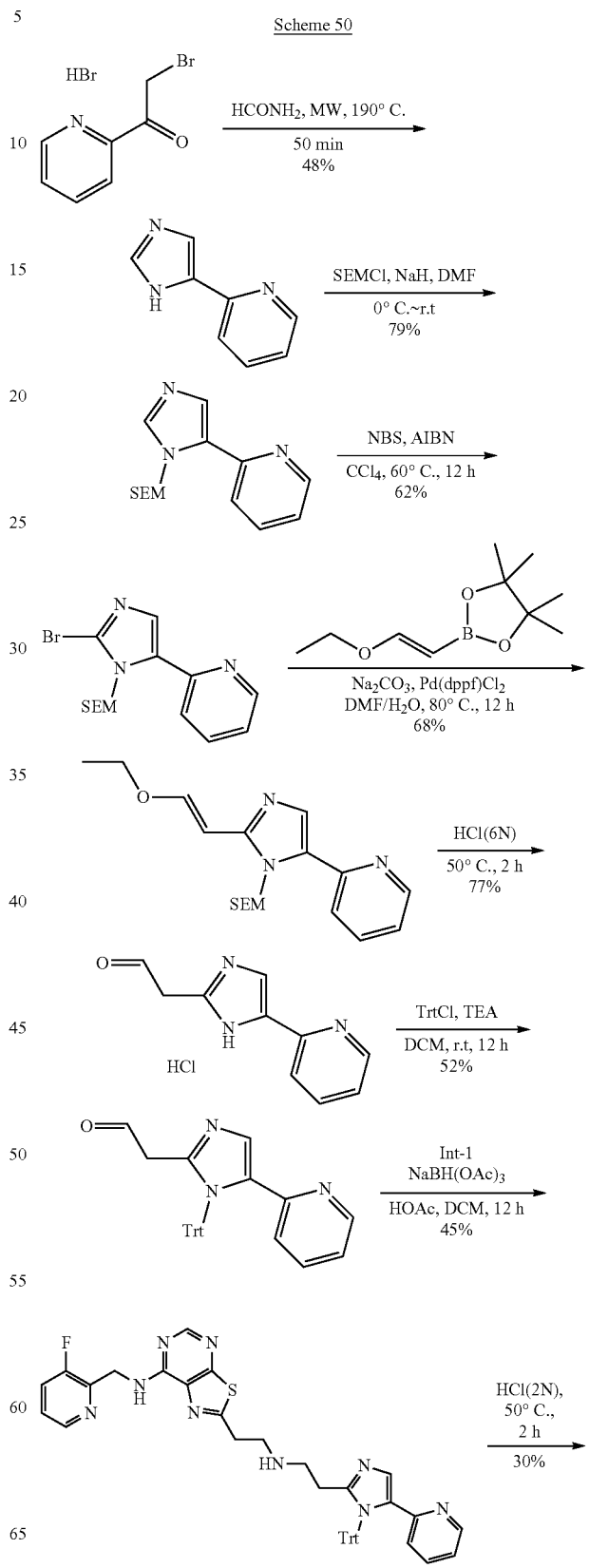

-continued

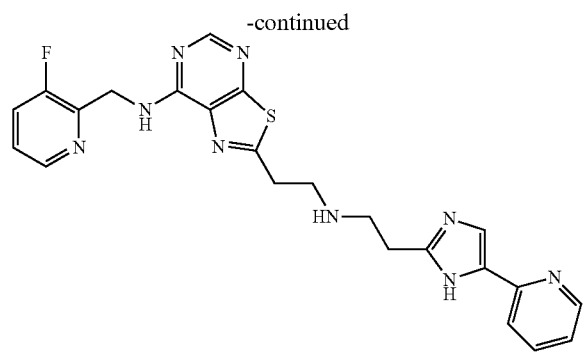

Step 1

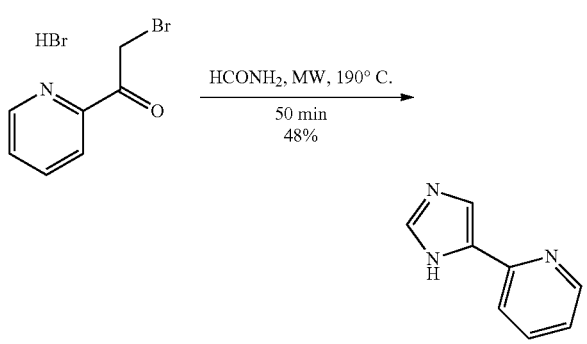

Into a 25-mL microwave tube, was placed 2-bromo-1-(pyridin-2-yl)ethan-1-one hydrobromide (1.0 g, 32.61 mmol, 1.0 equiv) and HCONH₂ (6 mL). The mixture was irradiated for 50 min at 190° C. The reaction mixture was cooled to room temperature, diluted with 10 mL MeOH, and purified by Prep-HPLC with the following conditions: C18-180 g column, CH₃CN/H₂O (0.05% NH₄OH), 80 mL/min, from 10% to 70% within 12 min. 1.0 g (4 batches, 48%) of 2-(3H-imidazol-4-yl)pyridine was obtained as a dark brown solid.

Step 2

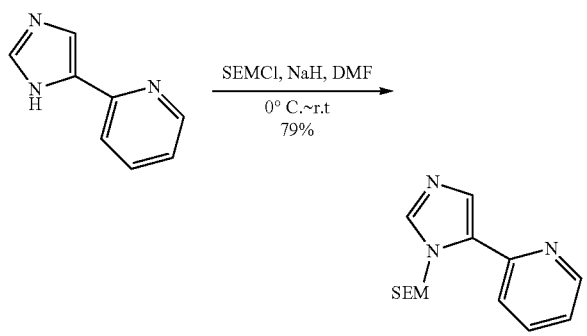

Into a 50-mL 3-necked round-bottom flask purged and maintained with an inert atmosphere of nitrogen, was placed 2-(3H-imidazol-4-yl)pyridine (1.0 g, 6.90 mmol, 1.0 equiv), DMF (15 mL). After being cooled to 0° C., NaH (60% in mineral oil) (0.33 g, 8.28 mmol, 1.2 equiv) was added in one portion carefully and stirred for 0.5 h, followed by SEMCl (1.27 g, 7.59 mmol, 1.1 equiv), which was added dropwise. The mixture was allowed to stir for 2 h at room temperature.

The reaction was then quenched by the addition of water/ice (20 mL), extracted with 2×50 mL of ethyl acetate, washed with brine (30 mL*3), dried over anhydrous sodium sulfate, filtered, and the filtrate was concentrated under reduced pressure. 1.5 g (79%) of 2-(3-[[2-(trimethylsilyl)ethoxy]methyl]imidazol-4-yl)pyridine was obtained as a brown oil and used in the next step directly without further purification.

Step 3

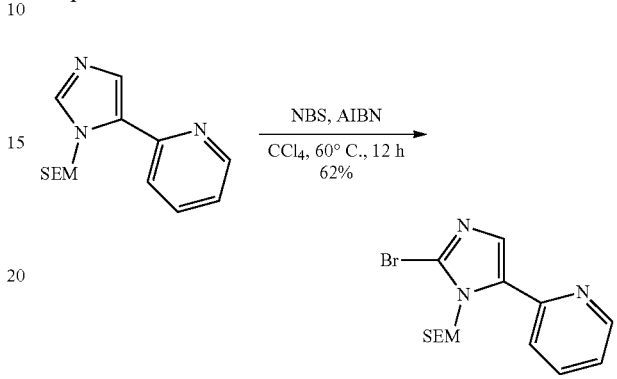

Into a 100-mL round-bottom flask, was placed 2-(1-((2-(trimethylsilyl)ethoxy)methyl)-1H-imidazol-5-yl)pyridine (1.5 g, 5.45 mmol, 1.0 equiv), CCl₄ (30 mL), NBS (1.16 g, 6.54 mmol, 1.2 equiv), and AIBN (90 mg, 0.55 mmol, 0.1 equiv). The mixture was stirred for 12 h at 60° C. The reaction mixture was cooled and purified by flash column with ethyl acetate/petroleum ether (1:3). 1.2 g (62%) of 2-(2-bromo-1-((2-(trimethyl silyl)ethoxy)methyl)-1H-imidazol-5-yl)pyridine was obtained as a yellow solid.

Step 4

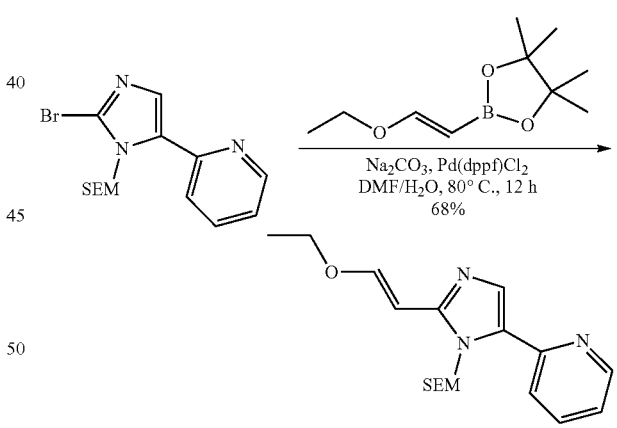

Into a 100-mL round-bottom flask purged and maintained with an inert atmosphere of nitrogen, was placed 2-(2-bromo-1-((2-(trimethylsilyl)ethoxy)methyl)-1H-imidazol-5-yl)pyridine (1.2 g, 3.40 mmol, 1.0 equiv), DMF/H₂O (8:1)(30 mL), 2-[(E)-2-ethoxyethenyl]-4,4,5,5-tetramethyl-1,3,2-dioxaborolane (808 mg, 4.08 mmol, 1.2 equiv), Na₂CO₃ (721 mg, 6.80 mmol, 2.0 equiv), and Pd(dppf)Cl₂ (124 mg, 0.17 mmol, 0.05 equiv). The mixture was stirred for 12 h at 80° C. The reaction mixture was cooled to room temperature and purified by flash column with (PE/EA=3:1). 800 mg (68%) of (E)-2-(2-(2-ethoxyvinyl)-1-((2-(trimethylsilyl)ethoxy)methyl)-1H-imidazol-5-yl)pyridine was obtained as a yellow solid.

Step 5

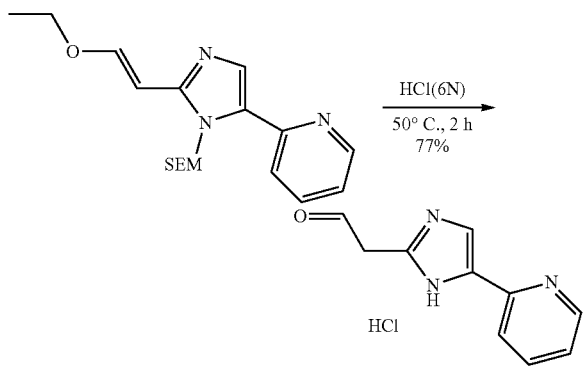

Into a 40-mL vial, was placed (E)-2-(2-(2-ethoxyvinyl)-1-((2-(trimethylsilyl)ethoxy)methyl)-1H-imidazol-5-yl)pyridine (800 mg, 2.32 mmol, 1.0 equiv), THF (10 mL), and HCl (6 N) (10 mL). The reaction solution was stirred for 2 h at 50° C. After being cooled to room temperature, the reaction solution was concentrated under reduced pressure. The residue was purified by Flash-Prep-HPLC with the following conditions (IntelFlash-1): Column, C18-120 g, mobile phase, $CH_3CN/H_2O$ (0.05% FA), Detector, 254 nm. 400 mg (77%) of 2-(5-(pyridin-2-yl)-1H-imidazol-2-yl)acetaldehyde hydrochloride was obtained as a light yellow solid.

Step 6

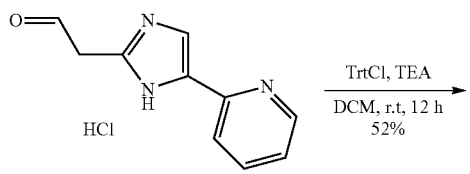

Into a 40-mL vial, was placed 2-(5-(pyridin-2-yl)-1H-imidazol-2-yl)acetaldehyde hydrochloride (400 mg, 1.79 mmol, 1.0 equiv), DCM (15 mL), TEA (362 mg, 3.58 mmol, 2.0 equiv), and Trt-Cl (548 mg, 1.97 mmol, 1.1 equiv). The reaction solution was stirred for 12 h at room temperature. The reaction was quenched with 10 mL of $H_2O$, the organic phase was separated out, dried over anhydrous $Na_2SO_4$, filtered, and the filtrate was concentrated under reduced pressure. 400 mg (52%) of 2-(5-(pyridin-2-yl)-1-trityl-1H-imidazol-2-yl)acetaldehyde was obtained as an off-white solid and used in the next step directly without further purification.

Step 7

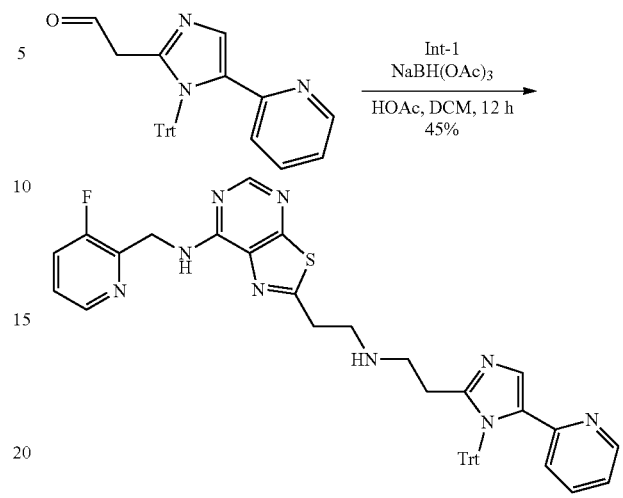

Into a 40-mL vial purged and maintained with an inert atmosphere of nitrogen, was placed 2-(2-aminoethyl)-N-[(3-fluoropyridin-2-yl)methyl]-[1,3]thiazolo[5,4-d]pyrimidin-7-amine (283 mg, 0.93 mmol, 1.0 equiv), DCM (20 mL), 2-(5-(pyridin-2-yl)-1-trityl-1H-imidazol-2-yl)acetaldehyde (400 mg, 0.93 mmol, 1.0 equiv), and HOAc (112 mg, 1.86 mmol, 2.0 equiv). After being stirred 0.5 h at room temperature, $NaBH(OAc)_3$ (591 mg, 2.79 mmol, 3.0 equiv) was added. The reaction solution was stirred for 12 h at room temperature. The reaction was then quenched by the addition of 10 mL of water. The pH value of the solution was adjusted to 8 with $Na_2CO_3$ (aq), extracted with DCM (30 mL), dried over anhydrous $Na_2SO_4$, filtered, and the filtrate was concentrated under reduced pressure. The residue was purified by flash column with dichloromethane/methanol (20:1). 300 mg (45%) of N-((3-fluoropyridin-2-yl)methyl)-2-(2-((2-(5-(pyridin-2-yl)-1-trityl-1H-imidazol-2-yl)ethyl)amino)ethyl)thiazolo[5,4-d]pyrimidin-7-amine was obtained as a yellow solid.

Step 8

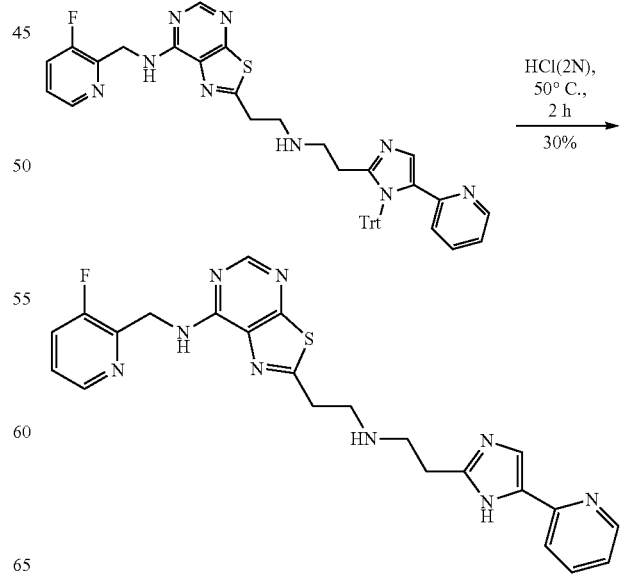

Into a 40-mL vial, was placed a mixture of N-((3-fluoropyridin-2-yl)methyl)-2-(2-((2-(5-(pyridin-2-yl)-1-trityl-1H-imidazol-2-yl)ethyl)amino)ethyl)thiazolo[5,4-d]pyrimidin-7-amine (300 mg, 0.42 mmol, 1.0 eq), HCl (2N) (10 mL), and THF (10 mL). The mixture was stirred for 2 h at 50° C. The mixture was then concentrated under reduced pressure to remove the solvent, the residue was dissolved in MeOH (5 mL), and subjected to reverse phase preparative (Prep-HPLC): Column, XBridge Shield RP18 OBD Column, 5 um, 19*150 mm; mobile phase, Water (10 mmol/L NH₄HCO₃+0.1% NH₃.H₂O) and ACN (16% Phase B up to 34% in 7 min) to provide the title compound as an off-white solid, 58.8 mg (30%). H NMR (300 MHz, DMSO-d₆) δ 8.46 (d, 1H, J=4.8 Hz), 8.33 (d, 2H, J=4.8 Hz), 8.30 (s, 1H), 7.73-7.67 (m, 3H), 7.51 (s, 1H), 7.41-7.35 (m, 1H), 7.16-7.11 (m, 1H), 4.87 (d, 2H, J=4.8 Hz), 3.27 (t, 2H, J=6.6 Hz), 3.08 (t, 2H, J=6.6 Hz), 3.01 (t, 2H, J=6.9 Hz), 2.86 (t, 2H, J=6.9 Hz). LCMS (ESI) m/z, [M+H]⁺: 476.2.

Example 1.72

Synthesis of N-[(3-fluoropyridin-2-yl)methyl]-2-[2-({2-[5-(pyridin-4-yl)-1H-imidazol-2-yl]ethyl}amino)ethyl]-[1,3]thiazolo[5,4-d]pyrimidin-7-amine (Compound 79)

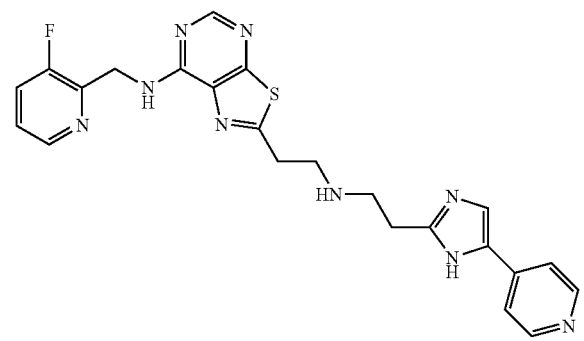 [SMILES: Fc1cccnc1CNc1ncnc2sc(CCNCCc3ncc(-c4ccncc4)[nH]3)nc12]

Scheme 51 depicts a synthetic route for preparing an exemplary compound.

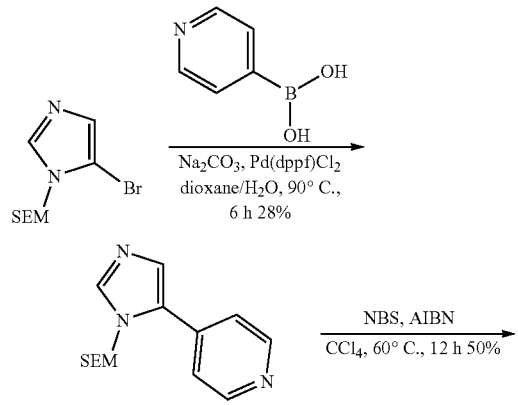

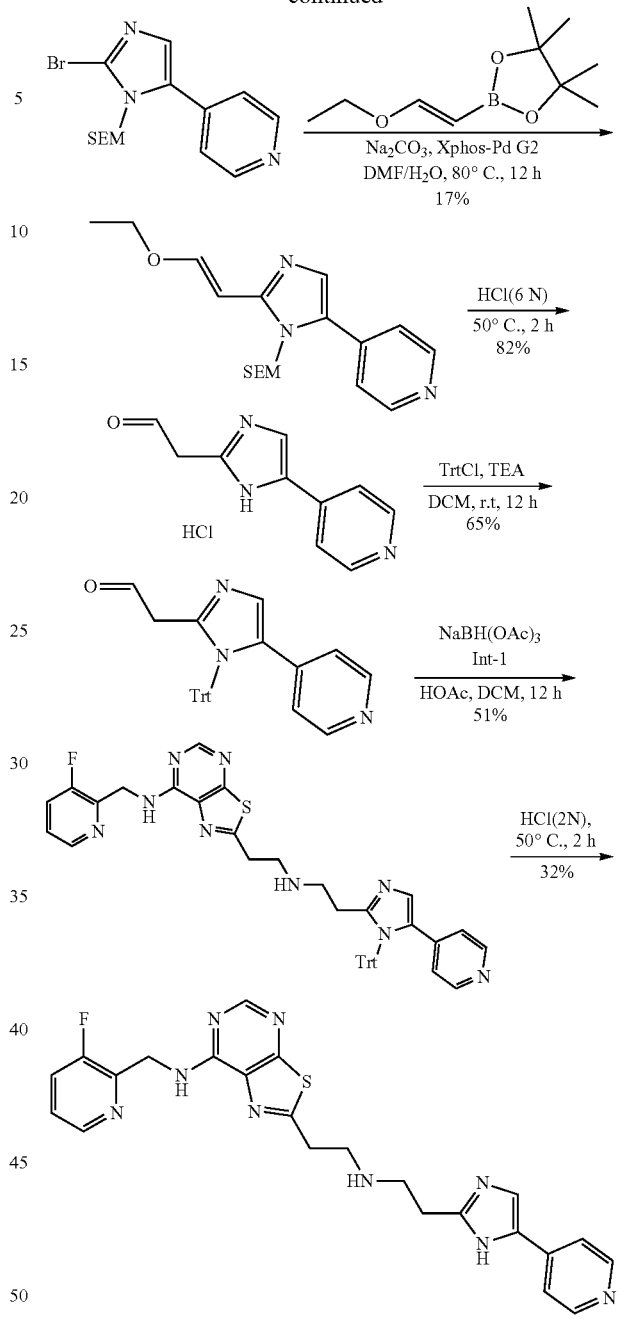

Step 1

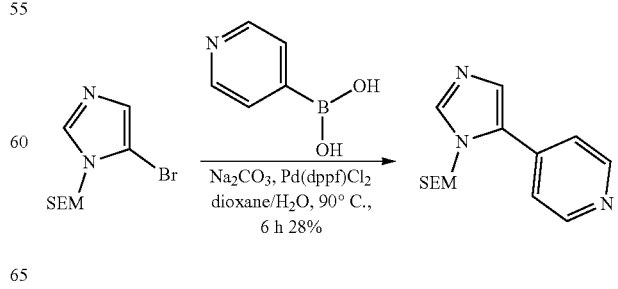

Into a 250-mL 3-necked round-bottom flask purged and maintained with an inert atmosphere of nitrogen, was placed 5-bromo-1-((2-(trimethylsilyl)ethoxy)methyl)-1H-imidazole (9.0 g, 32.61 mmol, 1.0 equiv), pyridin-4-ylboronic acid (5.22 g, 42.39 mmol, 1.3 equiv), dioxane/H$_2$O (8:1)(90 mL), Na$_2$CO$_3$ (6.91 g, 65.22 mmol, 2.0 equiv), and Pd(dppf)Cl$_2$ (1.19 g, 1.63 mmol, 0.05 equiv). The mixture was stirred for 6 h at 90° C. The reaction mixture was cooled to room temperature. The reaction solution was concentrated under reduced pressure to remove the solvent and extracted with 2×100 mL of ethyl acetate. Following this, the organic phase was combined, dried over anhydrous sodium sulfate, filtered, and the filtrate was concentrated. The residue was then purified by silica gel column with dichloromethane/methanol (20:1). 2.8 g (28%) of 4-(1-((2-(trimethyl silyl)ethoxy)methyl)-1H-imidazol-5-yl)pyridine was obtained as a brown solid.

Step 2

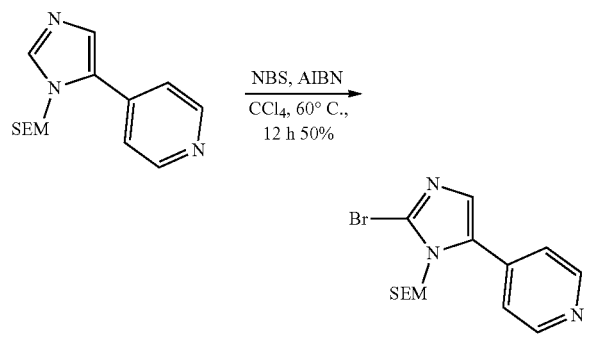

Into a 250-mL round-bottom flask, was placed 4-(1-((2-(trimethylsilyl)ethoxy)methyl)-1H-imidazol-5-yl)pyridine (2.80 g, 10.19 mmol, 1.0 equiv), CCl$_4$ (50 mL), NBS (2.18 g, 12.22 mmol, 1.2 equiv), and AIBN (167 mg, 1.02 mmol, 0.1 equiv). The mixture was stirred for 12 h at 60° C. The reaction mixture was cooled and purified by silica gel column with ethyl acetate/petroleum ether (1:3). 1.8 g (50%) of 4-(2-bromo-1-((2-(trimethylsilyl)ethoxy)methyl)-1H-imidazol-5-yl)pyridine was obtained as a yellow solid.

Step 3

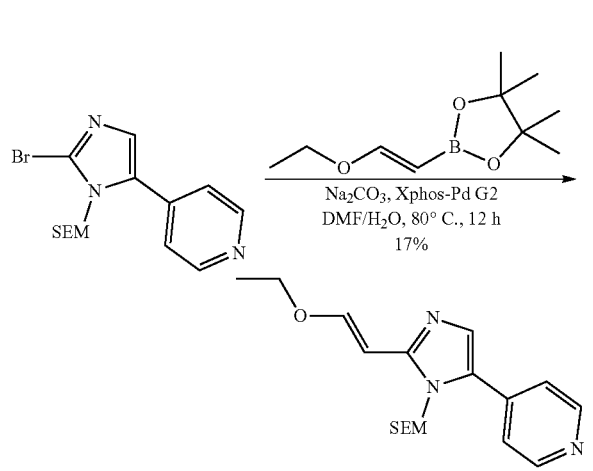

Into a 50-mL round-bottom flask purged and maintained with an inert atmosphere of nitrogen, was placed 4-(2-bromo-1-((2-(trimethylsilyl)ethoxy)methyl)-1H-imidazol-5-yl)pyridine (3.6 g, 10.20 mmol, 1.0 equiv), DMF/H$_2$O (8:1)(60 mL), 2-[(E)-2-ethoxyethenyl]-4,4,5,5-tetramethyl-1,3,2-dioxaborolane (2.42 g, 12.24 mmol, 1.2 equiv), Na$_2$CO$_3$ (2.16 g, 20.40 mmol, 2.0 equiv), and Xphos-Pd G2 (400 mg, 0.51 mmol, 0.05 equiv). The mixture was stirred for 12 h at 80° C. The reaction mixture was cooled to room temperature and purified by silica gel column with (PE/EA=3:1). 600 mg (17%) of (E)-4-(2-(2-ethoxyvinyl)-1-((2-(trimethylsilyl)ethoxy)methyl)-1H-imidazol-5-yl)pyridine was obtained as a yellow solid.

Step 4

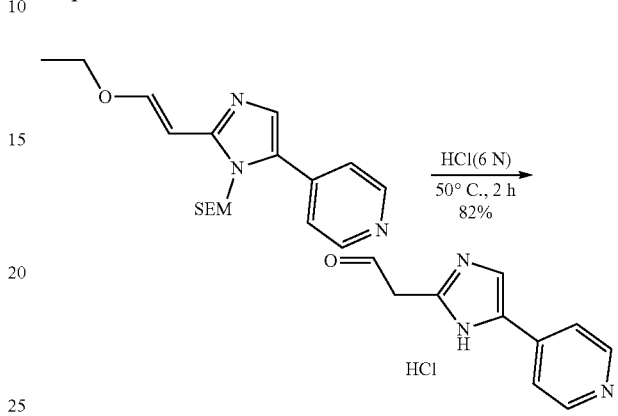

Into a 20-mL vial, was placed (E)-4-(2-(2-ethoxyvinyl)-1-((2-(trimethylsilyl)ethoxy)methyl)-1H-imidazol-5-yl)pyridine (600 mg, 1.74 mmol, 1.0 equiv), THF (10 mL), and HCl (6 N) (10 mL). The reaction solution was stirred for 2 h at 50° C. After being cooled to room temperature, the reaction solution was concentrated under reduced pressure. The residue was purified by Flash-Prep-HPLC with the following conditions (IntelFlash-1): Column, C18-120 g, mobile phase, CH$_3$CN/H$_2$O (0.05% FA), Detector, 254 nm. 320 mg (82%) of 2-(5-(pyridin-4-yl)-1H-imidazol-2-yl)acetaldehyde hydrochloride was obtained as a light yellow solid.

Step 5

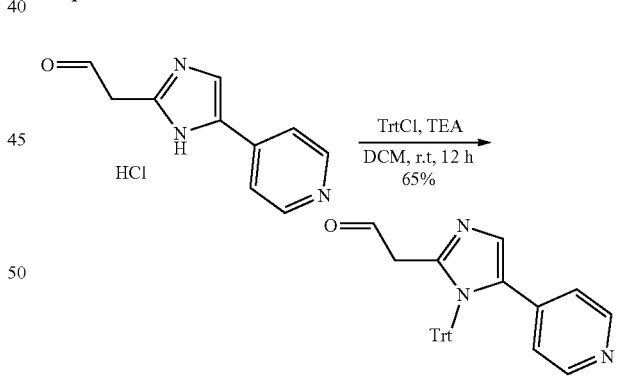

Into a 40-mL vial, was placed 2-(5-(pyridin-4-yl)-1H-imidazol-2-yl)acetaldehyde hydrochloride (320 mg, 1.44 mmol, 1.0 equiv), DCM (15 mL), TEA (291 mg, 2.88 mmol, 2.0 equiv), and Trt-Cl (440 mg, 1.58 mmol, 1.1 equiv). The reaction solution was stirred for 12 h at room temperature. The reaction was quenched with 10 mL of H$_2$O, the organic phase was separated out, dried over anhydrous Na$_2$SO$_4$, filtered, and the filtrate was concentrated under reduced pressure. 400 mg (65%) of 2-(5-(pyridin-4-yl)-1-trityl-1H-imidazol-2-yl)acetaldehyde was obtained as an off-white solid and used in the next step directly without further purification.

Step 6

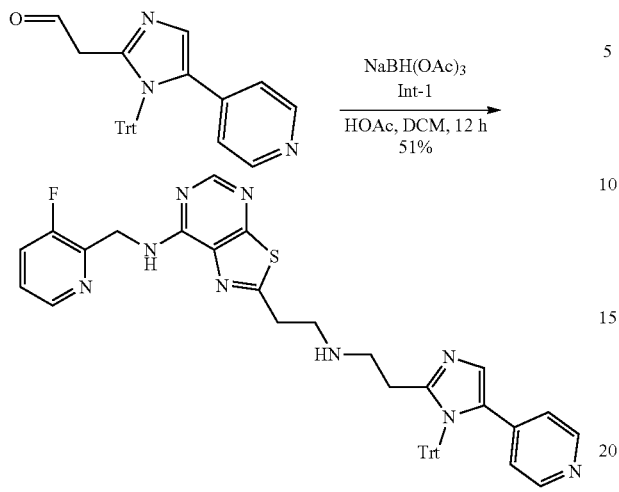

Into a 40-mL vial purged and maintained with an inert atmosphere of nitrogen, was placed 2-(2-aminoethyl)-N-[(3-fluoropyridin-2-yl)methyl]-[1,3]thiazolo[5,4-d]pyrimidin-7-amine (283 mg, 0.93 mmol, 1.0 equiv), DCM (20 mL), 2-(5-(pyridin-4-yl)-1-trityl-1H-imidazol-2-yl)acetaldehyde (400 mg, 0.93 mmol, 1.0 equiv), and HOAc (112 mg, 1.86 mmol, 2.0 equiv). After being stirred for 0.5 h at room temperature, NaBH(OAc)$_3$ (591 mg, 2.79 mmol, 3.0 equiv) was added. The reaction solution was then stirred for 12 h at room temperature. The reaction was then quenched by the addition of 10 mL of water. The pH value of the solution was adjusted to 8 with Na$_2$CO$_3$(aq), extracted with DCM (30 mL), dried over anhydrous Na$_2$SO$_4$, filtered, and the filtrate was concentrated under reduced pressure. The residue was purified by silica gel column with dichloromethane/methanol (20:1). 340 mg (51%) of N-((3-fluoropyridin-2-yl)methyl)-2-(2-((2-(5-(pyridin-4-yl)-1-trityl-1H-imidazol-2-yl)ethyl)amino)ethyl)thiazolo[5,4-d]pyrimidin-7-amine was obtained as a yellow solid.

Step 7

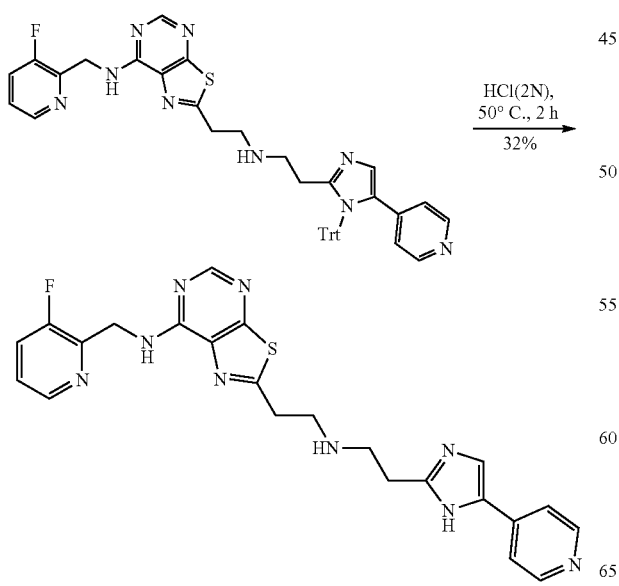

Into a 40-mL vial, was placed a mixture of N-((3-fluoropyridin-2-yl)methyl)-2-(2-((2-(5-(pyridin-4-yl)-1-trityl-1H-imidazol-2-yl)ethyl)amino)ethyl)thiazolo[5,4-d]pyrimidin-7-amine (340 mg, 0.47 mmol, 1.0 eq), HCl (2N)(10 mL), and THF (10 mL). The mixture was stirred for 2 h at 50° C. The mixture was then concentrated under reduced pressure to remove the solvent, the residue was dissolved in MeOH (5 mL), and then subjected to reverse phase preparative (Prep-HPLC): Column, XBridge Shield RP18 OBD Column, 5 um, 19*150 mm; mobile phase, Water (10 mmol/L NH$_4$HCO$_3$+0.1% NH$_3$.H$_2$O) and ACN (16% Phase B up to 34% in 7 min) to provide the title compound as a yellow solid, 71.2 mg (32%).

Example 1.73

Synthesis of 2-[2-({2-[5-(2-fluorophenyl)-1H-imidazol-2-yl]ethyl}amino)ethyl]-N-[(3-fluoropyridin-2-yl)methyl]-[1,3]thiazolo[5,4-d]pyrimidin-7-amine (Compound 66)

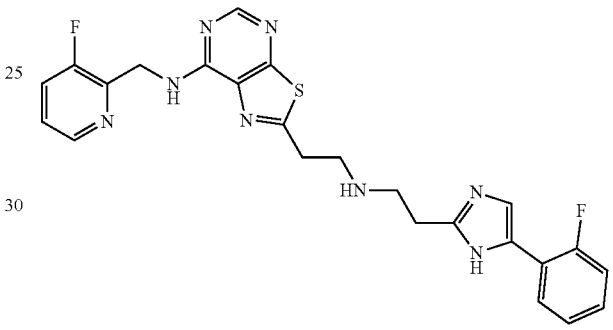

Compound 66 was synthesized in a similar fashion to that of Compound 79, replacing pyridin-4-ylboronic acid with 2-fluorophenyl)boronic acid. $^1$H NMR (300 MHz, DMSO-d$_6$) δ 8.39-8.33 (m, 2H), 8.32 (s, 1H), 7.96-7.90 (m, 1H), 7.74-7.67 (m, 1H), 7.41-7.34 (m, 2H), 7.22-7.11 (m, 3H), 4.87 (d, 2H, J=5.1 Hz), 3.41 (t, 2H, J=6.0 Hz), 3.28 (t, 2H, J=6.0 Hz), 3.20 (t, 2H, J=7.2 Hz), 2.98 (t, 2H, J=7.2 Hz). LCMS (ESI) m/z, [M+H]$^+$: 493.2.

Example 1.74

Synthesis of 2-[2-({2-[5-(3-fluorophenyl)-1H-imidazol-2-yl]ethyl}amino)ethyl]-N-[(3-fluoropyridin-2-yl)methyl]-[1,3]thiazolo[5,4-d]pyrimidin-7-amine (Compound 67)

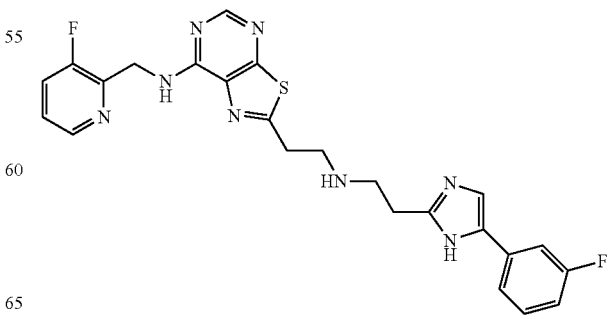

Compound 67 was synthesized in a similar fashion to that of Compound 79, replacing pyridin-4-ylboronic acid with 3-fluorophenyl)boronic acid. ¹H NMR (300 MHz, DMSO-d₆) δ 8.39-8.33 (m, 2H), 8.32 (s, 1H), 7.96-7.90 (m, 1H), 7.74-7.67 (m, 1H), 7.41-7.34 (m, 2H), 7.22-7.11 (m, 3H), 4.87 (d, 2H, J=5.1 Hz), 3.41 (t, 2H, J=6.0 Hz), 3.28 (t, 2H, J=6.0 Hz), 3.20 (t, 2H, J=7.2 Hz), 2.98 (t, 2H, J=7.2 Hz). LCMS (ESI) m/z, [M+H]⁺: 493.2.

Example 1.75

Synthesis of 2-[2-({2-[5-(4-fluorophenyl)-1H-imidazol-2-yl]ethyl}amino)ethyl]-N-[(3-fluoropyridin-2-yl)methyl]-[1,3]thiazolo[5,4-d]pyrimidin-7-amine (Compound 68)

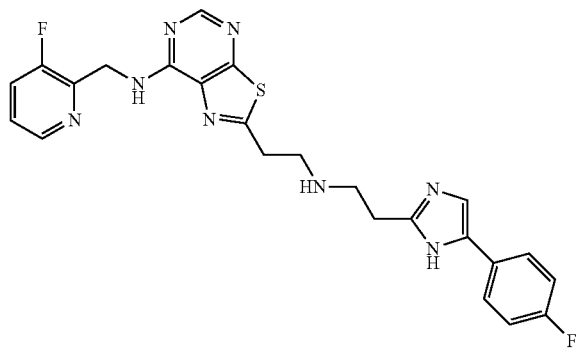 [SMILES: Fc1ccc(-c2cnc(CCNCCc3nc4c(NCc5ncccc5F)ncnc4s3)[nH]2)cc1]

Compound 68 was synthesized in a similar fashion to that of Compound 79, replacing pyridin-4-ylboronic acid with 4-fluorophenyl)boronic acid. ¹H NMR (300 MHz, DMSO-d₆) δ 11.75 (br, 1H), 8.35-8.29 (m, 3H), 7.74-7.67 (m, 3H), 7.42-7.36 (m, 2H), 7.15-7.09 (m, 2H), 4.88 (d, 2H, J=4.5 Hz), 3.23 (t, 2H, J=6.6 Hz), 3.02 (t, 2H, J=6.6 Hz), 2.94 (t, 2H, J=6.9 Hz), 2.80 (t, 2H, J=6.9 Hz). LCMS (ESI) m/z, [M+H]⁺: 493.2.

Example 1.76

Synthesis of 2-({6-[(1H-1,3-benzodiazol-2-yl)methyl]piperidin-2-yl}methyl)-N-[(3-fluoropyridin-2-yl)methyl]-[1,3]thiazolo[5,4-d]pyrimidin-7-amine (Compound 71)

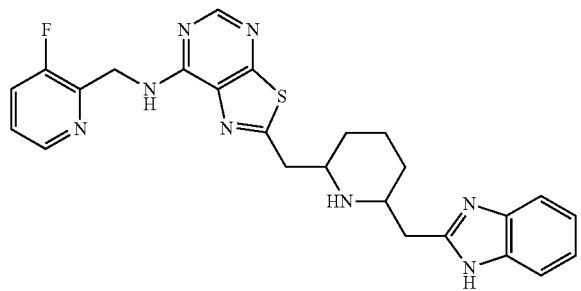 [SMILES: Fc1cccnc1CNc1ncnc2sc(CC3CCCC(Cc4nc5ccccc5[nH]4)N3)nc12]

Scheme 52 depicts a synthetic route for preparing an exemplary compound.

Scheme 52

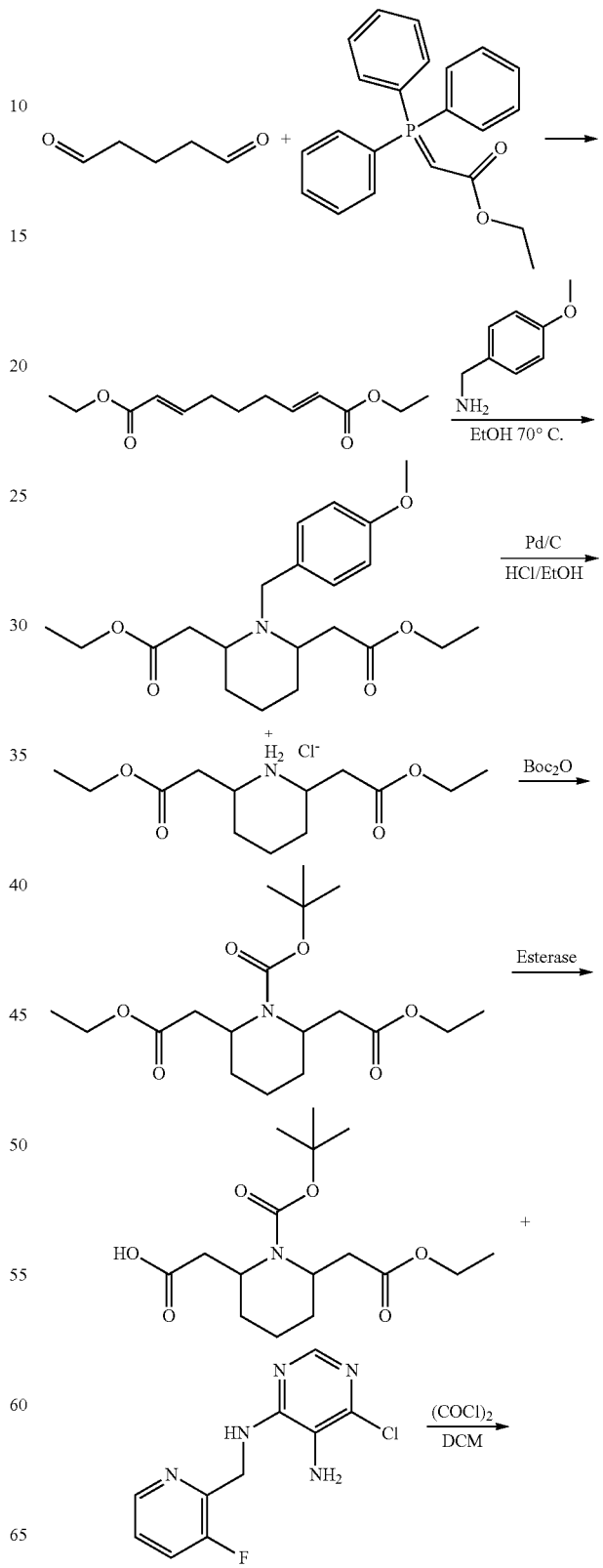

331
-continued

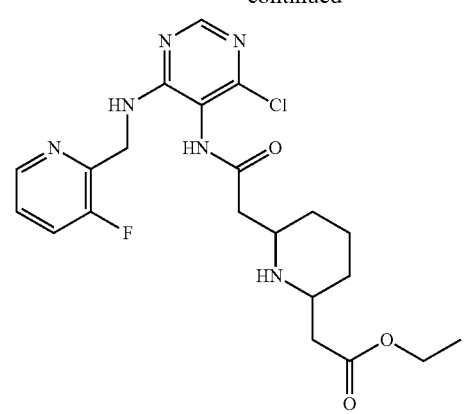

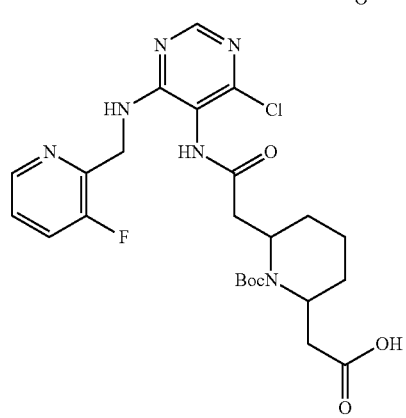

332
-continued

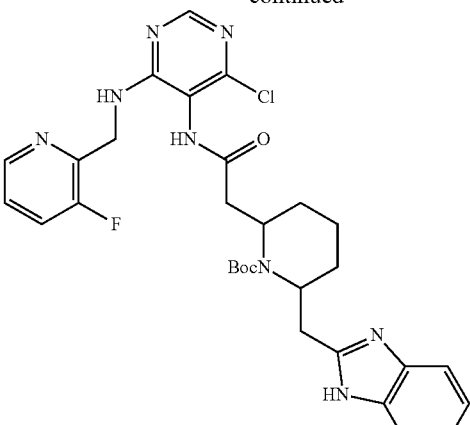

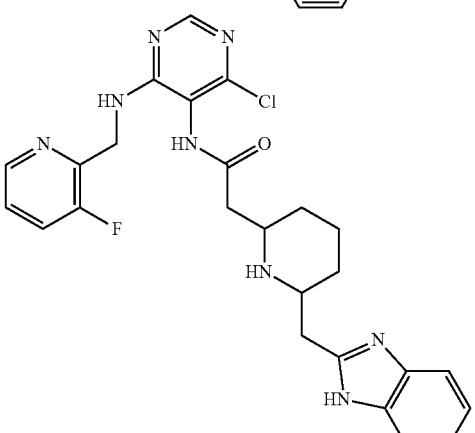

Step 1

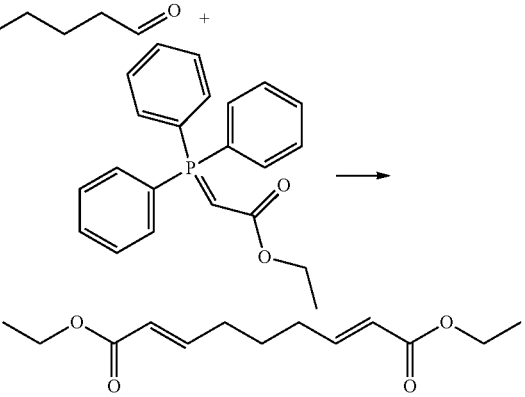

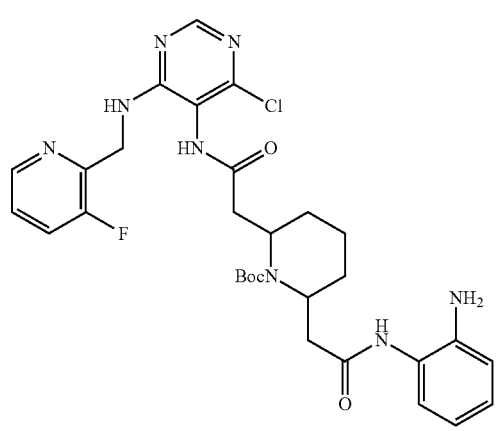

Pentanedial (3.00 mL; 8.25 mmol; 1.00 eq., 3 ml of a 50% water solution) was combined with DCM (10 ml). Sodium chloride (1.1 g) was added to saturate the water and extract the aldehyde. The organic phase was separated and dried over magnesium sulfate. The solution was filtered and rinsed with additional DCM (10 ml), to which was added ethyl (triphenylphosphoranylidene)acetate (6.04 g; 17.32 mmol; 2.10 eq.) in portions. After 1.5 h, the reaction was evaporated to a white solid and taken up in methyl tert-butyl ether (25 ml). Insoluble solids were filtered off and rinsed with more methyl tert-butyl ether. After evaporation, the residue was purified by silica gel chromatography (ethyl acetate/ hexanes gradient) to give 1,9-diethyl (2E,7E)-nona-2,7-dienedioate (1.09 g, 55%) as a colorless liquid. $^1$H NMR (400 MHz, Chloroform-d) δ 6.93 (dt, J=15.7, 6.9 Hz, 2H), 5.83 (dt, J=15.6, 1.5 Hz, 2H), 4.23-4.16 (m, 4H), 2.27-2.20 (m, 4H), 1.69-1.60 (m, 2H), 1.31-1.27 (m, 6H). MS (ES+): (M+H)$^+$=241.0.

Step 2

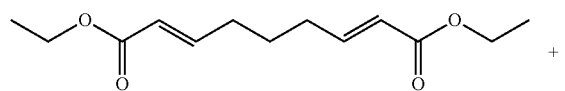

+

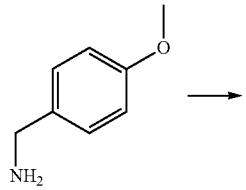

→

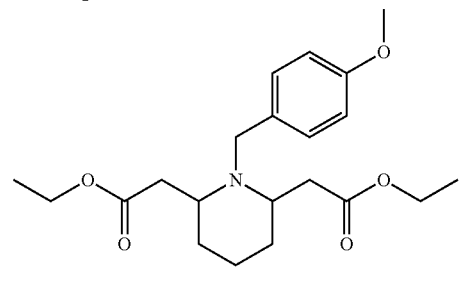

1,9-Diethyl (2E,7E)-nona-2,7-dienedioate (960.00 mg; 4.00 mmol; 1.00 eq.) was dissolved in ethanol (4 ml). 4-methoxyphenyl)methanamine (1.57 mL; 12 mmol; 3.00 eq.) was added and the reaction was stirred in a heat block at 70° C. for 6 h, and then at 60° C. for 15 h. The reaction was then evaporated and purified by silica gel chromatography (ethyl acetate/hexanes gradient) to give ethyl 2-[6-(2-ethoxy-2-oxoethyl)-1-[(4-methoxyphenyl)methyl]piperidin-2-yl]acetate (0.79 g, 52%) as a colorless oil. $^1$H NMR (400 MHz, Chloroform-d) δ 7.26-7.17 (m, 2H), 6.85-6.78 (m, 2H), 4.12-4.02 (m, 4H), 3.79 (s, 3H), 3.69-3.61 (m, 2H), 3.32-3.24 (m, 1H), 3.23-3.14 (m, 1H), 2.63-2.49 (m, 2H), 2.38 (dd, J=14.5, 8.1 Hz, 1H), 2.18 (dd, J=14.8, 9.7 Hz, 1H), 1.71-1.59 (m, 4H), 1.47-1.34 (m, 2H), 1.20 (t, J=7.2 Hz, 6H). MS (ES+): (M+H)$^+$=378.0.

Step 3

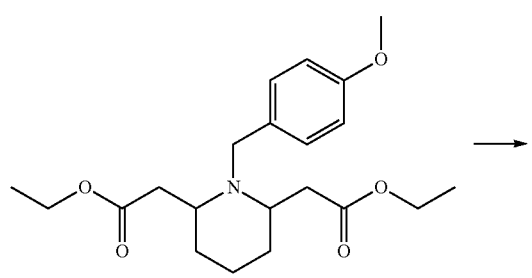

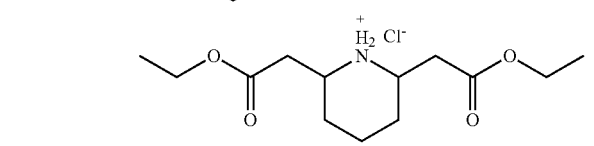

Ethyl 2-[6-(2-ethoxy-2-oxoethyl)-1-[(4-methoxyphenyl)methyl]piperidin-2-yl]acetate (825 mg; 2.19 mmol; 1.00 eq.) was dissolved in ethanol (20 ml). Hydrochloric acid (0.73 mL; 6.00 mol/L; 4.37 mmol; 2.00 eq.) and palladium on carbon (698 mg; 0.66 mmol; 0.30 eq., suspended in ethanol (10 ml)) were added, and the vessel was charged with a balloon containing H$_2$ gas. After 4 h, the reaction was filtered through Celite, rinsed through with ethanol and methanol, and evaporated to give 2,6-bis(2-ethoxy-2-oxoethyl)piperidin-1-ium chloride as a solid. MS (ES+): (M+H)$^+$=258.

Step 4

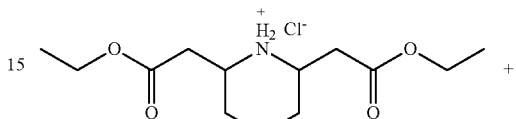

+

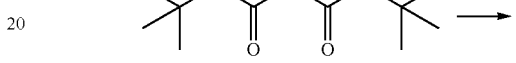

→

2,6-Bis(2-ethoxy-2-oxoethyl)piperidin-1-ium chloride (0.65 g; 2.20 mmol; 1.00 eq.) was dissolved in a mixture of THF (11 ml) and saturated sodium bicarbonate soln. (11 ml). Di-tert-butyl dicarbonate (0.96 g; 4.39 mmol; 2.00 eq.) in THF (3 ml) was added and the mixture was stirred for 18 h. More di-tert-butyl dicarbonate (0.2 g) in THF (1 ml) was added three times over 20 h. After 6 h more, the reaction was partitioned into water (50 ml) and ethyl acetate (100 ml). The phases were separated, the aqueous phase was extracted with ethyl acetate (100 ml), the combined organic phases were washed with sodium chloride solution (50 ml) and dried over sodium sulfate. After evaporation, the residue was purified by silica gel chromatography (ethyl acetate/hexanes gradient) to give tert-butyl 2,6-bis(2-ethoxy-2-oxoethyl)piperidine-1-carboxylate (0.62 g, 79%) as a viscous oil. $^1$H NMR (400 MHz, Chloroform-d) δ 4.31-4.22 (m, 2H), 4.13 (q, J=7.2 Hz, 4H), 2.74 (dd, J=15.0, 4.5 Hz, 2H), 2.50 (dd, J=15.0, 9.9 Hz, 2H), 1.86-1.66 (m, 6H), 1.46 (s, 9H), 1.29-1.22 (m, 6H).

Step 5

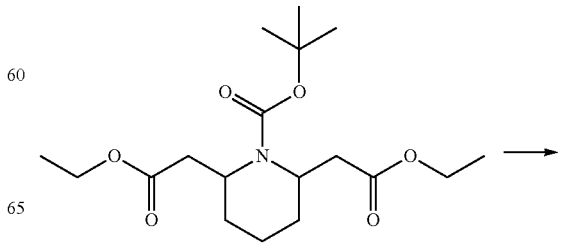

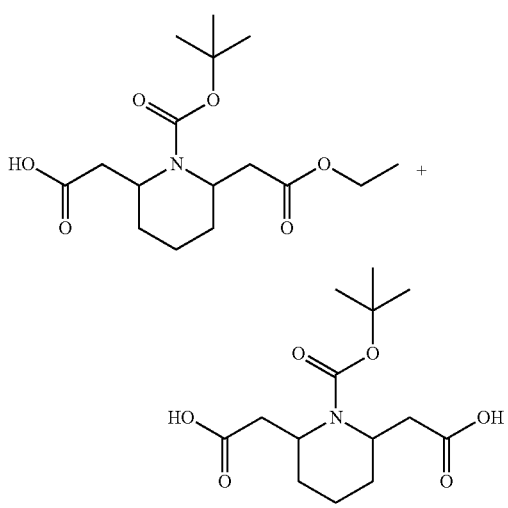

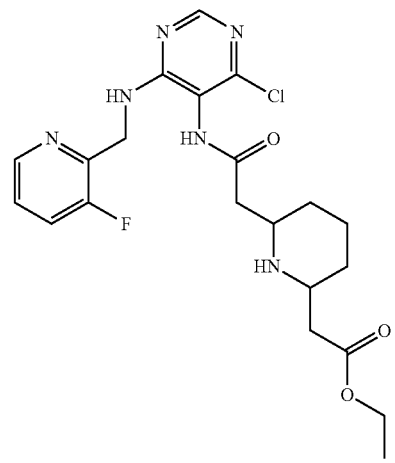

Tert-butyl 2,6-bis(2-ethoxy-2-oxoethyl)piperidine-1-carboxylate (499 mg; 1.40 mmol; 1.00 eq.) was mixed with an aqueous solution of potassium phosphate (3 mM) and sodium chloride (10 mM), and adjusted to pH >7 with 1 M HCl (70 ml). The mixture was stirred vigorously and Esterase from porcine liver (108.5 mg, 18 units/mg) was added and stirred in a heat block at 30° C. After 40 h, more esterase (60 mg) was added, and the pH was adjusted by addition of potassium phosphate as needed. After another 24 h, the mixture of di-acid, mono-acid and starting material was acidified to pH 2 with 1 M HCl and extracted with ethyl acetate (200 ml). The residue from evaporation was purified by reverse phase chromatography (Waters XSelect CSH C18 column, 0-95% acetonitrile/0.1% aqueous formic acid gradient) to give 2-{1-[(tert-butoxy)carbonyl]-6-(2-ethoxy-2-oxoethyl)piperidin-2-yl}acetic acid (113 mg, 24%). MS (ES+): (M+Na)$^+$=352.2.

Step 6

2-{1-[(Tert-butoxy)carbonyl]-6-(2-ethoxy-2-oxoethyl)piperidin-2-yl}acetic acid (119.00 mg; 0.36 mmol; 1.00 eq.) was dissolved in DCM (3.5 ml) and cooled in an ice bath. Oxalyl chloride (0.06 mL; 0.72 mmol; 2.00 eq.) was added slowly, followed by addition of 1 drop of DMF. The reaction was stirred at 25° C. for 2.5 h and then evaporated to dryness. 6-chloro-4-N-[(3-fluoropyridin-2-yl)methyl]pyrimidine-4,5-diamine (80.00 mg; 0.32 mmol; 1.00 eq.) was added to the above residue dissolved in N,N-dimethylacetamide (1 ml). After 16 h, the reaction was taken up in sodium bicarbonate solution (20 ml) and ethyl acetate (100 ml). The phases were separated, the aqueous phase was extracted with ethyl acetate (50 ml), and the combined organics phases were dried over sodium sulfate. After evaporation of solvent, the residue was purified by silica gel chromatography (methanol/dichloromethane gradient) to give ethyl 2-(6-{[(4-chloro-6-{[(3-fluoropyridin-2-yl)methyl]amino}pyrimidin-5-yl)carbamoyl]methyl}piperidin-2-yl)acetate (50 mg, 34%). MS (ES+): (M+H)$^+$=465.1.

Step 7

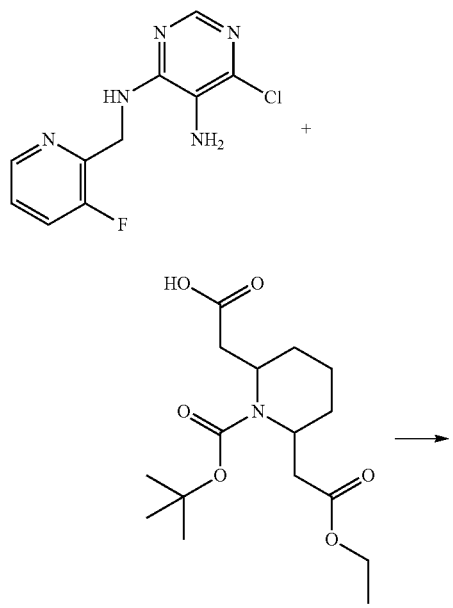

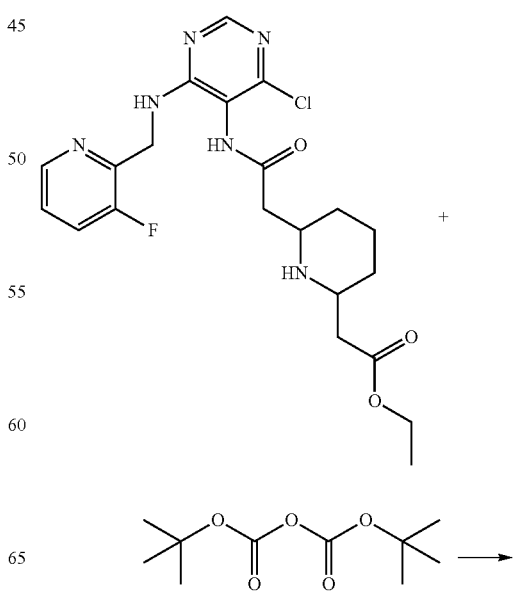

337

-continued

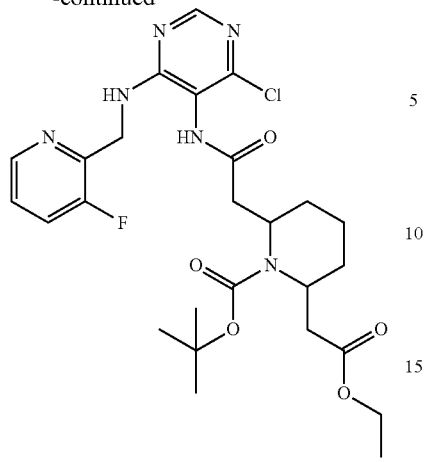

Ethyl 2-(6-{[(4-chloro-6-{[(3-fluoropyridin-2-yl)methyl] amino}pyrimidin-5-yl)carbamoyl]methyl}piperidin-2-yl) acetate (50.00 mg; 0.11 mmol; 1.00 eq.) was dissolved in DCM (1 ml). N,N-diisopropylethylamine (0.07 mL; 0.43 mmol; 4.00 eq.) and then di-tert-butyl dicarbonate (35.21 mg; 0.16 mmol; 1.50 eq.) in 1 DCM (1 ml) were added and the reaction was stirred for 15 h. More N,N-diisopropylethylamine (0.1 mL) and di-tert-butyl dicarbonate (50 mg in 1.5 ml of DCM) were added in portions over 8 h while the reaction was stirred at 40° C. After 22 h, sodium bicarbonate solution (10 ml) and ethyl acetate (50 ml) were added, and the phases were separated. The aqueous phase was extracted with ethyl acetate (20 ml) and the combined organic phases were dried over sodium sulfate. After evaporation of solvent, the residue was purified by silica gel chromatography (methanol/dichloromethane gradient) to give tert-butyl 2-{[(4-chloro-6-{[(3-fluoropyridin-2-yl)methyl]amino}pyrimidin-5-yl)carbamoyl]methyl}-6-(2-ethoxy-2-oxoethyl)piperidine-1-carboxylate (25 mg, 41%). $^1$H NMR (400 MHz, Chloroform-d) δ 8.53 (s, 1H), 8.38 (d, J=4.8 Hz, 1H), 8.29 (s, 1H), 7.54-7.46 (m, 1H), 7.37-7.28 (m, 1H), 7.10 (s, 1H), 4.97-4.84 (m, 2H), 4.49-4.40 (m, 1H), 4.26-4.17 (m, 1H), 4.12 (q, J=7.2 Hz, 2H), 2.99 (dd, J=14.0, 6.5 Hz, 1H), 2.86 (dd, J=15.5, 5.9 Hz, 1H), 2.66-2.50 (m, 2H), 1.90-1.70 (m, 6H), 1.43 (s, 9H), 1.24 (t, J=7.1 Hz, 3H). MS (ES+): (M+H)$^+$=565.2.

Step 8

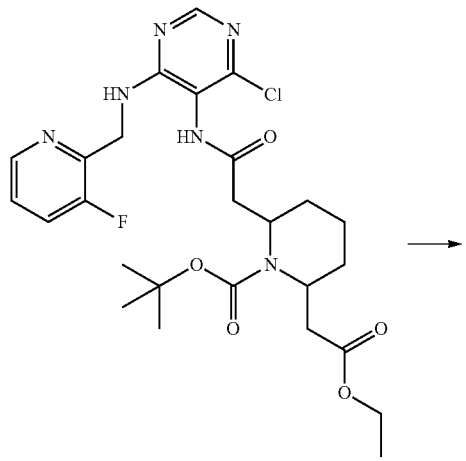

338

-continued

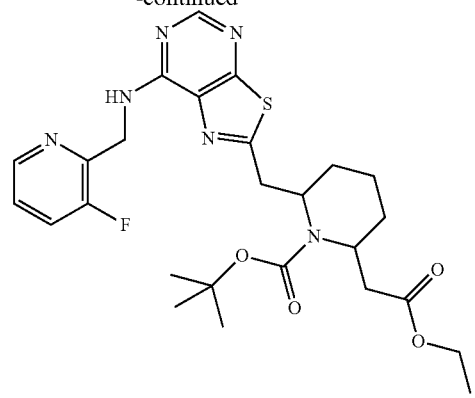

Tert-butyl 2-{[(4-chloro-6-{[(3-fluoropyridin-2-yl)methyl]amino}pyrimidin-5-yl)carbamoyl]methyl}-6-(2-ethoxy-2-oxoethyl)piperidine-1-carboxylate (25.00 mg; 0.04 mmol; 1.00 eq.) was dissolved in 1,4-dioxane (1 ml). 2,4-Bis(4-methoxyphenyl)-1,3,2,4-dithiadiphosphetane 2,4-disulfide (21 mg; 0.05 mmol; 1.15 eq.) (Lawesson reagent) was added and the reaction was stirred in a heat block at 95° C. for 2 h. The reaction was cooled and more Lawesson reagent (7 mg) was added and heating continued for 1 h more. The solvent was evaporated, and the residue was purified by silica gel chromatography (methanol/dichloromethane gradient) to give tert-butyl 2-(2-ethoxy-2-oxoethyl)-6-[(7-{[(3-fluoropyridin-2-yl)methyl]amino}-[1,3]thiazolo[5,4-d]pyrimidin-2-yl)methyl]piperidine-1-carboxylate (16 mg, 68%). MS (ES+): (M+H)$^+$=545.2.

Step 9

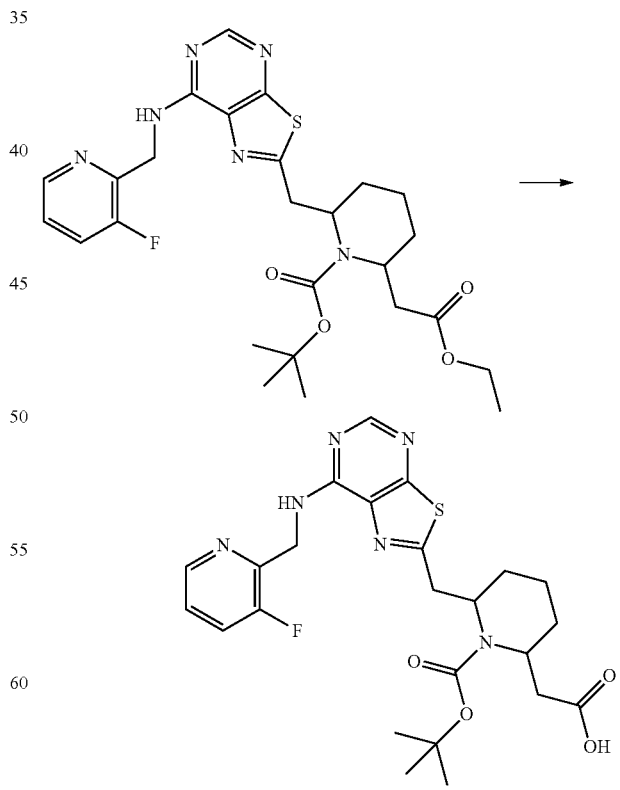

Tert-butyl 2-(2-ethoxy-2-oxoethyl)-6-[(7-{[(3-fluoropyridin-2-yl)methyl]amino}-[1,3]thiazolo[5,4-d]pyrimidin-2- yl)methyl]piperidine-1-carboxylate (16.40 mg; 0.03 mmol; 1.00 eq.) was dissolved in THF (1 ml) and methanol (0.3 ml). Lithium hydroxide (anhydrous) (3.6 mg; 0.15 mmol; 5.00 eq.) dissolved in water (0.5 ml) was added dropwise. After 2.5 h, the reaction was acidified carefully with 6 M HCl to pH 3 and evaporated to dryness. The residue was co-evaporated from toluene two times and dried under high vacuum. MS (ES+): (M+H)$^+$=517.

Step 10

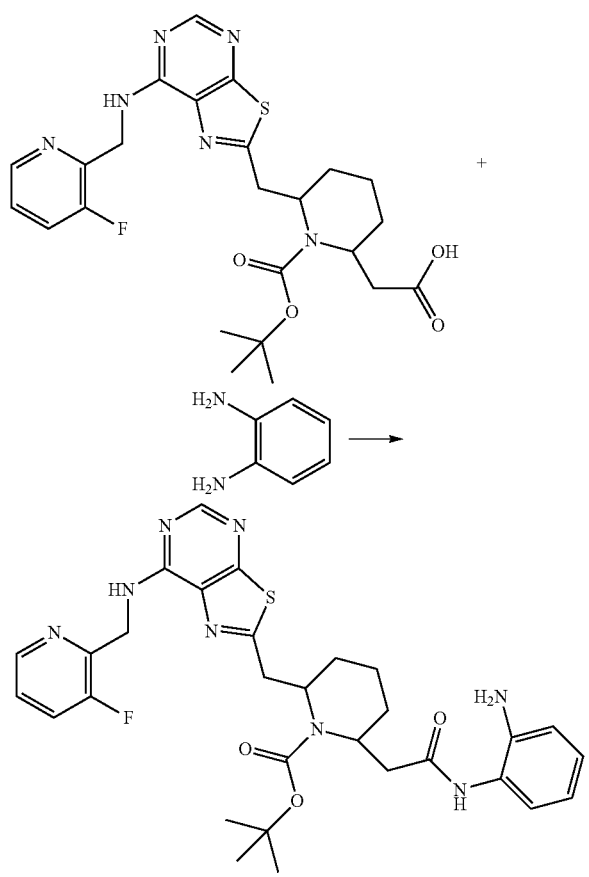

2-{1-[(Tert-butoxy)carbonyl]-6-[(7-{[(3-fluoropyridin-2-yl)methyl]amino}-[1,3]thiazolo[5,4-d]pyrimidin-2-yl)methyl]piperidin-2-yl}acetic acid (16.00 mg; 0.03 mmol; 1.00 eq.) was dissolved in N,N-dimethylformamide (1 ml). 1,2-Benzenediamine (4.5 mg; 0.04 mmol; 1.35 eq.), N,N-diisopropylethylamine (7.3 µL; 0.04 mmol; 1.35 eq.) and 1-[bis(dimethylamino)methylene]-1H-1,2,3-triazolo[4,5-b]pyridinium 3-oxid hexafluorophosphate (HATU, 15.90 mg; 0.04 mmol; 1.35 eq.) were added and the reaction was stirred for 5 h. The reaction was then taken up in ethyl acetate (50 ml) and sodium bicarbonate solution (10 ml). The phases were separated, and the aqueous phase was extracted with ethyl acetate (20 ml). The combined organic phases were washed w/sodium chloride solution (10 ml) and dried over sodium sulfate. After evaporation of solvent, the residue was purified by silica gel chromatography (methanol/dichloromethane gradient) to give tert-butyl 2-{[(2-aminophenyl)carbamoyl]methyl}-6-[(7-{[(3-fluoropyridin-2-yl)methyl]amino}-[1,3]thiazolo[5,4-d]pyrimidin-2-yl)methyl]piperidine-1-carboxylate. MS (ES+): (M+H)$^+$=607.3.

Step 11

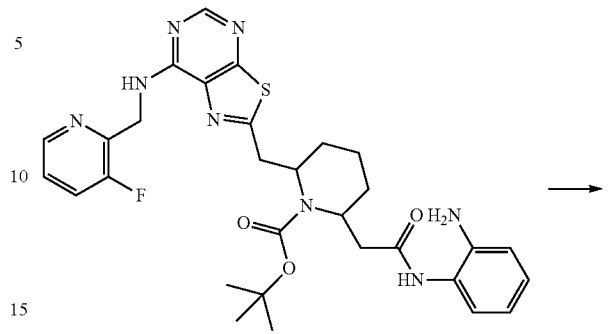

Tert-butyl 2-{[(2-aminophenyl)carbamoyl]methyl}-6-[(7-{[(3-fluoropyridin-2-yl)methyl]amino}-[1,3]thiazolo[5,4-d]pyrimidin-2-yl)methyl]piperidine-1-carboxylate (18.00 mg; 0.03 mmol; 1.00 eq.) was dissolved in acetic acid (1 ml) and stirred in a heat block at 80° C. After 1 h, solvent was evaporated, and the residue was taken up in ethyl acetate (50 ml) and sodium bicarbonate solution (10 ml). The phases were separated, the aqueous phase was extracted with ethyl acetate (20 ml), and the combined organic phases were dried over sodium sulfate. The solvent was evaporated, leaving a residue of tert-butyl 2-(1H-1,3-benzodiazol-2-ylmethyl)-6-[(7-{[(3-fluoropyridin-2-yl)methyl]amino}-[1,3]thiazolo[5,4-d]pyrimidin-2-yl)methyl]piperidine-1-carboxylate. MS (ES+): (M+H)$^+$=589.3.

Step 12

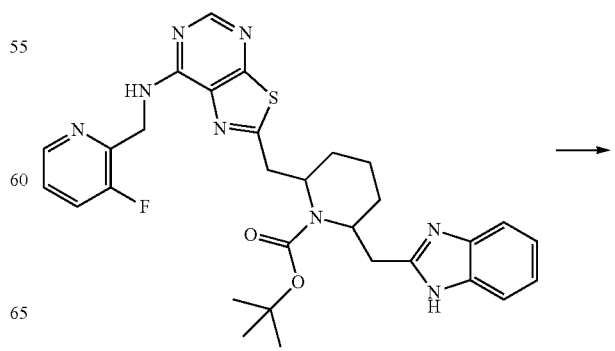

-continued

Tert-butyl 2-(1H-1,3-benzodiazol-2-ylmethyl)-6-[(7-{[(3-fluoropyridin-2-yl)methyl]amino}-[1,3]thiazolo[5,4-d]pyrimidin-2-yl)methyl]piperidine-1-carboxylate (18.00 mg; 0.03 mmol; 1.00 eq.) was dissolved in dichloromethane (1 ml). Trifluoroacetic acid (0.5 ml) was added slowly. After 1 h, solvent was evaporated, the residue was co-evaporated from toluene and dried under high vacuum. The dried residue was purified by reverse phase chromatography (Waters XSelect CSH C18 column, 0-65% acetonitrile/0.1% aqueous formic acid gradient) to give 2-({6-[(1H-1,3-benzodiazol-2-yl)methyl]piperidin-2-yl}methyl)-N-[(3-fluoropyridin-2-yl)methyl]-[1,3]thiazolo[5,4-d]pyrimidin-7-amine (formate salt, 7.5 mg, 46%) as a white solid. $^1$H NMR (400 MHz, DMSO-d$_6$) δ 8.32 (d, J=4.6 Hz, 1H), 8.29 (s, 1H), 8.27-8.14 (m, 2H), 7.74-7.65 (m, 1H), 7.43-7.34 (m, 1H), 7.30 (dd, J=6.0, 3.2 Hz, 2H), 7.03 (dd, J=6.0, 3.2 Hz, 2H), 4.85 (d, J=5.6 Hz, 2H), 3.50-3.45 (m, 2H), 3.33-3.16 (m, 2H), 2.94 (ddd, J=44.6, 14.6, 7.0 Hz, 2H), 1.74-1.55 (m, 4H), 1.43-1.28 (m, 2H). MS (ES$^+$): (M+H)$^+$=489.1.

Example 1.77

Synthesis of 2-[2-({2-[5-(5-chlorothiophen-2-yl)-1H-imidazol-2-yl]ethyl}amino)ethyl]-N-[(3-fluoropyridin-2-yl)methyl]-[1,3]thiazolo[5,4-d]pyrimidin-7-amine (Compound 72)

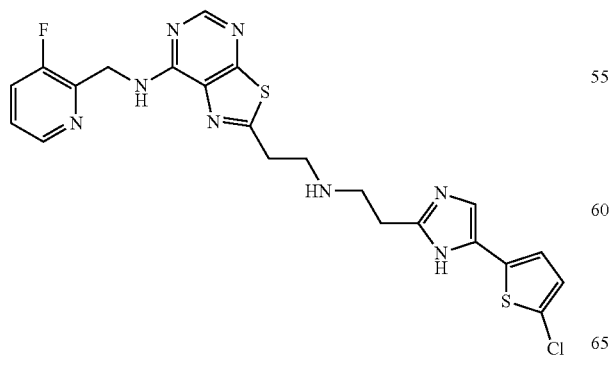

Scheme 53 depicts a synthetic route for preparing an exemplary compound.

Scheme 53

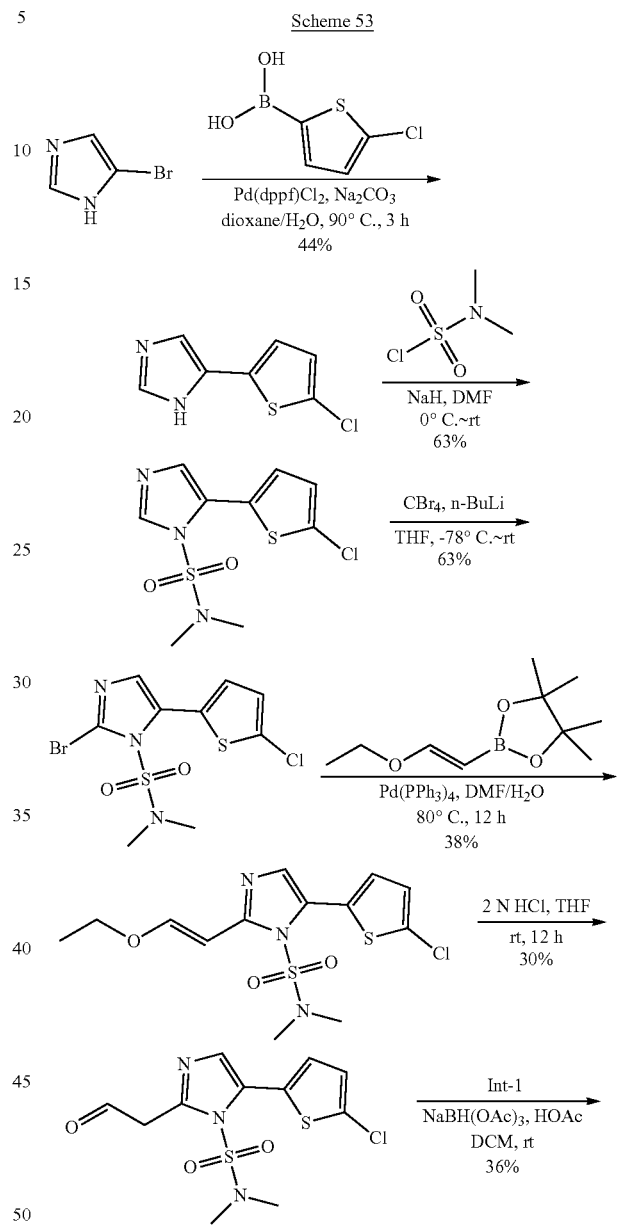

-continued

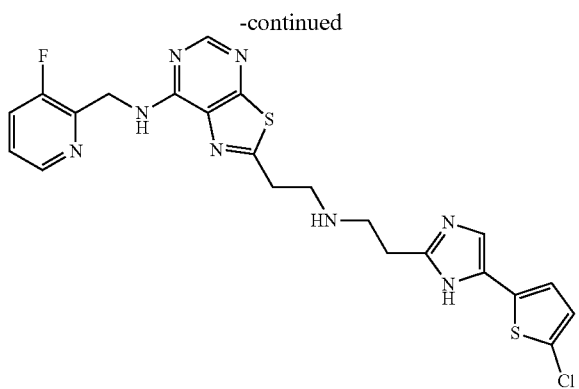

Step 1

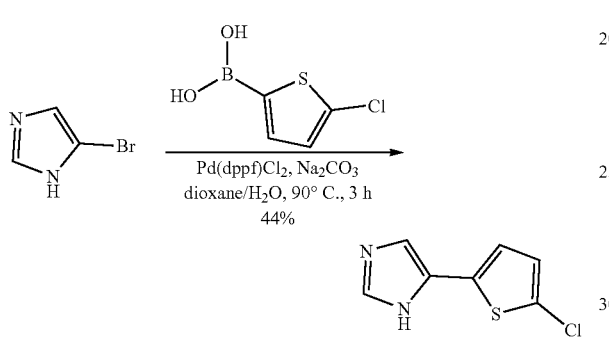

Into a 100-mL round-bottom flask purged and maintained with an inert atmosphere of nitrogen, was placed 4-bromo-3H-imidazole (3.78 g, 25.72 mmol, 1.0 equiv), 5-chlorothiophen-2-ylboronic acid (5.0 g, 30.79 mmol, 1.2 equiv), Na$_2$CO$_3$ (5.45 g, 51.42 mmol, 2.0 equiv), dioxane (40 mL), H$_2$O (4 mL), and Pd(dppf)Cl$_2$ (1.05 g, 1.44 mmol, 0.06 equiv). The mixture was stirred for 3 h at 90° C. After being cooled to room temperature, the reaction solution was concentrated in vacuo to remove the solvent. The residue was purified by silica gel column with DCM/MeOH (10:1). 2.1 g (44%) of 5-(5-chlorothiophen-2-yl)-1H-imidazole was obtained as a yellow solid. LCMS (ES) [M+1]$^+$ m/z: 185.

Step 2

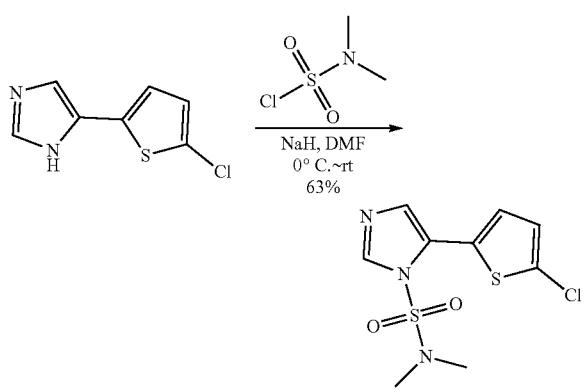

Into a 100-mL 3-necked round-bottom flask, was placed 5-(5-chlorothiophen-2-yl)-1H-imidazole (2.0 g, 10.83 mmol, 1.0 equiv), DMF (20 mL). This was followed by the addition of NaH (60% in mineral oil) (1.08 g, 27.04 mmol, 2.5 equiv) at 0° C. The reaction was then stirred for 0.5 h. To this, dimethylsulphamoyl chloride (1.87 g, 13.02 mmol, 1.2 equiv) was added. After addition, the mixture was stirred for 2 h at room temperature. The reaction was then quenched by the addition of water (20 mL), and extracted with 3×30 mL of ethyl acetate. The combined organic phase was washed with brine (30 mL*3), dried over anhydrous Na$_2$SO$_4$, filtered, and the filtrate was concentrated under reduced pressure. The residue was purified by silica column with ethyl acetate/petroleum ether (1:3). 2.0 g (63%) of 5-(5-chlorothiophen-2-yl)-N,N-dimethyl-1H-imidazole-1-sulfonamide was obtained as a yellow oil. LCMS (ES) [M+1]$^+$ m/z: 292.

Step 3

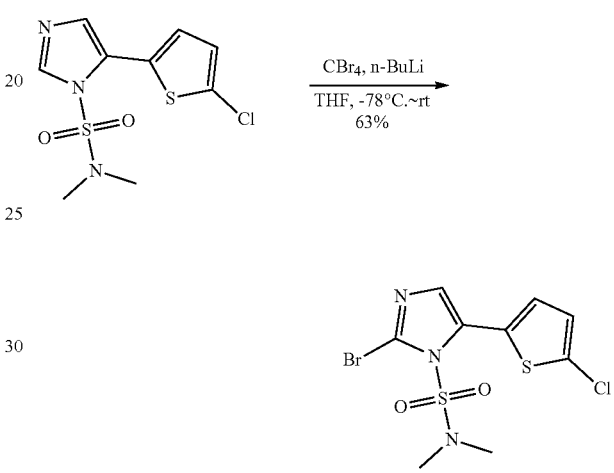

Into a 50-mL 3-necked round-bottom flask purged and maintained with an inert atmosphere of nitrogen, was placed 5-(5-chlorothiophen-2-yl)-N,N-dimethyl-1H-imidazole-1-sulfonamide (2.0 g, 6.86 mmol, 1.0 equiv), tetrahydrofuran (20 mL). This was followed by the addition of n-BuLi (2.5 M in hexane) (3.3 mL, 8.25 mmol, 1.2 equiv) at −78° C. The reaction solution was stirred for 30 min at −78° C. To this, CBr$_4$ (2.50 g, 7.54 mmol, 1.1 equiv) was added at −78° C., and stirred for 0.5 h at the same temperature, and then for 2 h at room temperature. The reaction was then quenched by the addition of NH$_4$Cl (aq) (30 mL) and extracted with 3×30 mL of ethyl acetate. The combined organic phase was dried over anhydrous Na$_2$SO$_4$, filtered, and the filtrate was concentrated in vacuo. The residue was purified by silica gel column with ethyl acetate/petroleum ether (1:4). 1.6 g (63%) of 2-bromo-5-(5-chlorothiophen-2-yl)-N,N-dimethyl-1H-imidazole-1-sulfonamide as a yellow oil. LCMS (ES) [M+1]$^+$ m/z: 370.

Step 4

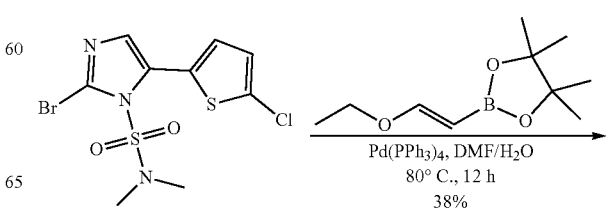

345
-continued

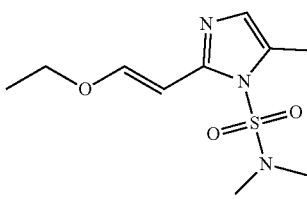

Into a 50-mL round-bottom flask purged and maintained with an inert atmosphere of nitrogen, was placed 2-bromo-5-(5-chlorothiophen-2-yl)-N,N-dimethyl-1H-imidazole-1-sulfonamide (1.60 g, 4.32 mmol, 1.0 equiv), 2-[(E)-2-ethoxyethenyl]-4,4,5,5-tetramethyl-1,3,2-dioxaborolane (1.28 g, 6.46 mmol, 1.5 equiv), Na$_2$CO$_3$ (912 mg, 8.61 mmol, 2.0 equiv), DMF (16 mL), H$_2$O (4 mL), and Pd(PPh$_3$)$_4$ (497 mg, 0.43 mmol, 0.1 equiv). The mixture was stirred for 12 h at 80° C. After being cooled to room temperature, the reaction was then diluted with water (20 mL), and extracted with 3×30 mL of ethyl acetate. The combined organic phase was washed with 2×20 ml of brine, dried over anhydrous Na$_2$SO$_4$, filtered, and the filtrate was concentrated in vacuo. The residue was purified by silica gel column with ethyl acetate/petroleum ether (1:3). 600 mg (38%) of (E)-5-(5-chlorothiophen-2-yl)-2-(2-ethoxyvinyl)-N,N-dimethyl-1H-imidazole-1-sulfonamide was obtained as a yellow solid. LCMS (ES) [M+1]$^+$ m/z: 362.

Step 5

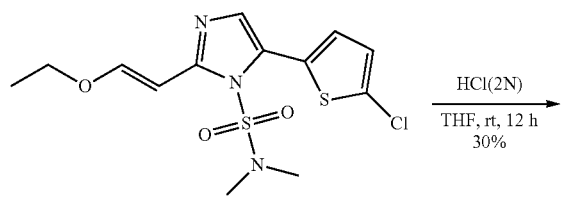

Into a 50-mL round-bottom flask, was placed (E)-5-(5-chlorothiophen-2-yl)-2-(2-ethoxyvinyl)-N,N-dimethyl-1H-imidazole-1-sulfonamide (600 mg, 1.66 mmol, 1.0 equiv), tetrahydrofuran (10 mL), HCl (2 M) (10 mL). The reaction solution was stirred for 12 h at room temperature. The reaction was diluted with H$_2$O (20 mL), the pH value was adjusted to 7 with NaHCO$_3$ solid, and then extracted with 3×30 mL of dichloromethane. The combined organic phase was dried over anhydrous sodium sulfate, filtered, and the filtrate was concentrated in vacuo. 165 mg (30%) of 5-(5-chlorothiophen-2-yl)-N,N-dimethyl-2-(2-oxoethyl)-1H-imidazole-1-sulfonamide was obtained as a yellow oil and used in the next step directly without further purification. LCMS (ES) [M+1]$^+$ m/z: 334.

346

Step 6

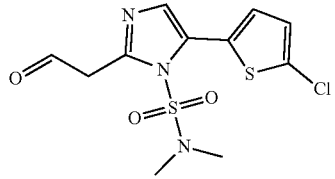

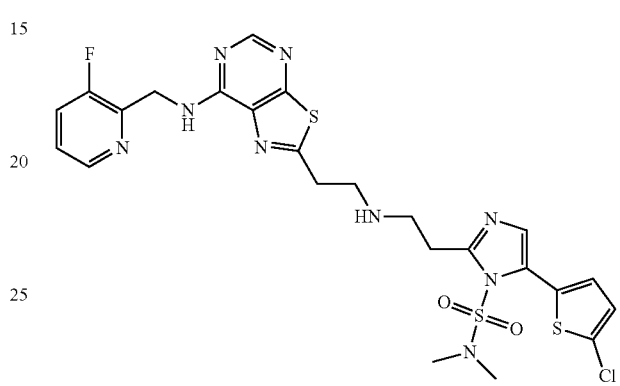

Into a 50-mL round-bottom flask, was placed 5-(5-chlorothiophen-2-yl)-N,N-dimethyl-2-(2-oxoethyl)-1H-imidazole-1-sulfonamide (165 mg, 0.49 mmol, 1.0 equiv), 2-(2-aminoethyl)-N-[(3-fluoropyridin-2-yl)methyl]-[1,3]thiazolo[5,4-d]pyrimidin-7-amine (150 mg, 0.49 mmol, 1.0 equiv), DCM (15 mL), and AcOH (30 mg, 0.50 mmol, 1.0 equiv). The mixture was stirred for 1 h at room temperature, followed by NaBH(OAc)$_3$ (315 mg, 1.49 mmol, 3.0 equiv), which was added in one portion. The reaction solution was allowed to stir for an additional 6 h at room temperature. The reaction was then quenched by the addition of water (30 mL). The pH value was adjusted to 8 with NaHCO$_3$ solid, and extracted with 3×20 mL of dichloromethane. The combined organic phase was dried over anhydrous sodium sulfate, filtered, and the filtrate was concentrated in vacuo. The residue was purified by silica column with dichloromethane/methanol (1/30). 110 mg (36%) of 5-(5-chlorothiophen-2-yl)-2-(2-((2-(7-(((3-fluoropyridin-2-yl)methyl)amino)thiazolo[5,4-d]pyrimidin-2-yl)ethyl)amino)ethyl)-N,N-dimethyl-1H-imidazole-1-sulfonamide was obtained as a yellow solid. LCMS (ES) [M+1]$^+$ m/z: 622.

Step 7

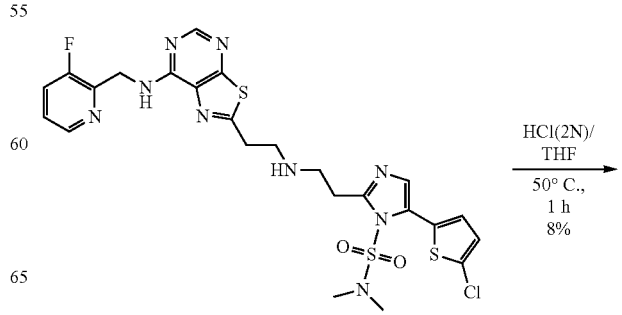

-continued

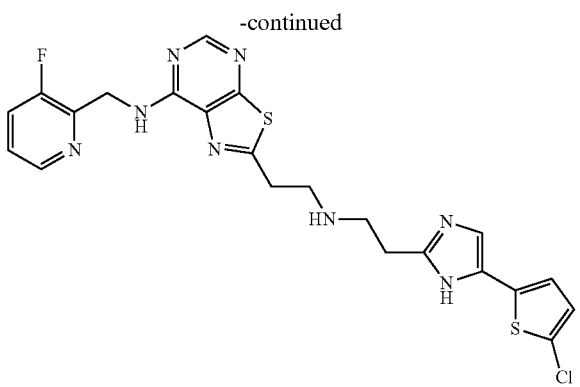

Into a 7-mL vial, was placed 5-(5-chlorothiophen-2-yl)-2-(2-((2-(7-(((3-fluoropyridin-2-yl)methyl)amino)thiazolo[5,4-d]pyrimidin-2-yl)ethyl)amino)ethyl)-N,N-dimethyl-1H-imidazole-1-sulfonamide (200 mg, 0.32 mmol, 1.0 equiv), THF (2 mL), HCl (2 M) (2 mL). The reaction solution was stirred for 1 h at 50° C. The resulting mixture was concentrated to remove the solvent. The pH value of the residue solution was adjusted to 7 with NH₄OH. The crude product was purified by Prep-HPLC with the following conditions: Column, Atlantis HILIC OBD Column, 19*150 mm*5 um; mobile phase, Water (0.05% NH₄OH) and CH₃CN (20% Phase B up to 60% within 12 min), Detector, UV 254 nm. 13.1 mg (8%) of 2-(2-((2-(5-(5-chlorothiophen-2-yl)-1H-imidazol-2-yl)ethyl)amino)ethyl)-N-((3-fluoropyridin-2-yl)methyl)thiazolo[5,4-d]pyrimidin-7-amine was obtained as an off-white solid. ¹H-NMR: (300 MHz, DMSO-d₆, ppm): δ 11.86 (br, 1H), 8.33 (d, J=9.6 Hz, 3H), 7.73-7.67 (m, 1H), 7.37 (d, J=12.6 Hz, 2H), 6.99 (d, J=8.4 Hz, 2H), 4.88 (s, 2H), 3.22 (s, 2H), 3.00 (s, 2H), 2.89 (t, J=8.1 Hz, 2H), 2.78 (t, J=8.4 Hz, 2H). LCMS: (ES, m/z): [M+H]⁺: 515.

Example 1.78

Synthesis of N-{[2-(2-{[2-(7-{[(3-fluoropyridin-2-yl)methyl]amino}-[1,3]thiazolo[5,4-d]pyrimidin-2-yl)ethyl]amino}ethyl)-1H-1,3-benzodiazol-5-yl]methyl})-3',6'-dihydroxy-3-oxo-3H-spiro[2-benzofuran-1,9'-xanthene]-6-carboxamide
(Compound 80)

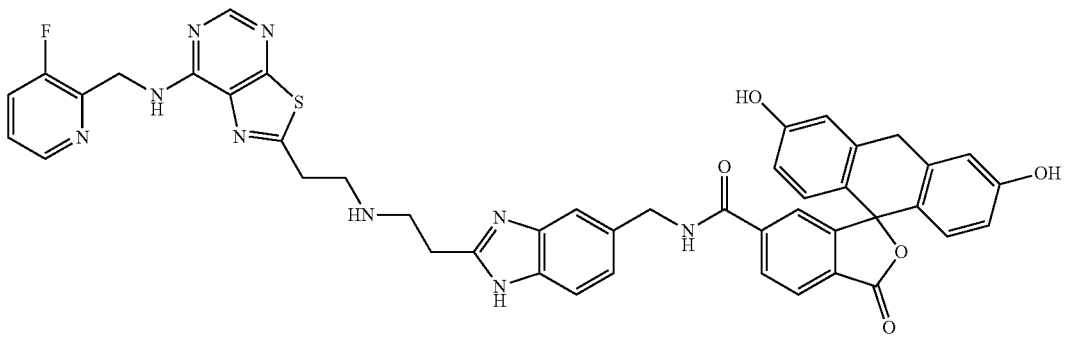 [SMILES: O=C(NCc1ccc2[nH]c(CCNCCc3nc4c(NCc5ncccc5F)ncnc4s3)nc2c1)c1ccc2c(c1)C1(OC2=O)c2ccc(O)cc2Cc2cc(O)ccc21]

Scheme 54 depicts a synthetic route for preparing an exemplary compound.

Scheme 54

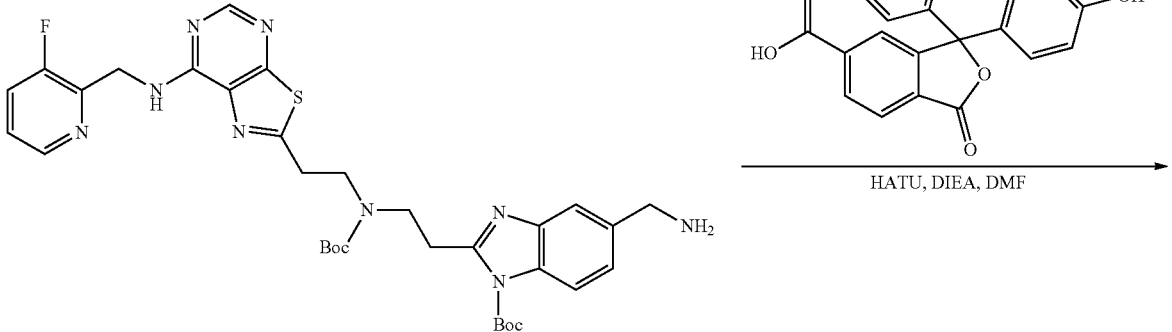

349 350
-continued
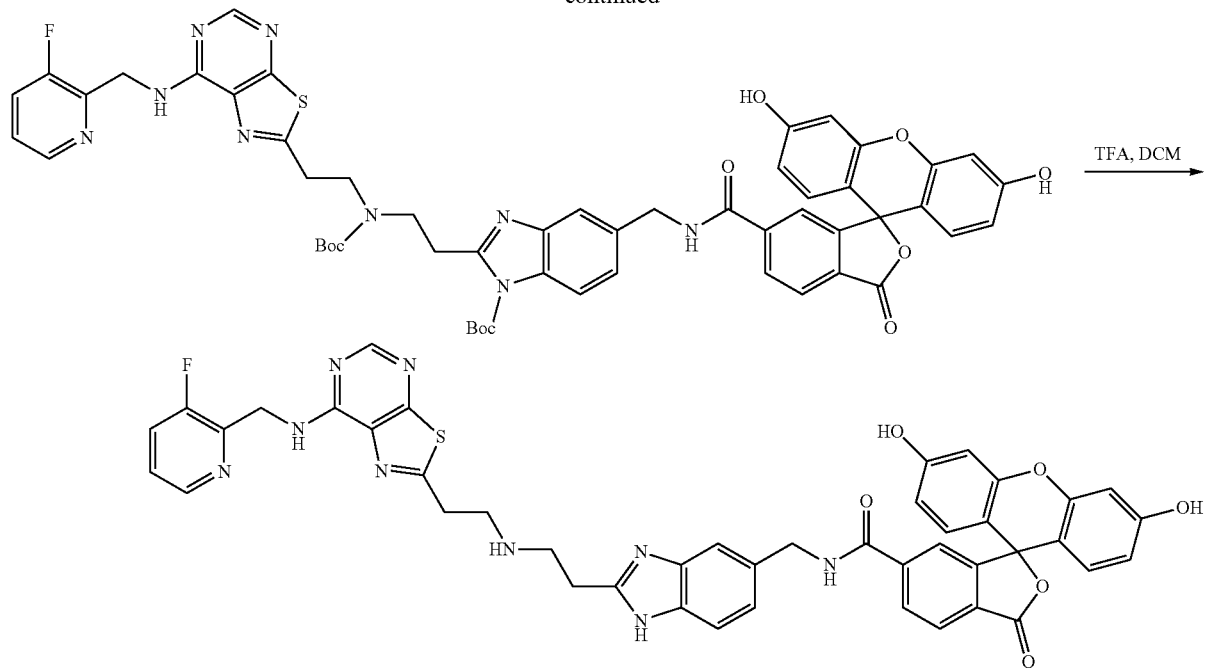
Step 1
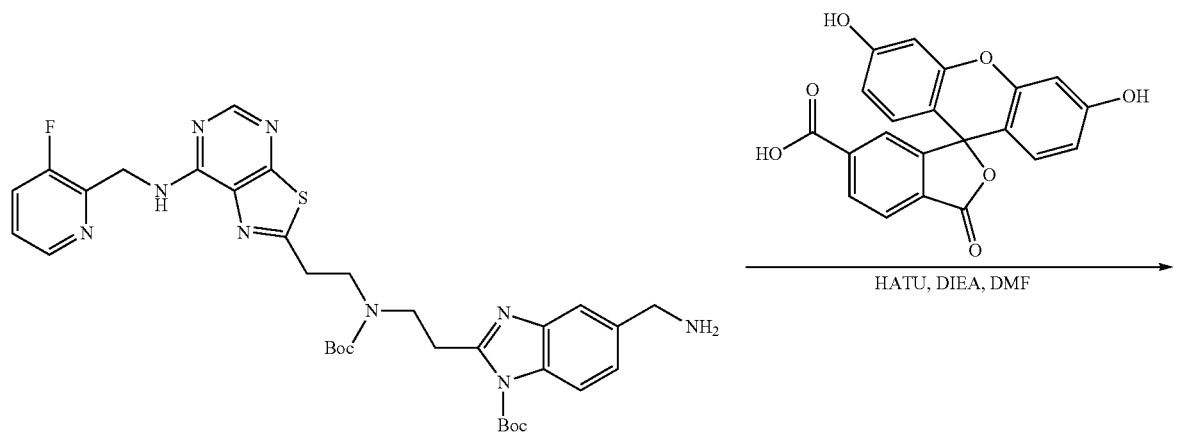
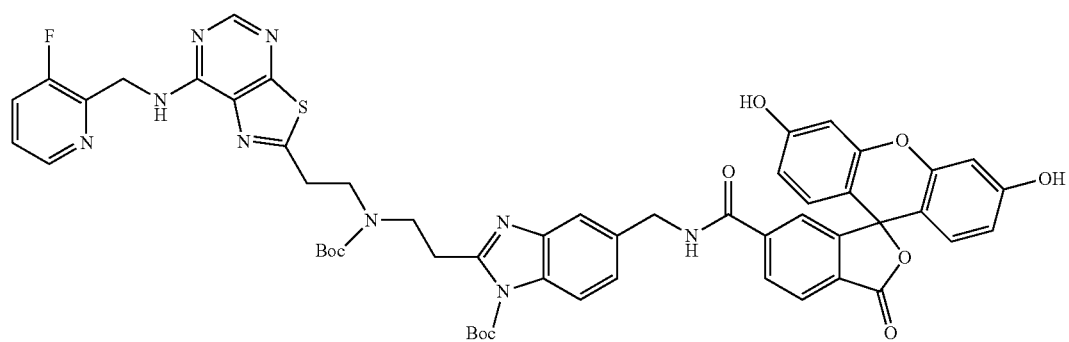

351

Into a 25-mL round-bottom flask purged and maintained with an inert atmosphere of nitrogen, was placed tert-butyl, 5-(aminomethyl)-2-[2-[(tert-butoxycarbonyl)[2-(7-[[(3-fluoropyridin-2-yl)methyl]amino]-[1,3]thiazolo[5,4-d]pyrimidin-2-yl)ethyl]amino]ethyl]-1,3-benzodiazole-1-carboxylate (40 mg, 0.059 mmol, 1.00 equiv), carboxyfluorescein (22 mg, 0.059 mmol, 1 equiv), DMF (5.00 mL), HATU (26.9 mg, 0.07 mmol, 1.2 equiv), and DIEA (9.0 mg, 0.07 mmol, 1.2 equiv). The resulting solution was stirred for 3 hr at room temperature. The crude product (80 mg) was purified by Prep-HPLC with the following conditions: mobile phase, ACN: H₂O (0.01% TFA); Detector. 35 mg product was obtained. This resulted in 35 mg (57.78%) of tert-butyl 2-[2-[(tert-butoxycarbonyl)[2-(7-[[(3-fluoropyridin-2-yl)methyl]amino]-[1,3]thiazolo[5,4-d]pyrimidin-2-yl)ethyl]amino]ethyl]-5-([3',6'-dihydroxy-3-oxospiro[2-benzofuran-1,9'-xanthen]-6-ylformamido]methyl)-1,3-benzodiazole-1-carboxylate as a light yellow solid. LCMS (ES) [M+1]⁺ m/z: 1036.

352

Into a 50-mL round-bottom flask, was placed a mixture of tert-butyl 2-[2-[(tert-butoxycarbonyl)[2-(7-[[(3-fluoropyridin-2-yl)methyl]amino]-[1,3]thiazolo[5,4-d]pyrimidin-2-yl)ethyl]amino]ethyl]-5-([3 (20.00 mg, 0.019 mmol, 1.00 equiv), DCM (15.00 mL), and TFA (2.00 mg, 0.018 mmol, 0.91 equiv). The resulting solution was stirred for 2 hours at room temperature. The crude product was purified by Prep-HPLC with the following conditions: Column, SunFire Prep C18 OBD Column 9*150 mm, 5 um; mobile phase, Water (0.1% FA) and ACN (41% Phase B up to 57% in 15 min); Detector, UV 254 nm. The resulting mixture was concentrated. This resulted in 1.40 mg (8.68%) of N-[[2-(2-[[2-(7-[[(3-fluoropyridin-2-yl)methyl]amino]-[1,3]thiazolo[5,4-d]pyrimidin-2-yl)ethyl]amino]ethyl)-1H-1,3-benzodiazol-5-yl]methyl]-3',6'-dihydroxy-3-oxospiro[2-benzofuran-1,9'-xanthene]-6-carboxamide as an orange solid. LCMS: (ES, m/z): [M+H]⁺: 836.

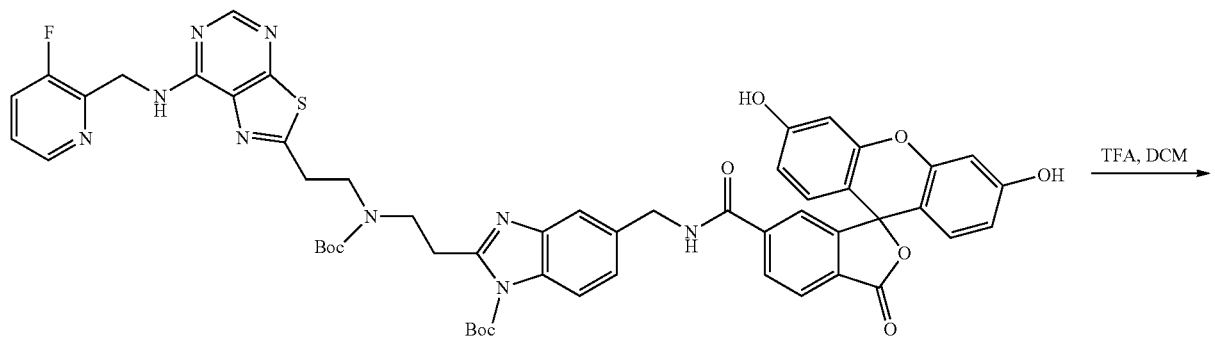

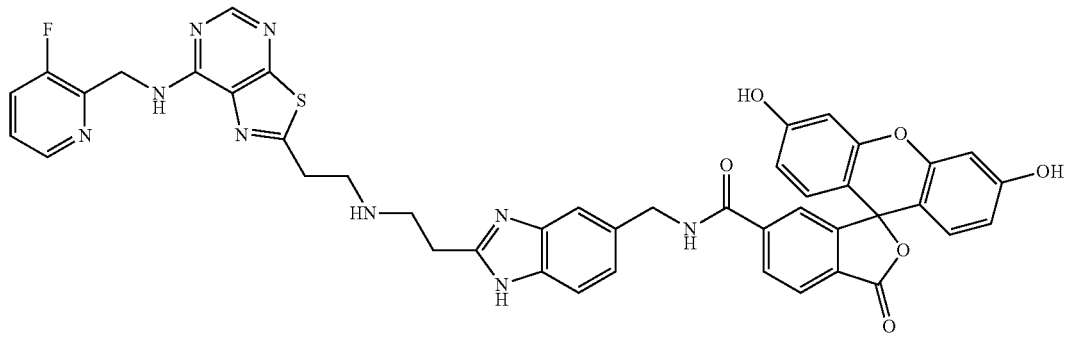

Example 1.79

Synthesis of 2-(2-{[2-(4,5-dimethyl-1H-imidazol-2-yl)ethyl]amino}ethyl)-N-[(3-fluoropyridin-2-yl)methyl]-[1,3]thiazolo[4,5-c]pyridin-4-amine (Compound 73)

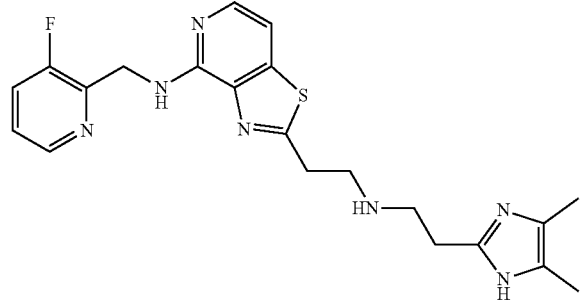 [SMILES: Cc1nc(CCNCCc2nc3c(NCc4ncccc4F)nccc3s2)[nH]c1C]

Scheme 55 depicts a synthetic route for preparing an exemplary compound.

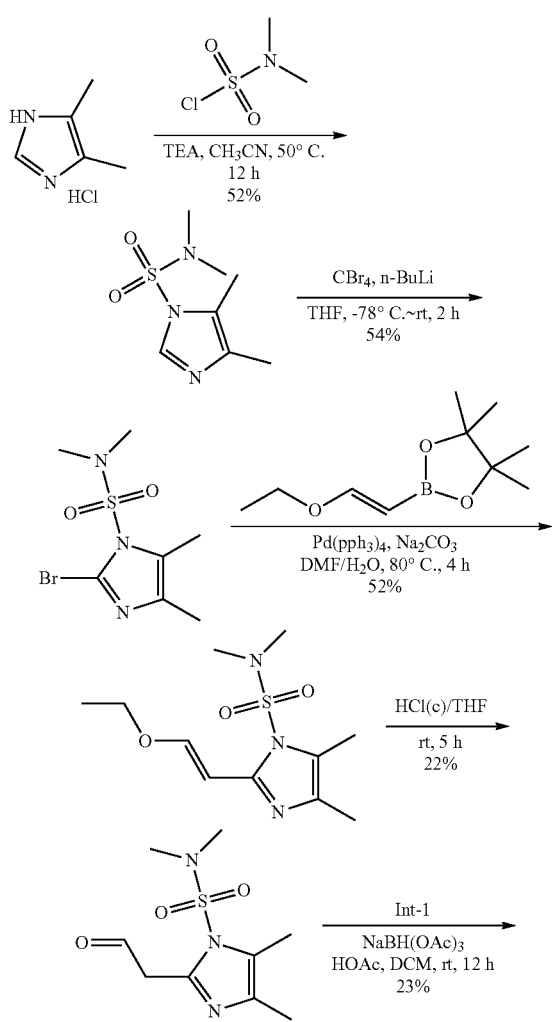

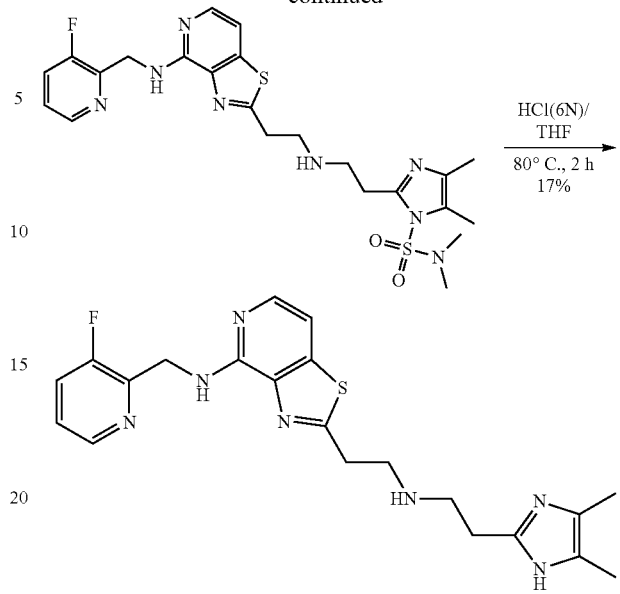

Step 1

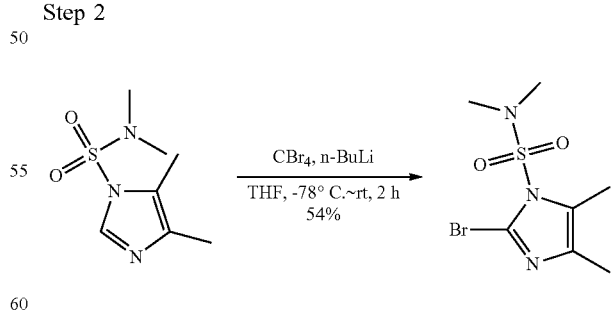

Into a 250-mL round-bottom flask, was placed 4,5-dimethyl-1H-imidazole hydrochloride (10.0 g, 75.42 mmol, 1.0 equiv), TEA (22.9 g, 226.26 mmol, 3.0 equiv), dimethylsulphamoyl-chloride (13.0 g, 90.51 mmol, 1.2 equiv), and CH$_3$CN (100 mL). The mixture was stirred for 12 h at 50° C. in oil bath. The reaction was cooled to room temperature and concentrated under reduced pressure. The residue was purified by silica gel column with ethyl acetate/petroleum ether (1:2). 8.0 g (52%) of N,N,4,5-tetramethylimidazole-1-sulfonamide was obtained as yellow oil. LCMS (ES) [M+1]$^+$ m/z: 204.

Step 2

Into a 250-mL round-bottom flask purged and maintained with an inert atmosphere of nitrogen, was placed N,N,4,5-tetramethylimidazole-1-sulfonamide (8.0 g, 39.36 mmol, 1.0 equiv) and THF (100 mL). This was followed by the addition of n-BuLi (31.5 mL, 78.72 mmol, 2.0 equiv) dropwise with stirring at −78° C. The mixture was then stirred for 0.5 h. To this, CBr$_4$ (14.4 g, 43.29 mmol, 1.1 equiv) was added dropwise with stirring at the same temperature. The reaction was left warm to room temperature and stirred for 2 h, quenched by the addition of 50 mL of H₂O, and extracted with 3×100 mL of ethyl acetate. The combined organic phase was dried over anhydrous sodium sulfate, filtered, and the filtrate was concentrated under reduced pressure. The residue was purified by silica gel column with ethyl acetate/petroleum ether (1:3). 6.0 g (54%) of 2-bromo-N,N,4,5-tetramethylimidazole-1-sulfonamide was obtained as a yellow oil. LCMS (ES) [M+1]⁺ m/z: 282.
Step 3

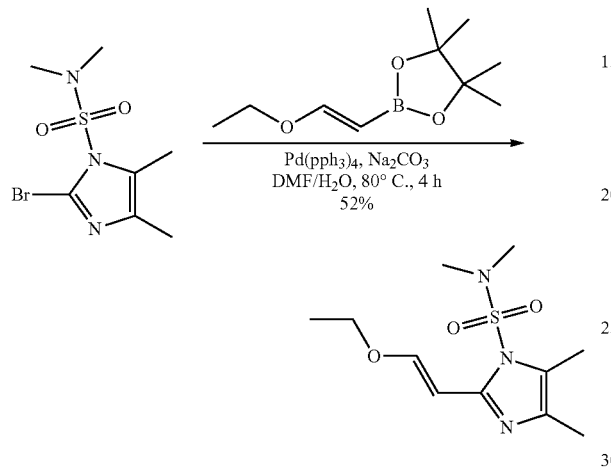

Into a 250-mL 3-necked round-bottom flask purged and maintained with an inert atmosphere of nitrogen, was placed 2-bromo-N,N,4,5-tetramethylimidazole-1-sulfonamide (6.0 g, 21.27 mmol, 1.0 equiv), DMF (100 mL), H₂O (40 mL), 2-[(E)-2-ethoxyethenyl]-4,4,5,5-tetramethyl-1,3,2-dioxaborolane (6.3 g, 31.89 mmol, 1.5 equiv), Na₂CO₃ (4.5 g, 42.46 mmol, 2.0 equiv), and Pd(pph₃)₄ (2.46 g, 2.13 mmol, 0.1 equiv). The reaction solution was stirred for 4 h at 80° C. After cooled to room temperature, the reaction was diluted with H₂O (100 mL), and extracted with 3×200 mL of ethyl acetate. The combined organic phase was washed with brine (100 mL*3), dried over anhydrous sodium sulfate, filtered, and the filtrate was concentrated under reduced pressure. The residue was purified by silica column with ethyl acetate/petroleum ether (1:2). 3.0 g (52%) of 2-[(E)-2-ethoxyethenyl]-N,N,4,5-tetramethylimidazole-1-sulfonamide was obtained as a light yellow solid. LCMS (ES) [M+1]+ m/z: 274.
Step 4

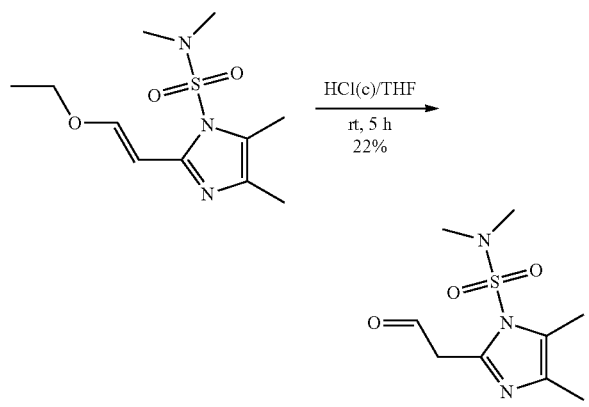

Into a 100-mL round-bottom flask, was placed 2-[(E)-2-ethoxyethenyl]-N,N,4,5-tetramethylimidazole-1-sulfonamide (3.0 g, 10.96 mmol, 1.0 equiv), THF (30 mL), and HCl (c) (30 mL). The mixture was stirred for 5 h at room temperature. The reaction solution was diluted with 40 mL of water and extracted with 3×100 mL of ethyl acetate. The combined organic phase was washed with of NaHCO₃ (aq) (50 mL*1), brine (50 mL*1), dried over anhydrous sodium sulfate, filtered, and the filtrate was concentrated under reduced pressure. 600 mg (22%) of N,N,4,5-tetramethyl-2-(2-oxoethyl)imidazole-1-sulfonamide as a colorless oil and used to the next step directly without further purification. LCMS (ES) [M+1]⁺ m/z: 246.

Step 5

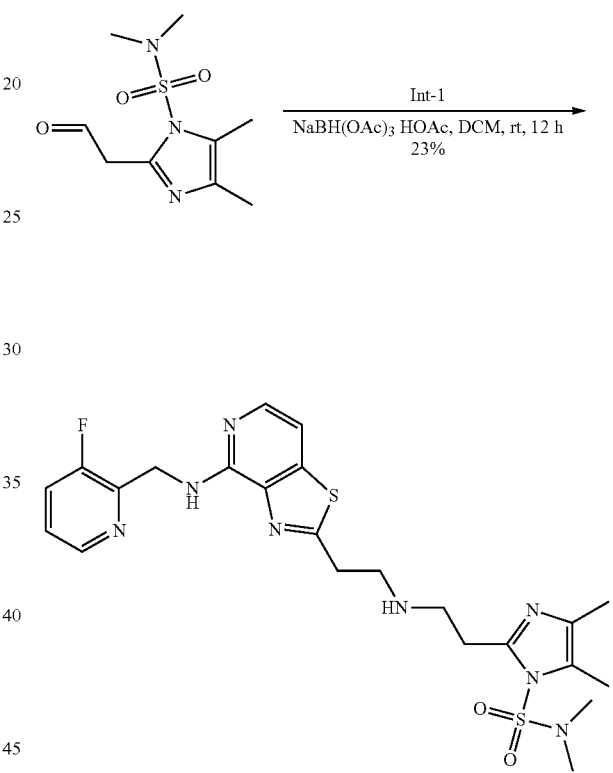

Into a 250-mL round-bottom flask, was placed N,N,4,5-tetramethyl-2-(2-oxoethyl)imidazole-1-sulfonamide (600 mg, 2.44 mmol, 1.0 equiv), DCM (60 mL), 2-(2-aminoethyl)-N-[(3-fluoropyridin-2-yl)methyl]-[1,3]thiazolo[4,5-c]pyridin-4-amine (742 mg, 2.45 mmol, 1.0 equiv), and HOAc (294 mg, 4.89 mmol, 2.0 equiv). After being stirred for 0.5 h, NaBH(OAc)₃ (1555 mg, 7.33 mmol, 3.0 equiv) was added at room temperature. The mixture was stirred for 12 h at room temperature. The reaction solution was diluted with 20 mL of saturated NaHCO₃ (aq), and then extracted with 3×100 mL of dichloromethane. The combined organic phase was dried over anhydrous sodium sulfate, filtered, and the filtrate was concentrated under reduced pressure. The residue was purified by silica column with dichloromethane/methanol (20:1). 300 mg (23%) of 2-(2-[[2-(4-[[(3-fluoropyridin-2-yl)methyl]amino]-[1,3]thiazolo[4,5-c]pyridin-2-yl)ethyl]amino]ethyl)-N,N,4,5-tetramethylimidazole-1-sulfonamide was obtained as a yellow oil. LCMS (ES) [M+1]⁺ m/z: 533.

Step 6

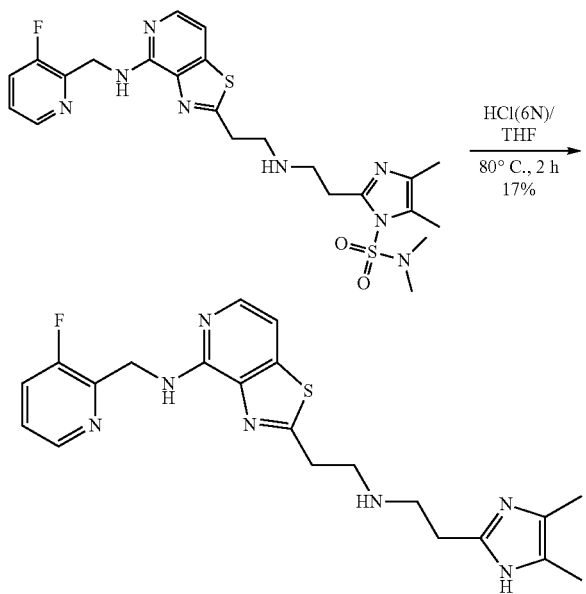

Into a 40-mL round-bottom flask, was placed 2-(2-[[2-(4-[[(3-fluoropyridin-2-yl)methyl]amino]-[1,3]thiazolo[4,5-c]pyridin-2-yl)ethyl]amino]ethyl)-N,N,4,5-tetramethylimidazole-1-sulfonamide (532 mg, 1.0 equiv), THF (10 mL), and HCl (6 N) (10 mL). The mixture was stirred for 2 h at 80° C. in an oil bath. The reaction was cooled to room temperature. After being cooled to room temperature, the pH value of the solution was adjusted to 8-9 with NH$_4$OH. The solution was filtered, and the filtrate was concentrated in vacuum, and then the residue was purified by Prep-HPLC with the following conditions: column, Ascentis Express C18, 50*3.0 mm, 2.7 um, Mobile Phase A: Water (0.05% TFA), Mobile Phase B: CH$_3$CN, Flow rate: 1.5 mL/min, Gradient: 5% to 100% within 10 min). 75.4 mg (17%) of 2-(2-[[2-(4,5-dimethyl-1H-imidazol-2-yl)ethyl]amino]ethyl)-N-[(3-fluoropyridin-2-yl)methyl]-[1,3]thiazolo[4,5-c]pyridin-4-amine was obtained as a light yellow solid. $^1$H NMR (300 MHz, DMSO-d$_6$): δ 11.08 (br, 1H), 8.40-8.38 (m, 1H), 7.86 (d, J=5.4 Hz, 1H), 7.74-7.68 (m, 1H), 7.43-7.37 (m, 1H), 7.31-7.27 (m, 1H), 7.18 (d, J=5.7 Hz, 1H), 4.85 (d, J=4.5 Hz, 2H), 3.42-3.32 (m, 1H), 3.23 (t, J=6.6 Hz, 2H), 2.98 (t, J=6.6 Hz, 2H), 2.83 (t, J=7.2 Hz, 2H), 2.63 (t, J=7.2 Hz, 2H), 1.96 (s, 6H). LCMS: (ES, m/z): [M+H]$^+$: 426.2.

Example 1.80

Synthesis of 2-[(1R)-2-{[2-(1H-1,3-benzodiazol-2-yl)ethyl]amino}-1-fluoroethyl]-N-[(3-fluoropyridin-2-yl)methyl]-[1,3]oxazolo[4,5-c]pyridin-4-amine and 2-[(1 S)-2-{[2-(1H-1,3-benzodiazol-2-yl)ethyl]amino}-1-fluoroethyl]-N-[(3-fluoropyridin-2-yl)methyl]-[1,3]oxazolo[4,5-c]pyridin-4-amine (Compounds 74 and 75)

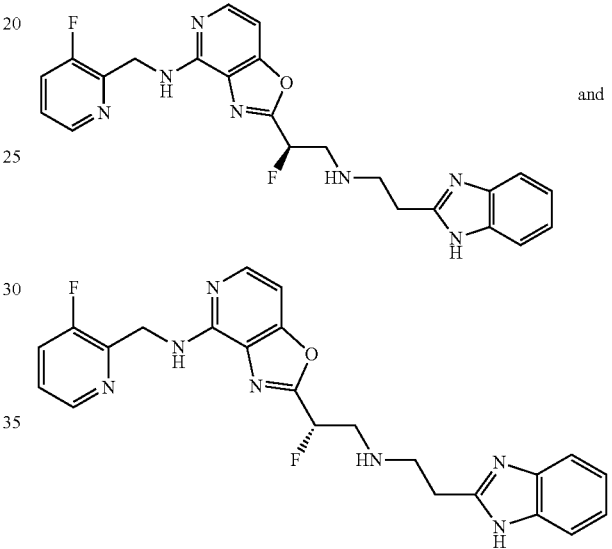

and

Scheme 56 depicts a synthetic route for preparing an exemplary compound.

Scheme 56

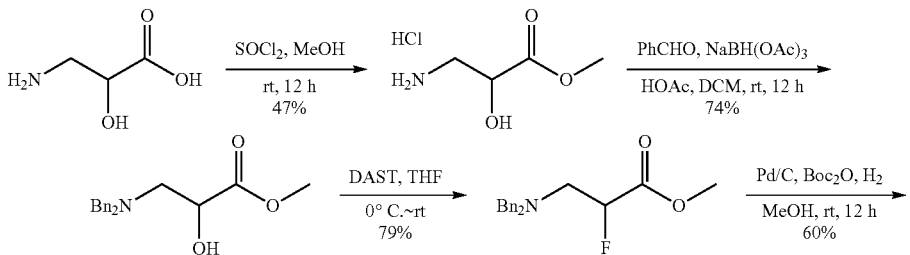

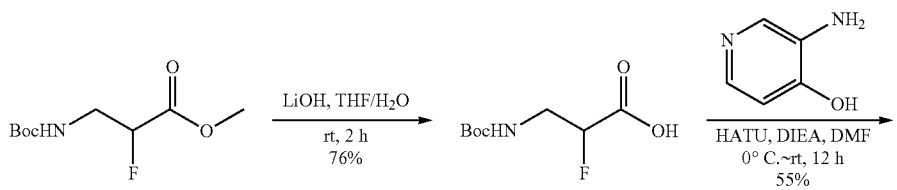

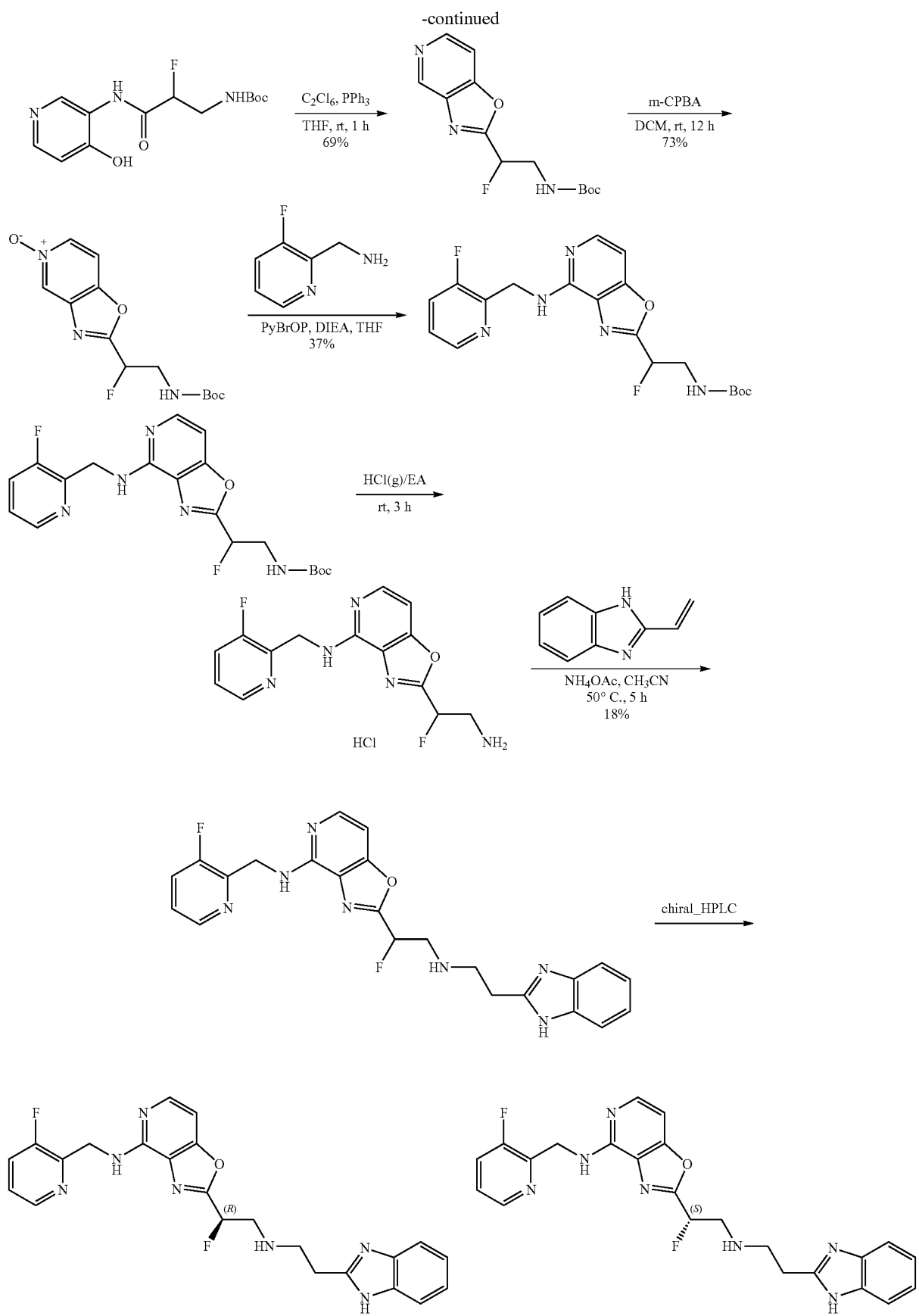

Step 1

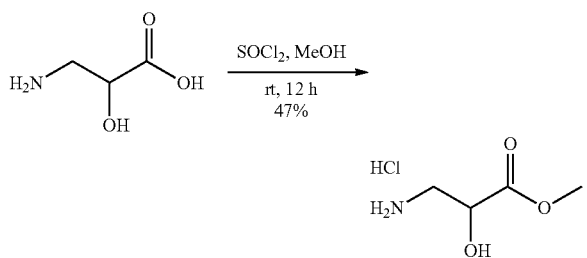

Into a 500-mL 3-necked round-bottom flask purged and maintained with an inert atmosphere of nitrogen, was placed isoserine (20.0 g, 190.31 mmol, 1.0 equiv) and MeOH (300 mL). This was followed by the addition of SOCl₂ (55.22 mL, 464.17 mmol, 4.0 equiv) dropwise with stirring at 0° C. After addition, the mixture was stirred for 12 h at room temperature. The reaction was concentrated under reduced pressure. 14 g (47%) of methyl 3-amino-2-hydroxypropanoate hydrochloride was obtained as a white solid and used in the next step without further purification. LCMS (ES) [M+1]⁺ m/z: 156.

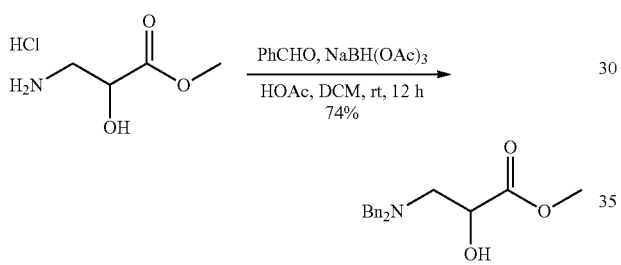

Into a 500-mL 3-necked round-bottom flask purged and maintained with an inert atmosphere of nitrogen, was placed methyl 3-amino-2-hydroxypropanoate hydrochloride (7.0 g, 44.99 mmol, 1.0 equiv), DCM (200 mL), TEA (9.11 g, 89.99 mmol, 2.0 equiv), HOAc (8.11 g, 134.98 mmol, 3.0 equiv), and benzaldehyde (11.46 g, 107.98 mmol, 2.4 equiv). The mixture was cooled to 0° C. and stirred for 0.5 h, and NaBH(OAc)₃ (28.61 g, 134.98 mmol, 3.0 equiv) was added. The reaction was left to stir for 12 h at room temperature. The reaction was concentrated to remove the solvent, the residue was diluted with 100 mL of HCl (2 M in H₂O), and then extracted with 200 mL of EA. The pH of the aqueous layer was adjusted to 8 with K₂CO₃ solid, extracted with 100 mL of dichloromethane, dried over anhydrous sodium sulfate, filtered, and the filtrate was concentrated under reduced pressure. 10 g (74%) of methyl 3-(dibenzylamino)-2-hydroxypropanoate was obtained as a white solid and used in the next step directly without further purification. LCMS (ES) [M+1]⁺ m/z: 300.

Step 3

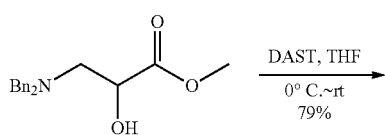

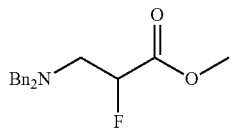

Into a 500-mL 3-necked round-bottom flask, was placed methyl 3-(dibenzylamino)-2-hydroxypropanoate (10.0 g, 33.40 mmol, 1.0 equiv) and THF (200 mL). This was followed by the addition of DAST (10.77 g, 66.81 mmol, 2.0 equiv) dropwise with stirring at 0° C. in 0.5 h. The reaction solution was stirred for 1 h at room temperature. The reaction was then quenched by the addition of 100 mL of ice-water, the pH value of the solution was adjusted to 8-9 with Na₂CO₃ solid, and extracted with 3×200 mL of ethyl acetate. The combined organic phase was dried over anhydrous sodium sulfate, filtered, and the filtrate was concentrated under reduced pressure. The residue was purified by silica gel column with ethyl acetate/petroleum ether (1:2). 8 g (79%) of methyl 3-(dibenzylamino)-2-fluoropropanoate was obtained as a light yellow oil. LCMS (ES) [M+1]⁺ m/z: 302.

Step 4

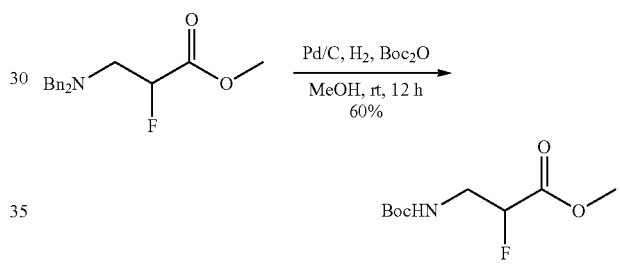

Into a 500-mL round-bottom flask, was placed methyl 3-(dibenzylamino)-2-fluoropropanoate (8.0 g, 26.55 mmol, 1.0 equiv), MeOH (100 mL), Boc₂O (8.69 g, 39.82 mmol, 1.5 equiv), and Pd/C (0.8 g, 10% Wt). The flask was evacuated and flushed three times with nitrogen, followed by flushing with hydrogen. The mixture was stirred for 12 h at room temperature under an atmosphere of hydrogen, filtered, and the filtrate was concentrated under reduced pressure. 3.5 g (60%) of methyl 3-[(tert-butoxycarbonyl)amino]-2-fluoropropanoate was obtained as a colorless oil and used in the next step directly without further purification. LCMS (ES) [M+1]⁺ m/z: 224.

Step 5

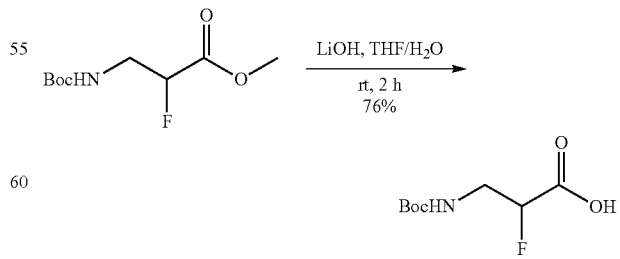

Into a 250-mL round-bottom flask, was placed methyl 3-[(tert-butoxycarbonyl)amino]-2-fluoropropanoate (3.50 g, 15.82 mmol, 1.0 equiv), THF (40 mL), H₂O (40 mL), and LiOH.H$_2$O (1.33 g, 31.64 mmol, 2.0 equiv). The mixture was stirred for 2 h at room temperature. The reaction solution was extracted with 50 mL of ethyl acetate. The pH value of the aqueous layer was adjusted to 3-4 with 1M HCl, extracted with 3×50 mL of dichloromethane, the organic layers combined, washed with 1×100 ml of brine, dried over anhydrous sodium sulfate, filtered, and the filtrate was concentrated under reduced pressure. 2.5 g (76%) of 3-[(tert-butoxycarbonyl)amino]-2-fluoropropanoic acid was obtained as a white solid. LCMS (ES) [M+1]$^+$ m/z: 208.
Step 6

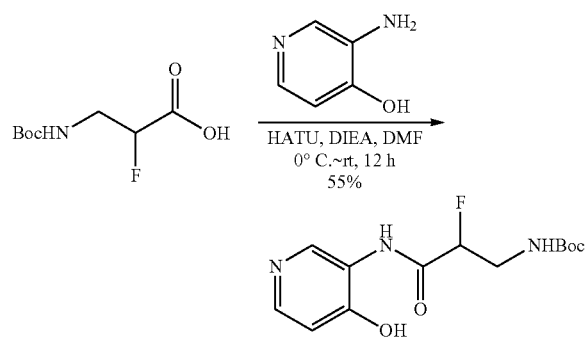

Into a 250-mL 3-necked round-bottom flask, was placed 3-[(tert-butoxycarbonyl)amino]-2-fluoropropanoic acid (2.50 g, 12.07 mmol, 1.0 equiv), 3-aminopyridin-4-ol (1.59 g, 14.48 mmol, 1.2 equiv), DMF (30 mL), and DIEA (4.68 g, 36.20 mmol, 3.0 equiv). This was followed by the addition of HATU (6.88 g, 18.10 mmol, 1.5 equiv) in three batches at 0° C. in 15 min. The mixture was stirred for 12 h at room temperature. The crude product was purified by Flash-Prep-HPLC with the following conditions: C18 column, CH$_3$CN/H$_2$O (0.05% NH$_4$OH) from 5% to 70% within 15 min, 70 mL/min, detector, 220 nm. 2 g (55%) of tert-butyl N-[2-fluoro-2-[(4-hydroxypyridin-3-yl)carbamoyl]ethyl]carbamate was obtained as a white solid. LCMS (ES) [M+1]$^+$ m/z: 300.
Step 7

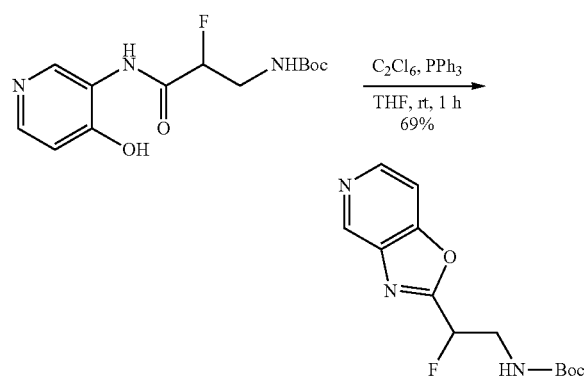

Into a 100-mL round-bottom flask, was placed PPh$_3$ (5.26 g, 20.05 mmol, 3.0 equiv), DCM (20 mL), C$_2$Cl$_6$ (3.95 g, 16.71 mmol, 2.5 equiv), and TEA (5.41 g, 53.46 mmol, 8.0 equiv). This was followed by the addition of tert-butyl N-[2-fluoro-2-[(4-hydroxypyridin-3-yl)carbamoyl]ethyl]carbamate (2.0 g, 6.68 mmol, 1.0 equiv) in four batches at room temperature in 10 min. The reaction solution was stirred for 1 h at room temperature. The reaction mixture was concentrated under reduced pressure to remove the solvent, the residue was purified by silica gel column with EA/PE=1:1. 1.3 g (69%) of tert-butyl N-(2-fluoro-2-[[1,3]oxazolo[4,5-c]pyridin-2-yl]ethyl)carbamate was obtained as a light yellow solid. LCMS (ES) [M+1]$^+$ m/z: 282.
Step 8

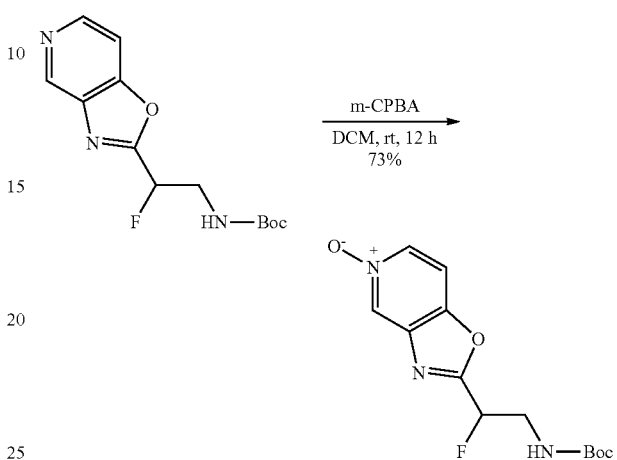

Into a 50-mL round-bottom flask, was placed tert-butyl N-(2-fluoro-2-[[1,3]oxazolo[4,5-c]pyridin-2-yl]ethyl)carbamate (1.30 g, 4.62 mmol, 1.0 equiv), DCM (20 mL), m-CPBA (1.60 g, 9.24 mmol, 2.0 equiv). The reaction solution was stirred for 12 h at room temperature. The reaction was then quenched by the addition of 20 mL of NaHCO$_3$ (aq) and extracted with 3×50 mL of dichloromethane. The combined organic phase was dried over anhydrous sodium sulfate, filtered, and the filtrate was concentrated under reduced pressure. The residue was purified by silica gel column with dichloromethane/methanol (10:1). 1 g (73%) of 2-[2-[(tert-butoxycarbonyl)amino]-1-fluoroethyl]-[1,3]oxazolo[4,5-c]pyridin-5-ium-5-olate was obtained as a white solid. LCMS (ES) [M+1]$^+$ m/z: 298.
Step 9

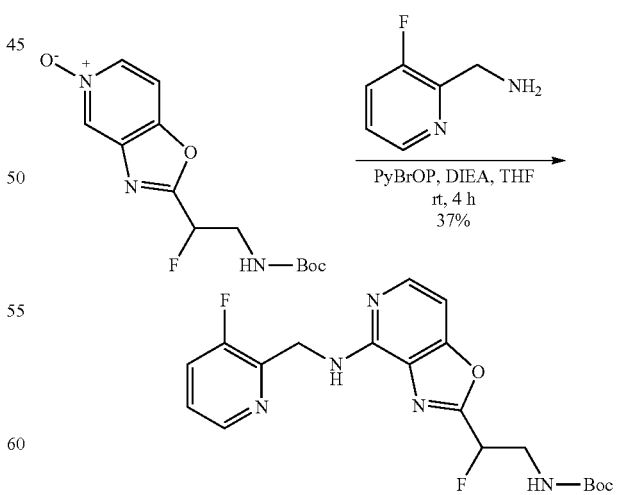

Into a 50-mL round-bottom flask purged and maintained with an inert atmosphere of nitrogen, was placed 2-[2-[(tert-butoxycarbonyl)amino]-1-fluoroethyl]-[1,3]oxazolo[4,5-c]pyridin-5-ium-5-olate (1.0 g, 3.36 mmol, 1.0 equiv), 1-(3- fluoropyridin-2-yl)methanamine (0.55 g, 4.37 mmol, 1.3 equiv), THF (20 mL), DIEA (2.61 g, 20.18 mmol, 6.0 equiv), and PyBrOP (2.35 g, 5.05 mmol, 1.5 equiv). The mixture was stirred for 4 h at room temperature. The mixture was concentrated under vacuum to remove the solvent, and the residue was purified by silica gel column with ethyl acetate/petroleum ether (1:1). 510 mg (37%) of tert-butyl N-[2-fluoro-2-(4-[[(3-fluoropyridin-2-yl)methyl]amino]-[1,3]oxazolo[4,5-c]pyridin-2-yl)ethyl]carbamate was obtained as a light yellow oil. LCMS (ES) [M+1]+ m/z: 406.
Step 10

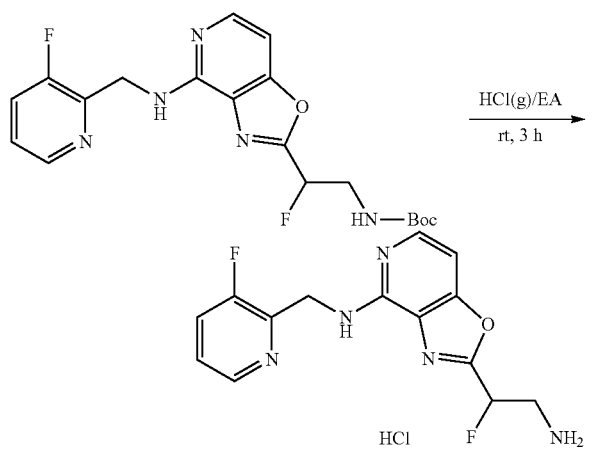

Into a 50-mL round-bottom flask, was placed tert-butyl N-[2-fluoro-2-(4-[[(3-fluoropyridin-2-yl)methyl]amino]-[1,3]oxazolo[4,5-c]pyridin-2-yl)ethyl]carbamate (500 mg, 1.23 mmol, 1.0 equiv) and DCM (10 mL). This was followed by the addition of HCl (g) (2 M in EA) (4 mL) dropwise with stirring at 0° C. The mixture was stirred for 3 h at room temperature. The reaction mixture was concentrated in vacuum, and 500 mg of 2-(2-amino-1-fluoroethyl)-N-[(3-fluoropyridin-2-yl)methyl]-[1,3]oxazolo[4,5-c]pyridin-4-amine hydrochloride was obtained as a white solid and used in the next step directly without further purification. LCMS (ES) [M+1]+ m/z: 342.

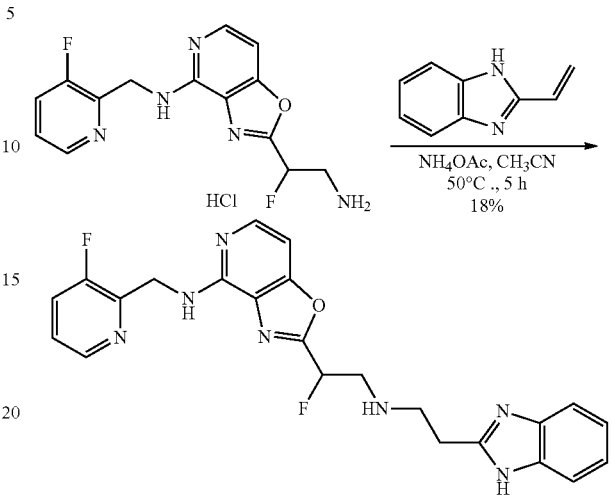

Into a 40-mL round-bottom flask, was placed 2-(2-amino-1-fluoroethyl)-N-[(3-fluoropyridin-2-yl)methyl]-[1,3]oxazolo[4,5-c]pyridin-4-amine hydrochloride (500 mg, 1.46 mmol, 1.1 equiv), 2-ethenyl-1H-1,3-benzodiazole (192 mg, 1.30 mmol, 1.0 equiv), TEA (808 mg, 8.00 mmol, 6.0 equiv), and CH₃CN (20 mL). The reaction solution was stirred for 5 h at 50° C. in an oil bath. The reaction was concentrated to remove the solvent, and the residue was purified by Flash-Prep-HPLC with the following conditions: Column, Kinetex EVO C18, 50*3.0 mm, 2.6 um, Mobile Phase A: Water/0.05% NH₃.H₂O, Mobile Phase B: CH₃CN; Flow rate: 1.2 mL/min, Gradient: 5% B to 100% B in 1.1 min, hold 0.7 min. 110 mg (18%) of 2-(2-[[2-(1H-1,3-benzodiazol-2-yl)ethyl]amino]-1-fluoroethyl)-N-[(3-fluoropyridin-2-yl)methyl]-[1,3]oxazolo[4,5-c]pyridin-4-amine was obtained as a white solid. LCMS (ES) [M+1]+ m/z: 342.

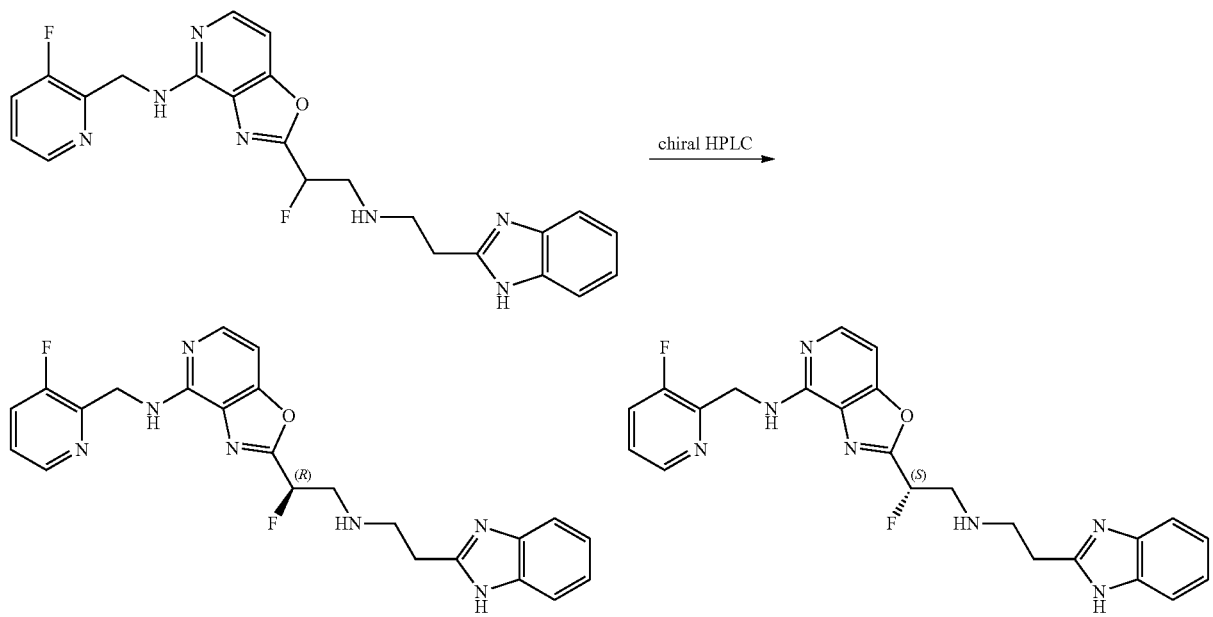

2-(2-[[2-(1H-1,3-benzodiazol-2-yl)ethyl]amino]-1-fluoroethyl)-N-[(3-fluoropyridin-2-yl)methyl]-[1,3]oxazolo[4,5-c]pyridin-4-amine (110.00 mg) was purified by chiral-HPLC with the following conditions: column, CHIRALPAK IA-3, Phase A: n-Hexane (0.1% DEA), Mobile Phase B: Ethanol. 39.8 mg (36%) of 2-[(1R)-2-{[2-(1H-1,3-benzodiazol-2-yl)ethyl]amino}-1-fluoroethyl]-N-[(3-fluoropyridin-2-yl)methyl]-[1,3]oxazolo[4,5-c]pyridin-4-amine was obtained as a white solid. $^1$H NMR (300 MHz, DMSO-$d_6$, ppm): δ 8.35 (dt, J=1.5, 4.8 Hz, 1H), 7.96 (d, J=6.0 Hz, 1H), 7.72-7.65 (m, 1H), 7.50-7.35 (m, 4H), 7.10 (dd, J=3.0, 6.3 Hz, 2H), 6.98 (d, J=5.7 Hz, 1H), 5.99 (t, J=6.0 Hz, 0.5H), 5.83 (t, J=6.0 Hz, 0.5H), 4.86 (d, J=4.8 Hz, 2H), 3.37-3.28 (m, 2H), 3.06 (t, J=6.6 Hz, 2H), 2.95 (t, J=6.6 Hz, 2H), 2.40 (br, 1H). LCMS: (ES, m/z): [M+H]$^+$: 450.2. and 43.9 mg (39%) of 2-[(1S)-2-{[2-(1H-1,3-benzodiazol-2-yl)ethyl]amino}-1-fluoroethyl]-N-[(3-fluoropyridin-2-yl)methyl]-[1,3]oxazolo[4,5-c]pyridin-4-amine was obtained as a white solid. $^1$H NMR (300 MHz, DMSO-$d_6$, ppm): δ 12.13 (br, 1H), 8.35 (dt, J=1.5, 4.8 Hz, 1H), 7.96 (d, J=6.0 Hz, 1H), 7.72-7.65 (m, 1H), 7.50-7.35 (m, 4H), 7.10 (dd, J=3.0, 6.3 Hz, 2H), 6.98 (d, J=5.7 Hz, 1H), 5.99 (t, J=6.0 Hz, 0.5H), 5.83 (t, J=6.0 Hz, 0.5H), 4.86 (d, J=4.8 Hz, 2H), 3.37-3.28 (m, 2H), 3.06 (t, J=6.6 Hz, 2H), 2.95 (t, J=6.6 Hz, 2H), 2.40 (br, 1H). LCMS: (ES, m/z): [M+H]$^+$: 450.2.

Example 1.81

Synthesis of 2-(2-{[2-(4,5-dimethyl-1H-imidazol-2-yl)ethyl]amino}ethyl)-7-{[(3-fluoropyridin-2-yl)methyl]amino}-[1,3]thiazolo[5,4-d]pyrimidin-5-ol (Compound 76)

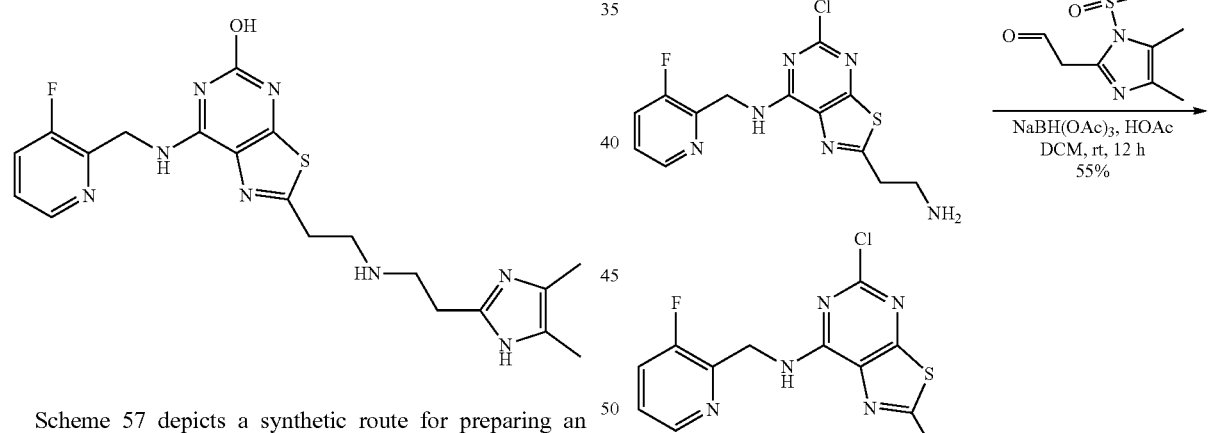

Scheme 57 depicts a synthetic route for preparing an exemplary compound.

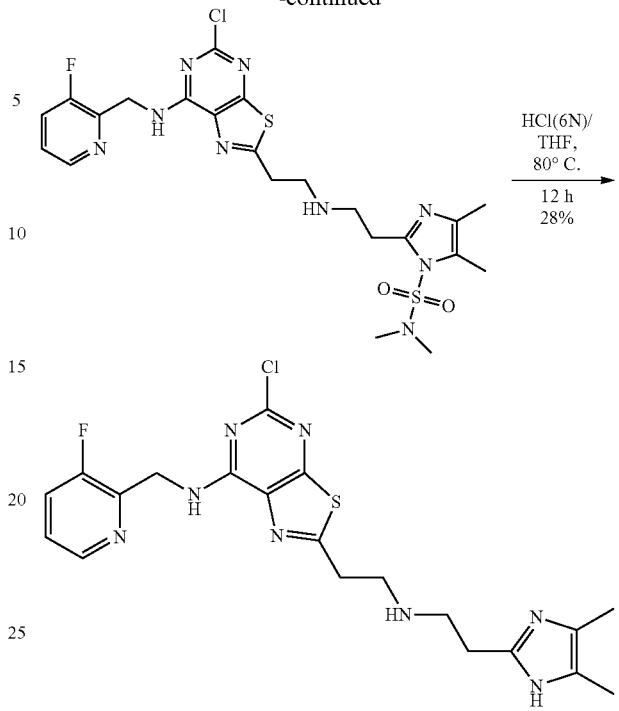

Step 1

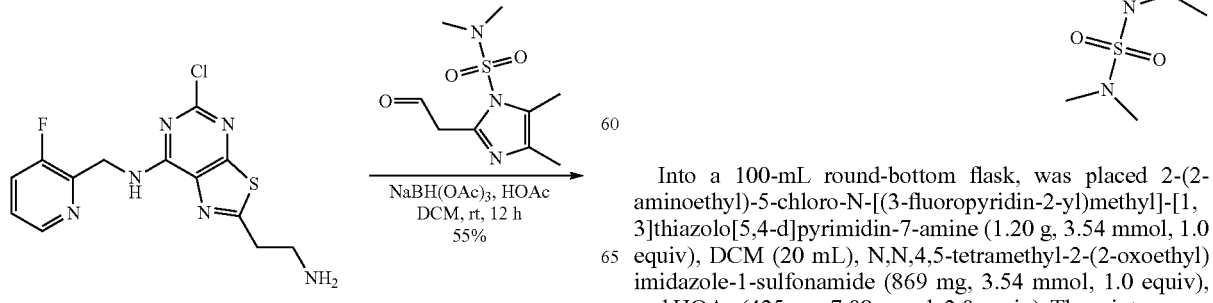

Into a 100-mL round-bottom flask, was placed 2-(2-aminoethyl)-5-chloro-N-[(3-fluoropyridin-2-yl)methyl]-[1,3]thiazolo[5,4-d]pyrimidin-7-amine (1.20 g, 3.54 mmol, 1.0 equiv), DCM (20 mL), N,N,4,5-tetramethyl-2-(2-oxoethyl) imidazole-1-sulfonamide (869 mg, 3.54 mmol, 1.0 equiv), and HOAc (425 mg, 7.08 mmol, 2.0 equiv). The mixture was stirred for 0.5 h at room temperature, followed by the addition of NaBH(OAc)$_3$ (2.25 g, 10.63 mmol, 3.0 equiv), which was added in one portion. The reaction was stirred for 12 h at room temperature. The reaction solution was diluted with 10 mL of H$_2$O and the pH value of the solution was adjusted to 8 with K$_2$CO$_3$ (4 M in H$_2$O). Following this, the reaction solution was extracted with 3×50 mL of dichloromethane. The combined organic phase was dried over anhydrous sodium sulfate, filtered, and the filtrate was concentrated under reduced pressure. The residue was purified by silica gel column with ethyl acetate/petroleum ether (1:1). 1.1 g (55%) of 2-(2-[[2-(5-chloro-7-[[(3-fluoropyridin-2-yl)methyl]amino]-[1,3]thiazolo[5,4-d]pyrimidin-2-yl)ethyl]amino]ethyl)-N,N,4,5-tetramethylimidazole-1-sulfonamide was obtained as a light yellow oil. LCMS (ES) [M+1]$^+$ m/z: 568.

Step 2

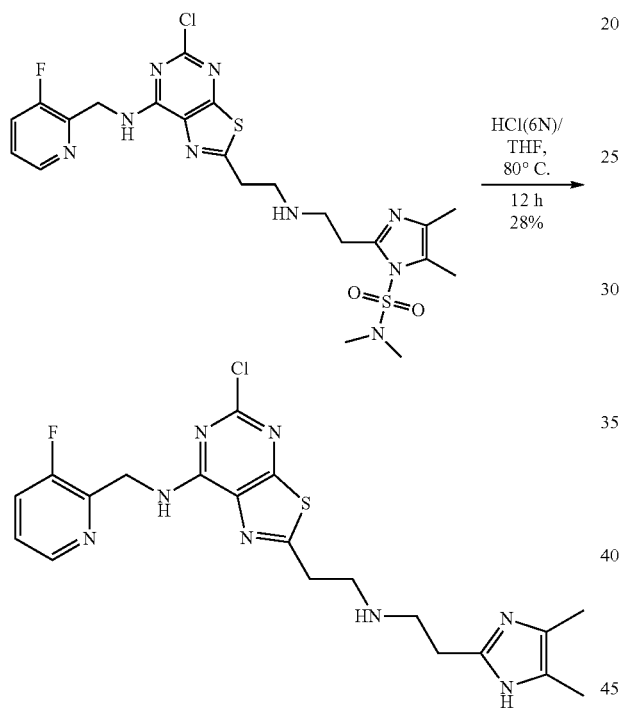

Into a 50-mL round-bottom flask, was placed 2-(2-[[2-(5-chloro-7-[[(3-fluoropyridin-2-yl)methyl]amino]-[1,3]thiazolo[5,4-d]pyrimidin-2-yl)ethyl]amino]ethyl)-N,N,4,5-tetramethylimidazole-1-sulfonamide (500 mg, 0.88 mmol, 1.0 equiv), THF (20 mL), and HCl (6 M) (20 mL). The reaction solution was stirred for 12 h at 80° C. in an oil bath. The reaction mixture was cooled to room temperature and concentrated under reduced pressure to remove the solvent. The pH value of the residue was adjusted to 8-9 with NH$_4$OH (30% in H$_2$O) and extracted with 3×100 mL solvent of DCM:MeOH=10:1. The combined organic phase was concentrated in vacuum and the crude product was purified by Flash-Prep-HPLC with the following conditions (IntelFlash-1): Column, HPH C18, 50*3.0 mm, 2.6 um, Mobile Phase A: Water/0.05% NH$_3$.H$_2$O, Mobile Phase B: CH$_3$CN, Flow rate: 1.2 mL/min, Gradient: 5% B to 100% B within 1.1 min, hold 0.7 min. 108.2 mg (28%) of 2-(2-[[2-(4,5-dimethyl-1H-imidazol-2-yl)ethyl]amino]ethyl)-7-[[(3-fluoropyridin-2-yl)methyl]amino]-[1,3]thiazolo[5,4-d]pyrimidin-5-ol was obtained as a white solid. $^1$H NMR (300 MHz, DMSO-d$_6$, ppm): δ 8.39-8.37 (m, 1H), 8.21 (br, 1H), 7.75-7.69 (m, 1H), 7.44-7.38 (m, 1H), 4.80 (s, 2H), 3.08 (t, J=6.3 Hz, 2H), 2.91 (t, J=6.3 Hz, 2H), 2.83 (d, J=7.2 Hz, 2H), 2.64 (t, J=7.2 Hz, 2H), 1.97 (s, 6H). LCMS: (ES, m/z): [M+H]$^+$: 443.1.

Example 1.82

Synthesis of 2-[(1R)-2-{[2-(1H-1,3-benzodiazol-2-yl)ethyl]amino}-1-fluoroethyl]-N-[(3-fluoropyridin-2-yl)methyl]-[1,3]thiazolo[5,4-d]pyrimidin-7-amine (Compound 77)

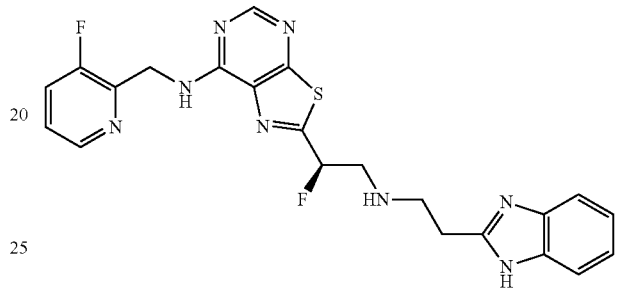

Scheme 58 depicts a synthetic route for preparing an exemplary compound.

Scheme 58

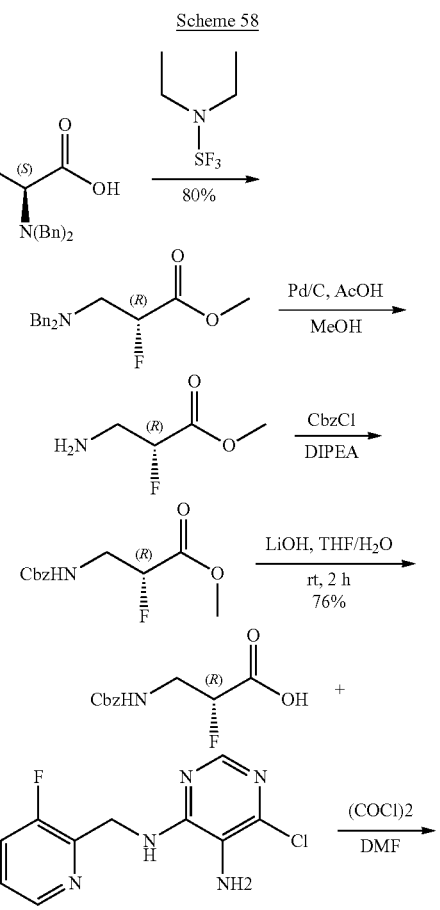

Step 2

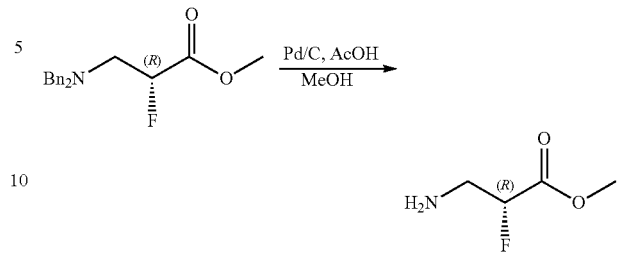

To a solution of methyl (2R)-3-(dibenzylamino)-2-fluoropropanoate (4.00 g; 13.27 mmol; 1.00 eq.) in MeOH (30 mL) was added AcOH (1.25 mL) followed by Pd/C (0.75 g). The solution was charged with $H_2$ balloon (1 atm) and stirred for 3 h. The HPLC check reaction was completed and the mixture was diluted with AcCN. Pd/C was filtered off and the filtrate was concentrated to give methyl (2R)-3-amino-2-fluoropropanoate as a yellow oil, which was used directly for the next step of the reaction without purification.

Step 3

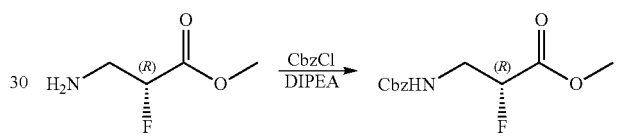

To a solution of methyl (2R)-3-amino-2-fluoropropanoate (0.80 g; 6.60 mmol; 1.00 eq.) in DCM (15 ml) was added Hunig's base (4.60 mL; 26.40 mmol; 4.00 eq.) and benzyl chloroformate (1.41 mL; 9.90 mmol; 1.50 eq.) at 0° C. The mixture was stirred further at room temperature for 15 h, diluted with EtOAc, washed with Sat. $NaHCO_3$, brine, dried, and concentrated to give the crude product, which was purified by column chromatography (Hexanes/EtOAc=40:60) to give methyl (2R)-3-{[(benzyloxy)carbonyl]amino}-2-fluoropropanoate (0.56 g, 33%).

Step 4

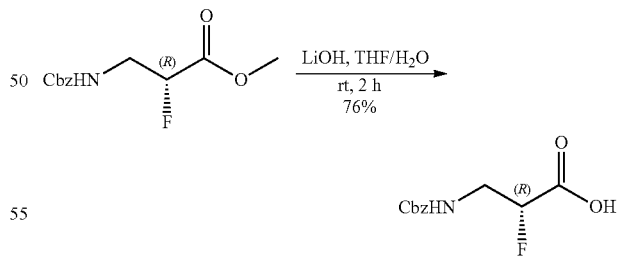

To a solution of methyl (2R)-3-{[(benzyloxy)carbonyl]amino}-2-fluoropropanoate (560.00 mg; 2.19 mmol; 1.00 eq.) in THF (2 mL) was added water (1 mL) and MeOH (1 mL), followed by lithiumol hydrate (184.14 mg; 4.39 mmol; 2.00 eq.). The mixture was stirred at room temperature for 2 h, concentrated, and was diluted with 1N HCl to pH=2. The precipitates were collected by filtration and dried under vacuum to give (2R)-3-{[(benzyloxy)carbonyl]amino}-2-fluoropropanoic acid (0.41 g, 77%).

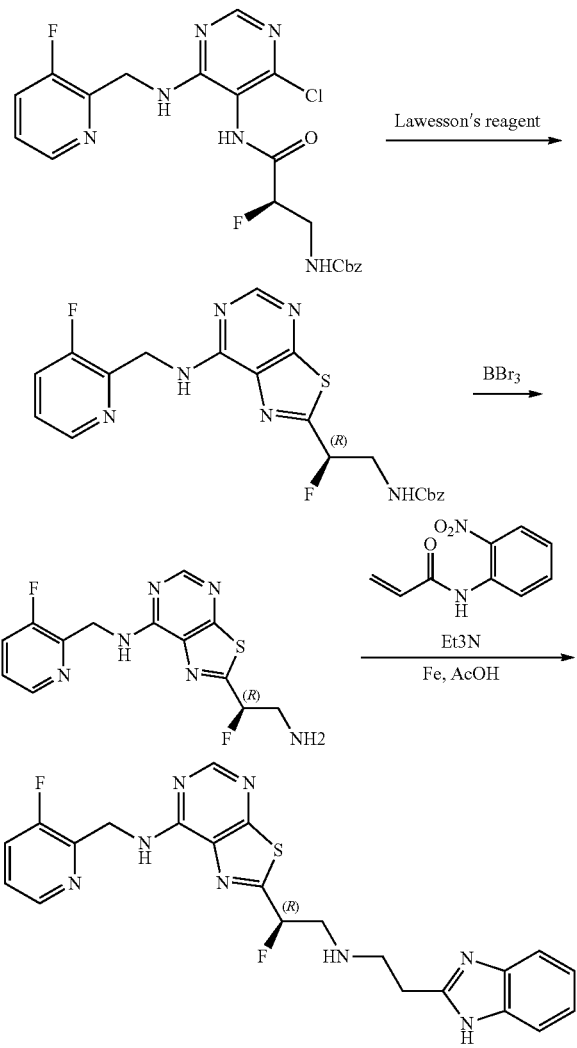

Step 1

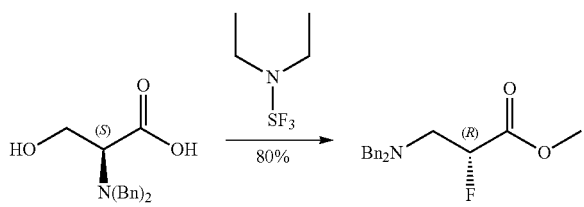

To a solution of dibenzyl-L-serine (5.00 g; 16.70 mmol; 1.00 eq.) in THF (35 mL) was added N-ethyl-N-(trifluoro-lambda~4~-sulfanyl)ethanamine (4.08 mL; 30.90 mmol; 1.85 eq.) in THF (5 mL) dropwise. After being stirred at room temperature for 1 h, the mixture was poured onto ice water and EtOAc and Sat $NaHCO_3$ were added. The organic layer was separated, and the aqueous layer was further extracted with EtOAc. Following this, the organic layers were combined, dried and concentrated, and the crude product was purified by column chromatography (hexanes/EtOAc=3:1) to give methyl (2R)-3-(dibenzylamino)-2-fluoropropanoate (4.02 g, 80%).

Step 5

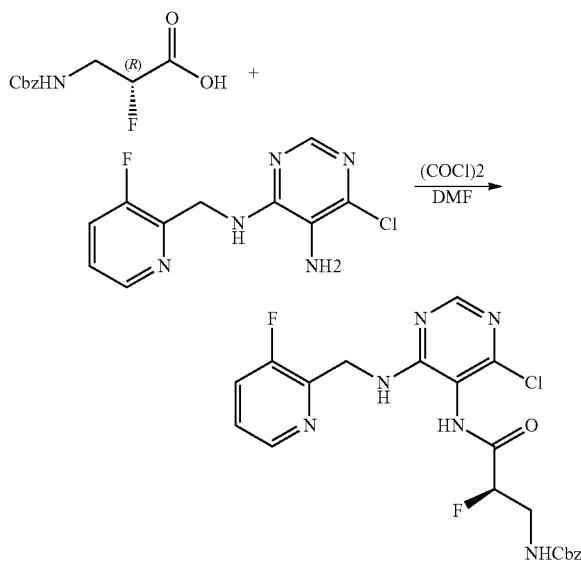

To a solution of (2R)-3-{[(benzyloxy)carbonyl]amino}-2-fluoropropanoic acid (397.49 mg; 1.65 mmol; 1.90 eq.) in DCM (8 mL) was added DMF (5 drops), followed by oxalyl chloride (0.21 mL; 2.43 mmol; 2.80 eq.). After being stirred at room temperature for 3 h, the mixture was concentrated to give the crude acid chloride. The crude acid chloride was dissolved in DMA (2 mL) and the solution was added to another solution of (2R)-3-{[(benzyloxy)carbonyl]amino}-2-fluoropropanoic acid (397.49 mg; 1.65 mmol; 1.90 eq.) in DMA (4 mL). The mixture was stirred for 1 h and was subjected to an aqueous workup and extracted with EtOAc. The organic layers were combined, dried, and concentrated to give benzyl N-[(2R)-2-[(4-chloro-6-{[(3-fluoropyridin-2-yl)methyl]amino}pyrimidin-5-yl)carbamoyl]-2-fluoroethyl]carbamate, which was used in the next step without purification (0.5 g, 120%).

Step 6

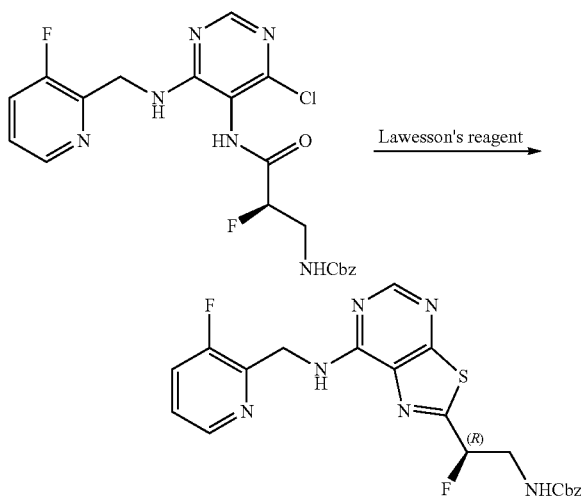

To a solution of benzyl N-[(2R)-2-[(4-chloro-6-{[(3-fluoropyridin-2-yl)methyl]amino}pyrimidin-5-yl)carbamoyl]-2-fluoroethyl]carbamate (413.00 mg; 0.87 mmol; 1.00 eq.) in Dioxane (10 mL) was added 2,4-bis(4-methoxyphenyl)-1,3,2,4-dithiadiphosphetane 2,4-disulfide (385.33 mg; 0.95 mmol; 1.10 eq.). The solution was degassed with N₂ and heated at 95° C. for 3 h. Following this, 200 mg more of Lawesson reagent was added and the mixture was further stirred for 30 min, cooled to room temperature, subjected to aqueous workup, and extracted with EtOAc. The organic layers were combined, dried and concentrated to give the crude product, which was purified by column chromatography (Hexanes/EtOAc=50:50 to 0:100) to give benzyl N-[(2R)-2-fluoro-2-(7-{[(3-fluoropyridin-2-yl)methyl]amino}-[1,3]thiazolo[5,4-d]pyrimidin-2-yl)ethyl]carbamate (0.38 g, 78%).

Step 7

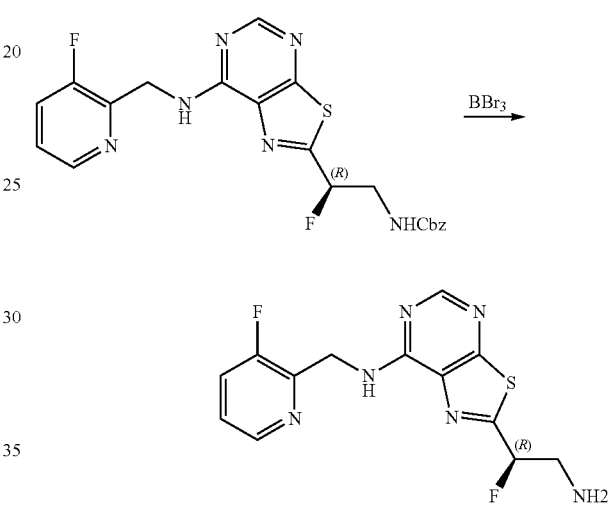

To a solution of benzyl N-[(2R)-2-fluoro-2-(7-{[(3-fluoropyridin-2-yl)methyl]amino}-[1,3]thiazolo[5,4-d]pyrimidin-2-yl)ethyl]carbamate (308.00 mg; 0.67 mmol; 1.00 eq.) in DCM (5 mL) was added boron tribromide (1.35 mL; 1.00 mol/L; 1.35 mmol; 2.00 eq.). The resulting slurry was stirred further for 2 h, and the mixture was concentrated, and the resulting slurry was washed with ether. The solid was filtered off and subjected to Sat. NaHCO₃ and EtOAc, the organic layer was separated, and the aqueous layer was further extracted with EtOAc. The organic layers were combined, dried, and concentrated to give 2-[(1R)-2-amino-1-fluoroethyl]-N-[(3-fluoropyridin-2-yl)methyl]-[1,3]thiazolo[5,4-d]pyrimidin-7-amine as a crude solid, which was used directly in the next step without purification (0.216 g, 99%).

Step 8

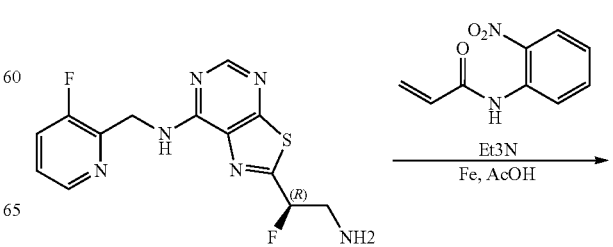

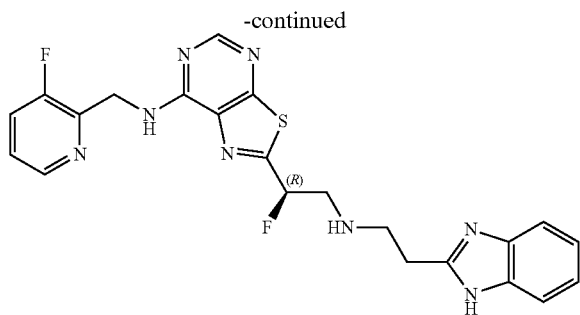

To a solution of 2-[(1R)-2-amino-1-fluoroethyl]-N-[(3-fluoropyridin-2-yl)methyl]-[1,3]thiazolo[5,4-d]pyrimidin-7-amine (216.00 mg; 0.67 mmol; 1.00 eq.) in AcCN (5 mL) was added triethylamine (0.28 mL; 2.01 mmol; 3.00 eq.), followed by N-(2-nitrophenyl)prop-2-enamide (128.78 mg; 0.67 mmol; 1.00 eq.). The reaction mixture was heated at 55° C. for 15 h, cooled, and concentrated to give the crude product. To the crude product in AcOH (3 mL) was added iron (187.11 mg; 3.35 mmol; 5.00 eq.) and the mixture was heated at 80° C. for 1 h, cooled, and diluted with AcCN/water. The mixture was filtered, and the filtrate was concentrated and subjected to preparative HPLC to give 2-[(1R)-2-{[2-(1H-1,3-benzodiazol-2-yl)ethyl]amino}-1-fluoroethyl]-N-[(3-fluoropyridin-2-yl)methyl]-[1,3]thiazolo[5,4-d]pyrimidin-7-amine (33.7 mg, 10.8%). $^1$H NMR (400 MHz, Methanol-$d_4$) δ 8.32 (d, J=22.9 Hz, 2H), 7.59 (ddd, J=9.7, 8.2, 1.3 Hz, 1H), 7.38 (ddt, J=13.1, 8.5, 3.8 Hz, 3H), 7.25-7.07 (m, 2H), 6.09 (d, J=6.2 Hz, 1H), 5.97 (s, 1H), 4.94 (s, 2H), 3.60-3.39 (m, 3H), 3.31-3.19 (m, 2H), 3.22-3.10 (m, 2H). LCMS: (ES, m/z): [M+H]$^+$: 467.0.

Example 1.83

Synthesis of N-{[2-(2-{[2-(1H-1,3-benzodiazol-2-yl)ethyl]amino}ethyl)-7-{[(3-fluoropyridin-2-yl)methyl]amino}-[1,3]thiazolo[5,4-d]pyrimidin-5-yl]oxy}acetamide (Compound 29)

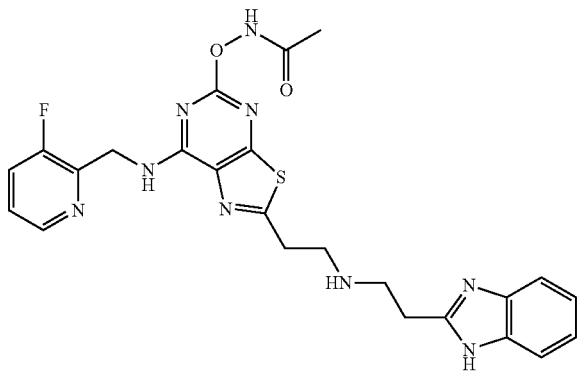 [SMILES: CC(=O)NOc1nc(NCc2ncccc2F)c2nc(CCNCCc3nc4ccccc4[nH]3)sc2n1]

Compound 29 was synthesized according to scheme 24. Into a 50-mL round-bottom flask, was placed 2-(2-((2-(1H-benzo[d]imidazol-2-yl)ethyl)amino)ethyl)-5-chloro-N-((3-fluoropyridin-2-yl)methyl)thiazolo[5,4-d]pyrimidin-7-amine (650.00 mg, 1.34 mmol, 1.00 equiv), DMSO (10.00 mL), K$_2$CO$_3$ (1.30 g, 9.421 mmol, 7.00 equiv), N-hydroxyacetamide (303 mg, 4.03 mmol, 3.00 equiv). The resulting solution was stirred for 16 hr at 80° C., cooled down and filtered. The crude product was purified by Prep-HPLC with the following conditions (Prep-HPLC-006): Column, XBridge Prep C$^{18}$ OBD Column, 19*150 mm 5 um; mobile phase, Water (10 MMOL/L NH$_4$HCO$_3$+0.1% NH$_3$.H$_2$O) and ACN (30% Phase B up to 40% in 7 min); Detector, UV. This resulted in 20.9 mg (3.0%) of N-((2-(2-((2-(1H-benzo[d]imidazol-2-yl)ethyl)amino)ethyl)-7-(((3-fluoropyridin-2-yl)methyl)amino)thiazolo[5,4-d]pyrimidin-5-yl)oxy)acetamide as a white solid and 101.3 mg (16.2%) of 2-(2-((2-(1H-benzo[d]imidazol-2-yl)ethyl)amino)ethyl)-7-(((3-fluoropyridin-2-yl)methyl)amino)thiazolo[5,4-d]pyrimidin-5-ol as a white solid. $^1$H NMR (300 MHz, DMSO-$d_6$) δ 12.25 (s, 1H), 11.31 (s, 1H), 8.37 (dt, J=4.7, 1.5 Hz, 1H), 8.22 (s, 1H), 7.71 (ddd, J=10.0, 8.3, 1.3 Hz, 1H), 7.52-7.35 (m, 3H), 7.19-7.04 (m, 2H), 6.64 (d, J=4.6 Hz, 1H), 4.80 (d, J=5.3 Hz, 2H), 3.68 (t, J=7.2 Hz, 2H), 3.57 (t, J=7.4 Hz, 2H), 3.16 (t, J=7.3 Hz, 2H), 3.03 (t, J=7.2 Hz, 2H), 2.59 (d, J=4.2 Hz, 3H). [M+1]$^+$ m/z: 522.2.

Example 1.83

Synthesis of 2-(2-{[2-(1H-1,3-benzodiazol-2-yl)ethyl]amino}-1,1-difluoroethyl)-N-[(3-fluoropyridin-2-yl)methyl]-[1,3]oxazolo[4,5-c]pyridin-4-amine (Compound 81)

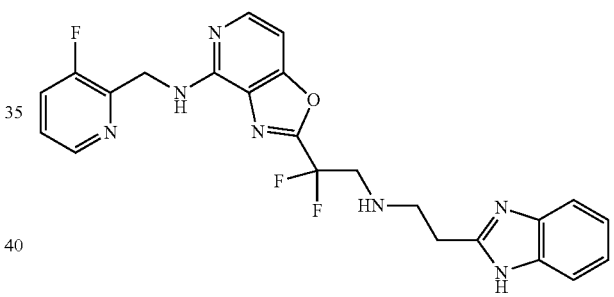

Scheme 59 depicts a synthetic route for preparing an exemplary compound.

Scheme 59

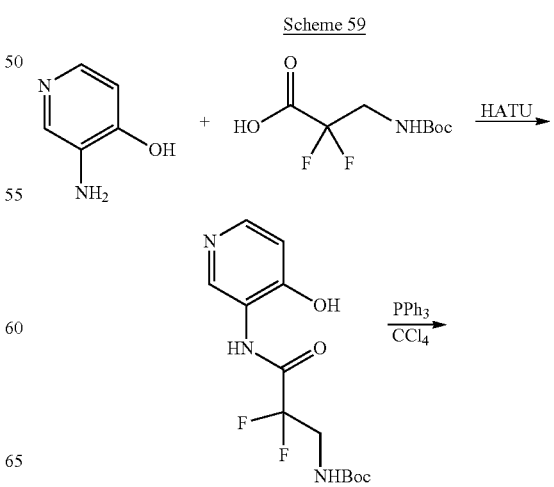

-continued

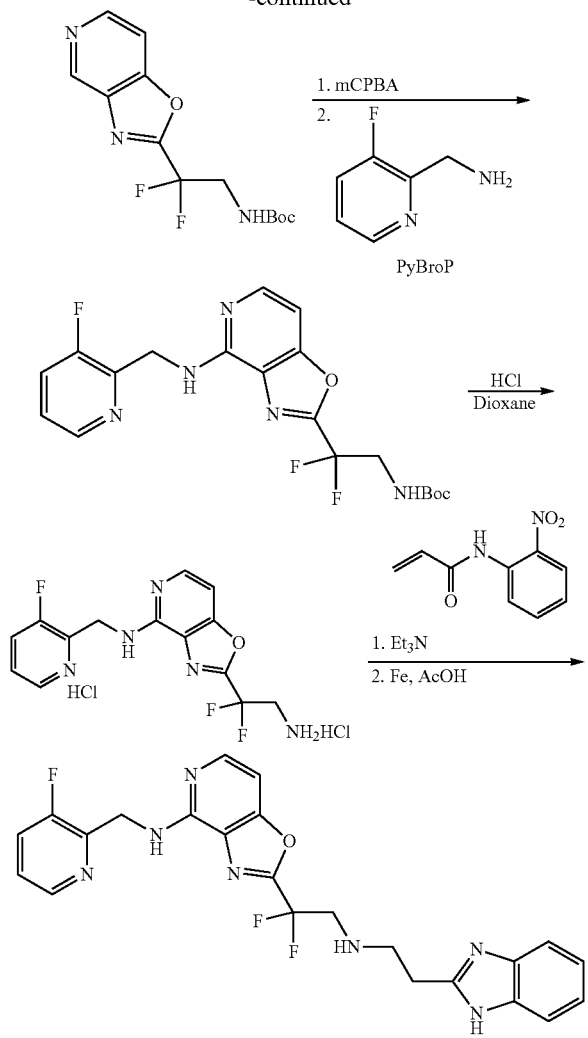

Step 1:

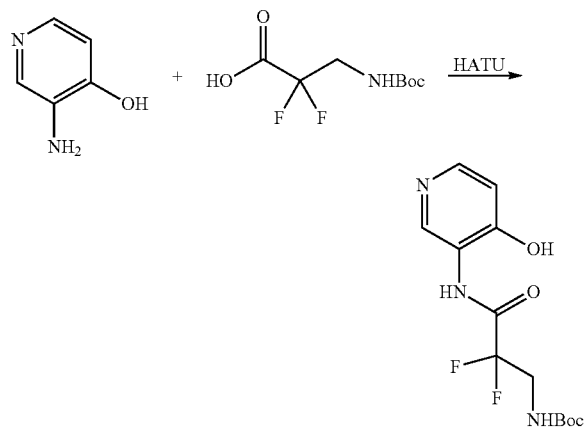

To a solution of 3-amino-4-pyridinol (268.94 mg; 2.44 mmol; 1.10 eq.) and 3-{[(tert-butoxy)carbonyl]amino}-2,2-difluoropropanoic acid (500.00 mg; 2.22 mmol; 1.00 eq.) in DMF (5 mL) was added Hunig's base (0.77 mL; 4.44 mmol; 2.00 eq.) and HATU (928.67 mg; 2.44 mmol; 1.10 eq.). The mixture was stirred further for 15 h. To the mixture was then added Sat. NaHCO₃ and the mixture was extracted with EtOAc. The organic layers were combined, washed with brine, dried over MgSO₄, and concentrated under vacuo to give tert-butyl N-{2,2-difluoro-2-[(4-hydroxypyridin-3-yl)carbamoyl]ethyl}carbamate (650 mg, 92.3% yield), which was used in the next step without purification. LCMS [M+1]⁺ m/z: 318.4.

Step 2:

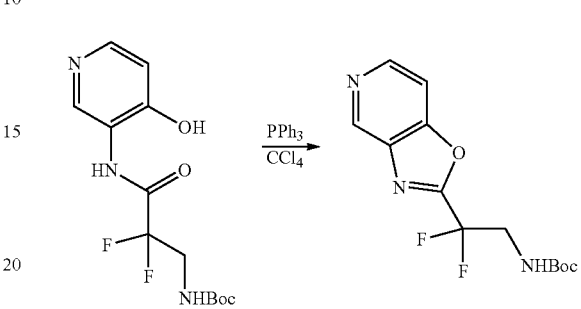

To a solution of tert-butyl N-{2,2-difluoro-2-[(4-hydroxypyridin-3-yl)carbamoyl]ethyl}carbamate (650.00 mg; 2.05 mmol; 1.00 eq.) in DCM (20 mL) was added triethylamine (1.15 mL; 8.19 mmol; 4.00 eq.), 1,1,1,2,2,2-hexachloroethane (727.48 mg; 3.07 mmol; 1.50 eq.) and polymer supported triphenylphosphine (805.98 mg; 3.07 mmol; 1.50 eq.). The reaction was stirred under N₂ for 2 h. The mixture was diluted with AcCN, filtered, and the filtrate was concentrated to give a crude product, which was purified by column chromatography (60% EtOAc in heptane) to give tert-butyl N-(2,2-difluoro-2-{[1,3]oxazolo[4,5-c]pyridin-2-yl}ethyl)carbamate (130 mg, 21.2% yield). LCMS [M+1]⁺ m/z: 300.1.

Step 3:

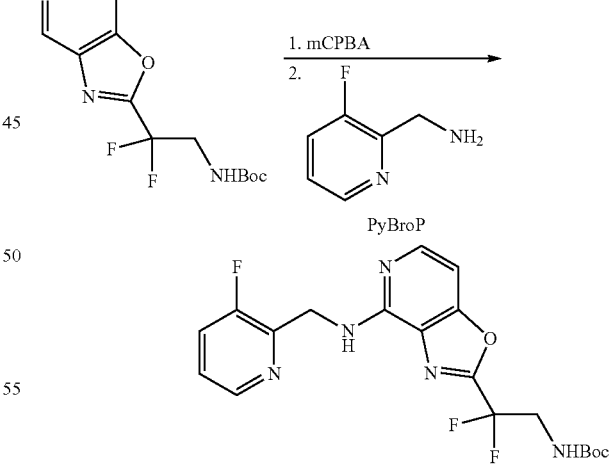

To a solution of tert-butyl N-(2,2-difluoro-2-{[1,3]oxazolo[4,5-c]pyridin-2-yl}ethyl)carbamate (130.00 mg; 0.43 mmol; 1.00 eq.) in DCM (4 mL) was added 3-chloroperoxybenzoic acid (128.50 mg; 0.52 mmol; 1.20 eq.) and the mixture was stirred for 2 h at room temperature. The mixture was then diluted with more DCM and washed with Sat. NaHCO₃ and brine, dried, and concentrated to give the desired crude pyridine oxide. The crude product was diluted with DMF (2 mL), and triethylamine (0.61 mL; 4.34 mmol; 10.00 eq.), (3-fluoropyridin-2-yl)methanamine (219.16 mg; 1.74 mmol; 4.00 eq.) and bromo[tri(1-pyrrolidinyl)]phosphonium hexafluorophosphate (810.01 mg; 1.74 mmol; 4.00 eq.) were added. After being stirred at room temperature for 15 h, the mixture was diluted with Sat. NaHCO₃. Following this, the mixture was extracted with EtOAc, the organic layers were combined, dried over MgSO₄, and concentrated to give a crude product, which was purified by silica gel column chromatography (hexanes/EtOAc=1:1) to give tert-butyl N-[2,2-difluoro-2-(4-{[(3-fluoropyridin-2-yl)methyl]amino}-[1,3]oxazolo[4,5-c]pyridin-2-yl)ethyl]carbamate (66 mg, 35.9% yield). LCMS [M+1]⁺ m/z: 424.5.

Step 4

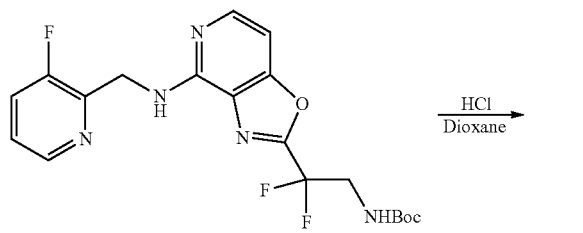

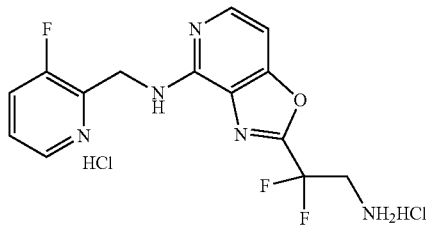

To a solution of tert-butyl N-[2,2-difluoro-2-(4-{[(3-fluoropyridin-2-yl)methyl]amino}-[1,3]oxazolo[4,5-c]pyridin-2-yl)ethyl]carbamate (66.00 mg; 0.16 mmol; 1.00 eq.) in DCM (1 mL) was added 4N HCl in dioxane (2 mL) and the mixture was stirred for 2 h at room temperature. The mixture was concentrated and diluted with 7N Ammonia in MeOH to neutralize the acid. The resulting mixture was concentrated, water and AcCN were added, and then the mixture was lyophilized to give 2-(2-amino-1,1-difluoroethyl)-N-[(3-fluoropyridin-2-yl)methyl]-[1,3]oxazolo[4,5-c]pyridin-4-amine bis HCl salt (65 mg, 105% yield), which was used in the next step without further purification. LCMS [M+1]⁺ m/z: 324.2.

Step 5

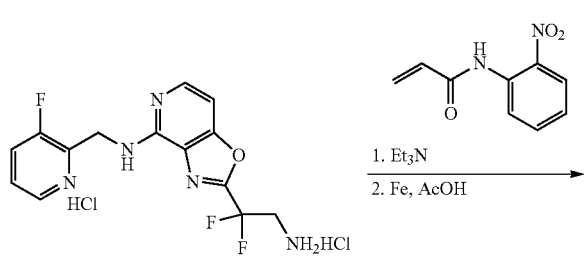

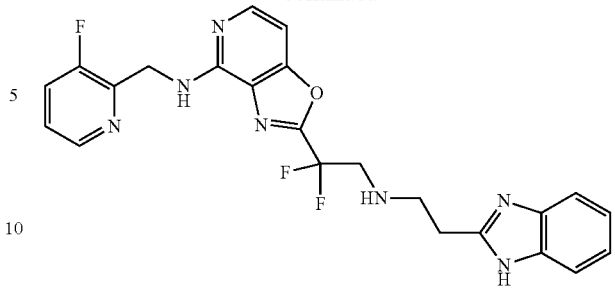

To a solution of 2-(2-amino-1,1-difluoroethyl)-N-[(3-fluoropyridin-2-yl)methyl]-[1,3]oxazolo[4,5-c]pyridin-4-amine bis HCl salt (63.4 mg; 0.16 mmol; 1.00 eq.) in AcCN (2 mL) was added triethylamine (0.07 mL; 0.48 mmol; 3.00 eq.) and N-(2-nitrophenyl)prop-2-enamide (30.75 mg; 0.16 mmol; 1.00 eq.). The mixture was heated at 55° C. for 15 h and at 80° C. for an additional 24 h. The mixture was cooled and concentrated to dryness; to this mixture was added AcOH (2 mL) and iron (26.81 mg; 0.48 mmol; 3.00 eq.). The mixture was heated at 80° C. for 2 h. HPLC indicated reaction completion. The mixture was cooled and diluted with AcCN and water. The insoluble material was filtered off and the filtrate was concentrated to give a crude product, which was purified by preparative HPLC to give 2-(2-{[2-(1H-1,3-benzodiazol-2-yl)ethyl]amino}-1,1-difluoroethyl)-N-[(3-fluoropyridin-2-yl)methyl]-[1,3]oxazolo[4,5-c]pyridin-4-amine (10.1 mg, 13.5% yield). LCMS [M+1]⁺ m/z: 468.2. ¹H NMR (400 MHz, Methanol-d₄) δ 8.39 (d, J=4.6 Hz, 1H), 8.05 (d, J=5.8 Hz, 1H), 7.65 (ddd, J=9.8, 8.3, 1.3 Hz, 1H), 7.47 (dt, J=7.0, 3.5 Hz, 2H), 7.41 (dt, J=8.5, 4.4 Hz, 1H), 7.20 (dd, J=6.0, 3.2 Hz, 2H), 6.99 (d, J=5.9 Hz, 1H), 4.96 (d, J=1.8 Hz, 2H), 3.65 (t, J=14.1 Hz, 2H), 3.21 (t, J=7.0 Hz, 2H), 3.06 (t, J=6.9 Hz, 2H).

Example 1.84

Synthesis of 2-[(1R)-2-{[2-(1H-1,3-benzodiazol-2-yl)ethyl]amino}-1-fluoroethyl]-N-[(3-fluoropyridin-2-yl)methyl]-[1,3]thiazolo[4,5-c]pyridin-4-amine (Compound 82)

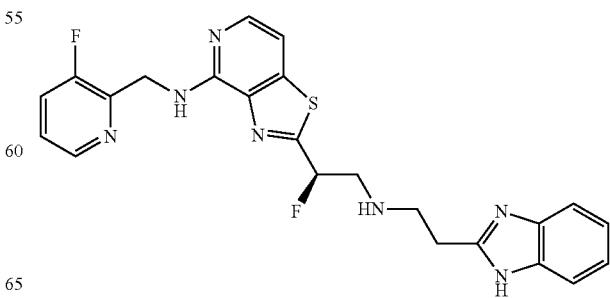

Scheme 60 depicts a synthetic route for preparing an exemplary compound.

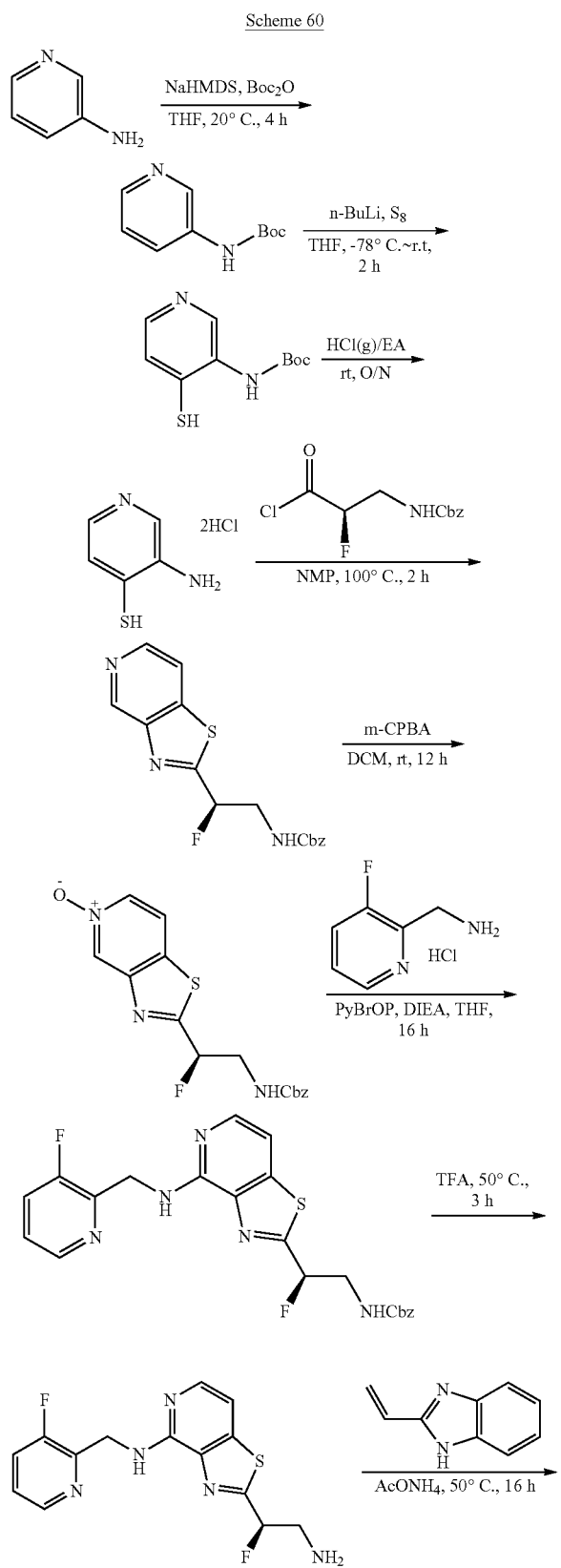

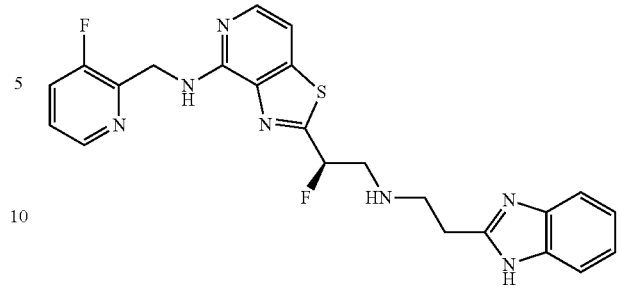

Compound 82 was synthesized in a similar manner to that of Compound 14. LCMS [M+1]+ m/z: 466.2. $^1$H NMR (300 MHz, DMSO-$d_6$) δ 8.37 (d, J=4.8 Hz, 2H), 7.91 (d, J=5.7 Hz, 1H), 7.72 (t, J=9.6 Hz, 1H), 7.48-7.36 (m, 4H), 7.17 (d, J=5.4 Hz, 1H), 7.14-7.11 (m, 2H), 6.08 (d, J=43.5 Hz, 1H), 4.87 (d, J=5.1 Hz, 2H), 3.20-2.97 (m, 7H).

Example 1.85

Synthesis of 2-[(1R)-2-{[2-(1H-1,3-benzodiazol-2-yl)ethyl]amino}-1-fluoroethyl]-7-{[(3-fluoropyridin-2-yl)methyl]amino}-[1,3]thiazolo[5,4-d]pyrimidin-5-ol (Compound 83)

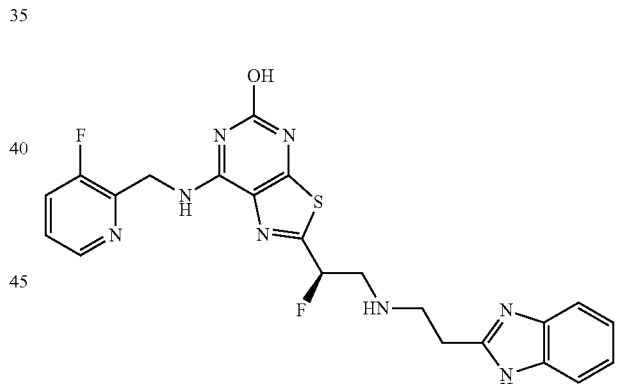

Scheme 61 depicts a synthetic route for preparing an exemplary compound.

Scheme 61

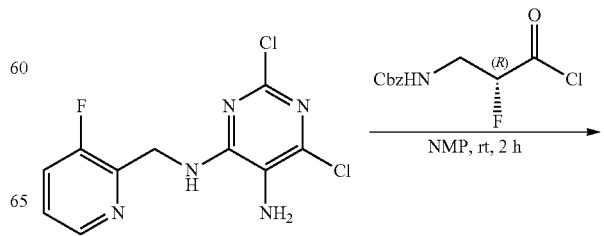

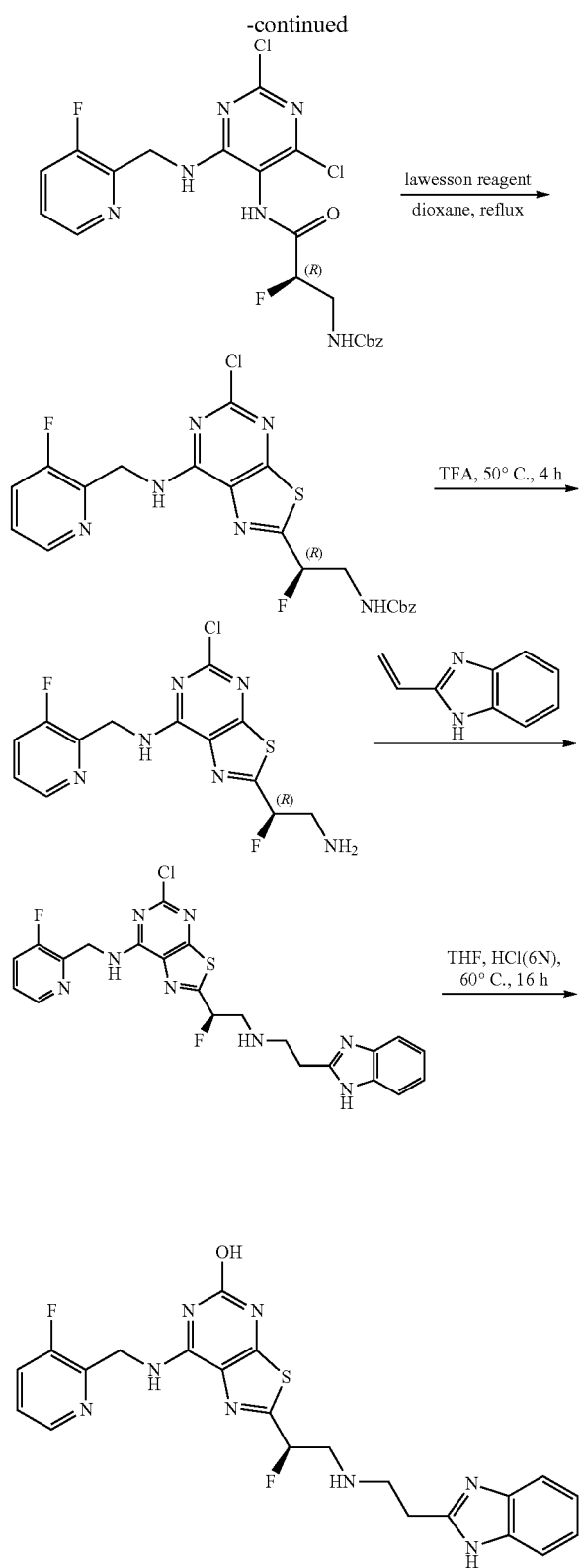

LCMS (ES) [M+1]$^+$: 483.1. $^1$H NMR (300 MHz, d$^6$-DMSO) ppm: 8.37 (d, J=1.5 Hz, 1H), 8.20 (s, 1H), 7.72 (t, J=9.6 Hz, 2H), 7.47-7.38 (m, 3H), 7.14-7.09 (m, 2H), 5.90 (d, J=42 Hz, 1H), 4.82 (d, J=4.8 Hz, 2H), 3.34-2.98 (m, 7H).

2. BIOLOGICAL EXAMPLES

Example 2.1

Biological In-Vitro Ferroportin Internalization Assay

The protocol for this assay is generally as described in WO2018/128828, incorporated herein by reference in its entirety. Functional internalization of ferroportin protein was measured using a stably-transfected CHO cell line expressing the human ferroportin tagged to a luciferase reporter. Cells were plated for 24 h in the presence of ferric ammonium citrate (FAC). Ferroportin protein expression was induced with doxycycline for 24 h. The next day, the compounds were added. Test compounds were dissolved in DMSO. Cells were incubated with the test compounds for 6 h, and subsequently luciferase activity was measured using the Nano-Glo Luciferase Assay System and Glomax (Promega, Madison, Wis.).

The average pEC$_{50}$ was determined for the test compounds. The data is provided in Table 2 below.

TABLE 2

| Compound No. from Table 1 | pEC50 |
|---|---|
| 1 | 7.8 |
| 2 | 7.3 |
| 3 | 7.1 |
| 4 | 6.6 |
| 5 | 6.8 |
| 6 | 7.8 |
| 7 | 6.7 |
| 8 | 6.4 |
| 9 | 6.3 |
| 10 | 5.7 |
| 11 | 6.7 |
| 12 | 7.3 |
| 13 | 8 |
| 14 | 7.8 |
| 15 | 6.8 |
| 16 | 5.6 |
| 17 | 7.7 |
| 18 | 5.7 |
| 19 | 6.2 |
| 20 | 7.5 |
| 21 | 6.2 |
| 22 | 6.5 |
| 23 | 8.8 |
| 24 | 5.8 |
| 25 | 6.3 |
| 26 | 6.5 |
| 27 | 6.2 |
| 28 | 6.3 |
| 29 | 5.2 |
| 30 | 7.3 |
| 31 | 5.6 |
| 32 | 6.9 |
| 33 | 6.2 |
| 34 | 5.1 |
| 35 | 7.1 |
| 36 | 6.4 |
| 37 | 5.6 |
| 38 | 4.9 |
| 39 | 6.9 |
| 40 | 6.2 |
| 41 | 7.2 |
| 42 | 7.3 |
| 43 | 8.4 |
| 44 | 4.9 |
| 45 | 6.4 |
| 46 | 7.1 |
| 47 | 5.8 |

TABLE 2-continued

| Compound No. from Table 1 | pEC50 |
|---|---|
| 48 | 7 |
| 49 | 6.9 |
| 50 | 5.1 |
| 51 | 8.2 |
| 52 | 6.6 |
| 53 | 7.3 |
| 54 | 5.1 |
| 55 | 7.6 |
| 56 | 6.7 |
| 57 | 5.4 |
| 58 | 5.7 |
| 59 | 6.2 |
| 60 | 5.8 |
| 61 | 6.9 |
| 62 | 7.7 |
| 63 | 5.1 |
| 64 | 7 |
| 65 | 6.2 |
| 66 | 5 |
| 67 | 6.2 |
| 68 | 5.8 |
| 69 | 5.2 |
| 70 | 5.6 |
| 71 | 5.2 |
| 72 | 6.4 |
| 73 | 7.6 |
| 74 | 6.9 |
| 75 | 7.1 |
| 76 | 8.1 |
| 77 | 7.8 |
| 78 | <5 |
| 79 | <5 |
| 80 | <5 |
| 81 | 6.3 |
| 82 | 6.4 |
| 83 | 7.1 |

Efforts have been made to ensure accuracy with respect to numbers used (e.g., amounts, temperature, etc.) but some experimental errors and deviations should be accounted for.

One skilled in the art will recognize many methods and materials similar or equivalent to those described herein, which could be used in the practicing the subject matter described herein. The present disclosure is in no way limited to just the methods and materials described.

Unless defined otherwise, technical and scientific terms used herein have the same meaning as commonly understood by one of ordinary skill in the art to which this subject matter belongs, and are consistent with: Singleton et al (1994) Dictionary of Microbiology and Molecular Biology, 2nd Ed., J. Wiley & Sons, New York, N.Y.; and Janeway, C., Travers, P., Walport, M., Shlomchik (2001) Immunobiology, 5th Ed., Garland Publishing, New York.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

Where a range of values is provided, it is understood that each intervening value, to the tenth of the unit of the lower limit, unless the context clearly dictates otherwise, between the upper and lower limit of the range and any other stated or intervening value in that stated range, is encompassed. The upper and lower limits of these small ranges which may independently be included in the smaller rangers is also encompassed, subject to any specifically excluded limit in the stated range. Where the stated range includes one or both of the limits, ranges excluding either or both of those included limits are also included.

Many modifications and other embodiments set forth herein will come to mind to one skilled in the art to which this subject matter pertains having the benefit of the teachings presented in the foregoing descriptions and the associated drawings. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A compound of Formula I:

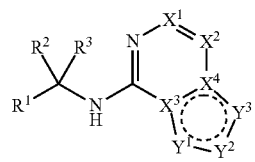

I wherein
$R^1$ is phenyl or a 6-membered heteroaryl, wherein the heteroaryl contains up to two ring heteroatoms, wherein the phenyl and heteroaryl are optionally substituted with one, two, three, or four substituents, each of which is independently selected from the group consisting of $C_1$-$C_6$ alkyl, halogen, —$OR^{1a}$, —$NR^{1b}R^{1c}$, —$N_3$, and —CN;
wherein $R^{1a}$, $R^{1b}$, and $R^{1c}$ are each independently selected from the group consisting of hydrogen and $C_1$-$C_6$ alkyl;
$R^2$ and $R^3$ are each independently hydrogen or $C_1$-$C_6$ alkyl; or $R^2$ and $R^3$ taken together with the carbon to which they are attached form a $C_3$-$C_6$ cycloalkyl;
$X^1$ is $CR^{10}$ and $X^2$ is N or $CR^{10}$; wherein
$R^{10}$ is selected from the group consisting of hydrogen, halogen, —CN, $C_1$-$C_3$ alkyl, —$OR^{15}$, and —$NR^{16}R^{17}$; wherein
$R^{15}$, $R^{16}$, and $R^{17}$ are each independently selected from the group consisting of hydrogen, $C_1$-$C_6$ alkyl, optionally substituted $C_3$-$C_7$ cycloalkyl, and —$NR^g(CO)R^h$; wherein
$R^g$ and $R^h$ are independently selected from the group consisting of hydrogen and $C_1$-$C_3$ alkyl;
$X^3$ and $X^4$ are each independently C;
$Y^1$ is N or $NR^{18}$;
$Y^2$ is $CJ^1$; and
$Y^3$ is N, O, S, $CR^{18}$, or $NR^{18}$;
wherein
$R^{18}$ is hydrogen or $C_1$-$C_3$ alkyl; and
$J^1$ is

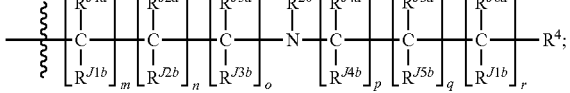

wherein
$R^{20}$ is selected from the group consisting of hydrogen and $C_1$-$C_6$ alkyl;

m, n, and o are each independently 0 or 1, provided that the sum of m, n, and o is at least 1;

p, q, and r are each independently 0 or 1, provided that the sum of p, q, and r is at least 1;

each $R^{J1a}$, $R^{J1b}$, $R^{J2a}$, $R^{J2b}$, $R^{J3a}$, $R^{J3b}$, $R^{J4a}$, $R^{J4b}$, $R^{J5a}$, $R^{J5b}$, $R^{J6a}$, and $R^{J6b}$ is independently selected from the group consisting of hydrogen, halogen, hydroxy, $C_1$-$C_3$ alkyl, $C_3$-$C_6$ cycloalkyl, and a 4- to 6-membered heterocycle; or wherein two of $R^{J1a}$, $R^{J2a}$, $R^{J3a}$, and $R^{20}$ or two of $R^{J4a}$, $R^{J5a}$, $R^{J6a}$, and $R^{20}$ or on of $R^{J1a}$, $R^{J2a}$, and $R^{J3a}$, and one of $R^{J4a}$, $R^{J5a}$, and $R^{J6a}$ take together with the atom to which they are attached form a $C_3$-$C_6$ cycloalkyl or a 4- to 6-membered heterocycle; and $R^4$ is $C_6$-$C_{10}$ aryl or 5- to 10-membered heteroaryl, each of which is optionally substituted;

or a pharmaceutically acceptable salt thereof.

2. The compound of claim 1, or a pharmaceutically acceptable salt thereof, wherein $R^{15}$, $R^{16}$, and $R^{17}$ are each independently selected from the group consisting of hydrogen and $C_1$-$C_6$ alkyl;

$Y^1$ is N;

each $R^{J1a}$, $R^{J1b}$, $R^{J2a}$, $R^{J2b}$, $R^{J3a}$, $R^{J3b}$, $R^{J4a}$, $R^{J4b}$, $R^{J5a}$, $R^{J5b}$, $R^{J6a}$, and $R^{J6b}$ is independently selected from the group consisting of hydrogen, fluorine, methyl, and hydroxy; or wherein two of $R^{J1a}$, $R^{J2a}$, $R^{J3a}$, and $R^{20}$ or two of $R^{J4a}$, $R^{J5a}$, $R^{J6a}$, and $R^{20}$ taken together with the atom to which they are attached form a $C_3$-$C_6$ cycloalkyl or a 4- to 6-membered heterocycle; and $R^4$ is $C_6$-$C_{10}$ aryl or 5- to 10-membered heteroaryl, wherein the aryl or heteroaryl is optionally substituted with one, two, three, or four substituents, each of which is independently selected from the group consisting of hydrogen, $C_3$-$C_6$ cycloalkyl, phenyl, benzyl, halo-$C_1$-$C_3$ alkyl, 5- to 7-membered heteroaryl, ($C_3$-$C_6$ cycloalkyl)-$C_1$-$C_3$ alkyl, $C_1$-$C_6$ alkyl, —C(O)O—$C_1$-$C_6$ alkyl, halogen, —$OR^{4a}$, —CN, —C(O)$NR^{4b}R^{4c}$, and —$NR^{4b}$(CO)$R^{4c}$;

wherein said phenyl or 5- to 7-membered heteroaryl is optionally substituted with one, two, or three substituents, each of which is independently selected from the group consisting of halogen, halo-$C_1$-$C_3$ alkyl, and $C_1$-$C_6$ alkyl;

wherein $R^{4a}$ is hydrogen; and $R^{4b}$ and $R^{4c}$ are independently selected from the group consisting of hydrogen and $C_1$-$C_3$ alkyl.

3. The compound of claim 1, wherein the compound is of Formula Ib:

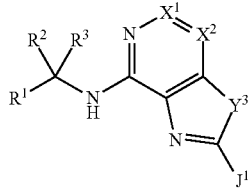

Ib wherein $Y^3$ is $NR^{18}$, O or S.

4. The compound of claim 1, wherein $Y^3$ is S or O.

5. The compound of claim 1, wherein the compound is of Formula Ic:

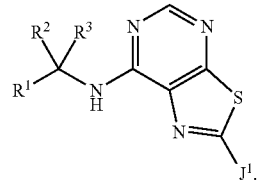

Ic

6. The compound of claim 1, wherein the compound is of Formula Id:

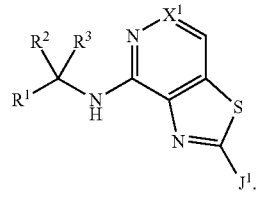

Id

7. The compound of claim 1, wherein the compound is of Formula Ie:

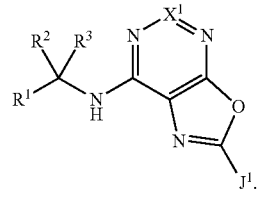

Ie

8. The compound of claim 1, wherein the compound is of Formula If:

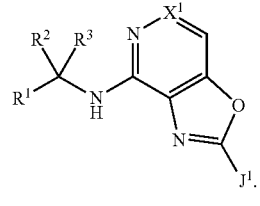

If

9. The compound of claim 1, wherein the compound is of Formula Ig:

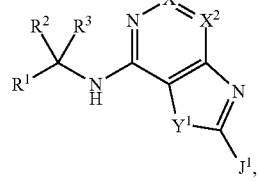

Ig wherein $Y^1$ is $NR^{18}$, O, or S.

10. The compound of claim 1, wherein $R^1$ is an optionally substituted, 6-membered heteroaryl containing one or two ring heteroatoms.

11. The compound of claim 1, wherein $R^1$ is optionally substituted pyridinyl.

12. The compound of claim 1, wherein $R^2$ and $R^3$ are each hydrogen.

13. The compound of claim 1, wherein $X^2$ is N.

14. The compound of claim 13, wherein $R^{10}$ is hydrogen.

15. The compound of claim 14, wherein $R^{20}$ is hydrogen.

16. The compound of claim 1, wherein the sum of m, n, and o is 2, and the sum of p, q, and r is 2.

17. The compound of claim 16, wherein n, o, p, and q, in each instance is 1.

18. The compound of claim 1, wherein each of $R^{J1a}$, $R^{J1b}$, $R^{J2a}$, $R^{J2b}$, $R^{J3a}$, $R^{J3b}$, $R^{J4a}$, $R^{J4b}$, $R^{J5a}$, $R^{J5b}$, $R^{J6a}$, and $R^{J6b}$, if present, is hydrogen.

19. The compound of claim 1, wherein m is 1; $R^{J1a}$ is fluorine; $R^{J1b}$ is hydrogen or fluorine; and each of $R^{J2a}$, $R^{J2b}$, $R^{J3a}$, $R^{J3b}$, $R^{J4a}$, $R^{J4b}$, $R^{J5a}$, $R^{J5b}$, $R^{J6a}$, and $R^{J6b}$, if present, is hydrogen.

20. The compound of claim 1, wherein $R^4$ is a 5- to 10-membered heteroaryl.

21. The compound of claim 1, wherein $R^4$ is a 9-membered bicyclic heteroaryl.

22. The compound of claim 1, wherein $R^4$ is

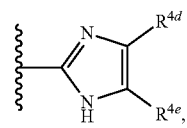

wherein $R^{4d}$ and $R^{4e}$ are independently selected from the group consisting of hydrogen, $C_1$-$C_3$ alkyl, halo-$C_1$-$C_3$ alkyl, 5- to 7-membered heteroaryl, ($C_3$-$C_6$ cycloalkyl)-$C_1$-$C_3$ alkyl, $C_3$-$C_6$ cycloalkyl, phenyl, and benzyl, and wherein said phenyl or 5- to 7-membered heteroaryl is optionally substituted with one, two, or three substituents, each of which is independently selected from the group consisting of halogen, halo-$C_1$-$C_3$ alkyl, and $C_1$-$C_6$ alkyl.

23. The compound of claim 1, wherein the compound has one of the following structures:

| Compound No. | Structure |
|---|---|
| 1 | 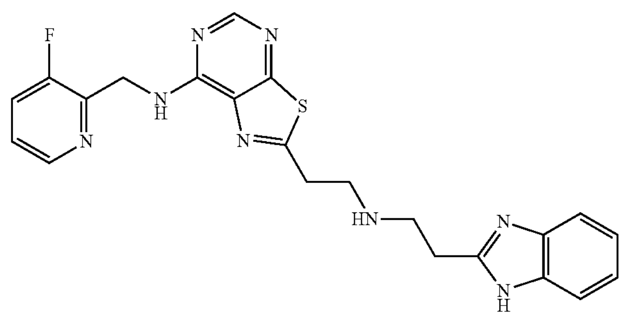 |
| 2 | 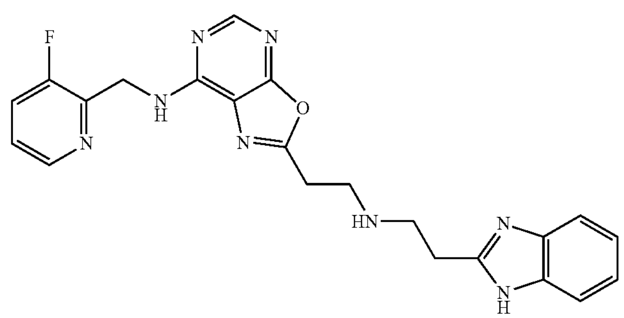 |
| 3 | 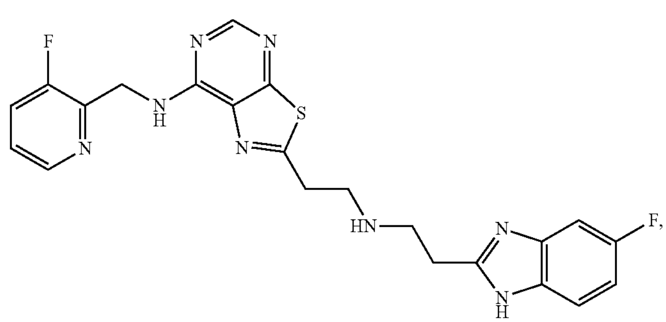 [SMILES: Fc1ccc2[nH]c(CCNCCc3nc4c(NCc5ncccc5F)ncnc4s3)nc2c1] |

| Compound No. | Structure |
|---|---|
| 4 | 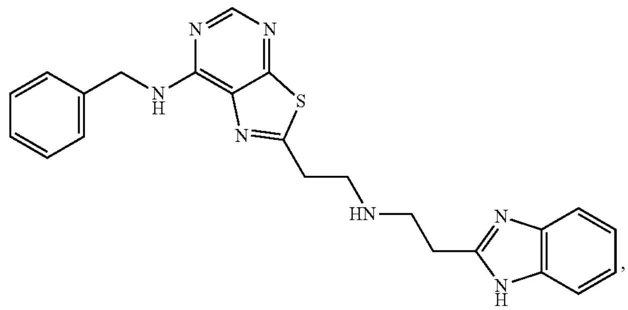 [SMILES: c1ccc(CNc2ncnc3sc(CCNCCc4nc5ccccc5[nH]4)nc23)cc1] |
| 5 | 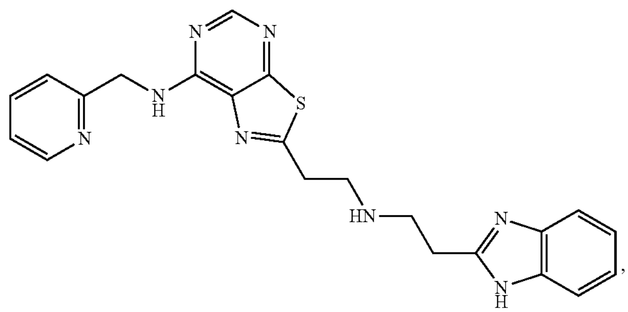 [SMILES: c1ccc(CNc2ncnc3sc(CCNCCc4nc5ccccc5[nH]4)nc23)nc1] |
| 6 | 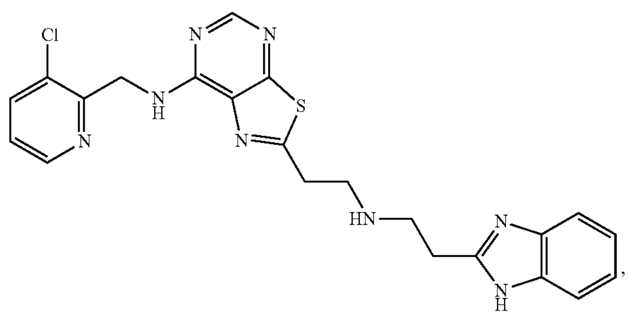 [SMILES: Clc1cccnc1CNc1ncnc2sc(CCNCCc3nc4ccccc4[nH]3)nc12] |
| 7 | 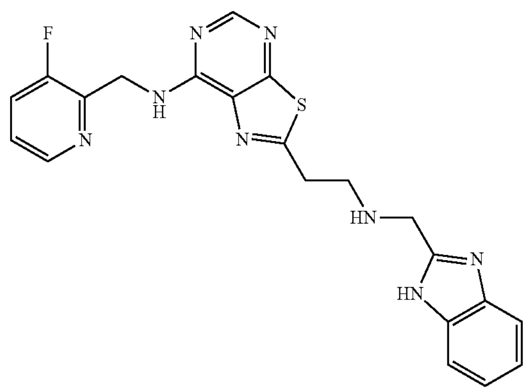 |

| Compound No. | Structure |
|---|---|
| 8 | 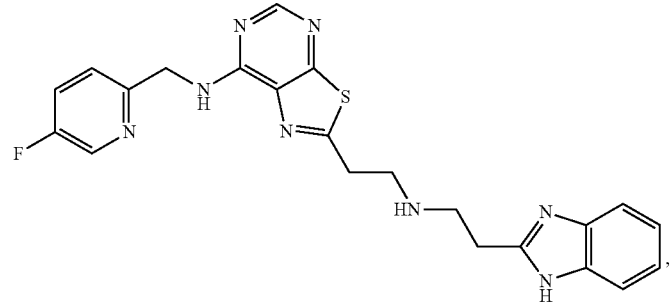 [SMILES: Fc1ccc(CNc2ncnc3sc(CCNCCc4nc5ccccc5[nH]4)nc23)nc1] |
| 9 | 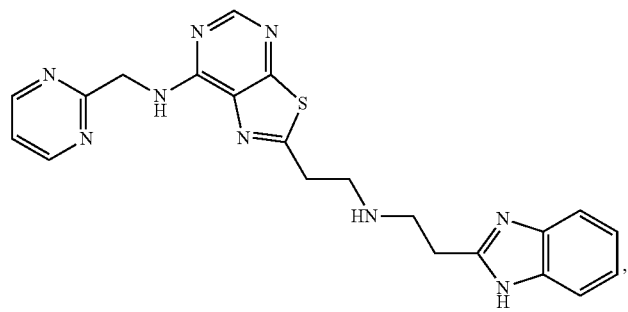 [SMILES: c1cnc(CNc2ncnc3sc(CCNCCc4nc5ccccc5[nH]4)nc23)nc1] |
| 10 | 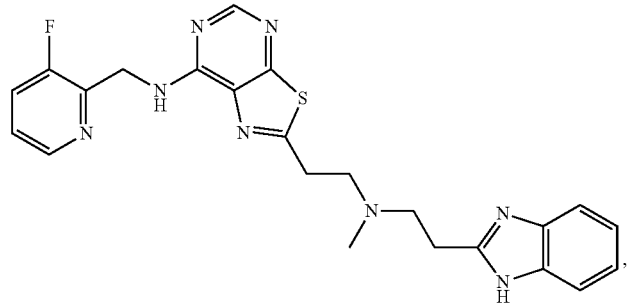 [SMILES: CN(CCc1nc2ccccc2[nH]1)CCc1nc2c(NCc3ncccc3F)ncnc2s1] |
| 11 | 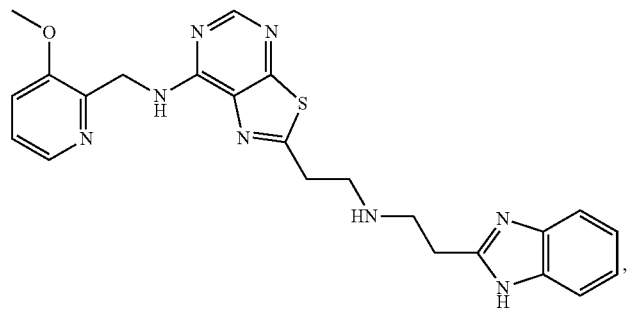 [SMILES: COc1cccnc1CNc1ncnc2sc(CCNCCc3nc4ccccc4[nH]3)nc12] |
| 12 | 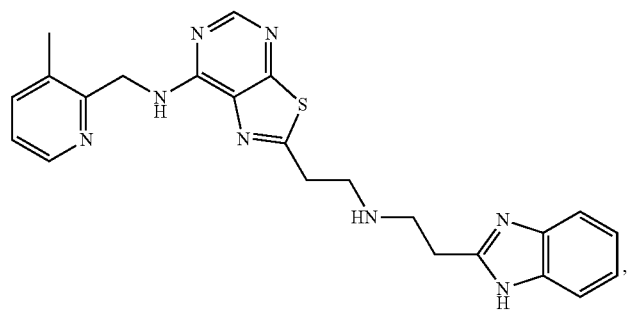 [SMILES: Cc1cccnc1CNc1ncnc2sc(CCNCCc3nc4ccccc4[nH]3)nc12] |

| Compound No. | Structure |
|---|---|
| 13 | 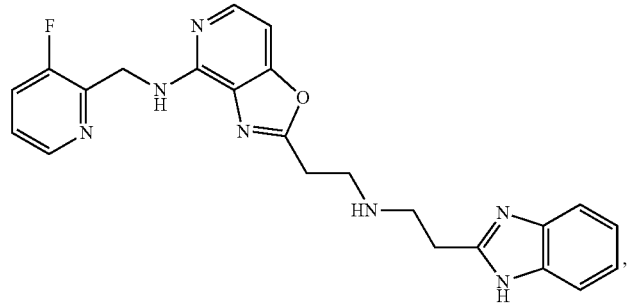 [SMILES: Fc1cccnc1CNc1nccc2oc(CCNCCc3nc4ccccc4[nH]3)nc12] |
| 14 | 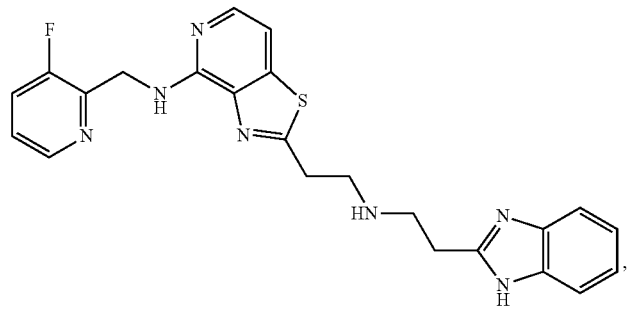 [SMILES: Fc1cccnc1CNc1nccc2sc(CCNCCc3nc4ccccc4[nH]3)nc12] |
| 15 | 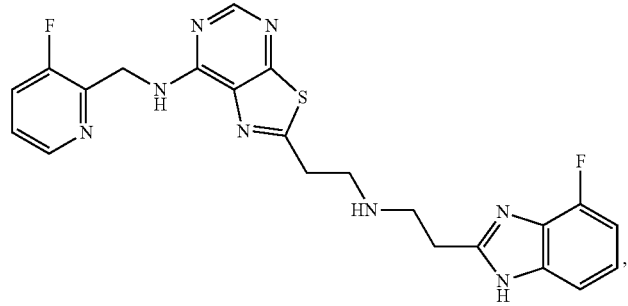 [SMILES: Fc1cccnc1CNc1ncnc2sc(CCNCCc3nc4c(F)cccc4[nH]3)nc12] |
| 16 | 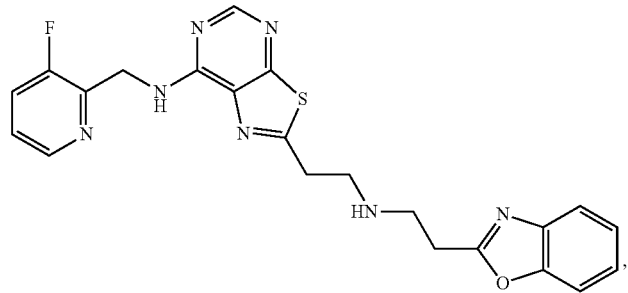 [SMILES: Fc1cccnc1CNc1ncnc2sc(CCNCCc3nc4ccccc4o3)nc12] |
| 17 | 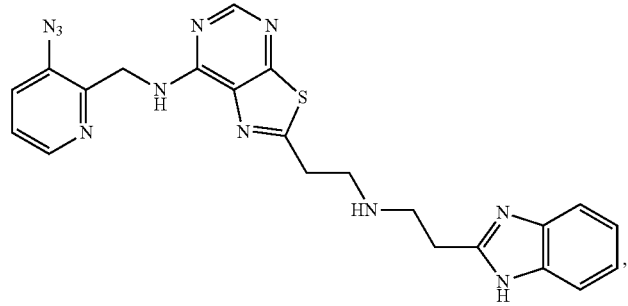 [SMILES: [N-]=[N+]=Nc1cccnc1CNc1ncnc2sc(CCNCCc3nc4ccccc4[nH]3)nc12] |

| Compound No. | Structure |
|---|---|
| 18 | 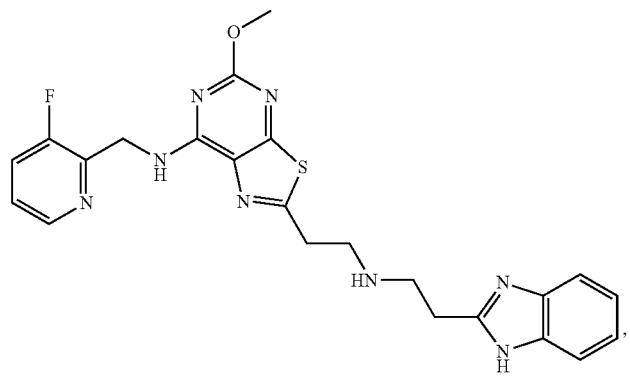 [SMILES: COc1nc(NCc2ncccc2F)c2nc(CCNCCc3nc4ccccc4[nH]3)sc2n1] |
| 19 | 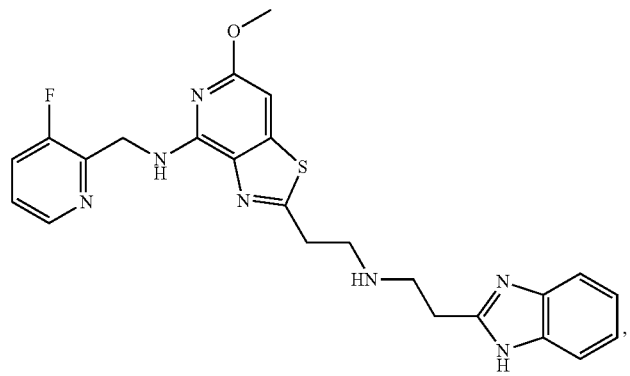 [SMILES: COc1cc2sc(CCNCCc3nc4ccccc4[nH]3)nc2c(NCc2ncccc2F)n1] |
| 20 | 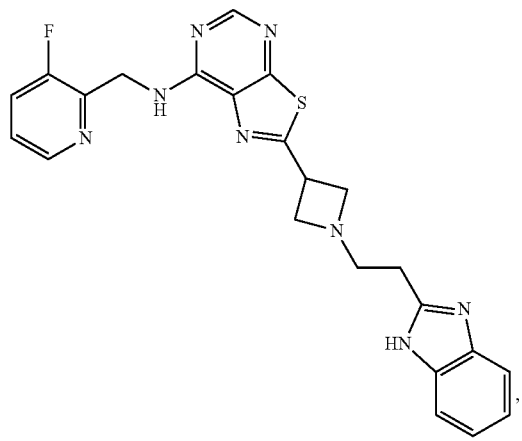 [SMILES: Fc1cccnc1CNc1ncnc2sc(C3CN(CCc4nc5ccccc5[nH]4)C3)nc12] |
| 21 | 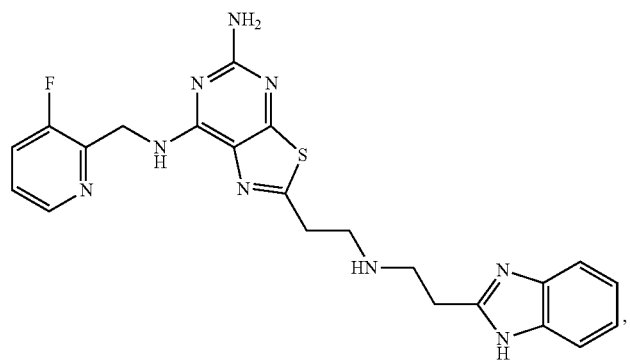 [SMILES: Nc1nc(NCc2ncccc2F)c2nc(CCNCCc3nc4ccccc4[nH]3)sc2n1] |

| Compound No. | Structure |
|---|---|
| 22 | (structure) |
| 23 | (structure) |
| 24 | (structure) |
| 25 | (structure) |

-continued
| Compound No. | Structure |
|---|---|
| 26 | 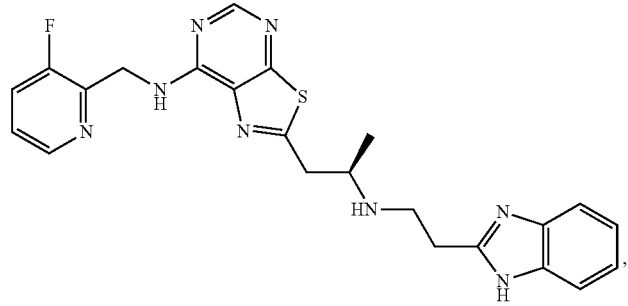 [SMILES: C[C@H](Cc1nc2c(NCc3ncccc3F)ncnc2s1)NCCc1nc2ccccc2[nH]1] |
| 27 | 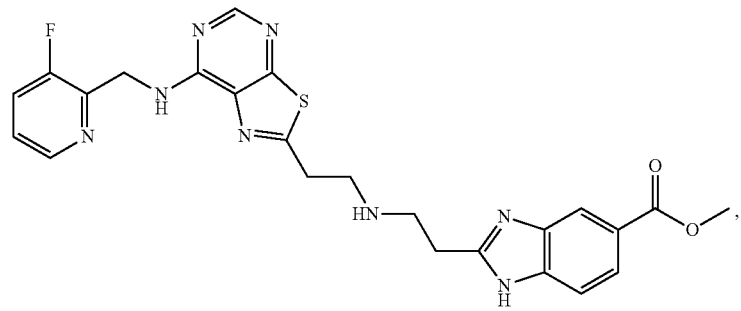 [SMILES: COC(=O)c1ccc2[nH]c(CCNCCc3nc4c(NCc5ncccc5F)ncnc4s3)nc2c1] |
| 28 | 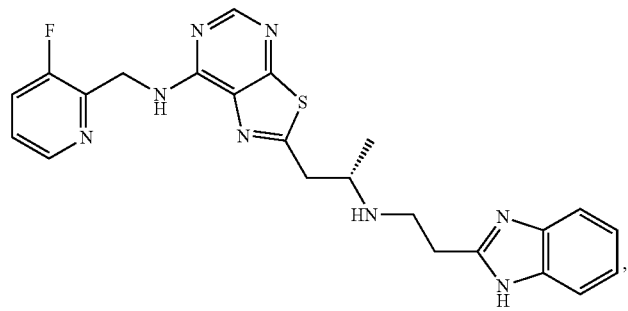 [SMILES: C[C@@H](Cc1nc2c(NCc3ncccc3F)ncnc2s1)NCCc1nc2ccccc2[nH]1] |
| 29 | 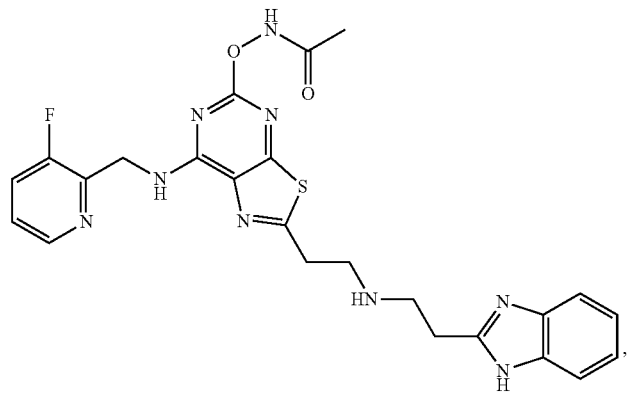 [SMILES: CC(=O)NOc1nc(NCc2ncccc2F)c2nc(CCNCCc3nc4ccccc4[nH]3)sc2n1] |

-continued

| Compound No. | Structure |
|---|---|
| 30 | 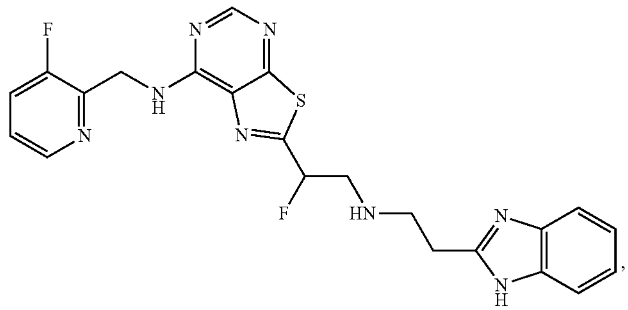 |
| 31 | 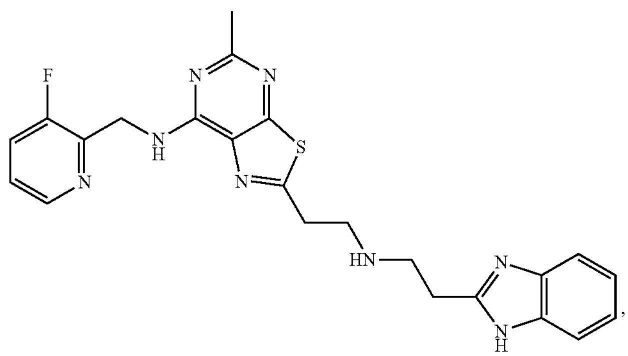 [SMILES: Cc1nc(NCc2ncccc2F)c2nc(CCNCCc3nc4ccccc4[nH]3)sc2n1] |
| 32 | 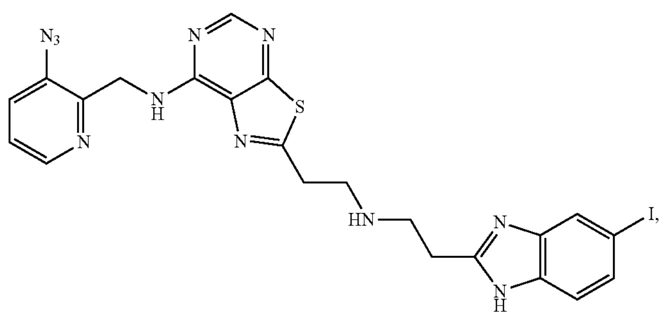 [SMILES: [N-]=[N+]=Nc1cccnc1CNc1ncnc2sc(CCNCCc3nc4cc(I)ccc4[nH]3)nc12] |
| 33 | 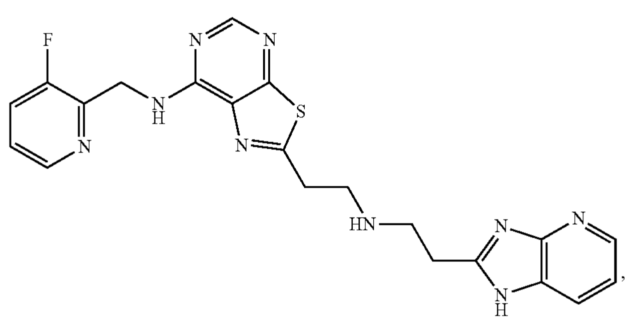 [SMILES: Fc1cccnc1CNc1ncnc2sc(CCNCCc3nc4ncccc4[nH]3)nc12] |

-continued
| Compound No. | Structure |
|---|---|
| 35 | 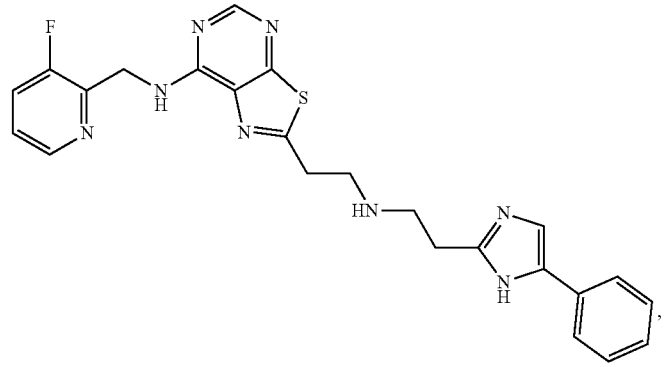 [SMILES: Fc1cccnc1CNc1ncnc2sc(CCNCCc3ncc(-c4ccccc4)[nH]3)nc12] |
| 36 | 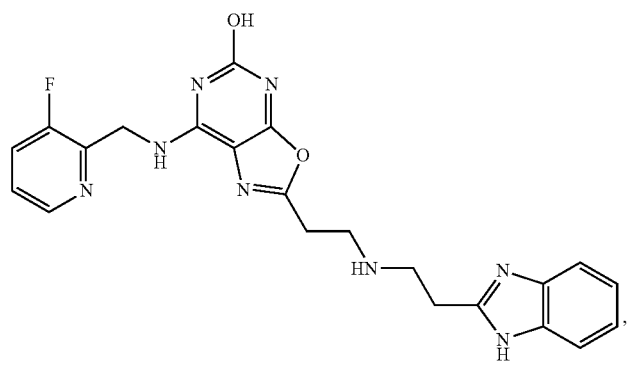 |
| 37 | 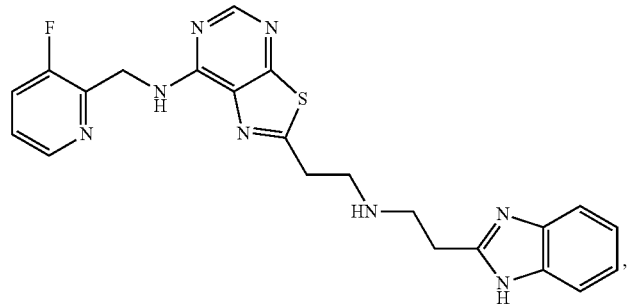 [SMILES: Fc1cccnc1CNc1ncnc2sc(CCNCCc3nc4ccccc4[nH]3)nc12] |
| 38 | 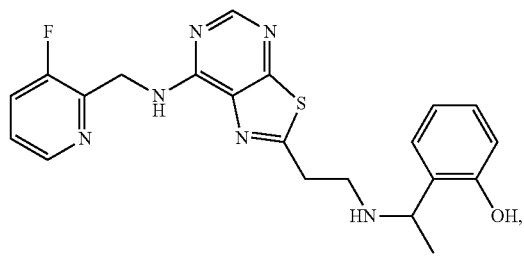 [SMILES: CC(NCCc1nc2c(NCc3ncccc3F)ncnc2s1)c1ccccc1O] |

-continued
| Compound No. | Structure |
|---|---|
| 39 | 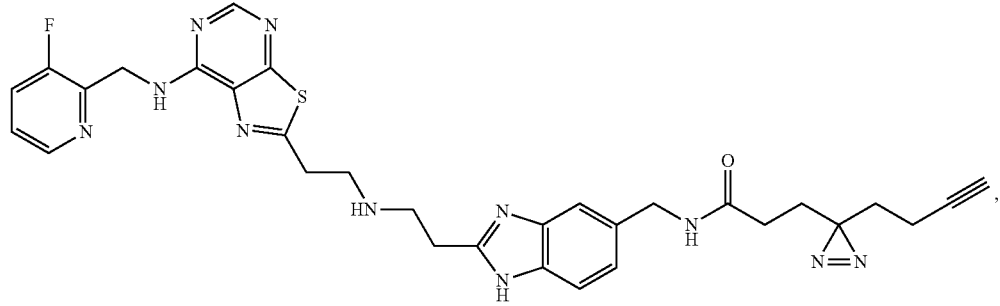 [SMILES: C#CCCC1(CCC(=O)NCc2ccc3[nH]c(CCNCCc4nc5c(NCc6ncccc6F)ncnc5s4)nc3c2)N=N1] |
| 40 | 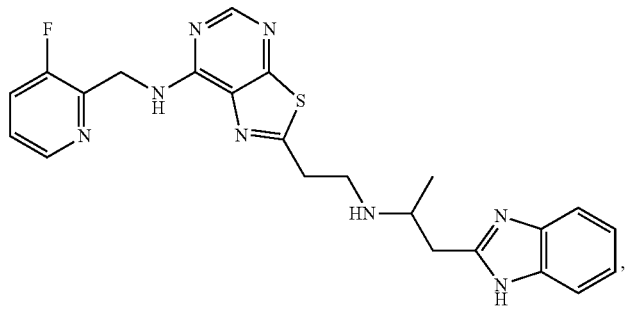 [SMILES: CC(Cc1nc2ccccc2[nH]1)NCCc1nc2c(NCc3ncccc3F)ncnc2s1] |
| 41 | 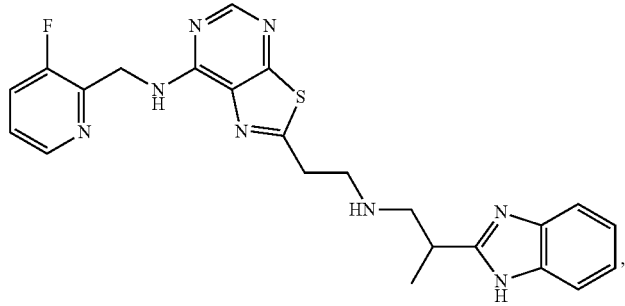 [SMILES: CC(CNCCc1nc2c(NCc3ncccc3F)ncnc2s1)c1nc2ccccc2[nH]1] |
| 42 | 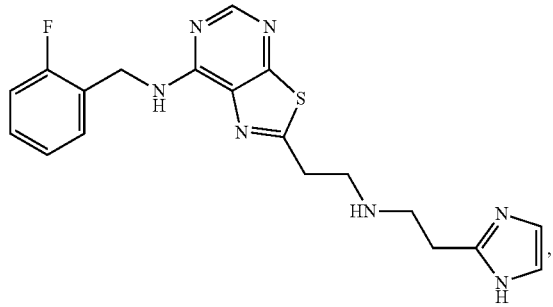 [SMILES: Fc1ccccc1CNc1ncnc2sc(CCNCCc3ncc[nH]3)nc12] |
| 43 | 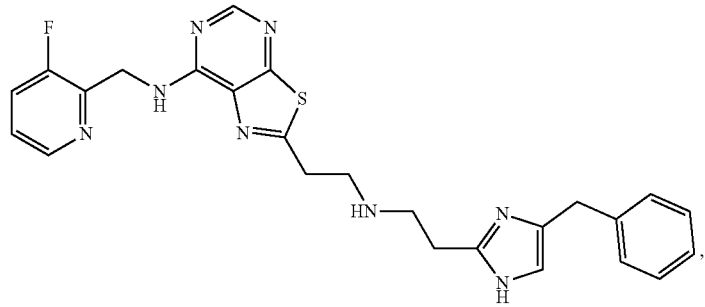 [SMILES: Fc1cccnc1CNc1ncnc2sc(CCNCCc3nc(Cc4ccccc4)c[nH]3)nc12] |

| Compound No. | Structure |
|---|---|
| 44 | 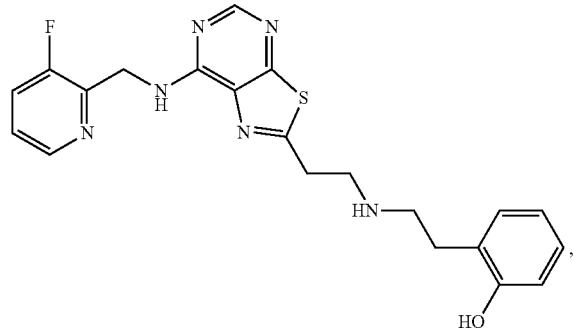 [SMILES: Oc1ccccc1CCNCCc1nc2c(NCc3ncccc3F)ncnc2s1] |
| 45 | 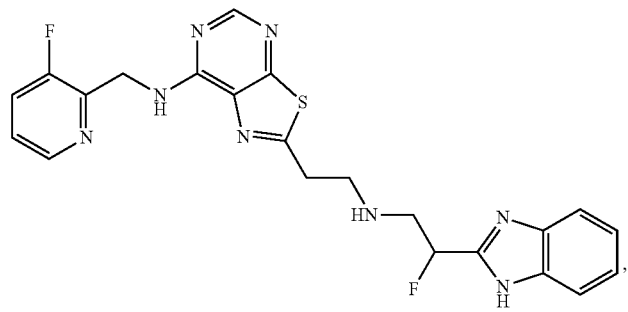 [SMILES: Fc1cccnc1CNc1ncnc2sc(CCNCC(F)c3nc4ccccc4[nH]3)nc12] |
| 46 | 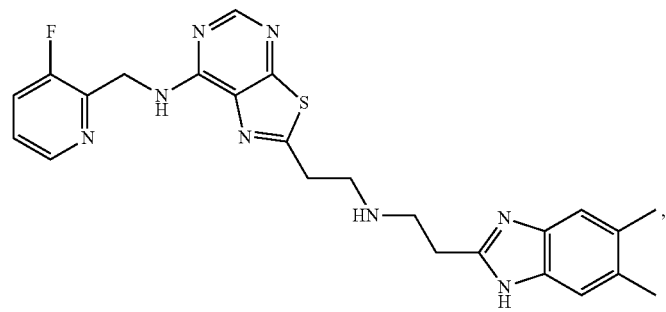 [SMILES: Cc1cc2nc(CCNCCc3nc4c(NCc5ncccc5F)ncnc4s3)[nH]c2cc1C] |
| 47 | 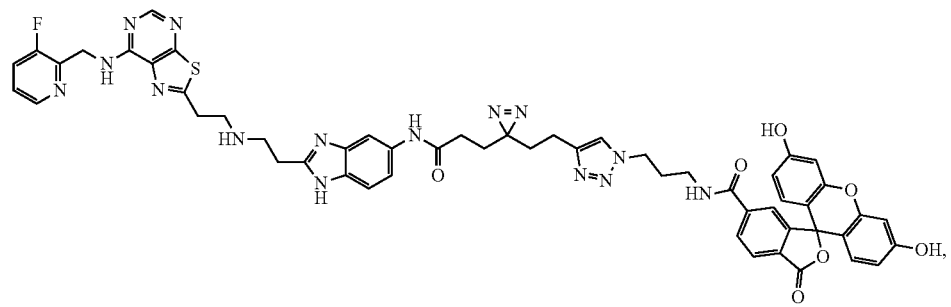 [SMILES: O=C(CCC1(CCc2cn(CCCNC(=O)c3ccc4c(c3)C3(OC4=O)c4ccc(O)cc4Oc4cc(O)ccc43)nn2)N=N1)Nc1ccc2[nH]c(CCNCCc3nc4c(NCc5ncccc5F)ncnc4s3)nc2c1] |

-continued
| Compound No. | Structure |
|---|---|
| 48 | 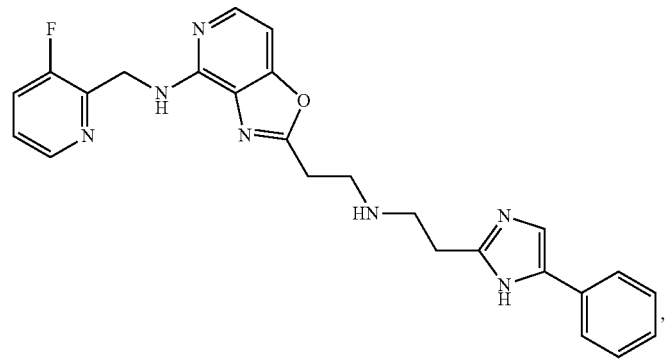 [SMILES: Fc1cccnc1CNc1nccc2oc(CCNCCc3ncc(-c4ccccc4)[nH]3)nc12] |
| 49 | 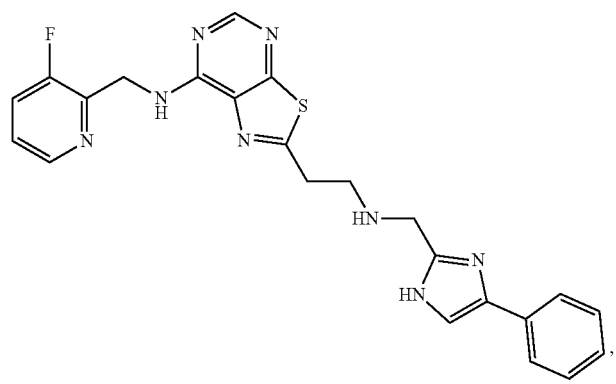 [SMILES: Fc1cccnc1CNc1ncnc2sc(CCNCc3nc(-c4ccccc4)c[nH]3)nc12] |
| 50 | 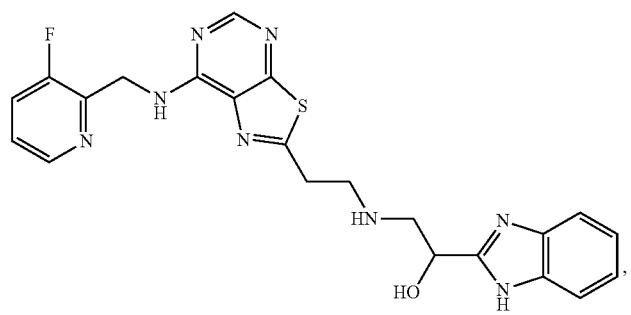 [SMILES: OC(CNCCc1nc2c(NCc3ncccc3F)ncnc2s1)c1nc2ccccc2[nH]1] |
| 51 | 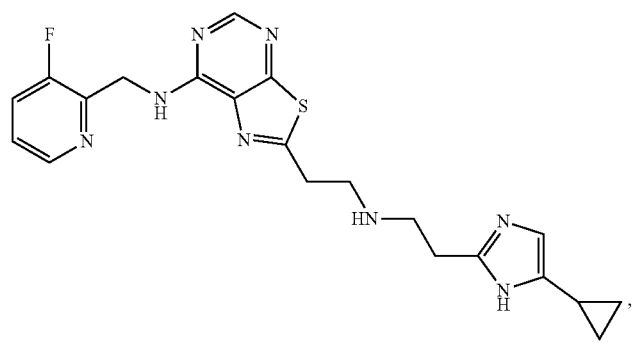 [SMILES: Fc1cccnc1CNc1ncnc2sc(CCNCCc3ncc(C4CC4)[nH]3)nc12] |

-continued
| Compound No. | Structure |
|---|---|
| 52 | 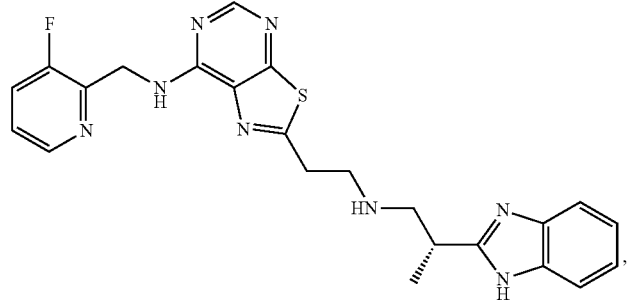 [SMILES: C[C@H](CNCCc1nc2c(NCc3ncccc3F)ncnc2s1)c1nc2ccccc2[nH]1] |
| 53 | 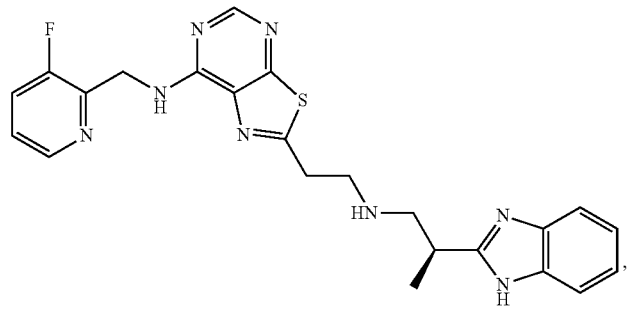 [SMILES: C[C@@H](CNCCc1nc2c(NCc3ncccc3F)ncnc2s1)c1nc2ccccc2[nH]1] |
| 54 | 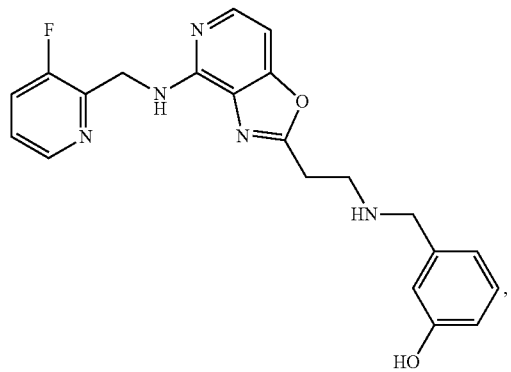 [SMILES: Oc1cccc(CNCCc2nc3c(NCc4ncccc4F)nccc3o2)c1] |
| 55 | 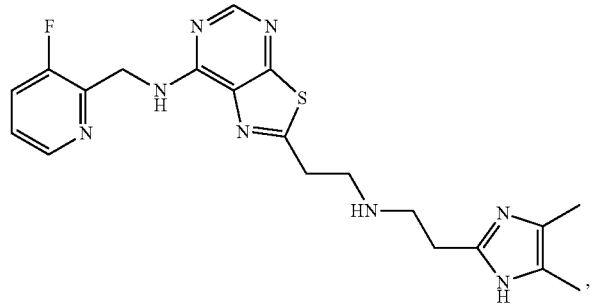 [SMILES: Cc1nc(CCNCCc2nc3c(NCc4ncccc4F)ncnc3s2)[nH]c1C] |

-continued
| Compound No. | Structure |
|---|---|
| 56 | 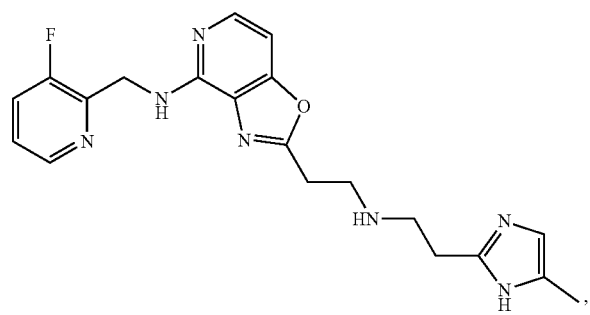 [SMILES: Cc1cnc(CCNCCc2nc3c(NCc4ncccc4F)nccc3o2)[nH]1] |
| 57 | 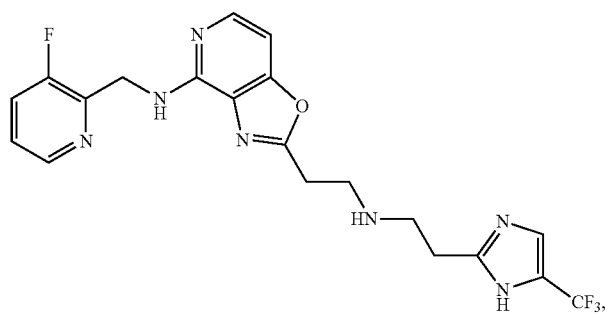 [SMILES: Fc1cccnc1CNc1nccc2oc(CCNCCc3ncc(C(F)(F)F)[nH]3)nc12] |
| 58 | 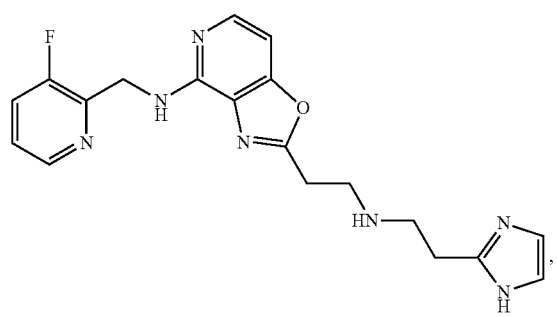 [SMILES: Fc1cccnc1CNc1nccc2oc(CCNCCc3ncc[nH]3)nc12] |
| 59 | 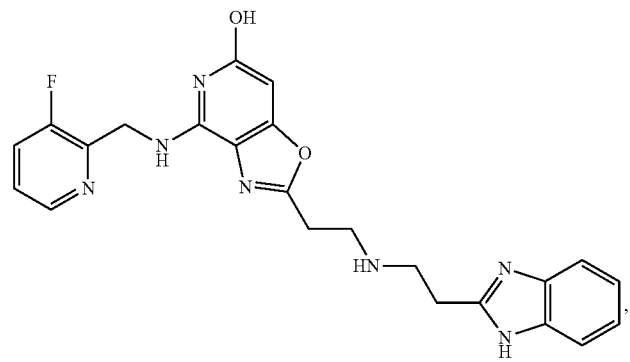 [SMILES: Oc1cc2oc(CCNCCc3nc4ccccc4[nH]3)nc2c(NCc2ncccc2F)n1] |

| Compound No. | Structure |
|---|---|
| 60 | 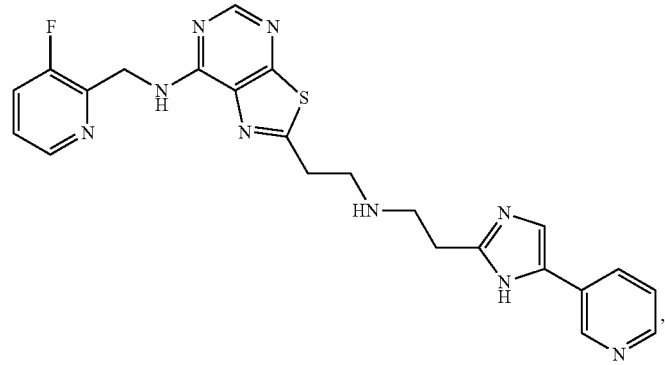 [SMILES: Fc1cccnc1CNc1ncnc2sc(CCNCCc3ncc(-c4cccnc4)[nH]3)nc12] |
| 61 | 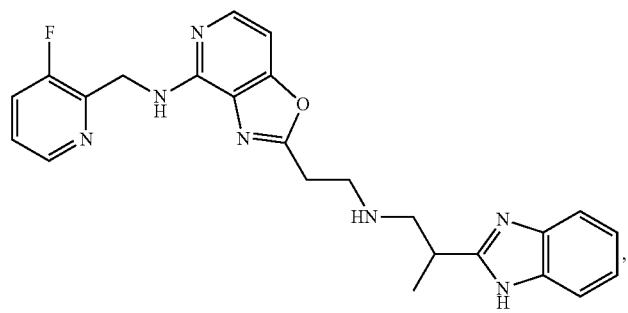 [SMILES: CC(CNCCc1nc2c(NCc3ncccc3F)nccc2o1)c1nc2ccccc2[nH]1] |
| 62 | 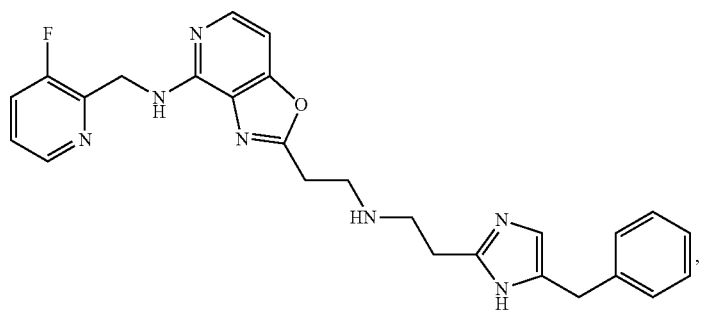 [SMILES: Fc1cccnc1CNc1nccc2oc(CCNCCc3ncc(Cc4ccccc4)[nH]3)nc12] |
| 63 | 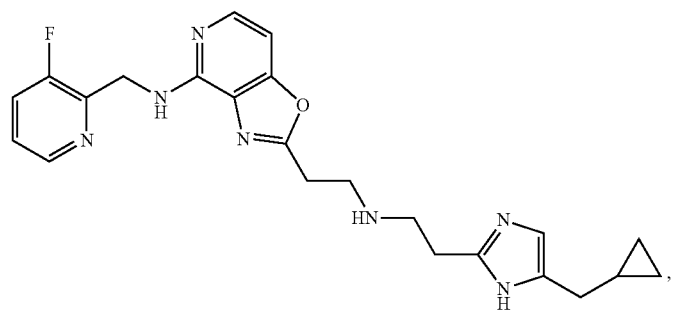 [SMILES: Fc1cccnc1CNc1nccc2oc(CCNCCc3ncc(CC4CC4)[nH]3)nc12] |

-continued
| Compound No. | Structure |
| --- | --- |
| 64 | 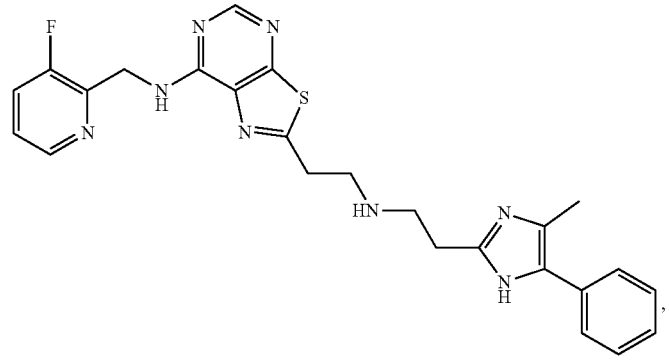 [SMILES: Cc1nc(CCNCCc2nc3c(NCc4ncccc4F)ncnc3s2)[nH]c1-c1ccccc1] |
| 65 | 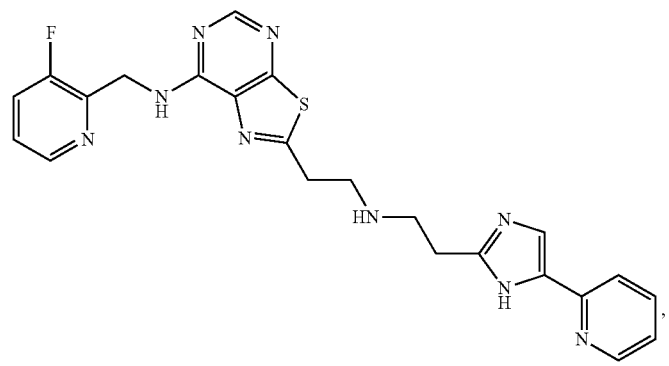 |
| 66 | 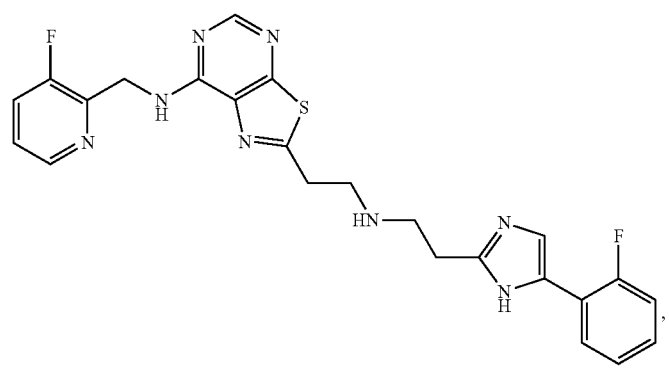 [SMILES: Fc1ccccc1-c1cnc(CCNCCc2nc3c(NCc4ncccc4F)ncnc3s2)[nH]1] |
| 67 | 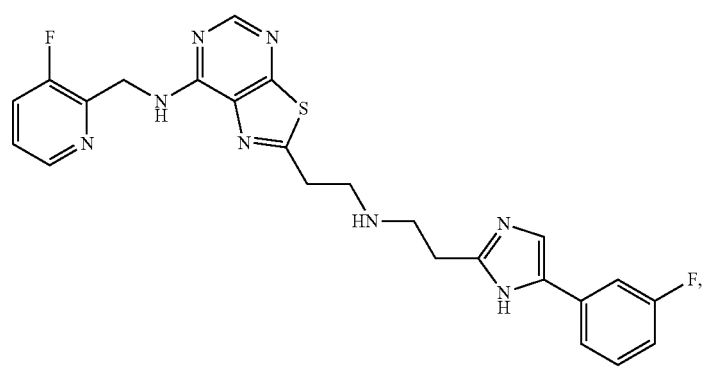 [SMILES: Fc1cccc(-c2cnc(CCNCCc3nc4c(NCc5ncccc5F)ncnc4s3)[nH]2)c1] |

-continued
| Compound No. | Structure |
|---|---|
| 68 | 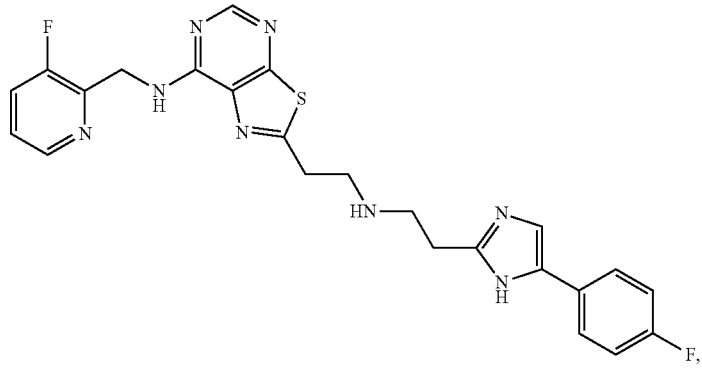 [SMILES: Fc1ccc(-c2cnc(CCNCCc3nc4c(NCc5ncccc5F)ncnc4s3)[nH]2)cc1] |
| 69 | 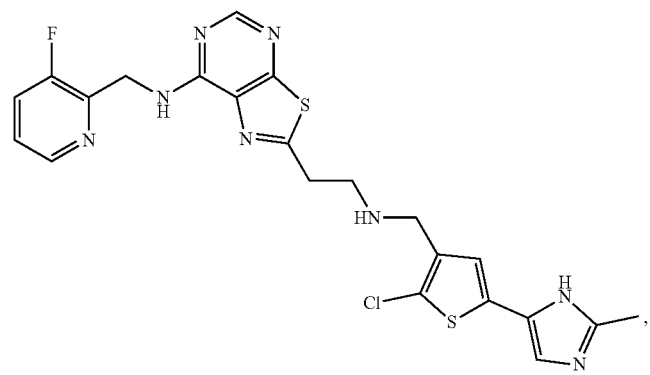 [SMILES: Cc1ncc(-c2cc(CNCCc3nc4c(NCc5ncccc5F)ncnc4s3)c(Cl)s2)[nH]1] |
| 70 | 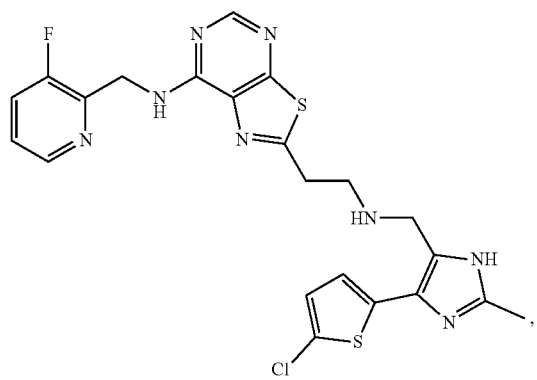 [SMILES: Cc1nc(-c2ccc(Cl)s2)c(CNCCc2nc3c(NCc4ncccc4F)ncnc3s2)[nH]1] |
| 71 | 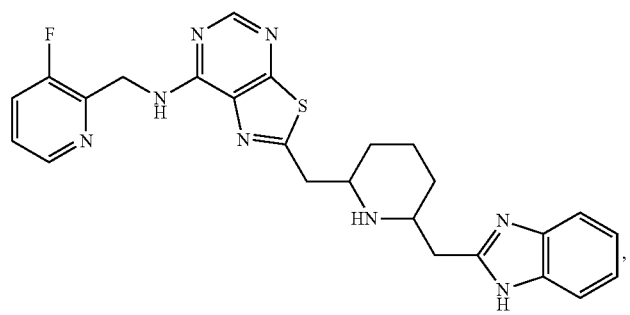 [SMILES: Fc1cccnc1CNc1ncnc2sc(CC3CCCC(Cc4nc5ccccc5[nH]4)N3)nc12] |

| Compound No. | Structure |
|---|---|
| 72 | 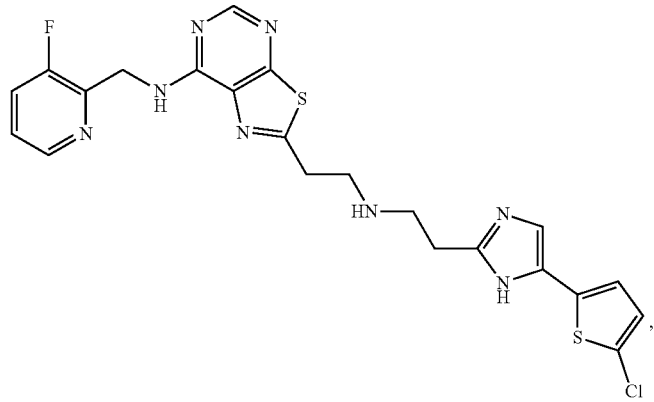 [SMILES: Fc1cccnc1CNc1ncnc2sc(CCNCCc3ncc(-c4ccc(Cl)s4)[nH]3)nc12] |
| 73 | 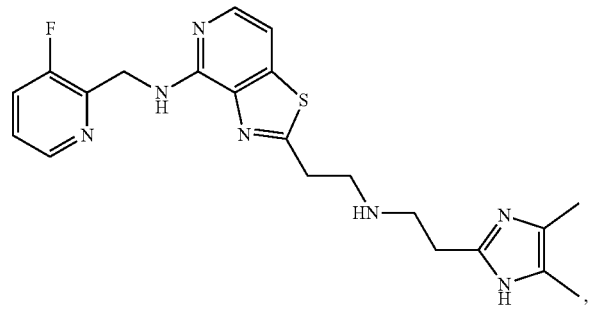 [SMILES: Cc1nc(CCNCCc2nc3c(NCc4ncccc4F)nccc3s2)[nH]c1C] |
| 74 | 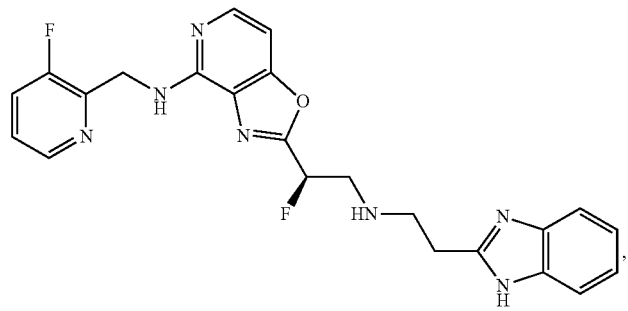 [SMILES: Fc1cccnc1CNc1nccc2oc([C@H](F)CNCCc3nc4ccccc4[nH]3)nc12] |
| 75 | 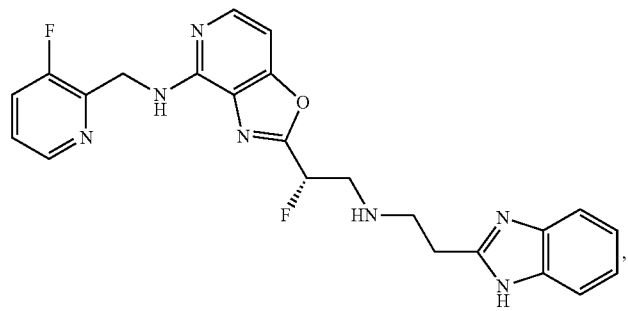 [SMILES: Fc1cccnc1CNc1nccc2oc([C@@H](F)CNCCc3nc4ccccc4[nH]3)nc12] |

| Compound No. | Structure |
|---|---|
| 76 | 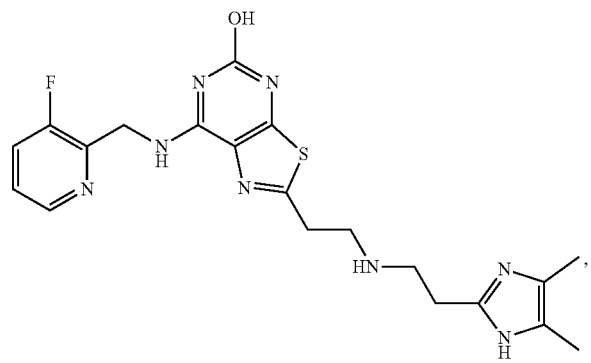 [SMILES: Cc1nc(CCNCCc2nc3c(NCc4ncccc4F)nc(O)nc3s2)[nH]c1C] |
| 77 | 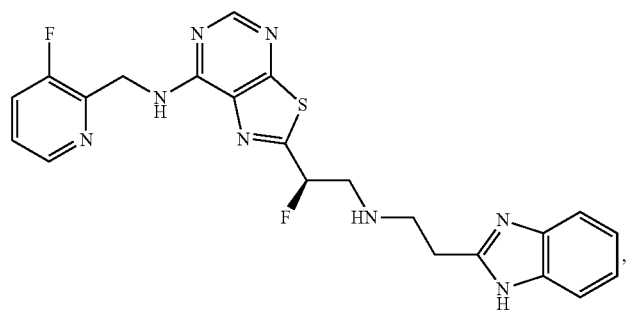 [SMILES: Fc1cccnc1CNc1ncnc2sc([C@H](F)CNCCc3nc4ccccc4[nH]3)nc12] |
| 78 | 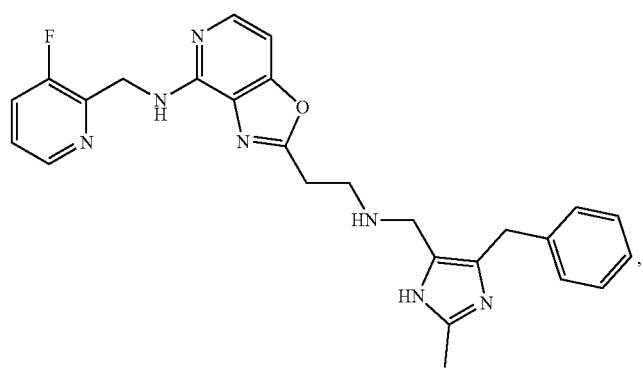 [SMILES: Cc1nc(Cc2ccccc2)c(CNCCc2nc3c(NCc4ncccc4F)nccc3o2)[nH]1] |
| 79 | 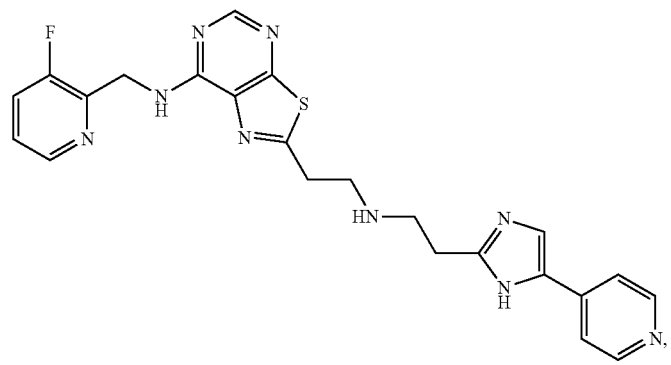 [SMILES: Fc1cccnc1CNc1ncnc2sc(CCNCCc3ncc(-c4ccncc4)[nH]3)nc12] |

| Compound No. | Structure |
|---|---|
| 80 | *(structure)* |
| 81 | *(structure)* |
| 82 | *(structure)*, and |
| 83 | *(structure)*. |

24. A pharmaceutical composition comprising a compound according to claim 1 or a pharmaceutically acceptable salt thereof, and a pharmaceutically acceptable excipient.

* * * * *

UNITED STATES PATENT AND TRADEMARK OFFICE
CERTIFICATE OF CORRECTION

PATENT NO. : 11,286,243 B2
APPLICATION NO. : 16/712628
DATED : March 29, 2022
INVENTOR(S) : Zhe Li et al.

Page 1 of 1

It is certified that error appears in the above-identified patent and that said Letters Patent is hereby corrected as shown below:

In the Claims

In Claim 1, at Column 387, Line 11, delete "on of" and insert -- one of --, therefor.
In Claim 1, at Column 387, Line 12, delete "take" and insert -- taken --, therefor.
In Claim 9, at Column 388, Line 66, delete ", O, or S" after "NR$^{18}$".

Signed and Sealed this
Eighth Day of October, 2024

Katherine Kelly Vidal
*Director of the United States Patent and Trademark Office*